(12) United States Patent
Saha et al.

(10) Patent No.: US 10,668,055 B2
(45) Date of Patent: Jun. 2, 2020

(54) CANCER TREATMENT USING COMBINATIONS OF ERK AND RAF INHIBITORS

(71) Applicant: BIOMED VALLEY DISCOVERIES, INC., Kansas City, MO (US)

(72) Inventors: Saurabh Saha, Wellesley Hills, MA (US); Dean Welsch, Parkville, MO (US); Gary DeCrescenzo, Parkville, MO (US); Jeffrey James Roix, Boston, MA (US)

(73) Assignee: BIOMED VALLEY DISCOVERIES, INC., Kansas City, MO (US)

( * ) Notice: Subject to any disclaimer, the term of this patent is extended or adjusted under 35 U.S.C. 154(b) by 0 days.

(21) Appl. No.: 15/105,904

(22) PCT Filed: Dec. 19, 2014

(86) PCT No.: PCT/US2014/071715
§ 371 (c)(1),
(2) Date: Jun. 17, 2016

(87) PCT Pub. No.: WO2015/095819
PCT Pub. Date: Jun. 25, 2015

(65) Prior Publication Data
US 2016/0310476 A1 Oct. 27, 2016

Related U.S. Application Data

(60) Provisional application No. 61/919,347, filed on Dec. 20, 2013.

(51) Int. Cl.
| | | |
|---|---|---|
| A61K 31/4439 | (2006.01) |
| A61K 31/437 | (2006.01) |
| A61K 31/506 | (2006.01) |
| A61K 45/06 | (2006.01) |
| A61K 31/519 | (2006.01) |
| A61K 31/555 | (2006.01) |
| A61K 31/5377 | (2006.01) |
| A61K 31/517 | (2006.01) |
| A61K 31/428 | (2006.01) |
| A61K 31/44 | (2006.01) |

(52) U.S. Cl.
CPC ........ *A61K 31/4439* (2013.01); *A61K 31/428* (2013.01); *A61K 31/437* (2013.01); *A61K 31/44* (2013.01); *A61K 31/506* (2013.01); *A61K 31/517* (2013.01); *A61K 31/519* (2013.01); *A61K 31/5377* (2013.01); *A61K 31/555* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 5,622,824 A | 4/1997 | Koster | |
| 6,140,053 A | 10/2000 | Koster | |
| 7,354,939 B2 * | 4/2008 | Martinez-Botella | ........................ C07F 9/65583 514/343 |
| 8,288,520 B2 | 10/2012 | Eder et al. | |
| 8,389,219 B2 | 3/2013 | Anthony et al. | |
| 2009/0306020 A1 | 12/2009 | Scheuring et al. | |
| 2011/0152230 A1 | 6/2011 | Mascharak | |
| 2012/0264632 A1 | 10/2012 | Leamon et al. | |
| 2013/0203632 A1 | 8/2013 | Nazarenko et al. | |
| 2013/0217721 A1 | 8/2013 | Lo et al. | |

FOREIGN PATENT DOCUMENTS

| | | | |
|---|---|---|---|
| CN | 1976919 A | 6/2007 | |
| WO | 2005021786 A1 | 3/2005 | |
| WO | 2005113541 A1 | 12/2005 | |
| WO | 2012046981 A2 | 4/2012 | |
| WO | WO 2012068562 A2 * | 5/2012 | ........... C12Q 1/6886 |
| WO | 2012125848 A2 | 9/2012 | |
| WO | 2013074594 A1 | 5/2013 | |

OTHER PUBLICATIONS

Roberts, Patrick J., and Channing J. Der. "Targeting the Raf-MEK-ERK mitogen-activated protein kinase cascade for the treatment of cancer." Oncogene 26.22 (2007): 3291-3310.*
Flaherty, Keith T. "BRAF inhibitors and melanoma." The Cancer Journal 17.6 (2011): 505-511.*
Trametinib (GSK1120212) product page from http://www.apexbt.com/trametinib.html, accessed Jun. 9, 2017.*
Avruch, J., et al., Ras Activation of the Raf Kinase: Tyrosine Kinase Recruitment of the MAP Kinase Cascade, Recent Prog Horm Res. 2001;56:127-55.
Brose, M.S., et al., BRAF and RAS Mutations in Human Lung cancer and Melanoma, Cancer Research, 62, 1997-7000, Dec. 1, 2002.
Davies, H., et al., Mutations of the BRAF gene in human cancer, Nature, vol. 417, Jun. 27, 2002, pp. 949-954.
Fransen, K., et al., Mutation analysis of the BRAF, ARAF and RAF-1 genes in human colorectal adenocarcinomas, Carcinogenesis. Apr. 2004;25(4):527-33.
Garnett, M. J., et al., Wild-Type and Mutant B-RAF Activate C-RAF through Distinct Mechanisms Involving Heterodimerization, Molecular Cell, vol. 20, 963-969, Dec. 22, 2005.

(Continued)

*Primary Examiner* — Nissa M Westerberg
(74) *Attorney, Agent, or Firm* — Bryan Cave Leighton Paisner, LLP

(57) ABSTRACT

The present invention provides, inter alia, methods of treating or ameliorating the effects of a cancer in a subject. The methods include administering to the subject an effective amount of (i) a first anti-cancer agent, which is BVD-523 or a pharmaceutically acceptable salt thereof and (ii) a second anti-cancer agent, which is a type 1 RAF inhibitor (such as dabrafenib) or another RAF inhibitor (such as regorafenib) or a pharmaceutically acceptable salt thereof, to treat or ameliorate the effects of the cancer. Also provided are pharmaceutical compositions and kits for treating or ameliorating the effects of a cancer in a subject.

27 Claims, 176 Drawing Sheets
Specification includes a Sequence Listing.

(56) References Cited

OTHER PUBLICATIONS

Greger, J. G., et al., Combinations of BRAF, MEK, na dPI3K/mTOR Inhibitors Overcome Acquired Resistance to the BRAF Inhibitor GSK2118436 Dabrafenib, Mediated by NRAS or MEK Mutations, Molecular Cancer Therapeutics, 11(4): 909-920, 2012.
Hocker, T., et al., Ultraviolet Radiation and Melanoma: A Systematic Review and Analysis of Reported Sequence Variants, Human Mutation 28(6), 578-599, 2007.
King, A. J., et al., Dabrafenib; Preclinical Characterization, Increased Efficacy when Combined with Trametinib, while BRAF/MEK Tool Combination Reduced Skin Lesions, PLOS One, vol. 8, Issue 7, e67583-e67583, (2013).
Liu, D., et al., BRAF V600E Maintains Proliferation, Transformation, and Tumorigencity of BRAF-Mutuan Papillary Thyroid Cancer Cells, Journal of Clinical Endocrinol. Metab. Jun. 2007; 92(6): 2264-2271.
Little, A. S., et al., Amplification of the Driving Oncogene, KRAS or BRAF, Underpins Acquired Resistance to MEK 1/2 Inhibitors in Colorectal Cancer Cells, Science Signaling 4(166), ra17, Mar. 29, 2011.
Long, G.V., et al., Prognostic and Clinicopathologic Associations of Oncogenic BRAF in Metastatic Melanoma, Journal of Clinical Oncology, vol. 29, No. 10, pp. 1239-1246, Apr. 2011.
Manandhar, S. P., et al., Small-Molecular Inhibitors of the Rce1p CaaX Protease, J. Biomol. Screen, Oct. 2007; 12(7): pp. 983-993.
Maurer, T., et al., Small-molecule ligands bind to a distinct pocket in Ras and inhibit SOS-mediated nucleotide exchange activity, PNAS, Apr. 3, 2012, vol. 109, No. 14, pp. 5299-5304.
Mittal, R. et al., The Acetyltransferase Activity of the Bacterial Toxin YopJ of Yersinia Is Activated by Eukaryotic Host Cell Inositol Hexakisphosphate, The J. of Biological Chemistry, vol. 285, No. 26, pp. 19927-19934, Jun. 25, 2016.
Patgiri, A., et al., An Orthosteric Inhibitor of the Ras-Sos Interaction, Nat. Chem. Biol., 2011; 7(9): 585-587.
Porter, S.B., Inhibition of the CaaX proteases Rce1p and Ste24p by peptidyl (acyloxy)methyl Ketones, Biochim. Biophys. Acta, 2007 une; 1773(6): 853-862.
Rushworth, L.K., et al., Regulation and Role of Raf-1/B-Raf Heterodimerization, Molecular and Cellular Biology, Mar. 2006, vol. 26, No. 6, pp. 2262-2272.
Seth, R., et al., Concomitant mutations and spice variants in KRAS and BRAF demonstrate complex perturbation of the Ras/Raf signalling pathway in advanced colorectal cancer, Gut, 2009, 58:1234-1241.
Shima, F., et al., In silico discovery of small-molecular Ras inhibitors that display antitumor activity by blocking the Ras-effector interaction, PNAS, May 14, 2013, vol. 110, No. 20.
Wan, P.T.C., Mechanism of activation of the RAF-ERK Signaling Pathway by Oncogenic Mutations of B-RAF, Cell, vol. 116, pp. 855-867, Mar. 19, 2004.
Weber, C.K., et al., Active Ras Induces Heterodimerization of the cRaf and BRaf, Cancer Research, vol. 61, 3595-3598, May 1, 2001.
Wellbrock, C., et al., The RAF Proteins Take Centre Stage, Nature Reviews, Molecular Cell Biology, vol. 5, Nov. 2004, pp. 875-885.
Xu, X., et al., High Prevalence of BRAF Gene Mutation in Papillary Thyroid Carcinomas and Thyroid Tumor Cell Lines, Cancer Research 63, 4561-4567, Aug. 1, 2003.
Metzker, M. L., et al., Emerging technologies in DNA sequencing, Human Genome, Sequencing Center and Dept. of Mol. and Human Genetics, Genome Research 15:1767-1776, 2005.
Ota, M., et al., Single Nucleotide polymorphism detection by polymerase chain reaction-restriction fragment length polymorphism, Nature Protocols, vol. 2, No. 11, pp. 2857-2864, 2007.
Absalan, F., et al., Molecular Inversion Probe Assay, Methods in Molecular Biology, vol. 396: Comparative Genomics, vol. 2, pp. 315-330 (2008).
Nilsson, M., et al., Padlock Probes: Circularizing Oligonucleotides for Localized DNA Detection, Science, vol. 265, Sep. 30, 1994.
Akinleye, A., et al., MEK and the inhibitors: from bench to bedside, Journal of Hematology & Oncology 2013, 6:27.
Hardenbol, P., et al., Multiplexed genotyping with sequence-tagged molecular inversion probes, Nature Biotechnology, vol. 21, No. 6, pp. 673-678, Jun. 2003.
Morris, et al., Discovery of Novel ERK Inhibitor with Activity in Models of Acquired Resistance to BRAF and MEK Inhibitors, Cancer Discovery, Jul. 2013, vol. 3, No. 7 pp. 742-750.
Jin, et al., Exploration of N-(2-aminoethyl) piperidine-4-carboxamide as a potential scaffold for development of VEGFR-2, ERK-2 and Abl-1 multikinase inhibitor, Bioorganic & Medicinal Chemistry, Sep. 15, 2013, vol. 21, No. 18, pp. 5694-5706.
Li et al., Recent Advances in the Research and Development of B-Raf Inhibitors, Current Medical Chemistry, 2010, vol. 17, No. 16, pp. 1618-1634.
International Search Report and Written Opinion issued by the International Bureau dated Jun. 10, 2015.
Darrin D. Stuart et al., "Abstract 3790: preclinical profile of LGX 818: a potent and selective RAF kinase inhibitor", Cancer Research, vol. 72, No. 16, supplement (Apr. 4, 2012).
Office Action, Chinese Appl. No. 201480074321.4, dated May 29, 2018.
Hoeflich et al. "In vivo Antitumor Activity of MEK and Phosphatidylinositol 3-Kinase Inhibitors in Basal-Like Breast Cancer Models." Clin Cancer Res. Jul. 15, 2009;15(14):4649-64.
Jing et al. "Comprehensive Predictive Biomarker Analysis for MEK Inhibitor GSK1120212." Mol Cancer Ther. Mar. 2012;11(3):720-9.
Kwong et al. "Oncogenic NRAS signaling differentially regulates survival and proliferation in melanoma." Nat Med. Oct. 2012;18(10):1503-10.
Serra et al. "PI3K inhibition results in enhanced HER signaling and acquired ERK dependency in HER2-overexpressing breast cancer." Oncogene. Jun. 2, 2011;30(22):2547-57.
Sherr and McCormick. "The RB and p53 pathways in cancer." Cancer Cell. Aug. 2002;2(2):103-12.
Tang et al. "Attenuation of the Retinoblastoma Pathway in Pancreatic Neuroendocrine Tumors Due to Increased Cdk4/Cdk6." Clin Cancer Res. Sep. 1, 2012;18(17):4612-20.
Hatzivassiliou, et al. "ERK Inhibition Overcomes Acquired Resistance to MEK Inhibitors," Mol Cancer Ther 2012; 11:1143-1154.

* cited by examiner

FIG. 1
A
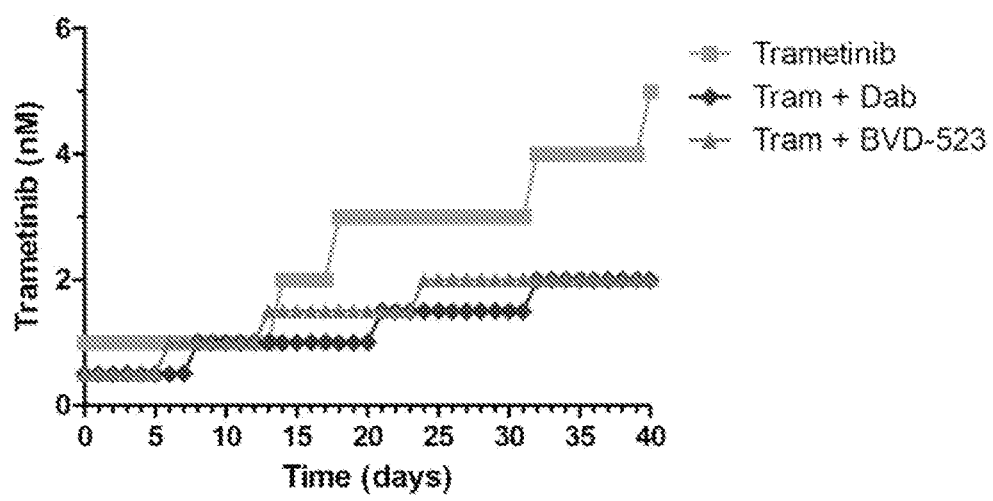
B
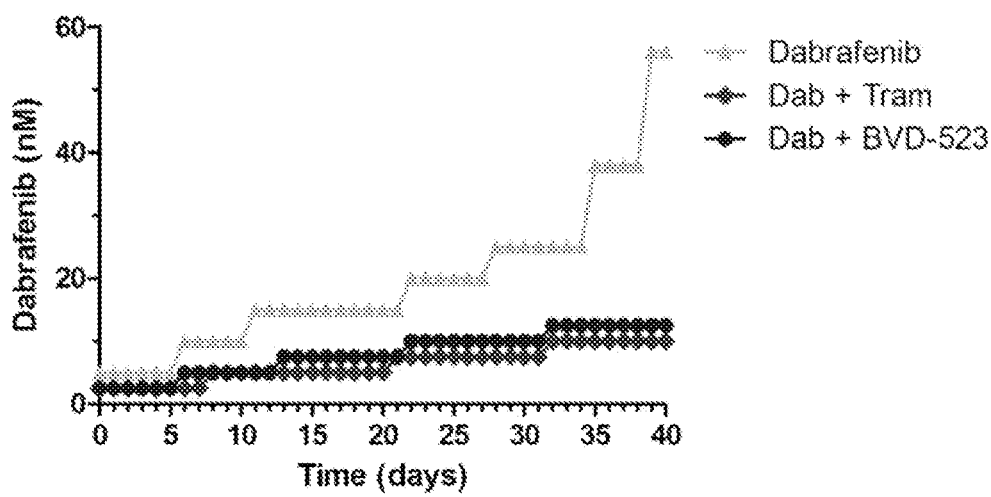

FIG. 1, Con't
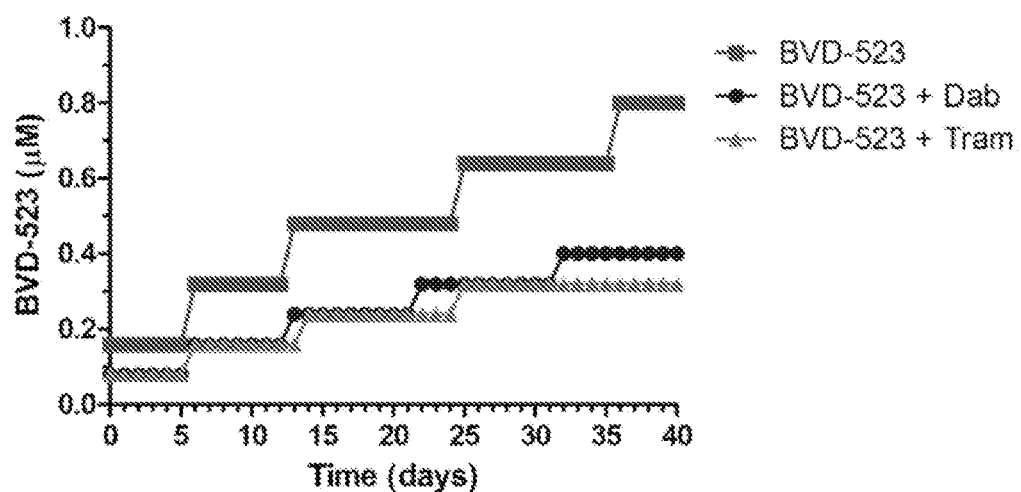

A

FIG. 2, Con't
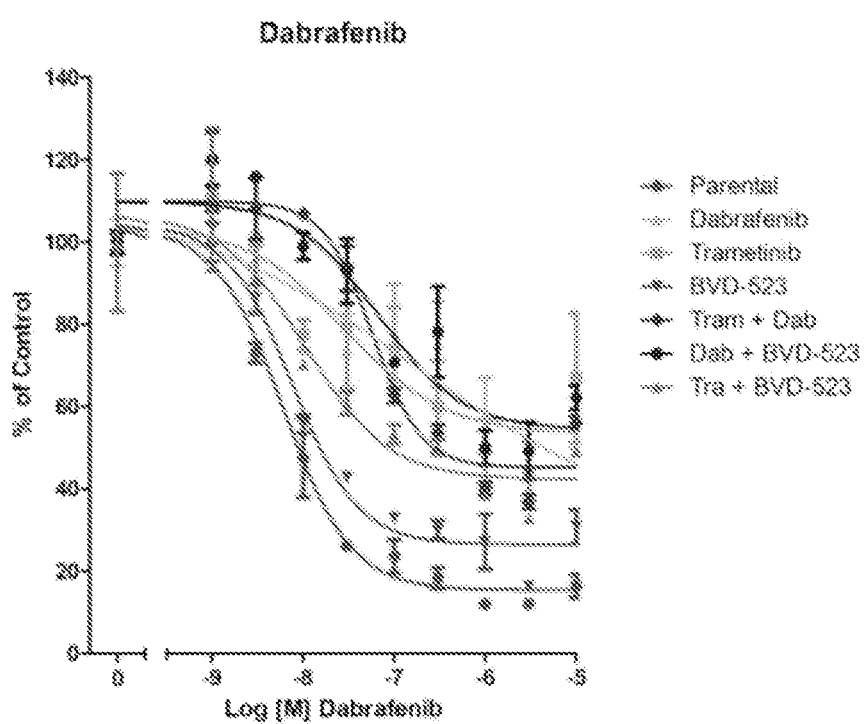

FIG. 2, Con't
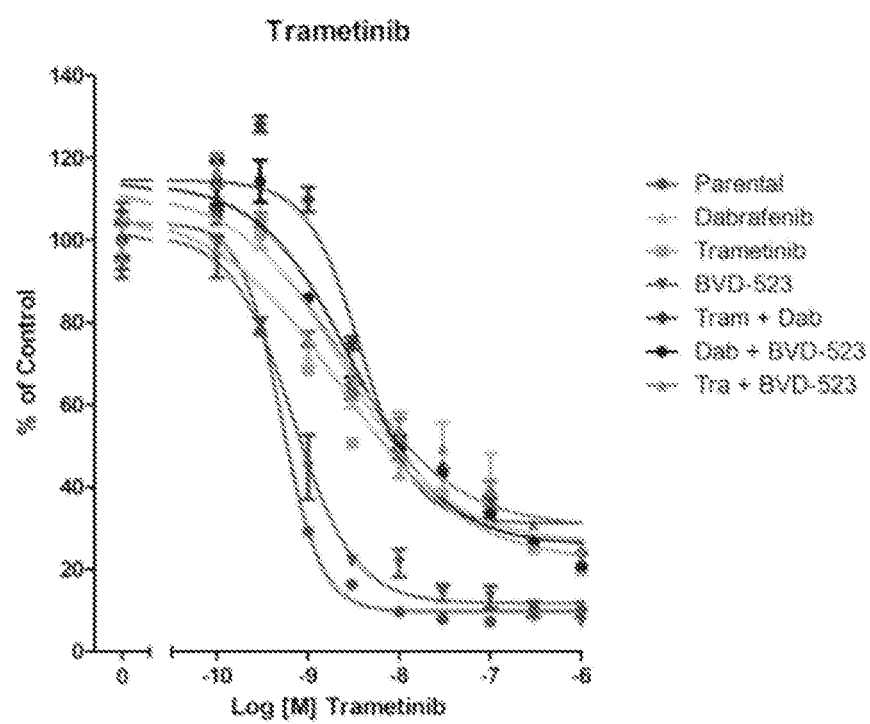

FIG. 2, Con't
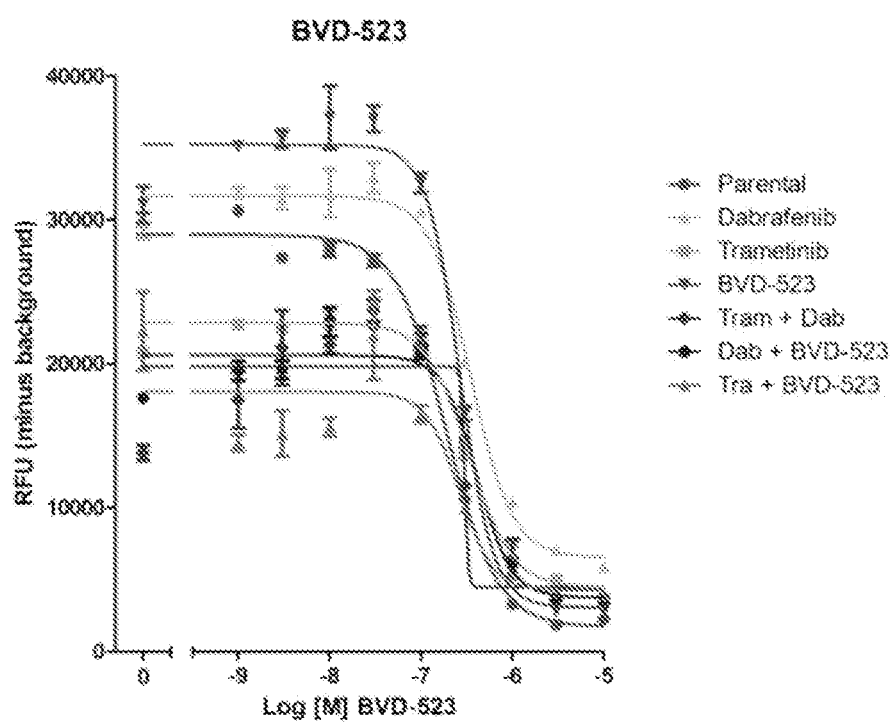

FIG. 2, Con't
E
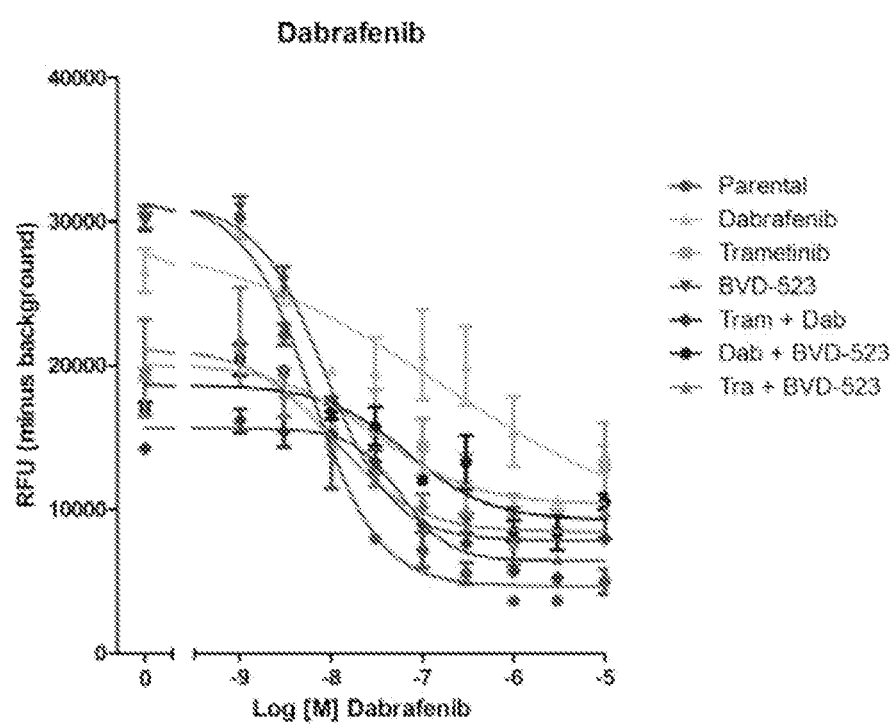

FIG. 2, Con't
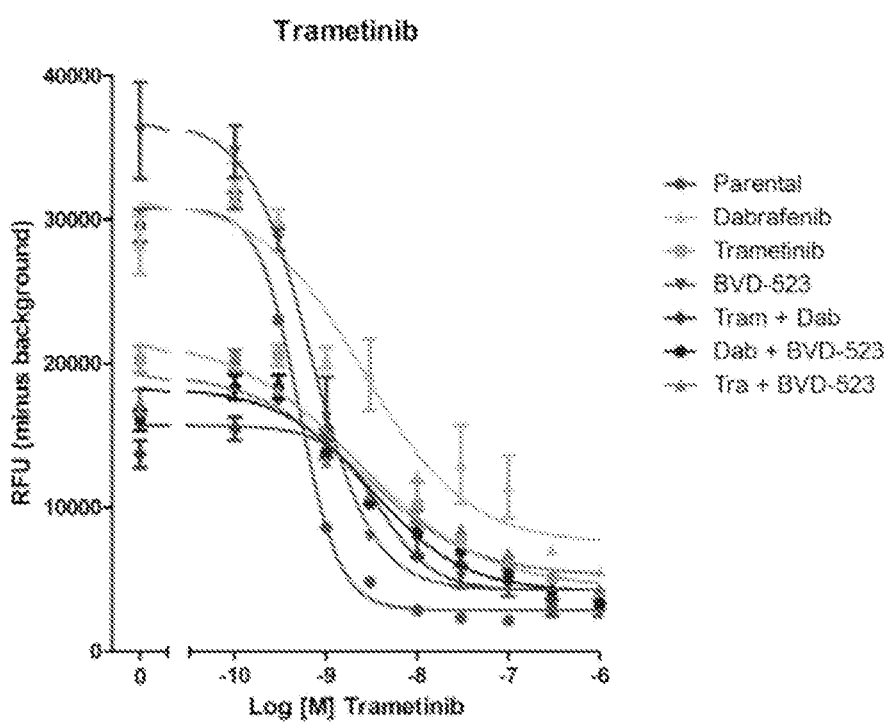

FIG. 2, Con't
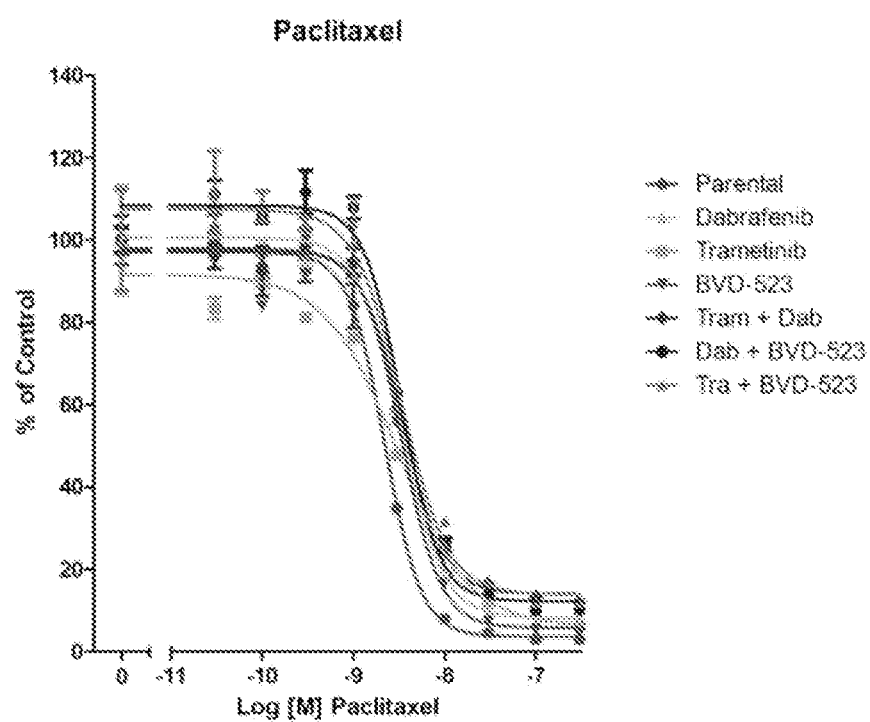

FIG. 2, Con't
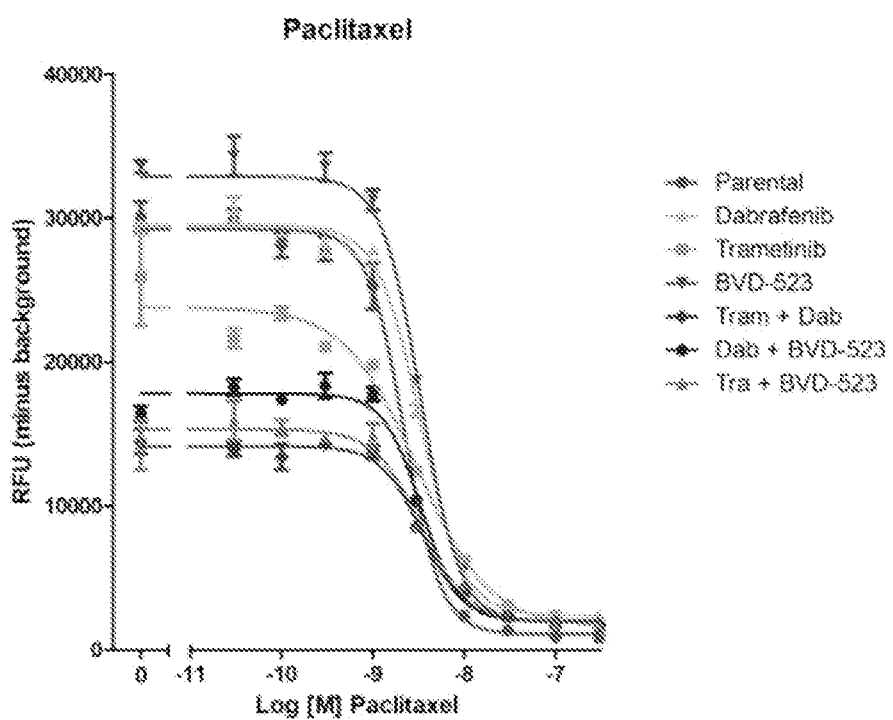

FIG. 3
A
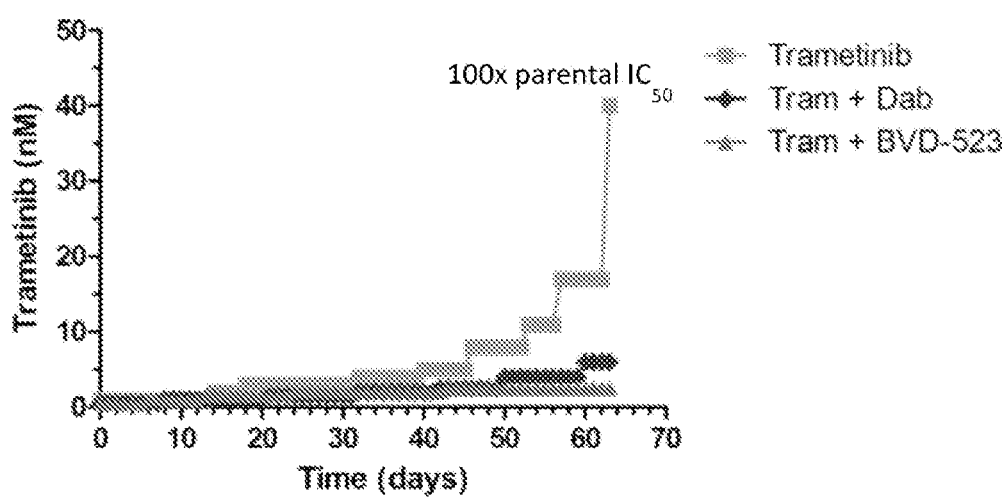
B
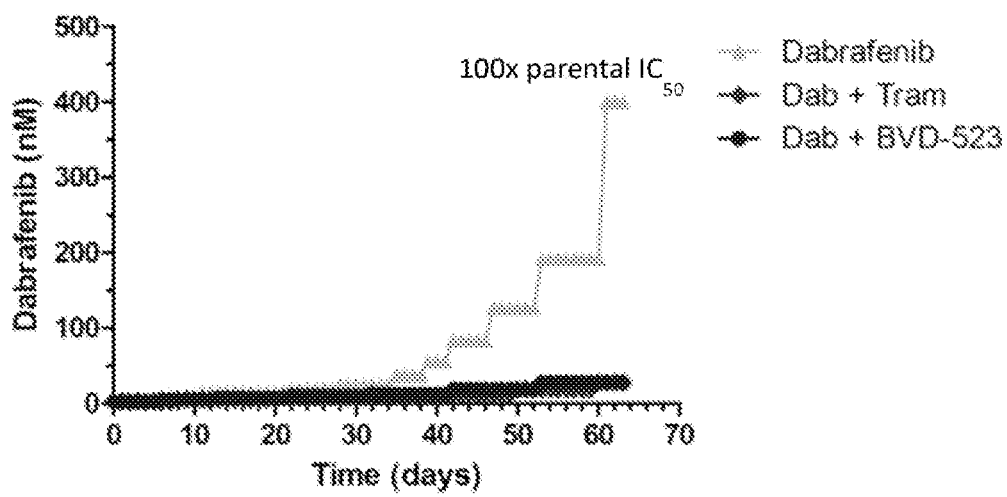

FIG. 3, Con't
C
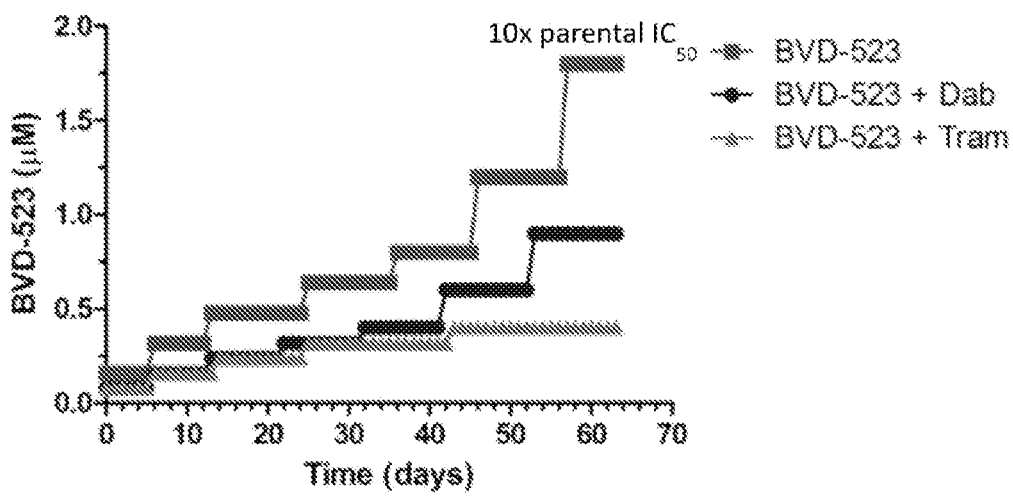
D
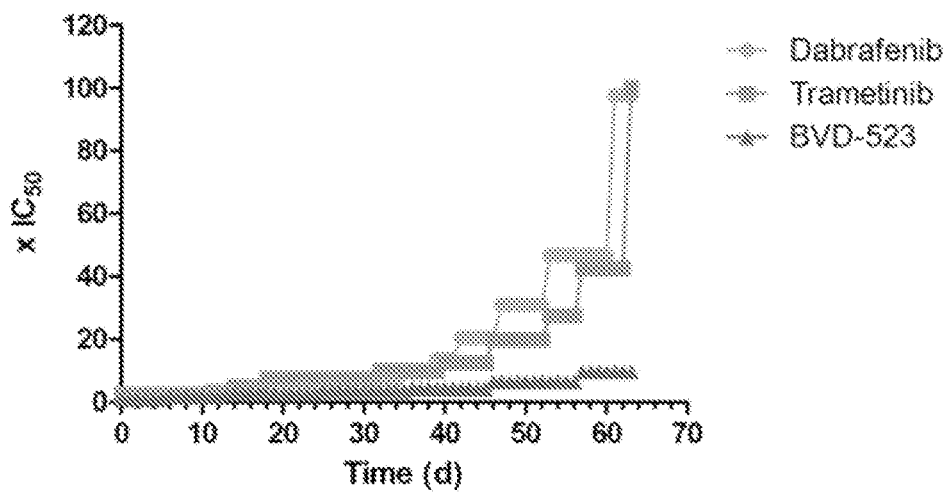

A

FIG. 4, Con't
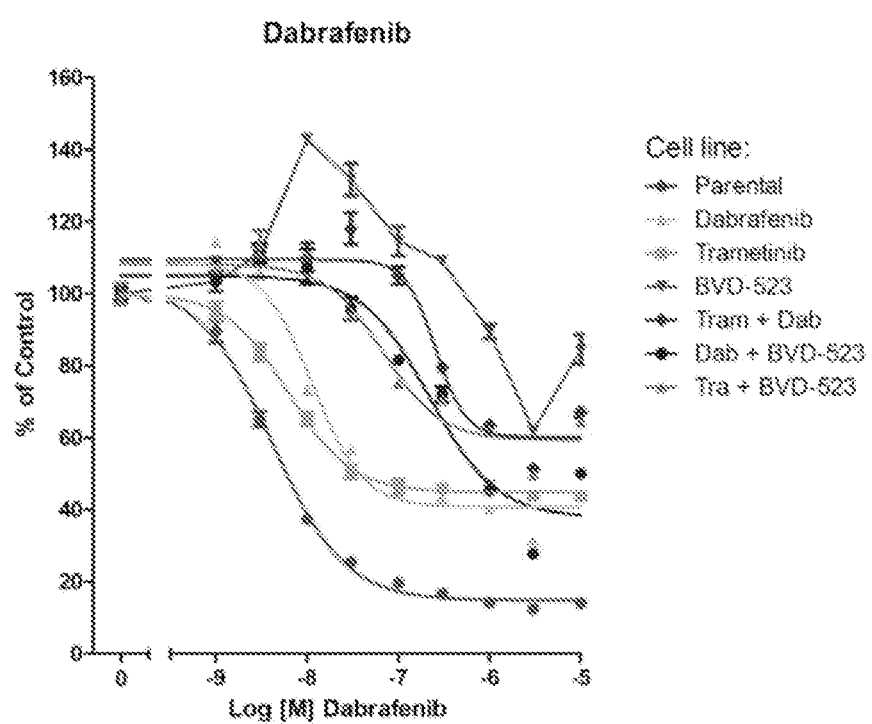

FIG. 4, Con't
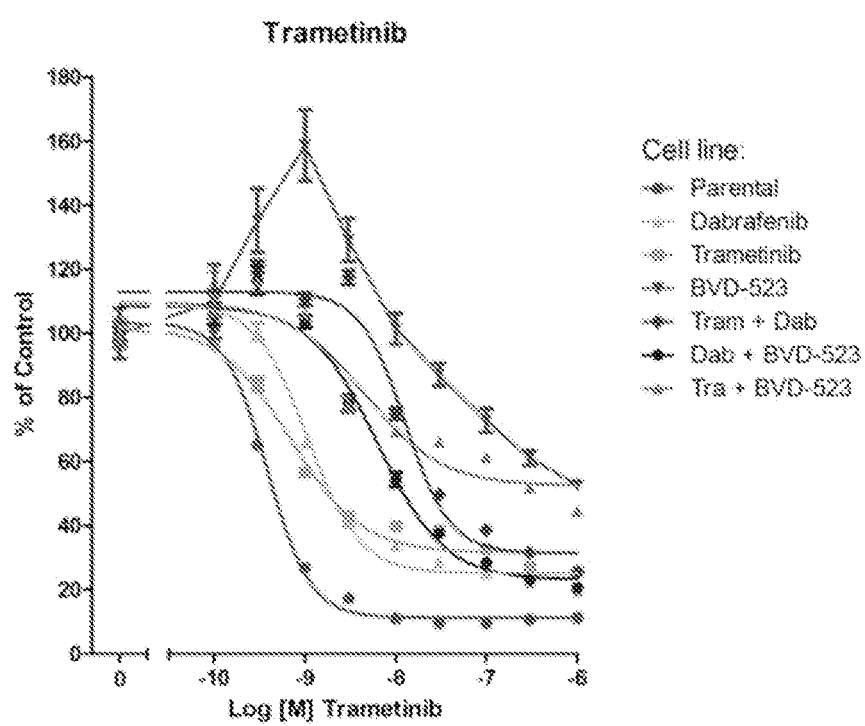

FIG. 4, Con't
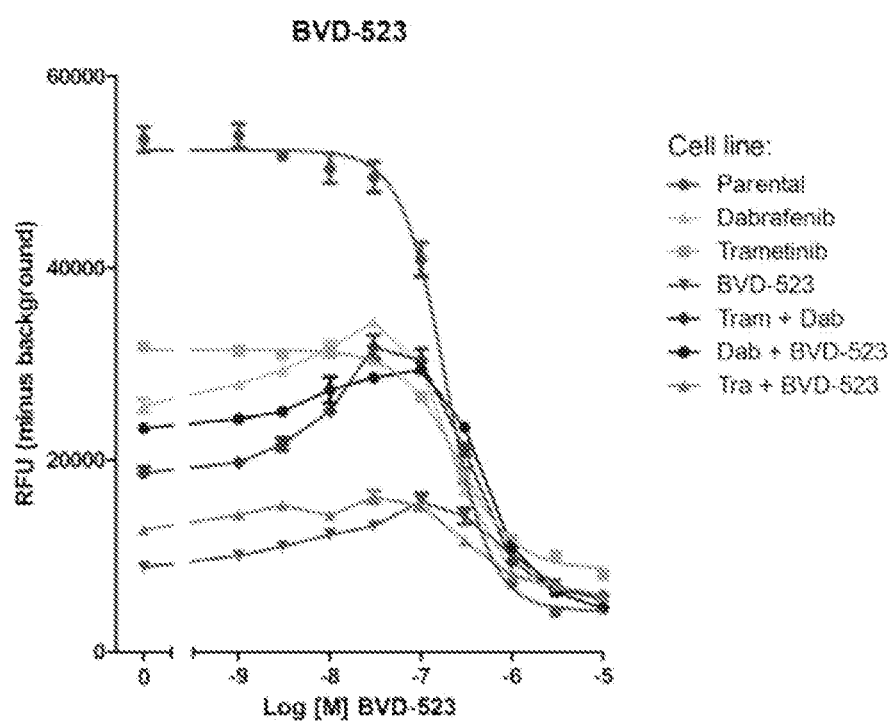

FIG. 4, Con't
E
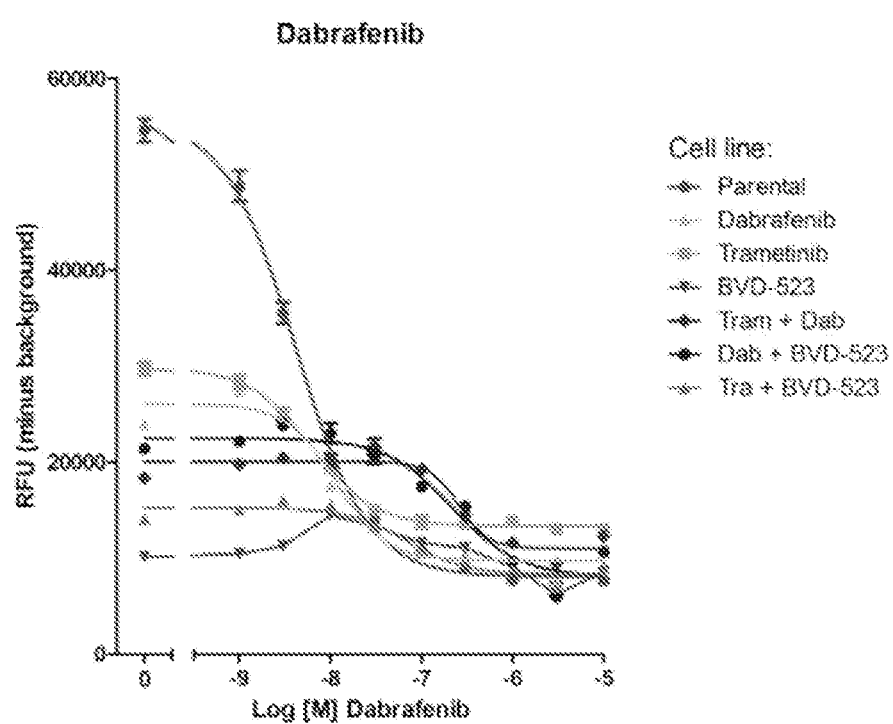

FIG. 4, Con't
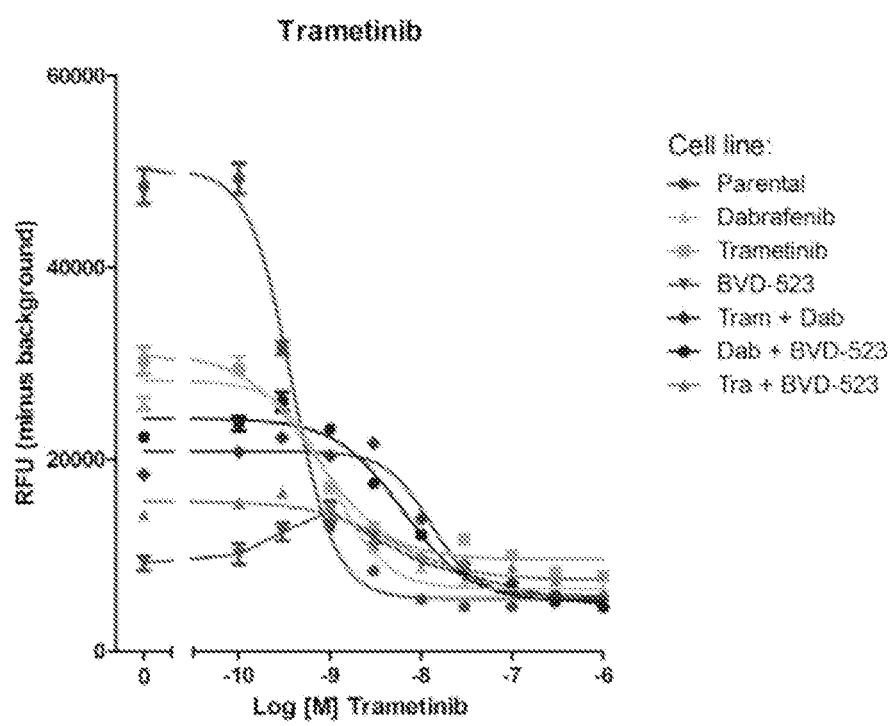

FIG. 4, Con't
G
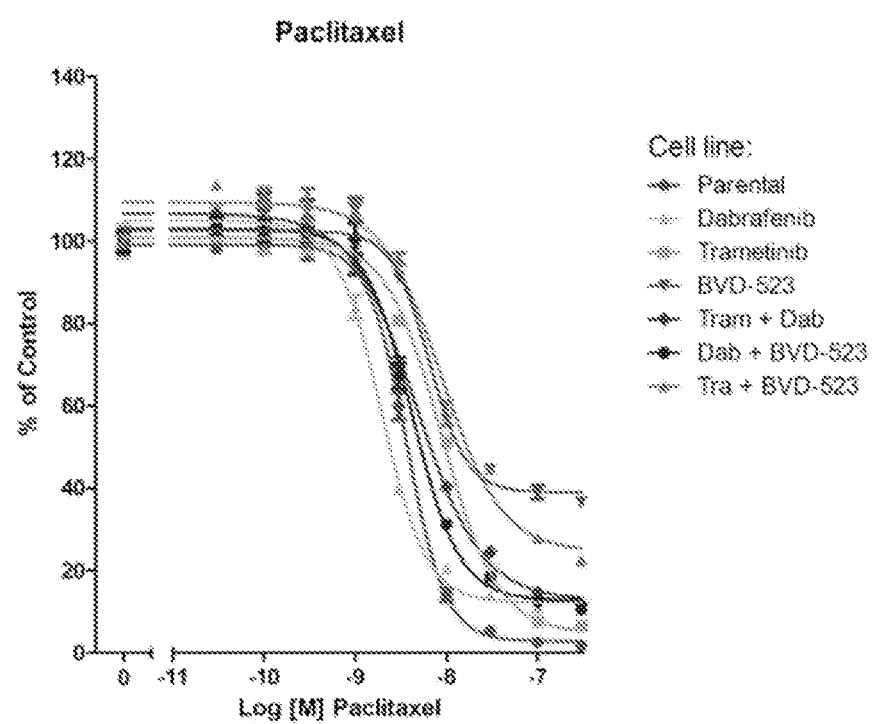

FIG. 4, Con't
H
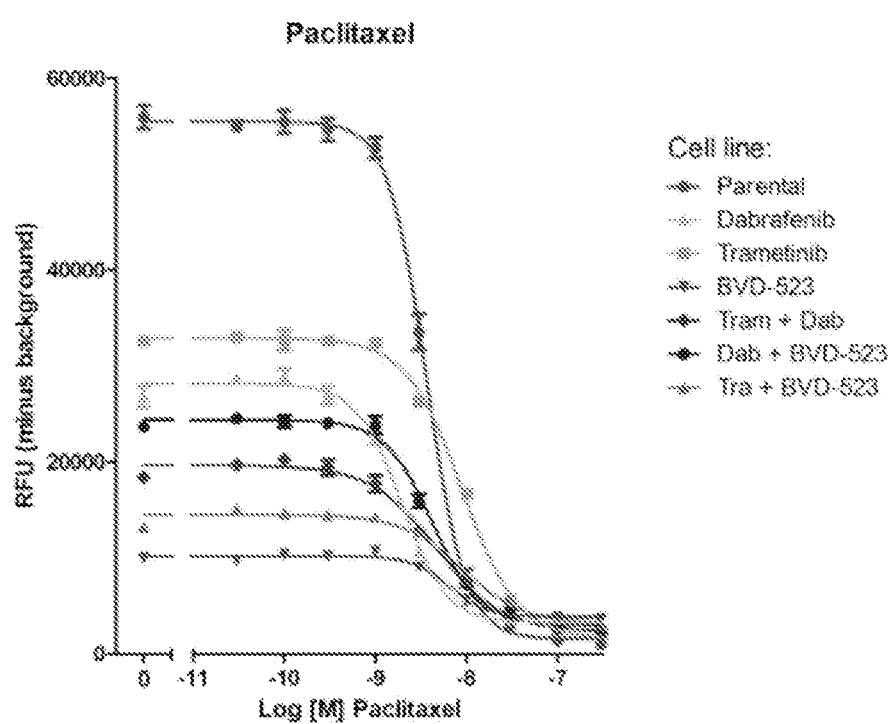

A

FIG. 5, Con't
B
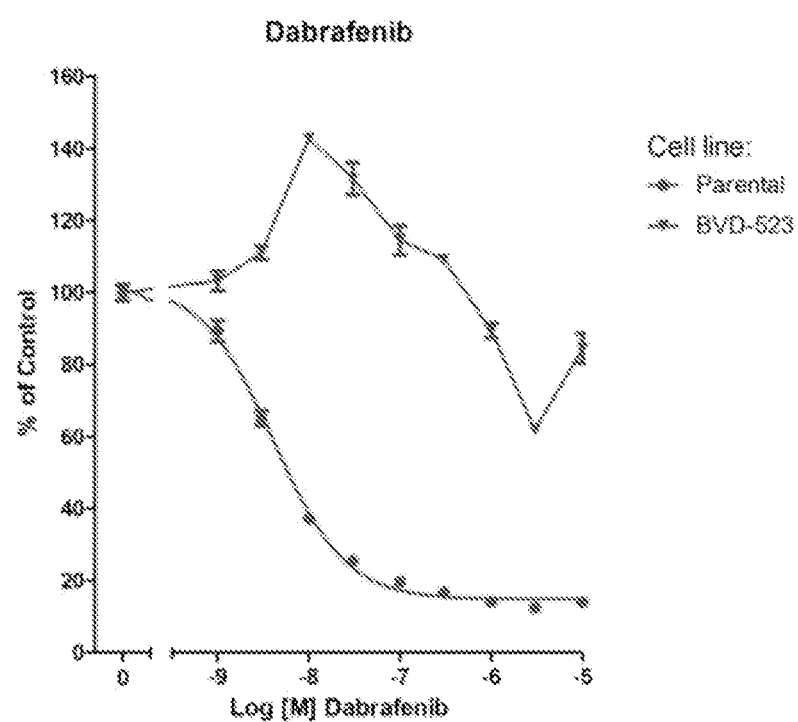

FIG. 5, Con't
C
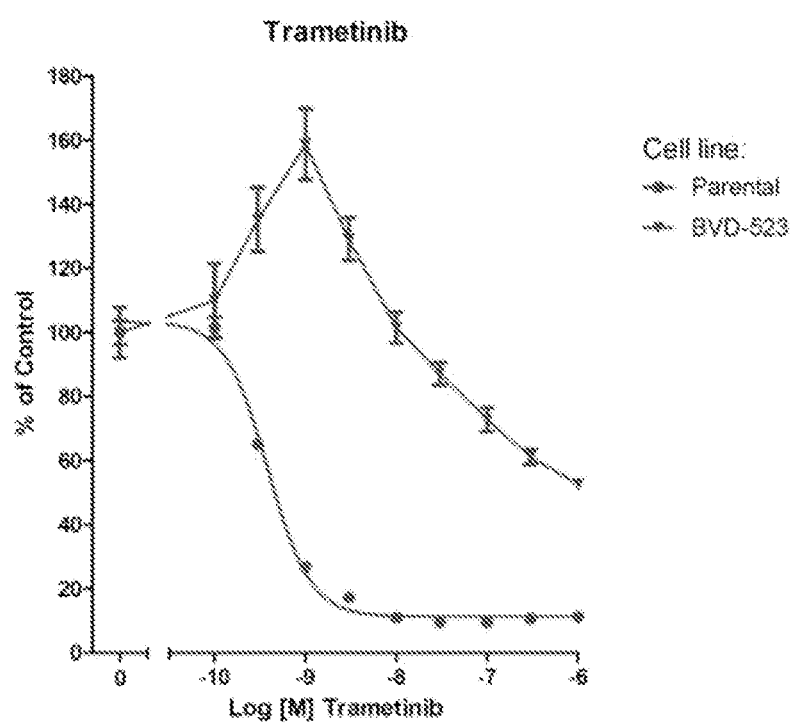

FIG. 5, Con't
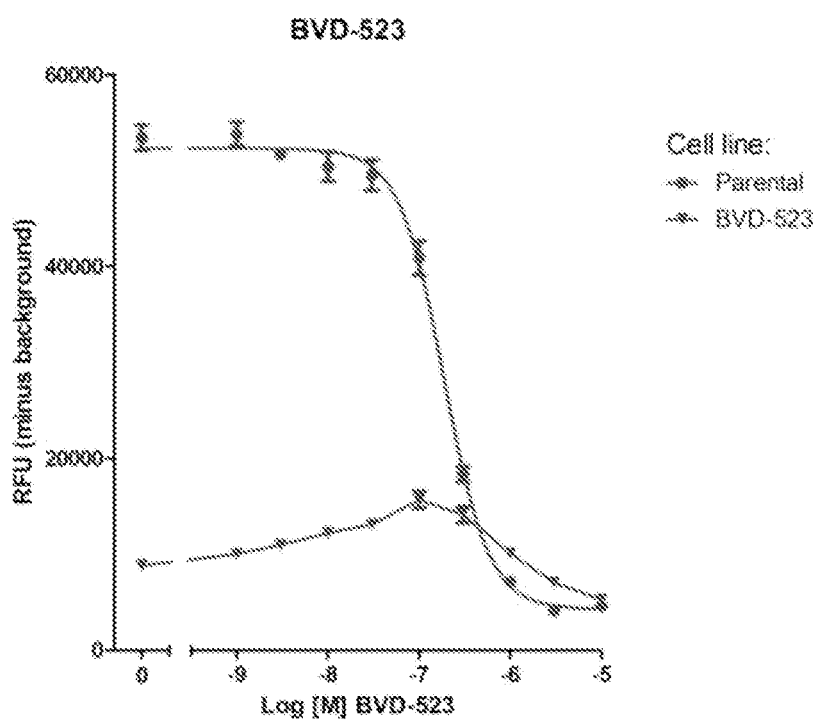

FIG. 5, Con't
E
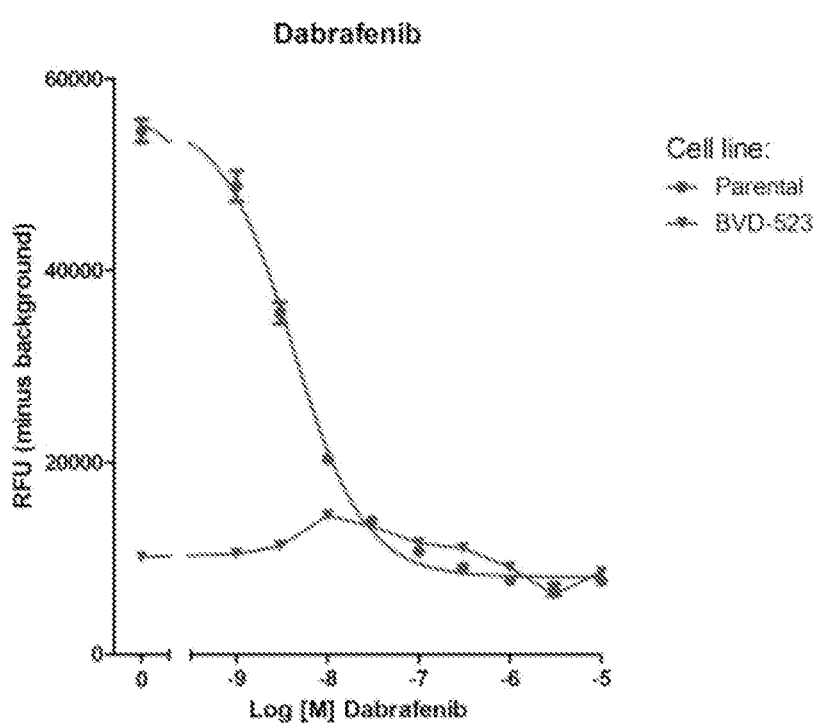

FIG. 5, Con't
F
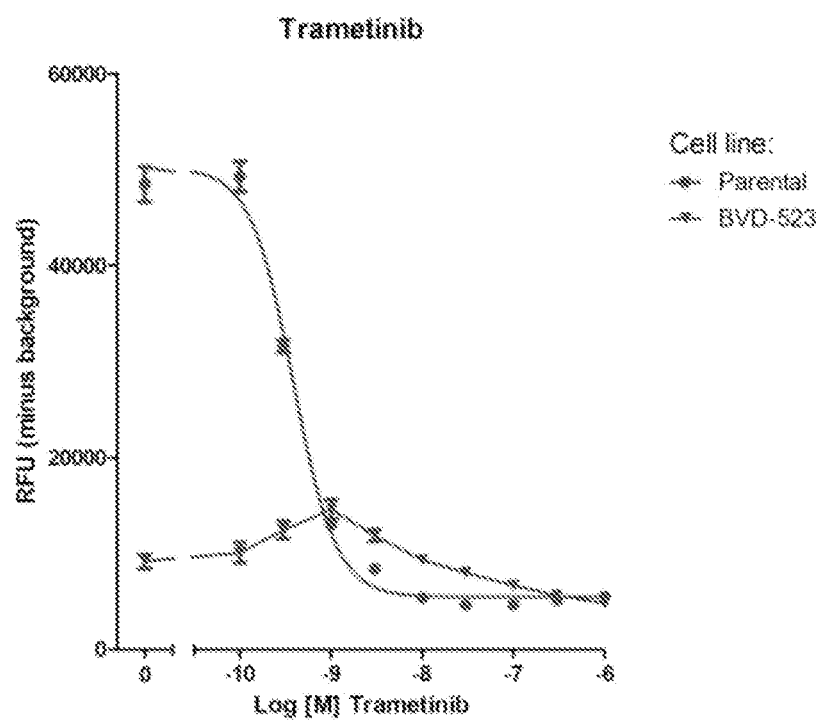

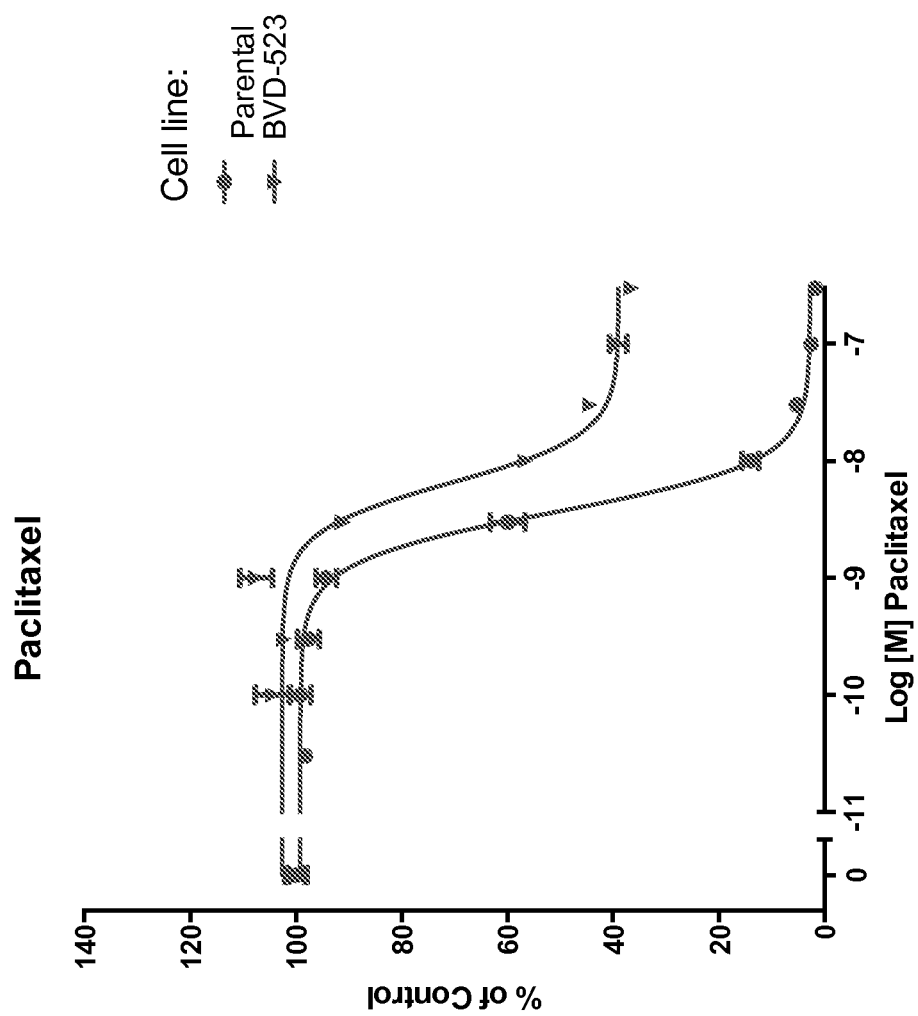
FIG. 5 Con't

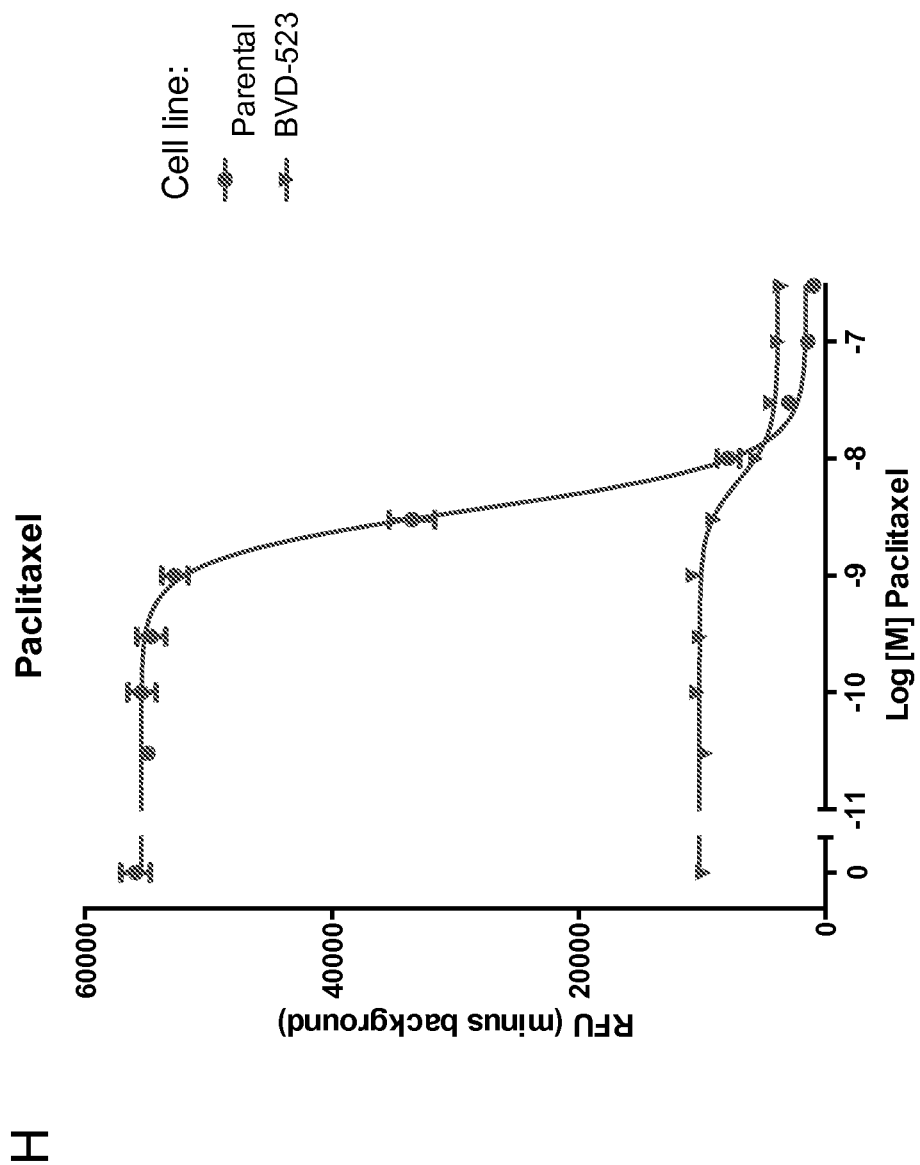

FIG. 6
A
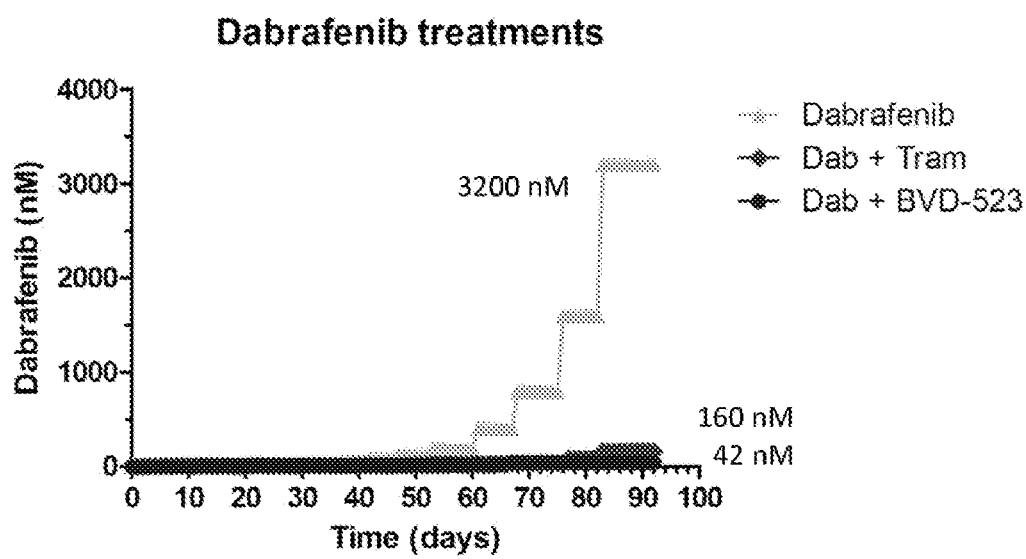
B
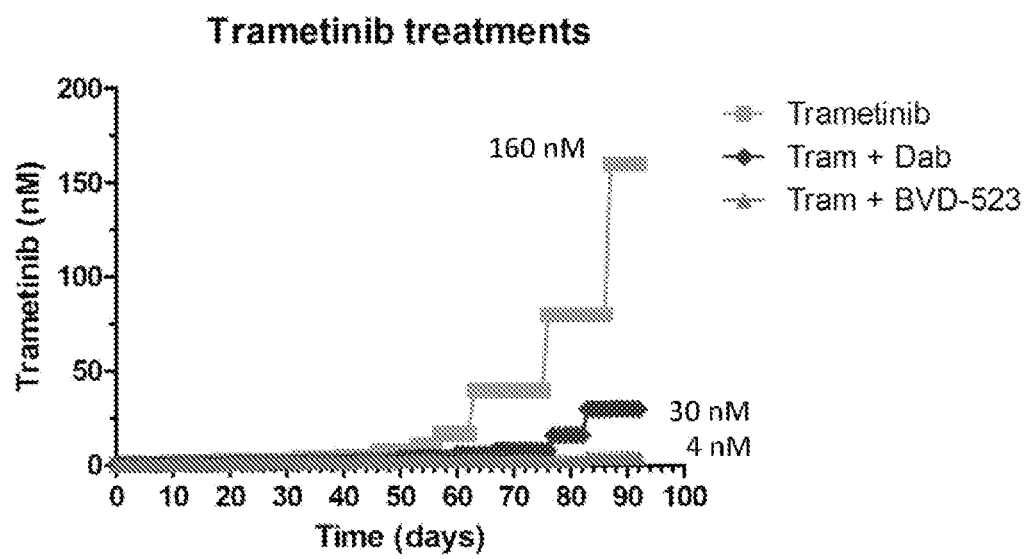

FIG. 6, Con't
C
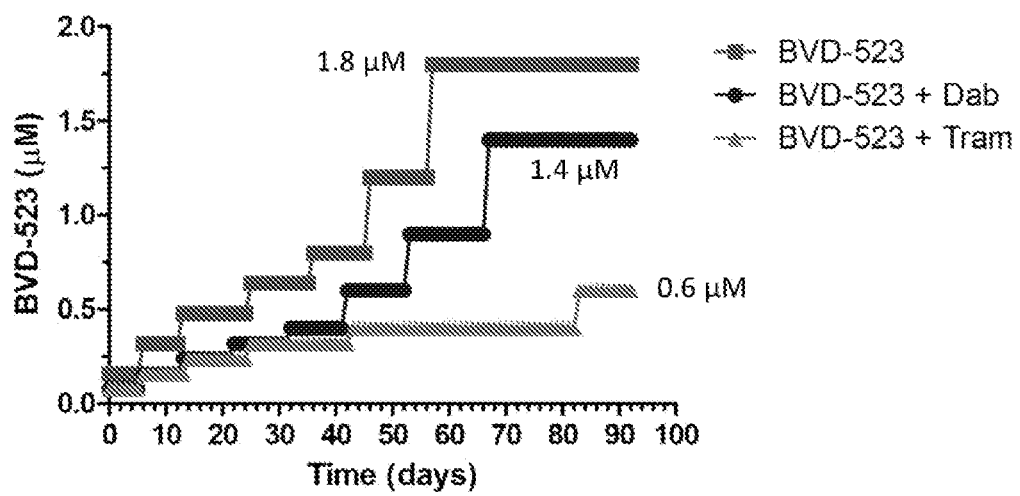
D
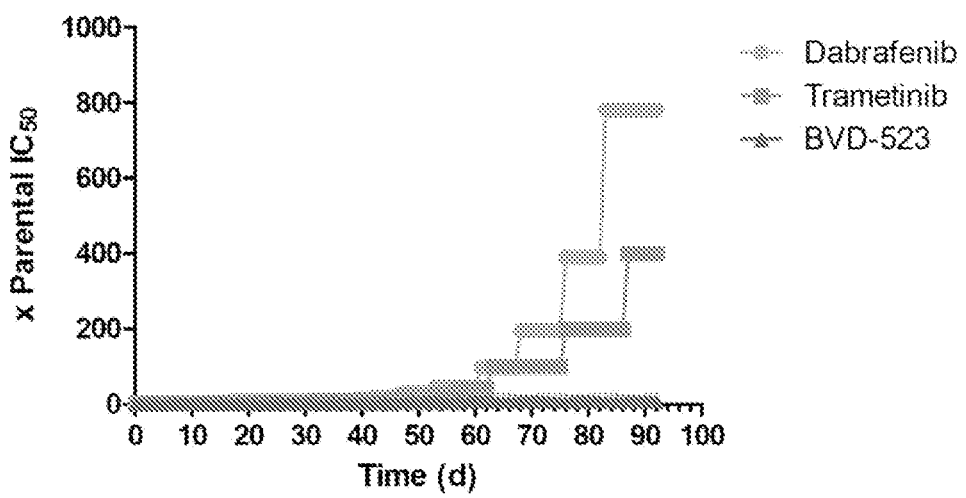

A

FIG. 8, Con't
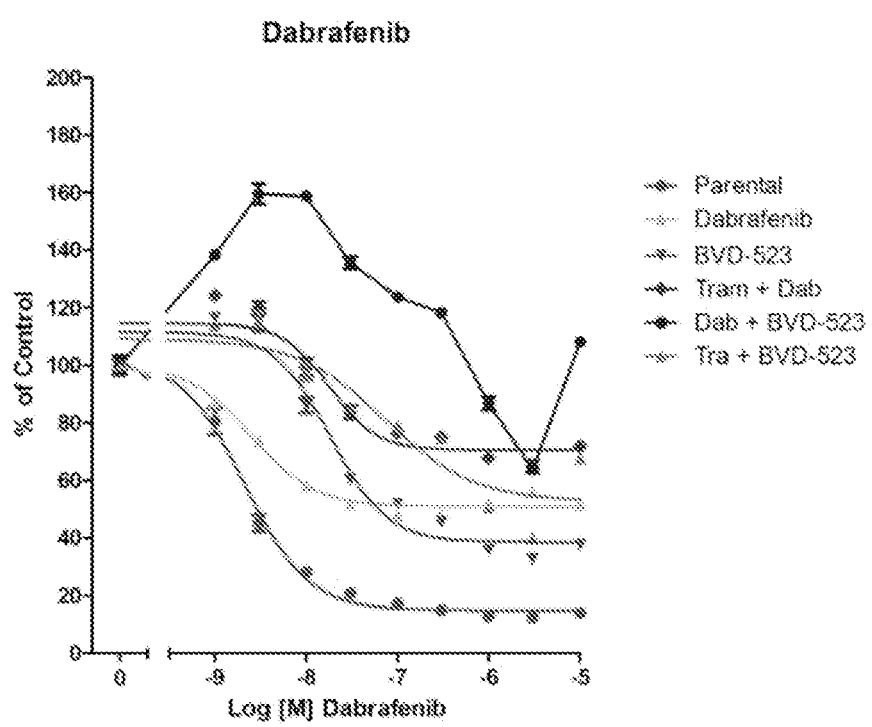

FIG. 8, Con't
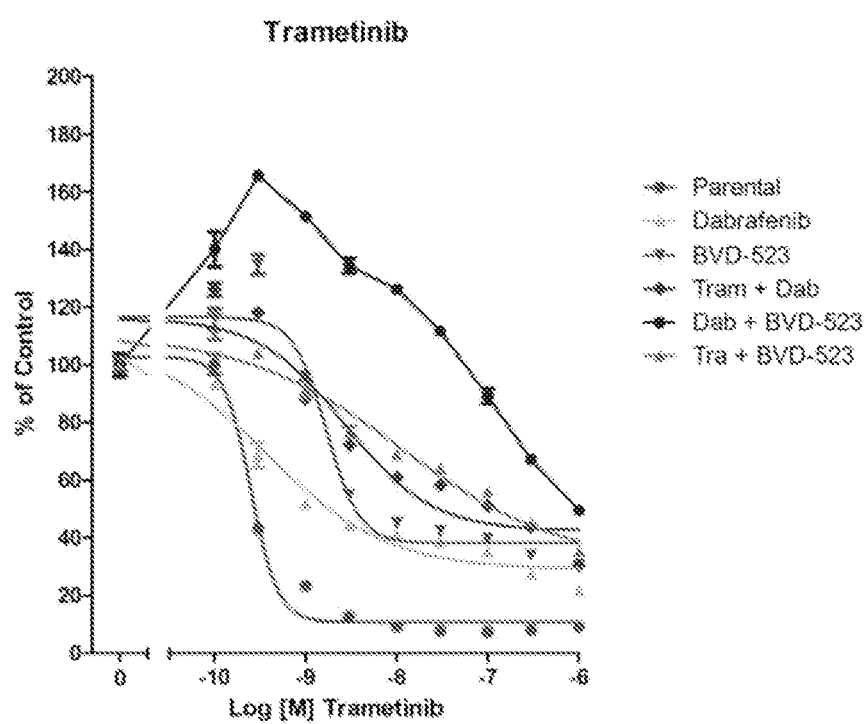

FIG. 8, Con't
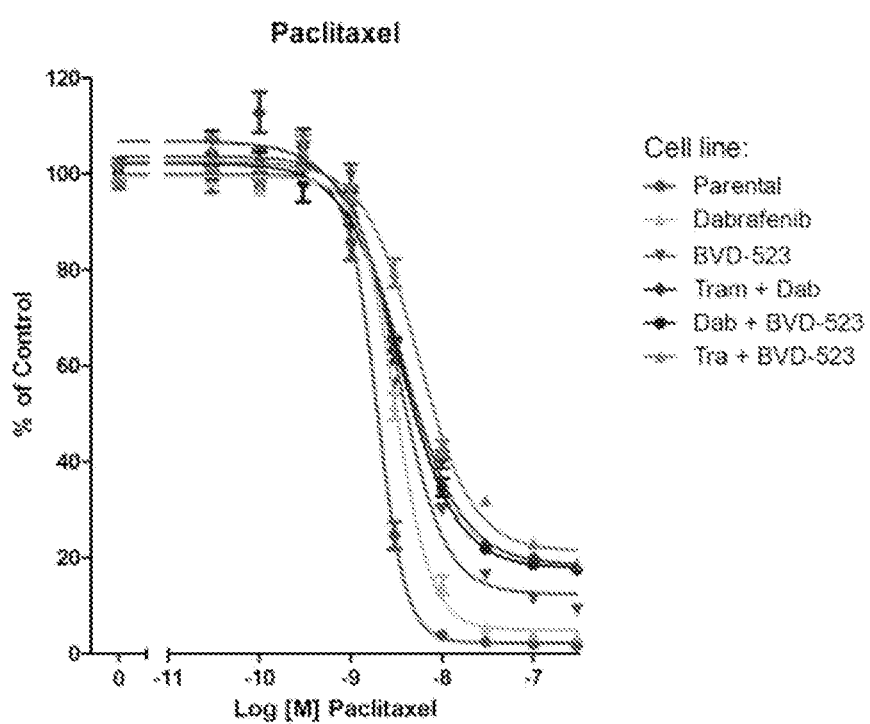

FIG. 9, Con't
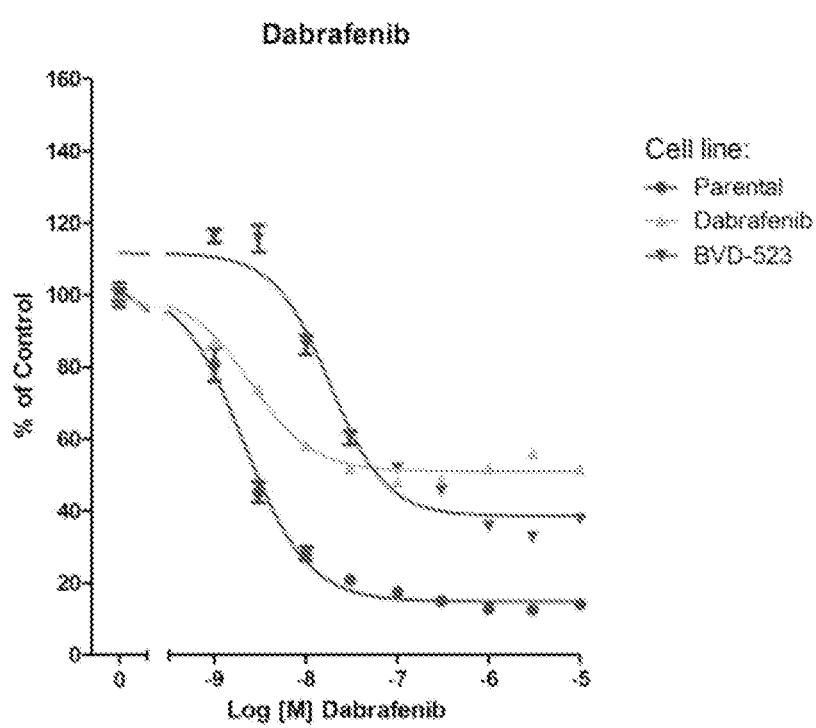

FIG. 9, Con't
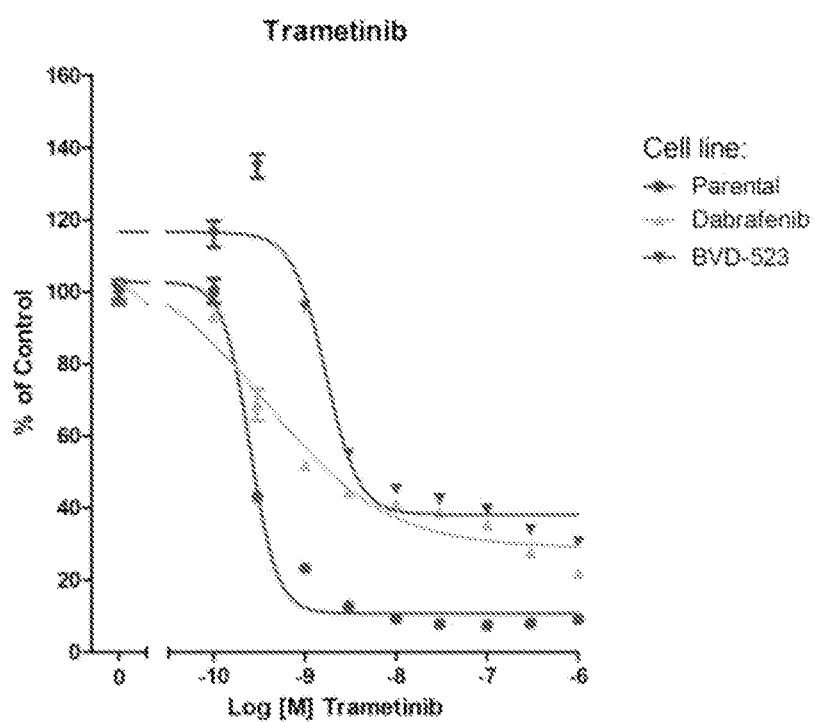

FIG. 9, Con't
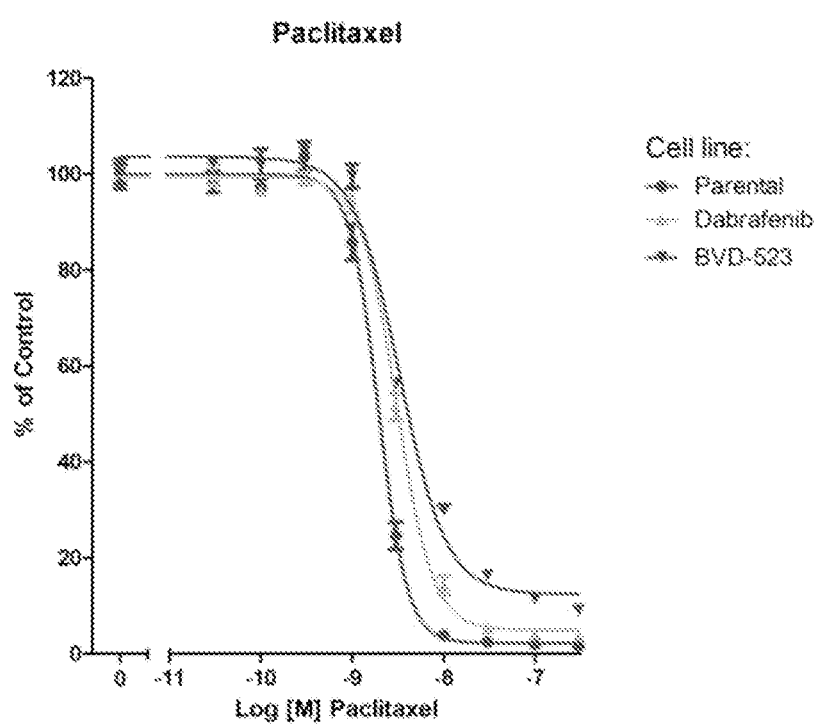

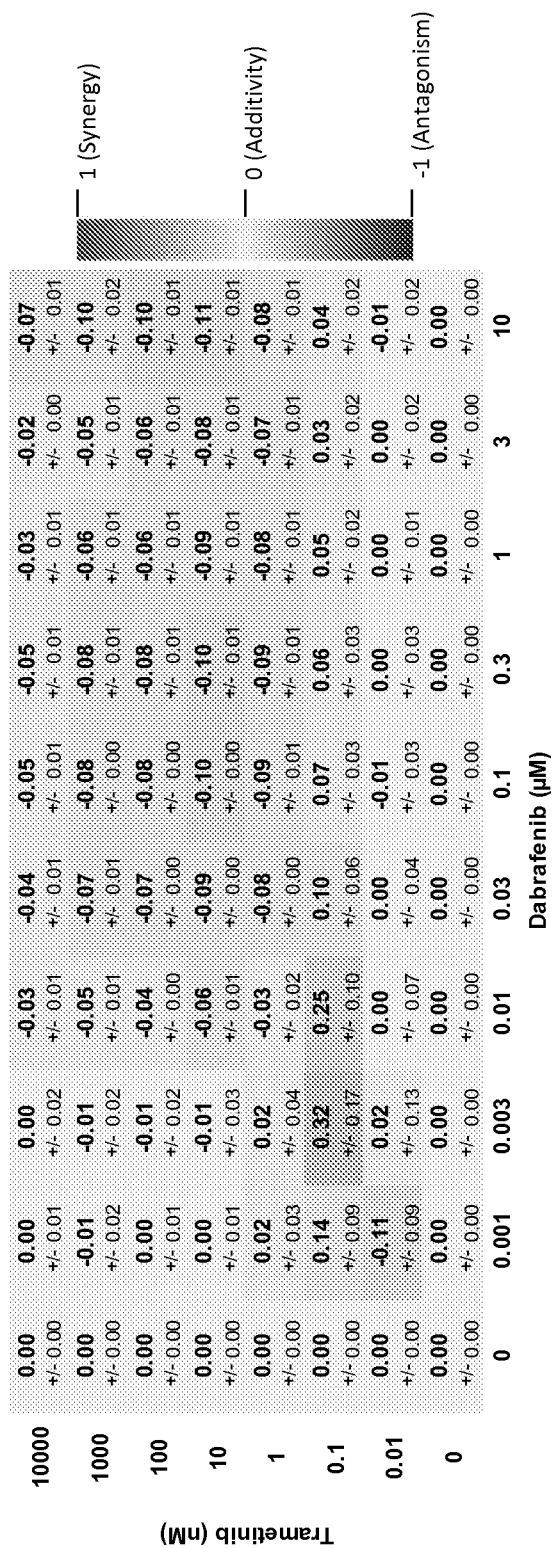
FIG. 10, Con't

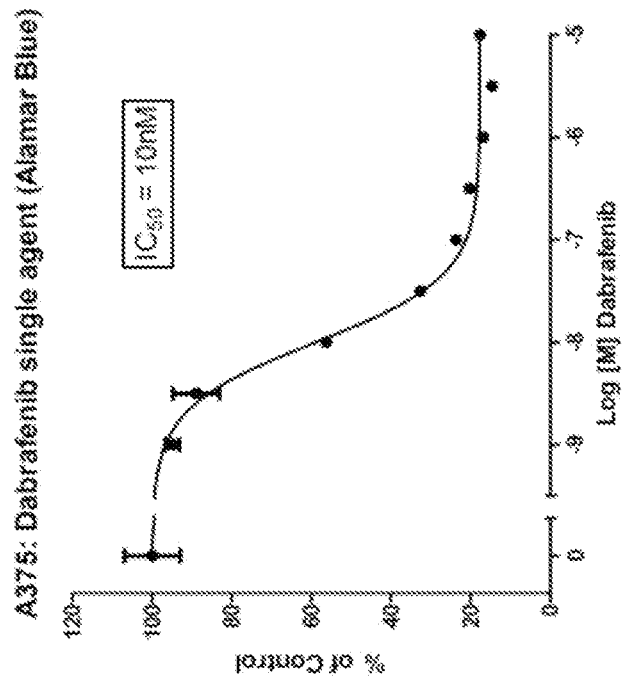
FIG. 10, Con't

FIG. 10, Con't

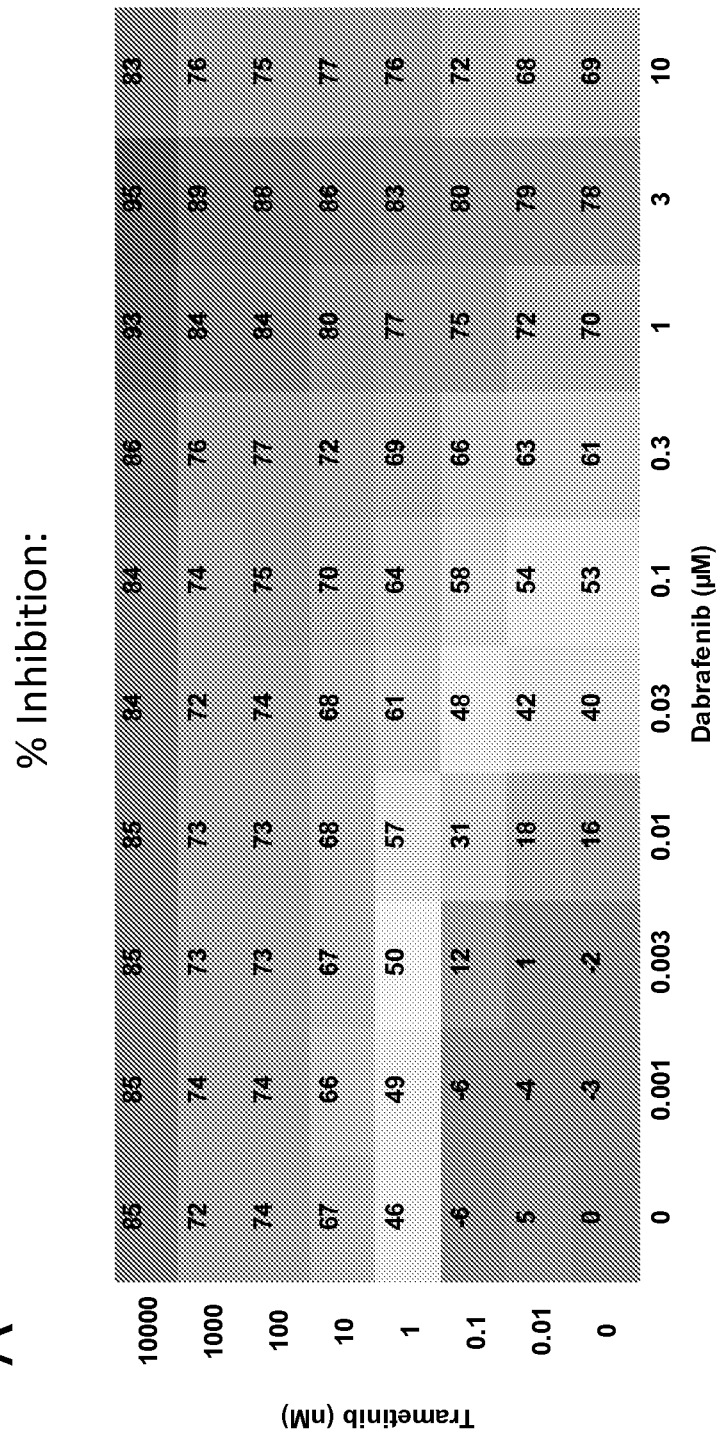

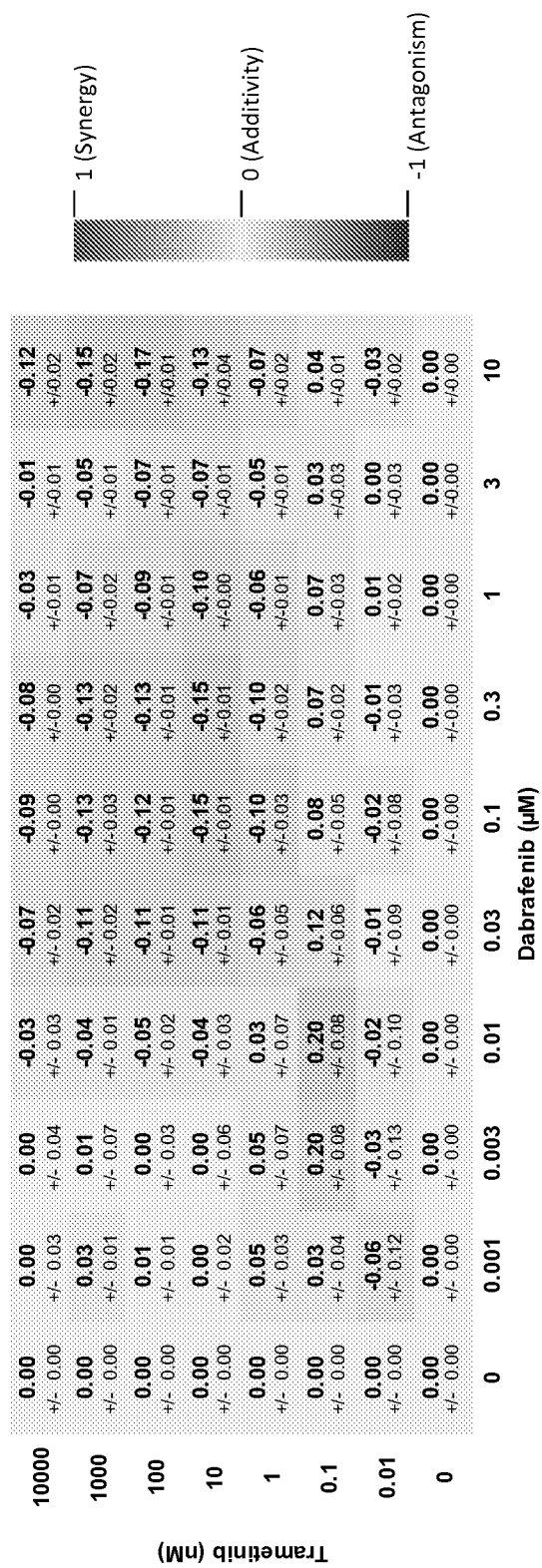
FIG. 11, Con't

FIG. 11, Con't
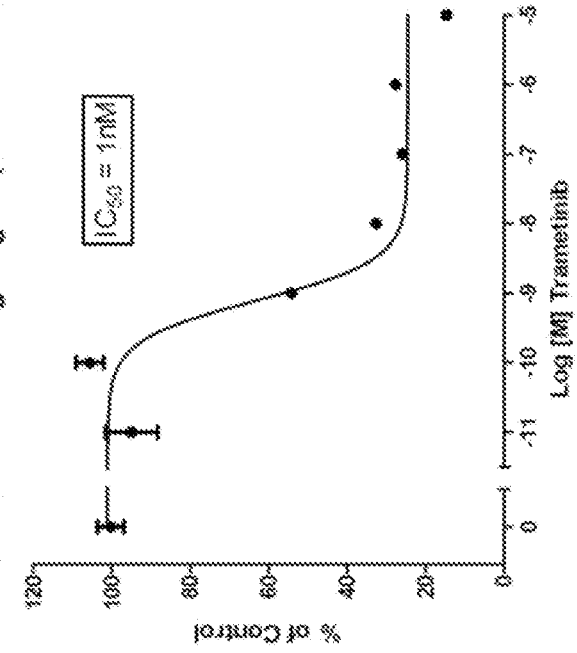
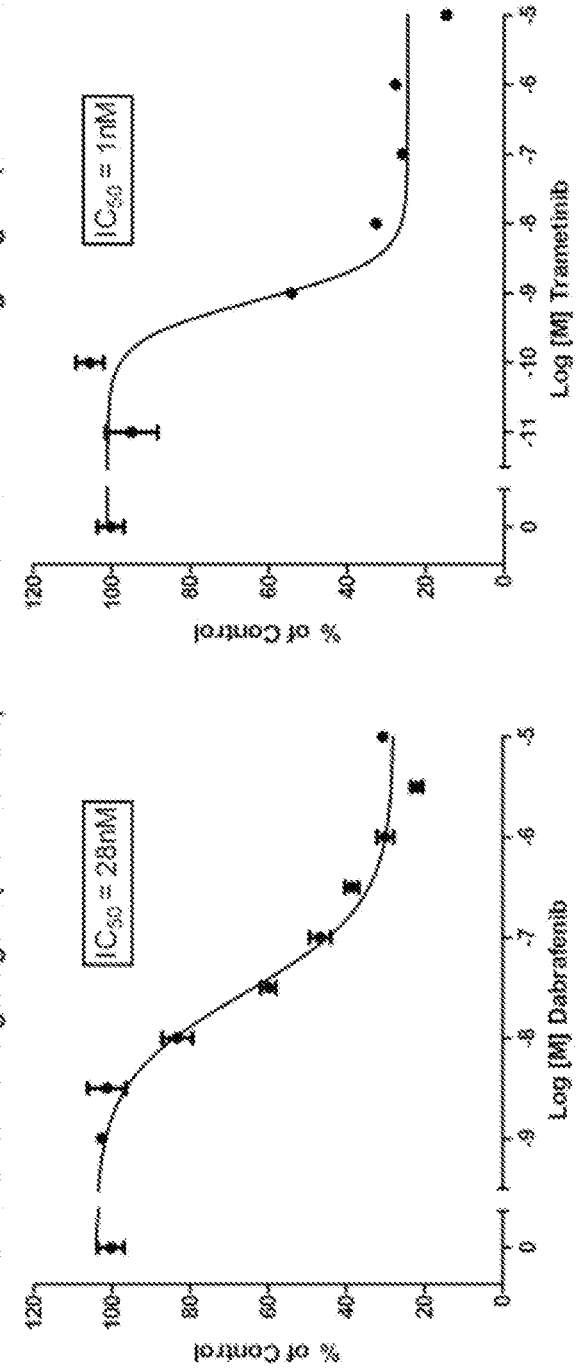

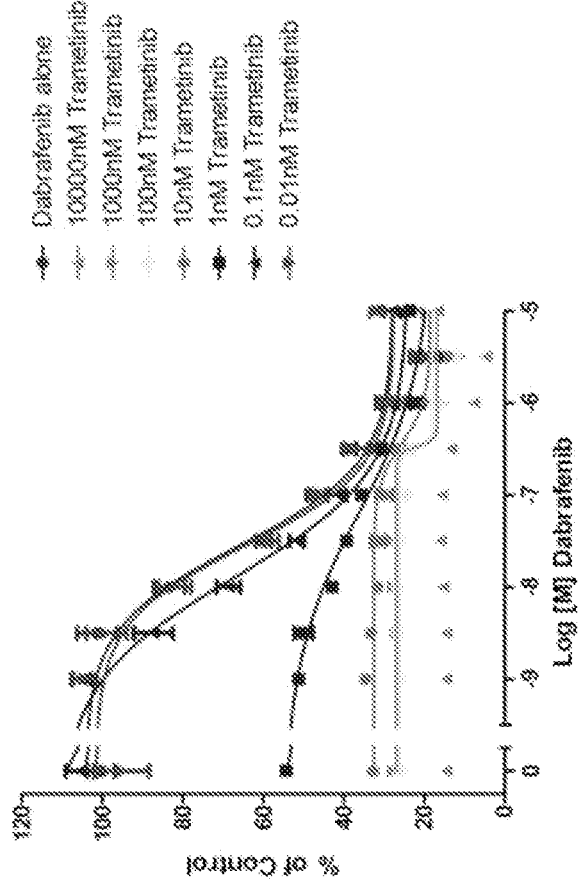
FIG. 11, Con't

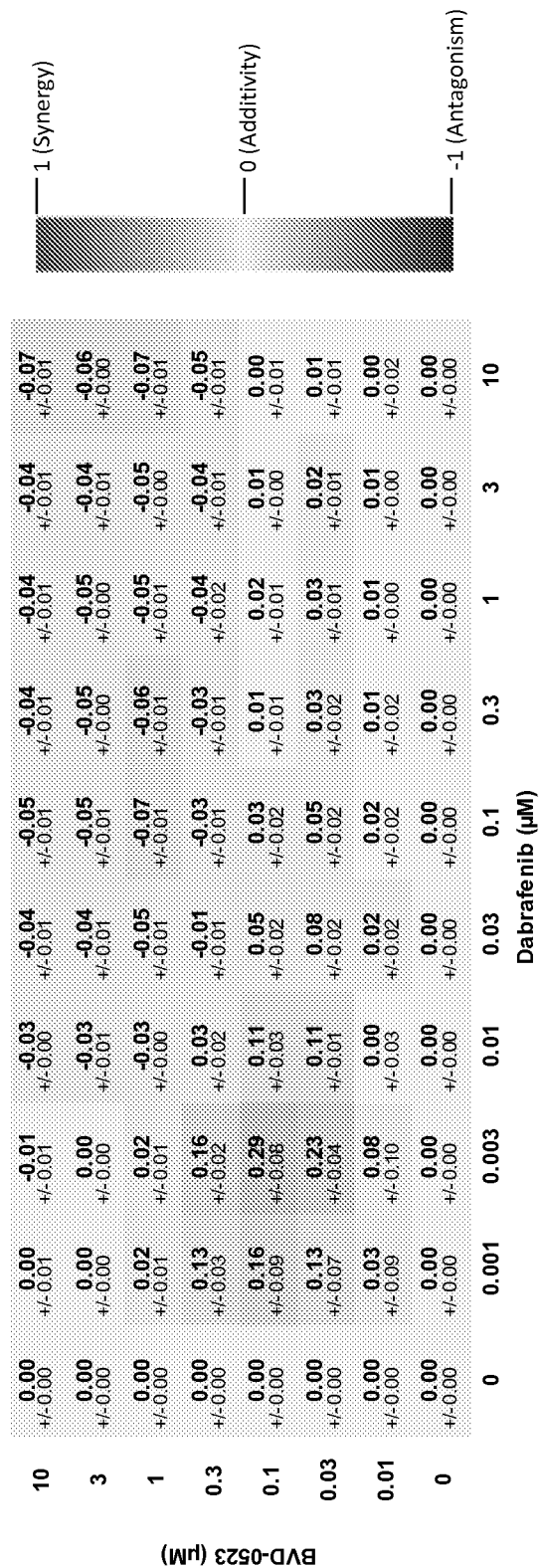
FIG. 12, Con't

FIG. 12, Con't
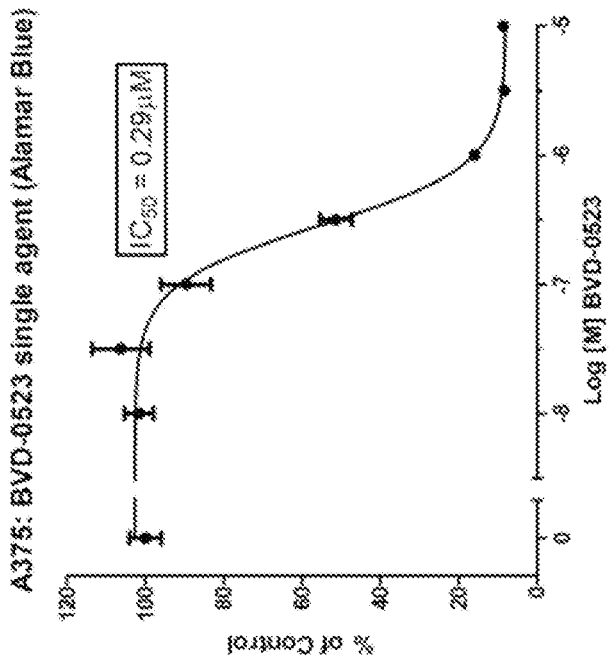
D
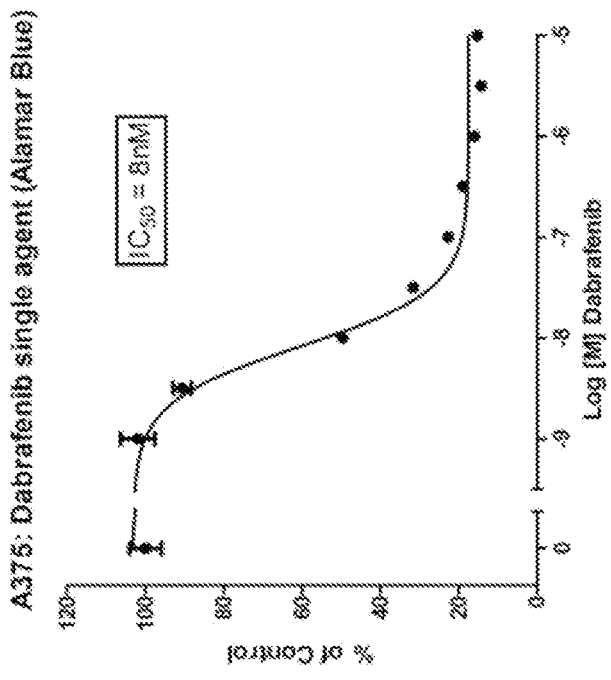
C

FIG. 12, Con't
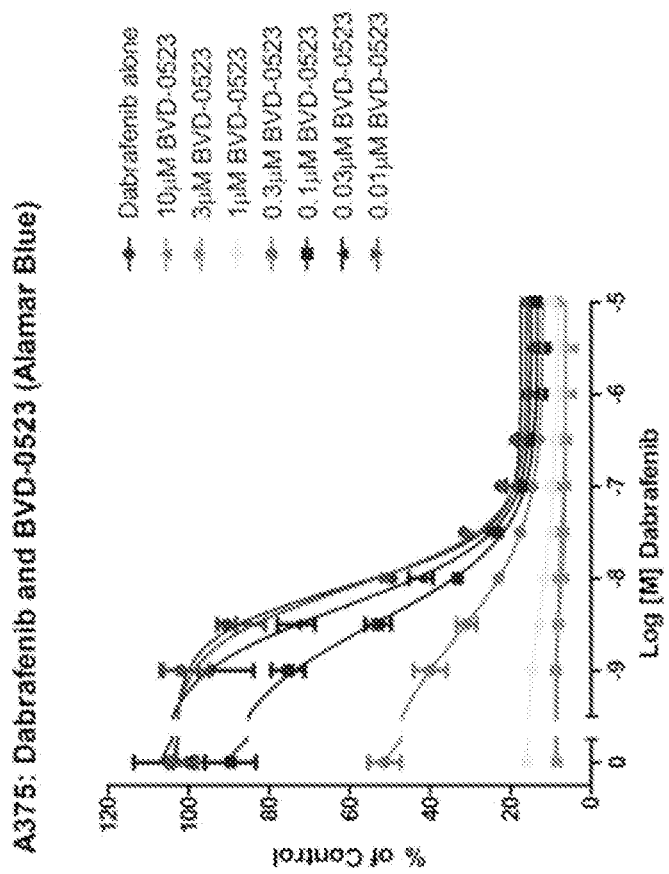
E

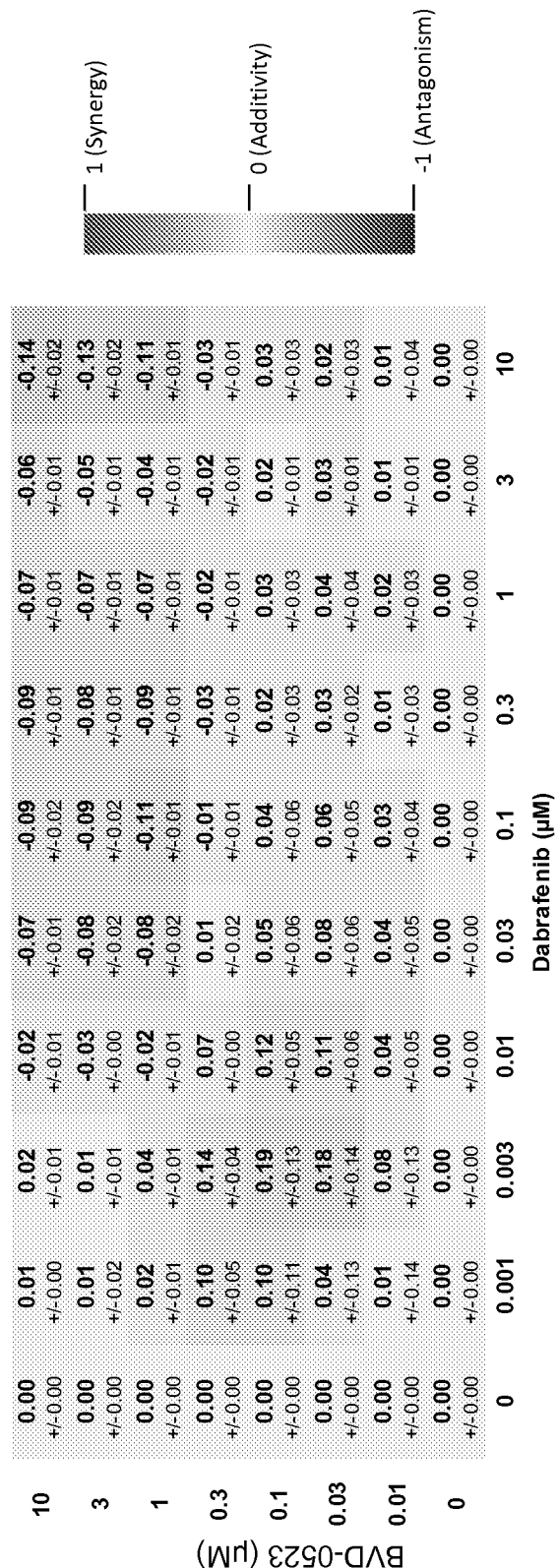
FIG. 13, Con't

FIG. 13, Con't
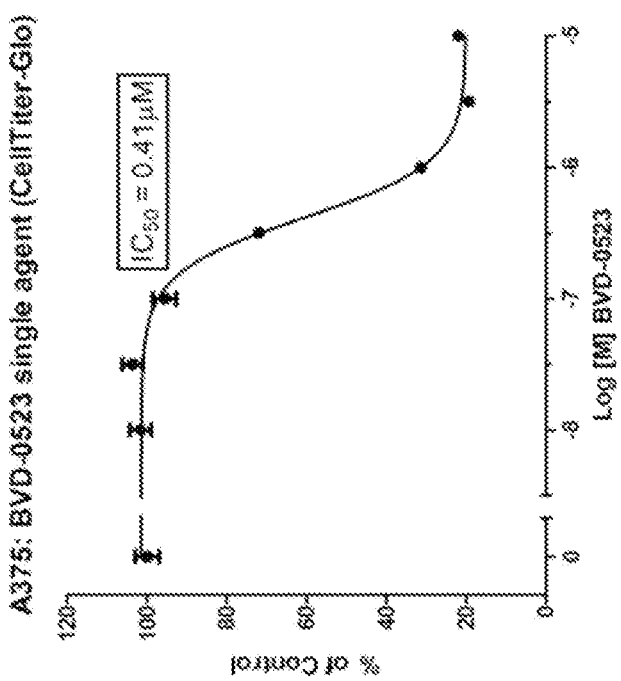
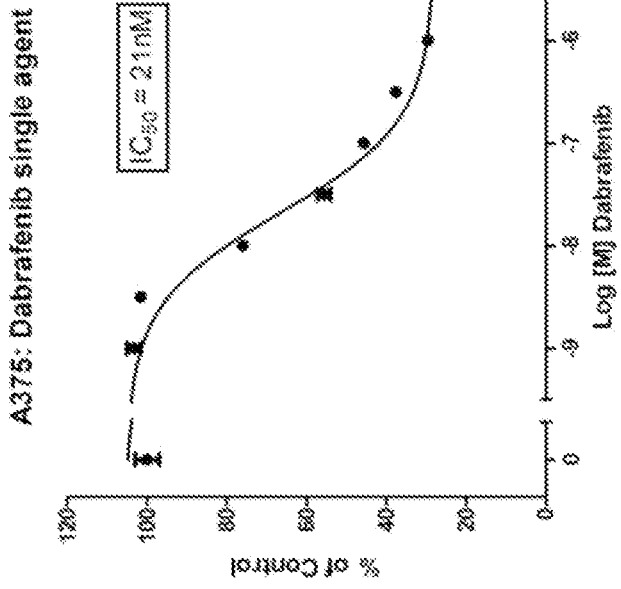

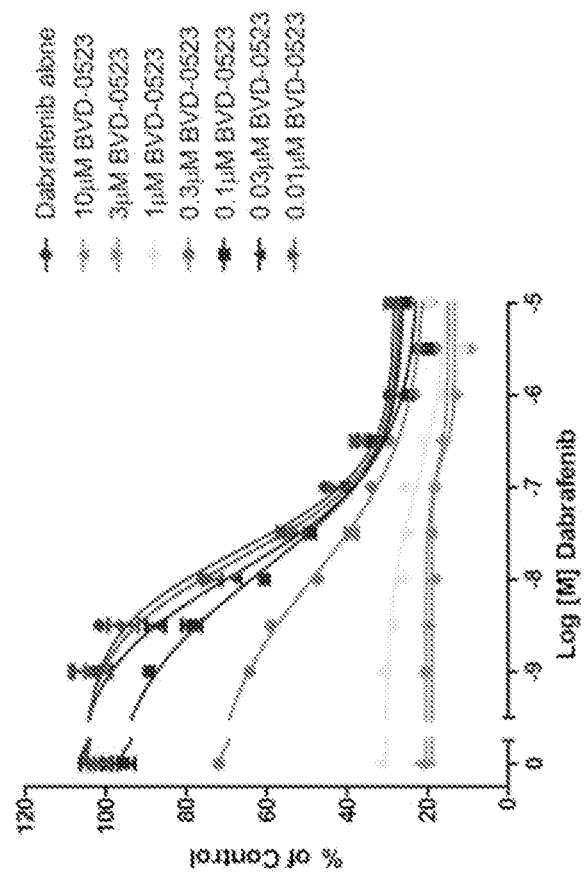
FIG. 13, Con't

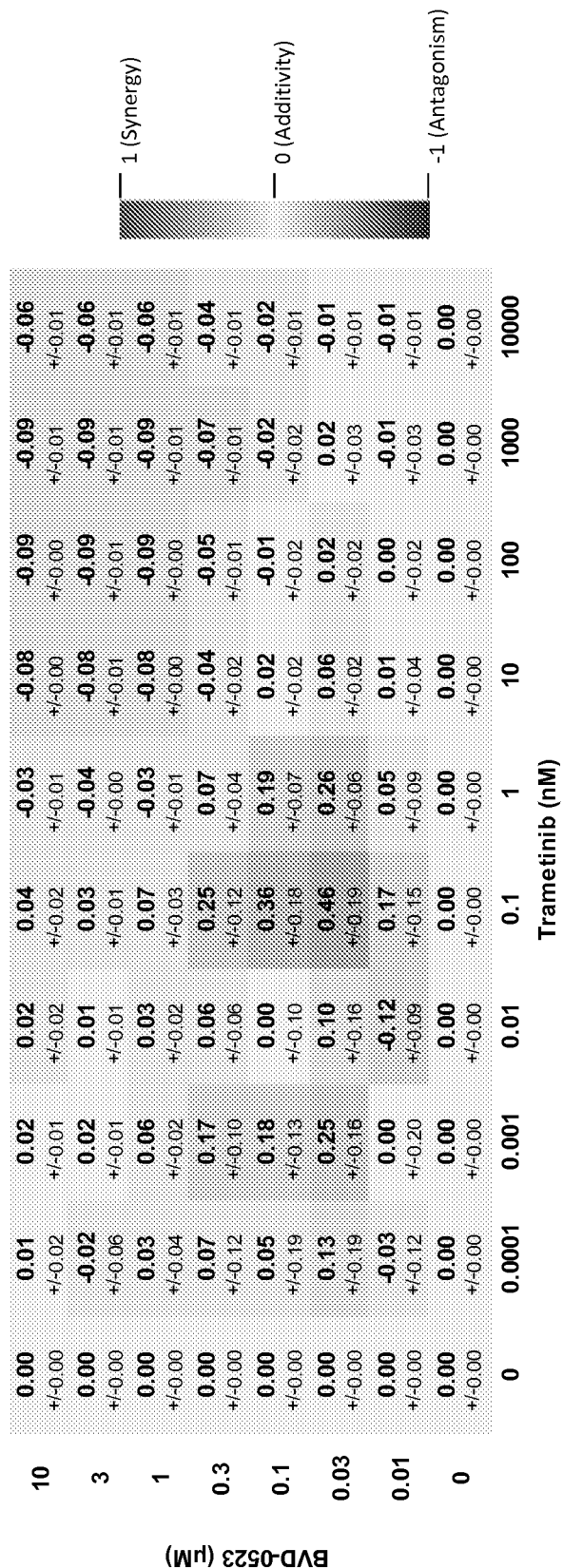
FIG. 14, Con't

FIG. 14, Con't
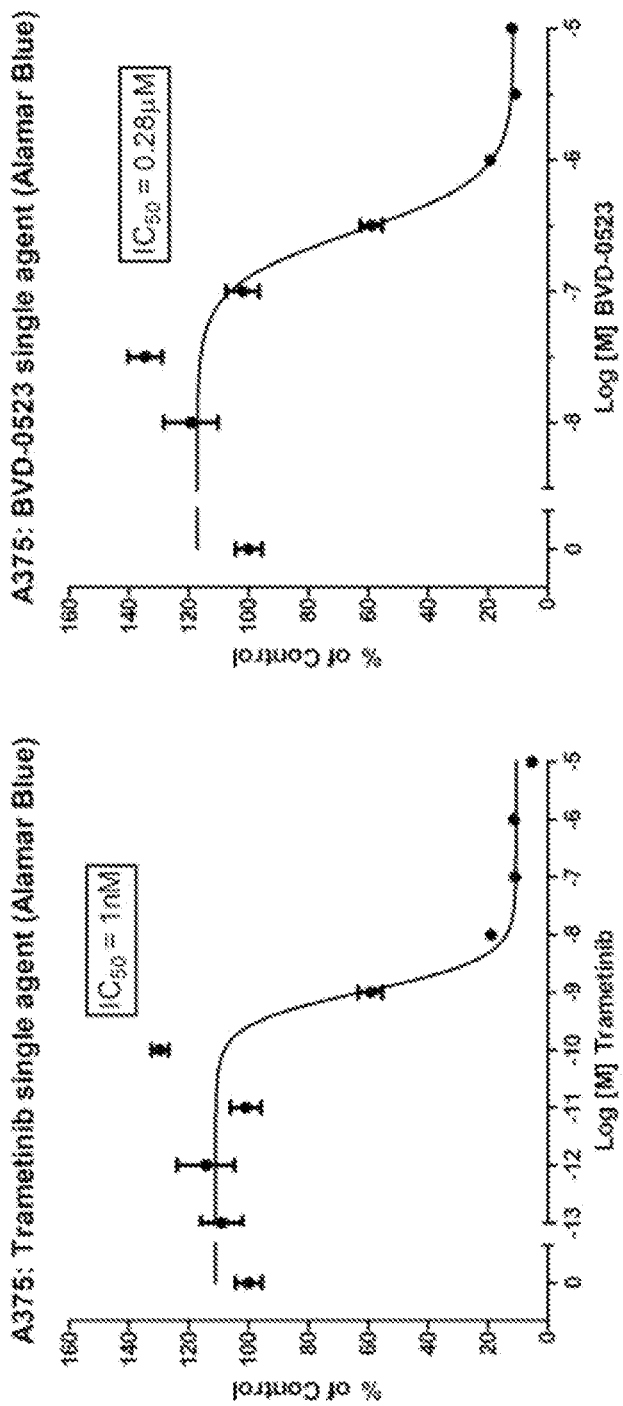

FIG. 14, Con't
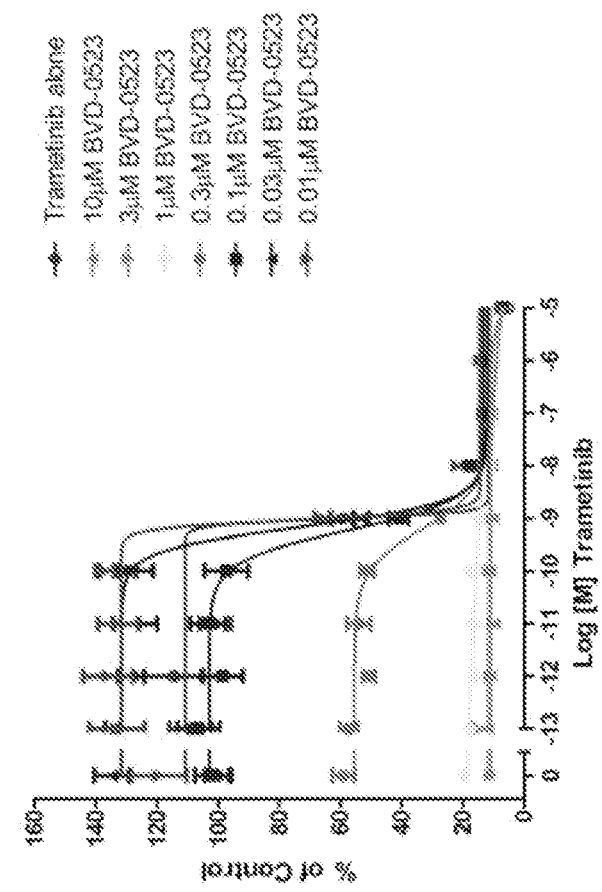
E

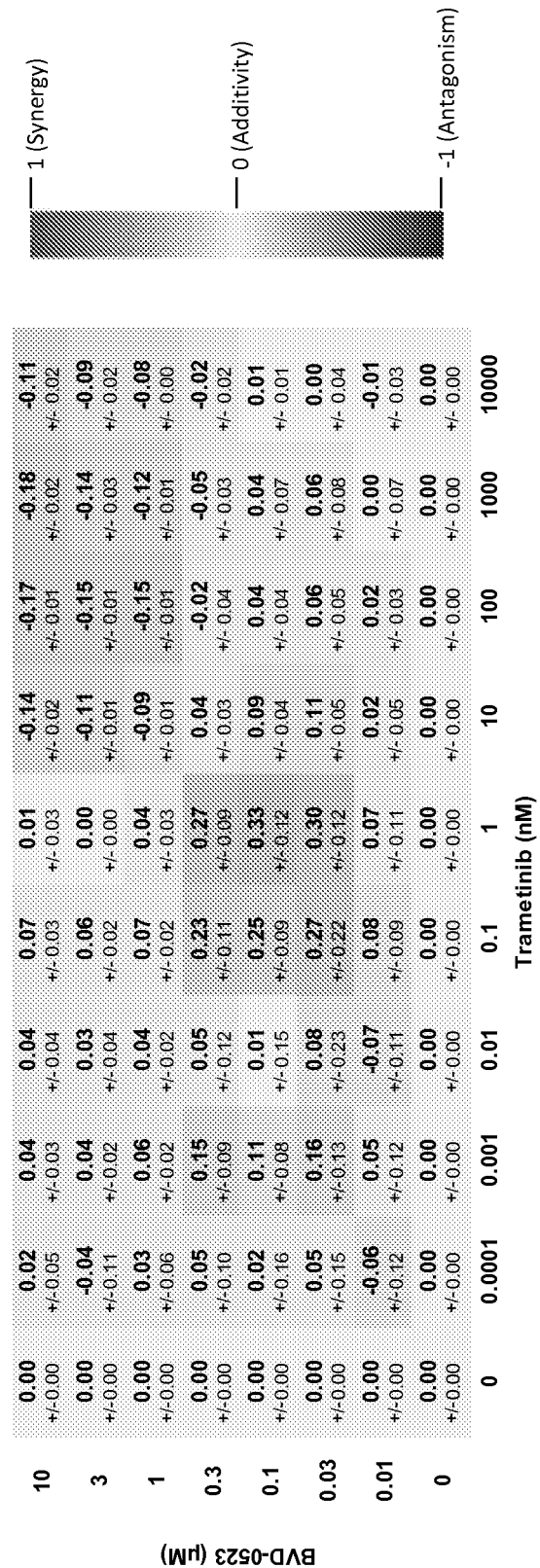
FIG. 15, Con't

FIG. 15, Con't
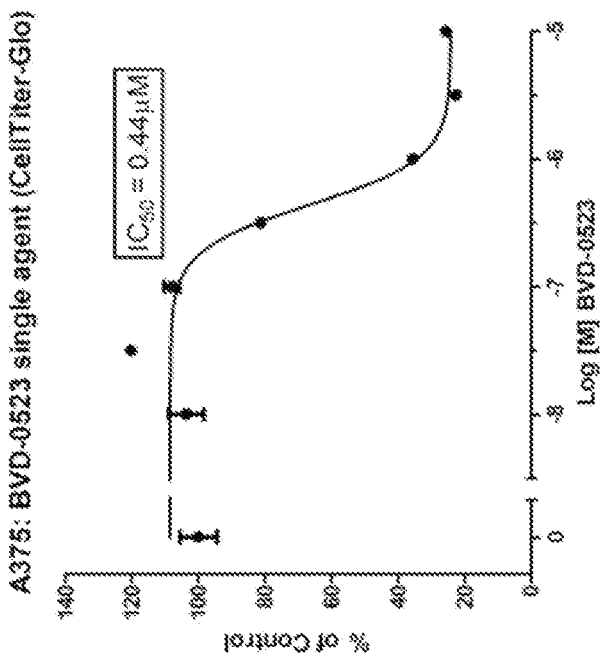
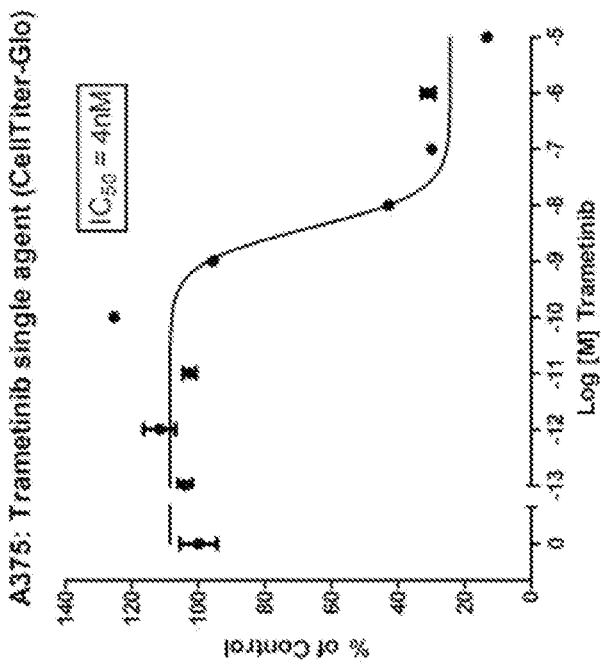

FIG. 15, Con't
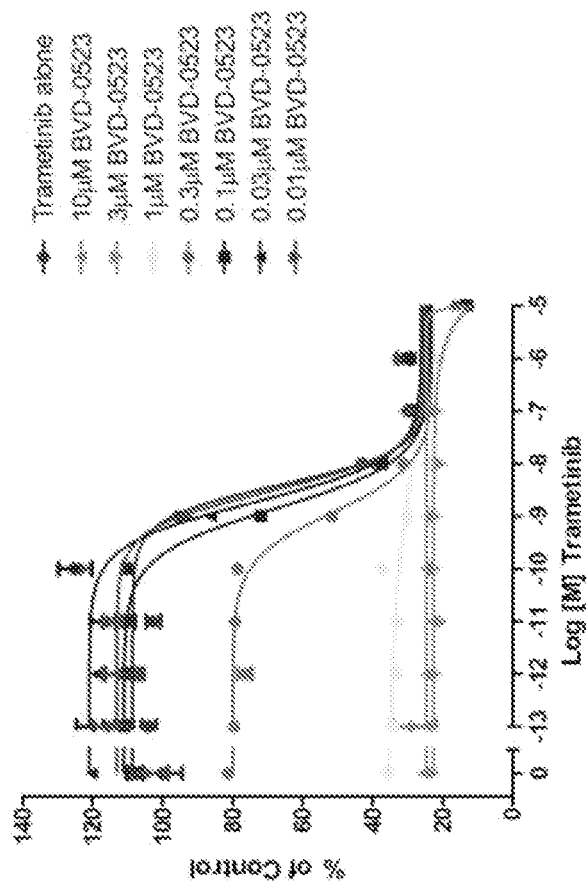
E

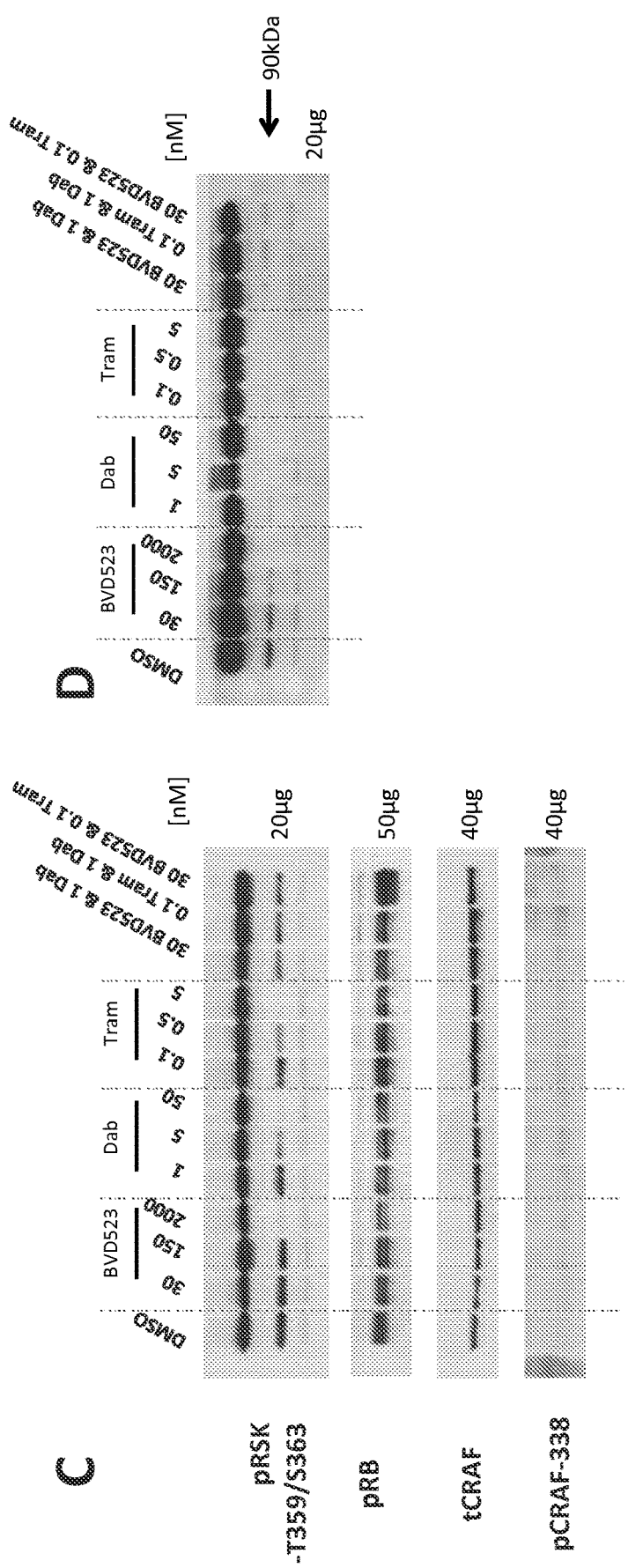
FIG. 16 Con't

FIG. 17 Con't
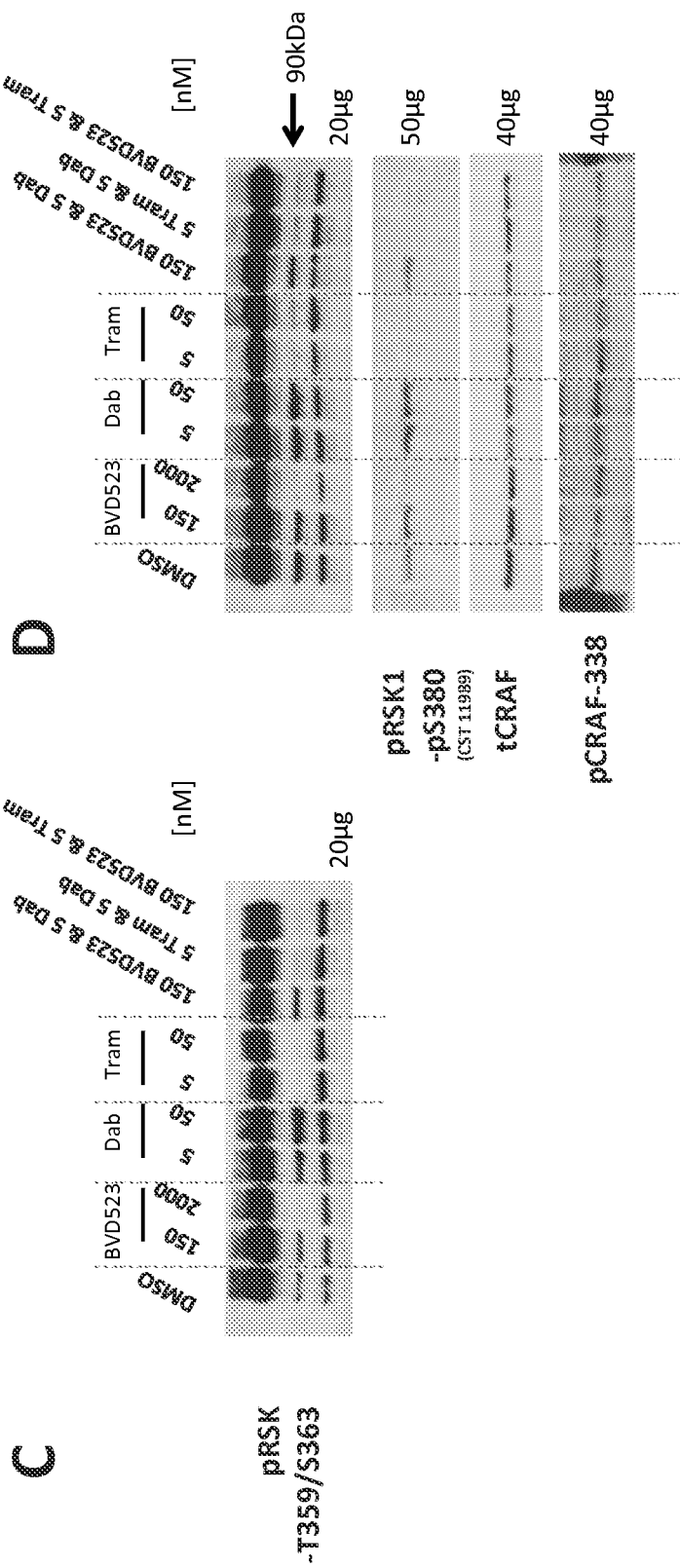

FIG. 18 Con't
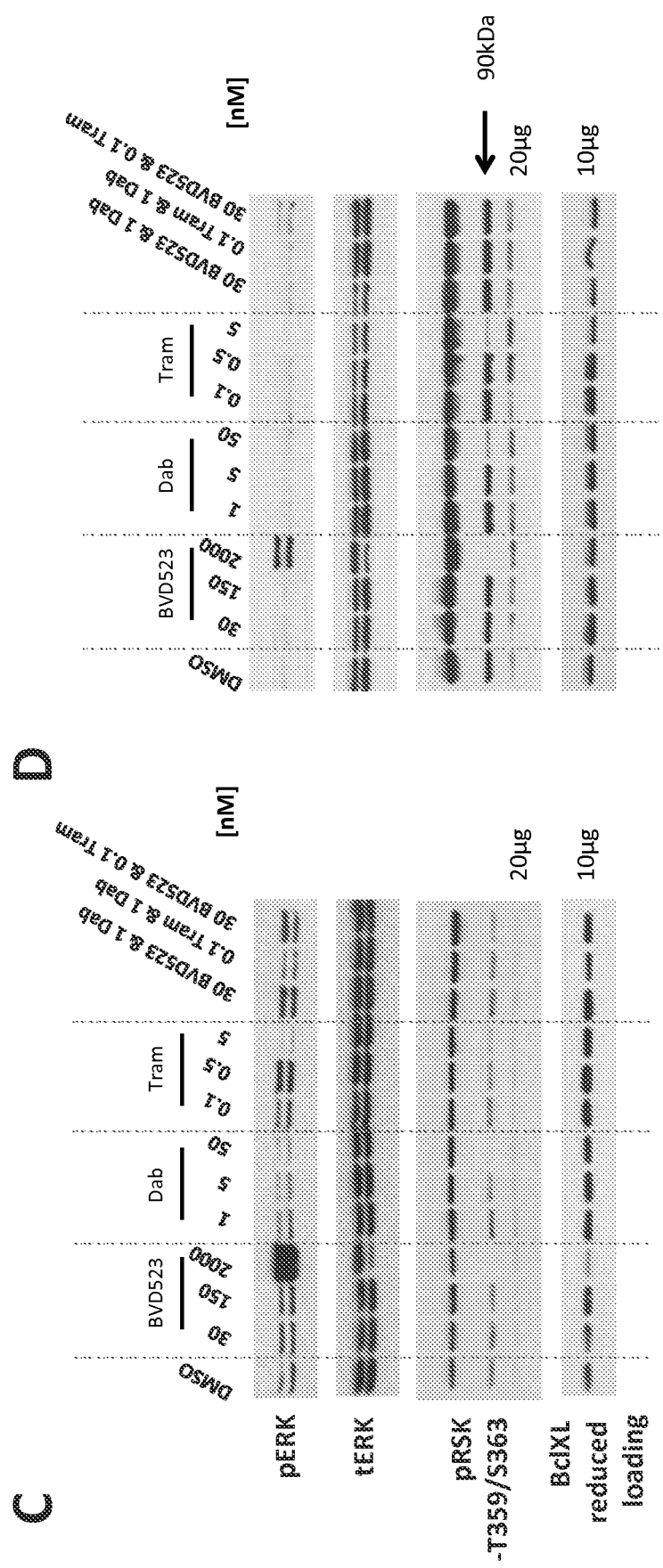

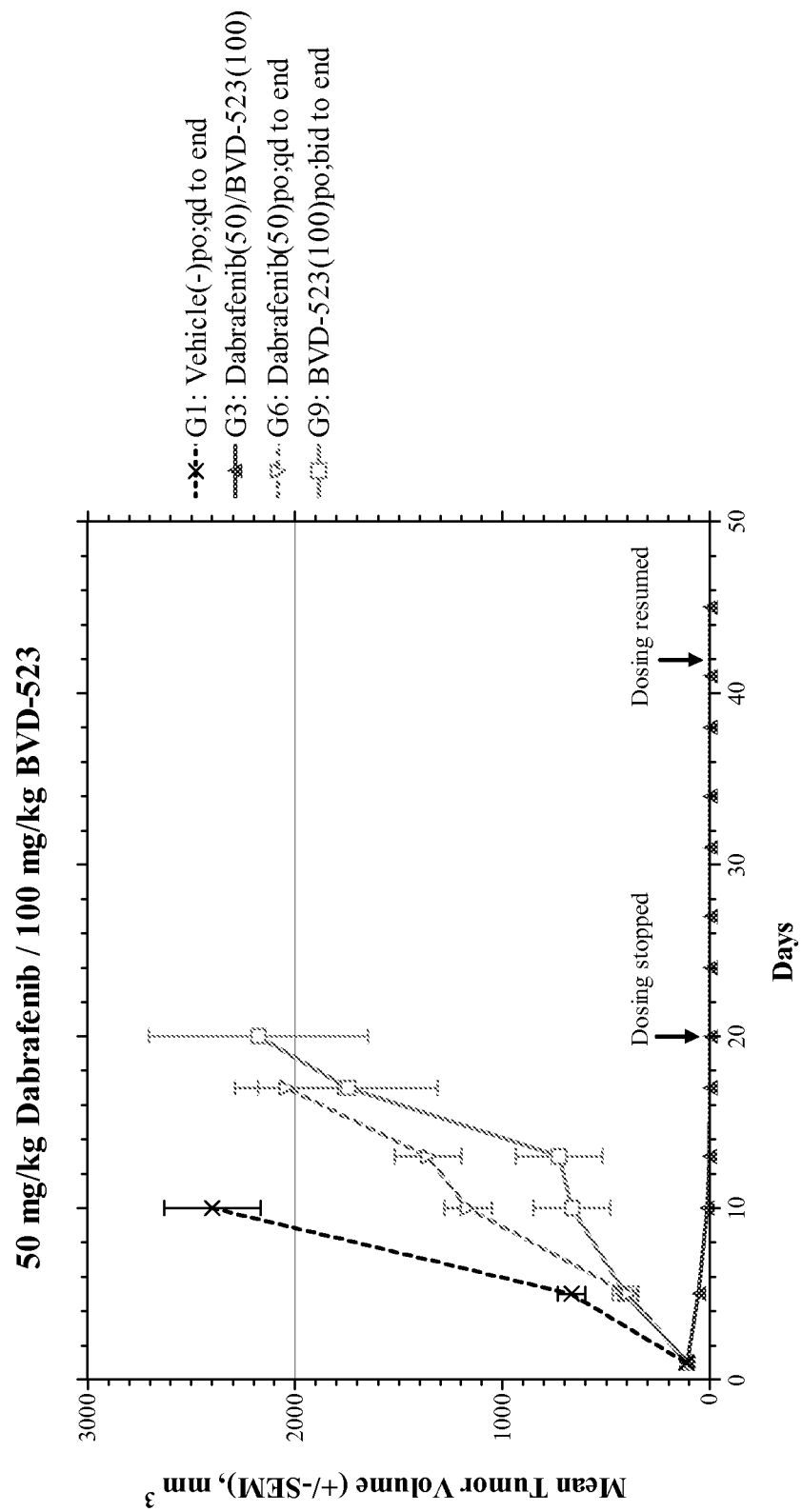
FIG. 28 Con't

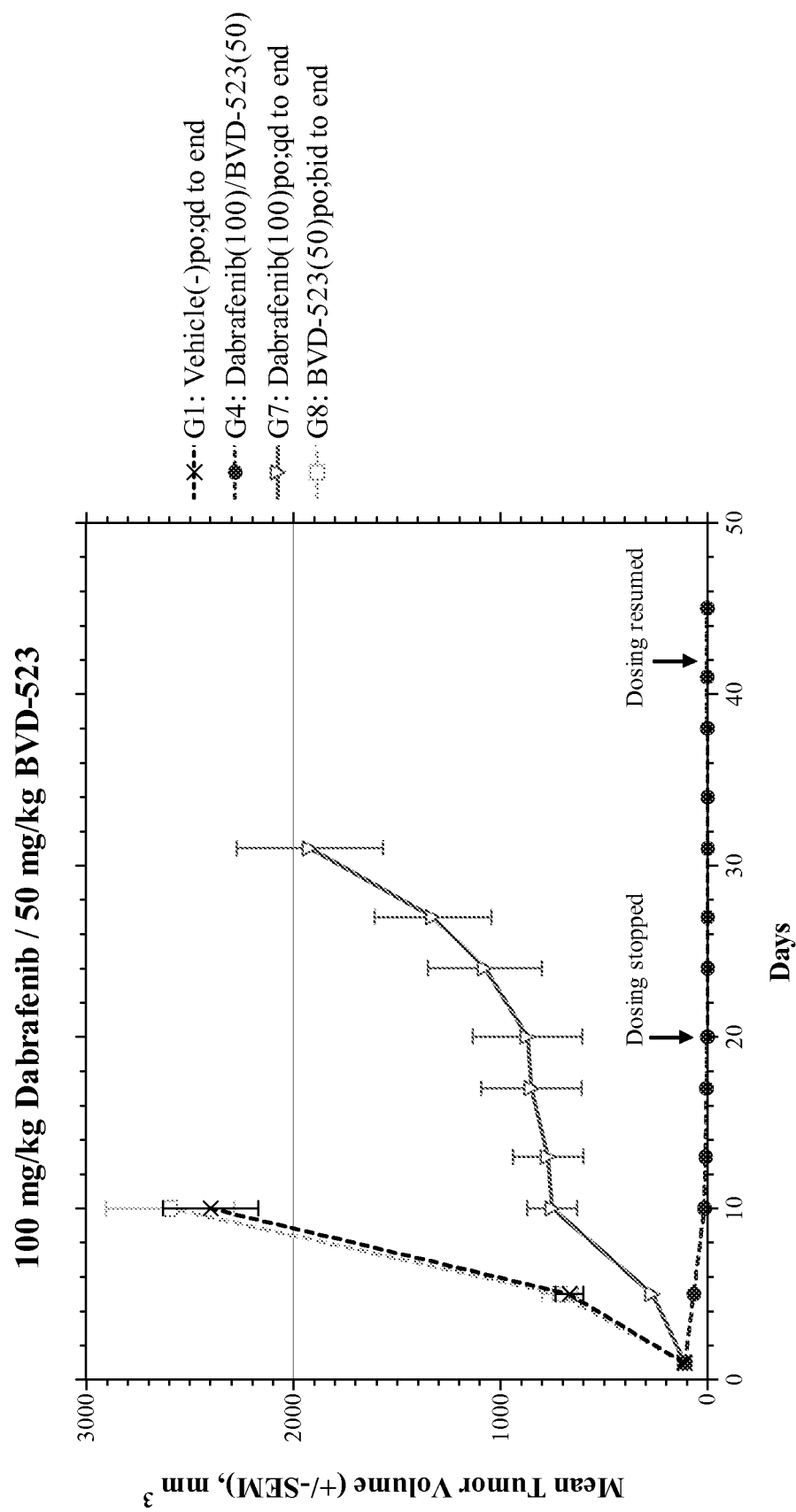
FIG. 28 Con't

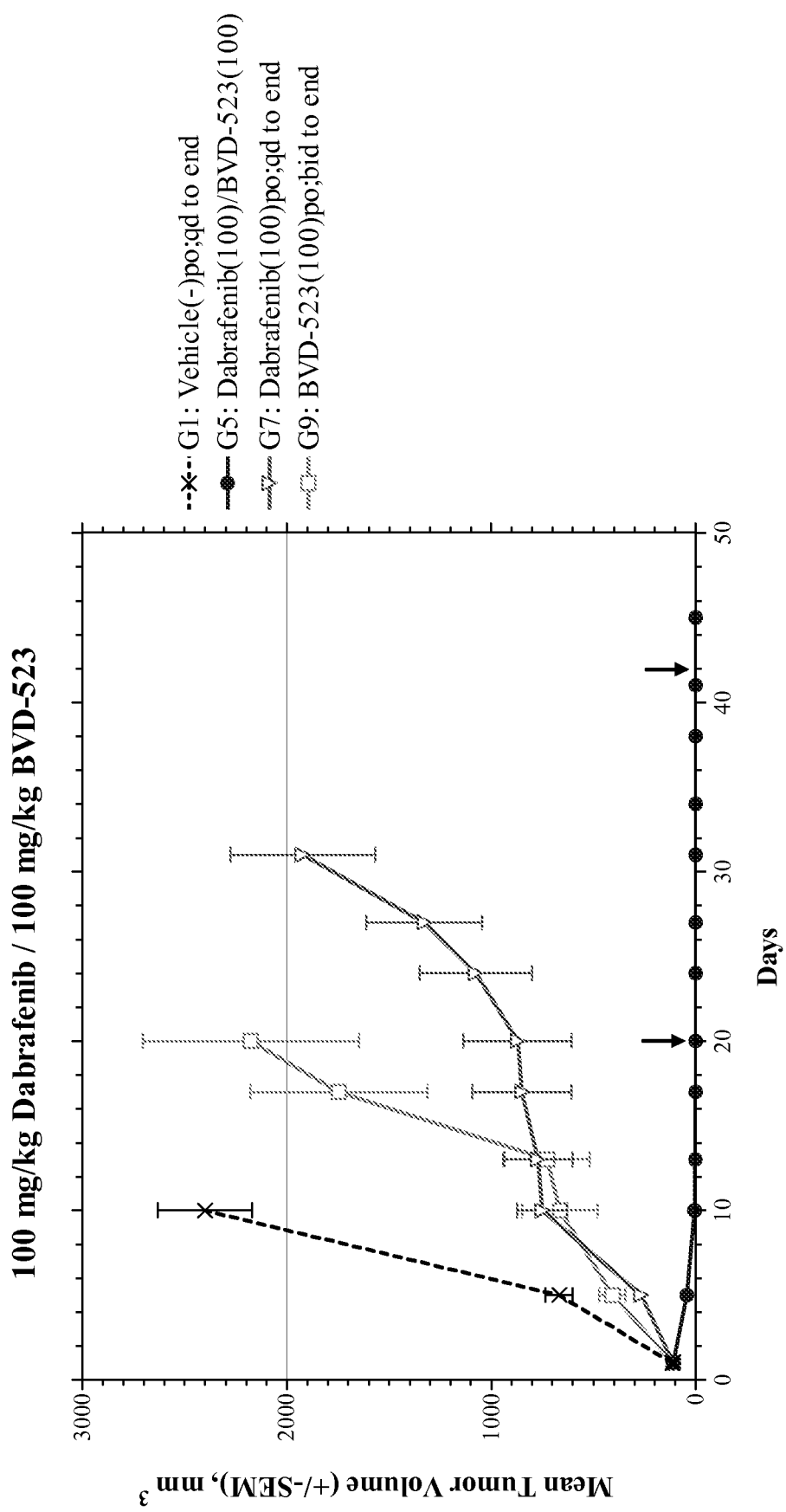
FIG. 28 Con't

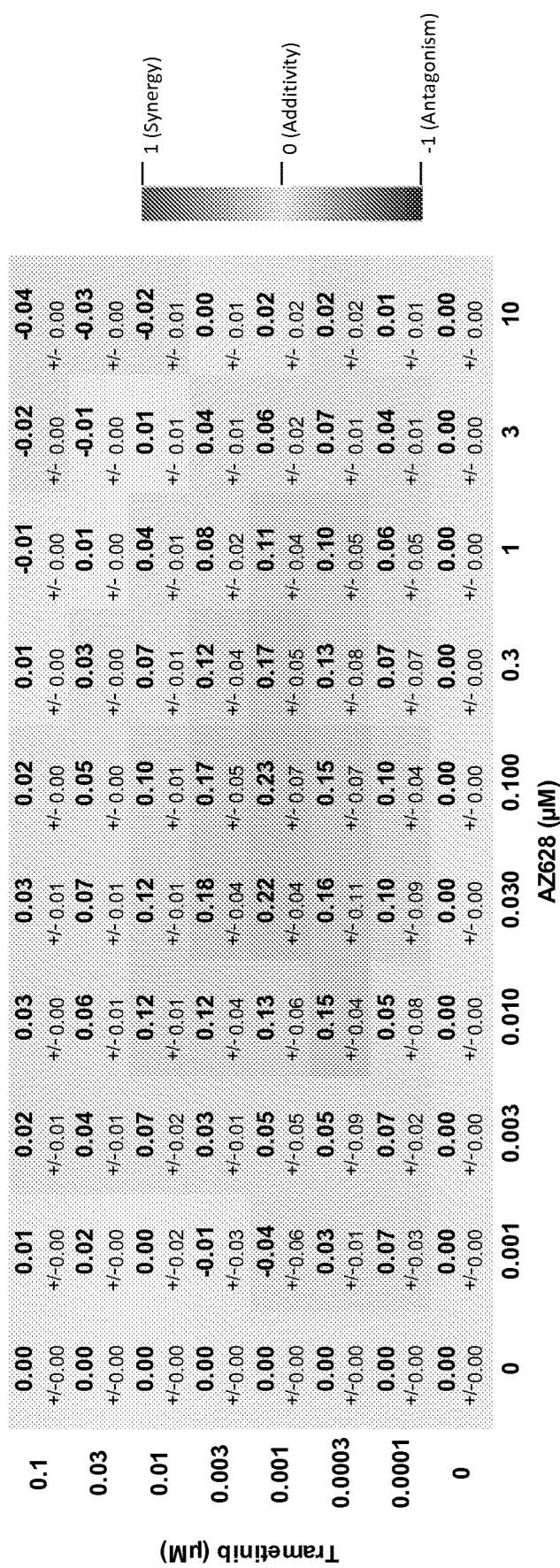
FIG. 31 Con't

FIG. 31 Con't
HCT116: AZ628/Trametinib Combination Assay – Alamar Blue
Single agent and Potentiation plots:
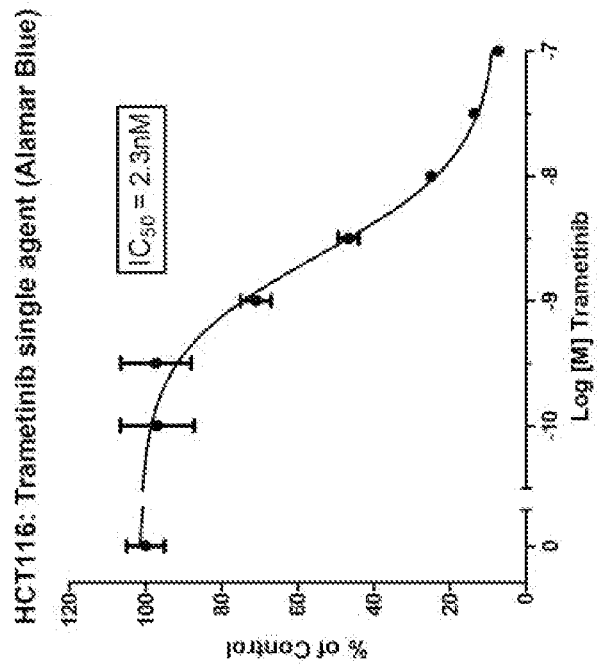
D
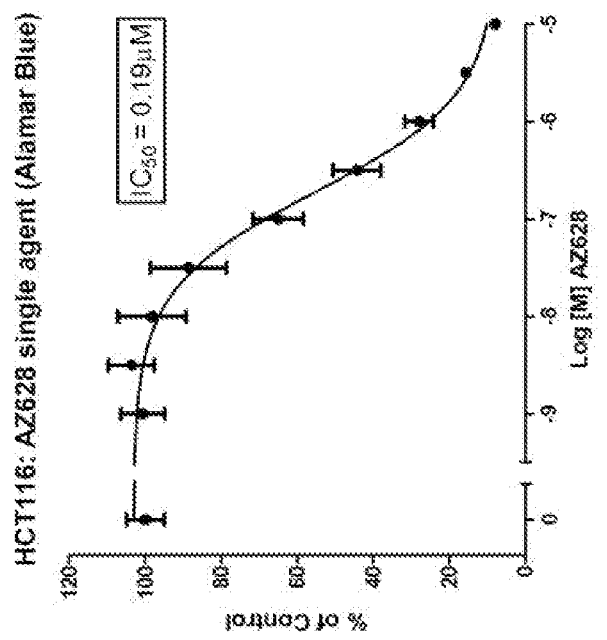
C

FIG. 31 Con't
HCT116: AZ628/Trametinib Combination Assay – Alamar Blue
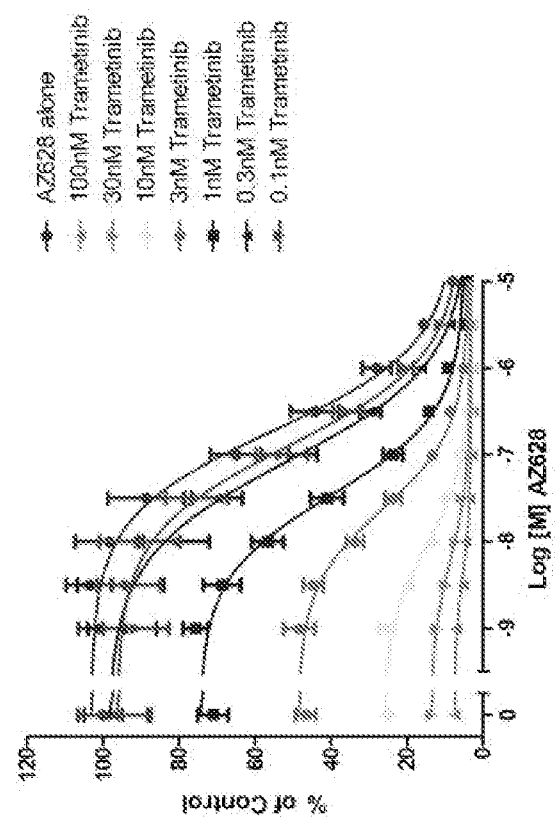

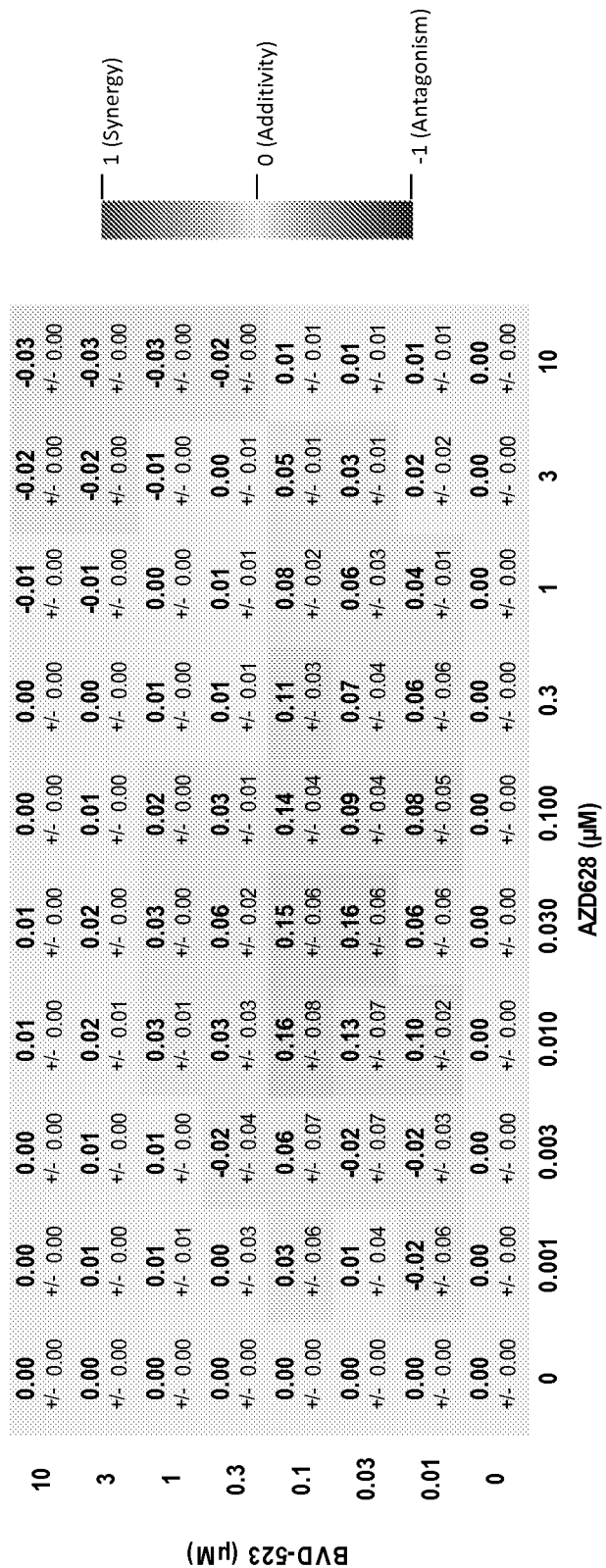

FIG. 32 Con't
HCT116: AZ628/BVD-523 Combination Assay – Alamar Blue
Single agent and Potentiation plots:
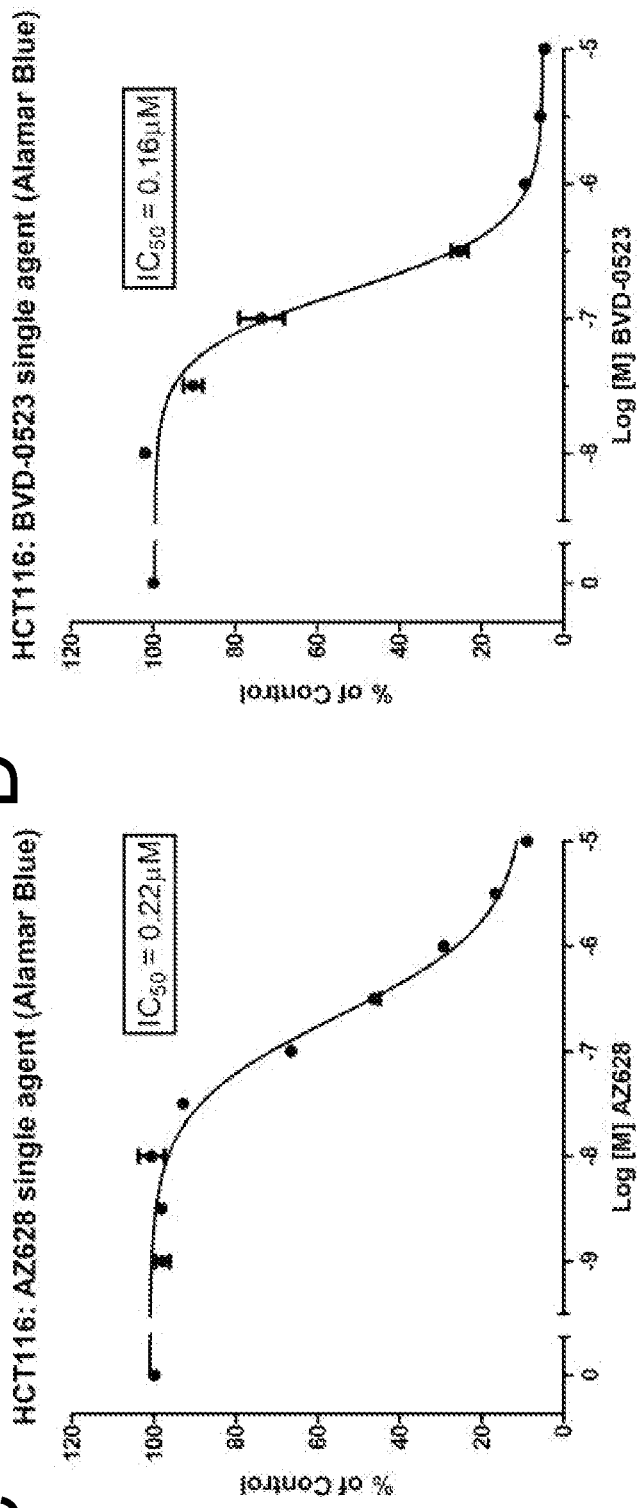
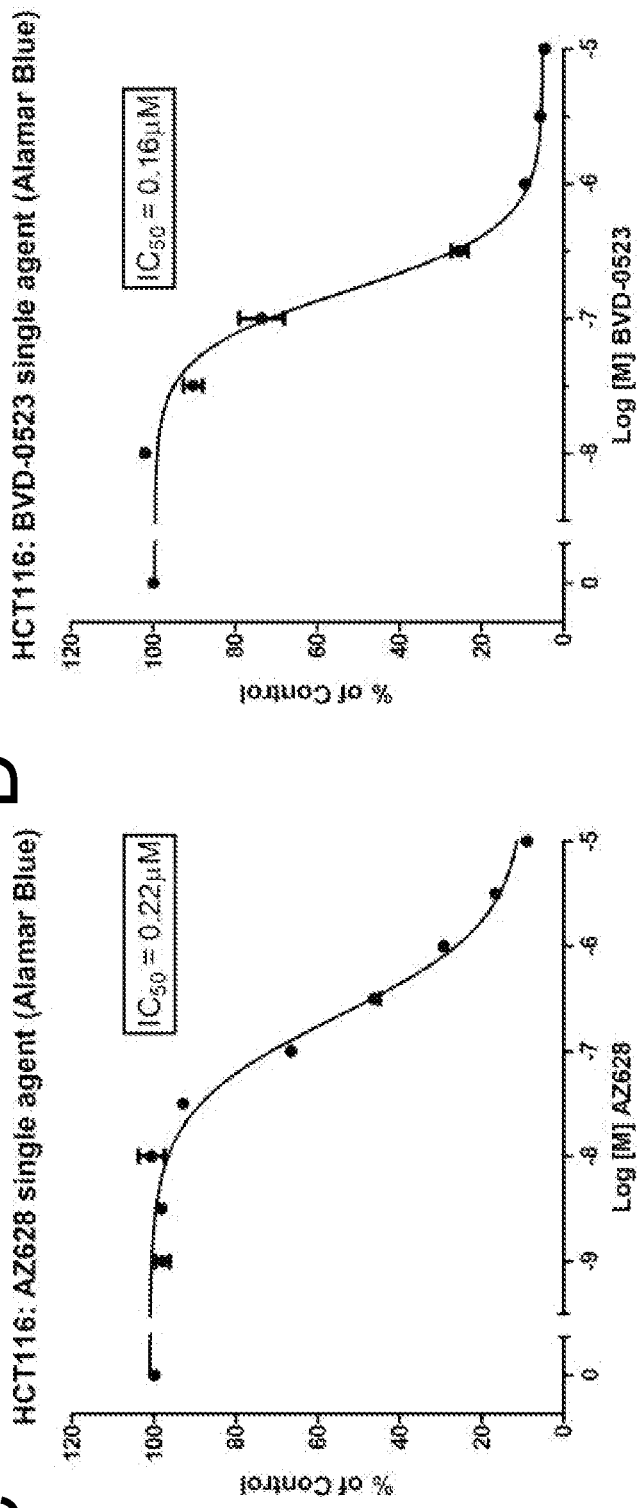

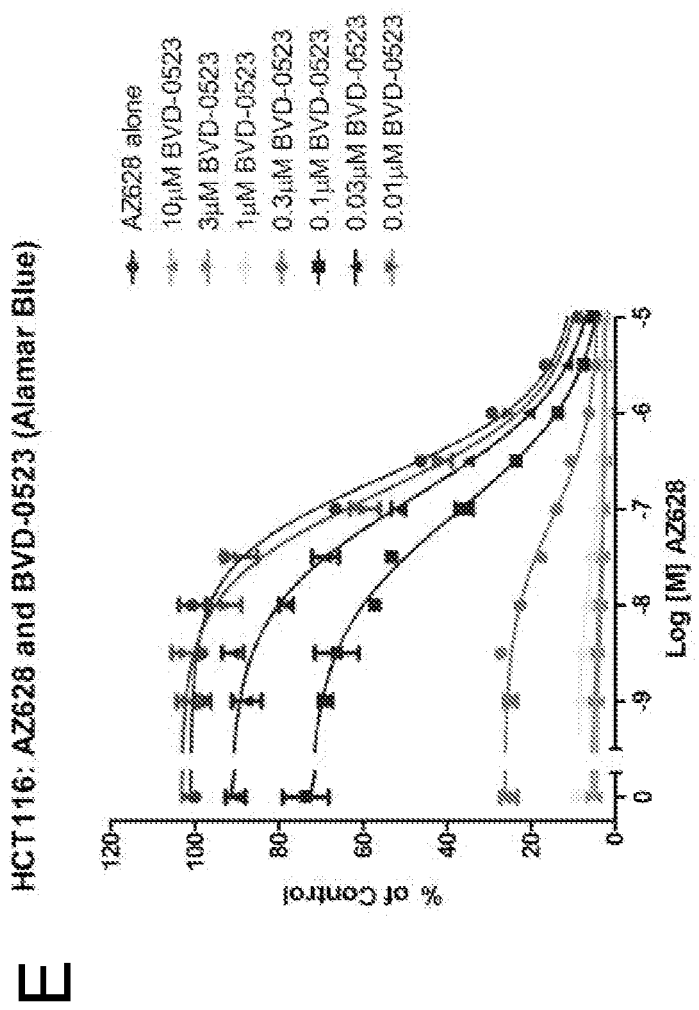
FIG. 32 Con't
HCT116: AZ628/BVD-523 Combination Assay – Alamar Blue

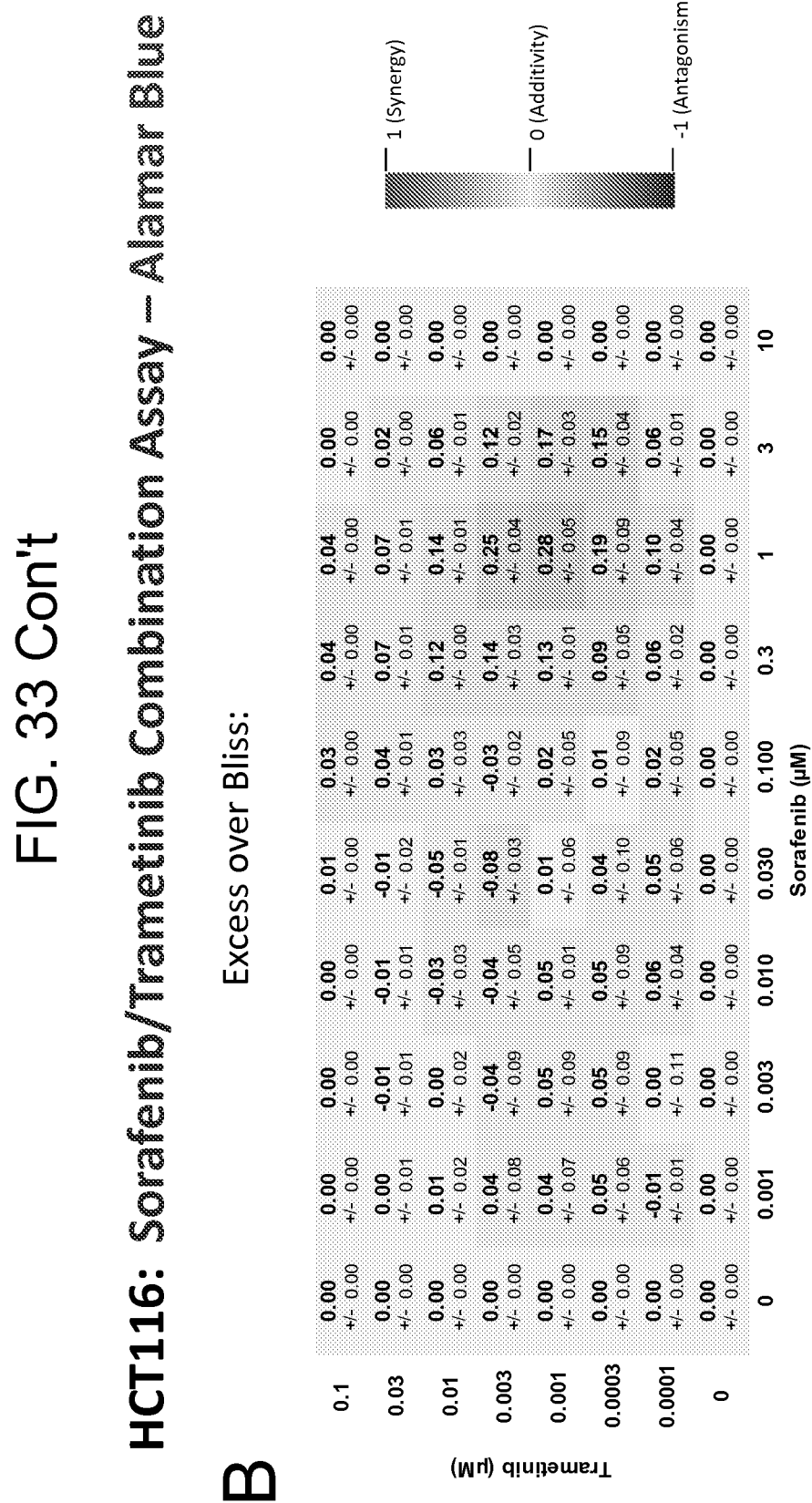
FIG. 33 Con't

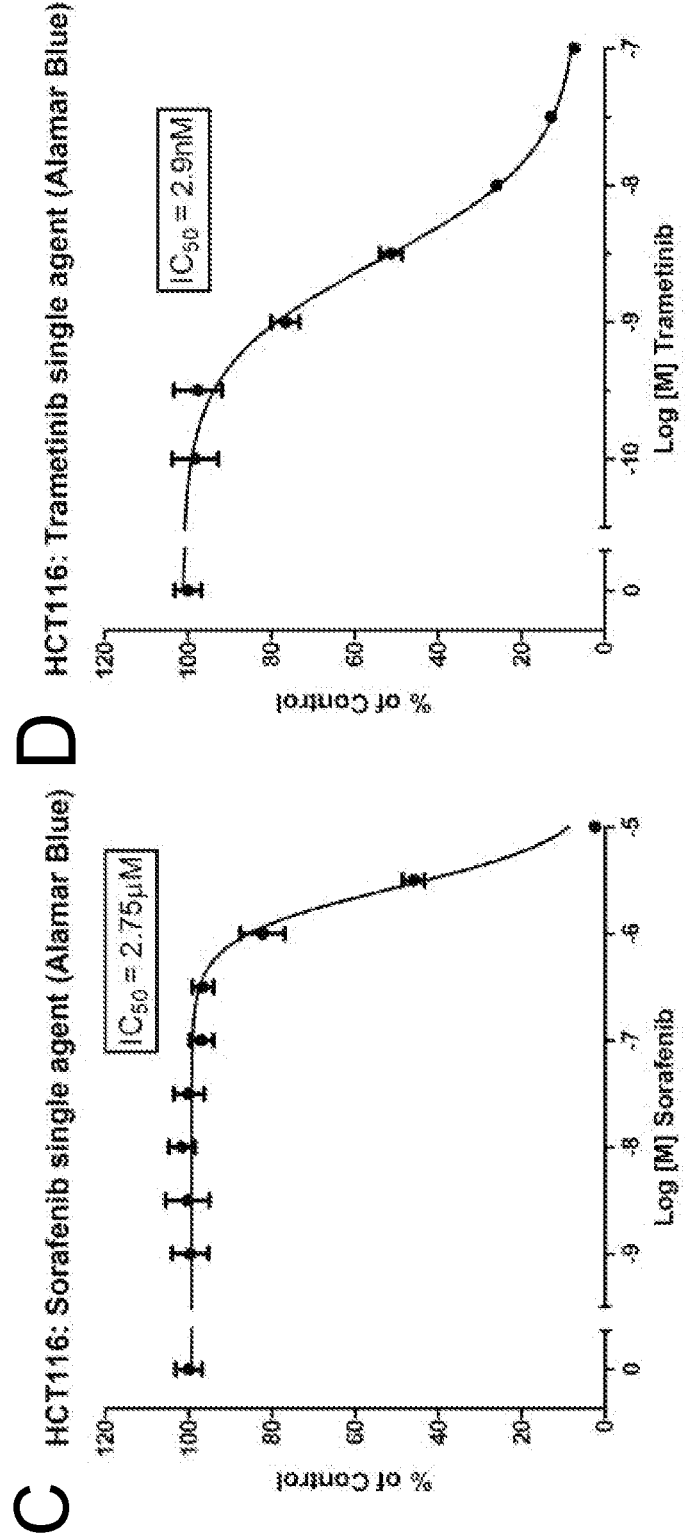
FIG. 33 Con't
HCT116: Sorafenib/Trametinib Combination Assay – Alamar Blue
Single agent and Potentiation plots:

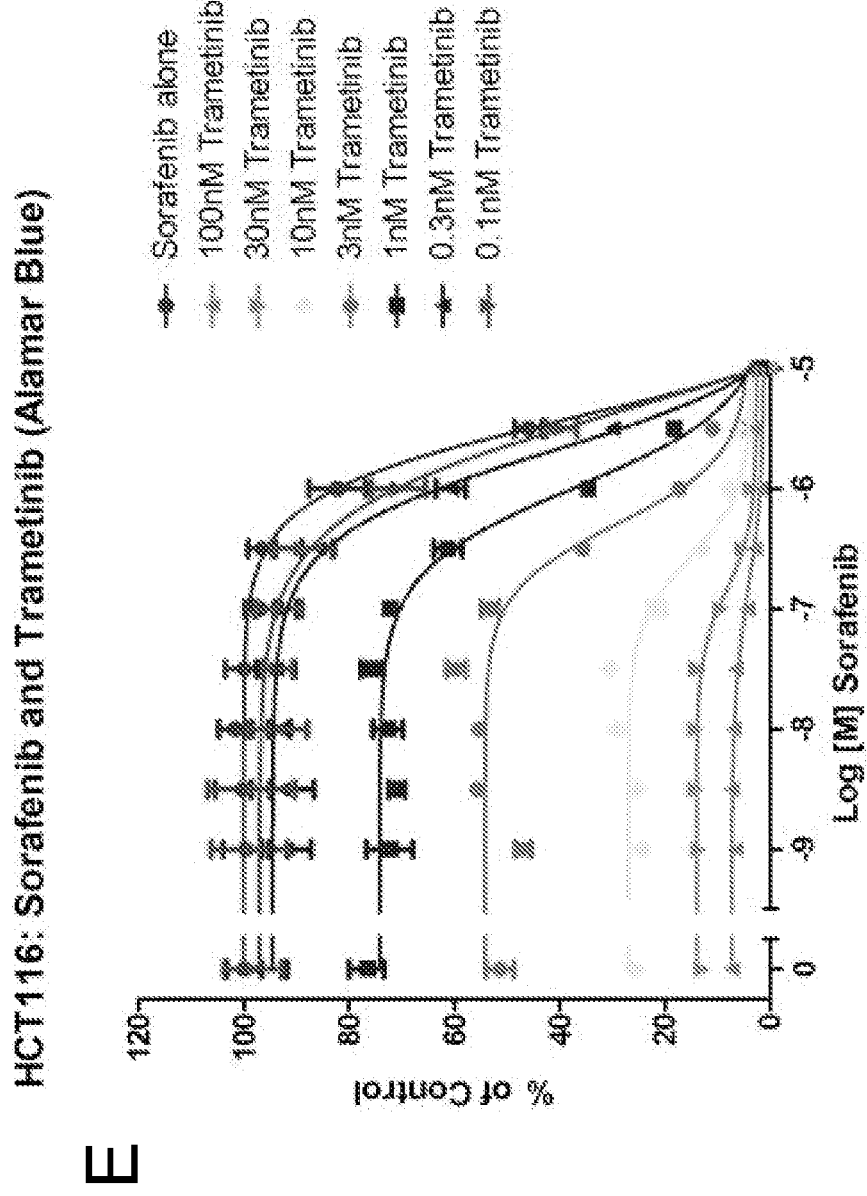
FIG. 33 Con't
HCT116: Sorafenib/Trametinib Combination Assay – Alamar Blue

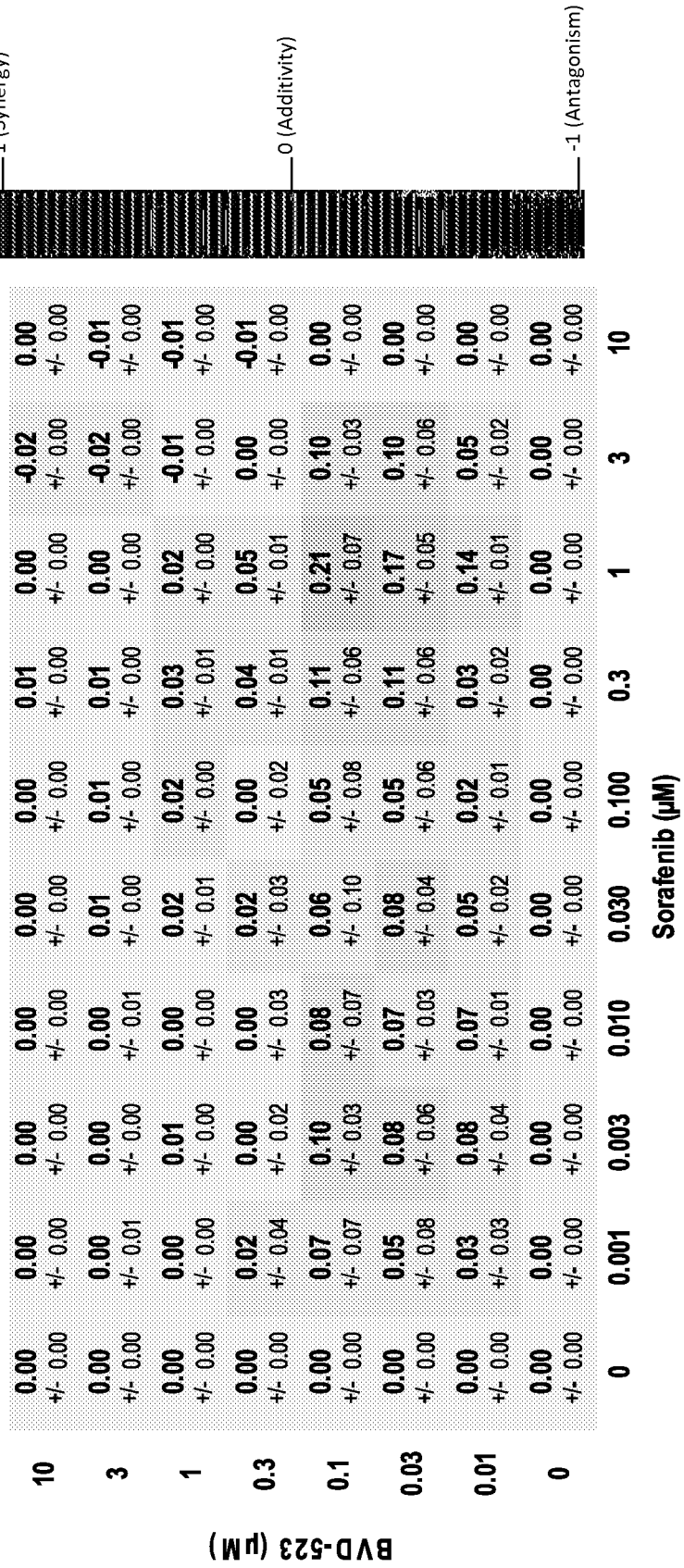
FIG. 34 Con't

FIG. 34 Con't
HCT116: Sorafenib/BVD-523 Combination Assay – Alamar Blue
Single agent and Potentiation plots:
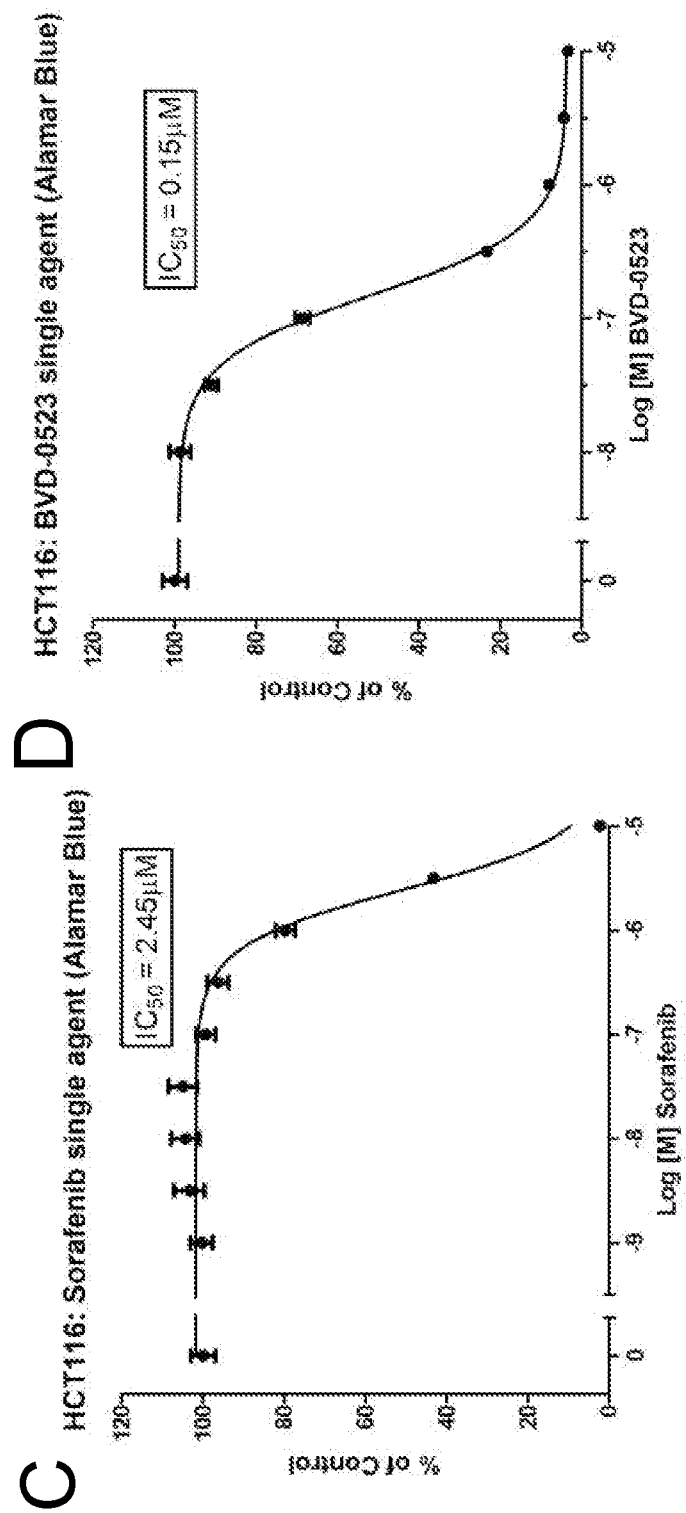

FIG. 34 Con't
HCT116: Sorafenib/BVD-523 Combination Assay – Alamar Blue
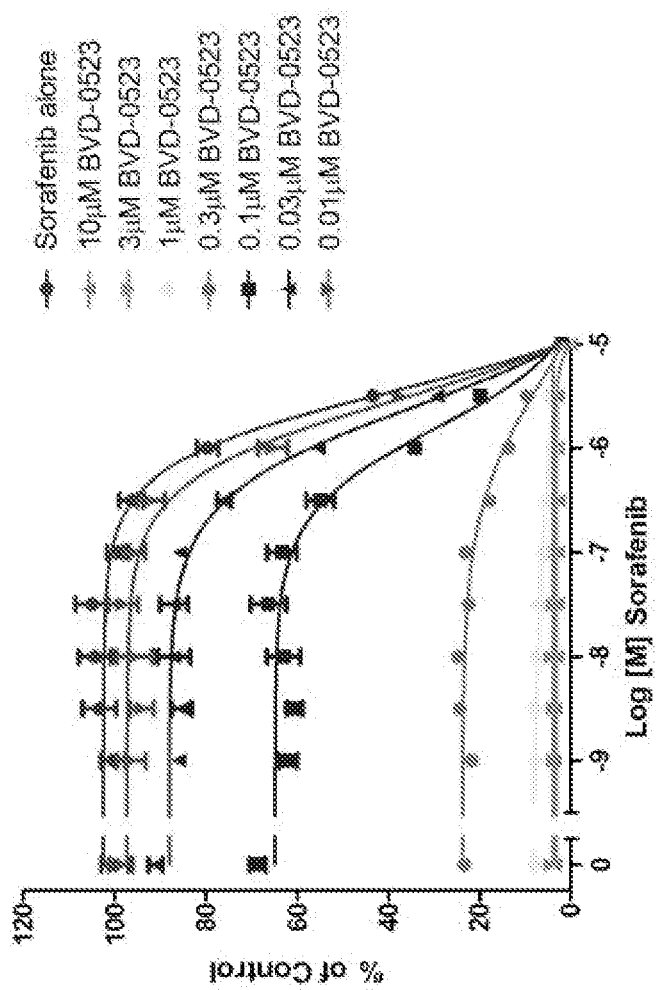

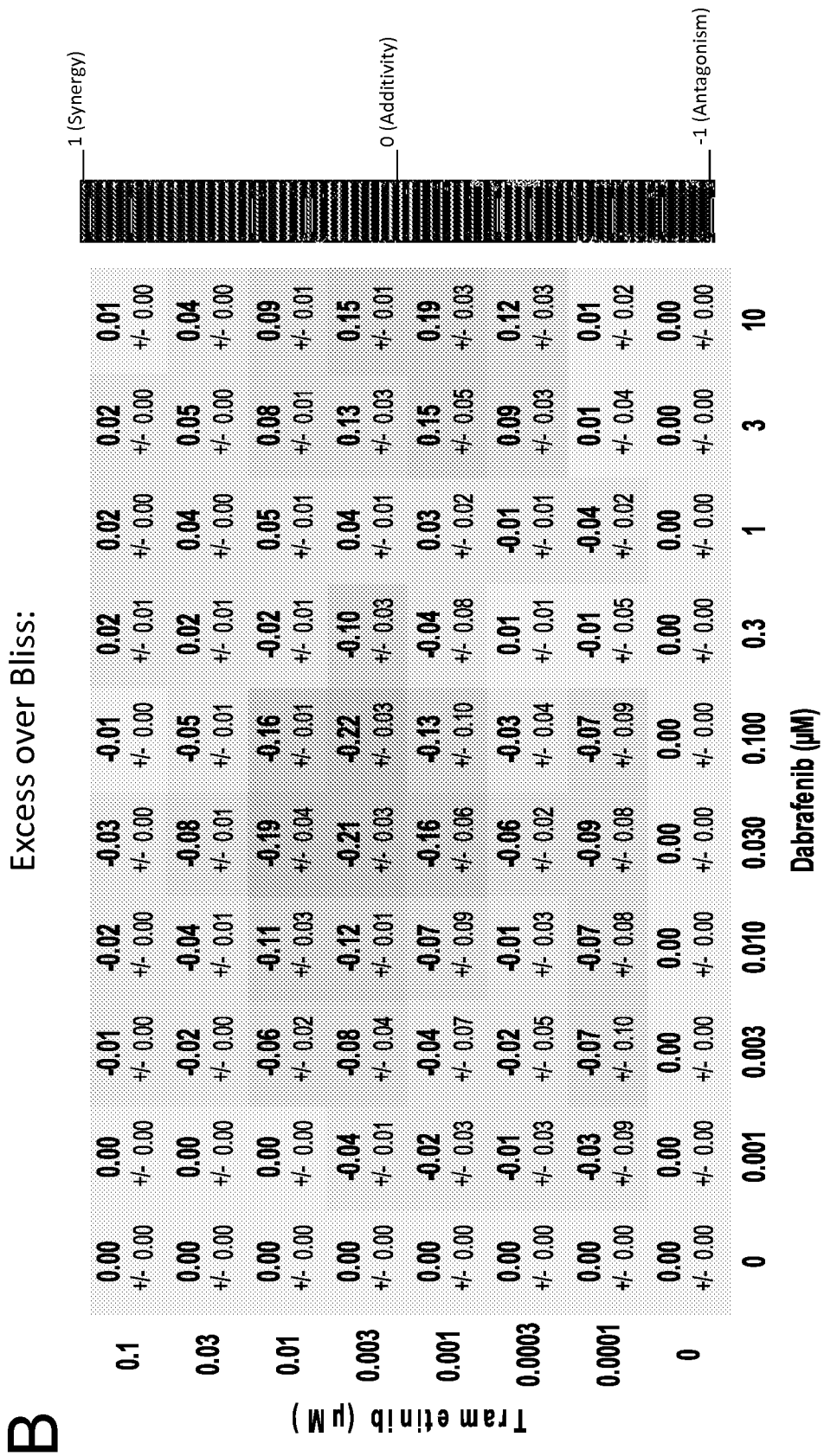
FIG. 35 Con't

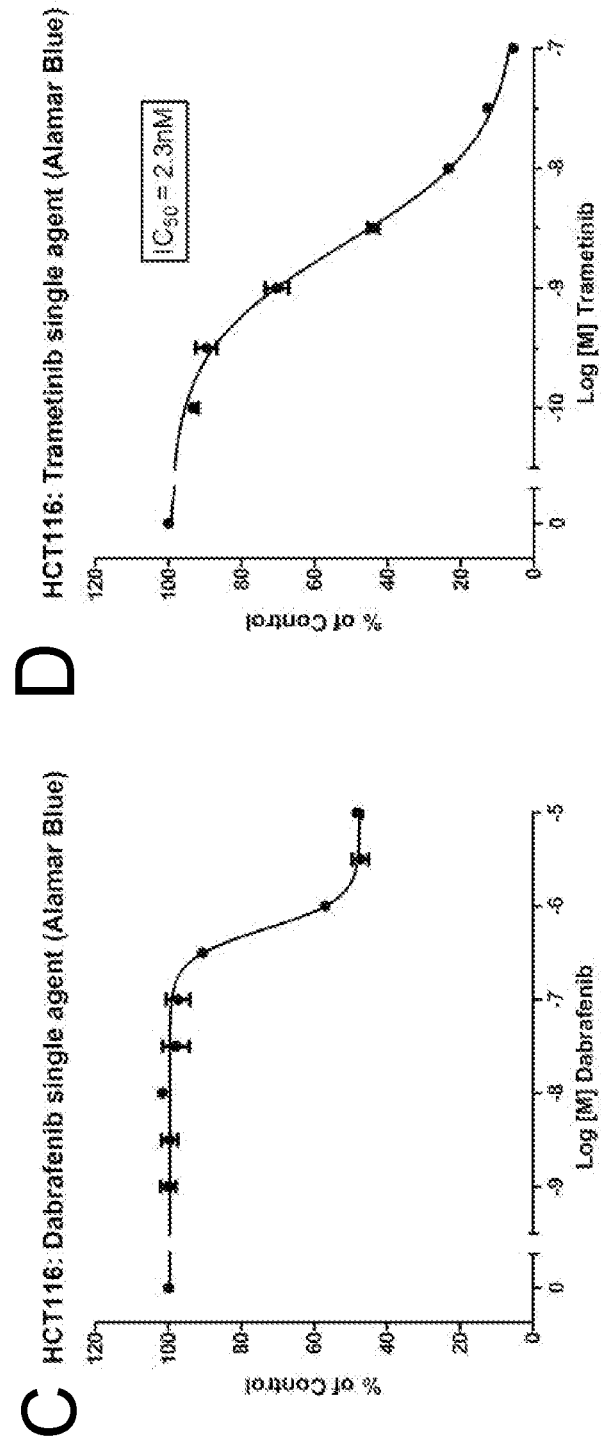
FIG. 35 Con't

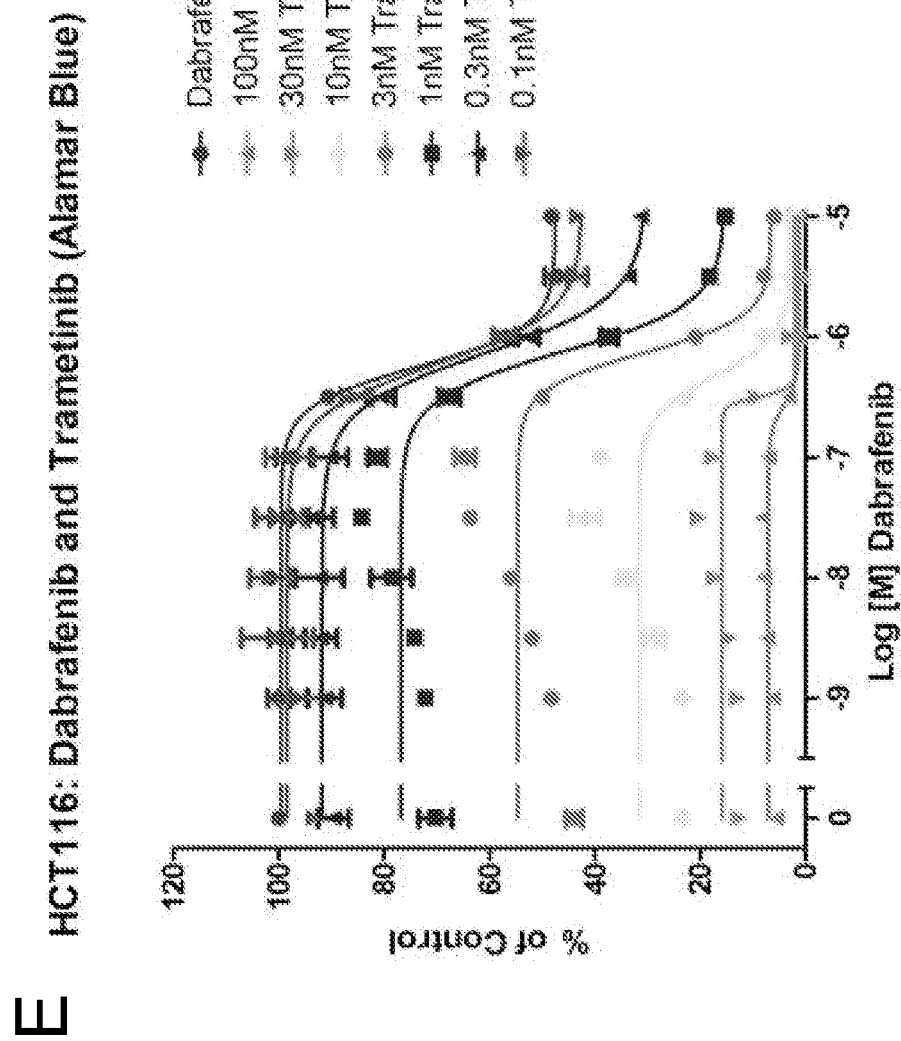
FIG. 35 Con't
HCT116: Dabrafenib/Trametinib Combination Assay – Alamar Blue

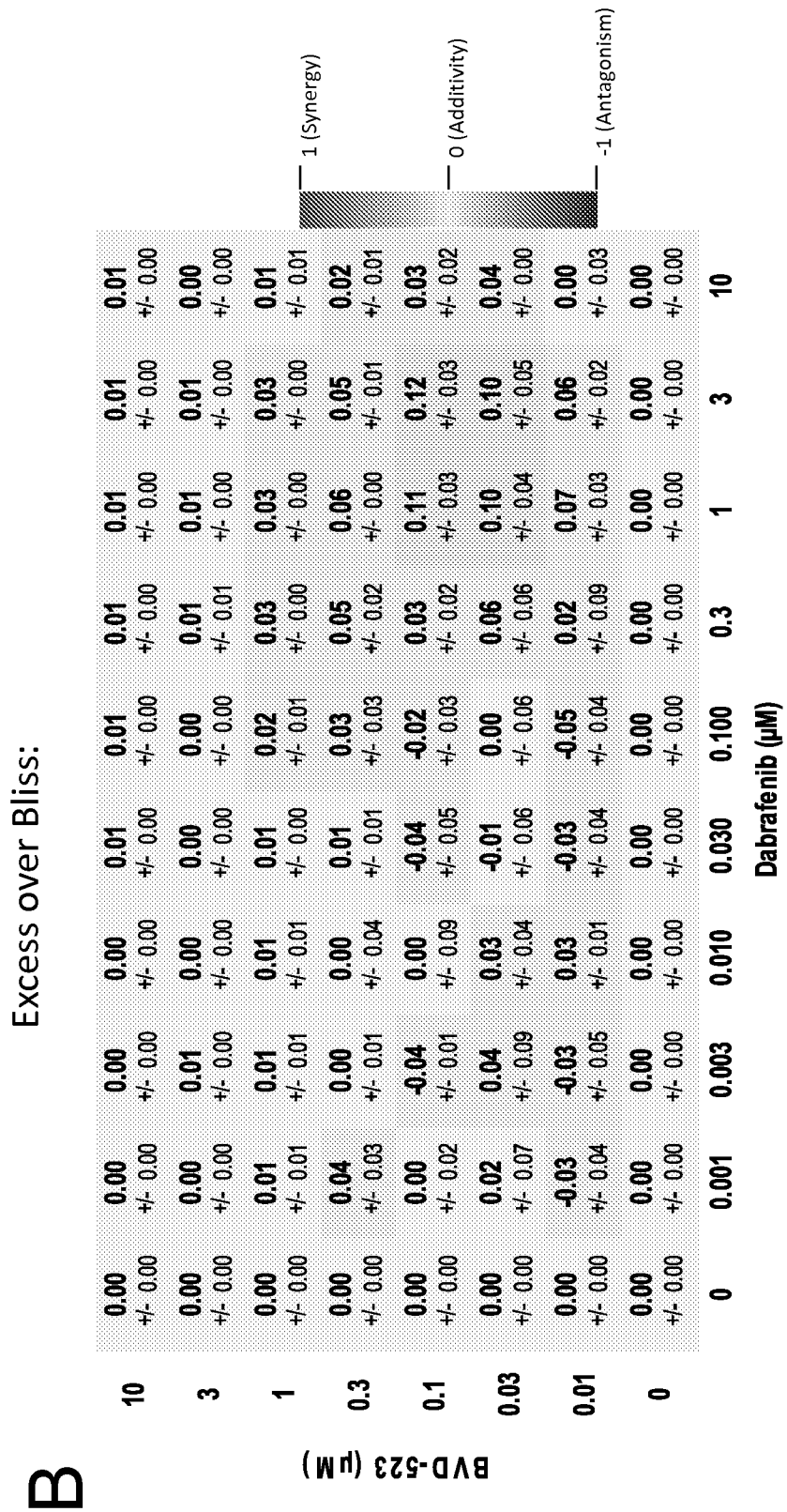

FIG. 36 Con't
HCT116: Dabrafenib/BVD-523 Combination Assay – Alamar Blue
Single agent and Potentiation plots:
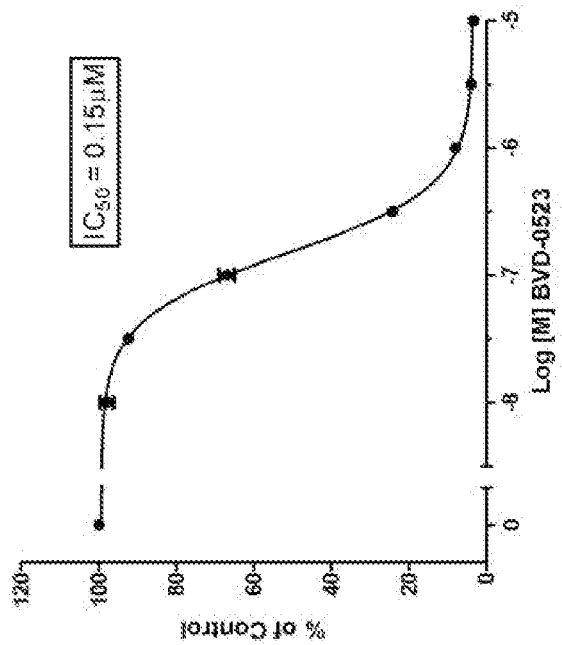
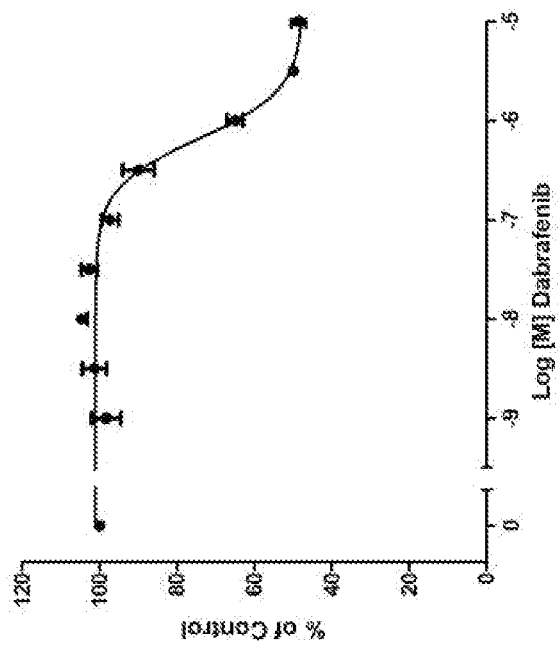

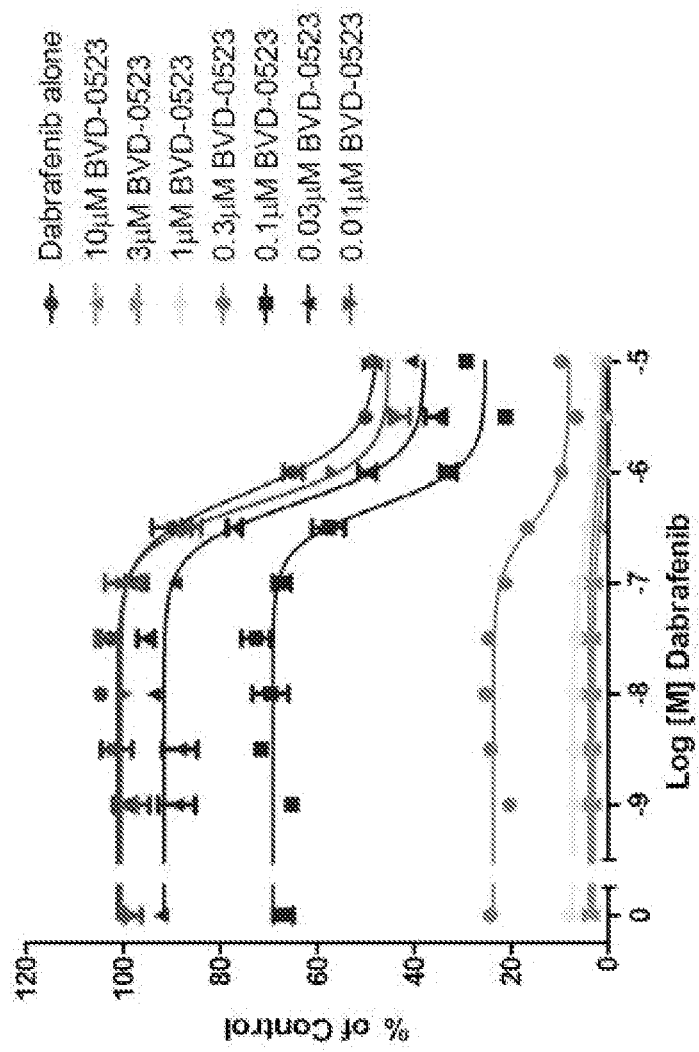
FIG. 36 Con't
HCT116: Dabrafenib/BVD-523 Combination Assay – Alamar Blue

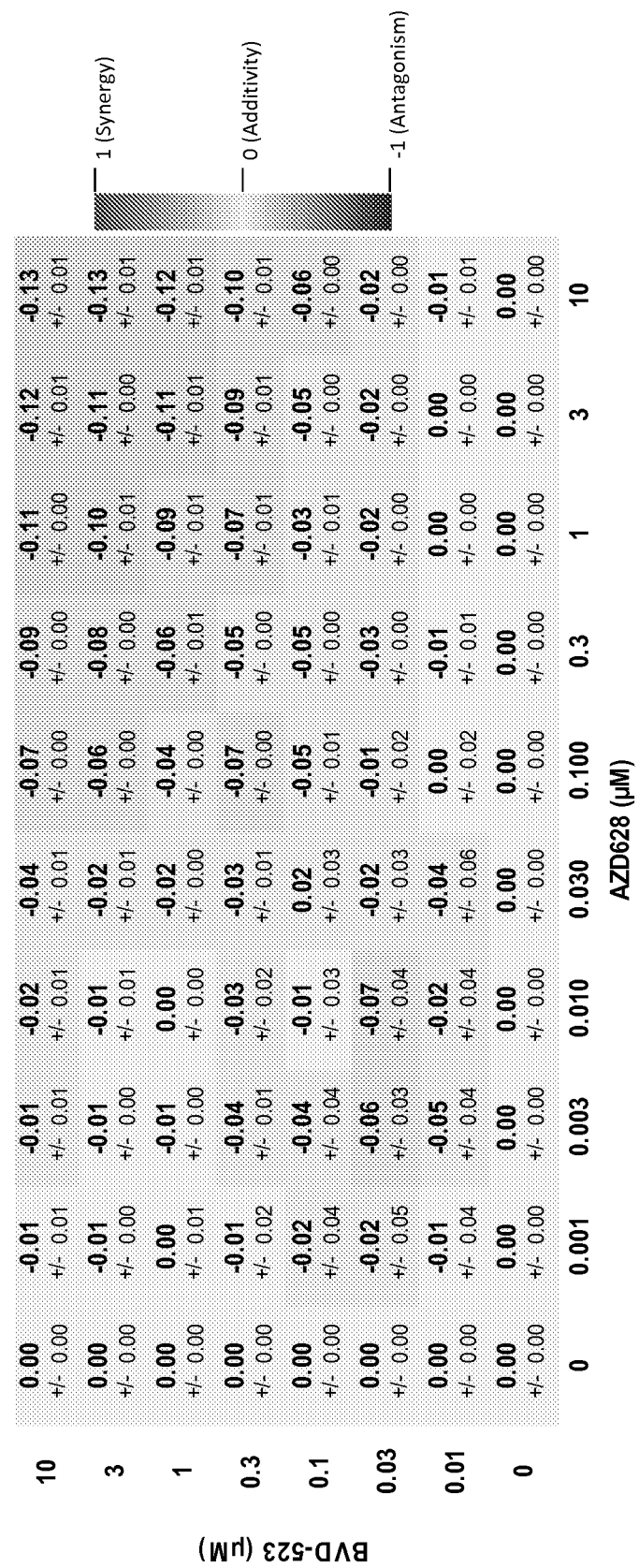
FIG. 37 Con't

FIG. 37 Con't
A375: AZ628/BVD-523 Combination Assay – Alamar Blue
Single agent and Potentiation plots:
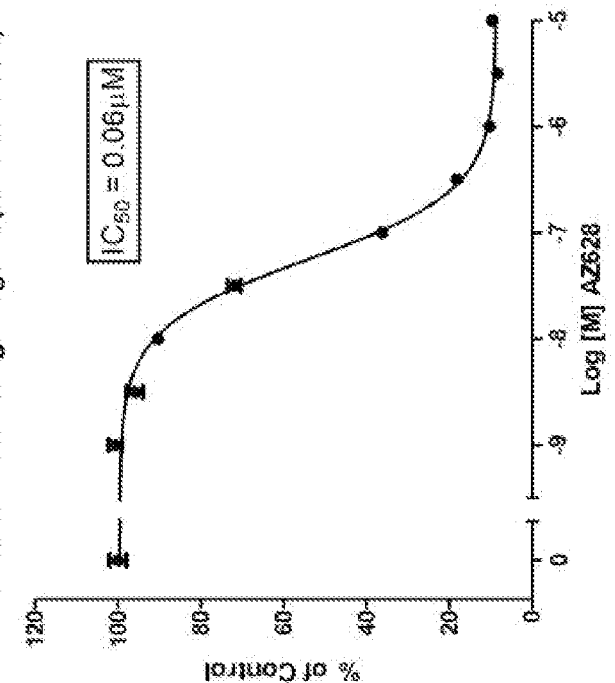

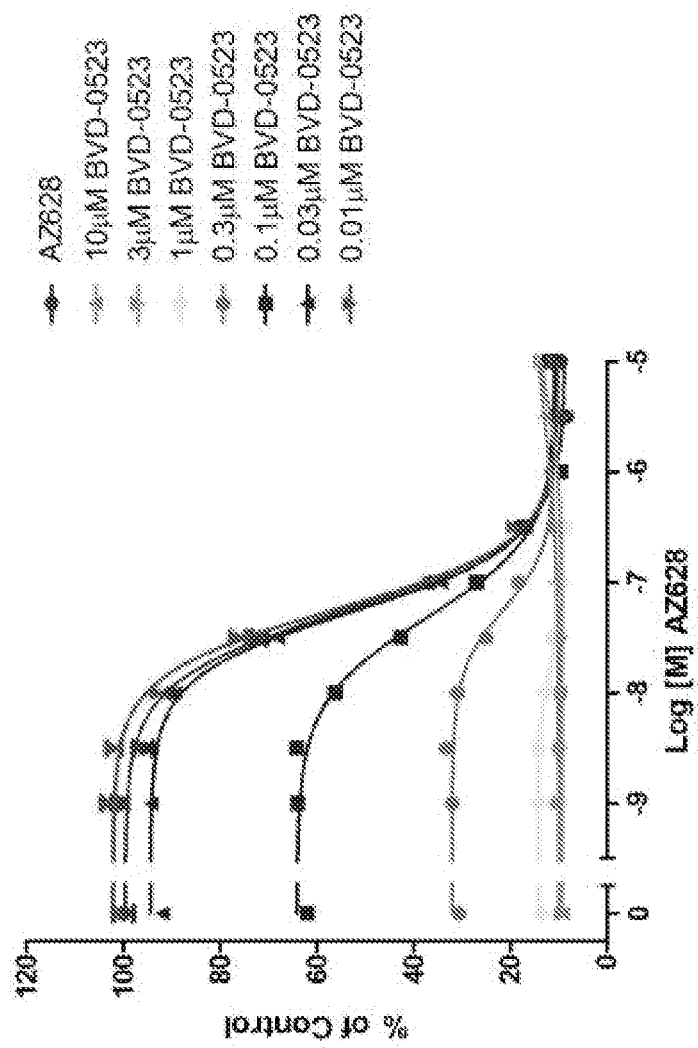
FIG. 37 Con't

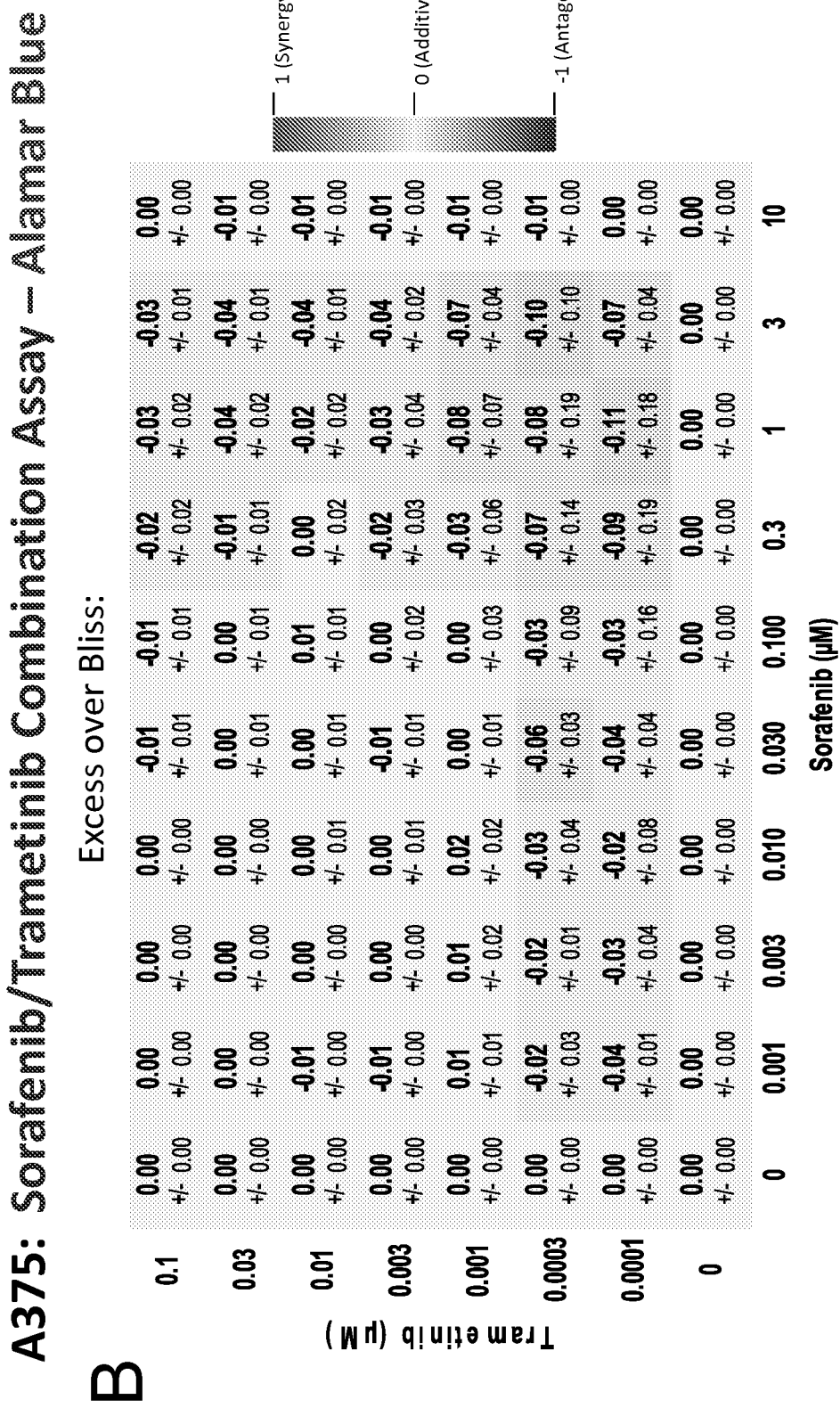
FIG. 38 Con't

FIG. 38 Con't
A375: Sorafenib/Trametinib Combination Assay – Alamar Blue
Single agent and Potentiation plots:
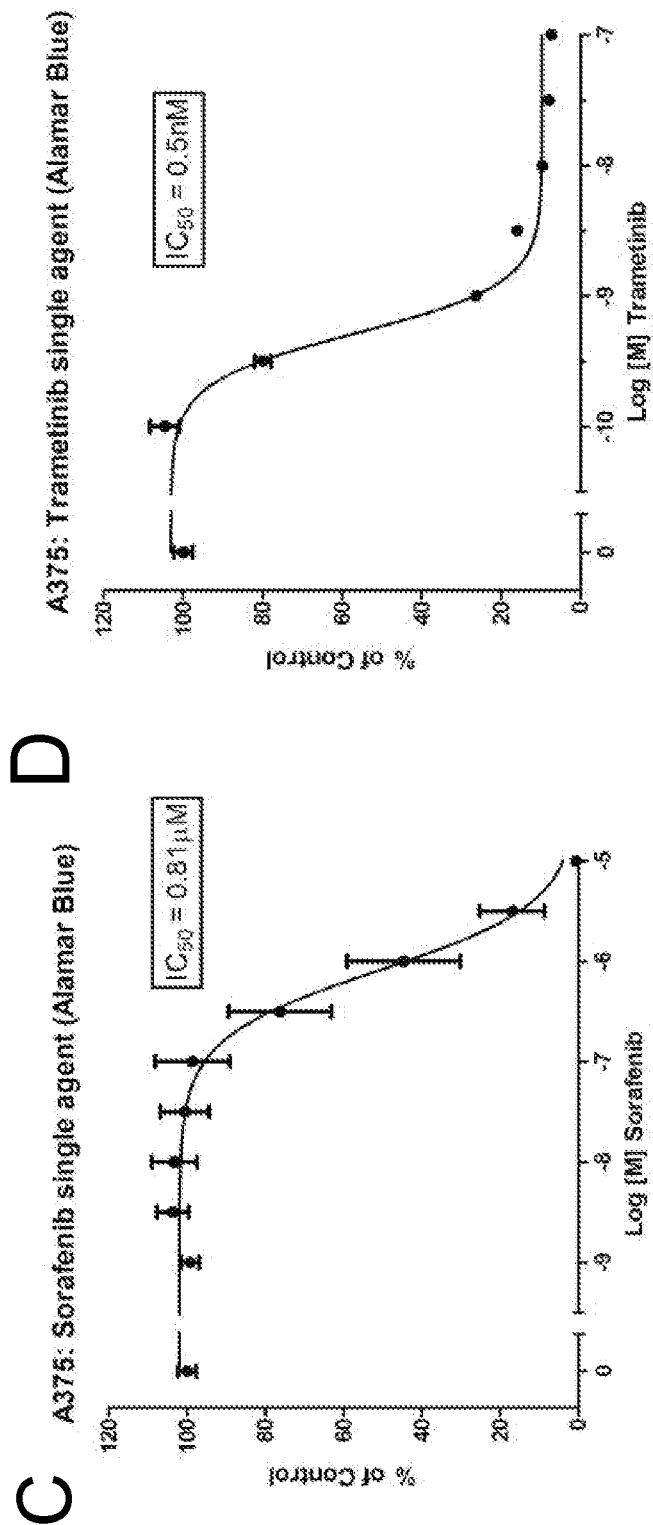

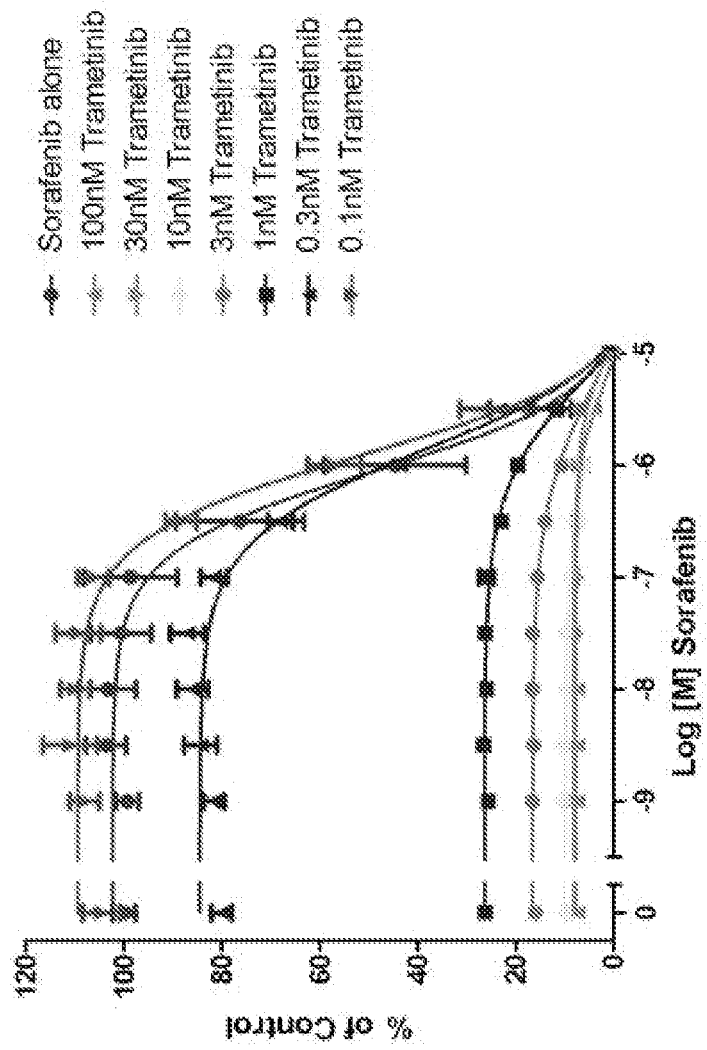
FIG. 38 Con't
A375: Sorafenib/Trametinib Combination Assay – Alamar Blue

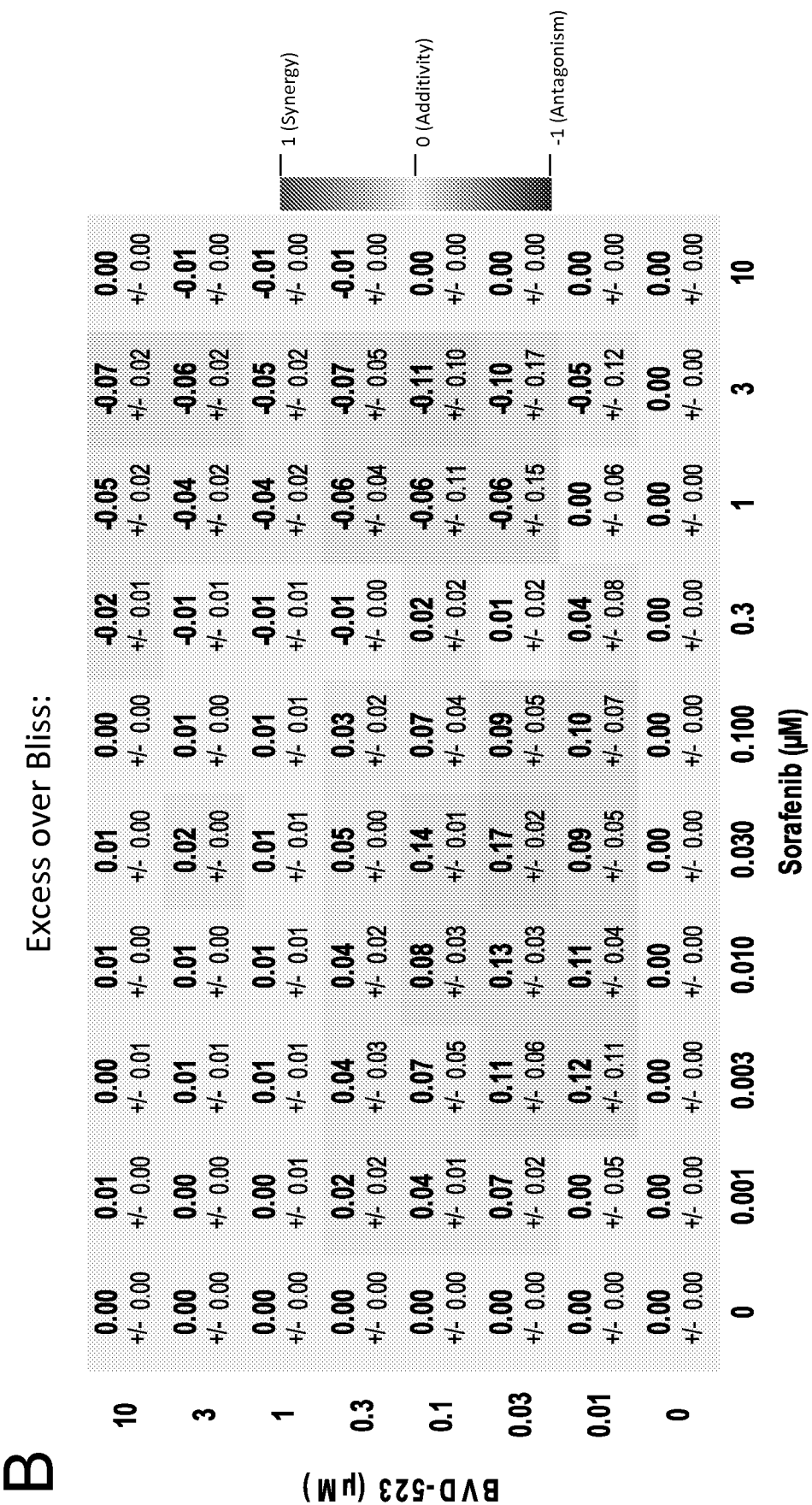
FIG. 39 Con't

FIG. 39 Con't
A375: Sorafenib/BVD-523 Combination Assay – Alamar Blue
Single agent and Potentiation plots:
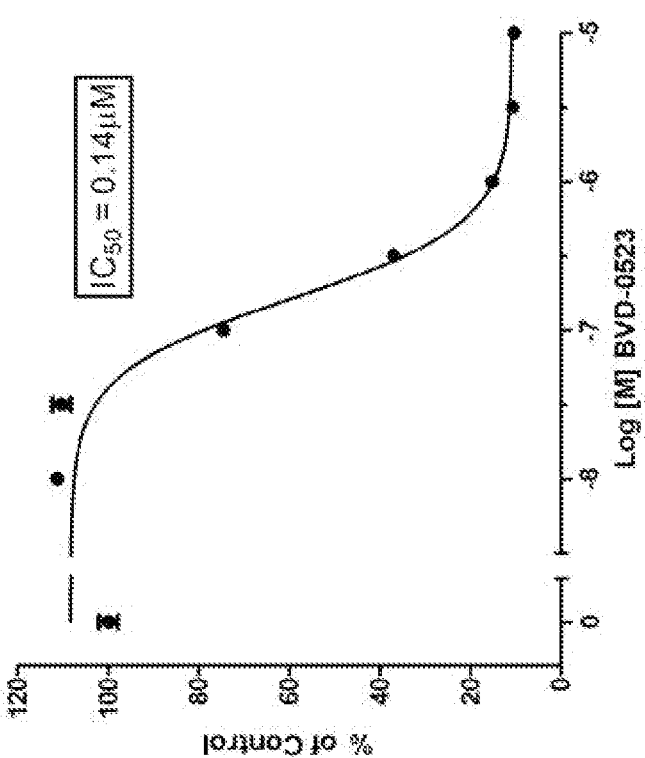
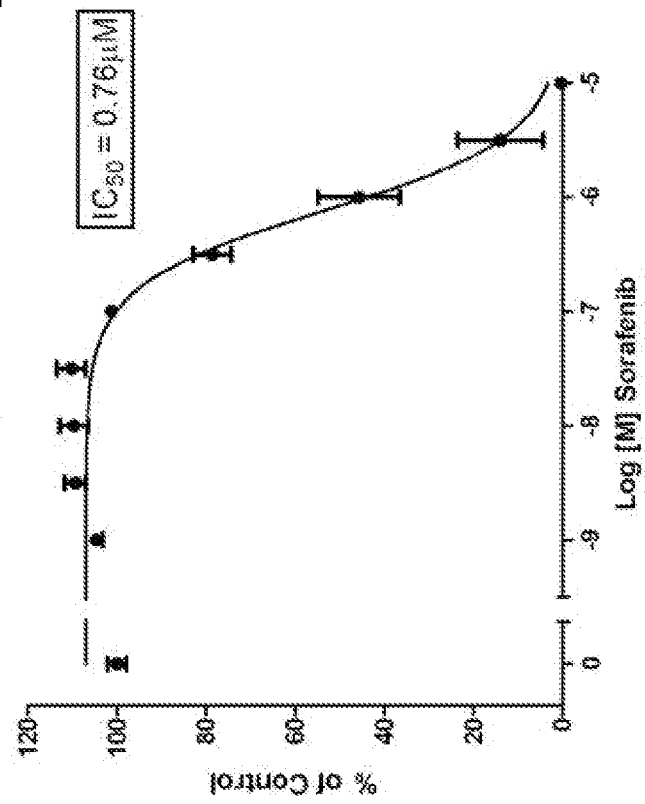

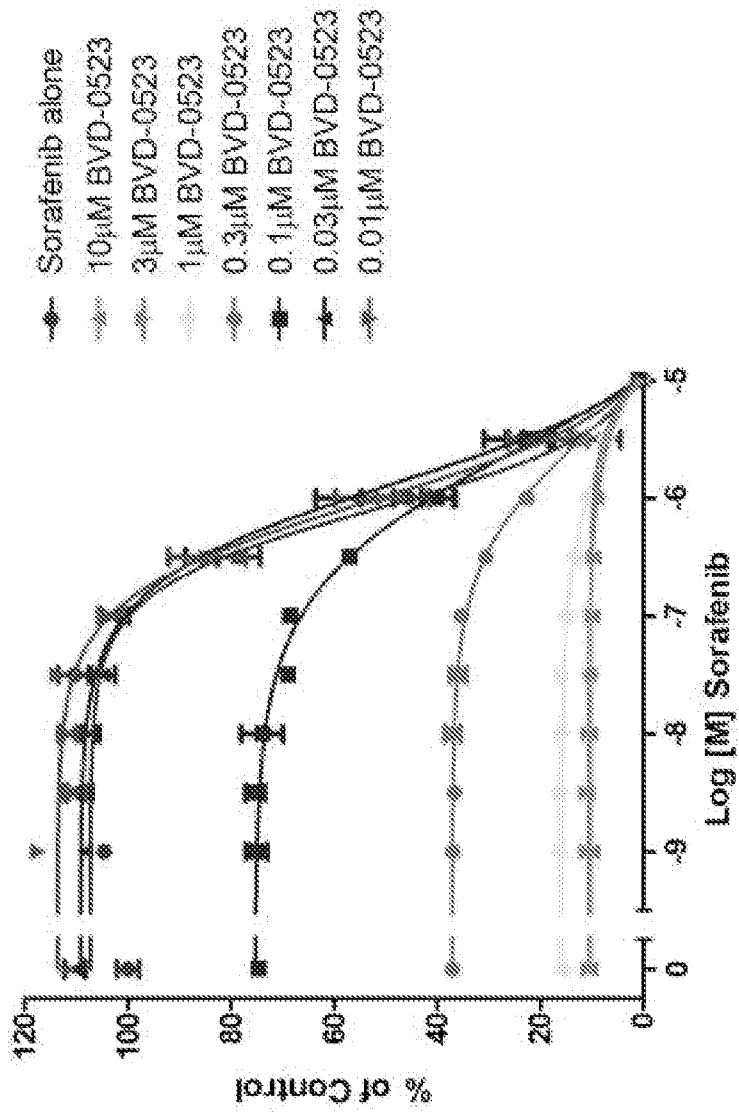
FIG. 39 Con't
A375: Sorafenib/BVD-523 Combination Assay – Alamar Blue

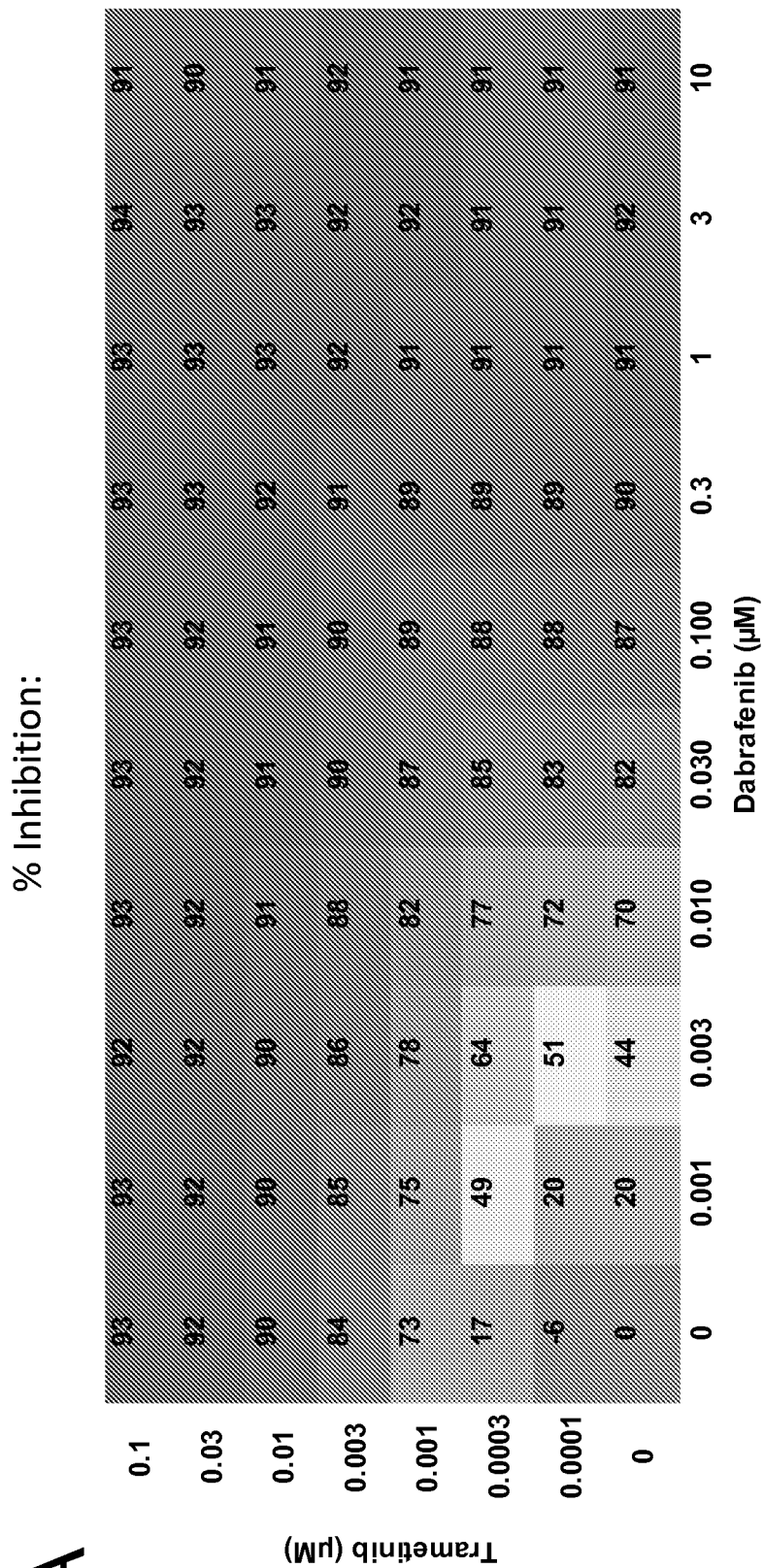

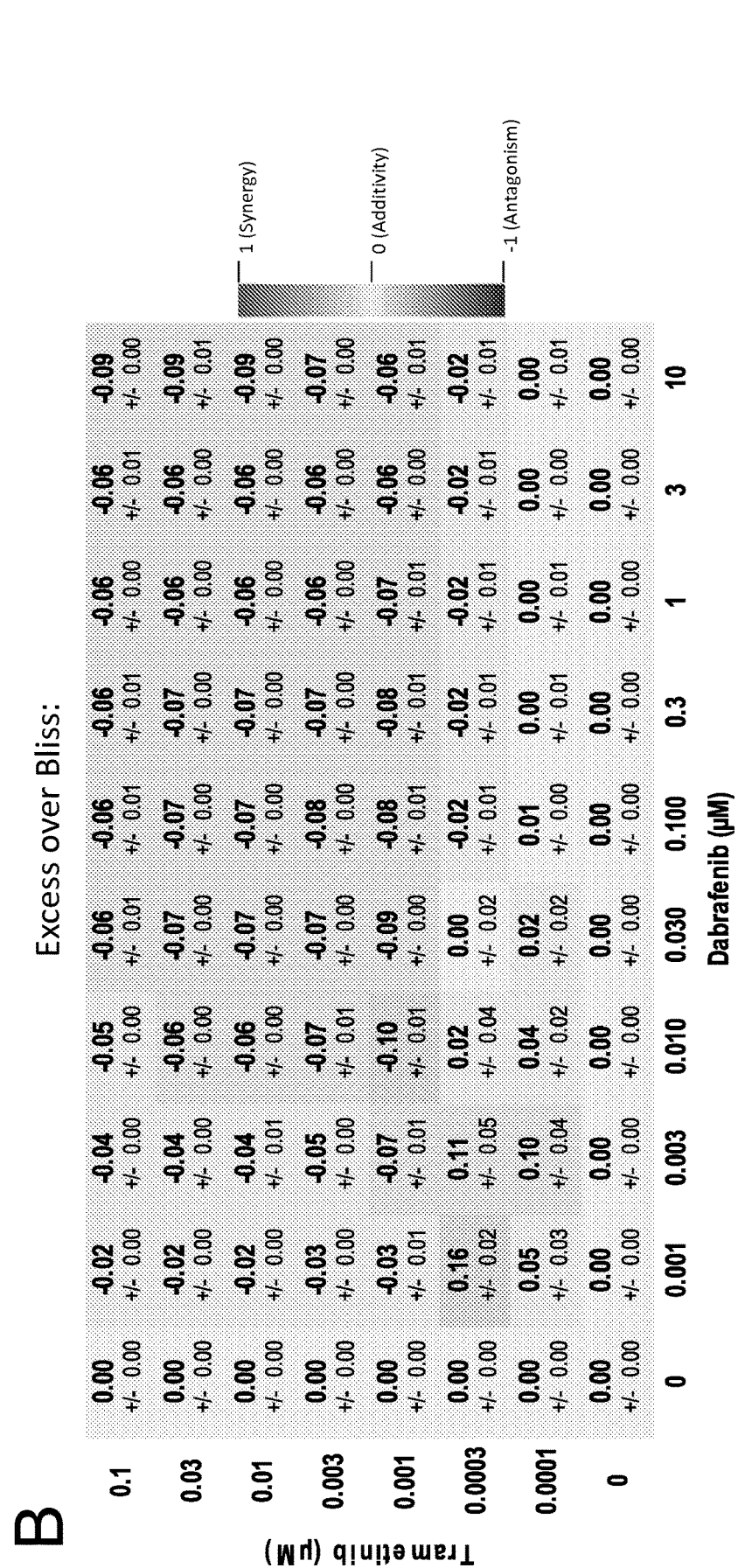

FIG. 40 Con't
A375: Dabrafenib/Trametinib Combination Assay – Alamar Blue
Single agent and Potentiation plots:
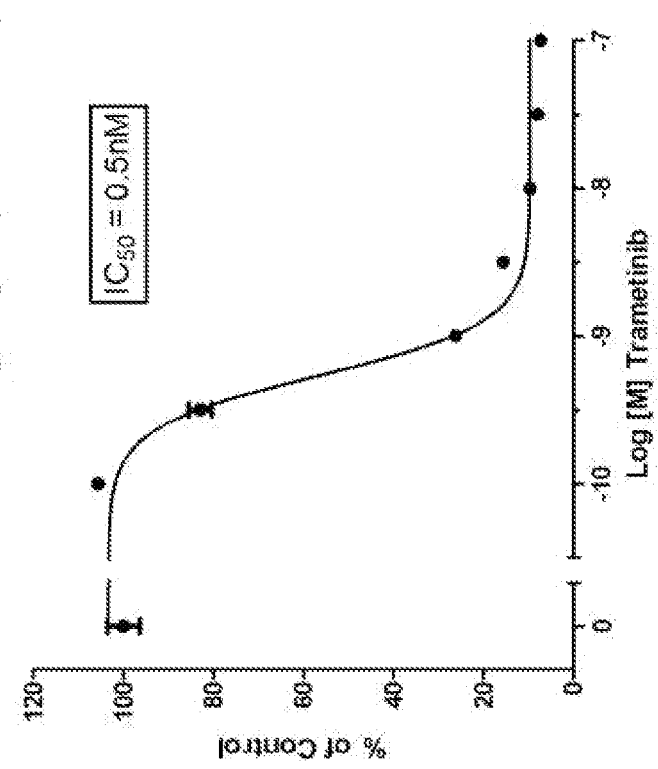
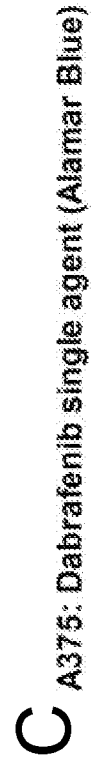
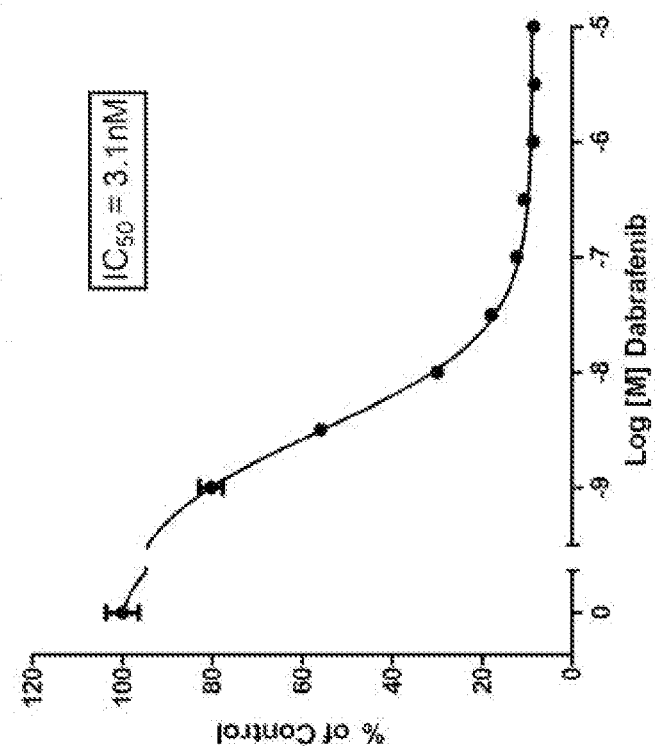

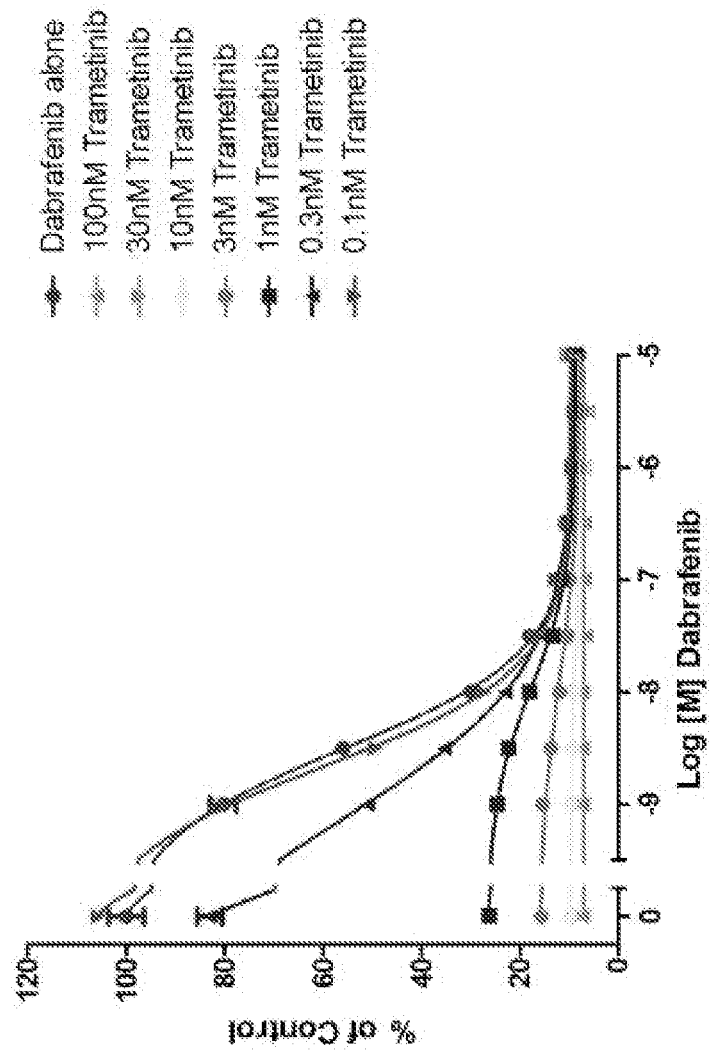
FIG. 40 Con't

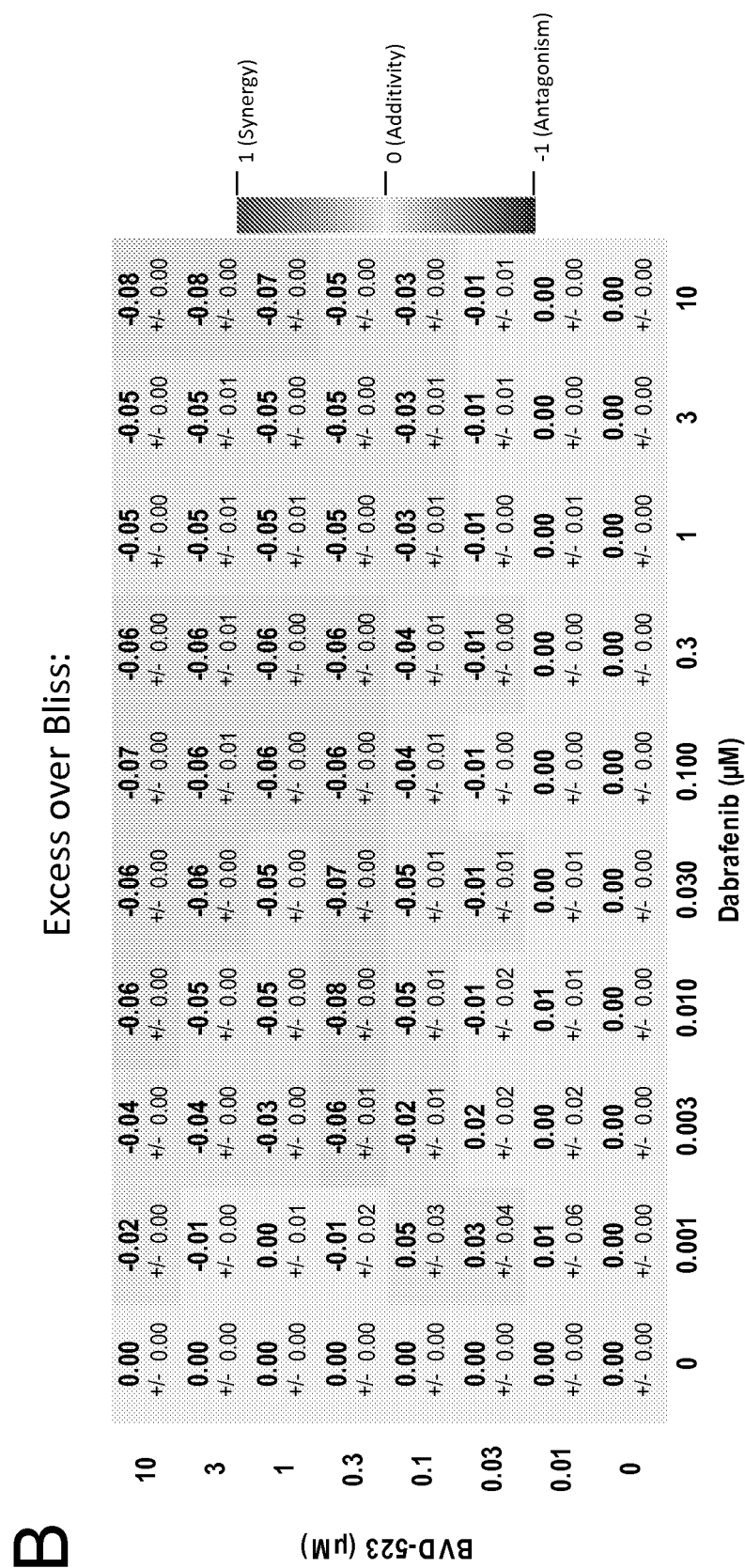
FIG. 41 Con't

FIG. 41 Con't
A375: Dabrafenib/BVD-523 Combination Assay – Alamar Blue
Single agent and Potentiation plots:
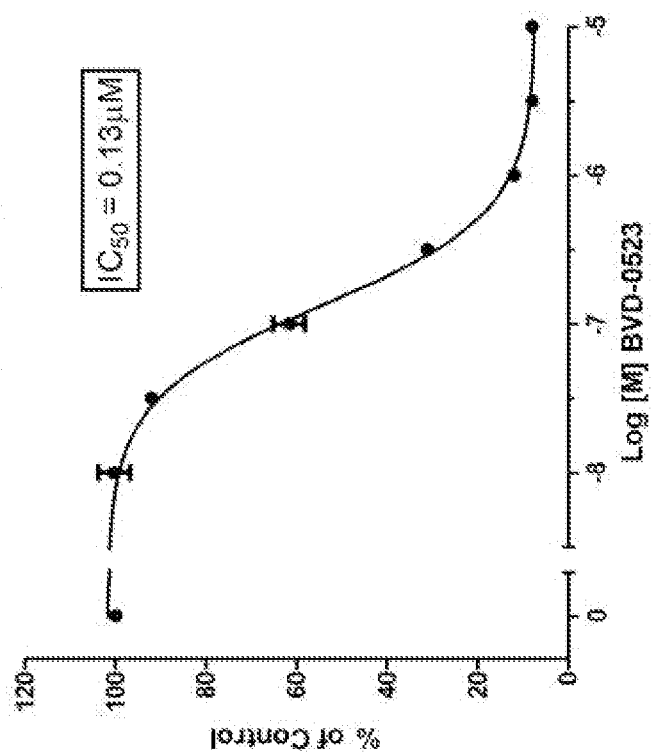
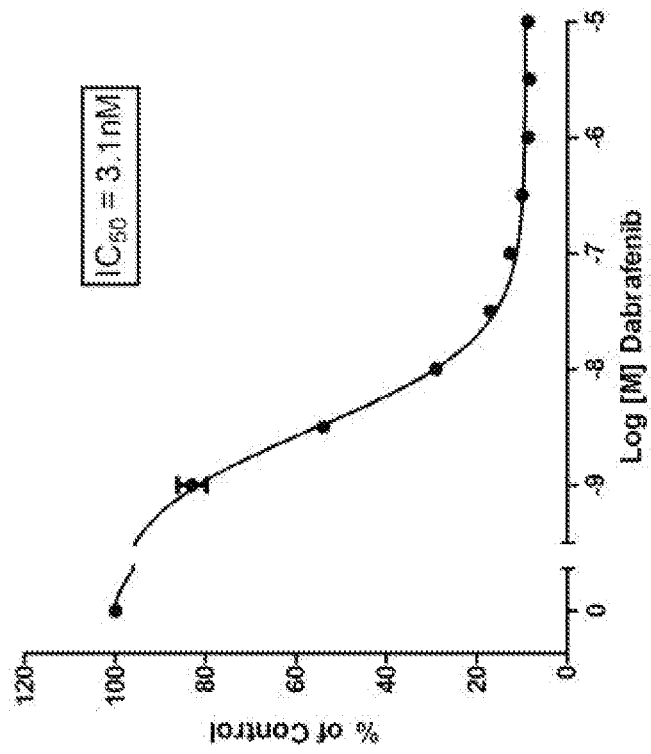

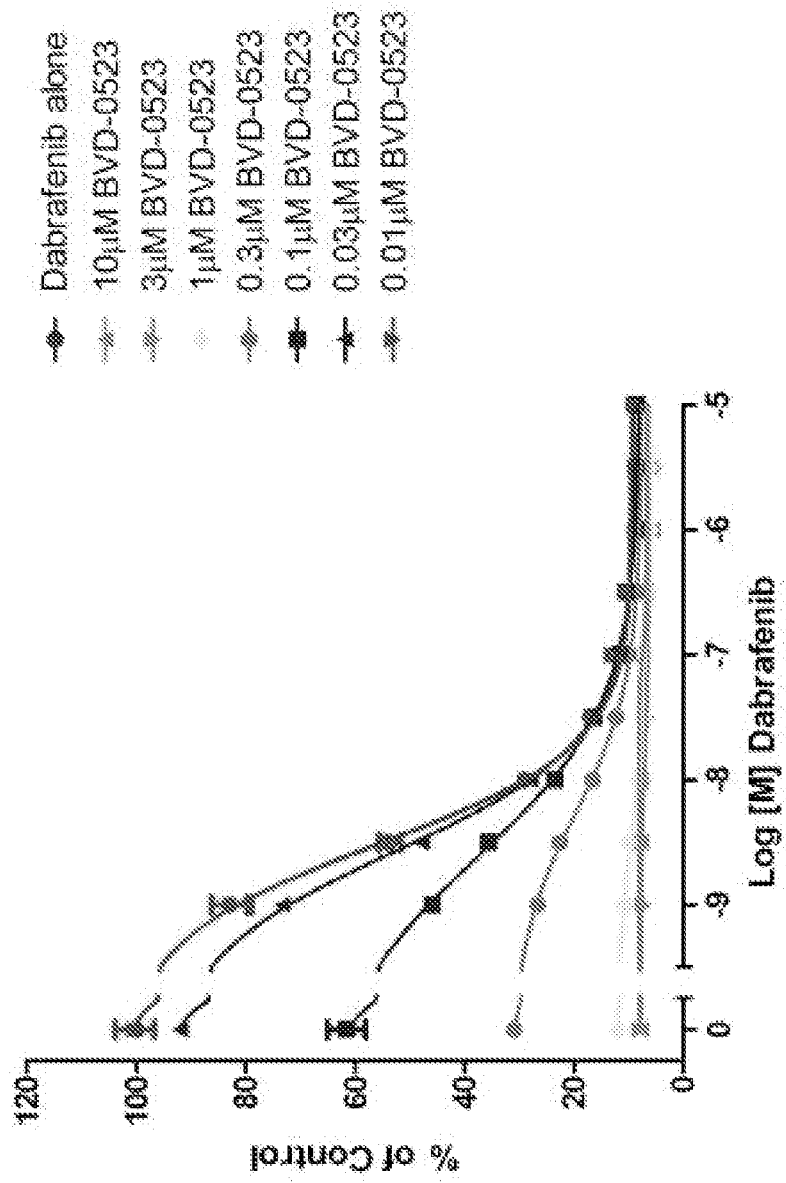
FIG. 41 Con't
A375: Dabrafenib/BVD-523 Combination Assay – Alamar Blue

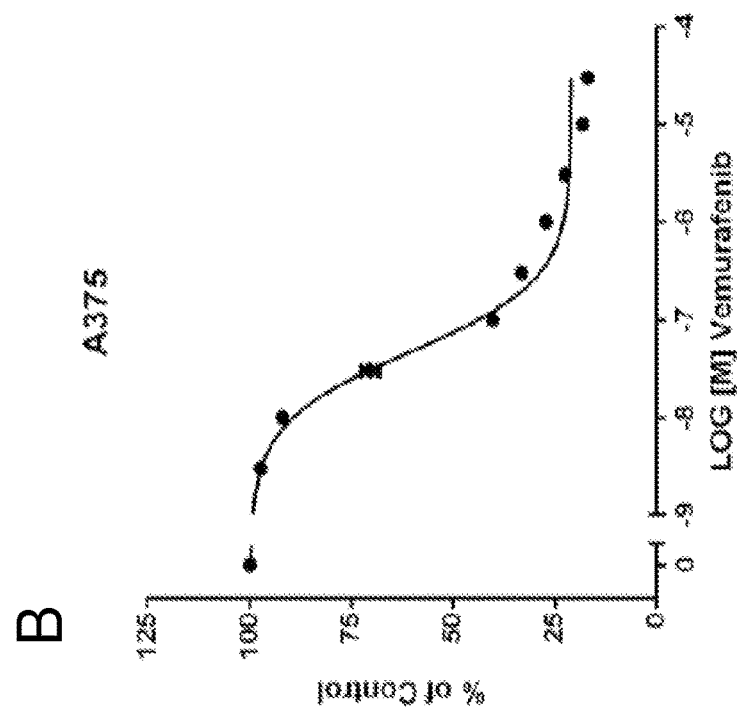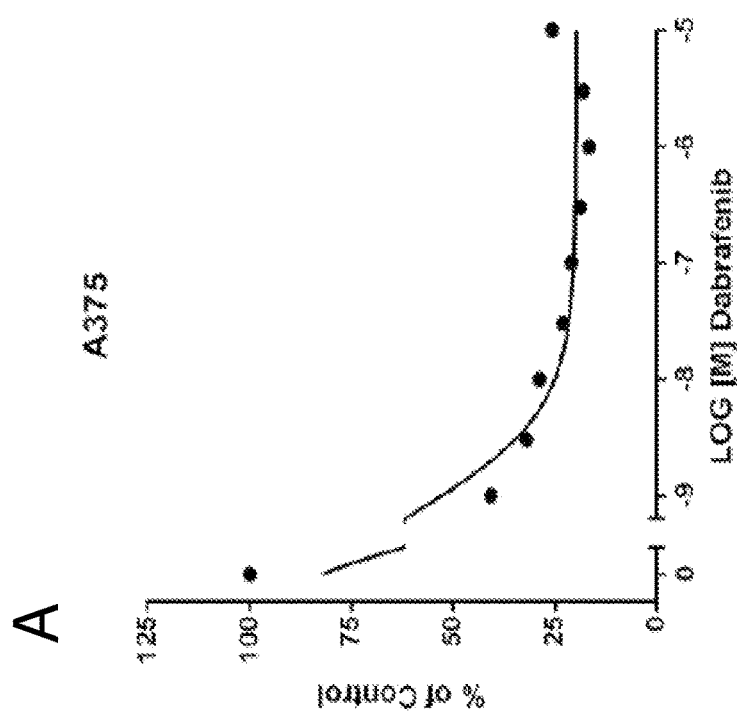
FIG. 42

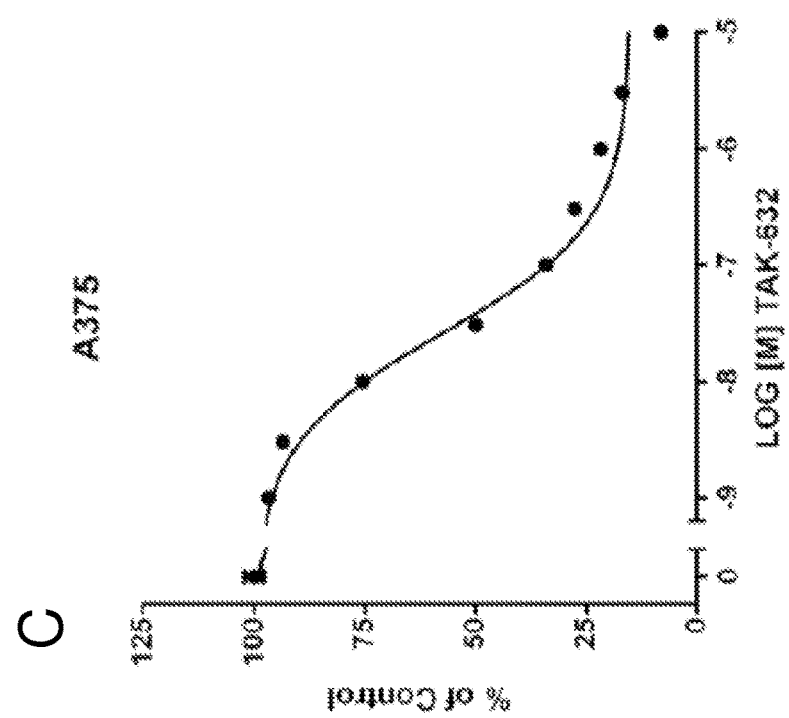
FIG. 42, Con't

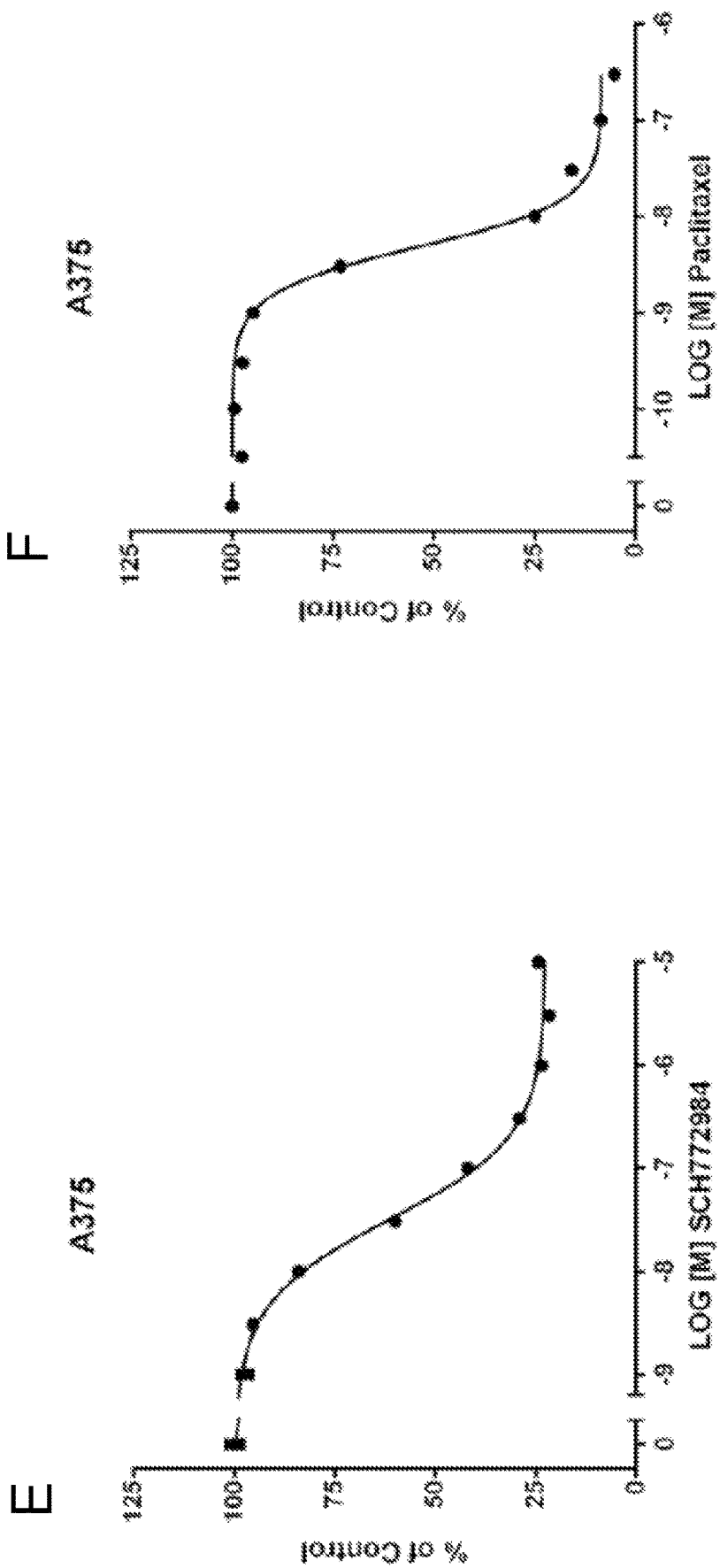
FIG. 42, Con't

FIG. 42, Con't
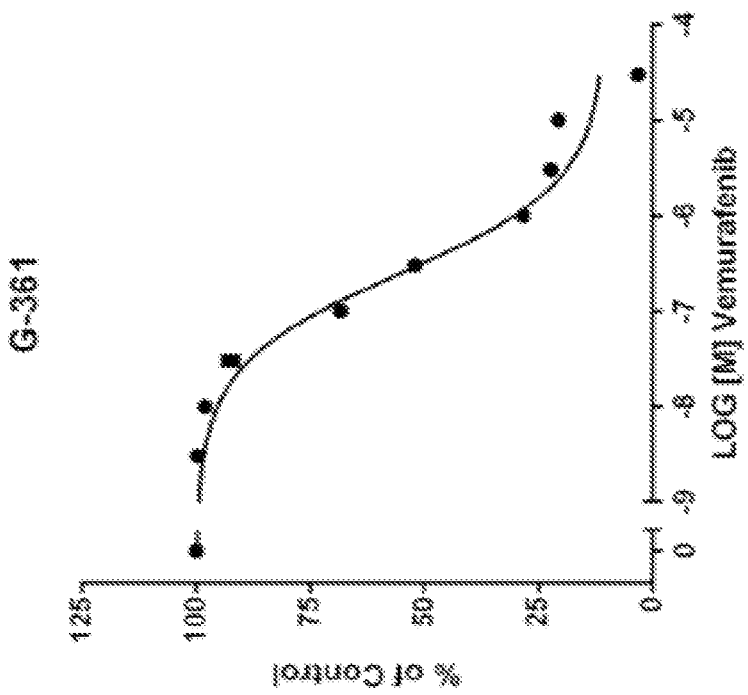
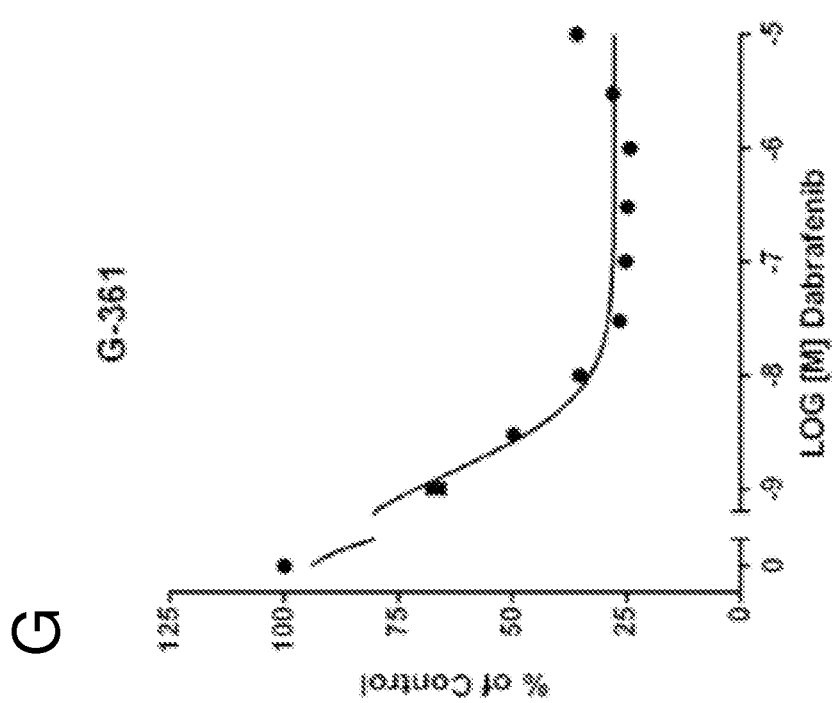

FIG. 42, Con't
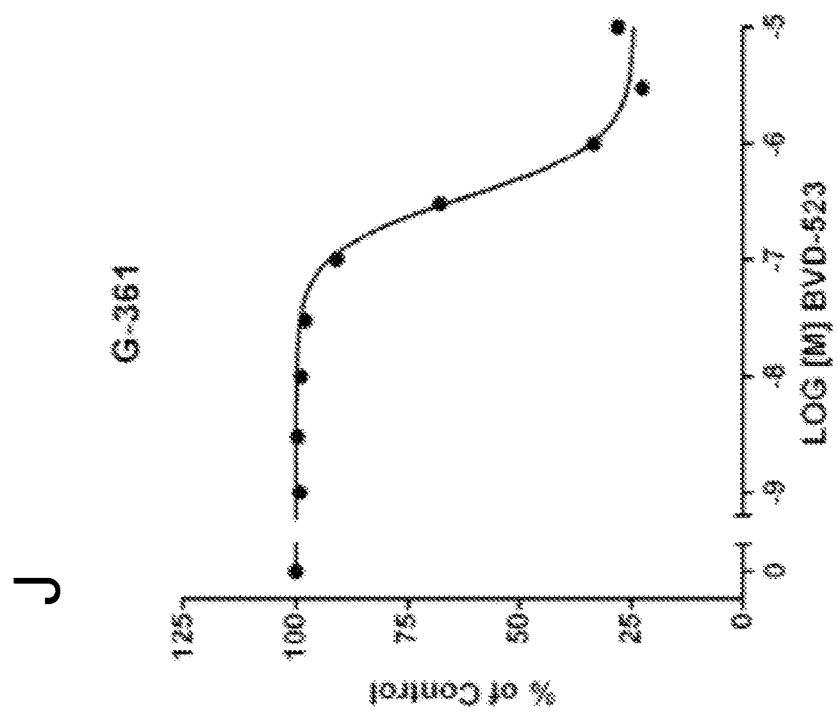
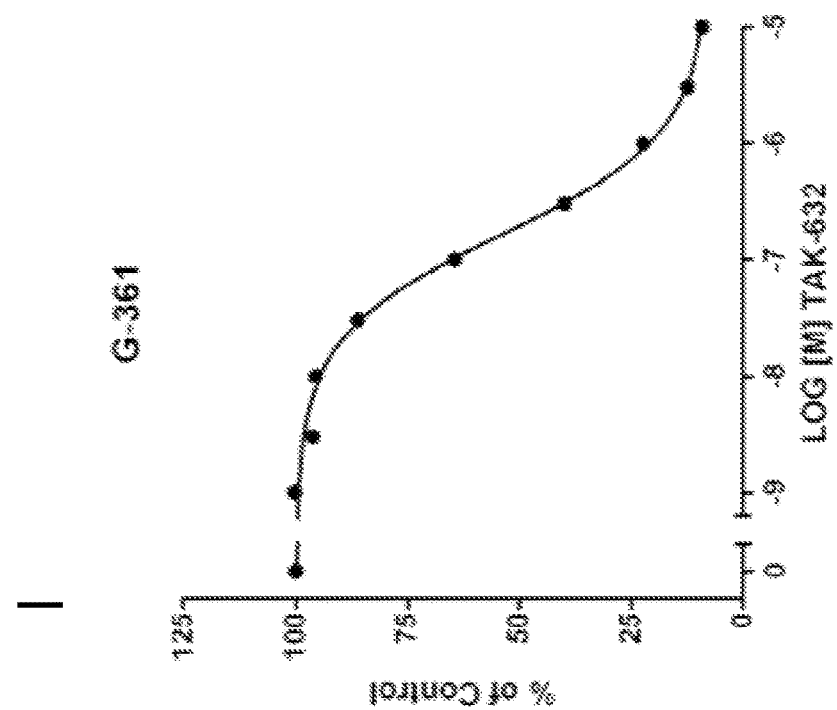

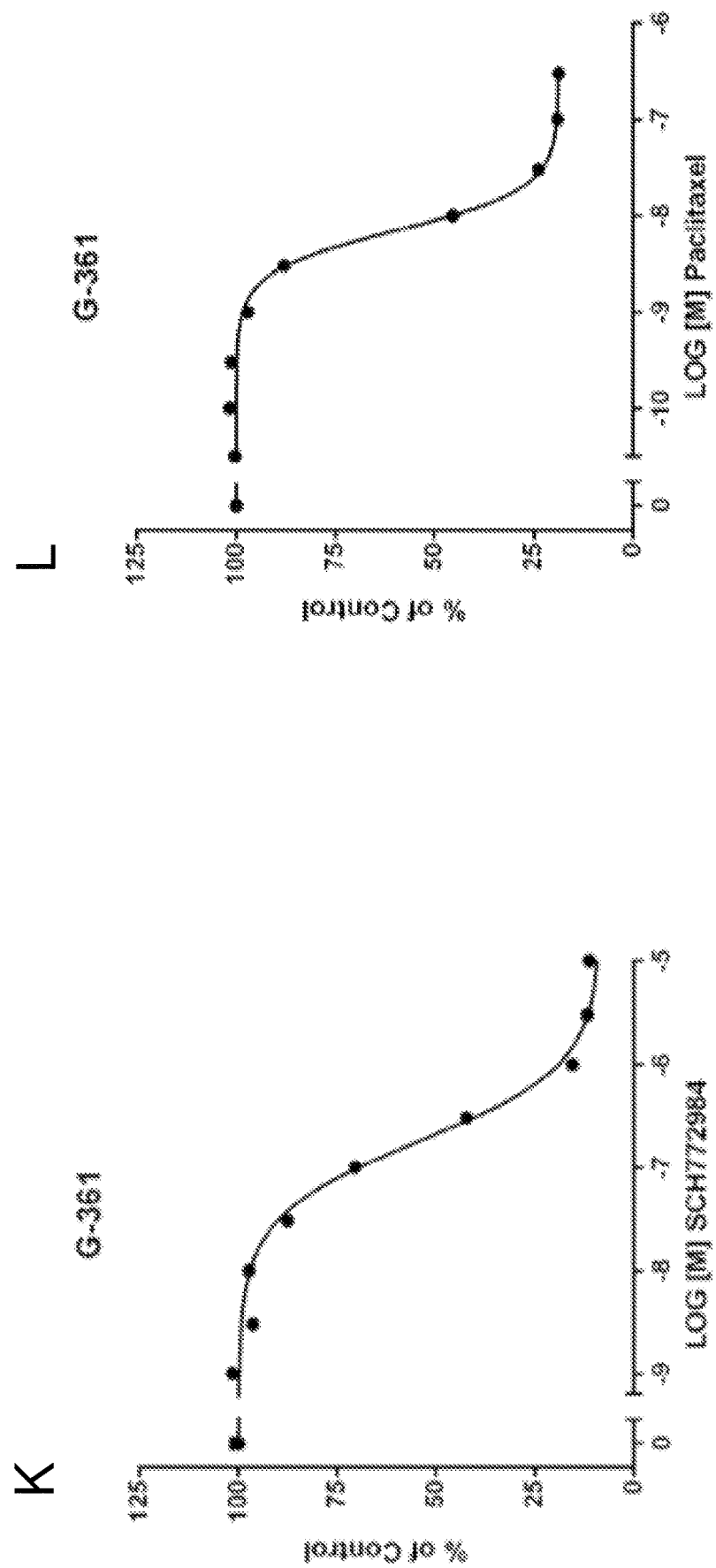
FIG. 42, Con't

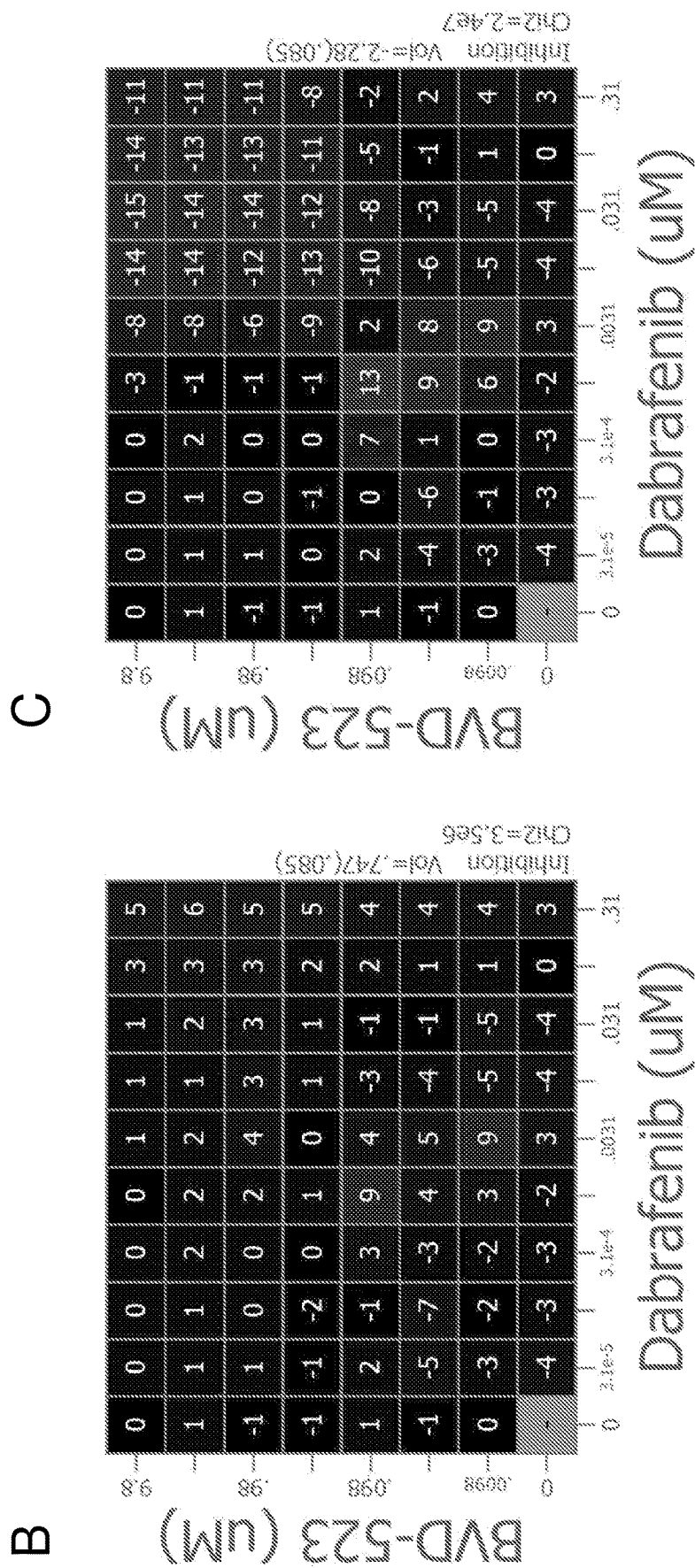
FIG. 43, Con't

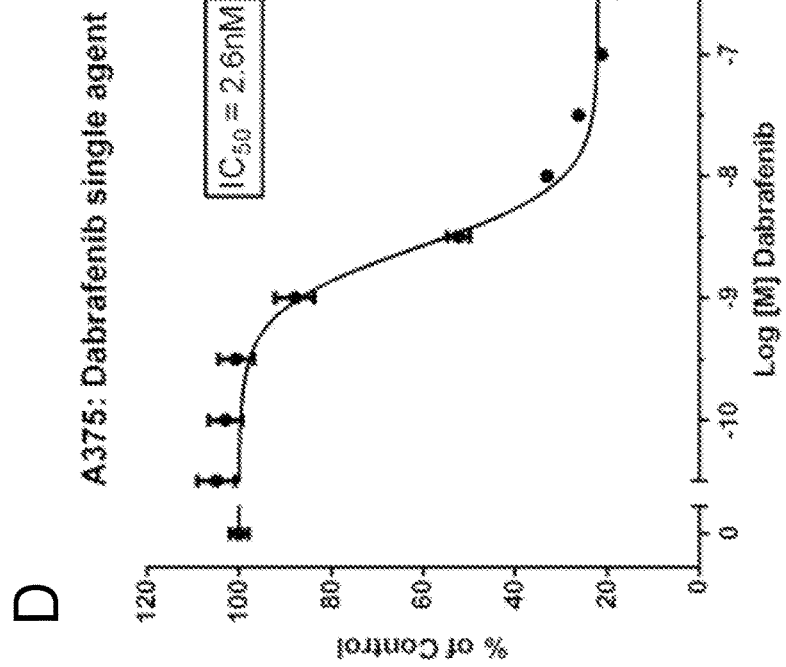
FIG. 43, Con't

FIG. 44, Con't
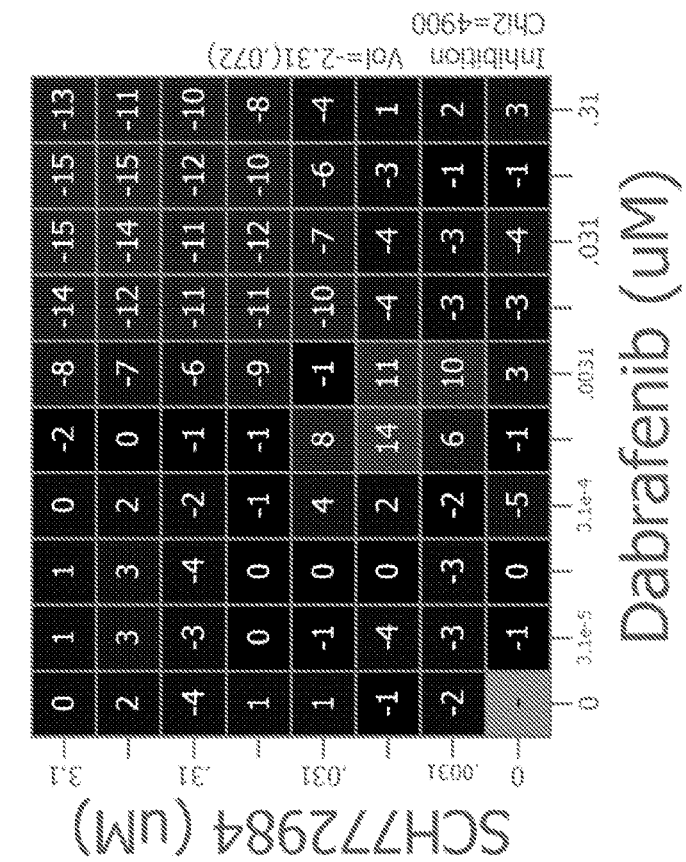
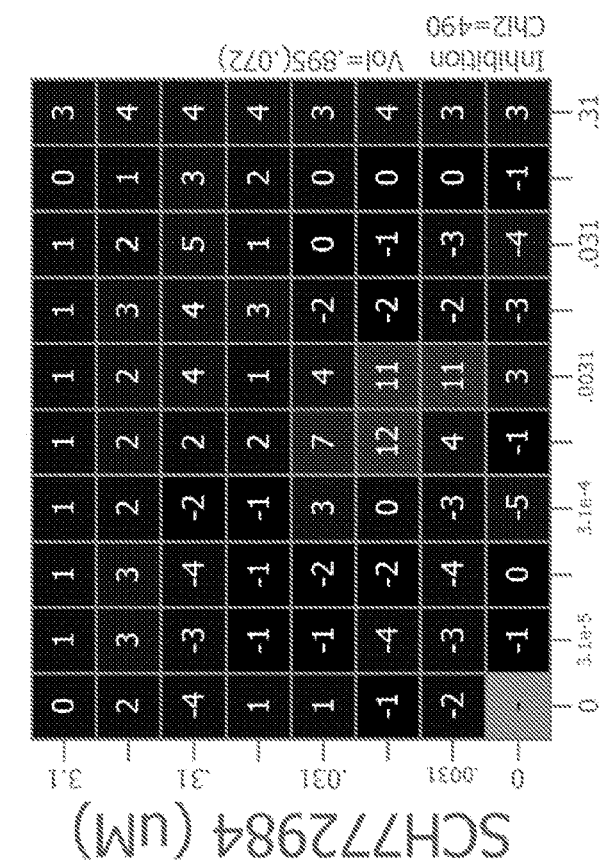

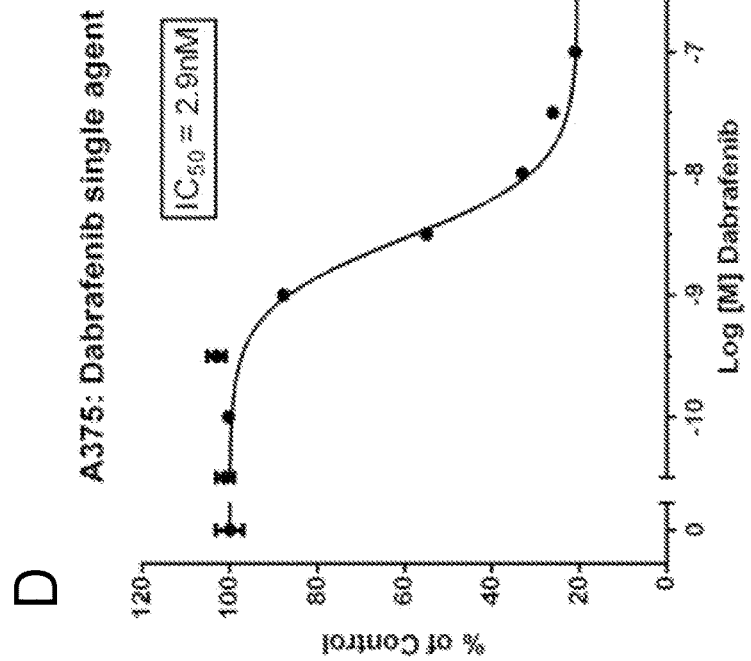
FIG. 44, Con't

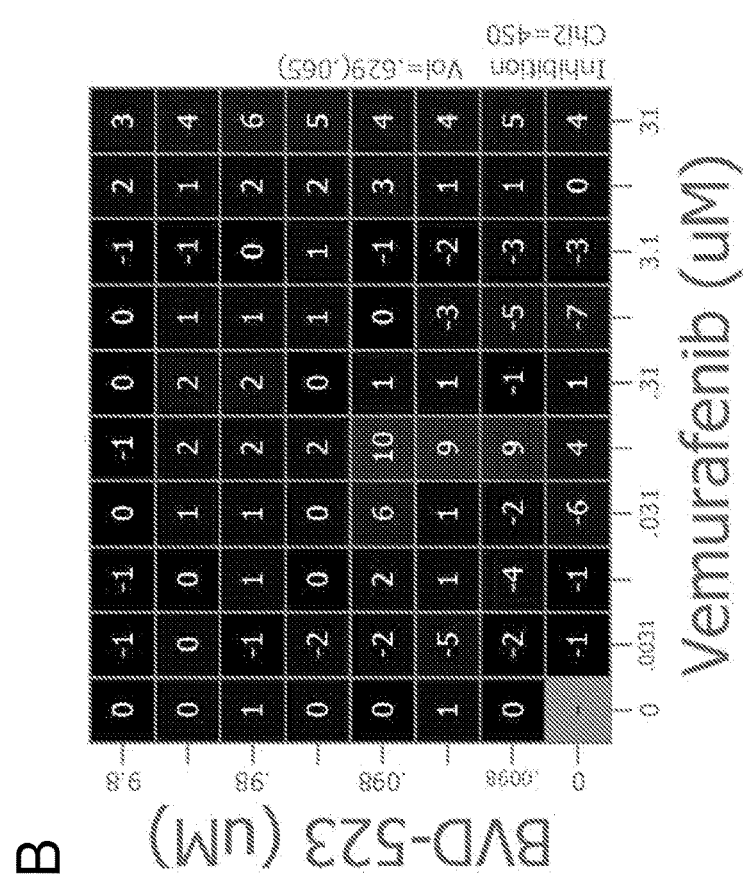
FIG. 45, Con't

FIG. 45, Con't
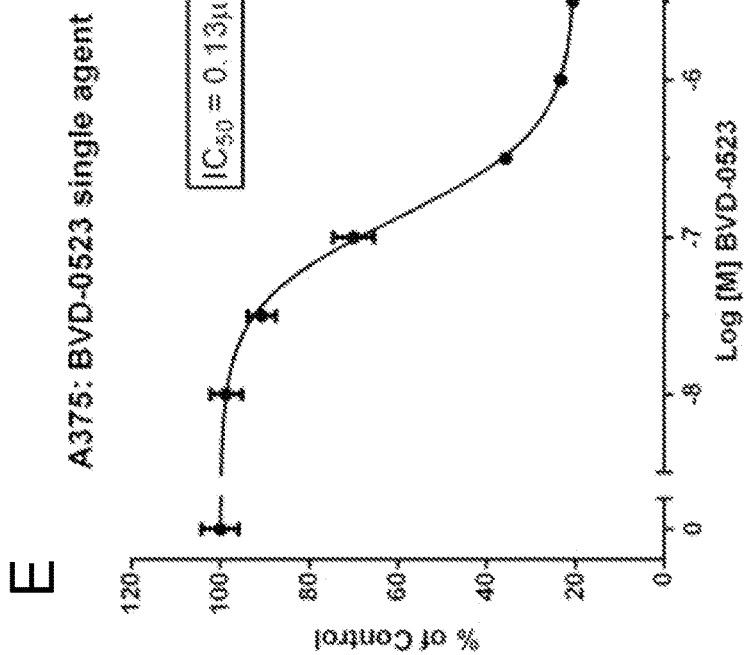
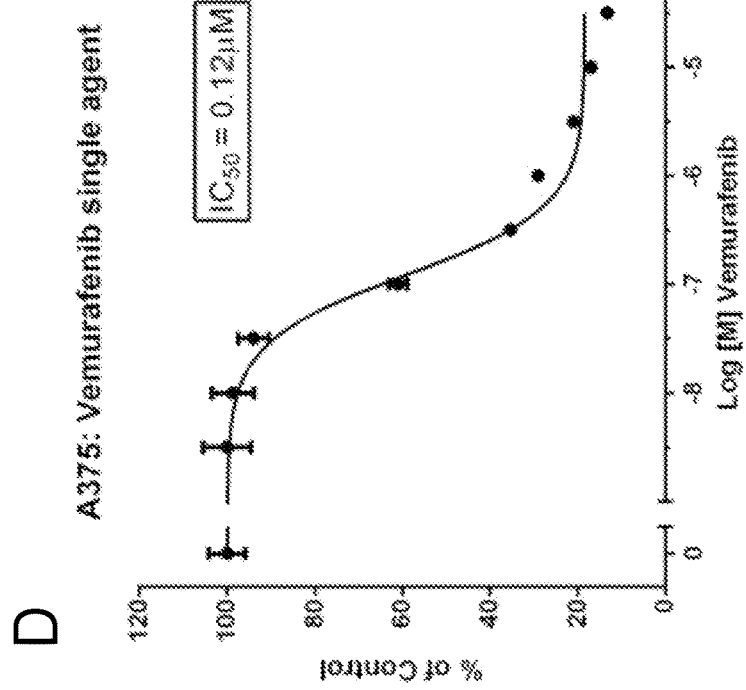

FIG. 46, Con't
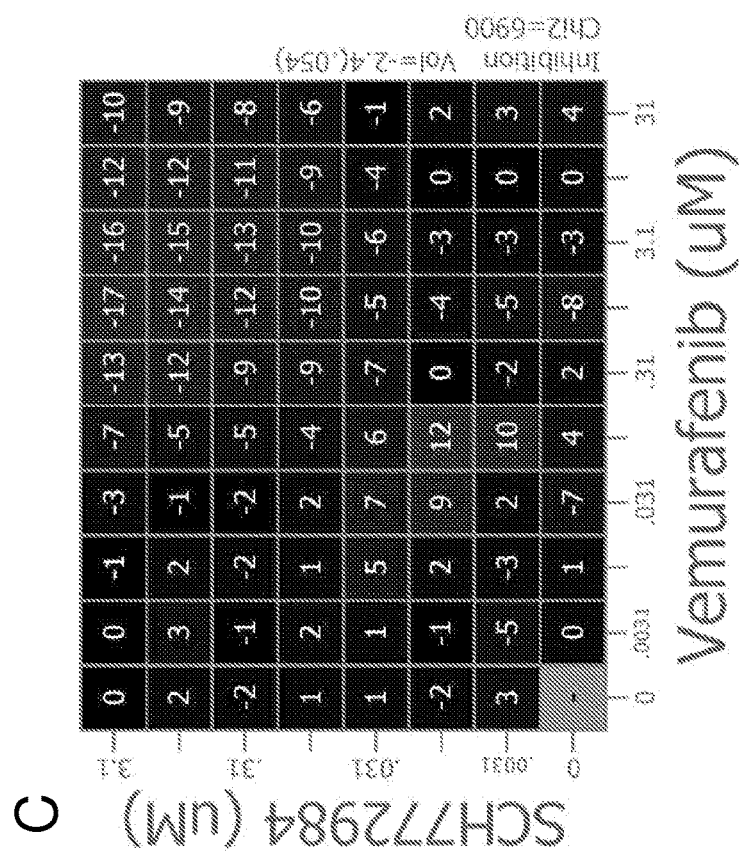
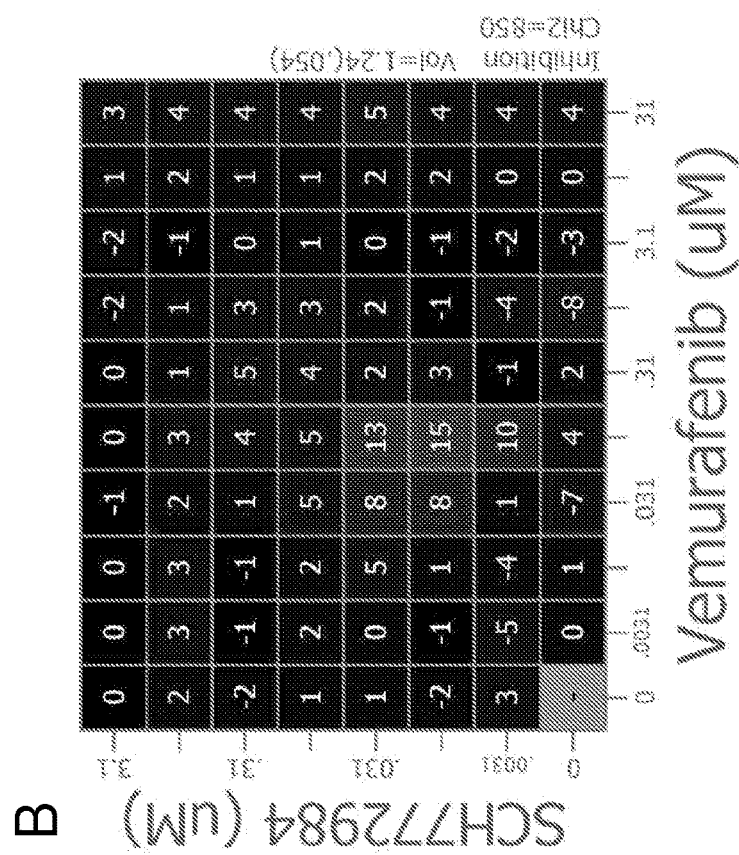

FIG. 46, Con't
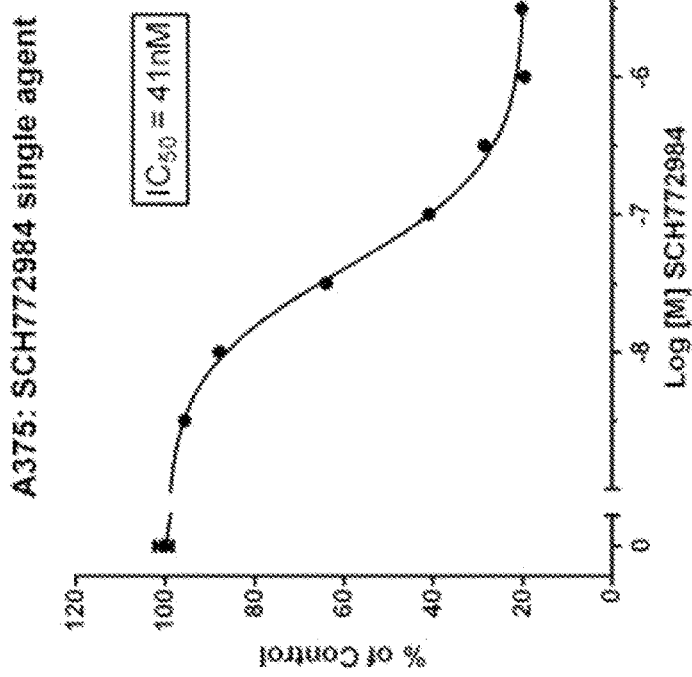
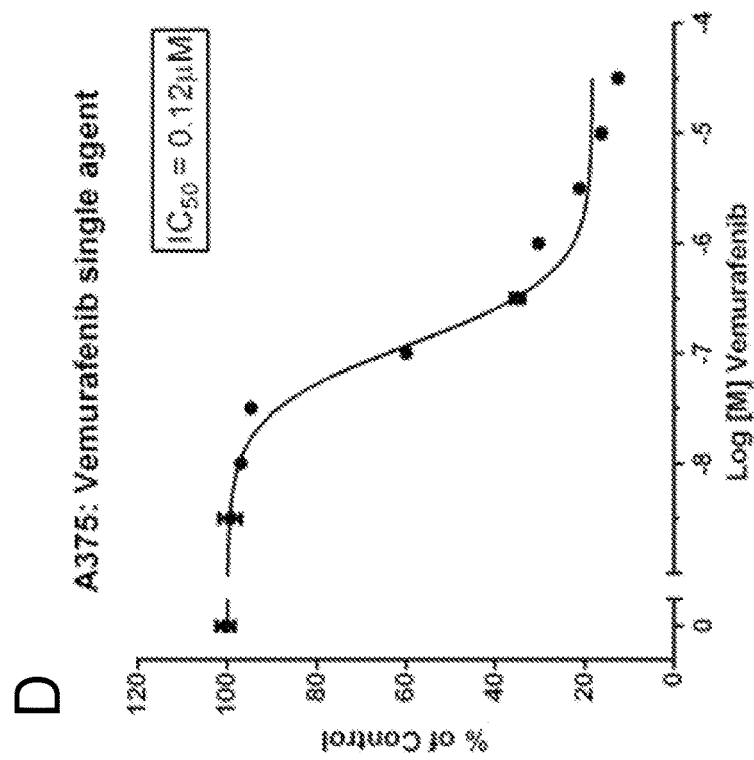

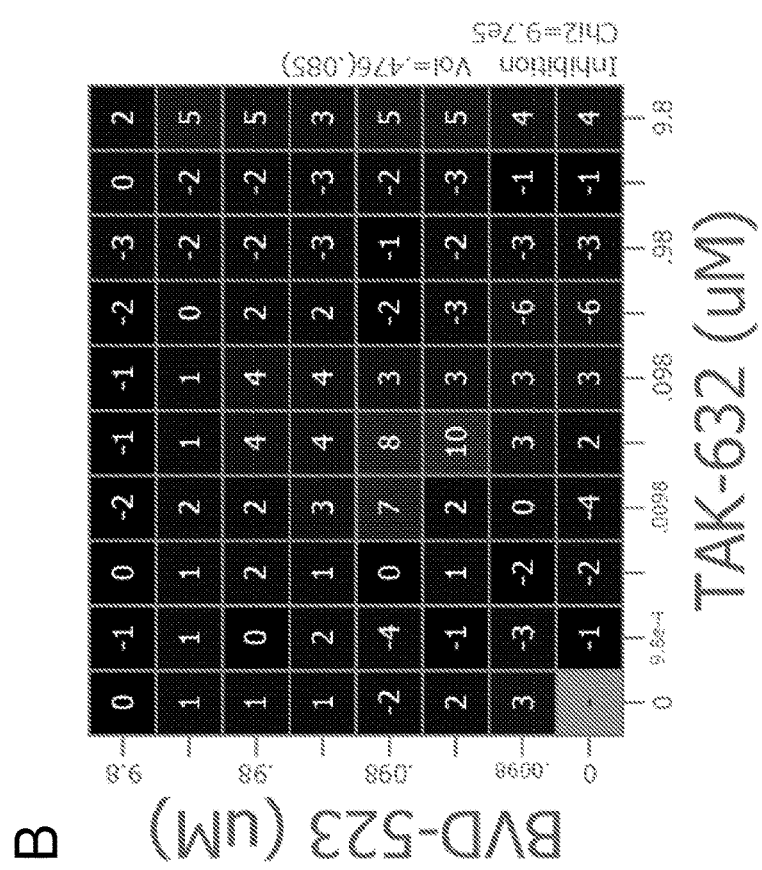
FIG. 47, Con't

FIG. 47, Con't
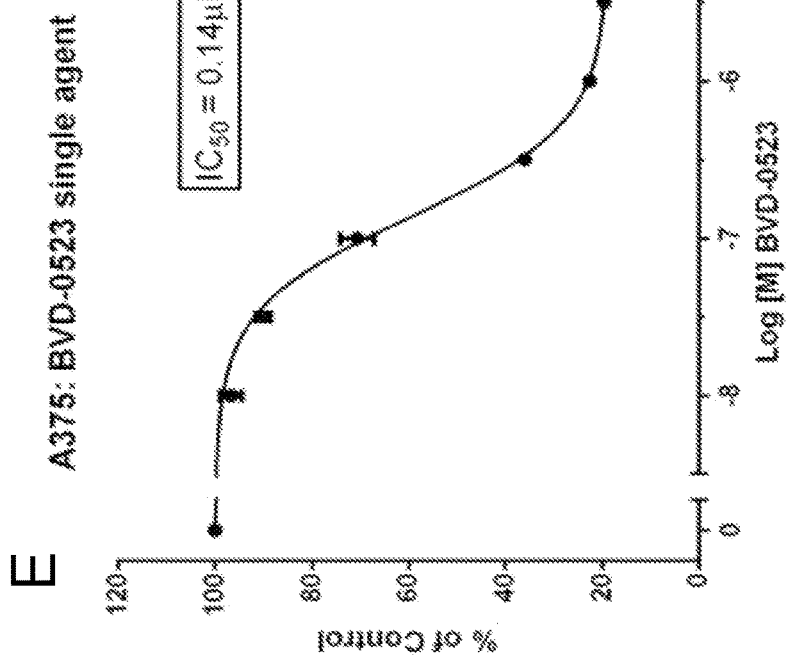
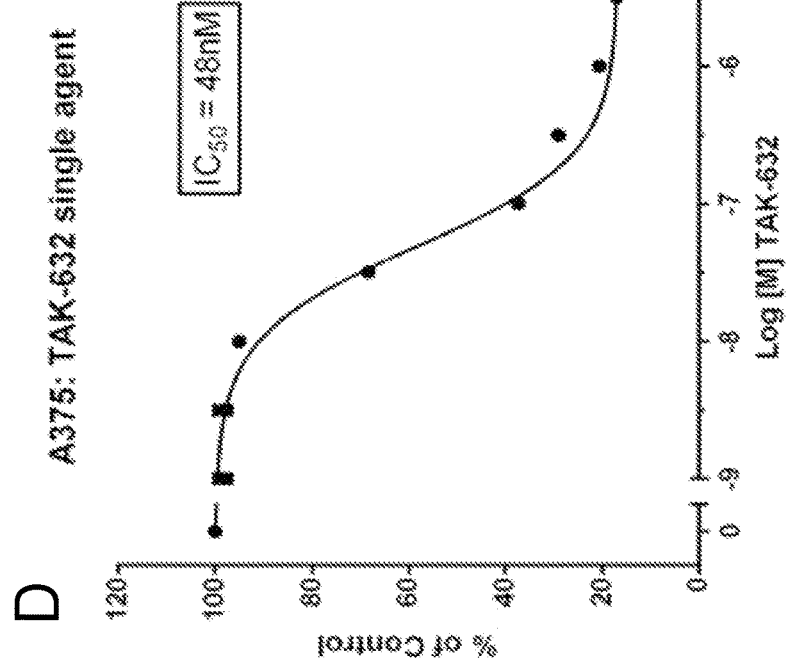

FIG. 48, Con't
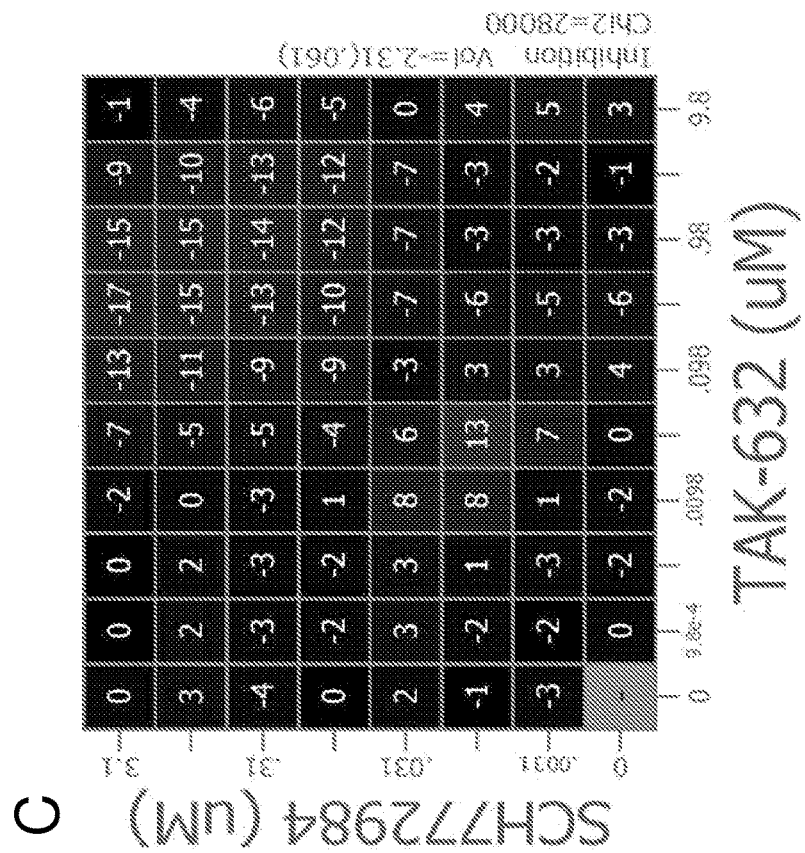
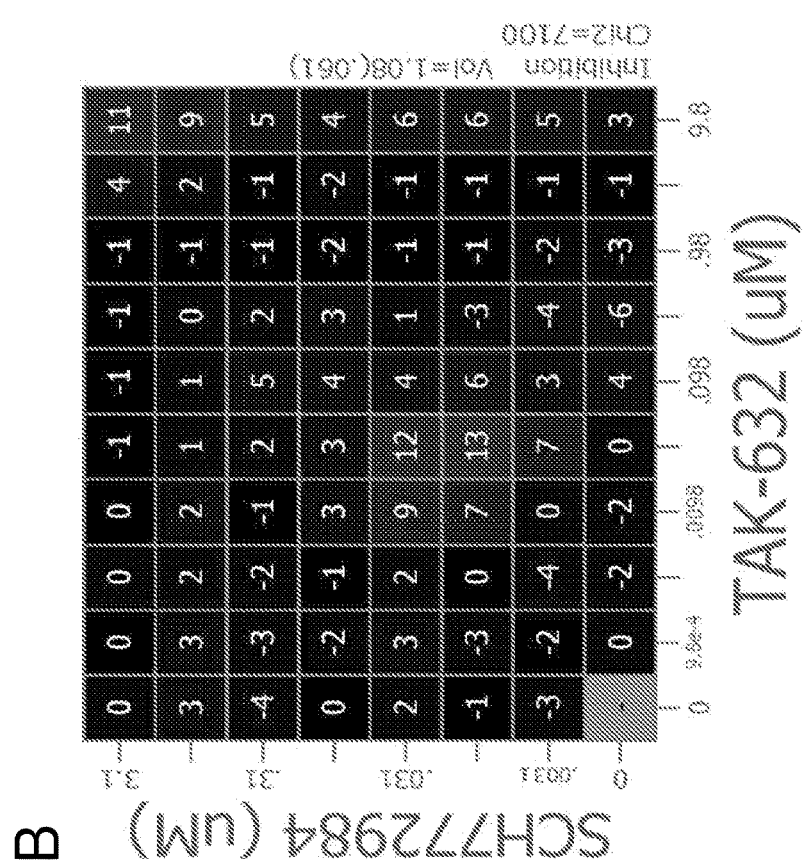

FIG. 48, Con't
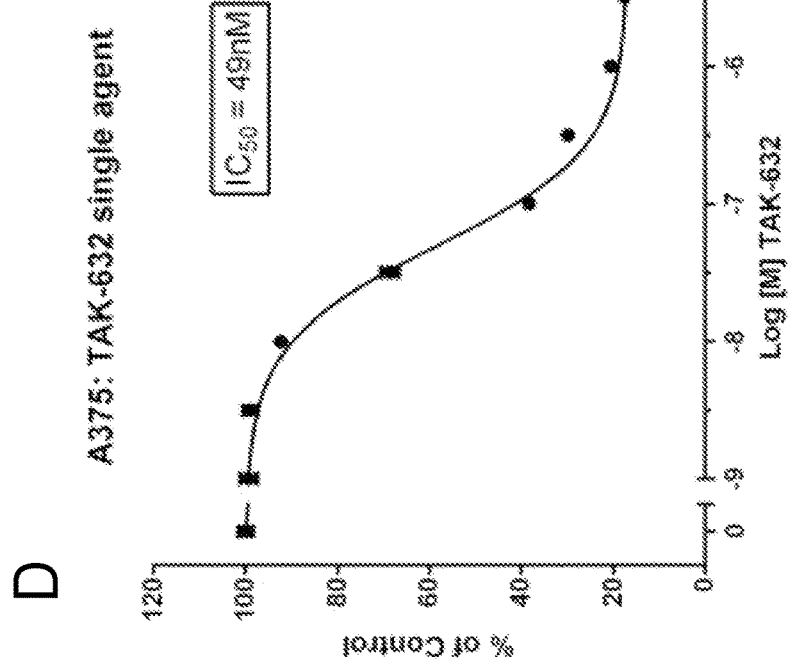

FIG. 49, Con't
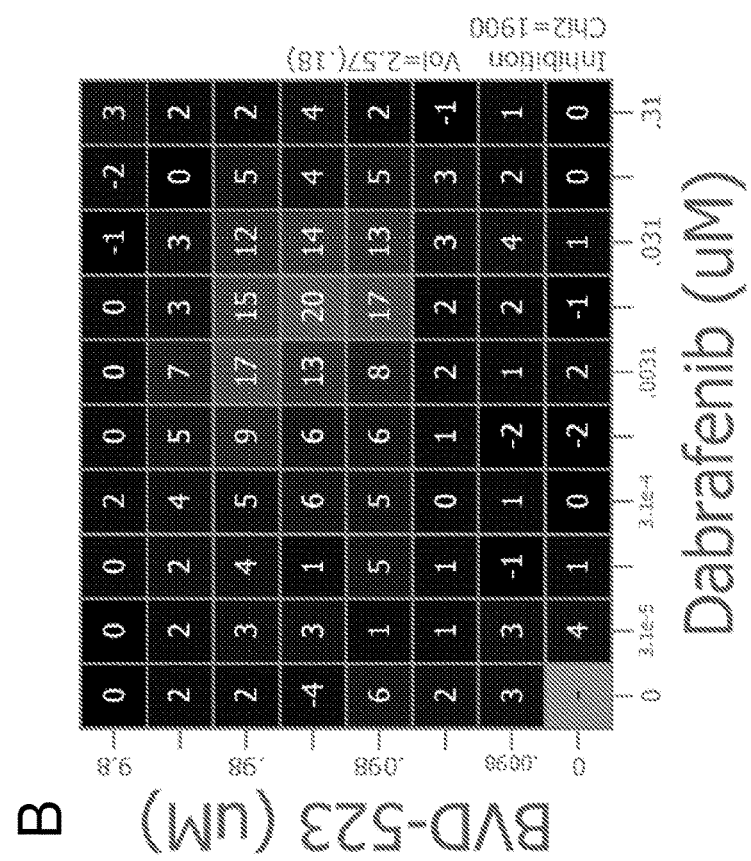

FIG. 49, Con't
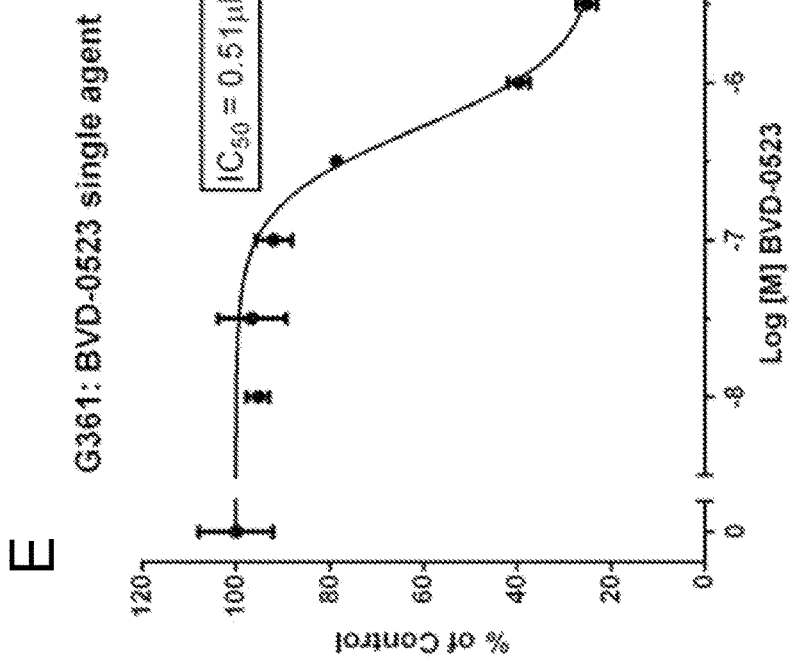
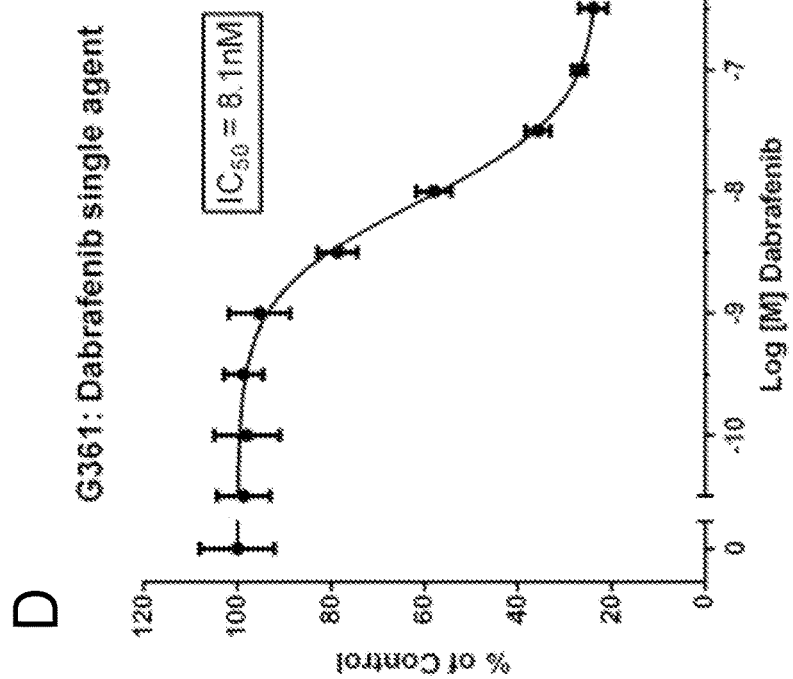

FIG. 50, Con't
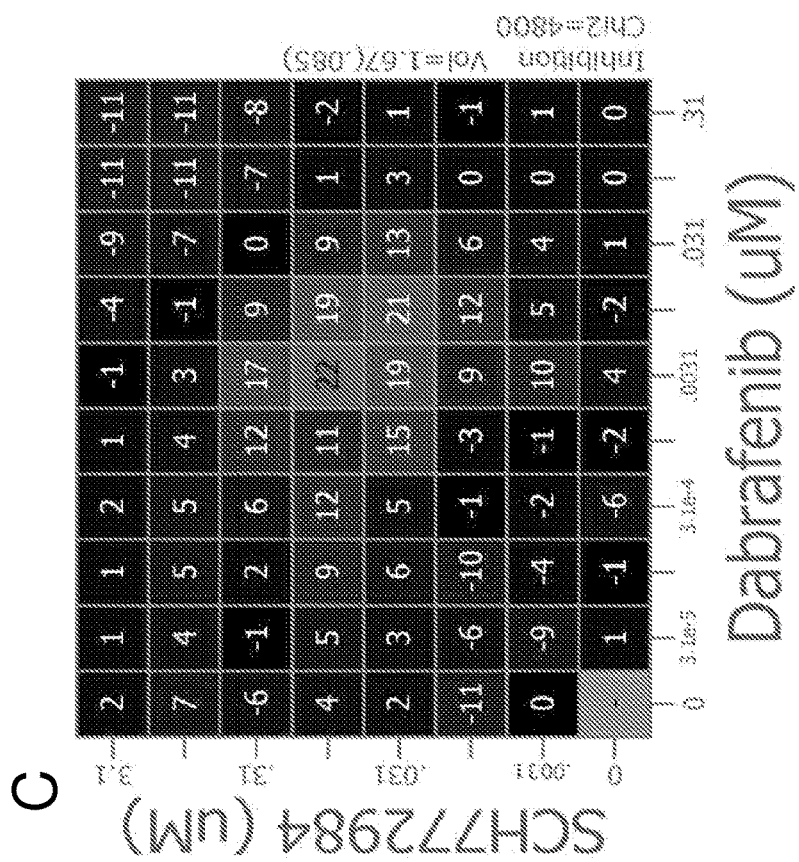
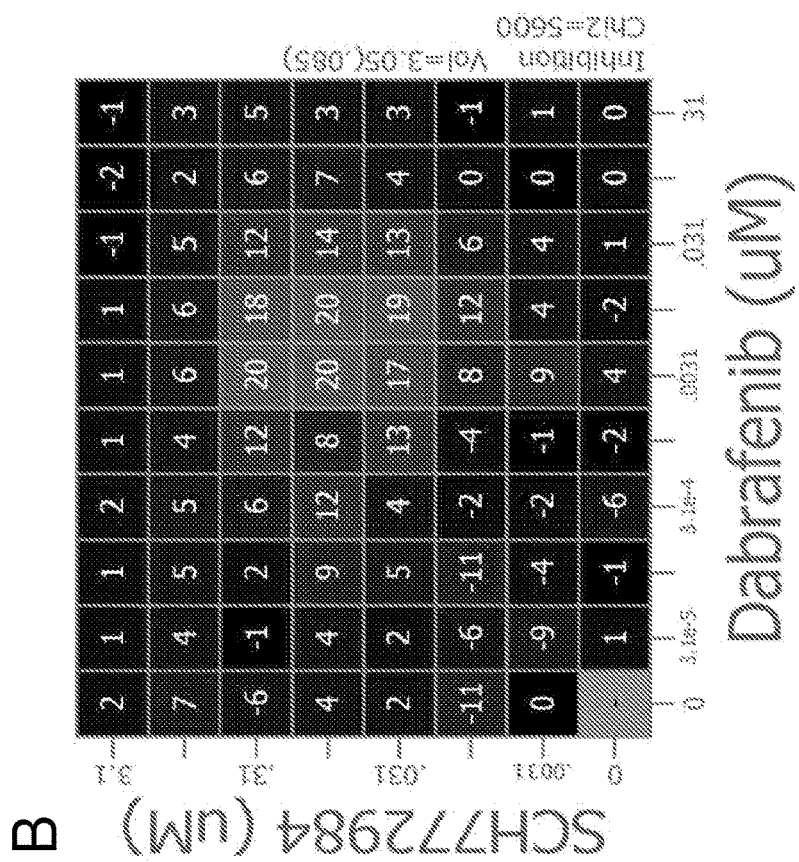

FIG. 50, Con't
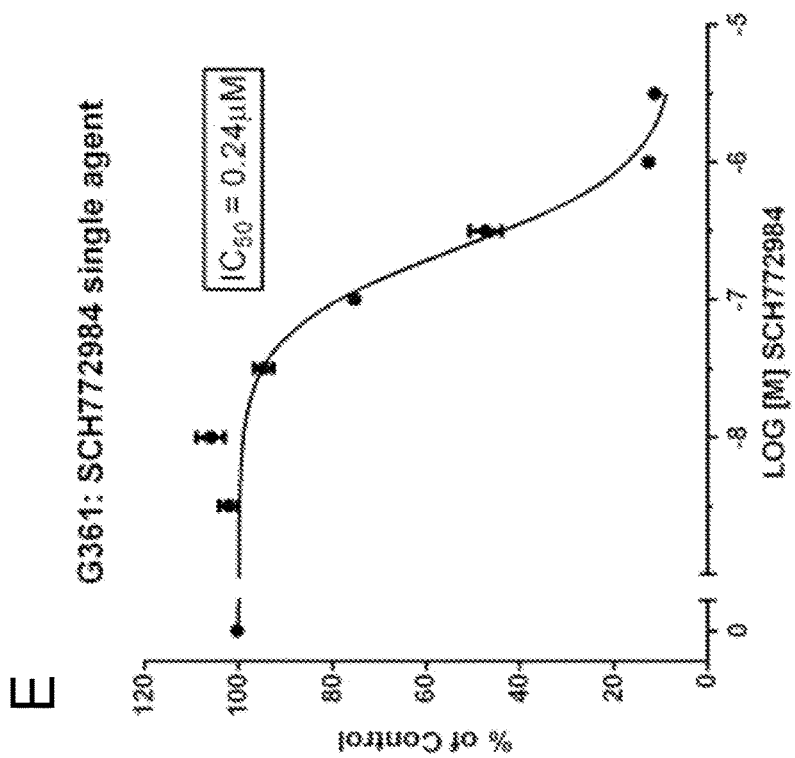
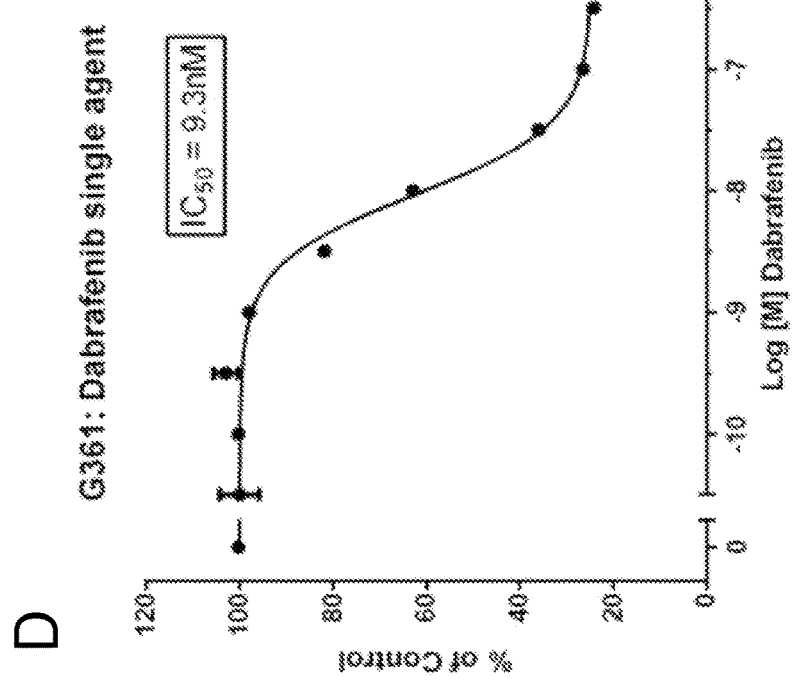

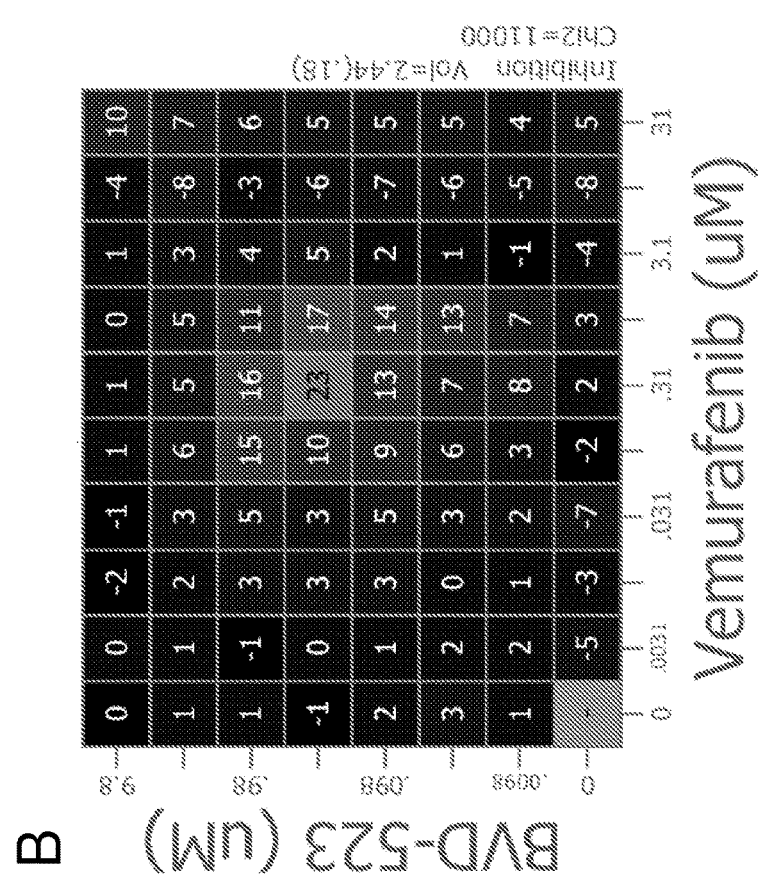
FIG. 51, Con't

FIG. 51, Con't
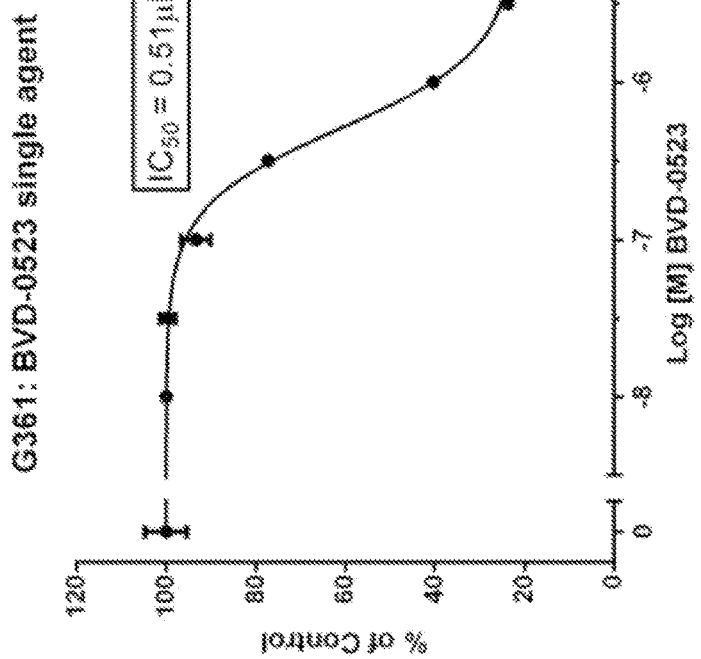
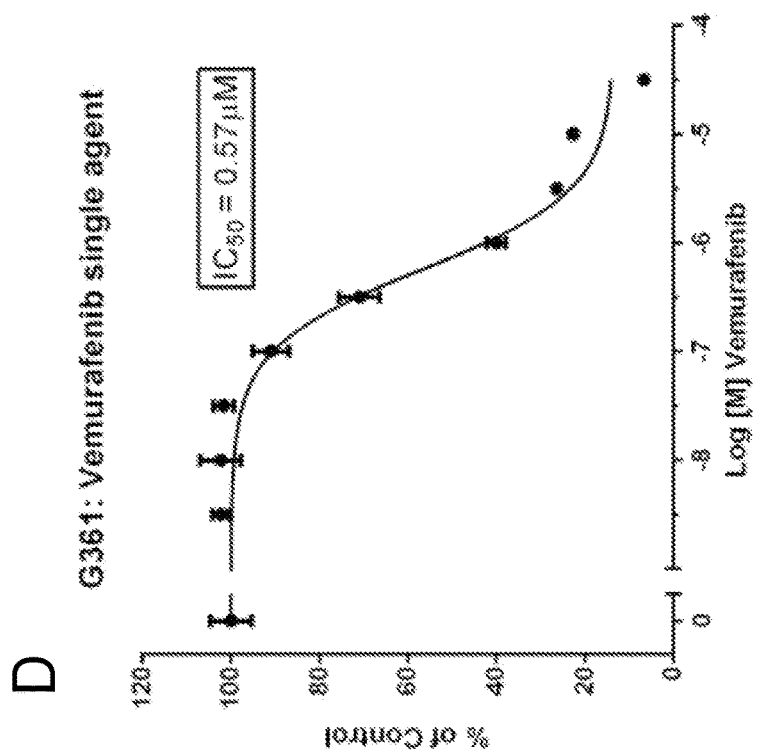

FIG. 52, Con't
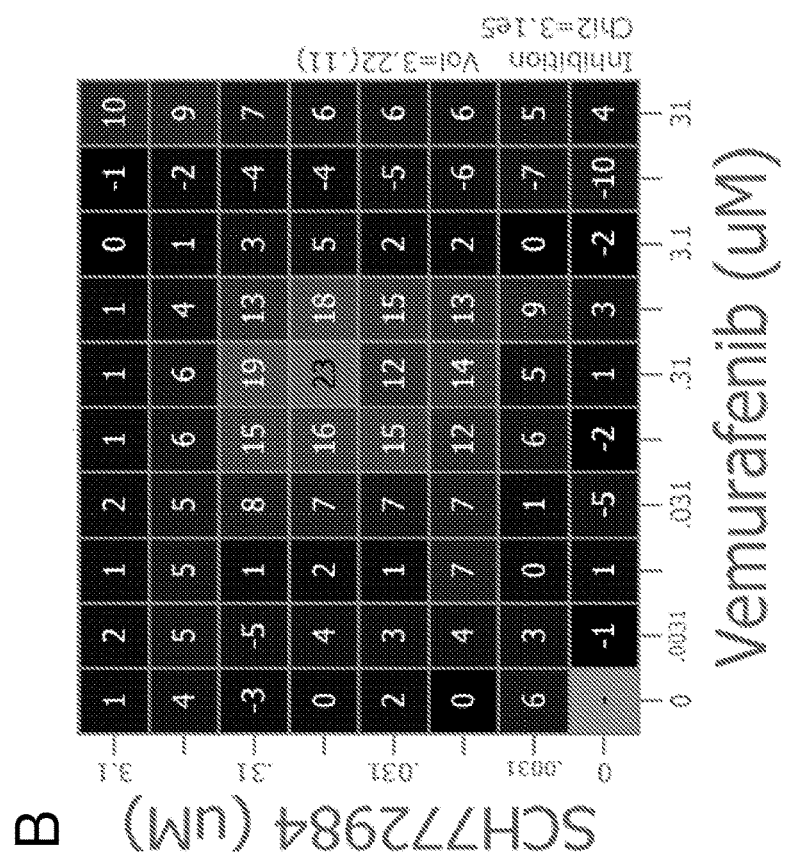

FIG. 52, Con't
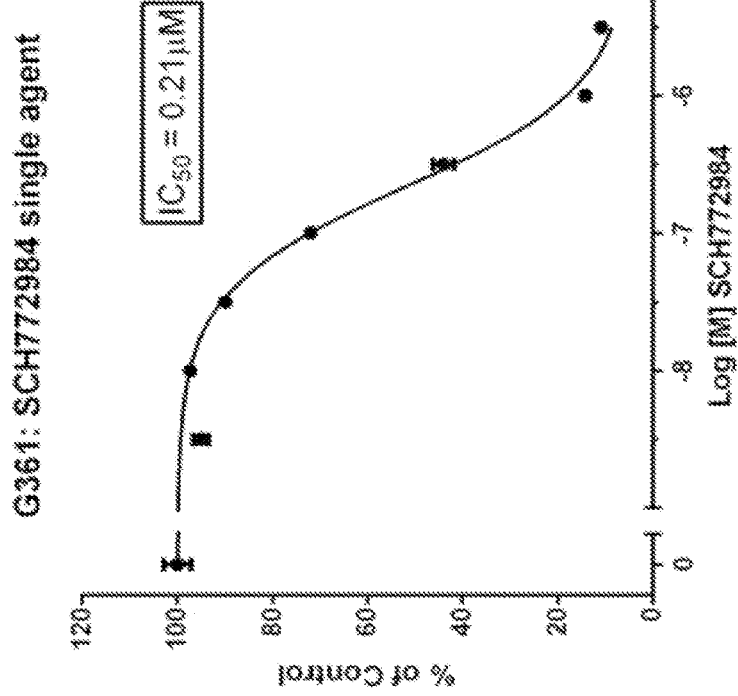
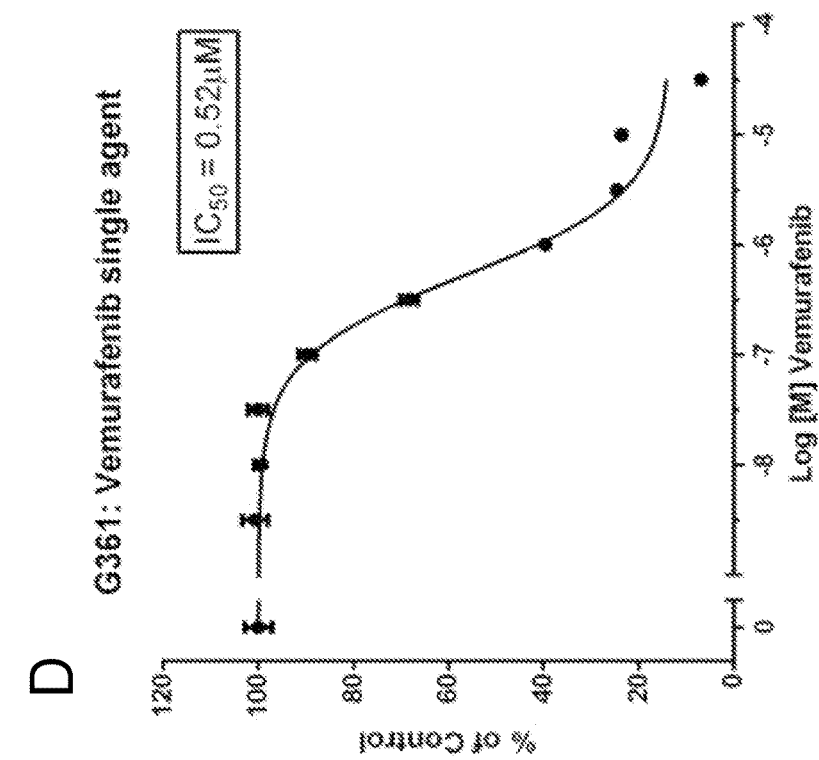

FIG. 53, Con't
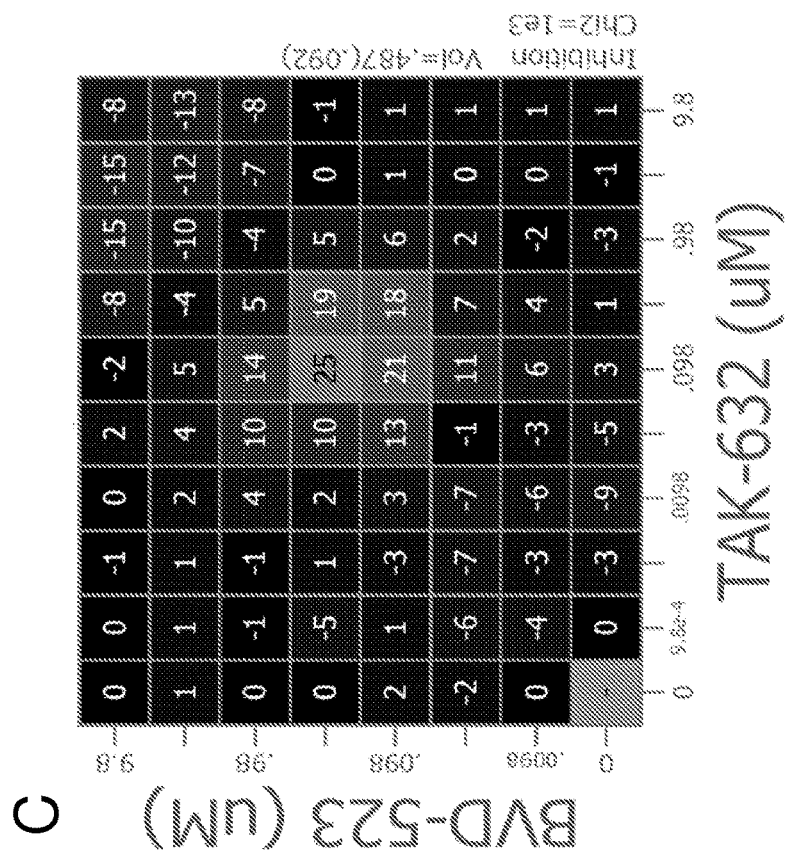
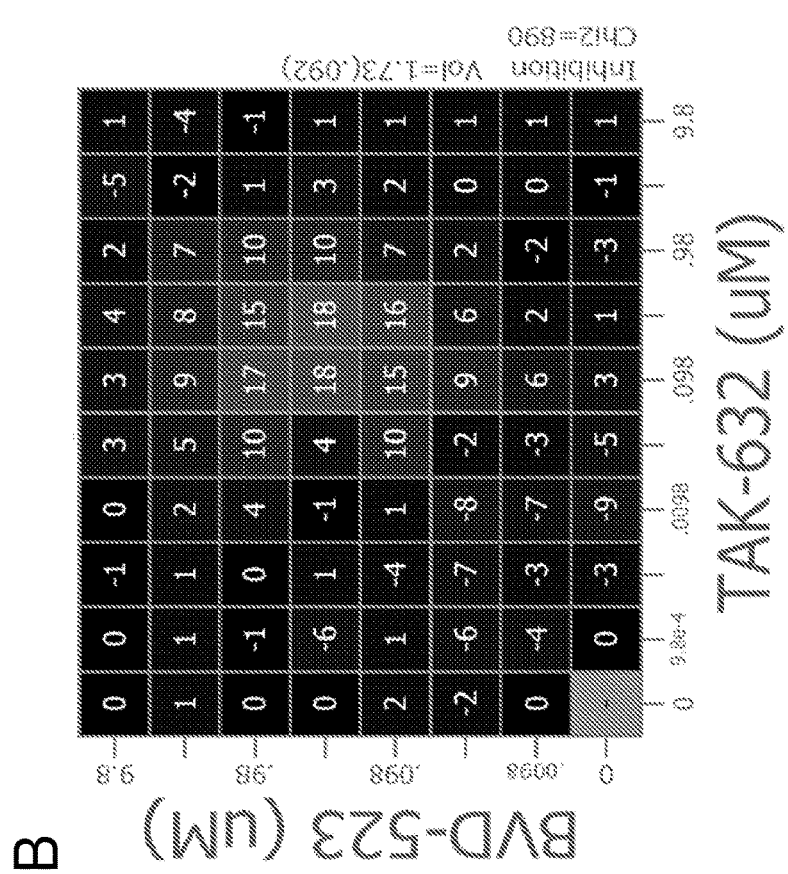

FIG. 53, Con't
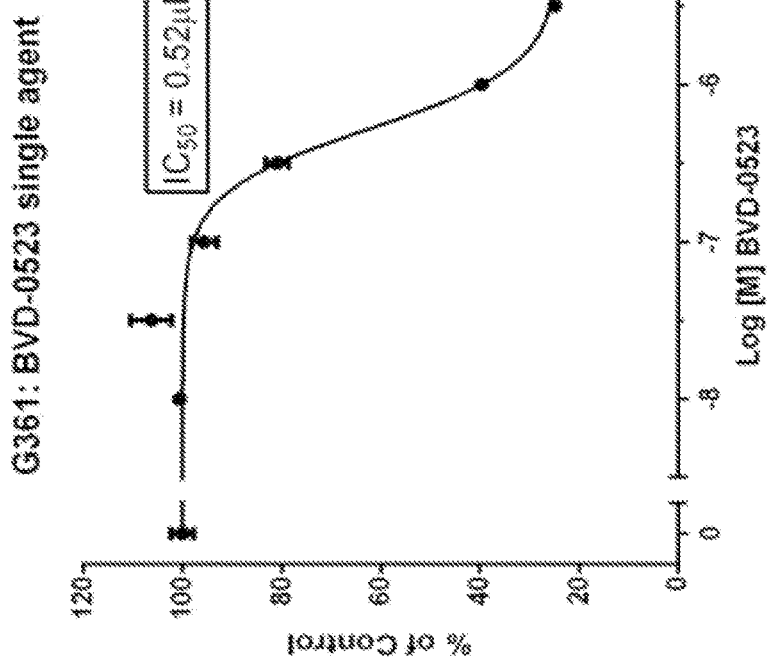
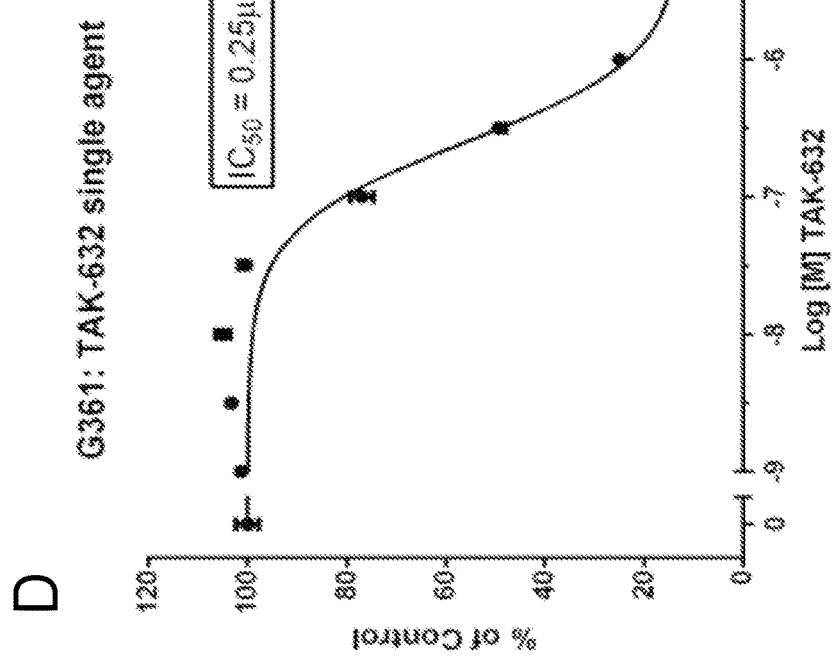

FIG. 54, Con't
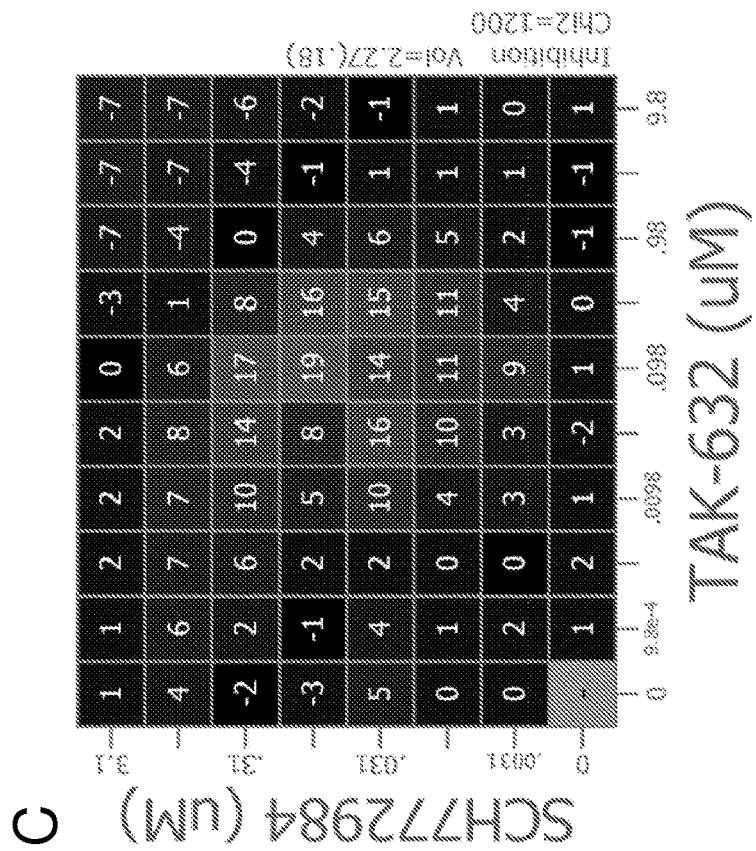
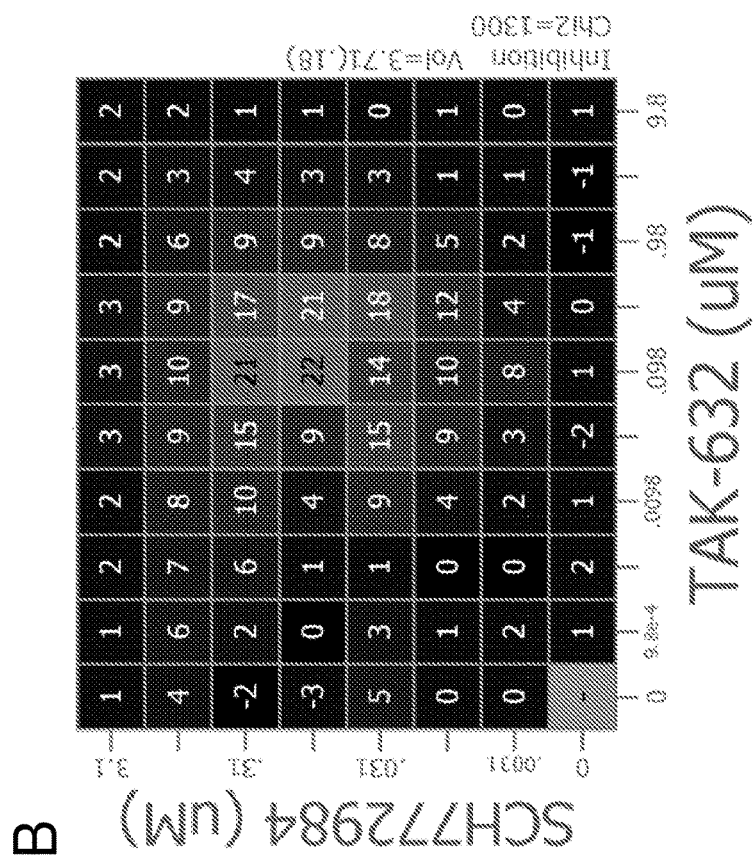

FIG. 54, Con't
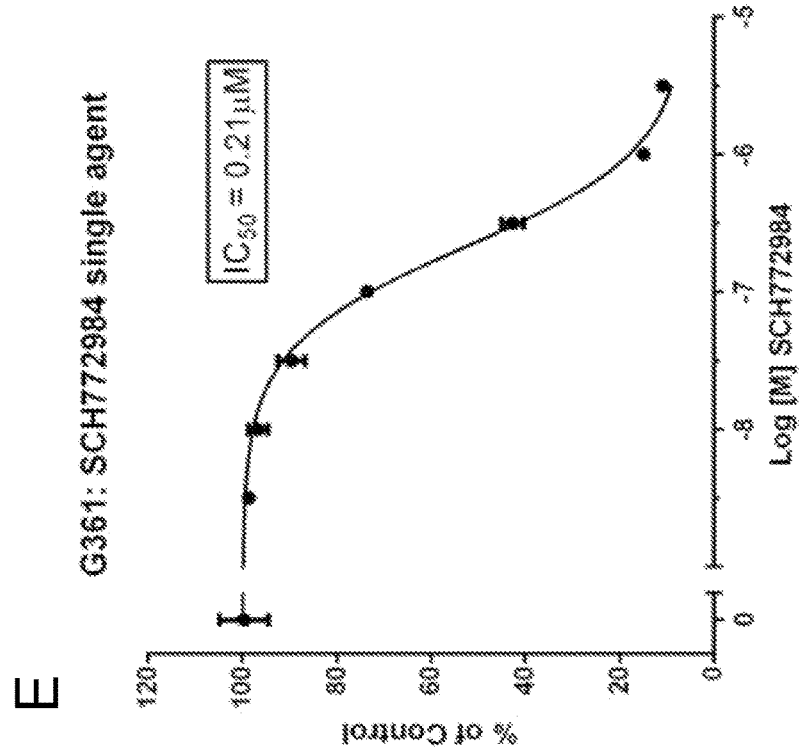
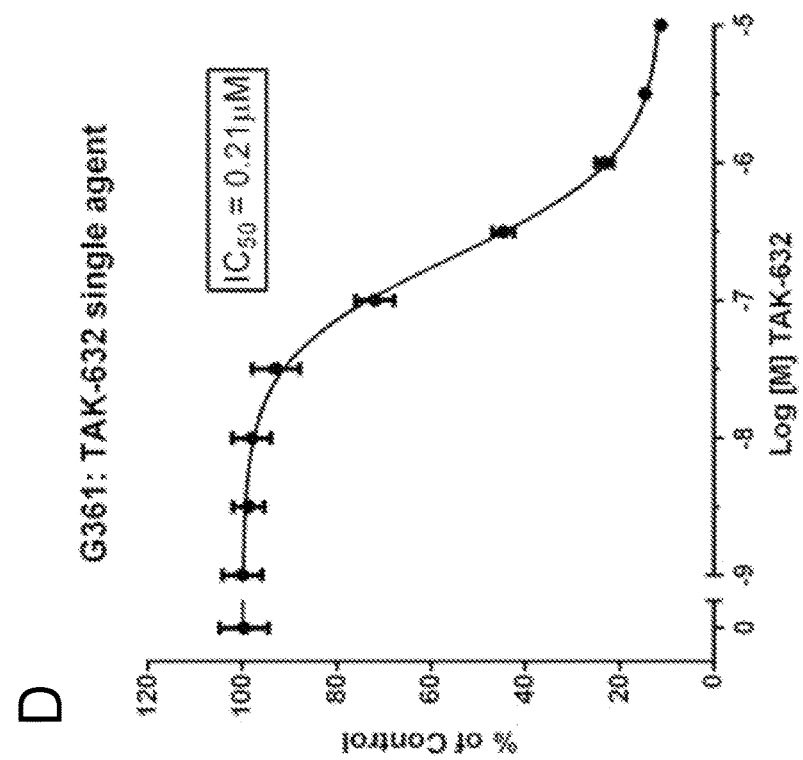

FIG. 57
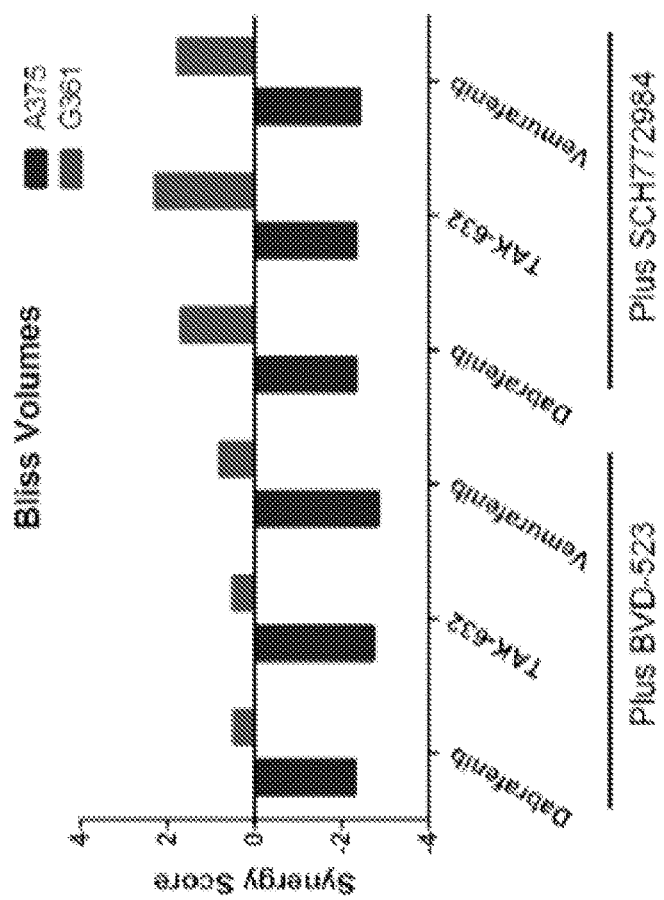
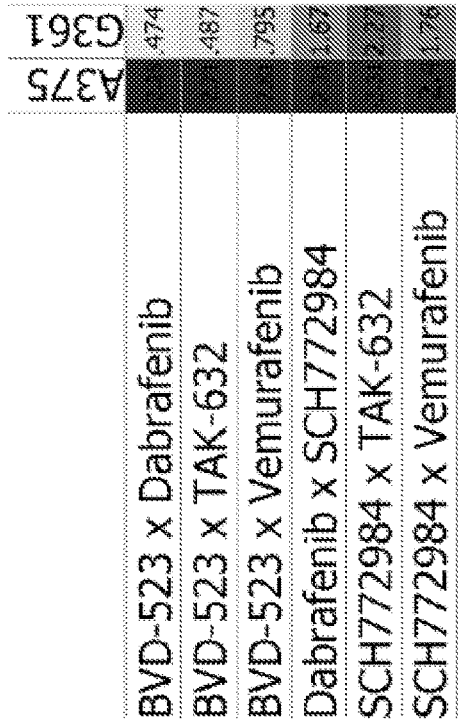

FIG. 58
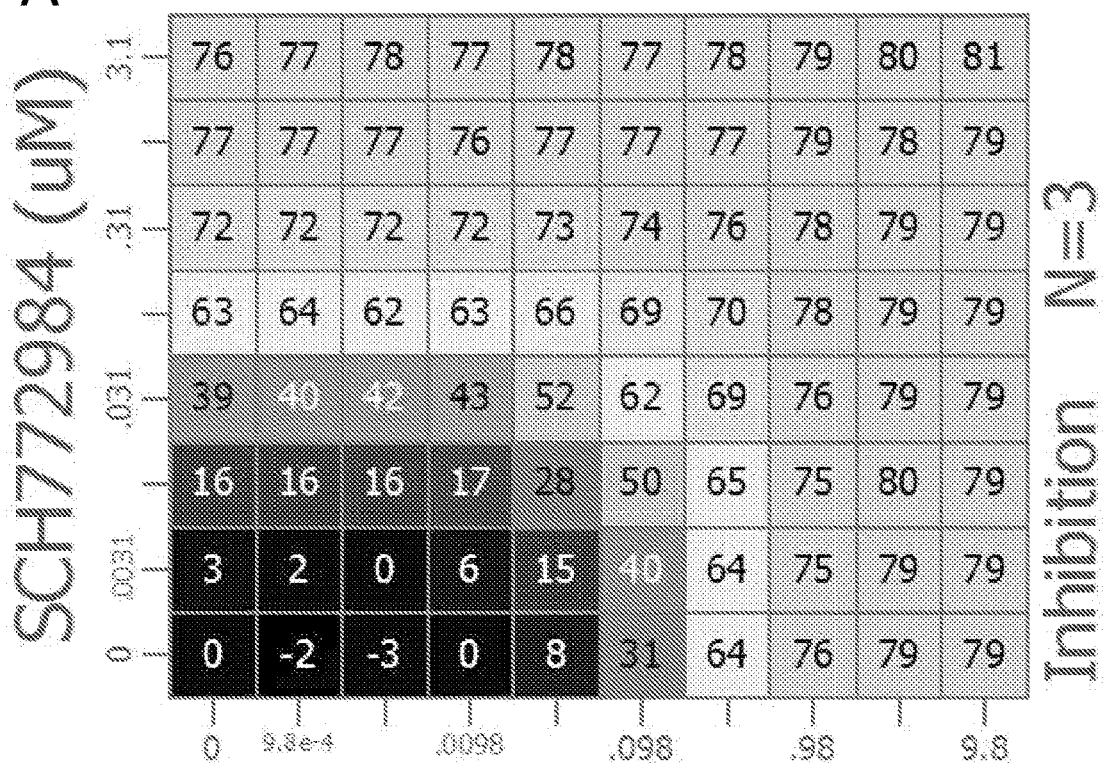
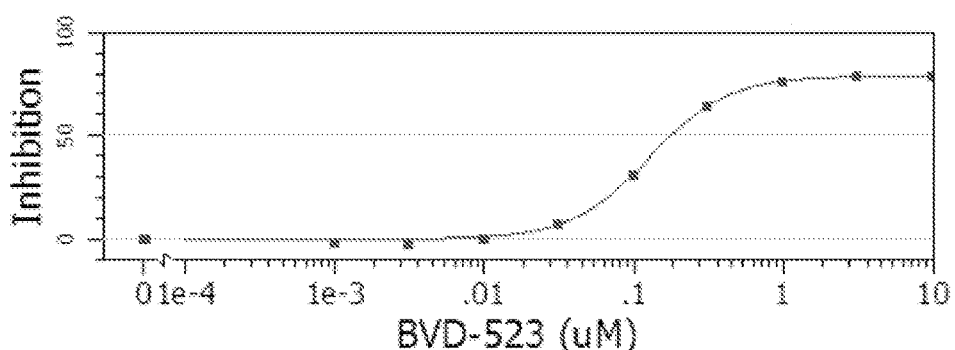
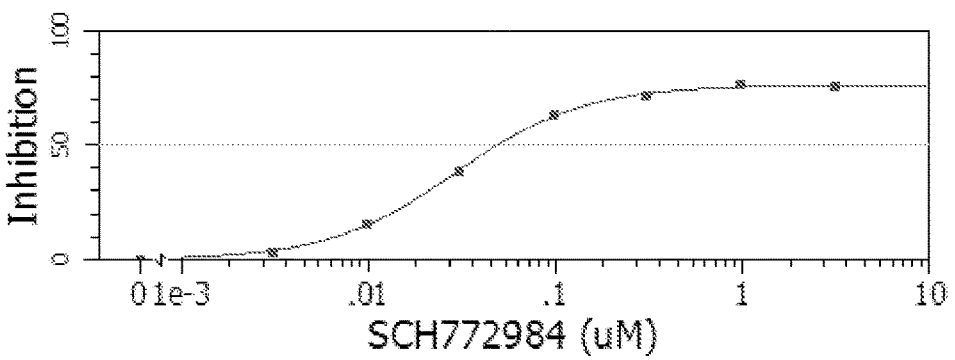

FIG. 58, Continued
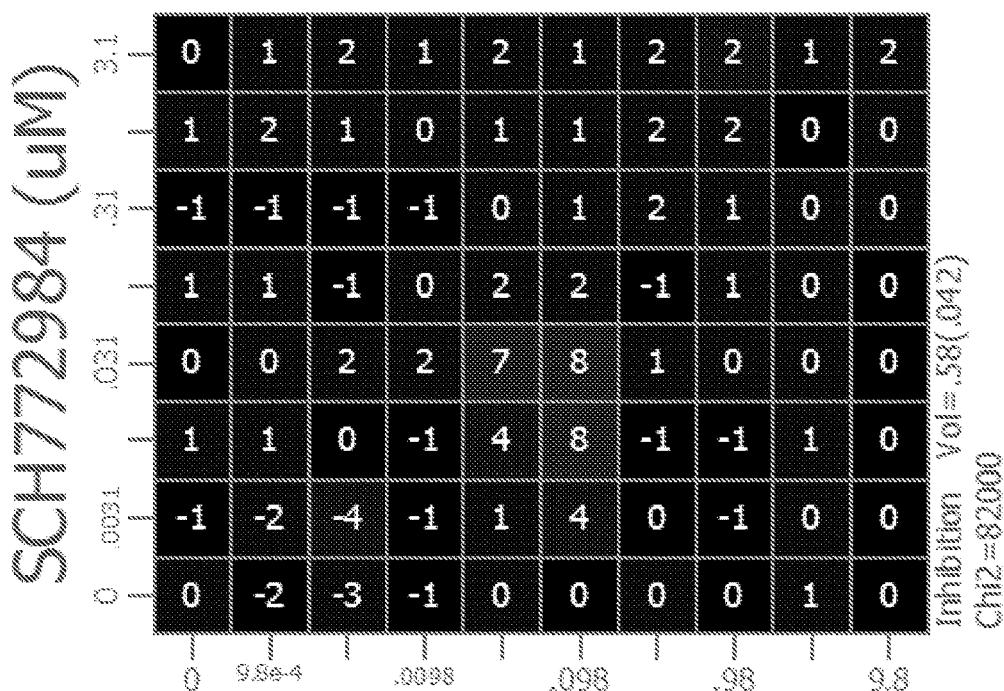
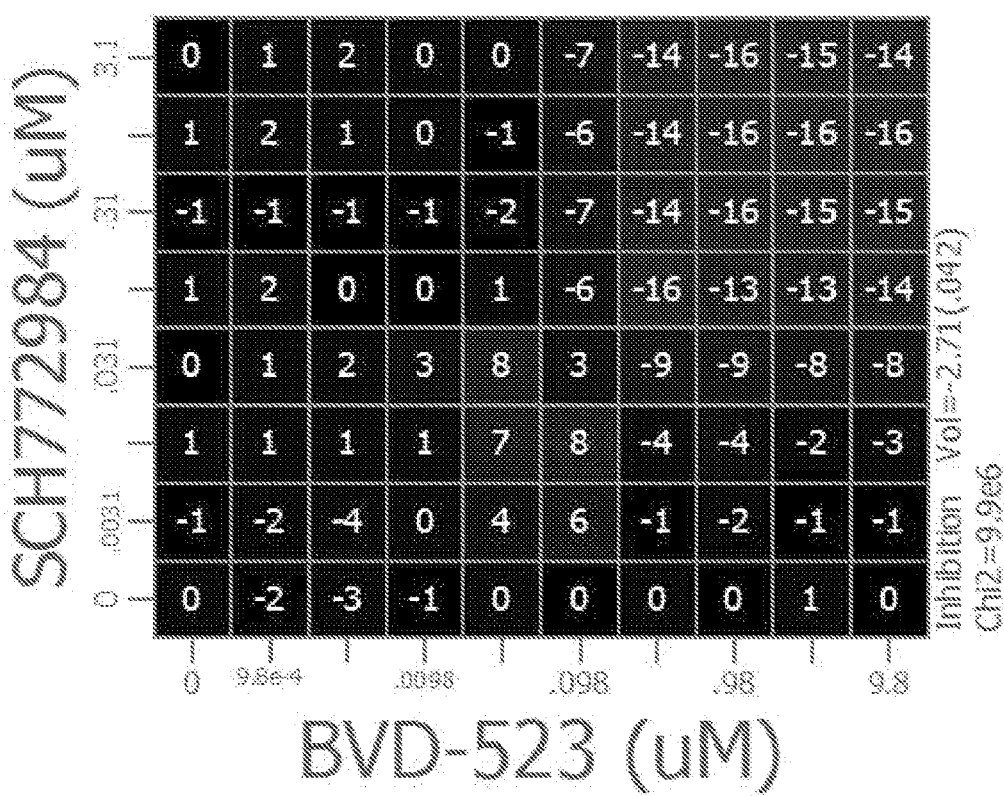

CANCER TREATMENT USING COMBINATIONS OF ERK AND RAF INHIBITORS

CROSS REFERENCE TO RELATED APPLICATIONS

This present application is the National Phase of International Application No. PCT/US2014/071715, filed on Dec. 19, 2014, which claims benefit to U.S. Provisional Application Ser. No. 61/919,347, filed on Dec. 20, 2013. The entire contents of the above applications are incorporated by reference as if recited in full herein.

FIELD OF INVENTION

The present invention provides, inter alia, methods, kits, and pharmaceutical compositions for treating or ameliorating the effects of a cancer in a subject using (i) a first anti-cancer agent, which is BVD-523 or a pharmaceutically acceptable salt thereof and (ii) a second anti-cancer agent, which is a type 1 RAF inhibitor, such as dabrafenib or a pharmaceutically acceptable salt thereof, to treat or ameliorate the effects of the cancer.

INCORPORATION BY REFERENCE OF SEQUENCE LISTING

This application contains references to amino acids and/or nucleic acid sequences that have been filed concurrently herewith as sequence listing text file "0375604.txt", file size of 255 KB, created on Dec. 19, 2014. The aforementioned sequence listing is hereby incorporated by reference in its entirety pursuant to 37 C.F.R. § 1.52(e)(5).

BACKGROUND OF THE INVENTION

Drug inhibitors that target components of the mitogen-activated protein kinases (MAPK) signaling pathway show clinical efficacy in a variety of cancers, particularly those bearing mutations in the BRAF protein kinase. Both RAF and MEK kinase inhibitors are approved for single-agent use in advanced metastatic BRAF mutant melanoma, and the combination of dabrafenib and trametinib is currently undergoing Food and Drug Administration (FDA) review for this indication. Either alone or in combination, BRAF and MEK inhibitors show variable activity in other cancers, with promising efficacy in BRAF mutant thyroid and lung cancer, as well as possible marginal activity in BRAF mutant colorectal cancer.

Varying patterns of clinical efficacy are seen with BRAF and MEK inhibitors. Both the extent and penetrance of initial tumor regression, as well as duration of response before disease progression, varies uniquely according to each drug class when given alone, or when administered in either sequential or concurrent combination strategies. To date, concurrent dabrafenib and trametinib combination therapy appears to be the preferred intervention for BRAF mutant melanoma.

As with other targeted therapies, patterns of disease response to RAF and MEK inhibitors appear to be influenced by the intrinsic genetic heterogeneity present in the cancers where the drugs are used. For instance, it has been shown that certain genetic alterations, including PTEN and other changes that activate the PI3K cell growth signals, may predict a poor initial response, and/or relatively rapid progression, in BRAF mutant melanoma treated with the RAF inhibitor vemurafenib. Likewise, direct mutations in MEK gene loci appear to emerge in tumors that have progressed following either BRAF, MEK or combined drug treatment. Several additional examples, from RAS and RAF gene amplification and splicing mutations, suggest that acquired drug resistance is produced when oncogenic pleiotropy encounters the selective pressure of targeted drug treatment.

Therefore, novel targeted agents would ideally inhibit diverse nodes of oncogenic pathways, and also be effective in combinations by inducing a burden of selective pressure that exceeds the adaptive capacity of diverse cancer genomes. The present application is directed to meeting, inter alia, the need for novel targeted agents.

SUMMARY OF THE INVENTION

One embodiment of the present invention is a method of treating or ameliorating the effects of a cancer in a subject in need thereof. This method comprises administering to the subject an effective amount of (i) a first anti-cancer agent, which is BVD-523 or a pharmaceutically acceptable salt thereof and (ii) a second anti-cancer agent, which is a type 1 RAF inhibitor or a pharmaceutically acceptable salt thereof, to treat or ameliorate the effects of the cancer.

Another embodiment of the present invention is a method of treating or ameliorating the effects of a cancer in a subject in need thereof. This method comprises administering to the subject an effective amount of (i) BVD-523 or a pharmaceutically acceptable salt thereof and (ii) a second anti-cancer agent, which is dabrafenib or a pharmaceutically acceptable salt thereof, to treat or ameliorate the effects of the cancer.

An additional embodiment of the present invention is a method of effecting cancer cell death. This method comprises contacting the cancer cell with an effective amount of (i) a first anti-cancer agent, which is BVD-523 or a pharmaceutically acceptable salt thereof and (ii) a second anti-cancer agent, which is a type 1 RAF inhibitor or a pharmaceutically acceptable salt thereof.

A further embodiment of the present invention is a kit for treating or ameliorating the effects of a cancer in a subject in need thereof. This kit comprises an effective amount of (i) a first anti-cancer agent, which is BVD-523 or a pharmaceutically acceptable salt thereof and (ii) a second anti-cancer agent, which is a type 1 RAF inhibitor or a pharmaceutically acceptable salt thereof, packaged together with instructions for their use.

An additional embodiment of the present invention is a pharmaceutical composition for treating or ameliorating the effects of a cancer in a subject in need thereof. This pharmaceutical composition comprises a pharmaceutically acceptable diluent or carrier and an effective amount of (i) a first anti-cancer agent, which is BVD-523 or a pharmaceutically acceptable salt thereof and (ii) a second anti-cancer agent, which is a type 1 RAF inhibitor or a pharmaceutically acceptable salt thereof, wherein administration of the first and second anti-cancer agents provides a synergistic effect compared to administration of either anti-cancer agent alone.

Another embodiment of the present invention is a method of treating or ameliorating the effects of a cancer in a subject in need thereof. This method comprises administering to the subject an effective amount of (i) a first anti-cancer agent, which is BVD-523 or a pharmaceutically acceptable salt thereof and (ii) a second anti-cancer agent, which is a RAF inhibitor selected from the group consisting of AAL881

(Novartis); AB-024 (Ambit Biosciences), ARQ-736 (ArQule), ARQ-761 (ArQule), AZ628 (Axon Medchem BV), BeiGene-283 (BeiGene), BUB-024 (MLN 2480) (Sunesis & Takeda), b-raf inhibitor (Sareum), BRAF kinase inhibitor (Selexagen Therapeutics), BRAF siRNA 313 (tacaccagcaagctagatgca) and 253 (cctatcgttagagtcttcctg) (Liu et al., 2007), CTT239065 (Institute of Cancer Research), DP-4978 (Deciphera Pharmaceuticals), HM-95573 (Hanmi), GW-5074 (Sigma Aldrich), ISIS 5132 (Novartis), LErafAON (NeoPharm, Inc.), LBT613 (Novartis), LGX-818 (Novartis), pazopanib (GlaxoSmithKline), PLX5568 (Plexxikon), RAF-265 (Novartis), RAF-365 (Novartis), regorafenib (Bayer Healthcare Pharmaceuticals, Inc.), RO 5126766 (Hoffmann-La Roche), TAK 632 (Takeda), TL-241 (Teligene), XL-281 (Exelixis), pharmaceutically acceptable salts thereof, and combinations thereof, to treat or ameliorate the effects of the cancer.

An additional embodiment of the present invention is a method of effecting cancer cell death. This method comprises contacting the cancer cell with an effective amount of (i) a first anti-cancer agent, which is BVD-523 or a pharmaceutically acceptable salt thereof and (ii) a second anti-cancer agent, which is a RAF inhibitor selected from the group consisting of AAL881 (Novartis); AB-024 (Ambit Biosciences), ARQ-736 (ArQule), ARQ-761 (ArQule), AZ628 (Axon Medchem BV), BeiGene-283 (BeiGene), BUB-024 (MLN 2480) (Sunesis & Takeda), b-raf inhibitor (Sareum), BRAF kinase inhibitor (Selexagen Therapeutics), BRAF siRNA 313 (tacaccagcaagctagatgca) and 253 (cctatcgttagagtcttcctg), CTT239065 (Institute of Cancer Research), DP-4978 (Deciphera Pharmaceuticals), HM-95573 (Hanmi), GW-5074 (Sigma Aldrich), ISIS 5132 (Novartis), LErafAON (NeoPharm, Inc.), LBT613 (Novartis), LGX-818 (Novartis), pazopanib (GlaxoSmithKline), PLX5568 (Plexxikon), RAF-265 (Novartis), RAF-365 (Novartis), regorafenib (Bayer Healthcare Pharmaceuticals, Inc.), RO 5126766 (Hoffmann-La Roche), TAK 632 (Takeda), TL-241 (Teligene), XL-281 (Exelixis), pharmaceutically acceptable salts thereof, and combinations thereof.

A further embodiment of the present invention is a kit for treating or ameliorating the effects of a cancer in a subject in need thereof. This kit comprises an effective amount of (i) a first anti-cancer agent, which is BVD-523 or a pharmaceutically acceptable salt thereof and (ii) a second anti-cancer agent, which is a RAF inhibitor selected from the group consisting of AAL881 (Novartis); AB-024 (Ambit Biosciences), ARQ-736 (ArQule), ARQ-761 (ArQule), AZ628 (Axon Medchem BV), BeiGene-283 (BeiGene), BUB-024 (MLN 2480) (Sunesis & Takeda), b-raf inhibitor (Sareum), BRAF kinase inhibitor (Selexagen Therapeutics), BRAF siRNA 313 (tacaccagcaagctagatgca) and 253 (cctatcgttagagtcttcctg), CTT239065 (Institute of Cancer Research), DP-4978 (Deciphera Pharmaceuticals), HM-95573 (Hanmi), GW-5074 (Sigma Aldrich), ISIS 5132 (Novartis), LErafAON (NeoPharm, Inc.), LBT613 (Novartis), LGX-818 (Novartis), pazopanib (GlaxoSmithKline), PLX5568 (Plexxikon), RAF-265 (Novartis), RAF-365 (Novartis), regorafenib (Bayer Healthcare Pharmaceuticals, Inc.), RO 5126766 (Hoffmann-La Roche), TAK 632 (Takeda), TL-241 (Teligene), XL-281 (Exelixis), pharmaceutically acceptable salts thereof, and combinations thereof, packaged together with instructions for their use.

Another embodiment of the present invention is a pharmaceutical composition for treating or ameliorating the effects of a cancer in a subject in need thereof. This pharmaceutical composition comprises a pharmaceutically acceptable diluent or carrier and an effective amount of (i) a first anti-cancer agent, which is BVD-523 or a pharmaceutically acceptable salt thereof and (ii) a second anti-cancer agent, which is a RAF inhibitor selected from the group consisting of AAL881 (Novartis); AB-024 (Ambit Biosciences), ARQ-736 (ArQule), ARQ-761 (ArQule), AZ628 (Axon Medchem BV), BeiGene-283 (BeiGene), BUB-024 (MLN 2480) (Sunesis & Takeda), b-raf inhibitor (Sareum), BRAF kinase inhibitor (Selexagen Therapeutics), BRAF siRNA 313 (tacaccagcaagctagatgca) and 253 (cctatcgttagagtcttcctg), CTT239065 (Institute of Cancer Research), DP-4978 (Deciphera Pharmaceuticals), HM-95573 (Hanmi), GW-5074 (Sigma Aldrich), ISIS 5132 (Novartis), LErafAON (NeoPharm, Inc.), LBT613 (Novartis), LGX-818 (Novartis), pazopanib (GlaxoSmithKline), PLX5568 (Plexxikon), RAF-265 (Novartis), RAF-365 (Novartis), regorafenib (Bayer Healthcare Pharmaceuticals, Inc.), RO 5126766 (Hoffmann-La Roche), TAK 632 (Takeda), TL-241 (Teligene), XL-281 (Exelixis), pharmaceutically acceptable salts thereof, and combinations thereof, wherein administration of the first and second anti-cancer agents provides a synergistic effect compared to administration of either anti-cancer agent alone.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A-C show the progress of a dose escalation study in a human malignant melanoma cell line (A375 cells) for month 1. Various treatments (trametinib (a type 2 MEK inhibitor), dabrafenib (a BRAF inhibitor), and BVD-523 (an ERK1/2 inhibitor)) are as labeled.

FIGS. 2A-2C and 2G are normalized to control, whereas FIGS. 2D-2F and 2H show the raw data.

FIGS. 3A-3D show the progress of a dose escalation study in A375 cells for month 2. Various treatments (trametinib, dabrafenib, and BVD-523) are as labeled.

FIGS. 4A-4C and 4G are normalized to control, whereas FIGS. 4D-4F and 4H show the raw data.

FIGS. 5A-5C and 5G are normalized to control, whereas FIGS. 5D-5F and 5H show the raw data.

FIGS. 6A-D show the progress of the dose escalation study in a human malignant cell line (A375 cells) for month 3. Various treatments (trametinib, dabrafenib, and BVD-523) are as labeled.

FIG. 11A is a dose matrix showing % inhibition of the trametinib/dabrafenib combination in A375 cells using the CellTiter-Glo cell viability assay. FIG. 11B is a dose matrix showing excess over Bliss for the trametinib/dabrafenib combination. FIGS. 11C and 11D show % viability relative to DMSO only treated controls for dabrafenib and trametinib single agent treatments in A375 cells using the CellTiter-Glo cell viability assay. FIG. 11E shows % viability relative to DMSO only treated controls for dabrafenib and trametinib combination treatments in A375 cells using the CellTiter-Glo cell viability assay.

FIGS. 16A and 16B show results from duplicate samples. Similarly, FIGS. 16C and 16D also show results from duplicate samples. In FIGS. 16A and 16B, pRSK1 had a relatively weak signal in A375 cells compared to other markers. A different pRSK1-S380 antibody from Cell Signaling (cat. #11989) was tested but did not give a detectable signal (data not shown). In FIGS. 16C and 16D, pCRAF-338 gave a minimal signal.

FIGS. 17A and 17B show results from duplicate samples. Similarly, FIGS. 17C and 17D also show results from duplicate samples. In FIGS. 17A-17B, pRSK1 levels appear to be very low in HCT116 cells, and in FIGS. 17C and 17D, pCRAF-338 signal was also very weak.

FIGS. 18A and 18B show results from duplicate samples. Similarly, FIGS. 18C and 18D also show results from duplicate samples. In FIGS. 18A and 18B, no band of a size corresponding to cleaved PARP (89 kDa) was apparent.

FIG. 40A is a dose matrix showing % inhibition of the dabrafenib/trametinib combination in A375 cells using the Alamar Blue cell viability assay. FIG. 40B is a dose matrix showing excess over Bliss for the dabrafenib/trametinib combination. FIGS. 40C and 40D show % viability relative to DMSO only treated controls for dabrafenib and trametinib single agent treatments in A375 cells using the Alamar Blue cell viability assay. FIG. 40E shows % viability relative to DMSO only treated controls for dabrafenib/trametinib combination treatments in A375 cells using the Alamar Blue cell viability assay.

FIG. 42 shows results of single agent proliferation assays in A375 (FIG. 42A-FIG. 42F) and G-361 (FIG. 42G-FIG. 42L) cells. Prolifferation results are shown for treatment with Dabrafenib (FIG. 42A and FIG. 42G), Vemurafenib (FIG. 42B and FIG. 42H), TAK-632 (FIG. 42C and FIG. 42I), BVD-523 (FIG. 42D and FIG. 42J), SCH772984 (FIG. 42E and FIG. 42K), and Paclitaxel (FIG. 42F and FIG. 42L).

FIG. 43B is a dose matrix showing Loewe excess for the Dabrafenib/SCH772984 combination. FIG. 43C is a dose matrix showing Bliss excess for the Dabrafenib/SCH772984 combination. FIGS. 43D and 43E, respectively, show % viability relative to DMSO only treated controls for Dabrafenib and SCH772984 single agent treatments in A375 cells.

FIG. 57A shows Bliss volumes for the tested combinations in both A375 and G-361 cells. FIG. 57B shows a graph of the values presented in FIG. 57A.

FIG. 58 shows the results of the combination of BVD-523 and SCH772984. FIG. 58A shows a dose matrix showing inhibition (%) for the combination in A375 cells. FIG. 58B-FIG. 58C show the results of single agent proliferation assays for the combination in 58A. FIG. 58D shows Loewe excess for the combination in 58A and FIG. 58E shows Bliss excess for the combination in 58A.

DETAILED DESCRIPTION OF THE INVENTION

One embodiment of the present invention is a method of treating or ameliorating the effects of a cancer in a subject in need thereof. This method comprises administering to the subject an effective amount of (i) a first anti-cancer agent, which is BVD-523 or a pharmaceutically acceptable salt thereof and (ii) a second anti-cancer agent, which is a type 1 RAF inhibitor or a pharmaceutically acceptable salt thereof, to treat or ameliorate the effects of the cancer.

As used herein, the terms "treat," "treating," "treatment" and grammatical variations thereof mean subjecting an individual subject to a protocol, regimen, process or remedy, in which it is desired to obtain a physiologic response or outcome in that subject, e.g., a patient. In particular, the methods and compositions of the present invention may be used to slow the development of disease symptoms or delay the onset of the disease or condition, or halt the progression of disease development. However, because every treated subject may not respond to a particular treatment protocol, regimen, process or remedy, treating does not require that the desired physiologic response or outcome be achieved in each and every subject or subject population, e.g., patient population. Accordingly, a given subject or subject population, e.g., patient population may fail to respond or respond inadequately to treatment.

As used herein, the terms "ameliorate", "ameliorating" and grammatical variations thereof mean to decrease the severity of the symptoms of a disease in a subject.

As used herein, a "subject" is a mammal, preferably, a human. In addition to humans, categories of mammals within the scope of the present invention include, for example, farm animals, domestic animals, laboratory animals, etc. Some examples of farm animals include cows, pigs, horses, goats, etc. Some examples of domestic animals include dogs, cats, etc. Some examples of laboratory animals include primates, rats, mice, rabbits, guinea pigs, etc.

Figure 18:
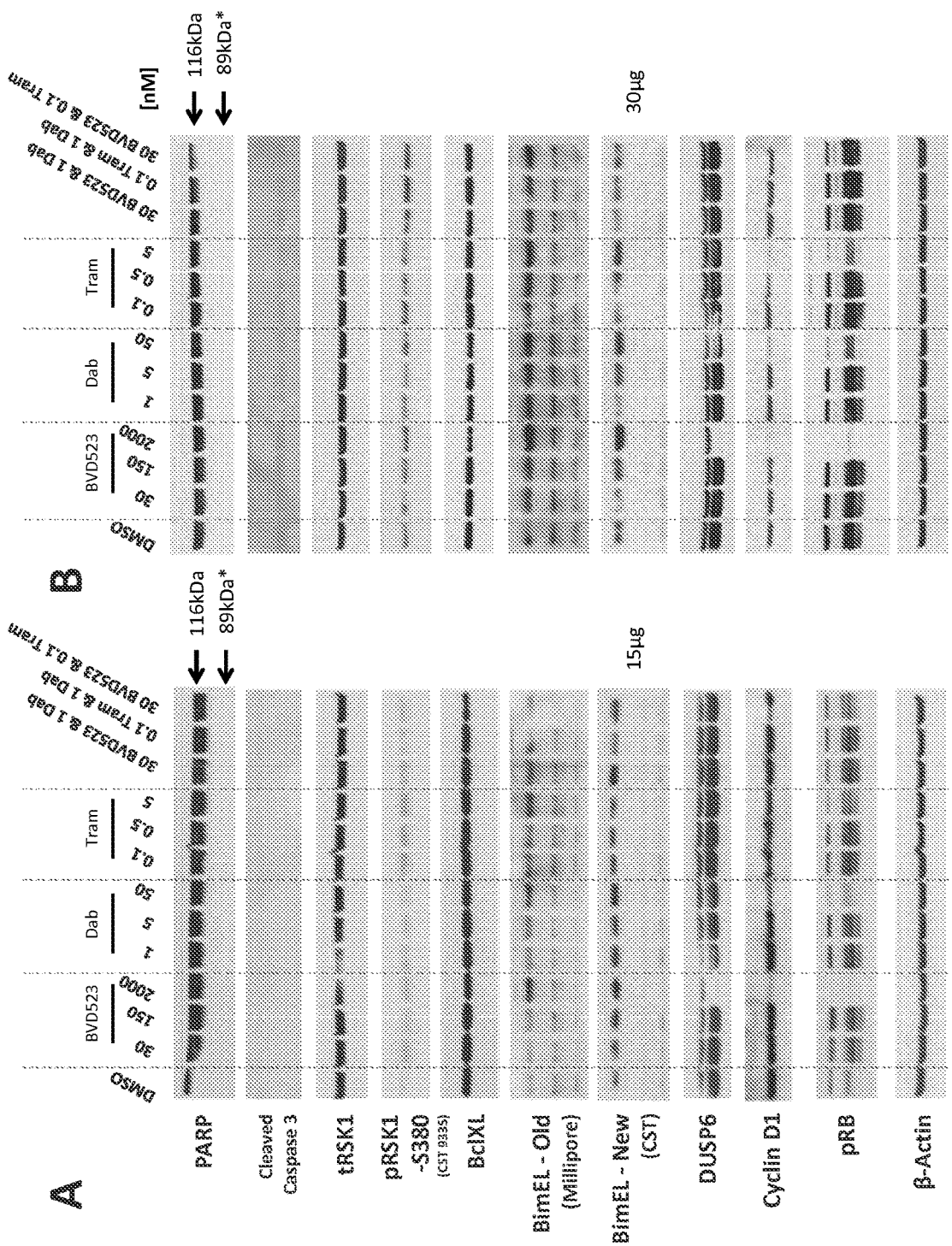
FIGS. 18A-D are a set of images showing Western blot analysis of cell cycle and apoptosis proteins in A375 melanoma cells after a 24 hour treatment with various concentrations (in nM) of BVD-523 ("BVD523"), trametinib ("tram") and/or dabrafenib ("Dab") as labelled. 50 µg of total protein was loaded in each lane except where indicated otherwise. In this experiment, duplicate samples were collected.
Figure 19:
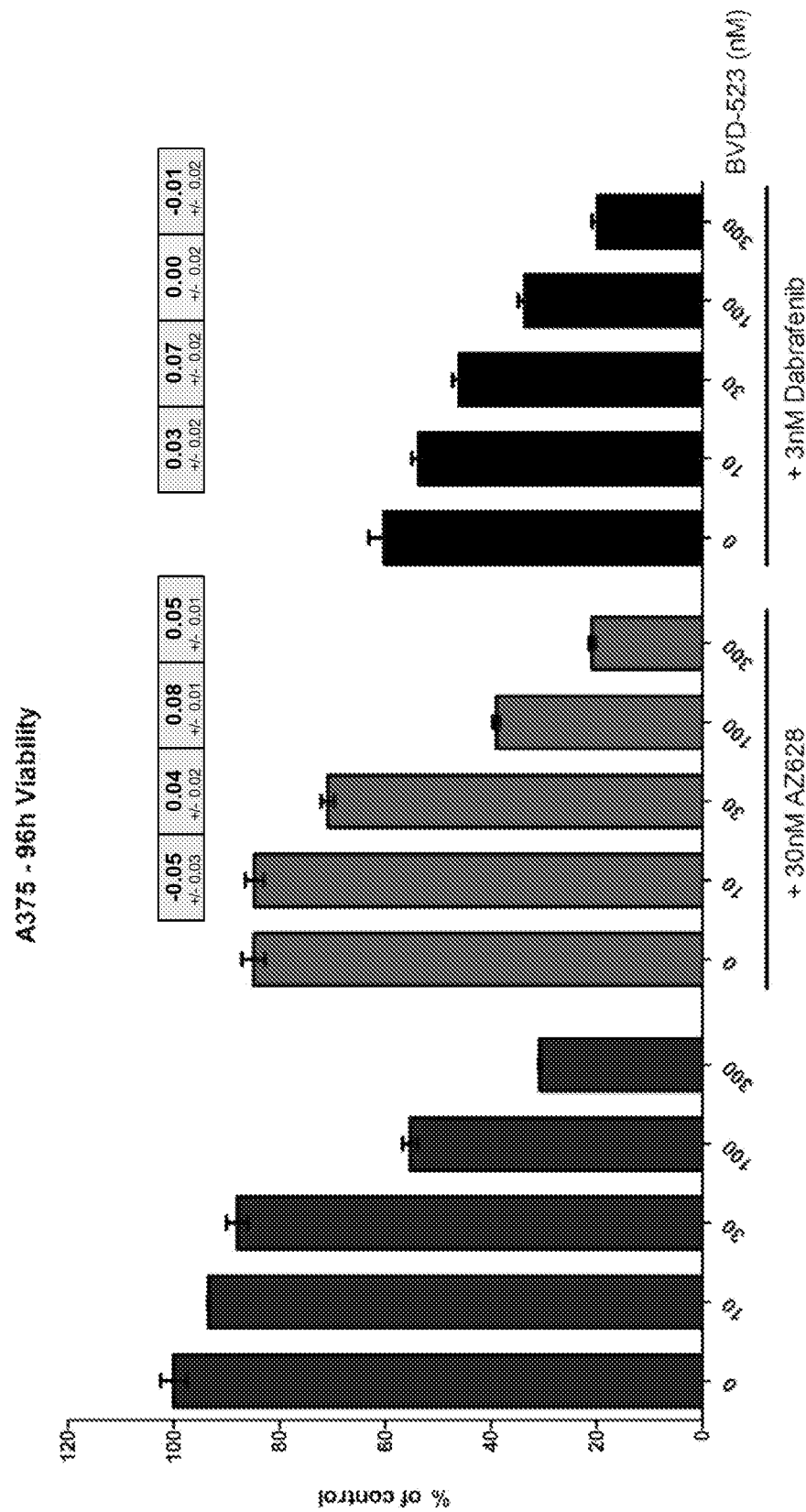
FIG. 19 is a histogram showing viability of A375 cells after 96 hours of incubation with various amounts of BVD-523 or BVD-523 in combination with 30 nM AZ628 (a RAF inhibitor) or 3 nM dabrafenib. The Bliss Scores are shown in the yellow boxes.
Figure 20:
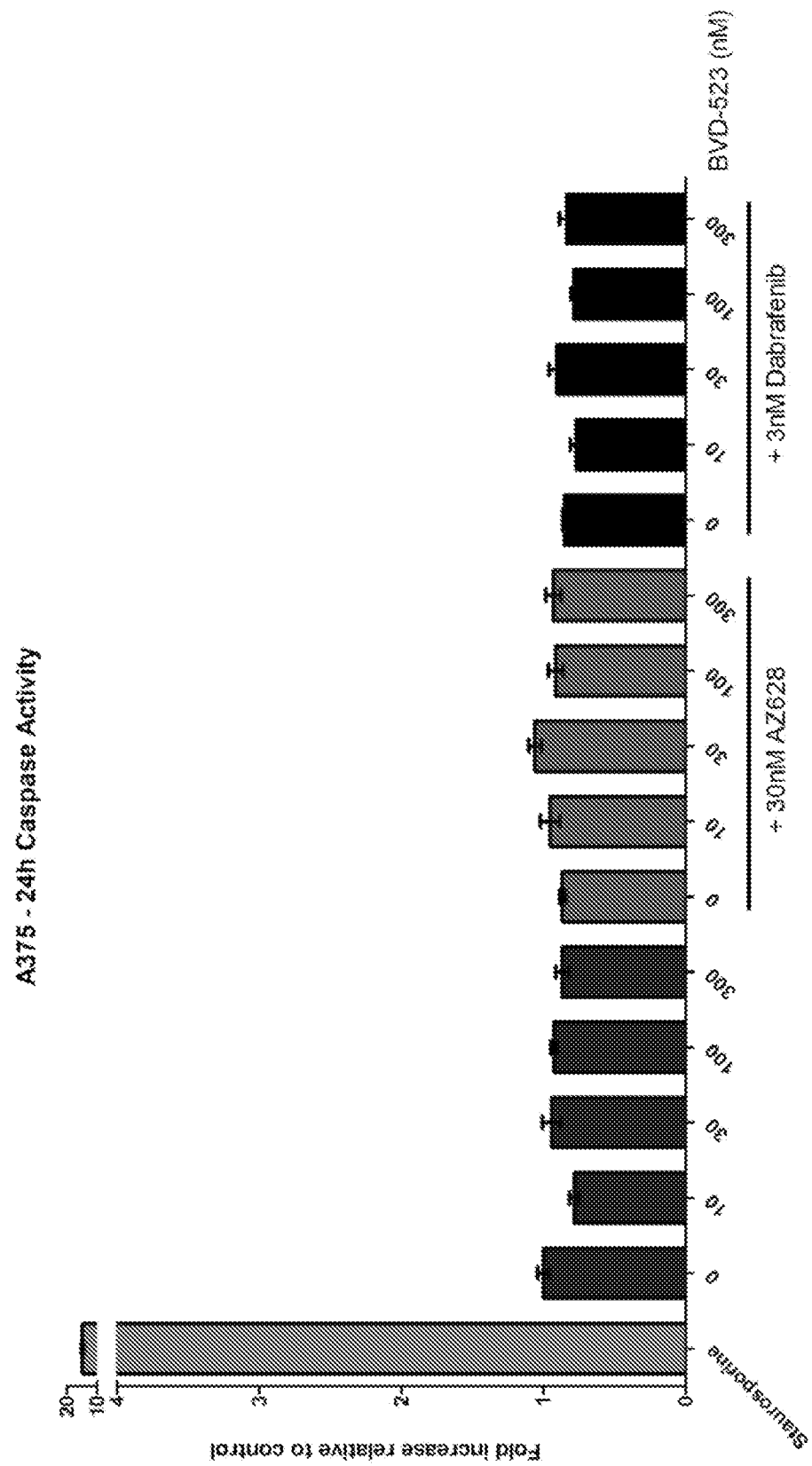
FIG. 20 is a histogram showing caspase activity in A375 cells after 24 hours of incubation with various amounts of BVD-523 or BVD-523 in combination with 30 nM AZ628 or 3 nM dabrafenib.
Figure 21:
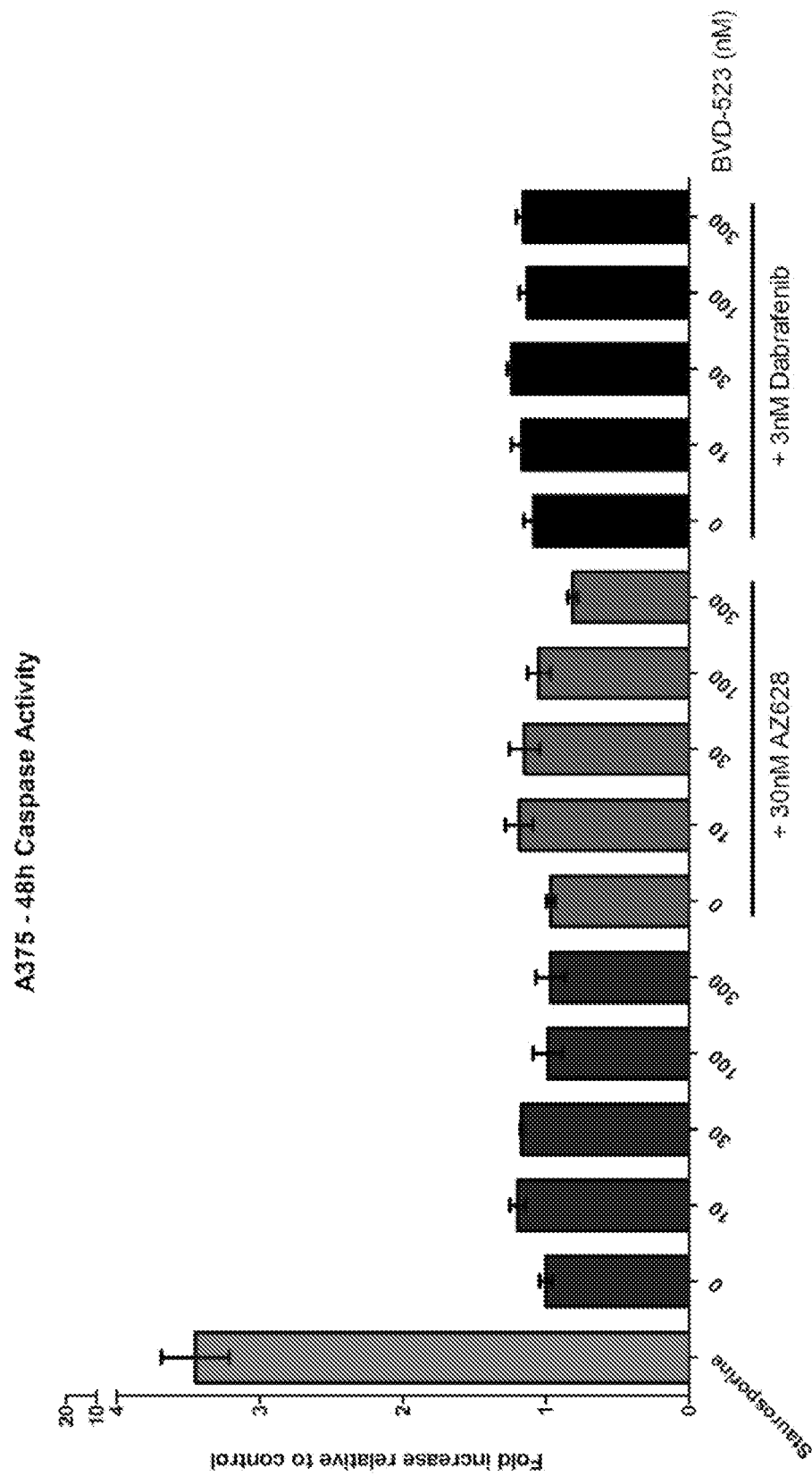
FIG. 21 is a histogram showing caspase activity in A375 cells after 48 hours of incubation with various amounts of BVD-523 or BVD-523 in combination with 30 nM AZ628 or 3 nM dabrafenib.
Figure 22:
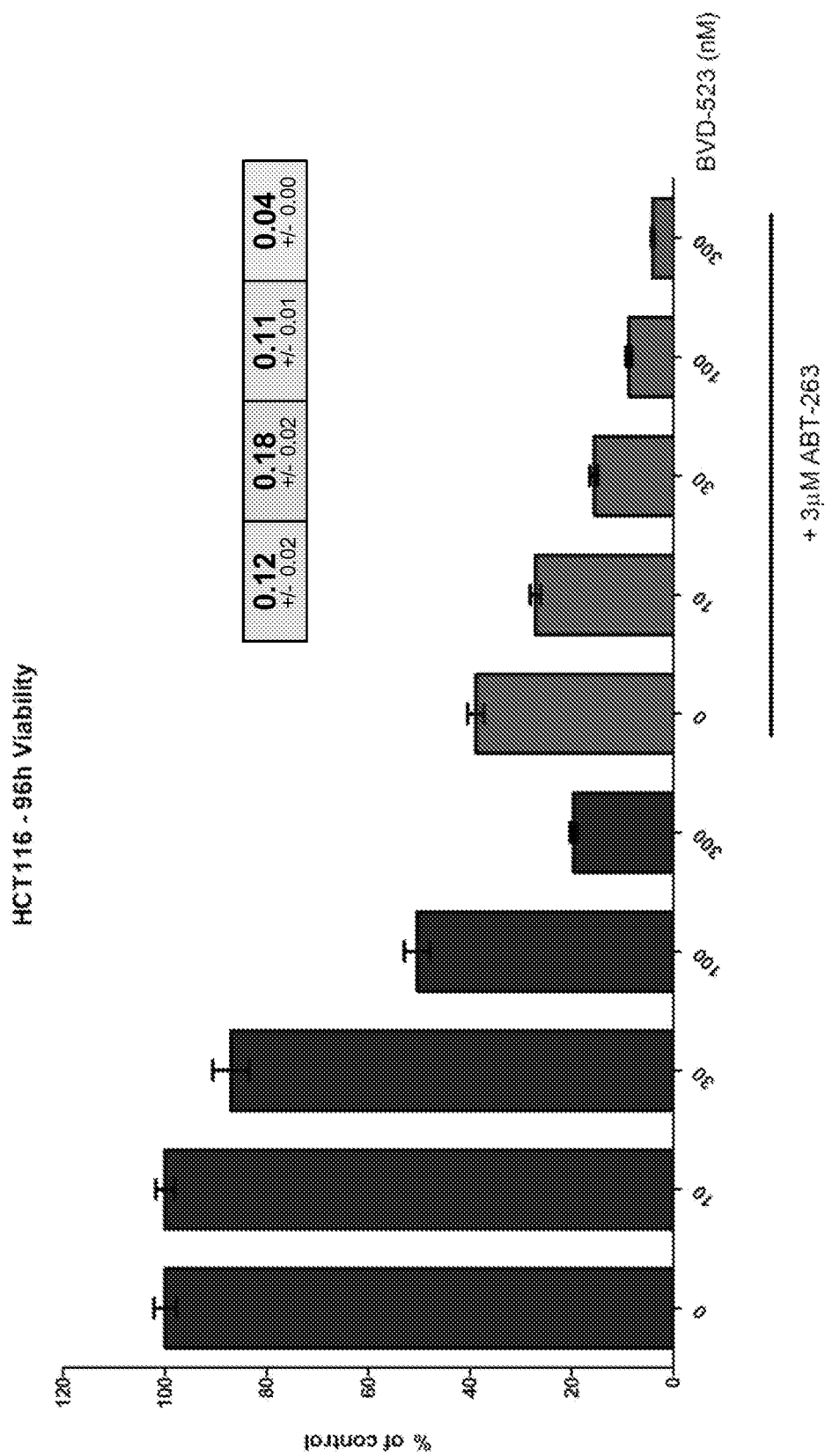
FIG. 22 is a histogram showing viability of HCT116 cells after 96 hours of incubation with various amounts of BVD-523 or BVD-523 in combination with 3 µM ABT-263. The Bliss Scores are shown in the yellow boxes.
Figure 23:
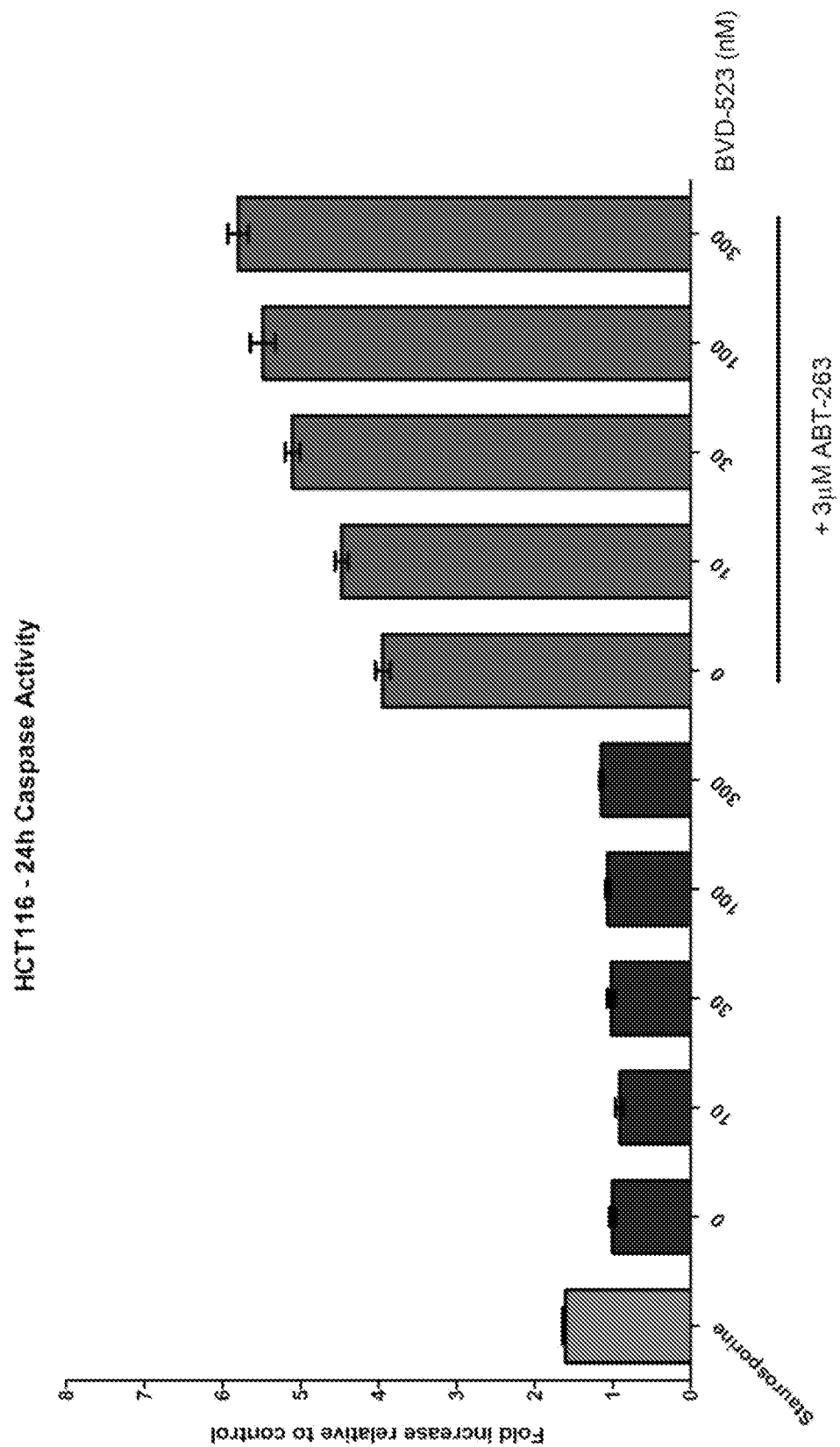
FIG. 23 is a histogram showing caspase activity in HCT116 cells after 24 hours of incubation with various amounts of BVD-523 or BVD-523 in combination with 3 µM ABT-263.
Figure 24:
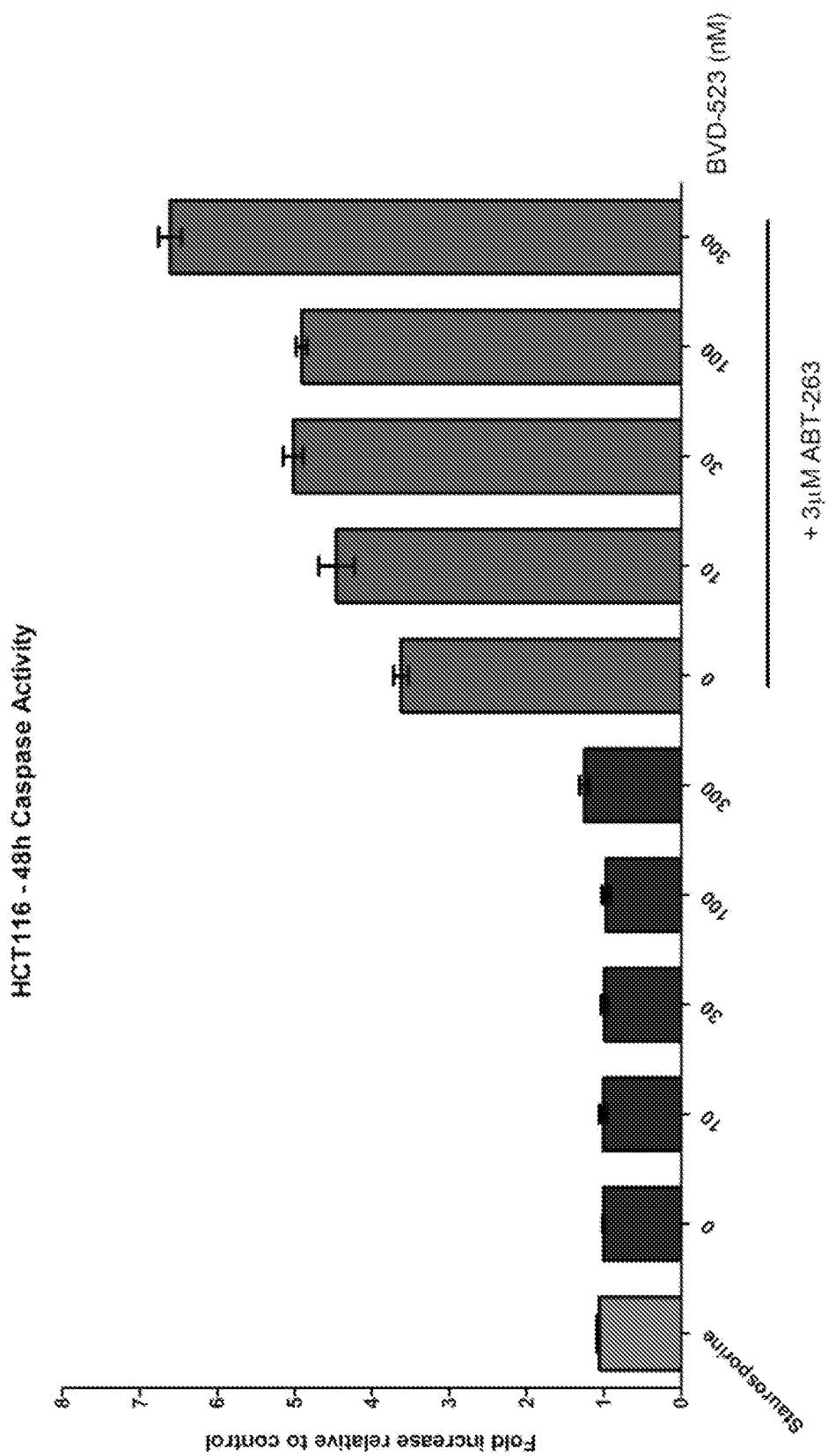
FIG. 24 is a histogram showing caspase activity in HCT116 cells after 48 hours of incubation with various amounts of BVD-523 or BVD-523 in combination with 3 µM ABT-263.

In the present invention, BVD-523 is a compound according to formula (I):

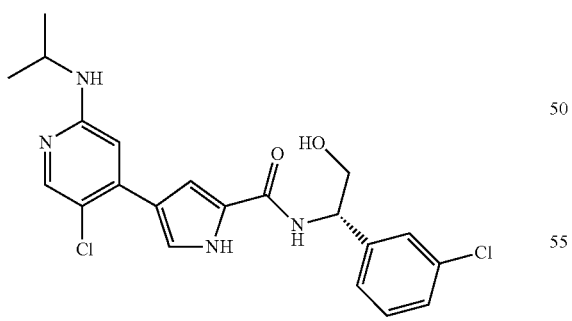

and pharmaceutically acceptable salts thereof. BVD-523 may be synthesized according to the methods disclosed in, e.g., U.S. Pat. No. 7,354,939. Enantiomers and racemic mixtures of both enantiomers of BVD-523 are also contemplated within the scope of the present invention. BVD-523 is an ERK1/2 inhibitor with a mechanism of action that is believed to be, e.g., unique and distinct from certain other ERK1/2 inhibitors, such as SCH772984. For example, other ERK1/2 inhibitors, such as SCH772984, inhibit autophosphorylation of ERK (Morris et al., 2013), whereas BVD-523 allows for the autophosphorylation of ERK while still inhibiting ERK (FIG. 18).

As used herein, a "RAF inhibitor" means those substances that (i) directly interact with RAF, e.g., by binding to RAF and (ii) decrease the expression or the activity of RAF. RAF inhibitors may be classified into two types by their respective binding modes. As used herein, "Type 1" RAF inhibitors are those inhibitors that target the ATP binding sites of the kinase in its active conformation. "Type 2" RAF inhibitors are those inhibitors that preferentially bind to an inactive conformation of the kinase. Non-limiting examples of Type 1 RAF inhibitors include:

Compound 7

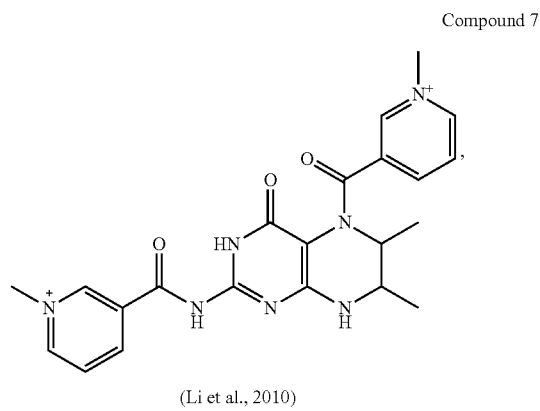

(Li et al., 2010)

Compound 9

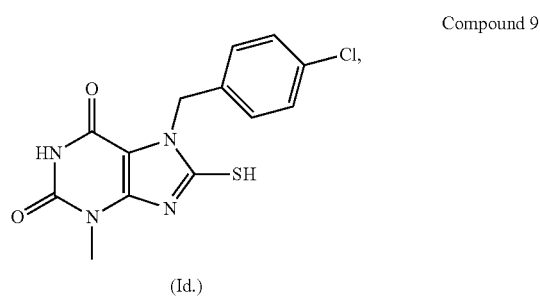

(Id.)

Compound 10

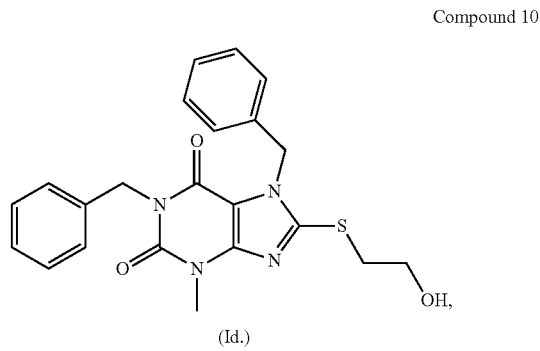

(Id.)

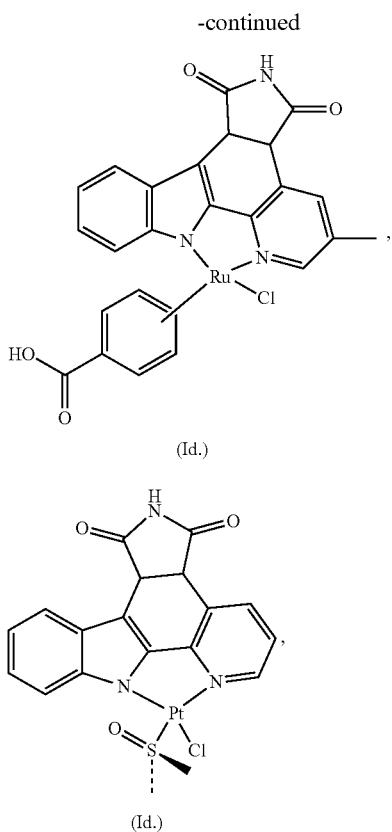

Compound 13 (Id.)

Compound 14 (Id.)

dabrafenib (GlaxoSmithKline), GDC-0879 (Genentech), L-779450 B-Raf (Merck), PLX3202 (Plexxikon), PLX4720 (Plexxikon), SB-590885 (GlaxoSmithKline), SB-699393 (GlaxoSmithKline), vemurafenib (Plexxikon), pharmaceutically acceptable salts thereof, and combinations thereof. Preferably, the type 1 RAF inhibitor is dabrafenib or a pharmaceutically acceptable salt thereof.

In one aspect of this embodiment, the subject with cancer has a somatic BRAF mutation or is refractory to MAPK pathway inhibitor treatment. Preferably, the subject is refractory to non-ERK MAPK pathway inhibitor treatment.

As used herein, "somatic mutation" means a change occurring in any cell that is not destined to become a germ cell. The mutation may be, e.g., a substitution, deletion, insertion, or a fusion. Table 1 below shows a distribution overview of BRAF mutations, as shown in the Sanger database.

TABLE 1

Distribution overview of BRAF mutations

| Mutation Type | Mutant samples | Percentage |
|---|---|---|
| Substitution nonsense | 23 | 0.07 |
| Substitution missense | 32955 | 99.07 |
| Substitution synonymous | 80 | 0.24 |
| Insertion inframe | 25 | 0.08 |
| Insertion frameshift | 1 | 0.00 |
| Deletion inframe | 13 | 0.04 |
| Deletion frameshift | 5 | 0.02 |
| Complex | 39 | 0.12 |
| Other | 172 | 0.52 |
| Total | 33263 | 100 |

BRAF mutations are found in approximately 66% melanoma (Davies et al., 2002; Brose et al., 2002; Hocket et al., 2007), and a relatively lower percentage in other cancers, 36% thyroid tumors and 10% colon cancers (Xu et al., 2003; Fransen et al., 2004). The most prevalent BRAF mutation occurs at amino acid 600 of the wild-type protein kinase (SEQ ID NO:2) by substituting valine with glutamic acid resulting in the mutant B-RafV600E, which accounts for about 80% of BRAF mutations (Davies et al., 2002; Hocker et al., 2007). B-RafV600E kinase domain has 500-fold higher kinase activity compared to the basal activity of wild-type B-Raf (Wan et al., 2004). Of the other BRAF mutations identified in melanoma, V600K and V600D/R are also common and represent 16% and 3% of all BRAF mutations, respectively (Long et al., 2011). In addition to melanoma, BRAF mutations are also common in many other cancers including papillary thyroid carcinoma, ovarian carcinoma, and colorectal carcinoma. (Wellbrock et al., 2004). In one study, BRAF splice variants (splicing out exons 14 and 15) were found in 5/24 (21%) colorectal cancers cell lines (Seth et al., 2009).

Table 2 below from the Sanger database shows the distribution and frequency of BRAF mutations in human tumors.

TABLE 2

| Primary Tissue | Unique Mutated Samples | Total Unique Samples | % Mutated |
|---|---|---|---|
| NS | 1071 | 1788 | 59.90 |
| Adrenal gland | 3 | 155 | 1.94 |
| Autonomic ganglia | 3 | 703 | 0.43 |
| Biliary tract | 36 | 684 | 5.26 |
| Bone | 5 | 284 | 1.76 |
| Breast | 27 | 2297 | 1.18 |
| Central nervous system | 206 | 3297 | 6.25 |
| Cervix | 6 | 473 | 1.27 |
| Endometrium | 40 | 2510 | 1.59 |
| Eye | 70 | 732 | 9.56 |
| Fallopian tube | 0 | 2 | 0 |
| Gastrointestinal tract (site indeterminate) | 5 | 514 | 0.97 |
| Genital tract | 4 | 54 | 7.41 |
| Haematopoietic and lymphoid tissue | 507 | 5388 | 9.41 |
| Kidney | 34 | 959 | 3.55 |
| Large intestine | 8301 | 67530 | 12.29 |
| Liver | 18 | 618 | 2.91 |
| Lung | 293 | 11249 | 2.60 |
| Meninges | 0 | 74 | 0 |
| Oesophagus | 5 | 927 | 0.54 |
| Ovary | 312 | 3922 | 7.96 |
| Pancreas | 16 | 1089 | 1.47 |
| Parathyroid | 0 | 20 | 0 |
| Penis | 0 | 28 | 0 |
| Peritoneum | 0 | 37 | 0 |
| Pituitary | 1 | 115 | 0.87 |
| Placenta | 0 | 2 | 0 |
| Pleura | 3 | 148 | 2.03 |
| Prostate | 25 | 1483 | 1.69 |
| Salivary gland | 1 | 131 | 0.76 |
| Skin | 7245 | 16943 | 42.76 |
| Small intestine | 12 | 251 | 4.78 |
| Soft tissue | 45 | 2160 | 2.08 |
| Stomach | 11 | 1473 | 0.75 |
| Testis | 7 | 251 | 2.79 |
| Thymus | 0 | 50 | 0 |
| Thyroid | 14929 | 38002 | 39.28 |
| Upper aerodigestive tract | 14 | 1352 | 1.04 |

TABLE 2-continued

| Primary Tissue | Unique Mutated Samples | Total Unique Samples | % Mutated |
|---|---|---|---|
| Urinary tract | 8 | 612 | 1.31 |
| Vagina | 0 | 1 | 0 |
| Vulva | 0 | 3 | 0 |
| Total | 33263 | 168311 | 19.76 |

Table 3 below shows select nucleic acid and amino acid sequences of BRAF. These sequences may be used in methods for identifying subjects with a mutant BRAF genotype (such as in the methods set forth below).

TABLE 3

| SEQ ID NO | Nucleic acid or polypeptide | Organism | Other information |
|---|---|---|---|
| 1 | nucleic acid | human | |
| 2 | polypeptide | human | |
| 3 | nucleic acid | rat (Rattus norvegicus) | |
| 4 | polypeptide | rat (Rattus norvegicus) | |
| 5 | nucleic acid | mouse, Mus musculus | |
| 6 | polypeptide | mouse, Mus musculus | |
| 7 | nucleic acid | rabbit, Oryctolagus cuniculus | |
| 8 | polypeptide | rabbit, Oryctolagus cuniculus | |
| 9 | nucleic acid | guinea pig, Cavia porcellus | |
| 10 | polypeptide | guinea pig, Cavia porcellus | |
| 11 | nucleic acid | dog, Canis lupus familiaris | variant x1 |
| 12 | polypeptide | dog, Canis lupus familiaris | variant x1 |
| 13 | nucleic acid | dog, Canis lupus familiaris | variant x2 |
| 14 | polypeptide | dog, Canis lupus familiaris | variant x2 |
| 15 | nucleic acid | cat, Felis catus | |
| 16 | polypeptide | cat, Felis catus | |
| 17 | nucleic acid | cow, Bos taurus | variant X1 |
| 18 | polypeptide | cow, Bos taurus | variant X1 |
| 19 | nucleic acid | cow, Bos taurus | variant X2 |
| 20 | polypeptide | cow, Bos taurus | variant X2 |
| 21 | nucleic acid | cow, Bos taurus | variant X3 |
| 22 | polypeptide | cow, Bos taurus | variant X3 |
| 23 | nucleic acid | cow, Bos taurus | variant X4 |
| 24 | polypeptide | cow, Bos taurus | variant X4 |
| 25 | nucleic acid | cow, Bos taurus | variant X5 |
| 26 | polypeptide | cow, Bos taurus | variant X5 |
| 27 | nucleic acid | cow, Bos taurus | variant X6 |
| 28 | polypeptide | cow, Bos taurus | variant X6 |
| 29 | nucleic acid | cow, Bos taurus | variant X7 |
| 30 | polypeptide | cow, Bos taurus | variant X7 |
| 31 | nucleic acid | cow, Bos taurus | variant X8 |
| 32 | polypeptide | cow, Bos taurus | variant X8 |
| 33 | nucleic acid | cow, Bos taurus | variant X9 |
| 34 | polypeptide | cow, Bos taurus | variant X9 |
| 35 | nucleic acid | cow, Bos taurus | variant X10 |
| 36 | polypeptide | cow, Bos taurus | variant X10 |
| 37 | nucleic acid | cow, Bos taurus | variant X11 |
| 38 | polypeptide | cow, Bos taurus | variant X11 |
| 39 | nucleic acid | cow, Bos taurus | variant 2 |
| 40 | polypeptide | cow, Bos taurus | variant 2 |
| 41 | nucleic acid | horse, Equus caballus | |
| 42 | polypeptide | horse, Equus caballus | |
| 43 | nucleic acid | chicken, Gallus gallus | |
| 44 | polypeptide | chicken, Gallus gallus | |

Methods for identifying mutations in nucleic acids, such as the above identified BRAF genes, are known in the art. Nucleic acids may be obtained from biological samples. In the present invention, biological samples include, but are not limited to, blood, plasma, urine, skin, saliva, and biopsies. Biological samples are obtained from a subject by routine procedures and methods which are known in the art.

Non-limiting examples of methods for identifying mutations include PCR, sequencing, hybrid capture, in-solution capture, molecular inversion probes, fluorescent in situ hybridization (FISH) assays, and combinations thereof.

Various sequencing methods are known in the art. These include, but are not limited to, Sanger sequencing (also referred to as dideoxy sequencing) and various sequencing-by-synthesis (SBS) methods as disclosed in, e.g., Metzker 2005, sequencing by hybridization, by ligation (for example, WO 2005021786), by degradation (for example, U.S. Pat. Nos. 5,622,824 and 6,140,053) and nanopore sequencing (which is commercially available from Oxford Nanopore Technologies, UK). In deep sequencing techniques, a given nucleotide in the sequence is read more than once during the sequencing process. Deep sequencing techniques are disclosed in e.g., U.S. Patent Publication No. 20120264632 and International Patent Publication No. WO2012125848.

The PCR-based methods for detecting mutations are known in the art and employ PCR amplification, where each target sequence in the sample has a corresponding pair of unique, sequence-specific primers. For example, the polymerase chain reaction-restriction fragment length polymorphism (PCR-RFLP) method allows for rapid detection of mutations after the genomic sequences are amplified by PCR. The mutation is discriminated by digestion with specific restriction endonucleases and is identified by electrophoresis. See, e.g., Ota et al., 2007. Mutations may also be detected using real time PCR. See, e.g., International Application publication No. WO2012046981.

Hybrid capture methods are known in the art and are disclosed in, e.g., U.S. Patent Publication No. 20130203632 and U.S. Pat. Nos. 8,389,219 and 8,288,520. These methods are based on the selective hybridization of the target genomic regions to user-designed oligonucleotides. The hybridization can be to oligonucleotides immobilized on high or low density microarrays (on-array capture), or solution-phase hybridization to oligonucleotides modified with a ligand (e.g. biotin) which can subsequently be immobilized to a solid surface, such as a bead (in-solution capture).

Molecular Inversion Probe (MIP) methods are known in the art and are disclosed in e.g., Absalan et al., 2008. Such methods use MIP molecules, which are special "padlock" probes (Nilsson et al., 1994) for genotyping. A MIP molecule is a linear oligonucleotide that contains specific regions, universal sequences, restriction sites and a Tag (index) sequence (16-22 bp). In such methods, a MIP hybridizes directly around the genetic marker/SNP of interest. The MIP method may also use a number of "padlock" probe sets that hybridize to genomic DNA in parallel (Hardenbol et al., 2003). In case of a perfect match, genomic homology regions are ligated by undergoing an inversion in configuration (as suggested by the name of the technique) and creating a circular molecule. After the first restriction, all molecules are amplified with universal primers. Amplicons are restricted again to ensure short fragments for hybridization on a microarray. Generated short fragments are labeled and, through a Tag sequence, hybridized to a cTag (complementary strand for index) on an array. After the formation of a Tag-cTag duplex, a signal is detected.

As used herein, being "refractory" to MAPK pathway inhibitor treatment means that one or more MAPK pathway inhibitors has reduced efficacy in treating cancer.

As used herein, a "mitogen-activated protein kinase (MAPK) pathway inhibitor" is any substance that reduces the activity, expression or phosphorylation of proteins in the MAPK pathway that result in a reduction of cell growth or an increase in cell death.

Figure 30:
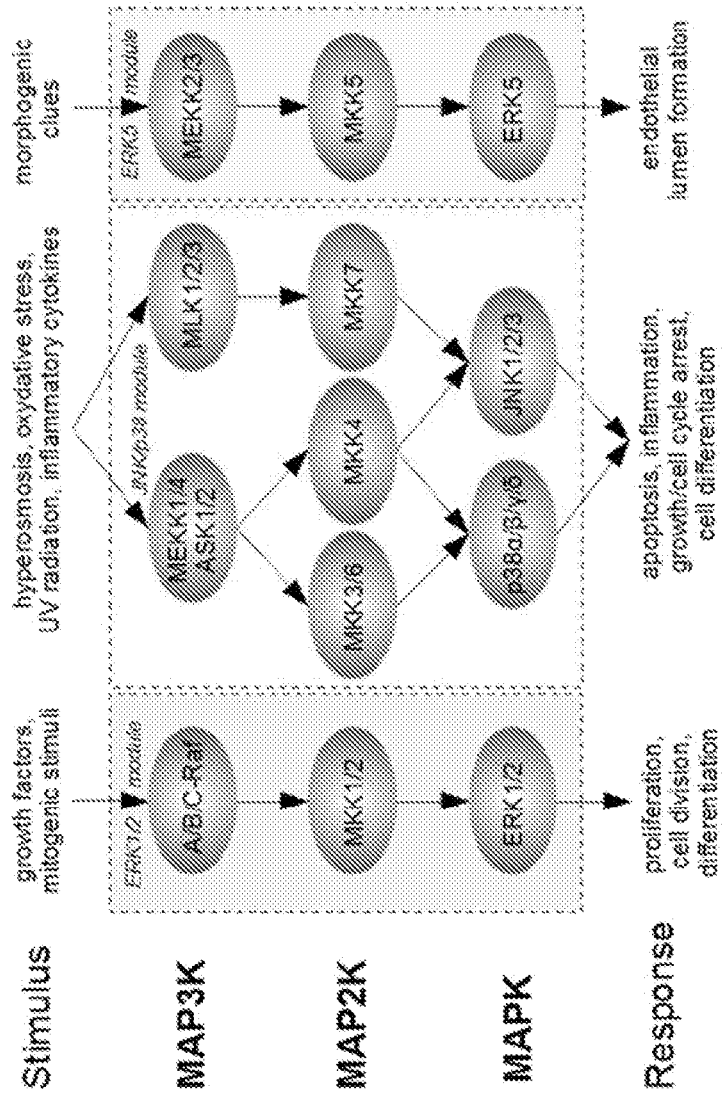
FIG. 30 shows a schematic of the mitogen-activated protein kinases (MAPK) pathway.
Figure 31:
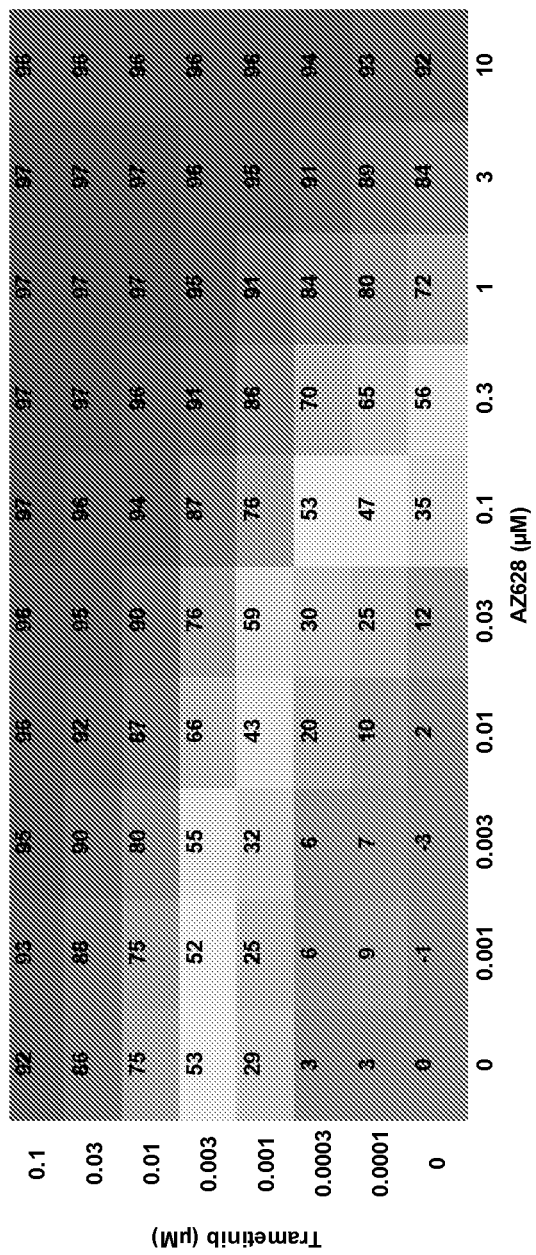
FIG. 31A is a dose matrix showing % inhibition of the AZ628/trametinib combination in HCT116 cells using the Alamar Blue cell viability assay.
FIG. 31B is a dose matrix showing excess over Bliss for the AZ628/trametinib combination.
FIGS. 31C and 31D show % viability relative to DMSO only treated controls for AZ628 and trametinib single agent treatments in HCT116 cells using the Alamar Blue cell viability assay.
FIG. 31E shows % viability relative to DMSO only treated controls for AZ628/trametinib combination treatments in HCT116 cells using the Alamar Blue cell viability assay.
Figure 32:
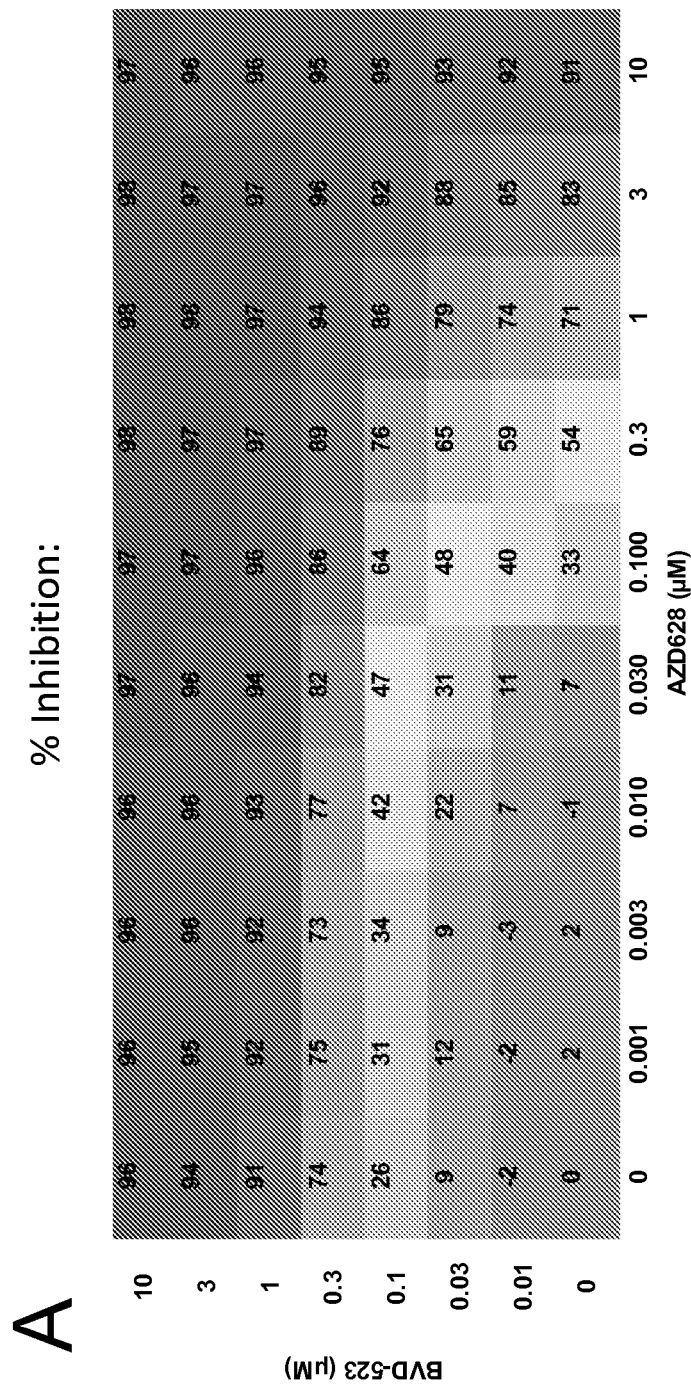
FIG. 32A is a dose matrix showing % inhibition of the AZ628/BVD-523 combination in HCT116 cells using the Alamar Blue cell viability assay.
FIG. 32B is a dose matrix showing excess over Bliss for the AZ628/BVD-523 combination.
FIGS. 32C and 32D show % viability relative to DMSO only treated controls for AZ628 and BVD-523 single agent treatments in HCT116 cells using the Alamar Blue cell viability assay.
FIG. 32E shows % viability relative to DMSO only treated controls for AZ628/BVD-523 combination treatments in HCT116 cells using the Alamar Blue cell viability assay.
Figure 33:
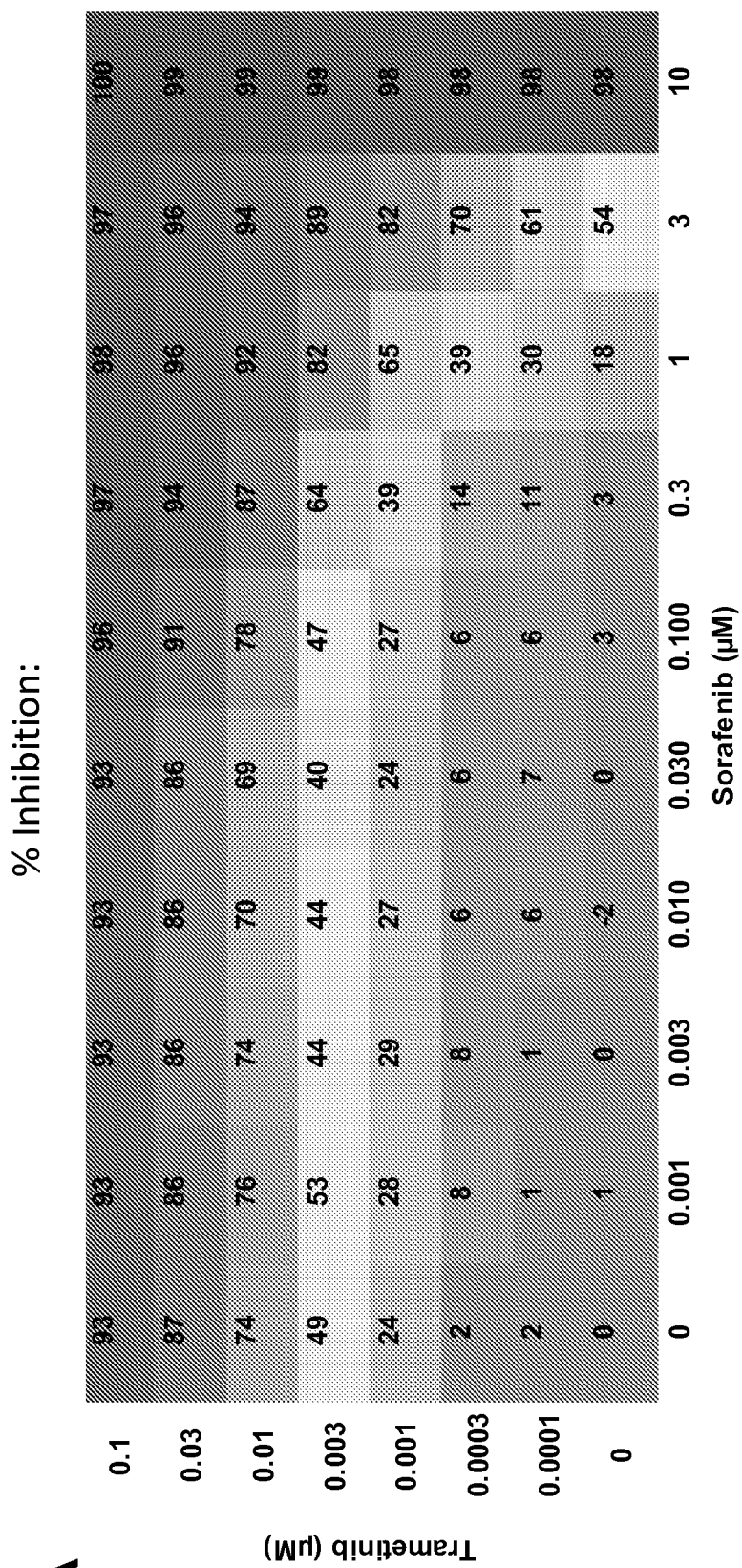
FIG. 33A is a dose matrix showing % inhibition of the sorafenib/trametinib combination in HCT116 cells using the Alamar Blue cell viability assay.
FIG. 33B is a dose matrix showing excess over Bliss for the sorafenib/trametinib combination.
FIGS. 33C and 33D show % viability relative to DMSO only treated controls for sorafenib and trametinib single agent treatments in HCT116 cells using the Alamar Blue cell viability assay.
FIG. 33E shows % viability relative to DMSO only treated controls for sorafenib/trametinib combination treatments in HCT116 cells using the Alamar Blue cell viability assay.
Figure 34:
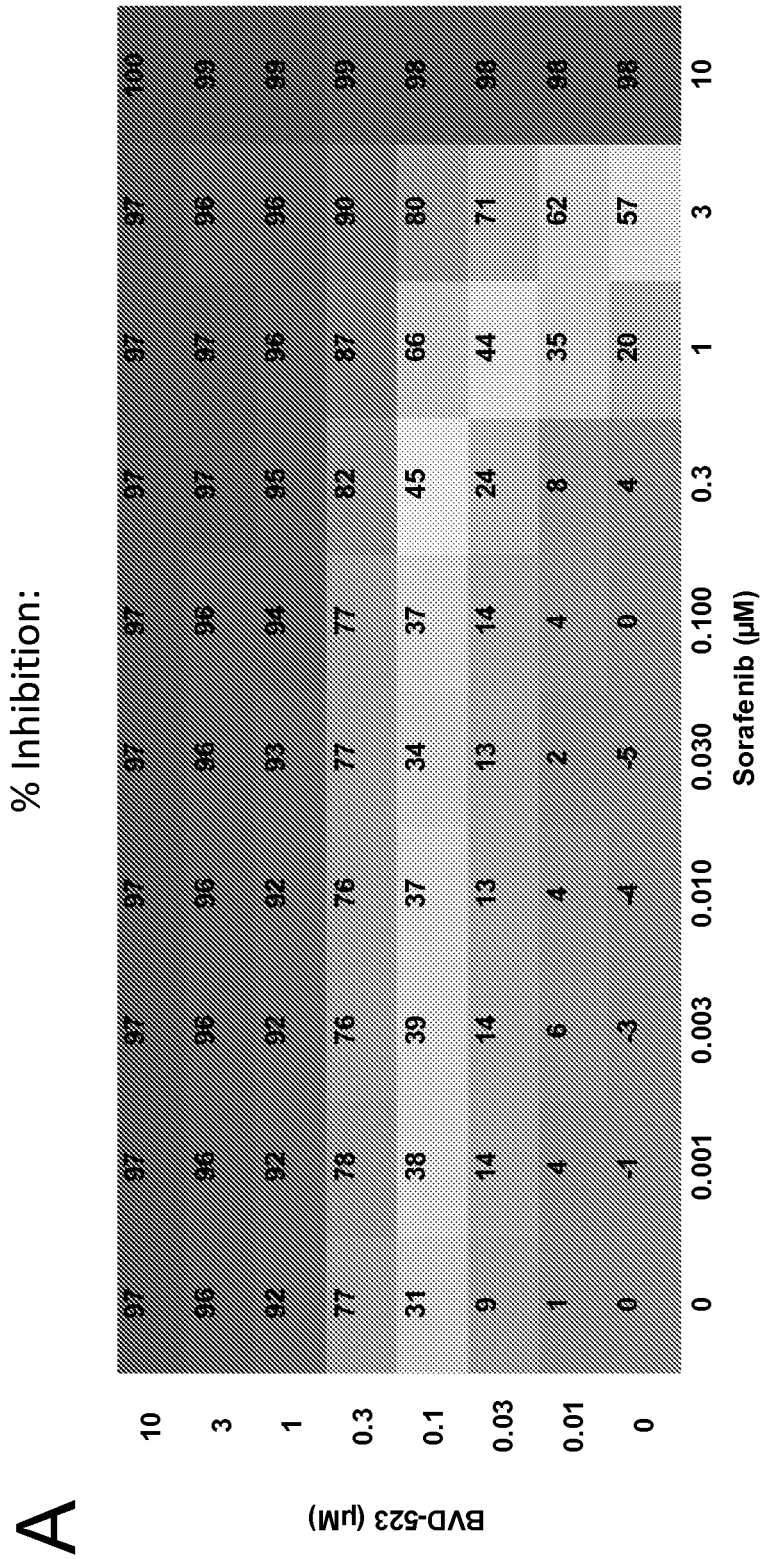
FIG. 34A is a dose matrix showing % inhibition of the sorafenib/BVD-523 combination in HCT116 cells using the Alamar Blue cell viability assay.
FIG. 34B is a dose matrix showing excess over Bliss for the sorafenib/BVD-523 combination.
FIGS. 34C and 34D show % viability relative to DMSO only treated controls for sorafenib and BVD-523 single agent treatments in HCT116 cells using the Alamar Blue cell viability assay.
FIG. 34E shows % viability relative to DMSO only treated controls for sorafenib/BVD-523 combination treatments in HCT116 cells using the Alamar Blue cell viability assay.
Figure 35:
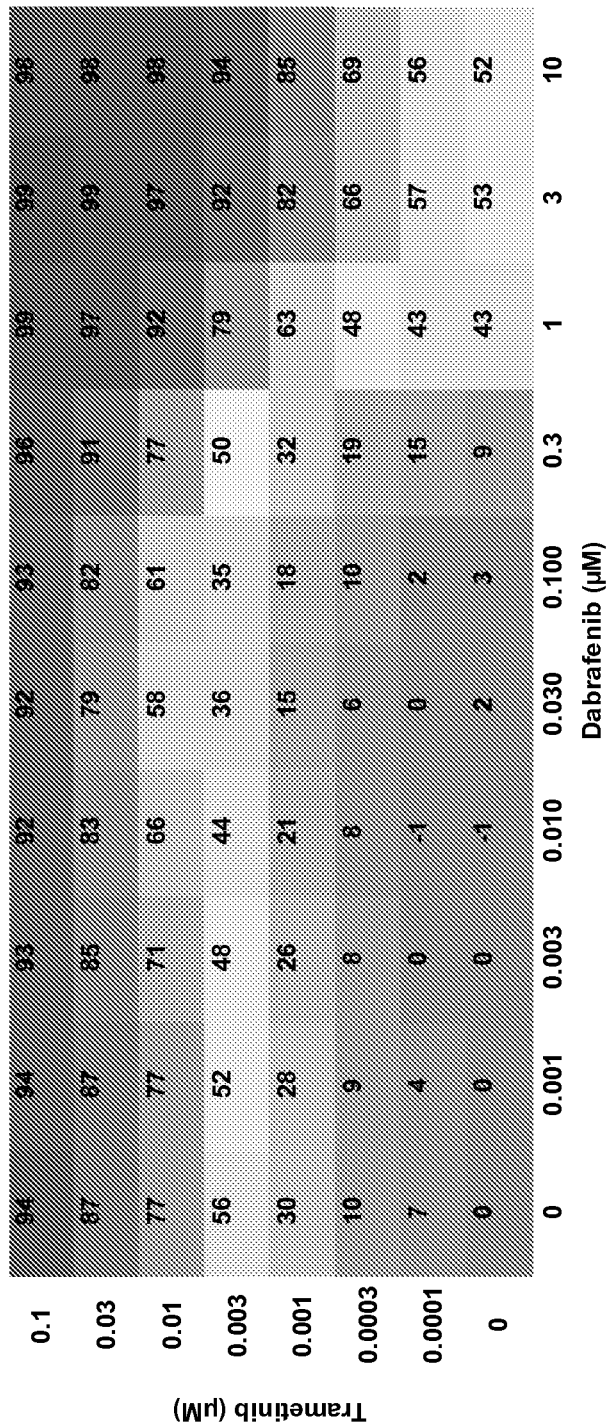
FIG. 35A is a dose matrix showing % inhibition of the dabrafenib/trametinib combination in HCT116 cells using the Alamar Blue cell viability assay.
FIG. 35B is a dose matrix showing excess over Bliss for the dabrafenib/trametinib combination.
FIGS. 35C and 35D show % viability relative to DMSO only treated controls for dabrafenib and trametinib single agent treatments in HCT116 cells using the Alamar Blue cell viability assay.
FIG. 35E shows % viability relative to DMSO only treated controls for dabrafenib/trametinib combination treatments in HCT116 cells using the Alamar Blue cell viability assay.
Figure 36:
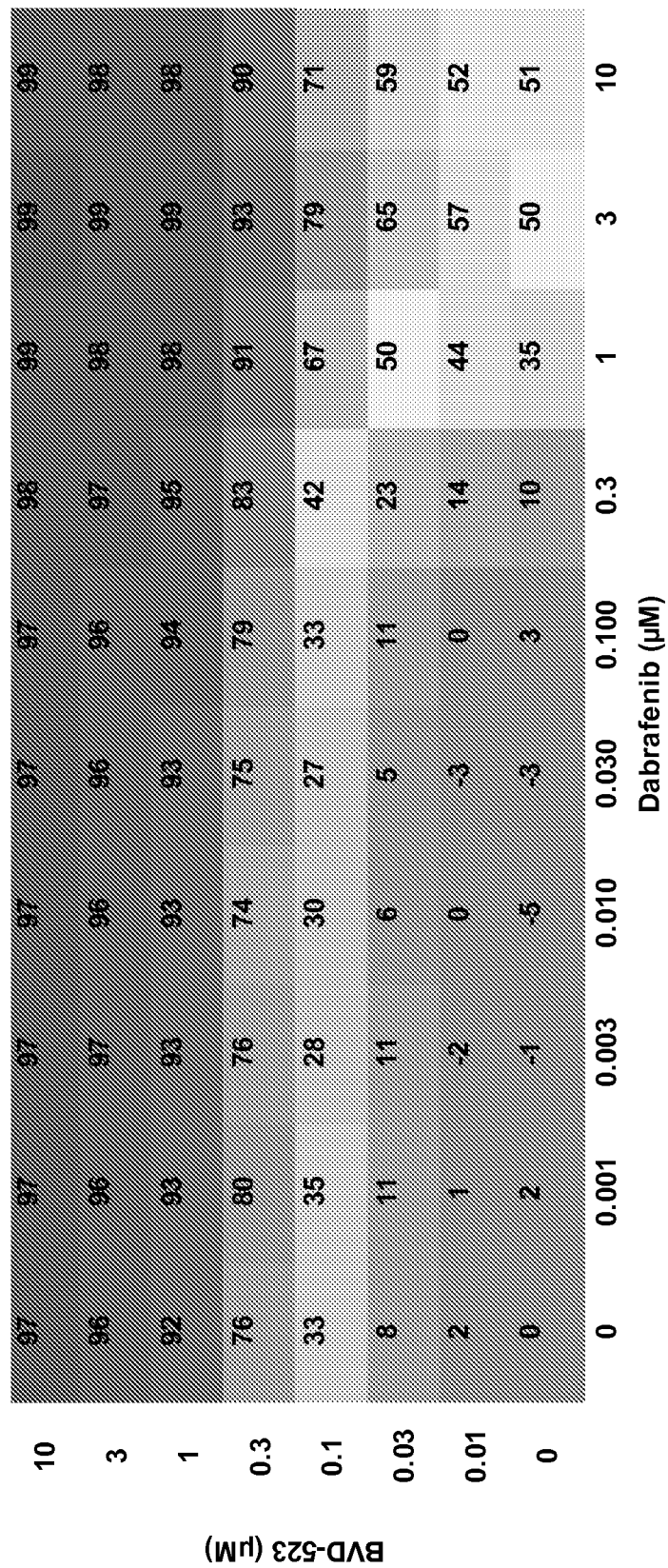
FIG. 36A is a dose matrix showing % inhibition of the dabrafenib/BVD-523 combination in HCT116 cells using the Alamar Blue cell viability assay.
FIG. 36B is a dose matrix showing excess over Bliss for the dabrafenib/BVD-523 combination.
FIGS. 36C and 36D show % viability relative to DMSO only treated controls for dabrafenib and BVD-523 single agent treatments in HCT116 cells using the Alamar Blue cell viability assay.
FIG. 36E shows % viability relative to DMSO only treated controls for dabrafenib/BVD-523 combination treatments in HCT116 cells using the Alamar Blue cell viability assay.
Figure 37:
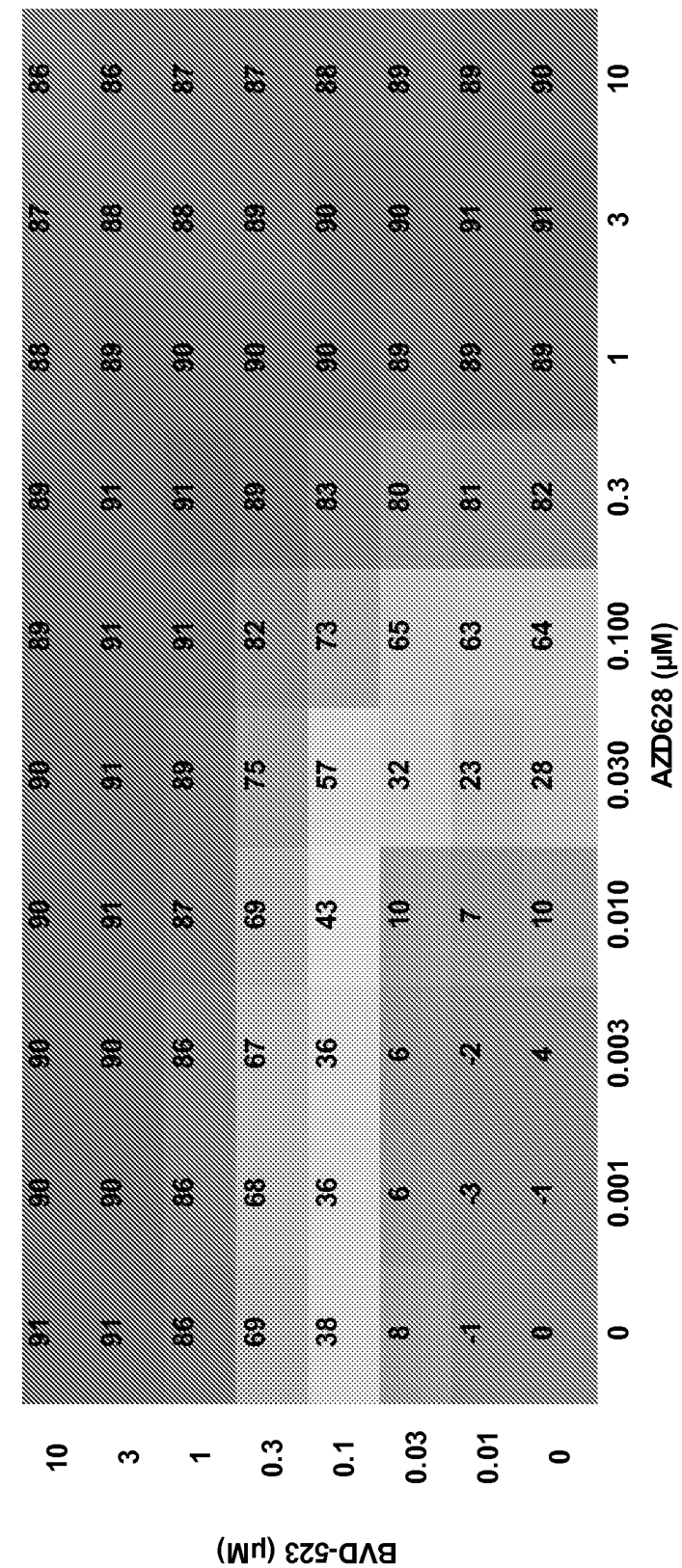
FIG. 37A is a dose matrix showing % inhibition of the AZ628/BVD-523 combination in A375 cells using the Alamar Blue cell viability assay.
FIG. 37B is a dose matrix showing excess over Bliss for the AZ628/BVD-523 combination.
FIGS. 37C and 37D show % viability relative to DMSO only treated controls for AZ628 and BVD-523 single agent treatments in A375 cells using the Alamar Blue cell viability assay.
FIG. 37E shows % viability relative to DMSO only treated controls for AZ628/BVD-523 combination treatments in A375 cells using the Alamar Blue cell viability assay.
Figure 38:
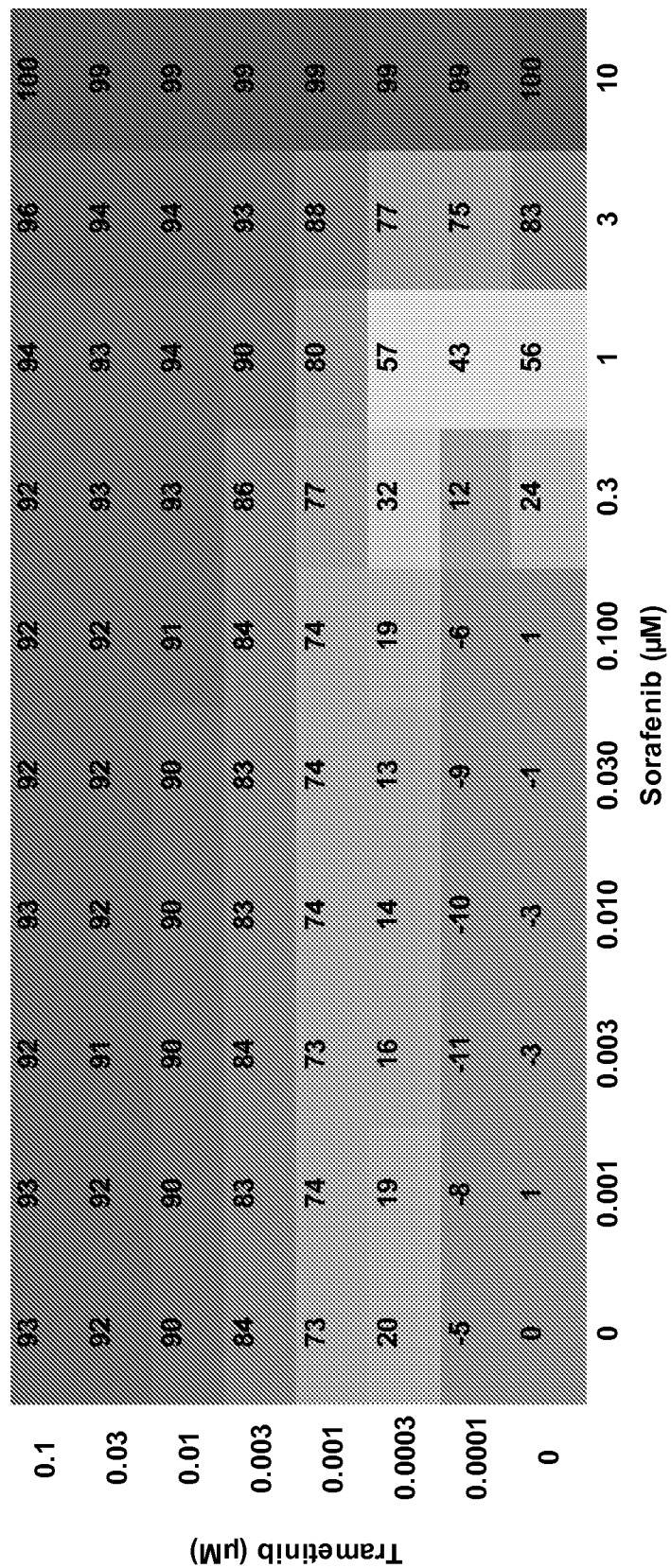
FIG. 38A is a dose matrix showing % inhibition of the sorafenib/trametinib combination in A375 cells using the Alamar Blue cell viability assay.
FIG. 38B is a dose matrix showing excess over Bliss for the sorafenib/trametinib combination.
FIGS. 38C and 38D show % viability relative to DMSO only treated controls for sorafenib and trametinib single agent treatments in A375 cells using the Alamar Blue cell viability assay.
FIG. 38E shows % viability relative to DMSO only treated controls for sorafenib/trametinib combination treatments in A375 cells using the Alamar Blue cell viability assay.
Figure 39:
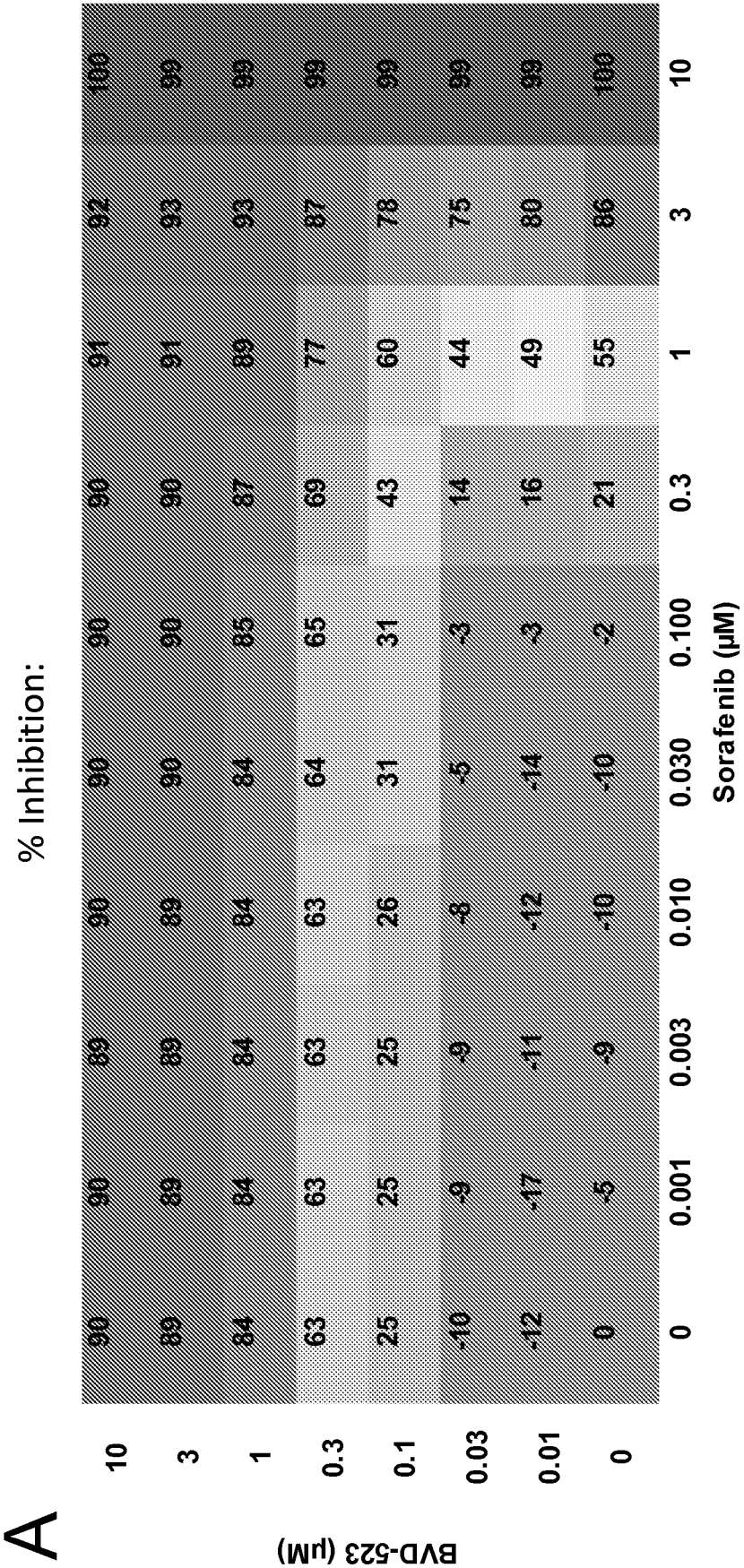
FIG. 39A is a dose matrix showing % inhibition of the sorafenib/BVD-523 combination in A375 cells using the Alamar Blue cell viability assay.
FIG. 39B is a dose matrix showing excess over Bliss for the sorafenib/BVD-523 combination.
FIGS. 39C and 39D show % viability relative to DMSO only treated controls for sorafenib and BVD-523 single agent treatments in A375 cells using the Alamar Blue cell viability assay.
FIG. 39E shows % viability relative to DMSO only treated controls for sorafenib/BVD-523 combination treatments in A375 cells using the Alamar Blue cell viability assay.
Figure 41:
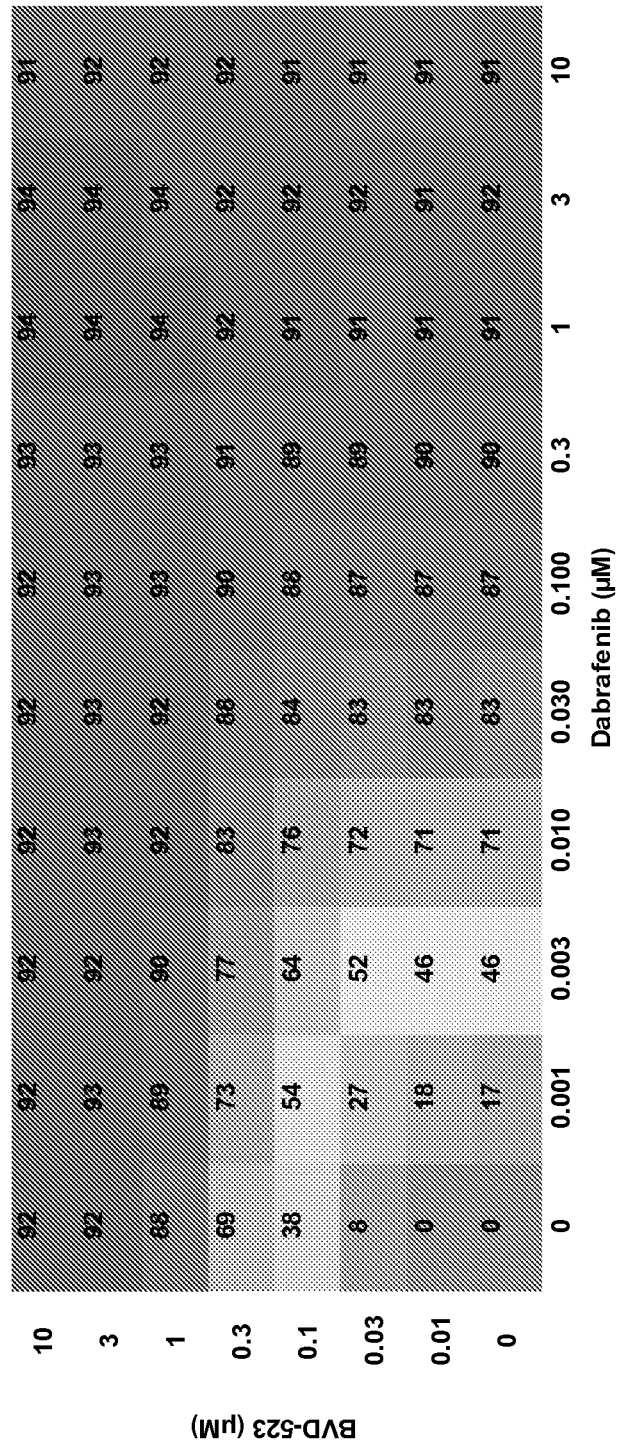
FIG. 41A is a dose matrix showing % inhibition of the dabrafenib/BVD-523 combination in A375 cells using the Alamar Blue cell viability assay.
FIG. 41B is a dose matrix showing excess over Bliss for the dabrafenib/BVD-523 combination.
FIGS. 41C and 41D show % viability relative to DMSO only treated controls for dabrafenib and BVD-523 single agent treatments in A375 cells using the Alamar Blue cell viability assay.
FIG. 41E shows % viability relative to DMSO only treated controls for dabrafenib/BVD-523 combination treatments in A375 cells using the Alamar Blue cell viability assay.
Figure 43:
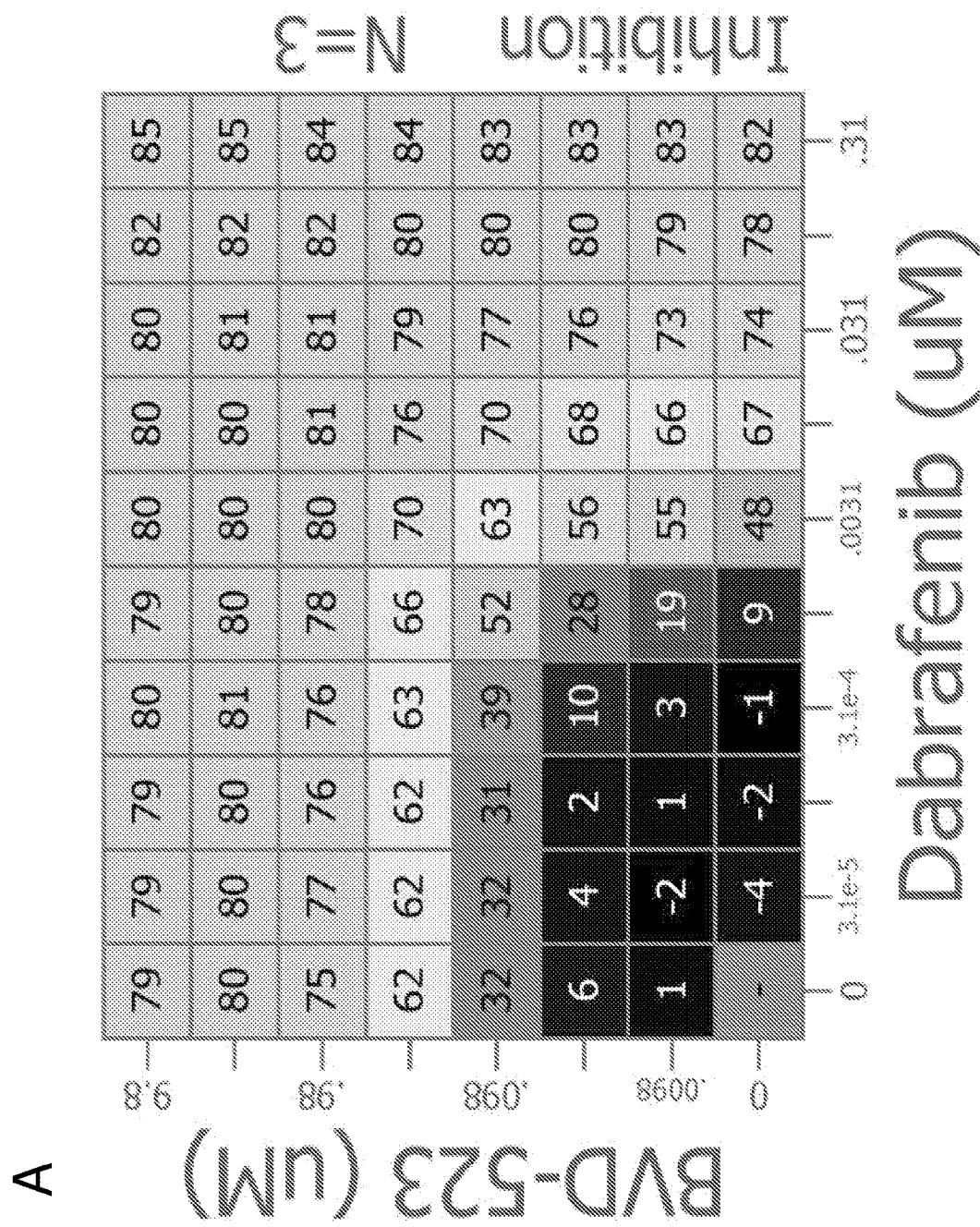
FIG. 43A is a dose matrix showing % inhibition of the Dabrafenib/BVD-523 combination in A375 cells.
FIG. 43B is a dose matrix showing Loewe excess for the Dabrafenib/BVD-523 combination.
FIG. 43C is a dose matrix showing Bliss excess for the Dabrafenib/BVD-523 combination.
FIGS. 43D and 43E, respectively, show % viability relative to DMSO only treated controls for Dabrafenib and BVD-523 single agent treatments in A375 cells.
Figure 44:
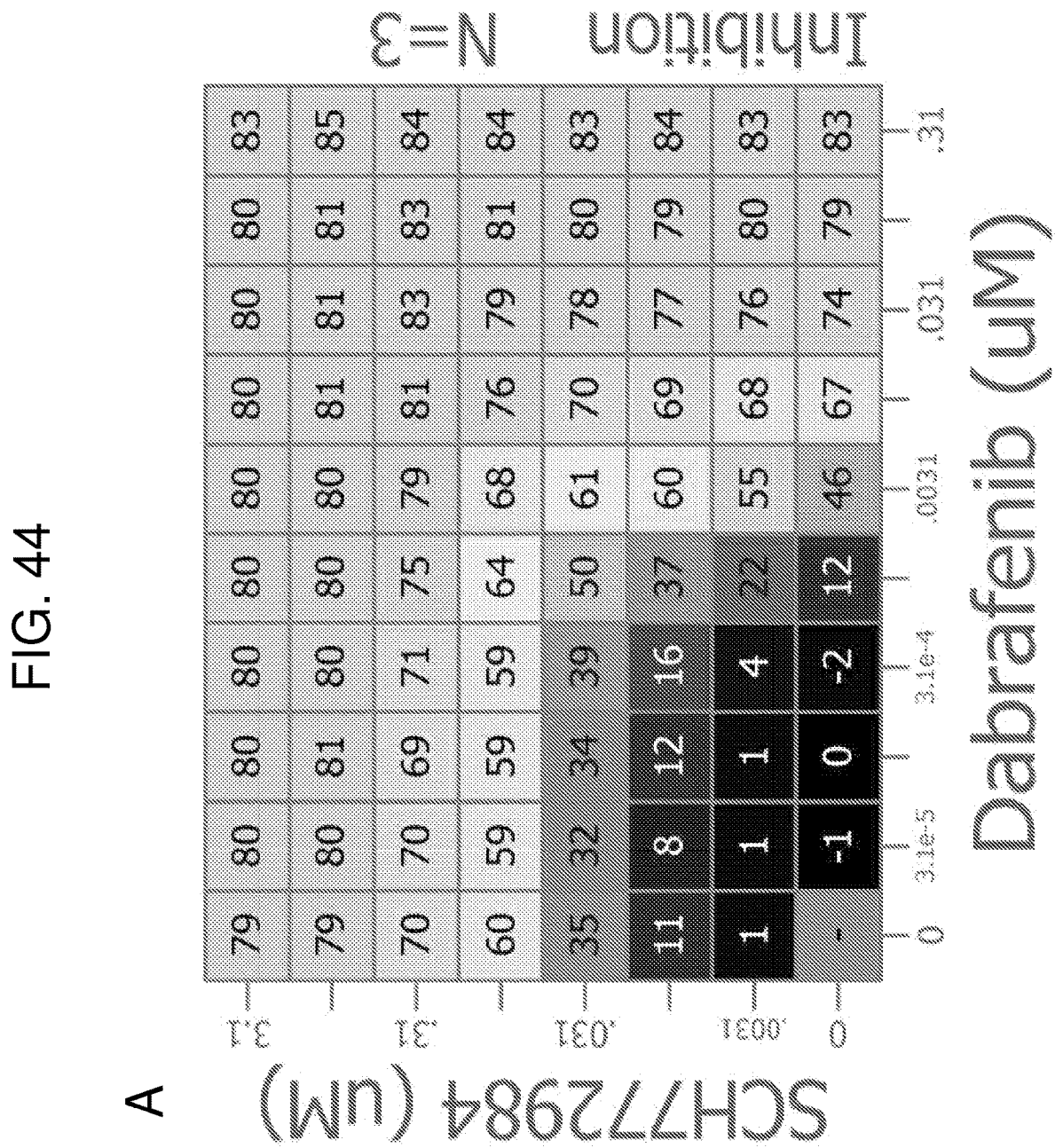
FIG. 44A is a dose matrix showing % inhibition of the Dabrafenib/SCH772984 combination in A375 cells.
Figure 45:
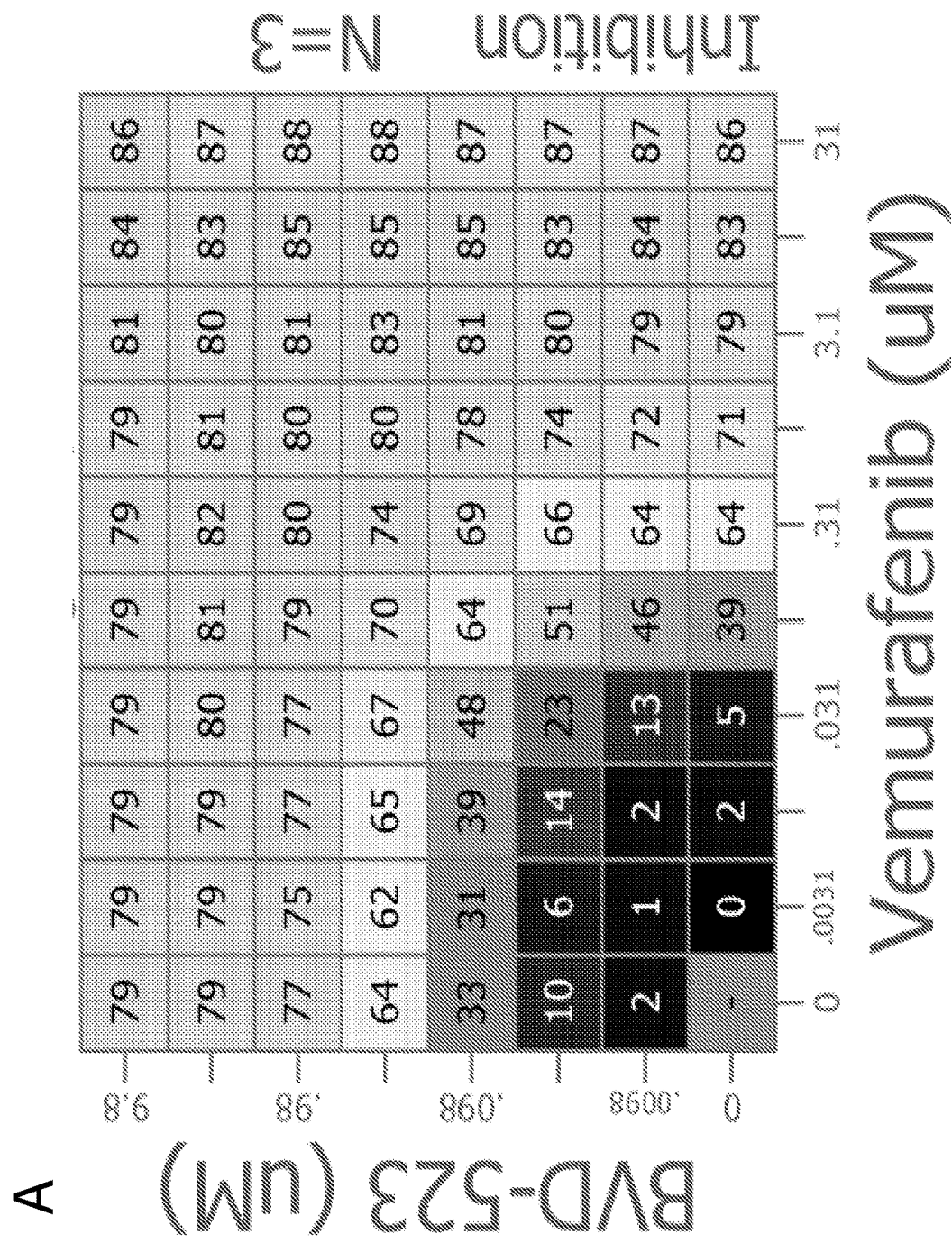
FIG. 45A is a dose matrix showing % inhibition of the Vemurafenib/BVD-523 combination in A375 cells.
FIG. 45B is a dose matrix showing Loewe excess for the Vemurafenib/BVD-523 combination.
FIG. 45C is a dose matrix showing Bliss excess for the Vemurafenib/BVD-523 combination.
FIGS. 45D and 45E, respectively, show % viability relative to DMSO only treated controls for Vemurafenib and BVD-523 single agent treatments in A375 cells.
Figure 46:
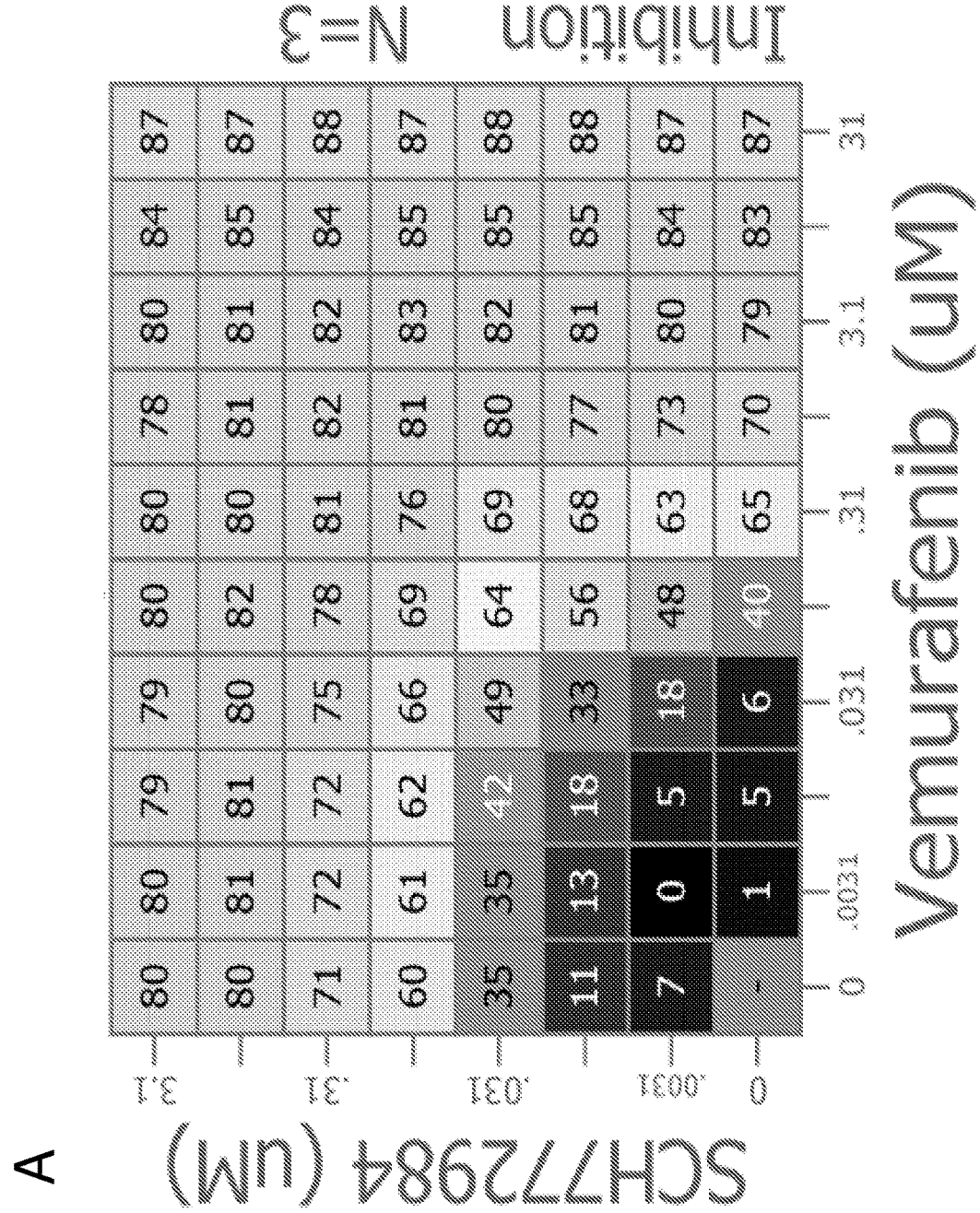
FIG. 46A is a dose matrix showing % inhibition of the Vemurafenib/SCH772984 combination in A375 cells.
FIG. 46B is a dose matrix showing Loewe excess for the Vemurafenib/SCH772984 combination.
FIG. 46C is a dose matrix showing Bliss excess for the Vemurafenib/SCH772984 combination.
FIGS. 46D and 46E, respectively, show % viability relative to DMSO only treated controls for Vemurafenib and SCH772984 single agent treatments in A375 cells.
Figure 47:
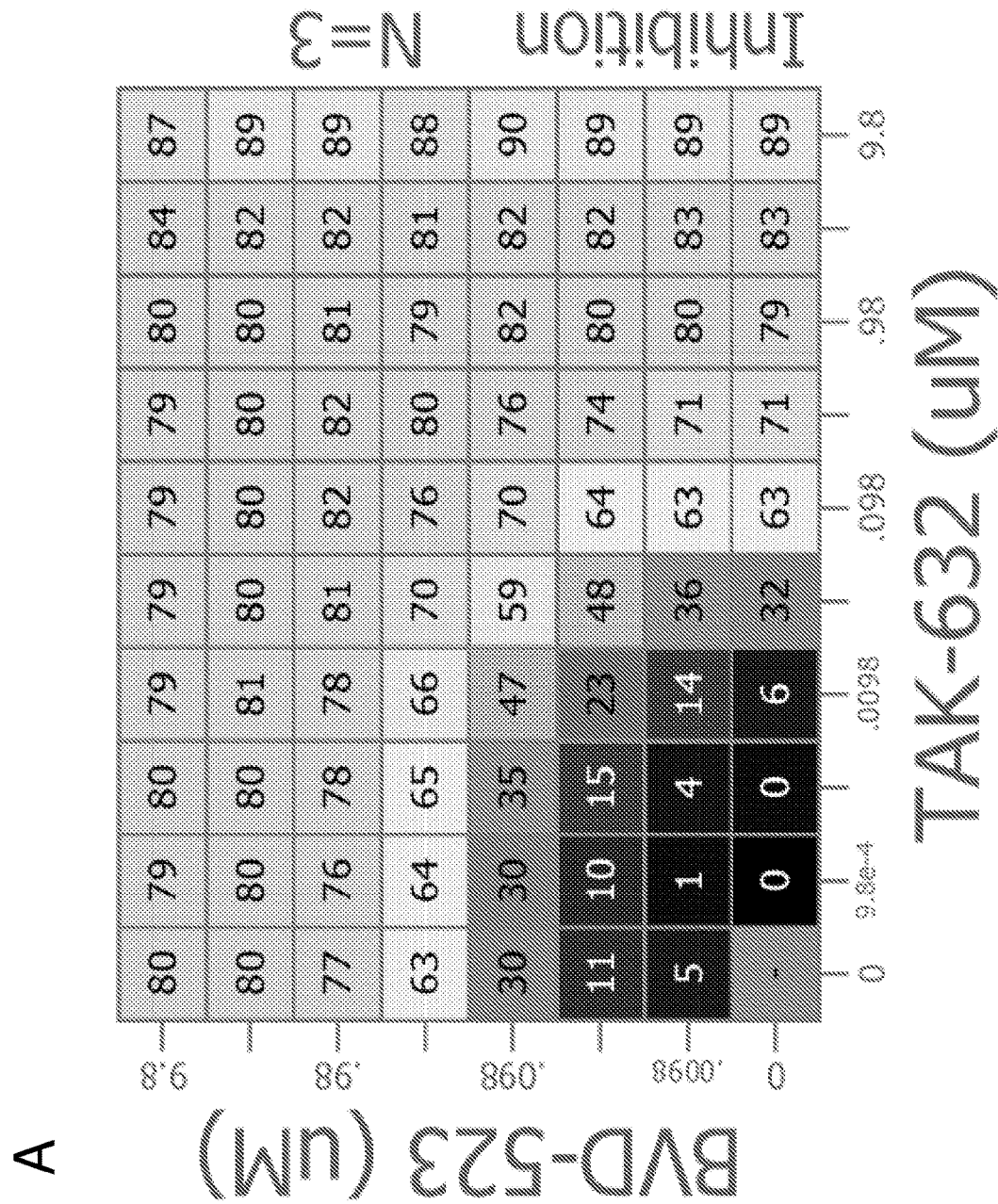
FIG. 47A is a dose matrix showing % inhibition of the TAK-632/BVD-523 combination in A375 cells.
FIG. 47B is a dose matrix showing Loewe excess for the TAK-632/BVD-523 combination.
FIG. 47C is a dose matrix showing Bliss excess for the TAK-632/BVD-523 combination.
FIGS. 47D and 47E, respectively, show % viability relative to DMSO only treated controls for TAK-632 and BVD-523 single agent treatments in A375 cells.
Figure 48:
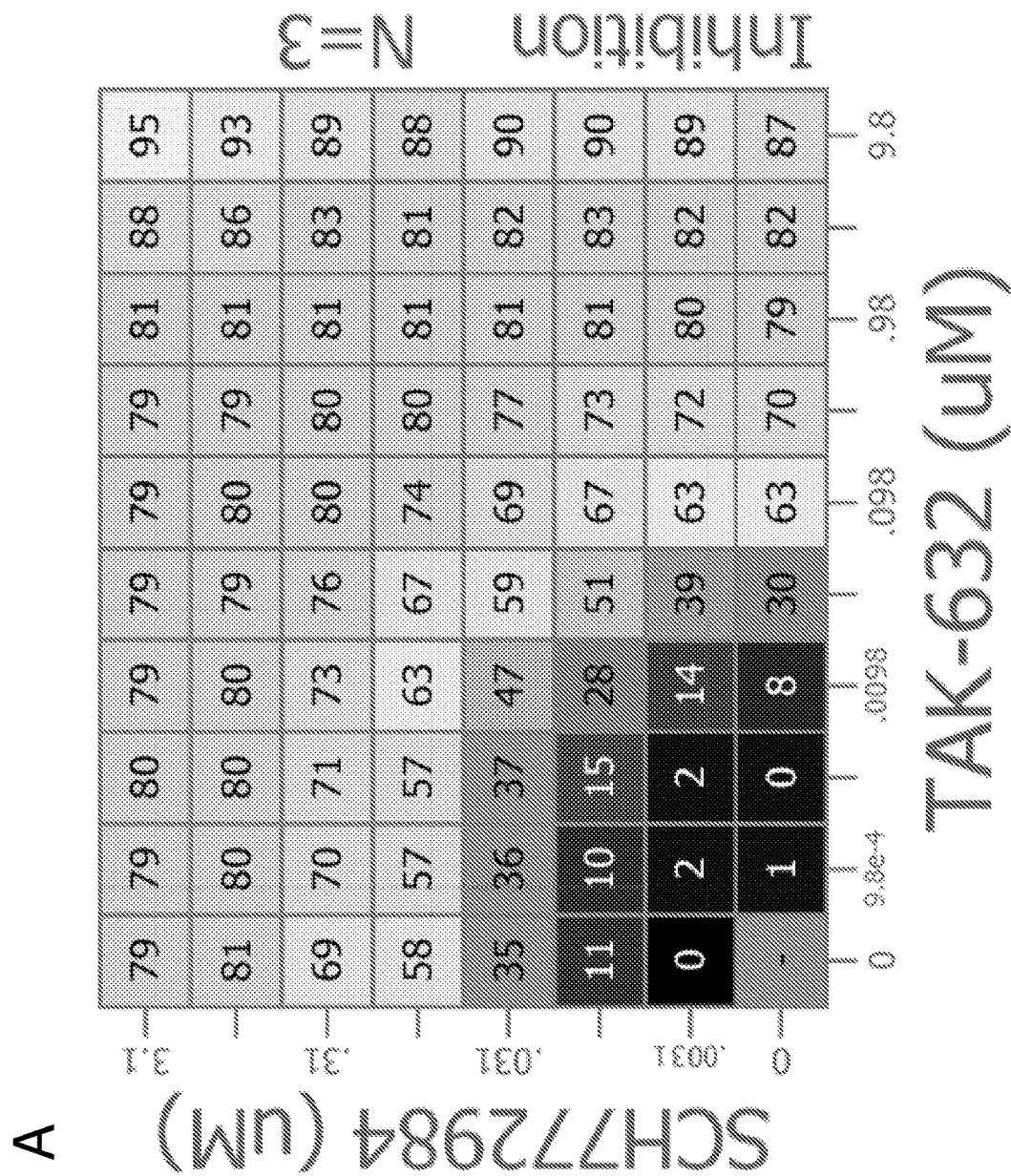
FIG. 48A is a dose matrix showing % inhibition of the TAK-632/SCH772984 combination in A375 cells.
FIG. 48B is a dose matrix showing Loewe excess for the TAK-632/SCH772984 combination.
FIG. 48C is a dose matrix showing Bliss excess for the TAK-632/SCH772984 combination.
FIGS. 48D and 48E, respectively, show % viability relative to DMSO only treated controls for TAK-632 and SCH772984 single agent treatments in A375 cells.
Figure 49:
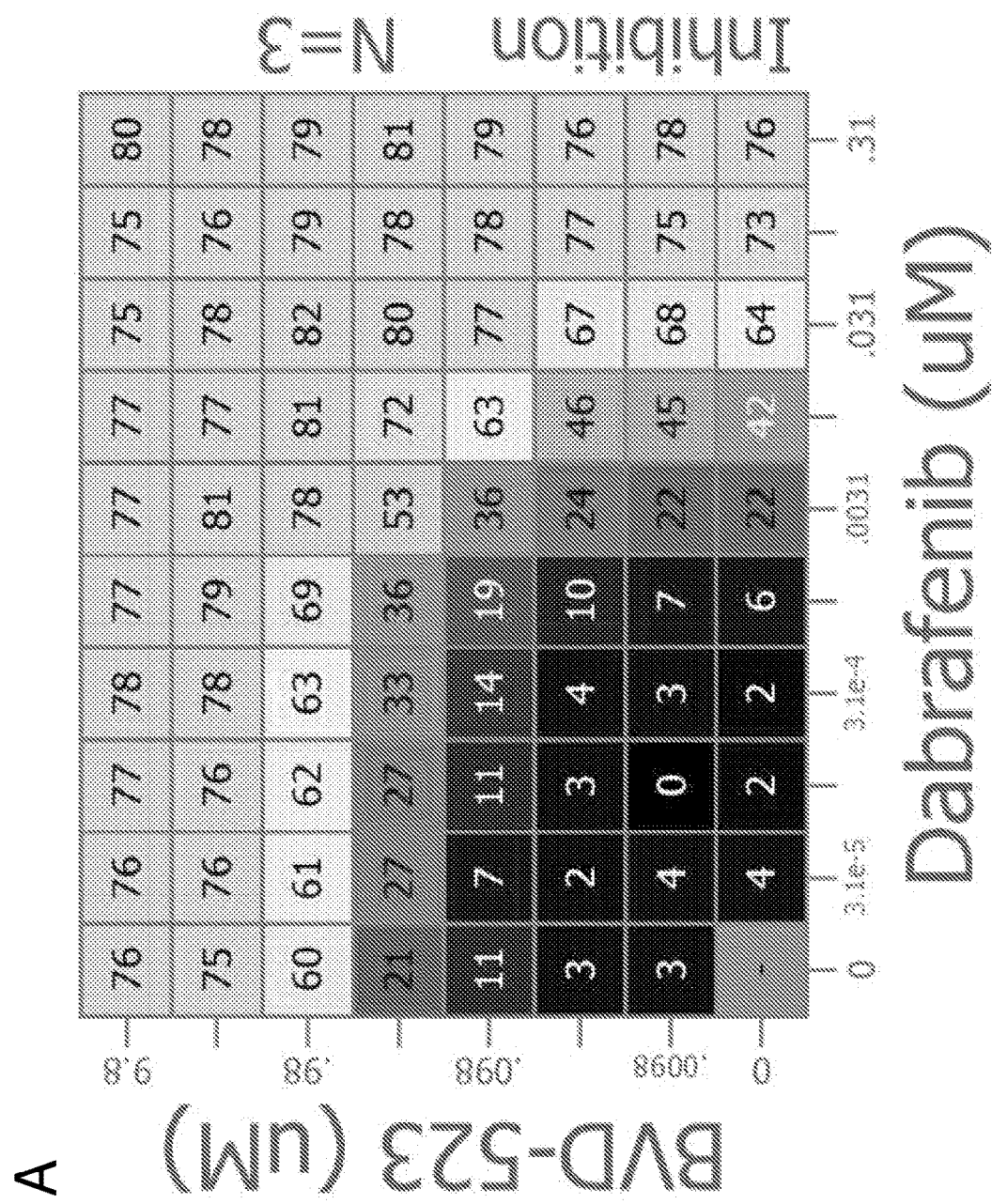
FIG. 49A is a dose matrix showing % inhibition of the Dabrafenib/BVD-523 combination in G-361 cells.
FIG. 49B is a dose matrix showing Loewe excess for the Dabrafenib/BVD-523 combination.
FIG. 49C is a dose matrix showing Bliss excess for the Dabrafenib/BVD-523 combination.
FIGS. 49D and 49E, respectively, show % viability relative to DMSO only treated controls for Dabrafenib and BVD-523 single agent treatments in G-361 cells.
Figure 50:
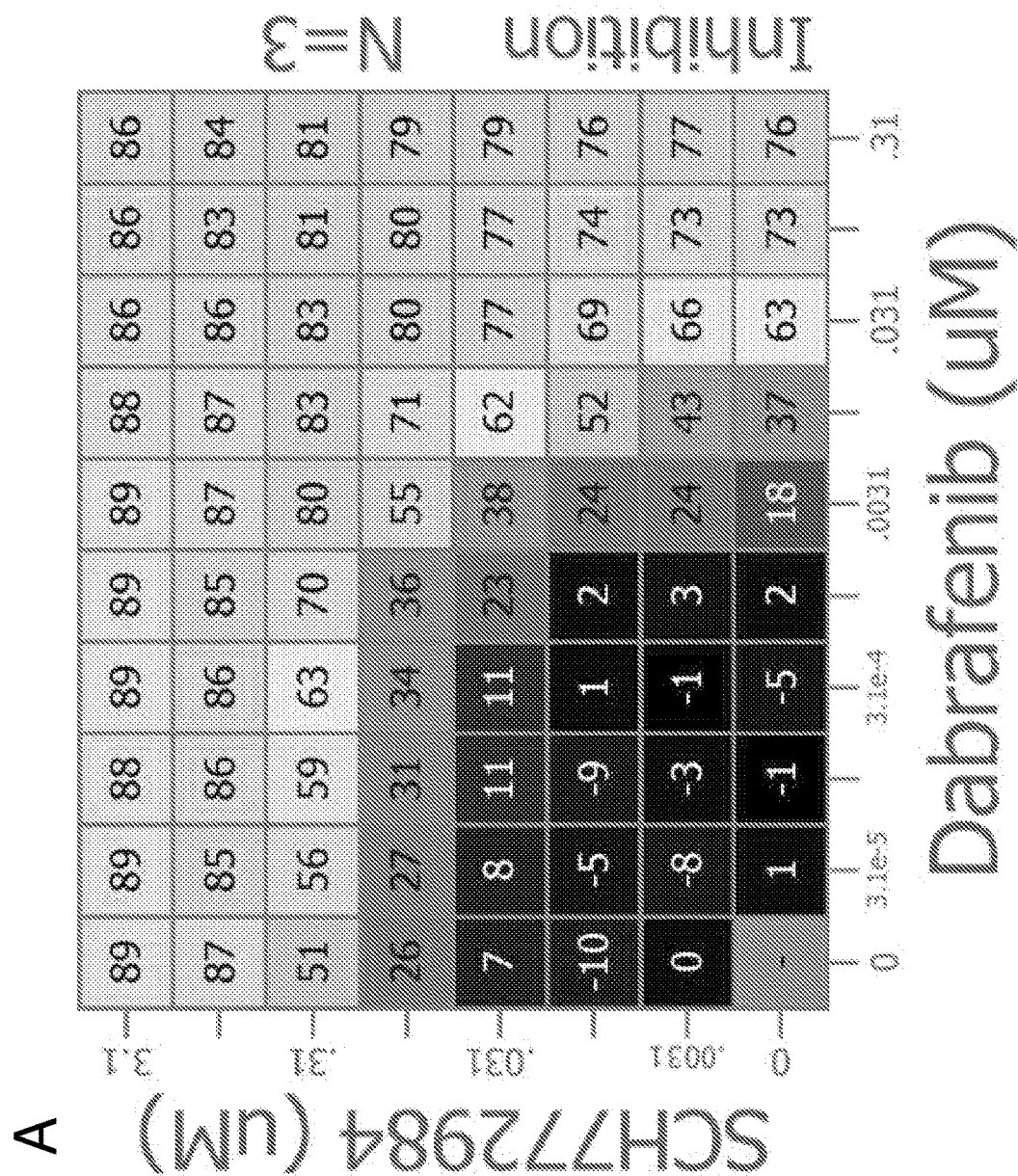
FIG. 50A is a dose matrix showing % inhibition of the Dabrafenib/SCH772984 combination in G-361 cells.
FIG. 50B is a dose matrix showing Loewe excess for the Dabrafenib/SCH772984 combination.
FIG. 50C is a dose matrix showing Bliss excess for the Dabrafenib/SCH772984 combination.
FIGS. 50D and 50E, respectively, show % viability relative to DMSO only treated controls for Dabrafenib and SCH772984 single agent treatments in G-361 cells.
Figure 51:
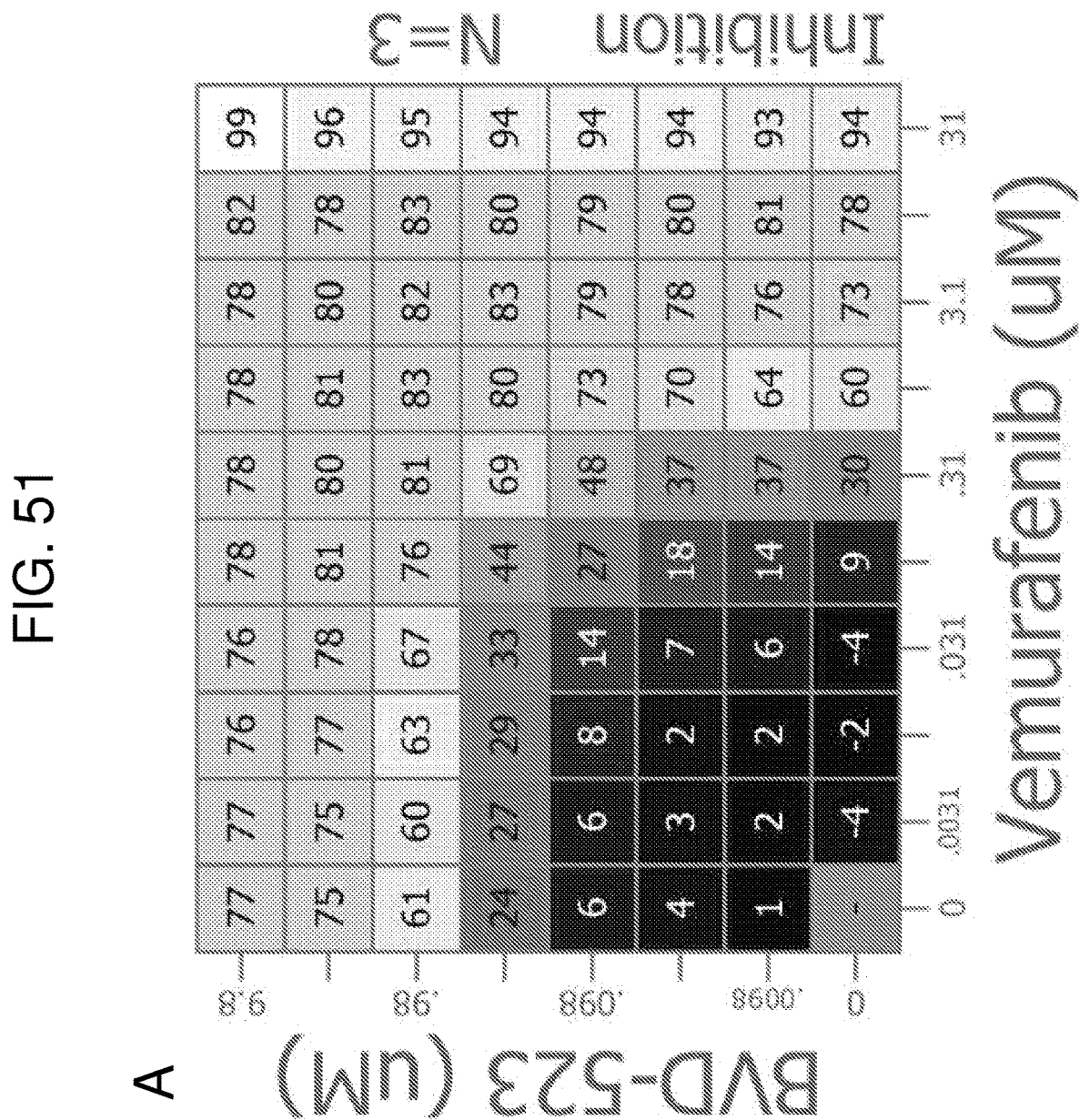
FIG. 51A is a dose matrix showing % inhibition of the Vemurafenib/BVD-523 combination in G-361 cells.
FIG. 51B is a dose matrix showing Loewe excess for the Vemurafenib/BVD-523 combination.
FIG. 51C is a dose matrix showing Bliss excess for the Vemurafenib/BVD-523 combination.
FIGS. 51D and 51E, respectively, show % viability relative to DMSO only treated controls for Vemurafenib and BVD-523 single agent treatments in G-361 cells.
Figure 52:
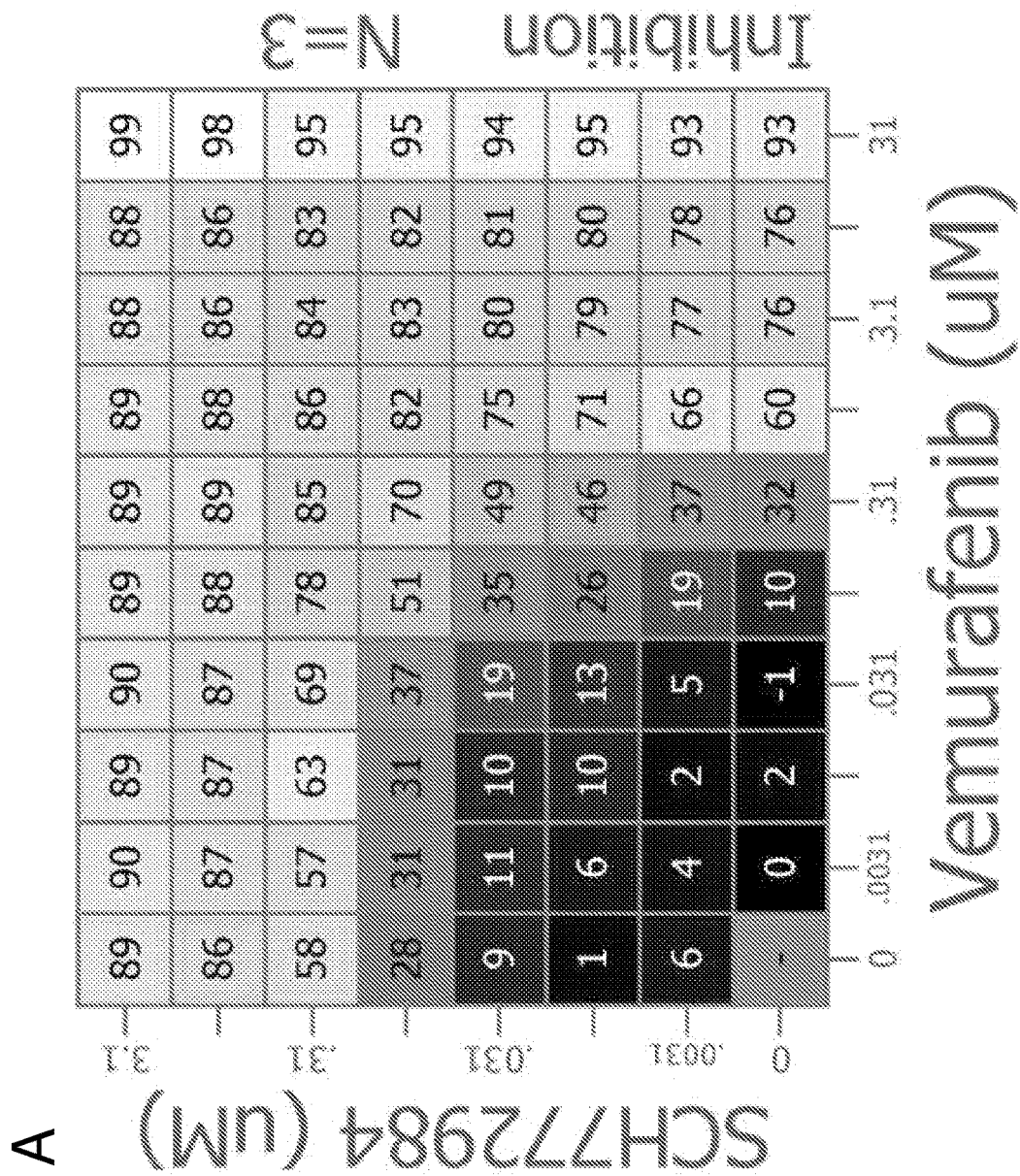
FIG. 52A is a dose matrix showing % inhibition of the Vemurafenib/SCH772984 combination in G-361 cells.
FIG. 52B is a dose matrix showing Loewe excess for the Vemurafenib/SCH772984 combination.
FIG. 52C is a dose matrix showing Bliss excess for the Vemurafenib/SCH772984 combination.
FIGS. 52D and 52E, respectively, show % viability relative to DMSO only treated controls for Vemurafenib and SCH772984 single agent treatments in G-361 cells.
Figure 53:
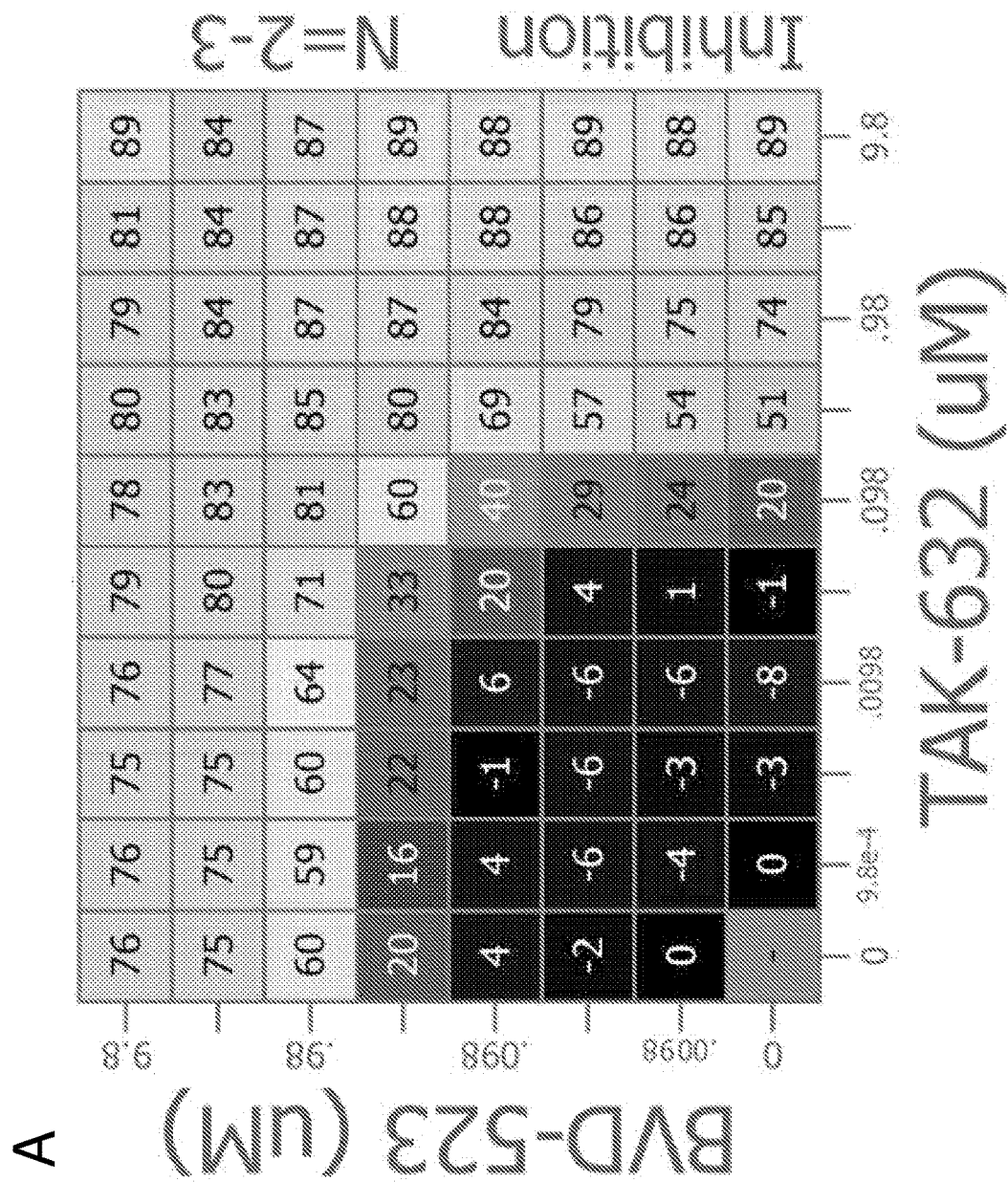
FIG. 53A is a dose matrix showing % inhibition of the TAK-632/BVD-523 combination in G-361 cells.
FIG. 53B is a dose matrix showing Loewe excess for the TAK-632/BVD-523 combination.
FIG. 53C is a dose matrix showing Bliss excess for the TAK-632/BVD-523 combination.
FIGS. 53D and 53E, respectively, show % viability relative to DMSO only treated controls for TAK-632 and BVD-523 single agent treatments in G-361 cells.
Figure 54:
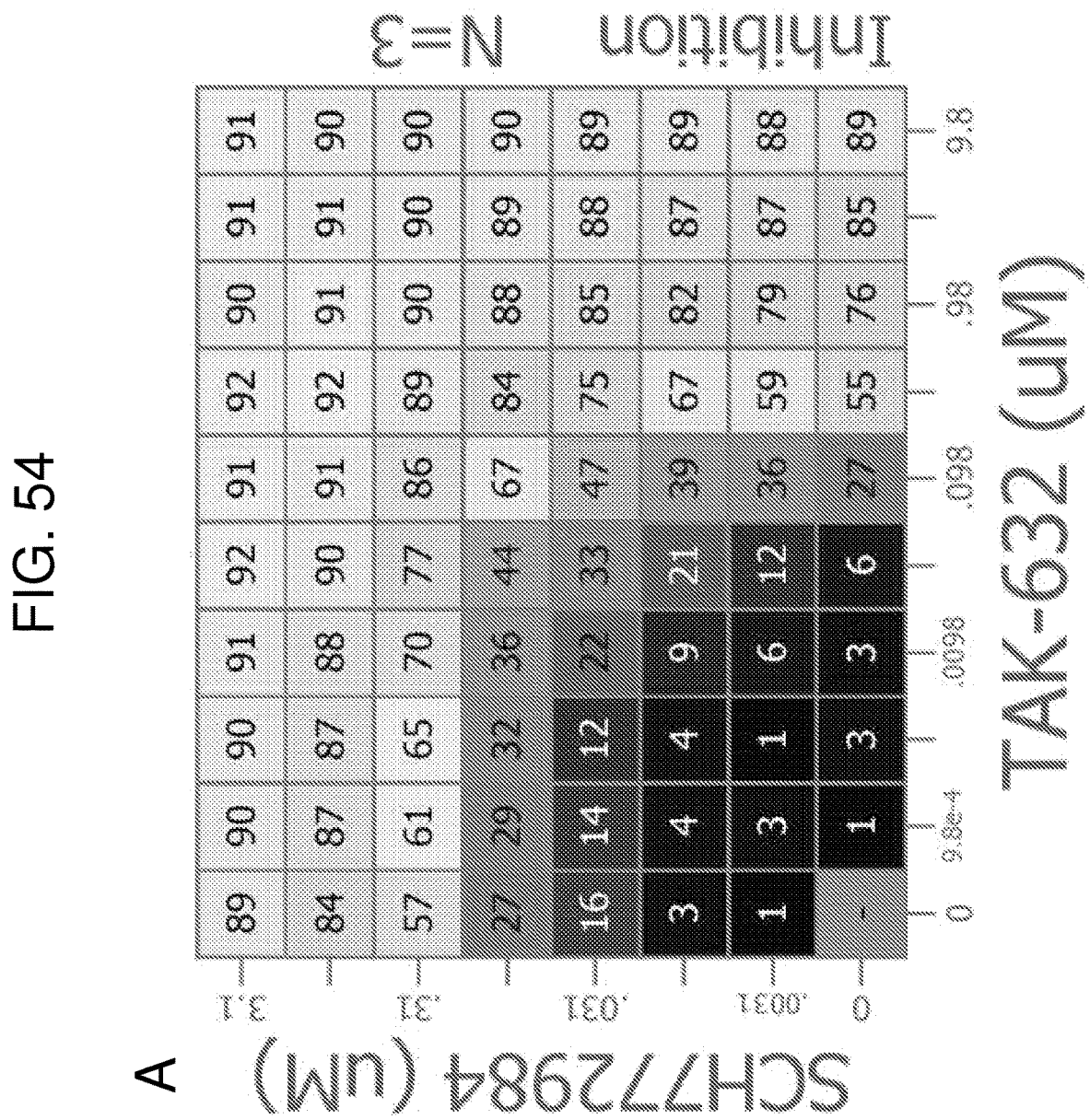
FIG. 54A is a dose matrix showing % inhibition of the TAK-632/SCH772984 combination in G-361 cells.
FIG. 54B is a dose matrix showing Loewe excess for the TAK-632/SCH772984 combination.
FIG. 54C is a dose matrix showing Bliss excess for the TAK-632/SCH772984 combination.
FIGS. 54D and 54E, respectively, show % viability relative to DMSO only treated controls for TAK-632 and SCH772984 single agent treatments in G-361 cells.

An overview of the mammalian MAPK cascades is shown in FIG. 30. The details of the MAPK pathways are reviewed in e.g., Akinleye et al., 2013. Briefly, with respect to the ERK1/2 module in FIG. 30 (light purple box), the MAPK 1/2 signaling cascade is activated by ligand binding to receptor tyrosine kinases (RTK). The activated receptors recruit and phosphorylate adaptor proteins Grb2 and SOS, which then interact with membrane-bound GTPase Ras and cause its activation. In its activated GTP-bound form, Ras recruits and activates Raf kinases (A-Raf, B-Raf, and C-Raf/RaF-1). The activated Raf kinases activate MAPK 1/2 (MKK1/2), which in turn catalyzes the phosphorylation of threonine and tyrosine residues in the activation sequence Thr-Glu-Tyr of ERK1/2. With respect to the JNK/p38 module (yellow box in FIG. 30), upstream kinases, MAP3Ks, such as MEKK1/4, ASK1/2, and MLK1/2/3, activate MAP2K3/6 (MKK3/6), MAP2K4 (MKK4), and MAP2K7 (MKK7). These MAP2Ks then activate JNK protein kinases, including JNK1, JNK2, and JNK3, as well as p38 α/β/γ/δ. To execute their functions, JNKs activate several transcription factors, including c-Jun, ATF-2, NF-ATc1, HSF-1 and STAT3. With respect to the ERK5 module (blue box in FIG. 30), the kinases upstream of MAP2K5 (MKK5) are MEKK2 and MEKK3. The best characterized downstream target of MEK5 is ERK5, also known as big MAP kinase 1 (BMK1) because it is twice the size of other MAPKs.

Non-limiting examples of MAPK pathway inhibitors include RAS inhibitors, RAF inhibitors, MEK inhibitors, ERK1/2 inhibitors, pharmaceutically acceptable salts thereof, and combinations thereof.

As used herein, a "RAS inhibitor" means those substances that (i) directly interact with RAS, e.g., by binding to RAS and (ii) decrease the expression or the activity of RAS. Non-limiting exemplary RAS inhibitors include, but are not limited to, farnesyl transferase inhibitors (such as, e.g., tipifarnib and lonafarnib), farnesyl group-containing small molecules (such as, e.g., salirasib and TLN-4601), DCAI, as disclosed by Maurer (Maurer et al., 2012), Kobe0065 and Kobe2602, as disclosed by Shima (Shima et al., 2013), HBS 3 (Patgiri et al., 2011), and AIK-4 (Allinky).

As used herein, a "RAF inhibitor" means those substances that (i) directly interact with RAF, e.g., by binding to RAF and (ii) decrease the expression or the activity of RAF, such as, e.g., A-RAF, B-RAF, and C-RAF (Raf-1). Non-limiting exemplary RAF inhibitors include:

Compound 7

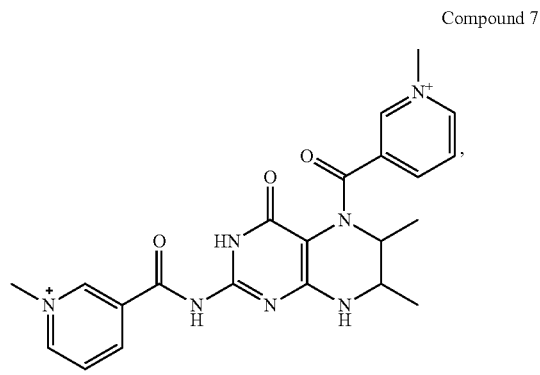

(Li et al., 2010)

Compound 9

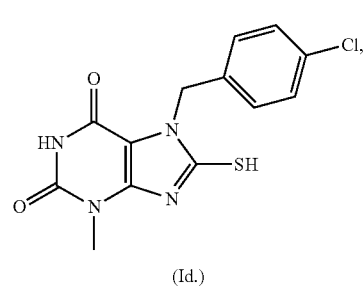

(Id.)

Compound 10

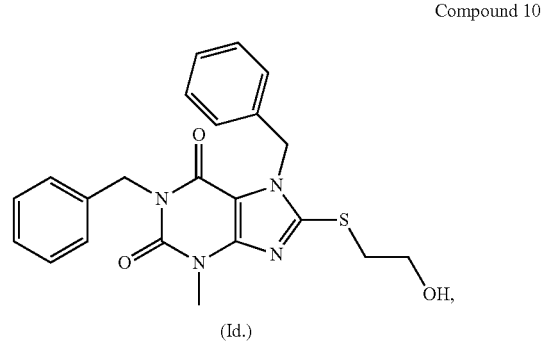

(Id.)

Compound 13

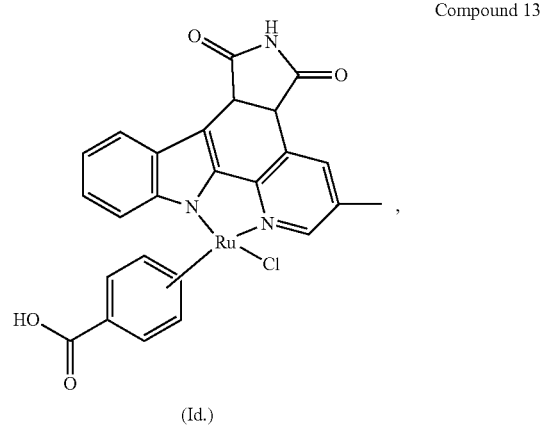

(Id.)

Compound 14

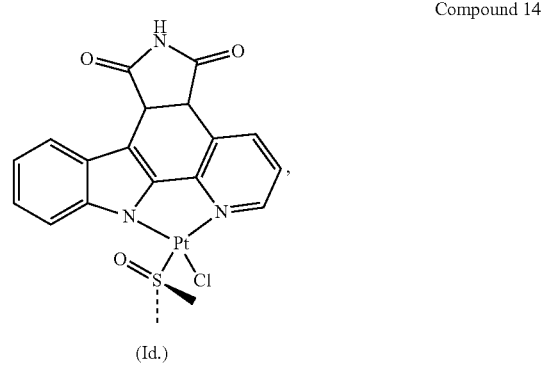

(Id.)

Compound 15

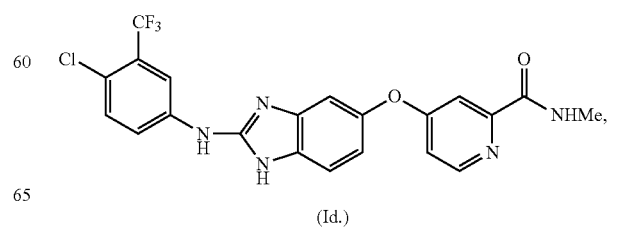

(Id.)

Compound 16
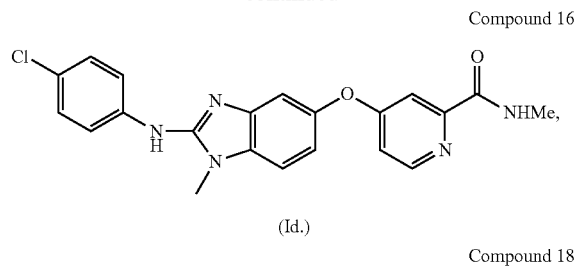
Compound 23
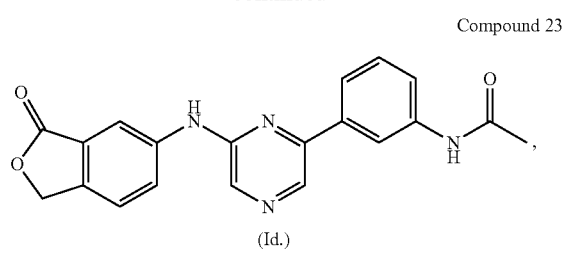
Compound 18
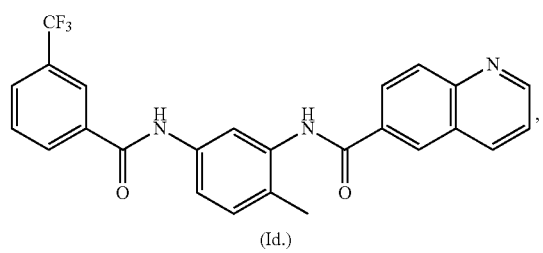
(Id.)
Compound 24
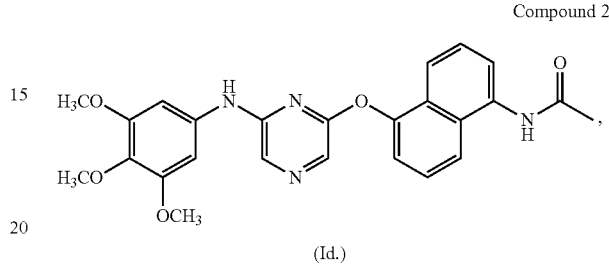
(Id.)
Compound 19
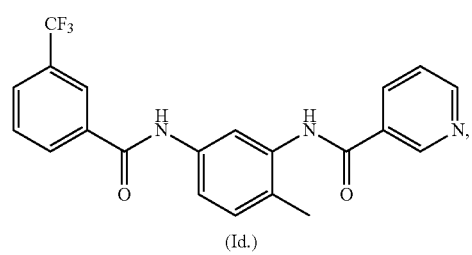
(Id.)
Compound 25
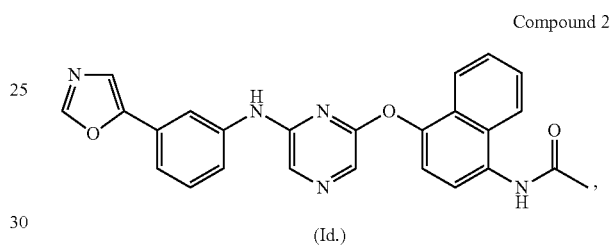
(Id.)
Compound 20
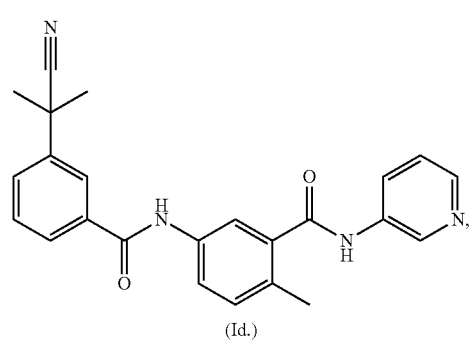
(Id.)
Compound 26
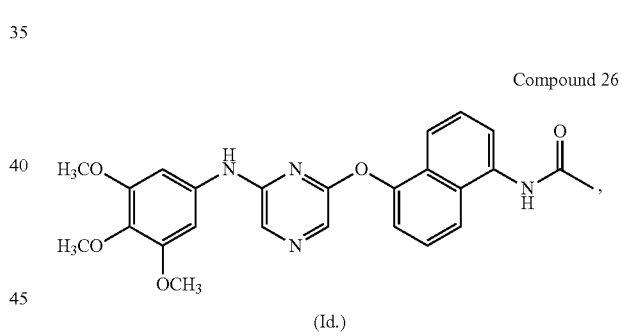
(Id.)
Compound 21
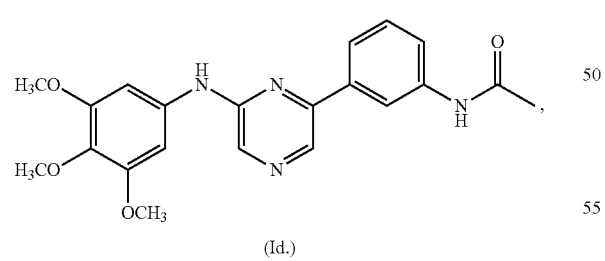
(Id.)
Compound 22
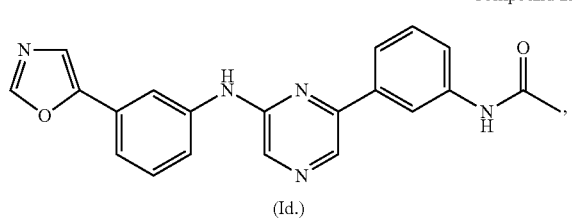
(Id.)
Compound 27
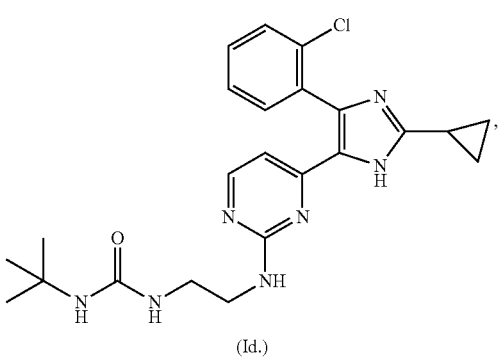
(Id.)

Compound 28
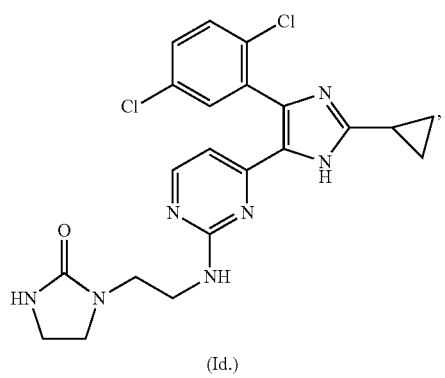
(Id.)
Compound 30
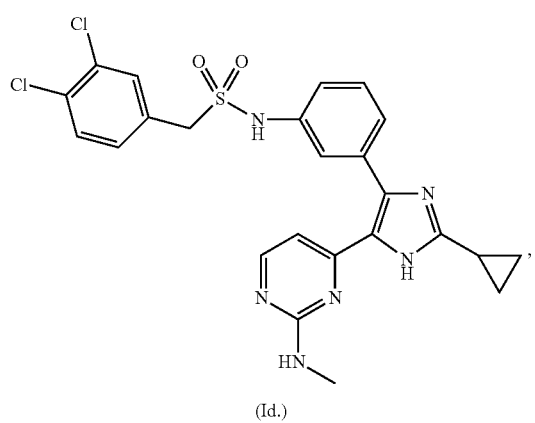
(Id.)
Compound 31
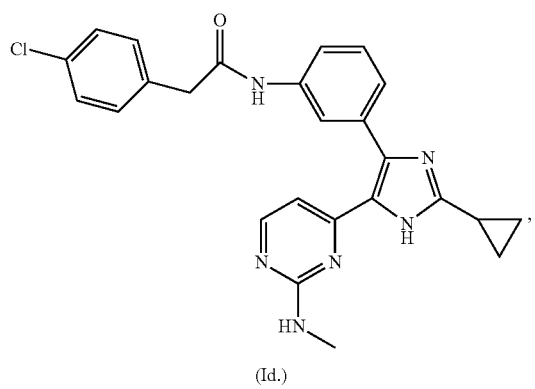
(Id.)
Compound 32
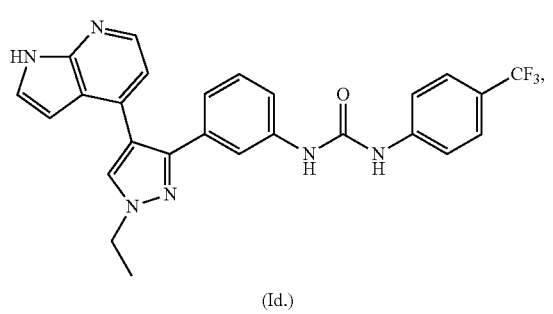
(Id.)
Compound 33
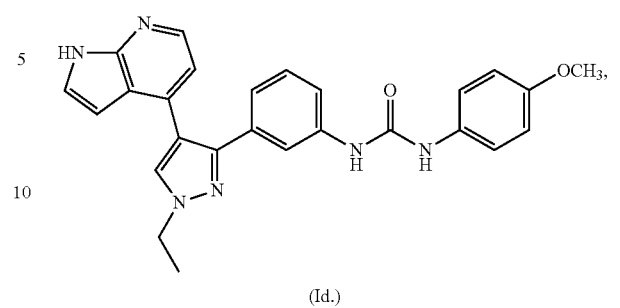
(Id.)
Compound 34
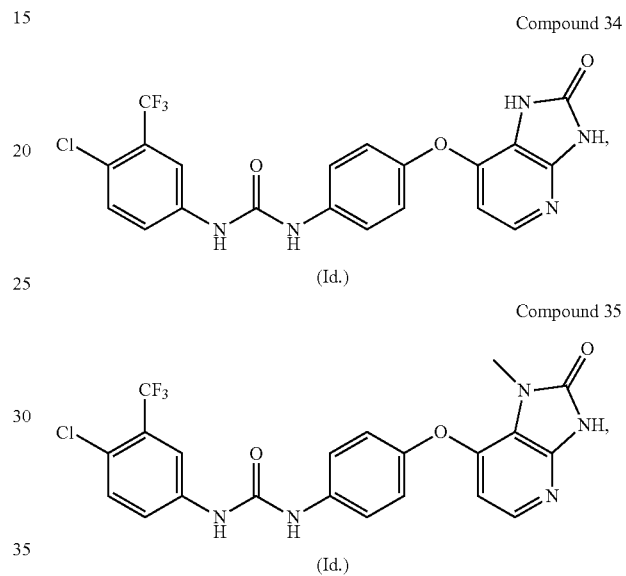
(Id.)
Compound 35
(Id.)
Compound 36
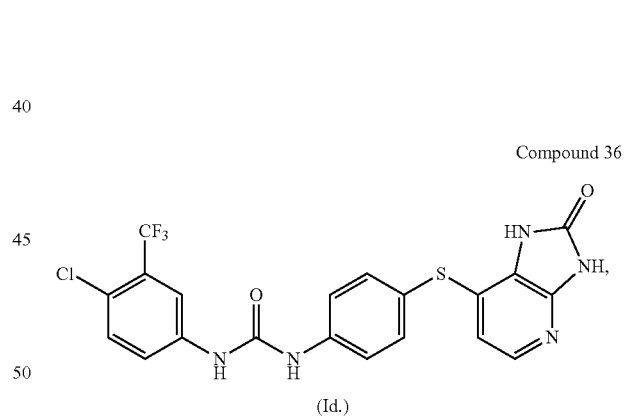
(Id.)
Compound 37
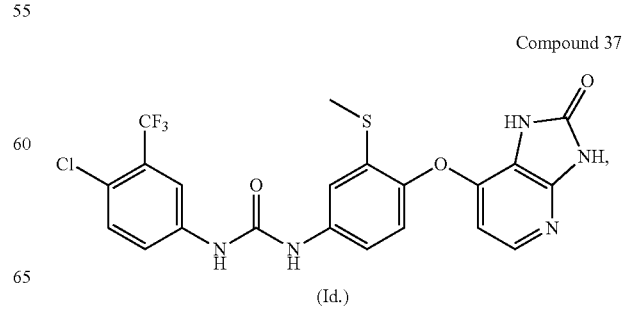
(Id.)

-continued

Compound 38

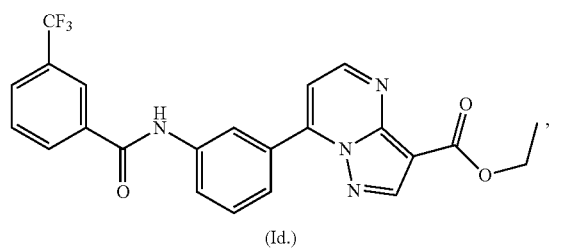

(Id.)

Compound 39

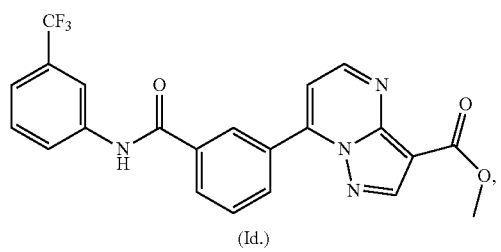

(Id.)

Compound 40

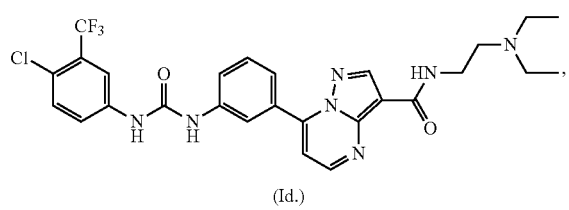

(Id.)

AAL881 (Novartis); AB-024 (Ambit Biosciences), ARQ-736 (ArQule), ARQ-761 (ArQule), AZ628 (Axon Medchem BV), BeiGene-283 (BeiGene), BUB-024 (MLN 2480) (Sunesis & Takeda), b-raf inhibitor (Sareum), BRAF kinase inhibitor (Selexagen Therapeutics), BRAF siRNA 313 (tacaccagcaagctagatgca) and 523 (cctatcgttagagtcttcctg) (Liu et al., 2007), CTT239065 (Institute of Cancer Research), dabrafenib (GSK2118436), DP-4978 (Deciphera Pharmaceuticals), HM-95573 (Hanmi), GDC-0879 (Genentech), GW-5074 (Sigma Aldrich), ISIS 5132 (Novartis), L779450 (Merck), LBT613 (Novartis), LErafAON (NeoPharm, Inc.), LGX-818 (Novartis), pazopanib (GlaxoSmithKline), PLX3202 (Plexxikon), PLX4720 (Plexxikon), PLX5568 (Plexxikon), RAF-265 (Novartis), RAF-365 (Novartis), regorafenib (Bayer Healthcare Pharmaceuticals, Inc.), RO 5126766 (Hoffmann-La Roche), SB-590885 (GlaxoSmithKline), SB699393 (GlaxoSmithKline), sorafenib (Onyx Pharmaceuticals), TAK 632 (Takeda), TL-241 (Teligene), vemurafenib (RG7204 or PLX4032) (Daiichi Sankyo), XL-281 (Exelixis), ZM-336372 (AstraZeneca), pharmaceutically acceptable salts thereof, and combinations thereof.

As used herein, a "MEK inhibitor" means those substances that (i) directly interact with MEK, e.g., by binding to MEK and (ii) decrease the expression or the activity of MEK. Thus, inhibitors that act upstream of MEK, such as RAS inhibitors and RAF inhibitors, are not MEF inhibitors according to the present invention. Non-limiting examples of MEK inhibitors include anthrax toxin, antroquinonol (Golden Biotechnology), ARRY-142886 (6-(4-bromo-2-chloro-phenylamino)-7-fluoro-3-methyl-3H-benzoimidazole-5-carboxylic acid (2-hydroxy-ethoxy)-amide) (Array BioPharma), ARRY-438162 (Array BioPharma), AS-1940477 (Astellas), AS-703988 (Merck KGaA), bentamapimod (Merck KGaA), BI-847325 (Boehringer Ingelheim), E-6201 (Eisai), GDC-0623 (Hoffmann-La Roche), GDC-0973 (cobimetinib) (Hoffmann-La Roche), L783277 (Merck), lethal factor portion of anthrax toxin, MEK162 (Array BioPharma), PD 098059 (2-(2'-amino-3'-methoxphenyl)-oxanaphthalen-4-one) (Pfizer), PD 184352 (CI-1040) (Pfizer), PD-0325901 (Pfizer), pimasertib (Santhera Pharmaceuticals), RDEA119 (Ardea Biosciences/Bayer), refametinib (AstraZeneca), RG422 (Chugai Pharmaceutical Co.), R0092210 (Roche), R04987655 (Hoffmann-La Roche), R05126766 (Hoffmann-La Roche), selumetinib (AZD6244) (AstraZeneca), SL327 (Sigma), TAK-733 (Takeda), trametinib (Japan Tobacco), U0126 (1,4-diamino-2,3-dicyano-1,4-bis(2-aminophenylthio)butadiene) (Sigma), WX-554 (Wilex), YopJ polypeptide (Mittal et al., 2010), pharmaceutically acceptable salts thereof, and combinations thereof.

As used herein, an "ERK1/2 inhibitor" means those substances that (i) directly interact with ERK1 and/or ERK2, e.g., by binding to ERK1/2 and (ii) decrease the expression or the activity of ERK1 and/or ERK2 protein kinases. Therefore, inhibitors that act upstream of ERK1/2, such as MEK inhibitors and RAF inhibitors, are not ERK1/2 inhibitors according to the present invention. Non-limiting examples of an ERK1/2 inhibitor include AEZS-131 (Aeterna Zentaris), AEZS-136 (Aeterna Zentaris), BVD-523, SCH-722984 (Merck & Co.), SCH-772984 (Merck & Co.), SCH-900353 (MK-8353) (Merck & Co.), pharmaceutically acceptable salts thereof, and combinations thereof.

In another aspect of this embodiment, the method further comprises administering to the subject at least one additional therapeutic agent effective for treating or ameliorating the effects of the cancer. The additional therapeutic agent may be selected from the group consisting of an antibody or fragment thereof, a cytotoxic agent, a toxin, a radionuclide, an immunomodulator, a photoactive therapeutic agent, a radiosensitizing agent, a hormone, an anti-angiogenesis agent, and combinations thereof.

As used herein, an "antibody" encompasses naturally occurring immunoglobulins as well as non-naturally occurring immunoglobulins, including, for example, single chain antibodies, chimeric antibodies (e.g., humanized murine antibodies), and heteroconjugate antibodies (e.g., bispecific antibodies). Fragments of antibodies include those that bind antigen, (e.g., Fab', F(ab')2, Fab, Fv, and rIgG). See also, e.g., Pierce Catalog and Handbook, 1994-1995 (Pierce Chemical Co., Rockford, Ill.); Kuby, J., Immunology, 3rd Ed., W.H. Freeman & Co., New York (1998). The term antibody also includes bivalent or bispecific molecules, diabodies, triabodies, and tetrabodies. The term "antibody" further includes both polyclonal and monoclonal antibodies.

Examples of therapeutic antibodies that may be used in the present invention include rituximab (Rituxan), Cetuximab (Erbitux), bevacizumab (Avastin), and Ibritumomab (Zevalin).

Cytotoxic agents according to the present invention include DNA damaging agents, antimetabolites, anti-microtubule agents, antibiotic agents, etc. DNA damaging agents include alkylating agents, platinum-based agents, intercalating agents, and inhibitors of DNA replication. Non-limiting examples of DNA alkylating agents include cyclophosphamide, mechlorethamine, uramustine, melphalan, chlorambucil, ifosfamide, carmustine, lomustine, streptozocin, busulfan, temozolomide, pharmaceutically acceptable salts thereof, prodrugs, and combinations thereof. Non-limiting examples of platinum-based agents include cisplatin, carboplatin, oxaliplatin, nedaplatin, satraplatin, triplatin tetranitrate, pharmaceutically acceptable salts thereof, prodrugs, and combinations thereof. Non-limiting examples of intercalating agents include doxorubicin, daunorubicin, idarubicin, mitoxantrone, pharmaceutically acceptable salts thereof, prodrugs, and combinations thereof. Non-limiting examples of inhibitors of DNA replication include irinotecan, topotecan, amsacrine, etoposide, etoposide phosphate, teniposide, pharmaceutically acceptable salts thereof, prodrugs, and combinations thereof. Antimetabolites include folate antagonists such as methotrexate and premetrexed, purine antagonists such as 6-mercaptopurine, dacarbazine, and fludarabine, and pyrimidine antagonists such as 5-fluorouracil, arabinosylcytosine, capecitabine, gemcitabine, decitabine, pharmaceutically acceptable salts thereof, prodrugs, and combinations thereof. Anti-microtubule agents include without limitation vinca alkaloids, paclitaxel (Taxol®), docetaxel (Taxotere®), and ixabepilone (Ixempra®). Antibiotic agents include without limitation actinomycin, anthracyclines, valrubicin, epirubicin, bleomycin, plicamycin, mitomycin, pharmaceutically acceptable salts thereof, prodrugs, and combinations thereof.

Cytotoxic agents according to the present invention also include an inhibitor of the PI3K/Akt pathway. Non-limiting examples of an inhibitor of the PI3K/Akt pathway include A-674563 (CAS #552325-73-2), AGL 2263, AMG-319 (Amgen, Thousand Oaks, Calif.), AS-041164 (5-benzo[1,3]dioxol-5-ylmethylene-thiazolidine-2,4-dione), AS-604850 (5-(2,2-Difluoro-benzo[1,3]dioxol-5-ylmethylene)-thiazolidine-2,4-dione), AS-605240 (5-quinoxilin-6-methylene-1,3-thiazolidine-2,4-dione), AT7867 (CAS #857531-00-1), benzimidazole series, Genentech (Roche Holdings Inc., South San Francisco, Calif.), BML-257 (CAS #32387-96-5), CAL-120 (Gilead Sciences, Foster City, Calif.), CAL-129 (Gilead Sciences), CAL-130 (Gilead Sciences), CAL-253 (Gilead Sciences), CAL-263 (Gilead Sciences), CAS #612847-09-3, CAS #681281-88-9, CAS #75747-14-7, CAS #925681-41-0, CAS #98510-80-6, CCT128930 (CAS #885499-61-6), CH5132799 (CAS #1007207-67-1), CHR-4432 (Chroma Therapeutics, Ltd., Abingdon, UK), FPA 124 (CAS #902779-59-3), GS-1101 (CAL-101) (Gilead Sciences), GSK 690693 (CAS #937174-76-0), H-89 (CAS #127243-85-0), Honokiol, IC87114 (Gilead Science), IPI-145 (Intellikine Inc.), KAR-4139 (Karus Therapeutics, Chilworth, UK), KAR-4141 (Karus Therapeutics), KIN-1 (Karus Therapeutics), KT 5720 (CAS #108068-98-0), Miltefosine, MK-2206 dihydrochloride (CAS #1032350-13-2), ML-9 (CAS #105637-50-1), Naltrindole Hydrochloride, OXY-111A (NormOxys Inc., Brighton, Mass.), perifosine, PHT-427 (CAS #1191951-57-1), PI3 kinase delta inhibitor, Merck KGaA (Merck & Co., Whitehouse Station, N.J.), PI3 kinase delta inhibitors, Genentech (Roche Holdings Inc.), PI3 kinase delta inhibitors, Incozen (Incozen Therapeutics, Pvt. Ltd., Hydrabad, India), PI3 kinase delta inhibitors-2, Incozen (Incozen Therapeutics), PI3 kinase inhibitor, Roche-4 (Roche Holdings Inc.), PI3 kinase inhibitors, Roche (Roche Holdings Inc.), PI3 kinase inhibitors, Roche-5 (Roche Holdings Inc.), PI3-alpha/delta inhibitors, Pathway Therapeutics (Pathway Therapeutics Ltd., South San Francisco, Calif.), PI3-delta inhibitors, Cellzome (Cellzome AG, Heidelberg, Germany), PI3-delta inhibitors, Intellikine (Intellikine Inc., La Jolla, Calif.), PI3-delta inhibitors, Pathway Therapeutics-1 (Pathway Therapeutics Ltd.), PI3-delta inhibitors, Pathway Therapeutics-2 (Pathway Therapeutics Ltd.), PI3-delta/gamma inhibitors, Cellzome (Cellzome AG), PI3-delta/gamma inhibitors, Cellzome (Cellzome AG), PI3-delta/gamma inhibitors, Intellikine (Intellikine Inc.), PI3-delta/gamma inhibitors, Intellikine (Intellikine Inc.), PI3-delta/gamma inhibitors, Pathway Therapeutics (Pathway Therapeutics Ltd.), PI3-delta/gamma inhibitors, Pathway Therapeutics (Pathway Therapeutics Ltd.), PI3-gamma inhibitor Evotec (Evotec), PI3-gamma inhibitor, Cellzome (Cellzome AG), PI3-gamma inhibitors, Pathway Therapeutics (Pathway Therapeutics Ltd.), PI3K delta/gamma inhibitors, Intellikine-1 (Intellikine Inc.), PI3K delta/gamma inhibitors, Intellikine-1 (Intellikine Inc.), pictilisib (Roche Holdings Inc.), PIK-90 (CAS #677338-12-4), SC-103980 (Pfizer, New York, N.Y.), SF-1126 (Semafore Pharmaceuticals, Indianapolis, Ind.), SH-5, SH-6, Tetrahydro Curcumin, TG100-115 (Targegen Inc., San Diego, Calif.), Triciribine, X-339 (Xcovery, West Palm Beach, Fla.), XL-499 (Evotech, Hamburg, Germany), pharmaceutically acceptable salts thereof, and combinations thereof.

In the present invention, the term "toxin" means an antigenic poison or venom of plant or animal origin. An example is diphtheria toxin or portions thereof.

In the present invention, the term "radionuclide" means a radioactive substance administered to the patient, e.g., intravenously or orally, after which it penetrates via the patient's normal metabolism into the target organ or tissue, where it delivers local radiation for a short time. Examples of radionuclides include, but are not limited to, I-125, At-211, Lu-177, Cu-67, I-131, Sm-153, Re-186, P-32, Re-188, In-114m, and Y-90.

In the present invention, the term "immunomodulator" means a substance that alters the immune response by augmenting or reducing the ability of the immune system to produce antibodies or sensitized cells that recognize and react with the antigen that initiated their production. Immunomodulators may be recombinant, synthetic, or natural preparations and include cytokines, corticosteroids, cytotoxic agents, thymosin, and immunoglobulins. Some immunomodulators are naturally present in the body, and certain of these are available in pharmacologic preparations. Examples of immunomodulators include, but are not limited to, granulocyte colony-stimulating factor (G-CSF), interferons, imiquimod and cellular membrane fractions from bacteria, IL-2, IL-7, IL-12, CCL3, CCL26, CXCL7, and synthetic cytosine phosphate-guanosine (CpG).

In the present invention, the term "photoactive therapeutic agent" means compounds and compositions that become active upon exposure to light. Certain examples of photoactive therapeutic agents are disclosed, e.g., in U.S. Patent Application Serial No. 2011/0152230 A1, "Photoactive Metal Nitrosyls For Blood Pressure Regulation And Cancer Therapy."

In the present invention, the term "radiosensitizing agent" means a compound that makes tumor cells more sensitive to radiation therapy. Examples of radiosensitizing agents include misonidazole, metronidazole, tirapazamine, and trans sodium crocetinate.

In the present invention, the term "hormone" means a substance released by cells in one part of a body that affects cells in another part of the body. Examples of hormones include, but are not limited to, prostaglandins, leukotrienes, prostacyclin, thromboxane, amylin, antimullerian hormone, adiponectin, adrenocorticotropic hormone, angiotensinogen, angiotensin, vasopressin, atriopeptin, brain natriuretic peptide, calcitonin, cholecystokinin, corticotropin-releasing hormone, encephalin, endothelin, erythropoietin, follicle-stimulating hormone, galanin, gastrin, ghrelin, glucagon, gonadotropin-releasing hormone, growth hormone-releasing hormone, human chorionic gonadotropin, human placental lactogen, growth hormone, inhibin, insulin, somatomedin, leptin, liptropin, luteinizing hormone, melanocyte stimulating hormone, motilin, orexin, oxytocin, pancreatic polypeptide, parathyroid hormone, prolactin, prolactin releasing hormone, relaxin, renin, secretin, somatostain, thrombopoietin, thyroid-stimulating hormone, testosterone, dehydroepiandrosterone, androstenedione, dihydrotestosterone, aldosterone, estradiol, estrone, estriol, cortisol, progesterone, calcitriol, and calcidiol.

Some compounds interfere with the activity of certain hormones or stop the production of certain hormones. These hormone-interfering compounds include, but are not limited to, tamoxifen (Nolvadex®), anastrozole (Arimidex®), letrozole (Femara®), and fulvestrant (Faslodex®). Such compounds are also within the meaning of hormone in the present invention.

As used herein, an "anti-angiogenesis" agent means a substance that reduces or inhibits the growth of new blood vessels, such as, e.g., an inhibitor of vascular endothelial growth factor (VEGF) and an inhibitor of endothelial cell migration. Anti-angiogenesis agents include without limitation 2-methoxyestradiol, angiostatin, bevacizumab, cartilage-derived angiogenesis inhibitory factor, endostatin, IFN-α, IL-12, itraconazole, linomide, platelet factor-4, prolactin, SU5416, suramin, tasquinimod, tecogalan, tetrathiomolybdate, thalidomide, thrombospondin, thrombospondin, TNP-470, ziv-aflibercept, pharmaceutically acceptable salts thereof, prodrugs, and combinations thereof.

In an additional aspect of this embodiment, administration of the first and second anti-cancer agents provides a synergistic effect compared to administration of either anti-cancer agent alone. As used herein, "synergistic" means more than additive. Synergistic effects may be measured by various assays known in the art, including but not limited to those disclosed herein, such as the excess over bliss assay.

Another embodiment of the present invention is a method of treating or ameliorating the effects of a cancer in a subject in need thereof. This method comprises administering to the subject an effective amount of (i) BVD-523 or a pharmaceutically acceptable salt thereof and (ii) a second anti-cancer agent, which is dabrafenib or a pharmaceutically acceptable salt thereof, to treat or ameliorate the effects of the cancer.

Suitable and preferred subjects are as disclosed herein. In this embodiment, the methods may be used to treat the cancers disclosed above, including those cancers with the mutational backgrounds identified above. Methods of identifying such mutations are also as set forth above.

In one aspect of this embodiment, the BVD-523 or a pharmaceutically acceptable salt thereof is administered in the form of a pharmaceutical composition further comprising a pharmaceutically acceptable carrier or diluent.

In a further aspect of this embodiment, the dabrafenib or a pharmaceutically acceptable salt thereof is administered in the form of a pharmaceutical composition further comprising a pharmaceutically acceptable carrier or diluent.

In a further aspect of this embodiment, the method further comprises administering at least one additional therapeutic agent, preferably an inhibitor of the PI3K/Akt pathway, as disclosed herein.

In an additional aspect of this embodiment, administration of the first and second anti-cancer agents provides a synergistic effect compared to administration of either anti-cancer agent alone.

Another embodiment of the present invention is a method of effecting cancer cell death. This method comprises contacting the cancer cell with an effective amount of (i) a first anti-cancer agent, which is BVD-523 or a pharmaceutically acceptable salt thereof and (ii) a second anti-cancer agent, which is a type 1 RAF inhibitor or a pharmaceutically acceptable salt thereof.

Suitable and preferred type 1 RAF inhibitors are as disclosed herein. In this embodiment, effecting cancer cell death may be accomplished in cancer cells having various mutational backgrounds and/or that are characterized as disclosed above. Methods of identifying such mutations are also as set forth above.

In an aspect of this embodiment, the methods may be carried out in vitro or in vivo, and may be used to effect cancer cell death, by e.g., killing cancer cells, in cells of the types of cancer disclosed herein.

In another aspect of this embodiment, the cancer cell is a mammalian cancer cell. Preferably, the mammalian cancer cell is obtained from a mammal selected from the group consisting of humans, primates, farm animals, and domestic animals. More preferably, the mammalian cancer cell is a human cancer cell.

In a further aspect of this embodiment, contacting the cancer cell with the first and second anti-cancer agents provides a synergistic effect compared to contacting the cancer cell with either anti-cancer agent alone.

In another aspect of this embodiment, the method further comprises contacting the cancer cell with at least one additional therapeutic agent, preferably an inhibitor of the PI3K/Akt pathway, as disclosed herein.

In a further aspect of this embodiment, contacting the cancer cell with the first and second anti-cancer agents provides a synergistic effect compared to contacting the cancer cell with either anti-cancer agent alone. In this embodiment, "contacting" means bringing BVD-523 and the type 1 RAF inhibitors, and optionally one or more additional therapeutic agents into close proximity to the cancer cells. This may be accomplished using conventional techniques of drug delivery to mammals or in the in vitro situation by, e.g., providing BVD-523 and the type 1 RAF inhibitors, and optionally other therapeutic agents to a culture media in which the cancer cells are located.

A further embodiment of the present invention is a kit for treating or ameliorating the effects of a cancer in a subject in need thereof. This kit comprises an effective amount of (i) a first anti-cancer agent, which is BVD-523 or a pharmaceutically acceptable salt thereof and (ii) a second anti-cancer agent, which is a type 1 RAF inhibitor or a pharmaceutically acceptable salt thereof, packaged together with instructions for their use.

The kits may also include suitable storage containers, e.g., ampules, vials, tubes, etc., for each anti-cancer agent of the present invention (which may e.g., may be in the form of pharmaceutical compositions) and other reagents, e.g., buffers, balanced salt solutions, etc., for use in administering the anti-cancer agents to subjects. The anti-cancer agents of the invention and other reagents may be present in the kits in any convenient form, such as, e.g., in a solution or in a powder form. The kits may further include a packaging container, optionally having one or more partitions for housing the pharmaceutical composition and other optional reagents.

Suitable and preferred subjects and type 1 RAF inhibitors are as disclosed herein. In this embodiment, the kit may be used to treat the cancers disclosed above, including those cancers with the mutational backgrounds identified herein. Methods of identifying such mutations are as set forth above.

In a further aspect of this embodiment, the kit further comprises at least one additional therapeutic agent, preferably an inhibitor of the PI3K/Akt pathway, as disclosed herein.

In an additional aspect of this embodiment, administration of the first and second anti-cancer agents provides a synergistic effect compared to administration of either anti-cancer agent alone.

Another embodiment of the present invention is a pharmaceutical composition for treating or ameliorating the effects of a cancer in a subject in need thereof. This pharmaceutical composition comprises a pharmaceutically acceptable diluent or carrier and an effective amount of (i) a first anti-cancer agent, which is BVD-523 or a pharmaceutically acceptable salt thereof and (ii) a second anti-cancer agent, which is a type 1 RAF inhibitor or a pharmaceutically acceptable salt thereof, wherein administration of the first and second anti-cancer agents provides a synergistic effect compared to administration of either anti-cancer agent alone. This pharmaceutical composition may further comprise a pharmaceutically acceptable diluent or carrier.

Suitable and preferred subjects and type 1 RAF inhibitors are as disclosed herein. The pharmaceutical compositions of the invention may be used to treat the cancers disclosed above, including those cancers with the mutational backgrounds identified herein. Methods of identifying such mutations are also as set forth above.

In a further aspect of this embodiment, the pharmaceutical composition further comprises at least one additional therapeutic agent, preferably an inhibitor of the PI3K/Akt pathway, as disclosed herein.

Another embodiment of the present invention is a method of treating or ameliorating the effects of a cancer in a subject in need thereof. This method comprises administering to the subject an effective amount of (i) a first anti-cancer agent, which is BVD-523 or a pharmaceutically acceptable salt thereof and (ii) a second anti-cancer agent, which is a RAF inhibitor selected from the group consisting of AAL881 (Novartis); AB-024 (Ambit Biosciences), ARQ-736 (ArQule), ARQ-761 (ArQule), AZ628 (Axon Medchem BV), BeiGene-283 (BeiGene), BUB-024 (MLN 2480) (Sunesis & Takeda), b-raf inhibitor (Sareum), BRAF kinase inhibitor (Selexagen Therapeutics), BRAF siRNA 313 (tacaccagcaagctagatgca) and 253 (cctatcgttagagtcttcctg), CTT239065 (Institute of Cancer Research), DP-4978 (Deciphera Pharmaceuticals), HM-95573 (Hanmi), GW-5074 (Sigma Aldrich), ISIS 5132 (Novartis), LErafAON (NeoPharm, Inc.), LBT613 (Novartis), LGX-818 (Novartis), pazopanib (GlaxoSmithKline), PLX5568 (Plexxikon), RAF-265 (Novartis), RAF-365 (Novartis), regorafenib (Bayer Healthcare Pharmaceuticals, Inc.), RO 5126766 (Hoffmann-La Roche), TAK 632 (Takeda), TL-241 (Teligene), XL-281 (Exelixis), pharmaceutically acceptable salts thereof, and combinations thereof, to treat or ameliorate the effects of the cancer. Preferably, the second anti-cancer agent is regorafenib or a pharmaceutically acceptable salt thereof.

In this embodiment, suitable and preferred subjects are as disclosed herein. In this embodiment, the methods may be used to treat the cancers disclosed above, including those cancers with the mutational backgrounds identified above. Methods of identifying such mutations are also as set forth above.

In a further aspect of this embodiment, the method further comprises administering at least one additional therapeutic agent, preferably an inhibitor of the PI3K/Akt pathway, as disclosed herein.

In another aspect of this embodiment, administration of the first and second anti-cancer agents provides a synergistic effect compared to administration of either anti-cancer agent alone.

An additional embodiment of the present invention is a method of effecting cancer cell death. This method comprises contacting the cancer cell with an effective amount of (i) a first anti-cancer agent, which is BVD-523 or a pharmaceutically acceptable salt thereof and (ii) a second anti-cancer agent, which is a RAF inhibitor selected from the group consisting of AAL881 (Novartis); AB-024 (Ambit Biosciences), ARQ-736 (ArQule), ARQ-761 (ArQule), AZ628 (Axon Medchem BV), BeiGene-283 (BeiGene), BUB-024 (MLN 2480) (Sunesis & Takeda), b-raf inhibitor (Sareum), BRAF kinase inhibitor (Selexagen Therapeutics), BRAF siRNA 313 (tacaccagcaagctagatgca) and 253 (cctatcgttagagtcttcctg), CTT239065 (Institute of Cancer Research), DP-4978 (Deciphera Pharmaceuticals), HM-95573 (Hanmi), GW-5074 (Sigma Aldrich), ISIS 5132 (Novartis), LErafAON (NeoPharm, Inc.), LBT613 (Novartis), LGX-818 (Novartis), pazopanib (GlaxoSmithKline), PLX5568 (Plexxikon), RAF-265 (Novartis), RAF-365 (Novartis), regorafenib (Bayer Healthcare Pharmaceuticals, Inc.), RO 5126766 (Hoffmann-La Roche), TAK 632 (Takeda), TL-241 (Teligene), XL-281 (Exelixis), pharmaceutically acceptable salts thereof, and combinations thereof. Preferably, the second anti-cancer agent is regorafenib or a pharmaceutically acceptable salt thereof.

Suitable and preferred cancer cells are as disclosed herein. In this embodiment, effecting cancer cell death may be accomplished in cancer cells having various mutational backgrounds and/or that are characterized as disclosed above. Methods of identifying such mutations are also as set forth above.

The methods of this embodiment, which may be carried out in vitro or in vivo, may be used to effect cancer cell death, by e.g., killing cancer cells, in cells of the types of cancer disclosed herein.

In one aspect of this embodiment, the cancer cell is a mammalian cancer cell. Preferably, the mammalian cancer cell is obtained from a mammal selected from the group consisting of humans, primates, farm animals, and domestic animals. More preferably, the mammalian cancer cell is a human cancer cell.

In another aspect of this embodiment, the method further comprises administering at least one additional therapeutic agent, preferably an inhibitor of the PI3K/Akt pathway, as disclosed herein.

In a further aspect of this embodiment, contacting the cancer cell with the first and second anti-cancer agents provides a synergistic effect compared to contacting the cancer cell with either anti-cancer agent alone.

In this embodiment, "contacting" means bringing BVD-523 and RAF inhibitors, and optionally one or more additional therapeutic agents into close proximity to the cancer cells. This may be accomplished using conventional techniques of drug delivery to mammals or in the in vitro situation by, e.g., providing BVD-523 and RAF inhibitors, and optionally other therapeutic agents to a culture media in which the cancer cells are located.

A further embodiment of the present invention is a kit for treating or ameliorating the effects of a cancer in a subject in need thereof. This kit comprises an effective amount of (i) a first anti-cancer agent, which is BVD-523 or a pharmaceutically acceptable salt thereof and (ii) a second anti-cancer agent, which is a RAF inhibitor selected from the group consisting of AAL881 (Novartis); AB-024 (Ambit Biosciences), ARQ-736 (ArQule), ARQ-761 (ArQule), AZ628 (Axon Medchem BV), BeiGene-283 (BeiGene), BUB-024 (MLN 2480) (Sunesis & Takeda), b-raf inhibitor (Sareum), BRAF kinase inhibitor (Selexagen Therapeutics), BRAF siRNA 313 (tacaccagcaagctagatgca) and 253 (cctatcgttagagtcttcctg), CTT239065 (Institute of Cancer Research), DP-4978 (Deciphera Pharmaceuticals), HM-95573 (Hanmi), GW-5074 (Sigma Aldrich), ISIS 5132 (Novartis), LErafAON (NeoPharm, Inc.), LBT613 (Novartis), LGX-818 (Novartis), pazopanib (GlaxoSmithKline), PLX5568 (Plexxikon), RAF-265 (Novartis), RAF-365 (Novartis), regorafenib (Bayer Healthcare Pharmaceuticals, Inc.), RO 5126766 (Hoffmann-La Roche), TAK 632 (Takeda), TL-241 (Teligene), XL-281 (Exelixis), pharmaceutically acceptable salts thereof, and combinations thereof, packaged together with instructions for their use. Preferably, the second anti-cancer agent is regorafenib or a pharmaceutically acceptable salt thereof.

In this embodiment, suitable and preferred subjects are as disclosed herein. In this embodiment, the kit may be used to treat the cancers disclosed above, including those cancers with the mutational backgrounds identified herein. Methods of identifying such mutations are as set forth above.

In a further aspect of this embodiment, the kit further comprises at least one additional therapeutic agent, preferably an inhibitor of the PI3K/Akt pathway, as disclosed herein.

In another aspect of this embodiment, administration of the first and second anti-cancer agents provides a synergistic effect compared to administration of either anti-cancer agent alone.

Another embodiment of the present invention is a pharmaceutical composition for treating or ameliorating the effects of a cancer in a subject in need thereof. This pharmaceutical composition comprises a pharmaceutically acceptable diluent or carrier and an effective amount of (i) a first anti-cancer agent, which is BVD-523 or a pharmaceutically acceptable salt thereof and (ii) a second anti-cancer agent, which is a RAF inhibitor selected from the group consisting of AAL881 (Novartis); AB-024 (Ambit Biosciences), ARQ-736 (ArQule), ARQ-761 (ArQule), AZ628 (Axon Medchem BV), BeiGene-283 (BeiGene), BUB-024 (MLN 2480) (Sunesis & Takeda), b-raf inhibitor (Sareum), BRAF kinase inhibitor (Selexagen Therapeutics), BRAF siRNA 313 (tacaccagcaagctagatgca) and 253 (cctatcgttagagtcttcctg), CTT239065 (Institute of Cancer Research), DP-4978 (Deciphera Pharmaceuticals), HM-95573 (Hanmi), GW-5074 (Sigma Aldrich), ISIS 5132 (Novartis), LErafAON (NeoPharm, Inc.), LBT613 (Novartis), LGX-818 (Novartis), pazopanib (GlaxoSmithKline), PLX5568 (Plexxikon), RAF-265 (Novartis), RAF-365 (Novartis), regorafenib (Bayer Healthcare Pharmaceuticals, Inc.), RO 5126766 (Hoffmann-La Roche), TAK 632 (Takeda), TL-241 (Teligene), XL-281 (Exelixis), pharmaceutically acceptable salts thereof, and combinations thereof, wherein administration of the first and second anti-cancer agents provides a synergistic effect compared to administration of either anti-cancer agent alone.

In this embodiment, suitable and preferred subjects are as disclosed herein. The pharmaceutical compositions of the invention may be used to treat the cancers disclosed above, including those cancers with the mutational backgrounds identified herein. Methods of identifying such mutations are also as set forth above.

In a further aspect of this embodiment, the pharmaceutical composition further comprises at least one additional therapeutic agent, preferably an inhibitor of the PI3K/Akt pathway, as disclosed herein.

The pharmaceutical compositions according to the present invention may be in a unit dosage form comprising both anti-cancer agents. In another aspect of this embodiment, the first anti-cancer agent is in a first unit dosage form and the second anti-cancer agent is in a second unit dosage form, separate from the first.

The first and second anti-cancer agents may be co-administered to the subject, either simultaneously or at different times, as deemed most appropriate by a physician. If the first and second anti-cancer agents are administered at different times, for example, by serial administration, the first anti-cancer agent may be administered to the subject before the second anti-cancer agent. Alternatively, the second anti-cancer agent may be administered to the subject before the first anti-cancer agent.

In the present invention, an "effective amount" or a "therapeutically effective amount" of an anti-cancer agent of the invention including pharmaceutical compositions containing same that are disclosed herein is an amount of such agent or composition that is sufficient to effect beneficial or desired results as described herein when administered to a subject. Effective dosage forms, modes of administration, and dosage amounts may be determined empirically, and making such determinations is within the skill of the art. It is understood by those skilled in the art that the dosage amount will vary with the route of administration, the rate of excretion, the duration of the treatment, the identity of any other drugs being administered, the age, size, and species of mammal, e.g., human patient, and like factors well known in the arts of medicine and veterinary medicine. In general, a suitable dose of an agent or composition according to the invention will be that amount of the agent or composition, which is the lowest dose effective to produce the desired effect. The effective dose of an agent or composition of the present invention may be administered as two, three, four, five, six or more sub-doses, administered separately at appropriate intervals throughout the day.

A suitable, non-limiting example of a dosage of BVD-523, a RAF inhibitor or another anti-cancer agent disclosed herein is from about 1 mg/kg to about 2400 mg/kg per day, such as from about 1 mg/kg to about 1200 mg/kg per day, 75 mg/kg per day to about 300 mg/kg per day, including from about 1 mg/kg to about 100 mg/kg per day. Other representative dosages of such agents include about 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 75 mg/kg, 80 mg/kg, 90 mg/kg, 100 mg/kg, 125 mg/kg, 150 mg/kg, 175 mg/kg, 200 mg/kg, 250 mg/kg, 300 mg/kg, 400 mg/kg, 500 mg/kg, 600 mg/kg, 700 mg/kg, 800 mg/kg, 900 mg/kg, 1000 mg/kg, 1100 mg/kg, 1200 mg/kg, 1300 mg/kg, 1400 mg/kg, 1500 mg/kg, 1600 mg/kg, 1700 mg/kg, 1800 mg/kg, 1900 mg/kg, 2000 mg/kg, 2100 mg/kg, 2200 mg/kg, and 2300 mg/kg per day. The effective dose of BVD-523, RAF inhibitors or other anti-cancer agents disclosed herein may be administered as two, three, four, five, six or more sub-doses, administered separately at appropriate intervals throughout the day.

The BVD-523, RAF inhibitors or other anti-cancer agents or pharmaceutical compositions containing same of the present invention may be administered in any desired and effective manner: for oral ingestion, or as an ointment or drop for local administration to the eyes, or for parenteral or other administration in any appropriate manner such as intraperitoneal, subcutaneous, topical, intradermal, inhalation, intrapulmonary, rectal, vaginal, sublingual, intramuscular, intravenous, intraarterial, intrathecal, or intralymphatic. Further, the BVD-523, RAF inhibitors or other anti-cancer agents or pharmaceutical compositions containing same of the present invention may be administered in conjunction with other treatments. The BVD-523, RAF inhibitors or other anti-cancer agents or pharmaceutical compositions containing the same may be encapsulated or otherwise protected against gastric or other secretions, if desired.

The pharmaceutical compositions of the invention comprise one or more active ingredients, e.g. anti-cancer agents, in admixture with one or more pharmaceutically-acceptable diluents or carriers and, optionally, one or more other compounds, drugs, ingredients and/or materials. Regardless of the route of administration selected, the agents/compounds of the present invention are formulated into pharmaceutically-acceptable dosage forms by conventional methods known to those of skill in the art. See, e.g., Remington, The Science and Practice of Pharmacy ($21^{st}$ Edition, Lippincott Williams and Wilkins, Philadelphia, Pa.).

Pharmaceutically acceptable diluents or carriers are well known in the art (see, e.g., Remington, The Science and Practice of Pharmacy ($21^{st}$ Edition, Lippincott Williams and Wilkins, Philadelphia, Pa.) and The National Formulary (American Pharmaceutical Association, Washington, D.C.)) and include sugars (e.g., lactose, sucrose, mannitol, and sorbitol), starches, cellulose preparations, calcium phosphates (e.g., dicalcium phosphate, tricalcium phosphate and calcium hydrogen phosphate), sodium citrate, water, aqueous solutions (e.g., saline, sodium chloride injection, Ringer's injection, dextrose injection, dextrose and sodium chloride injection, lactated Ringer's injection), alcohols (e.g., ethyl alcohol, propyl alcohol, and benzyl alcohol), polyols (e.g., glycerol, propylene glycol, and polyethylene glycol), organic esters (e.g., ethyl oleate and tryglycerides), biodegradable polymers (e.g., polylactide-polyglycolide, poly(orthoesters), and poly(anhydrides)), elastomeric matrices, liposomes, microspheres, oils (e.g., corn, germ, olive, castor, sesame, cottonseed, and groundnut), cocoa butter, waxes (e.g., suppository waxes), paraffins, silicones, talc, silicylate, etc. Each pharmaceutically acceptable diluent or carrier used in a pharmaceutical composition of the invention must be "acceptable" in the sense of being compatible with the other ingredients of the formulation and not injurious to the subject. Diluents or carriers suitable for a selected dosage form and intended route of administration are well known in the art, and acceptable diluents or carriers for a chosen dosage form and method of administration can be determined using ordinary skill in the art.

The pharmaceutical compositions of the invention may, optionally, contain additional ingredients and/or materials commonly used in pharmaceutical compositions. These ingredients and materials are well known in the art and include (1) fillers or extenders, such as starches, lactose, sucrose, glucose, mannitol, and silicic acid; (2) binders, such as carboxymethylcellulose, alginates, gelatin, polyvinyl pyrrolidone, hydroxypropylmethyl cellulose, sucrose and acacia; (3) humectants, such as glycerol; (4) disintegrating agents, such as agar-agar, calcium carbonate, potato or tapioca starch, alginic acid, certain silicates, sodium starch glycolate, cross-linked sodium carboxymethyl cellulose and sodium carbonate; (5) solution retarding agents, such as paraffin; (6) absorption accelerators, such as quaternary ammonium compounds; (7) wetting agents, such as cetyl alcohol and glycerol monostearate; (8) absorbents, such as kaolin and bentonite clay; (9) lubricants, such as talc, calcium stearate, magnesium stearate, solid polyethylene glycols, and sodium lauryl sulfate; (10) suspending agents, such as ethoxylated isostearyl alcohols, polyoxyethylene sorbitol and sorbitan esters, microcrystalline cellulose, aluminum metahydroxide, bentonite, agar-agar and tragacanth; (11) buffering agents; (12) excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, and polyamide powder; (13) inert diluents, such as water or other solvents; (14) preservatives; (15) surface-active agents; (16) dispersing agents; (17) control-release or absorption-delaying agents, such as hydroxypropylmethyl cellulose, other polymer matrices, biodegradable polymers, liposomes, microspheres, aluminum monostearate, gelatin, and waxes; (18) opacifying agents; (19) adjuvants; (20) wetting agents; (21) emulsifying and suspending agents; (22), solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan; (23) propellants, such as chlorofluorohydrocarbons and volatile unsubstituted hydrocarbons, such as butane and propane; (24) antioxidants; (25) agents which render the formulation isotonic with the blood of the intended recipient, such as sugars and sodium chloride; (26) thickening agents; (27) coating materials, such as lecithin; and (28) sweetening, flavoring, coloring, perfuming and preservative agents. Each such ingredient or material must be "acceptable" in the sense of being compatible with the other ingredients of the formulation and not injurious to the subject. Ingredients and materials suitable for a selected dosage form and intended route of administration are well known in the art, and acceptable ingredients and materials for a chosen dosage form and method of administration may be determined using ordinary skill in the art.

The pharmaceutical compositions of the present invention suitable for oral administration may be in the form of capsules, cachets, pills, tablets, powders, granules, a solution or a suspension in an aqueous or non-aqueous liquid, an oil-in-water or water-in-oil liquid emulsion, an elixir or syrup, a pastille, a bolus, an electuary or a paste. These formulations may be prepared by methods known in the art, e.g., by means of conventional pan-coating, mixing, granulation or lyophilization processes.

Solid dosage forms for oral administration (capsules, tablets, pills, dragees, powders, granules and the like) may be prepared, e.g., by mixing the active ingredient(s) with one or more pharmaceutically-acceptable diluents or carriers and, optionally, one or more fillers, extenders, binders, humectants, disintegrating agents, solution retarding agents, absorption accelerators, wetting agents, absorbents, lubricants, and/or coloring agents. Solid compositions of a similar type may be employed as fillers in soft and hard-filled gelatin capsules using a suitable excipient. A tablet may be made by compression or molding, optionally with one or more accessory ingredients. Compressed tablets may be prepared using a suitable binder, lubricant, inert diluent, preservative, disintegrant, surface-active or dispersing agent. Molded tablets may be made by molding in a suitable machine. The tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein. They may be sterilized by, for example, filtration through a bacteria-retaining filter. These compositions may also optionally contain opacifying agents and may be of a composition such that they release the active ingredient only, or preferentially, in a certain portion of the gastrointestinal tract, optionally, in a delayed manner. The active ingredient can also be in microencapsulated form.

Liquid dosage forms for oral administration include pharmaceutically-acceptable emulsions, microemulsions, solutions, suspensions, syrups and elixirs. The liquid dosage forms may contain suitable inert diluents commonly used in the art. Besides inert diluents, the oral compositions may also include adjuvants, such as wetting agents, emulsifying and suspending agents, sweetening, flavoring, coloring, perfuming and preservative agents. Suspensions may contain suspending agents.

The pharmaceutical compositions of the present invention for rectal or vaginal administration may be presented as a suppository, which may be prepared by mixing one or more active ingredient(s) with one or more suitable nonirritating diluents or carriers which are solid at room temperature, but liquid at body temperature and, therefore, will melt in the rectum or vaginal cavity and release the active compound. The pharmaceutical compositions of the present invention which are suitable for vaginal administration also include pessaries, tampons, creams, gels, pastes, foams or spray formulations containing such pharmaceutically-acceptable diluents or carriers as are known in the art to be appropriate.

Dosage forms for the topical or transdermal administration include powders, sprays, ointments, pastes, creams, lotions, gels, solutions, patches, drops and inhalants. The active agent(s)/compound(s) may be mixed under sterile conditions with a suitable pharmaceutically-acceptable diluent or carrier. The ointments, pastes, creams and gels may contain excipients. Powders and sprays may contain excipients and propellants.

The pharmaceutical compositions of the present invention suitable for parenteral administrations may comprise one or more agent(s)/compound(s) in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain suitable antioxidants, buffers, solutes which render the formulation isotonic with the blood of the intended recipient, or suspending or thickening agents. Proper fluidity can be maintained, for example, by the use of coating materials, by the maintenance of the required particle size in the case of dispersions, and by the use of surfactants. These pharmaceutical compositions may also contain suitable adjuvants, such as wetting agents, emulsifying agents and dispersing agents. It may also be desirable to include isotonic agents. In addition, prolonged absorption of the injectable pharmaceutical form may be brought about by the inclusion of agents which delay absorption.

In some cases, in order to prolong the effect of a drug (e.g., pharmaceutical formulation), it is desirable to slow its absorption from subcutaneous or intramuscular injection. This may be accomplished by the use of a liquid suspension of crystalline or amorphous material having poor water solubility.

The rate of absorption of the active agent/drug then depends upon its rate of dissolution which, in turn, may depend upon crystal size and crystalline form. Alternatively, delayed absorption of a parenterally-administered agent/drug may be accomplished by dissolving or suspending the active agent/drug in an oil vehicle. Injectable depot forms may be made by forming microencapsule matrices of the active ingredient in biodegradable polymers. Depending on the ratio of the active ingredient to polymer, and the nature of the particular polymer employed, the rate of active ingredient release can be controlled. Depot injectable formulations are also prepared by entrapping the drug in liposomes or microemulsions which are compatible with body tissue. The injectable materials can be sterilized for example, by filtration through a bacterial-retaining filter.

The formulations may be presented in unit-dose or multi-dose sealed containers, for example, ampules and vials, and may be stored in a lyophilized condition requiring only the addition of the sterile liquid diluent or carrier, for example water for injection, immediately prior to use. Extemporaneous injection solutions and suspensions may be prepared from sterile powders, granules and tablets of the type described above.

The present invention provides combinations shown to enhance the effects of ERK inhibitors. Herein, applicants have also shown that the combination of different ERK inhibitors is likewise synergistic. Therefore, it is contemplated that the effects of the combinations described herein can be further improved by the use of one or more additional ERK inhibitors. Accordingly, some embodiments of the present invention include one or more additional ERK inhibitors.

The following examples are provided to further illustrate the methods of the present invention. These examples are illustrative only and are not intended to limit the scope of the invention in any way.

EXAMPLES

Example 1

Materials and Methods

Cancer cell lines were maintained in cell culture under standard media and serum conditions. For dose escalation studies, A375 cells were split, grown to about 40-60% confluence, and then treated with the initial dose of the specified drug. Table 4 shows a summary of drug treatments that were escalated.

TABLE 4

Summary of Treatments Being Escalated

| Treatment | Inhibitor |
|---|---|
| 1 | Trametinib (MEKi) |
| 2 | Dabrafenib (BRAFi) |
| 3 | BVD-523 (ERKi) |
| 4 | Dabrafenib (BRAFi) + Trametinib (MEKi) |
| 5 | Dabrafenib (BRAFi) + BVD-523 (ERKi) |
| 6 | Trametinib (MEKi) + BVD-523 (ERKi) |

Figure 25:
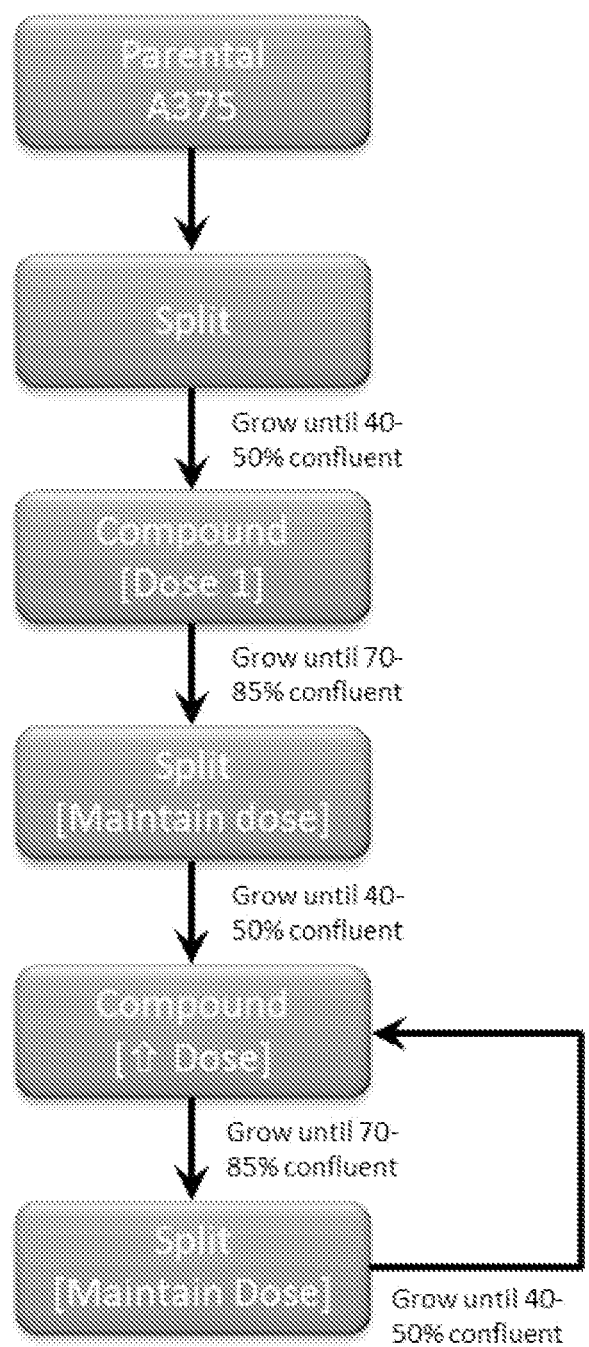
FIG. 25 is a flowchart showing the dose escalation protocol used herein.

Single agent dose escalations were performed based on Little et al., 2011 and is outlined in FIG. 25. Cells were then allowed to grow until 70-90% confluence and split. Split ratios were kept as "normal" as possible and reasonably consistent between treatments (e.g. a minimum of 50% of the normal split ratio of the parentals). Medium was refreshed every 3-4 days. When cells again reached about 40-60% confluence, the dose was escalated. In the event that the 40-60% window was missed, the cells were split again and dosed once they reached 40-60% confluence. Again, medium was refreshed every 3-4 days. The process was repeated as required (FIG. 25).

For single agent treatments, starting concentrations and dose increases were conducted by starting with the approximate $IC_{50}$, escalating in small increments or, gently, for the initial 4-5 doses, doubling the dose, increasing by the same increment for the next 4 doses, then moving to 1.5-fold increases in concentration for subsequent doses.

For combination treatments, starting concentrations and dose increases were conducted by starting with half of the approximate $IC_{50}$ of each compound (combination assay suggests this will result in about 40-70% inhibition range), escalating as per single agents (i.e. doing an initial doubling and then increasing by the same increment for the next 4 doses, then moving to 1.5-fold increases in concentration). Table 5 shows the projected dose increases using these schemes.

TABLE 5

Projected Dose Increases - Month 1

| | | | Dab/Tram | | Dab/523 | | Tram/523 | |
| --- | --- | --- | --- | --- | --- | --- | --- | --- |
| Dose | Tram (nM) | Dab (nM) | BVD-523 (μM) | Dab (nM) | Tram (nM) | Dab (nM) | 523 (μM) | Tram (nM) | 523 (μM) |
| 1 | 1 | 5 | 0.16 | 2.5 | 0.5 | 2.5 | 0.08 | 0.5 | 0.08 |
| 2 | 2 | 10 | 0.32 | 5 | 1 | 5 | 0.16 | 1 | 0.16 |
| 3 | 3 | 15 | 0.48 | 7.5 | 1.5 | 7.5 | 0.24 | 1.5 | 0.24 |
| 4 | 4 | 20 | 0.64 | 10 | 2 | 10 | 0.32 | 2 | 0.32 |
| 5 | 5 | 25 | 0.80 | 12.5 | 2.5 | 12.5 | 0.40 | 2.5 | 0.40 |
| 6 | 8 | 38 | 1.2 | 19 | 4 | 19 | 0.6 | 4 | 0.6 |
| 7 | 11 | 56 | 1.8 | 28 | 6 | 28 | 0.9 | 6 | 0.9 |
| 8 | 17 | 84 | 2.7 | 42 | 8 | 42 | 1.4 | 8 | 1.4 |
| 9 | 25 | 127 | 4.1 | 63 | 13 | 63 | 2.0 | 13 | 2.0 |
| 10 | 38 | 190 | 6.1 | 95 | 19 | 95 | 3.0 | 19 | 3.0 |
| 11 | 57 | 285 | 9.1 | 142 | 28 | 142 | 4.6 | 28 | 4.6 |
| 12 | 85 | 427 | 13.7 | 214 | 43 | 214 | 6.8 | 43 | 6.8 |
| 13 | 128 | 641 | 20.5 | 320 | 64 | 320 | 10.3 | 64 | 10.3 |
| 14 | 192 | 961 | 30.8 | 481 | 96 | 481 | 15.4 | 96 | 15.4 |
| 15 | 288 | 1442 | 46.1 | 721 | 144 | 721 | 23.1 | 144 | 23.1 |
| 16 | 432 | 2162 | 69.2 | 1081 | 216 | 1081 | 34.6 | 216 | 34.6 |
| 17 | 649 | 3244 | 103.8 | 1622 | 324 | 1622 | 51.9 | 324 | 51.9 |
| 18 | 973 | 4865 | 155.7 | 2433 | 487 | 2433 | 77.8 | 487 | 77.8 |
| 19 | 1460 | 7298 | 233.5 | 3649 | 730 | 3649 | 116.8 | 730 | 116.8 |
| 20 | 2189 | 10947 | 350.3 | 5474 | 1095 | 5474 | 175.2 | 1095 | 175.2 |

Clonal resistant cell populations were derived from resistant cell pools by limiting dilution.

Proliferation assays were used to track changes in sensitivity to the escalated agent(s) at appropriate time intervals (e.g. each month, although the timing is dependent on adequate cell numbers being available). For proliferation assays, cells were seeded in 96-well plates at 3000 cells per well in drug-free DMEM medium containing 10% FBS and allowed to adhere overnight prior to addition of compound or vehicle control. Compounds were prepared from DMSO stocks to give a final concentration range as shown in FIGS. 2A-H. The final DMSO concentration was constant at 0.1%. Test compounds were incubated with the cells for 96 hours at 37° C. and 5% $CO_2$ in a humidified atmosphere. Alamar Blue 10% (v/v) was then added and incubated for 4 hours and fluorescent product was detected using a BMG FLUO-star plate reader. The average media only background value was deducted and the data analyzed using a 4-parameter logistic equation in GraphPad Prism. Paclitaxel was used as a positive control.

Proliferation assays for month 1 were initiated at day 28 using cells growing in the concentrations of each agent indicated in Table 6.

TABLE 6

Initial Concentrations of Drugs Used in Proliferation Assays - Month 1

| Line | Dab | Tram | BVD-523 |
| --- | --- | --- | --- |
| Parental | — | — | — |
| Tram | — | 2 nM | — |
| Dab | 15 nM | — | — |
| BVD-523 | — | — | 0.48 μM |
| Tram + Dab | 5 nM | 1 nM | — |
| Dab + BVD-523 | 7.5 nM | — | 0.24 μM |
| Tram + BVD-523 | — | 1 nM | 0.16 μM |

Proliferation assays for month 2 were initiated at day 56 using cells growing in the concentrations of each agent indicated in Table 7.

TABLE 7

Initial Concentrations of Drugs Used in Proliferation Assays - Month 2

| Line | Dab | Tram | BVD-523 |
| --- | --- | --- | --- |
| Parental | — | — | — |
| Tram | — | 8 nM | — |
| Dab | 127 nM | — | — |
| BVD-523 | — | — | 0.8 μM |
| Tram + Dab | 10 nM | 2 nM | — |
| Dab + BVD-523 | 12.5 nM | — | 0.4 μM |
| Tram + BVD-523 | — | 2 nM | 0.32 μM |

At the end of the 3 month escalation period, cultures were maintained at the top concentration for 2 weeks prior to the final round of proliferation assays and potential single cell cloning. As the proliferation assays/single cell cloning required actively proliferating cells, for treatments where cells were proliferating very slowly at the top concentration or that were only recently escalated, a backup culture was also maintained at a lower concentration (Table 8). For the BVD-523 treatment, where cells appeared to have almost completely stopped growing and looked particularly fragile at the top concentration (1.8 µM), cultures were maintained at a lower concentration for the 2 week period.

TABLE 8

Details of Treatments Being Cultured at a Fixed Concentration for 2 Weeks

| Treatment | Inhibitor | Culture 1 | Backup Culture |
|---|---|---|---|
| 1 | Tram | 160 nM | 80 nM |
| 2 | Dab | 3.2 µM | — |
| 3 | BVD-523 | 1.2 µM | 0.8 µM |
| 4 | Dab + Tram | D: 160 nM<br>T: 30 nM | D: 80 nM<br>T: 16 nM |
| 5 | Dab + BVD-523 | D: 42 nM<br>523: 1.4 µM | D: 28 nM<br>523: 0.9 µM |
| 6 | Tram + BVD-523 | T: 4 nM<br>523: 0.6 µM | T: 2.5 nM<br>523: 0.4 µM |

Proliferation assays for month 3 used cells growing in the concentrations of each agent indicated in Table 9.

TABLE 9

Initial Concentrations of Drugs Used in Proliferation Assays - Month 3

| Line | Dab | Tram | BVD-523 |
|---|---|---|---|
| Parental | — | — | — |
| Tram | — | 160 nM | — |
| Dab | 3.2 µM | — | — |
| BVD-523 | — | — | 1.2 µM |
| Tram + Dab | 80 nM | 16 nM | — |
| Dab + BVD-523 | 28 nM | — | 0.9 µM |
| Tram + BVD-523 | — | 2.5 nM | 0.4 µM |

For combination studies, A375 cells (ATCC) were seeded into triplicate 96-well plates at a cell density of 3000 cells/well in DMEM plus 10% FBS and allowed to adhere overnight prior to addition of test compound or vehicle control. Combinations were tested using a 10×8 dose matrix with a final DMSO concentration of 0.2%. A 96 hour assay incubation period followed, with subsequent addition of Alamar Blue 10% (v/v) and 4 hours incubation prior to reading on a fluorescent plate reader. After reading Alamar Blue, the medium/Alamar Blue mix was flicked off and 100 µl of CellTiter-Glo/PBS (1:1) added and the plates processed as per the manufacturer's instructions (Promega). Media only background values were subtracted before the data was analysed. The Bliss additivity model was then applied.

In brief, predicted fractional inhibition values for combined inhibition were calculated using the equation $C_{bliss}=A+B-(A \times B)$ where A and B are the fractional inhibitions obtained by drug A alone or drug B alone at specific concentrations. $C_{bliss}$ is the fractional inhibition that would be expected if the combination of the two drugs were exactly additive. $C_{bliss}$ values are subtracted from the experimentally observed fractional inhibition values to give an 'excess over Bliss' value. Excess over Bliss values greater than 0 indicate synergy, whereas values less than 0 indicate antagonism. Excess over Bliss values are plotted as heat maps ±SD.

The single and combination data are also presented as dose-response curves generated in GraphPad Prism (plotted using % viability relative to DMSO only treated controls).

For focused combination studies, the Alamar Blue viability assays were performed as described above for combination studies. Additionally, Caspase-Glo 3/7 assays were performed. In brief, HCT116 cells were seeded in triplicate in white 96-well plates at a cell density of 5000 cells/well in McCoy's 5A plus 10% FBS. A375 cells were seeded at a density of 5000 cells/well in DMEM plus 10% FBS. Cells were allowed to adhere overnight prior to addition of the indicated amount of test compound or vehicle control. The final concentration of DMSO was 0.2%, and 800 nM staurosporine was included as a positive control. 24 and 48 hour assay incubation periods were used. Then, Caspase-Glo® 3/7 50% (v/v) was added, plates were mixed for 5 minutes on an orbital shaker and incubated for 1 hour at room temperature prior to reading on a luminescent plate reader. Media only background values were subtracted before the data was analysed.

Example 2

Dose Escalation and Proliferation Assays—Month 1

Dose Escalation Progress—Month 1

A375 cells were dose escalated using BVD-523, dabrafenib, and trametinib either as single agents or in combination. Doses were increased in small increments during the first month. Other than a marked reduction in growth rate, cells generally tolerated the escalations well and the doses were planned to be more aggressively escalated using larger increments in month 2. FIGS. 1A-C show month 1 progress for the dose escalation studies.

Proliferation Assay Results—Month 1

Proliferation assays were performed to assess the response of the escalated cells lines vs. parental cell line, to BVD-523, dabrafenib, and trametinib treatments.

FIGS. 2A-H show normalized and raw proliferation assay results from month 1 of the studies. Note that differences in max signals in DMSO controls between different treatments (FIGS. 2D-F, 2H) suggest differential growth rates between treatments. These differences may influence the responses of lines to inhibitors in the proliferation assays.

Table 10 shows $IC_{50}$ data for month 1 of the studies.

TABLE 10

$IC_{50}$ Data - Month 1

| | Cell Line, Relative $IC_{50}$ (nM) | | | | | | |
|---|---|---|---|---|---|---|---|
| Compound | Par* | Tram | Dab | BVD-523 | Dab/Tram | Dab/523 | Tram/523 |
| Dabrafenib | 6 | 29 | about 161 | 8 | 58 | 68 | 11 |
| Trametinib | 0.5 | 2.2 | 2.5 | 0.7 | 3.9 | 3.1 | 2.5 |
| BVD-523 | 189 | 335 | 350 | 268 | 300 | 412 | 263 |
| Paclitaxel | 2.2 | 3.0 | 3.3 | 3.4 | 3.5 | 3.4 | 3.4 |

*Par = Parental cell line

There were early hints that cells grown in the presence of escalating doses of dabrafenib or trametinib, either as single agents or in combinations, were exhibiting decreased responses to these two agents in proliferation assays.

In the early stages of month 2, the growth rate of cells in the dabrafenib only treatment notably increased relative to the early stages of month 1. This enabled an increased rate of progression and suggested that resistance was becoming apparent.

Example 3

Dose Escalation and Proliferation Assays—Month 2

Dose Escalation Progress—Month 2

The second month of studies saw most treatments move into a phase where doses were increased in greater increments (1.5-fold) compared to the initial gentle escalation phase. The single agent escalation of dabrafenib and trametinib was quickest, with cells growing in concentrations equivalent to 100× parental cell $IC_{50}$ (FIGS. 3A,B). The single agent escalation of BVD-523 progressed more slowly compared to dabrafenib and trametinib (FIG. 3C). See FIG. 3D for a comparison of the single agent escalations. BVD-523 escalated cells had a more "fragile" appearance and there was a greater number of floating cells compared to the dabrafenib and trametinib escalated populations.

The combined agent escalations progressed more slowly than the single agent treatments. The BVD-523/trametinib combination was particularly effective in preventing cells from progressing.

Proliferation Assay Results—Month 2

Proliferation assays on single agent escalated dabrafenib and trametinib cell populations revealed modest shifts in the dose response curves, suggesting that an additional period of escalation would be beneficial to further enrich for resistant cells. Interestingly, in the proliferations assay, there was evidence to suggest that cells exposed to BVD-523 grew less well upon inhibitor withdrawal, perhaps indicating a level of addiction.

FIGS. 4A-H show normalized and raw proliferation assay results from month 2 of the studies. Note that differences in max signals in DMSO controls between different treatments (FIGS. 4D-F, 4H) suggest differential growth rates between treatments. These differences may influence the responses of lines to inhibitors in the proliferation assays.

FIGS. 5A-H show normalized and raw proliferation assay results from month 2 of the studies with a focus on parental and BVD-523 line data only.

Table 11 shows $IC_{50}$ data for month 2 of the studies. Relative $IC_{50}$s were determined from 4-parameter curve fits in Prism.

TABLE 11

$IC_{50}$ Data - Month 2

Cell Line, Relative $IC_{50}$ (nM)

| Compound | Par* | Tra | Dab | BVD-523 | Dab/Tram | Dab/523 | Tram/523 |
|---|---|---|---|---|---|---|---|
| Dabrafenib | 4.1 | 6.2 | 11.5 | 697 | 256 | 218 | 68 |
| Trametinib | 0.4 | 0.7 | 1.1 | 24.3 | 12.6 | 6.2 | 4.6 |
| BVD-523 | 187 | 252 | 284 | 1706 | 561 | 678 | 435 |
| Paclitaxel | 3.7 | 8.9 | 1.9 | 6.5 | 4.7 | 4.2 | 8.9 |

*Par = Parental cell line

Example 4

Dose Escalation and Proliferation Assays—Month 3

Dose Escalation Progress—Month 3

FIGS. 6A-C show single and combination agent escalation for month 3 of the studies. FIG. 6D shows a comparison of single agent escalations.

Proliferation Assay Results—Month 3

Figure 2:
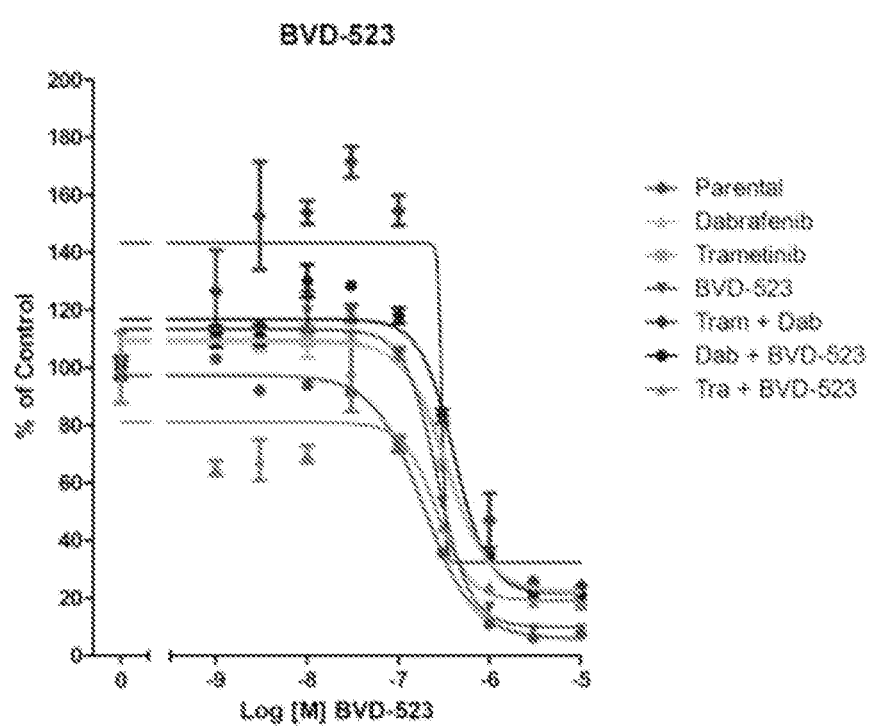
FIGS. 2A-H show the results of a proliferation assay that tracks changes in sensitivity to the escalated agent(s) at month 1. Various treatments (trametinib, dabrafenib, BVD-523, and pacitaxel) are as labeled on the top of the graph. The caption to the right of the graph shows the various types of cells generated from the dose escalation study. For example, "dabrafenib" refers to the cells that have been treated with the highest dose of dabrafenib from month 1 of the dose escalation study. Parental refers to the control cells that have not been treated with drugs.
Figure 4:
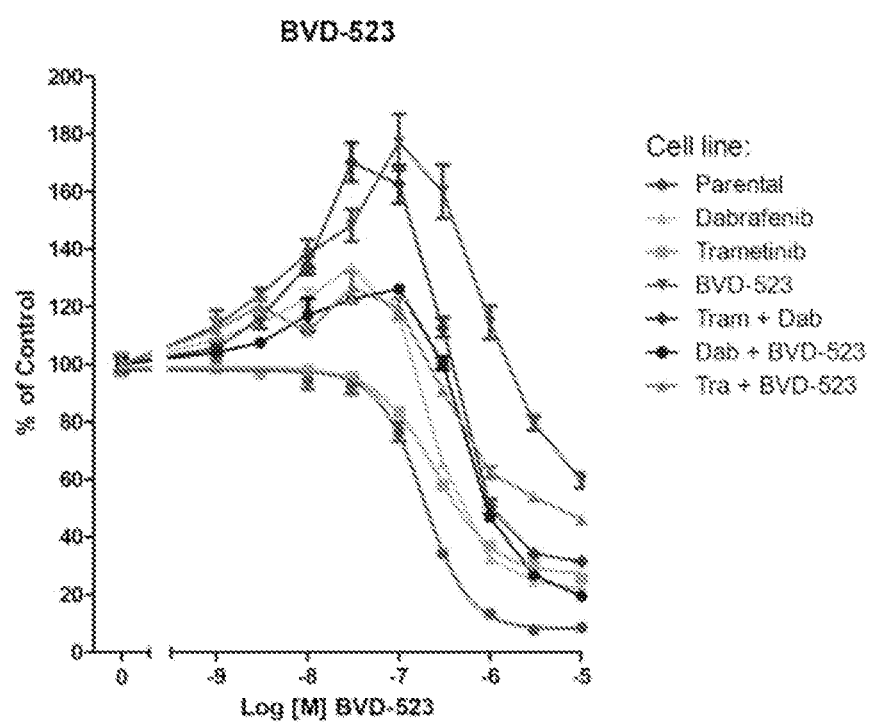
FIGS. 4A-H show the results of a proliferation assay that tracks changes in sensitivity to the escalated agent(s) at month 2. Various treatments (trametinib, dabrafenib, BVD-523, and pacitaxel) are as labeled on the top of the graph. The caption to the right of the graph shows the various types of cells generated from the dose escalation study. For example, "dabrafenib" refers to the cells that have been treated with the highest dose of dabrafenib from month 2 of the dose escalation study. Parental refers to the control cells that have not been treated with drugs.
Figure 5:
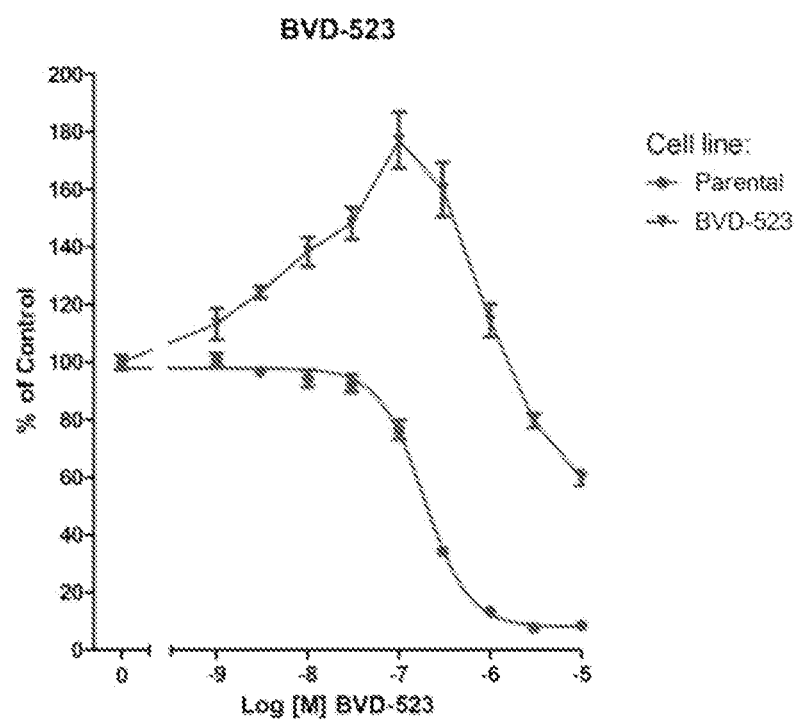
FIGS. 5A-H show only the parental and BVD-523 cell line data from FIG. 4. Various treatments (trametinib, dabrafenib, BVD-523, and pacitaxel) are as labeled.
Figure 7:
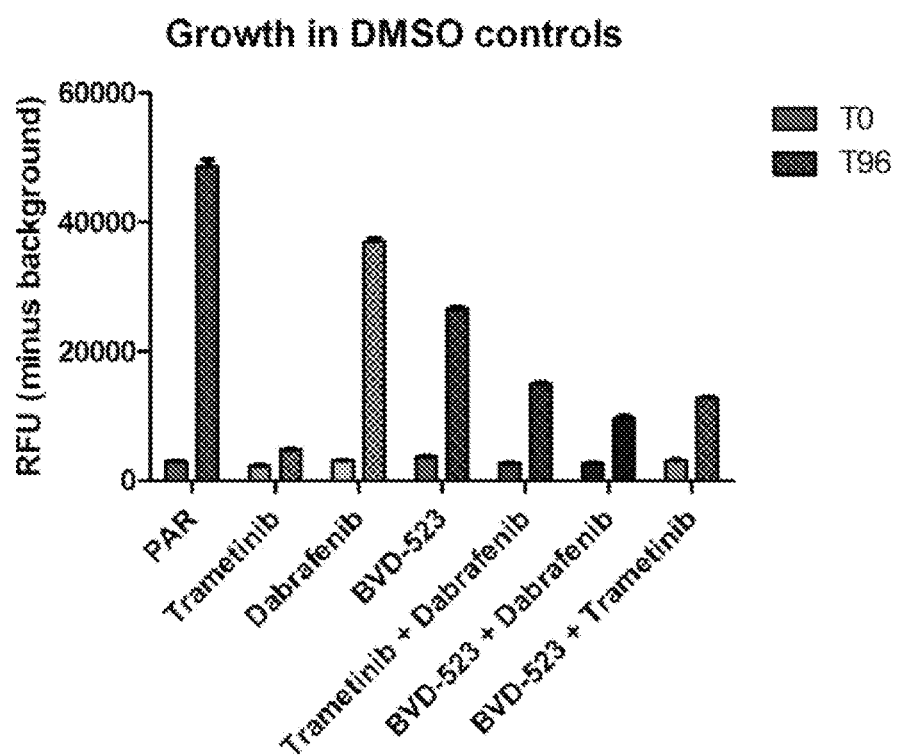
FIG. 7 is a histogram showing the results of a proliferation assay as applied to cells grown in the DMSO control wells from the dose escalation assay.
Figure 8:
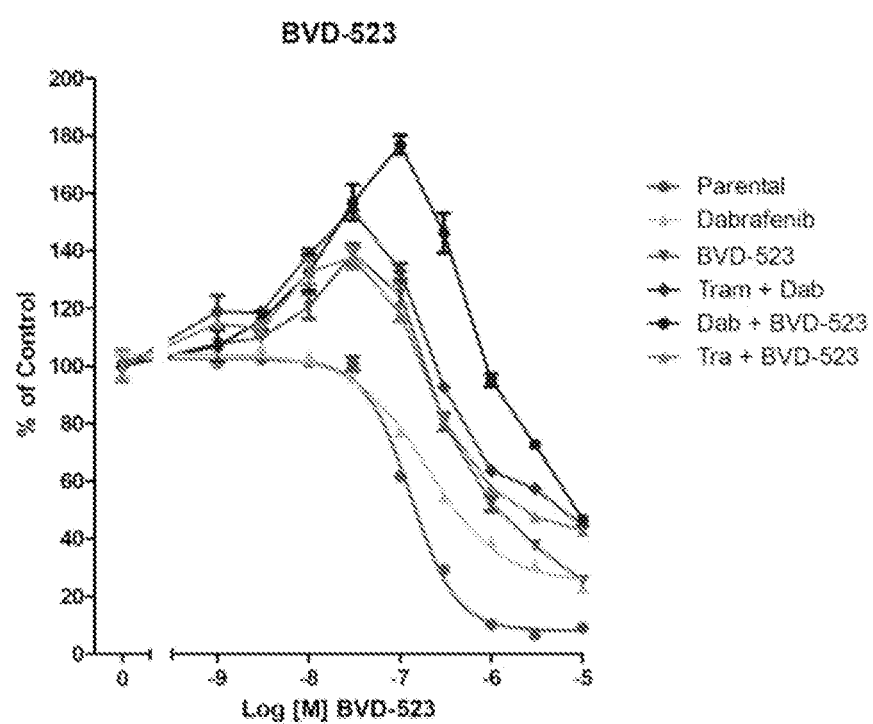
FIGS. 8A-D are a set of line graphs showing proliferation assays for month 3 of the study. Various treatments (trametinib, dabrafenib, BVD-523, and pacitaxel) are as labeled on the top of the graph. The caption to the right of the graph shows the various types of cells generated from the dose escalation study. For example, "dabrafenib" refers to the cells that have been treated with the highest dose of dabrafenib from month 3 of the dose escalation study. Parental refers to the control cells that have not been treated with drugs.
Figure 9:
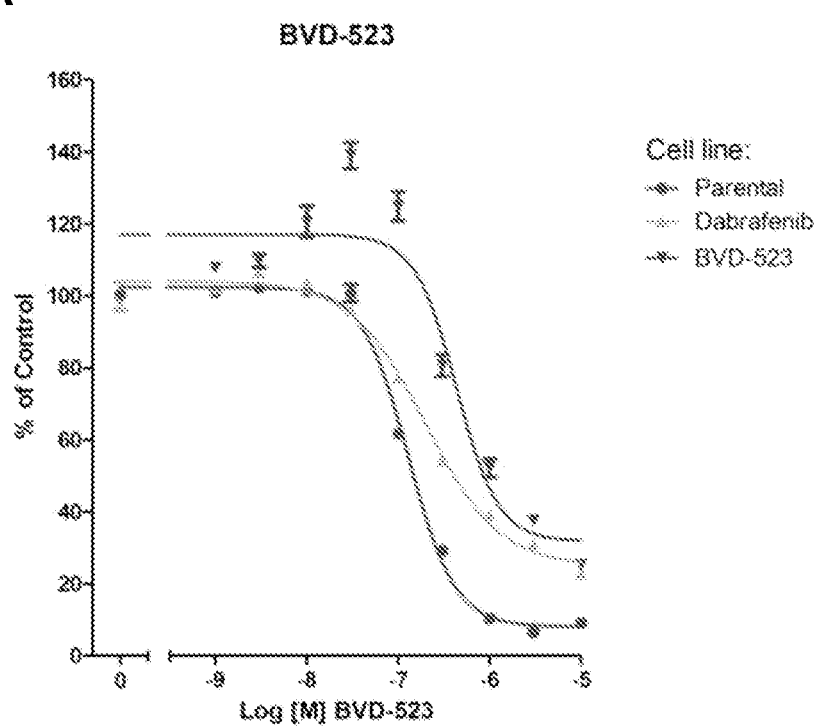
FIGS. 9A-D show only the parental, dabrafenib, and BVD-523 cell line data from FIG. 8.

FIG. 7 shows an assessment of growth during the proliferation assay in DMSO control wells. FIGS. 8A-D show results from month 3 of the studies. FIGS. 9A-D show results from month 3 of the studies with a focus on single treatment cell lines.

Table 12 shows $IC_{50}$ data for month 3 of the studies. Relative $IC_{50}$s were determined from 4-parameter curve fits in Prism. $IC_{50}$ values were not determined for the cell line escalated with trametinib due to a lack of growth during the assay (ND: not done).

TABLE 12

$IC_{50}$ Data - Month 3

Cell Line, Relative $IC_{50}$ (nM)

| Compound | Par* | Tram | Dab | BVD-523 | Dab/Tram | Dab/523 | Tram/523 |
|---|---|---|---|---|---|---|---|
| Dabrafenib | 2.1 | ND | 2.5 | 18.4 | 17.9 | 337 | 73 |
| Trametinib | 0.2 | ND | 0.4 | 1.7 | 2.7 | 90 | 11.2 |
| BVD-523 | 129 | ND | 198 | 433 | 323 | 1151 | 296 |
| Paclitaxel | 1.9 | ND | 1.9 | 6.5 | 4.7 | 4.2 | 8.9 |

*Par = Parental cell line

Example 5

Combination Study Results

Figure 10:
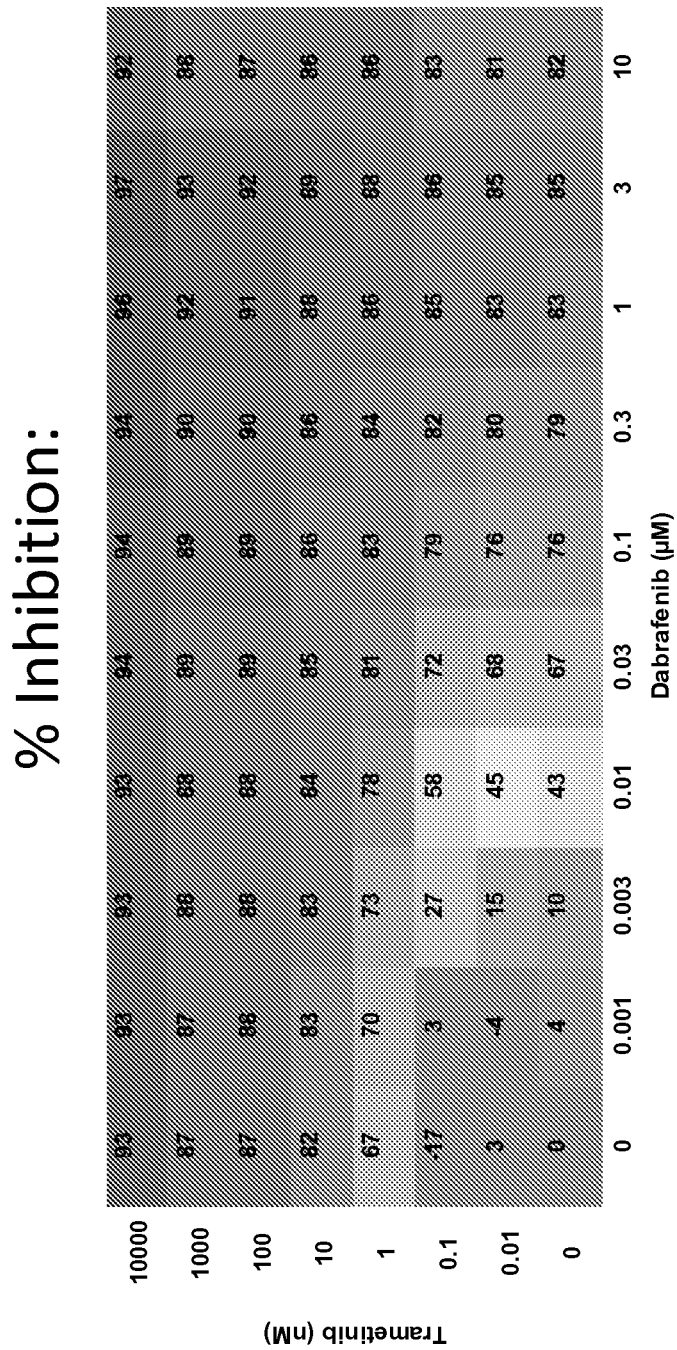
FIG. 10A is a dose matrix showing % inhibition of the trametinib/dabrafenib combination in A375 cells using the Alamar Blue cell viability assay.
FIG. 10B is a dose matrix showing excess over Bliss for the trametinib/dabrafenib combination.
FIGS. 10C and 10D show % viability relative to DMSO only treated controls for dabrafenib and trametinib single agent treatments in A375 cells using the Alamar Blue cell viability assay.
FIG. 10E shows % viability relative to DMSO only treated controls for dabrafenib and trametinib combination treatments in A375 cells using the Alamar Blue cell viability assay.
Figure 12:
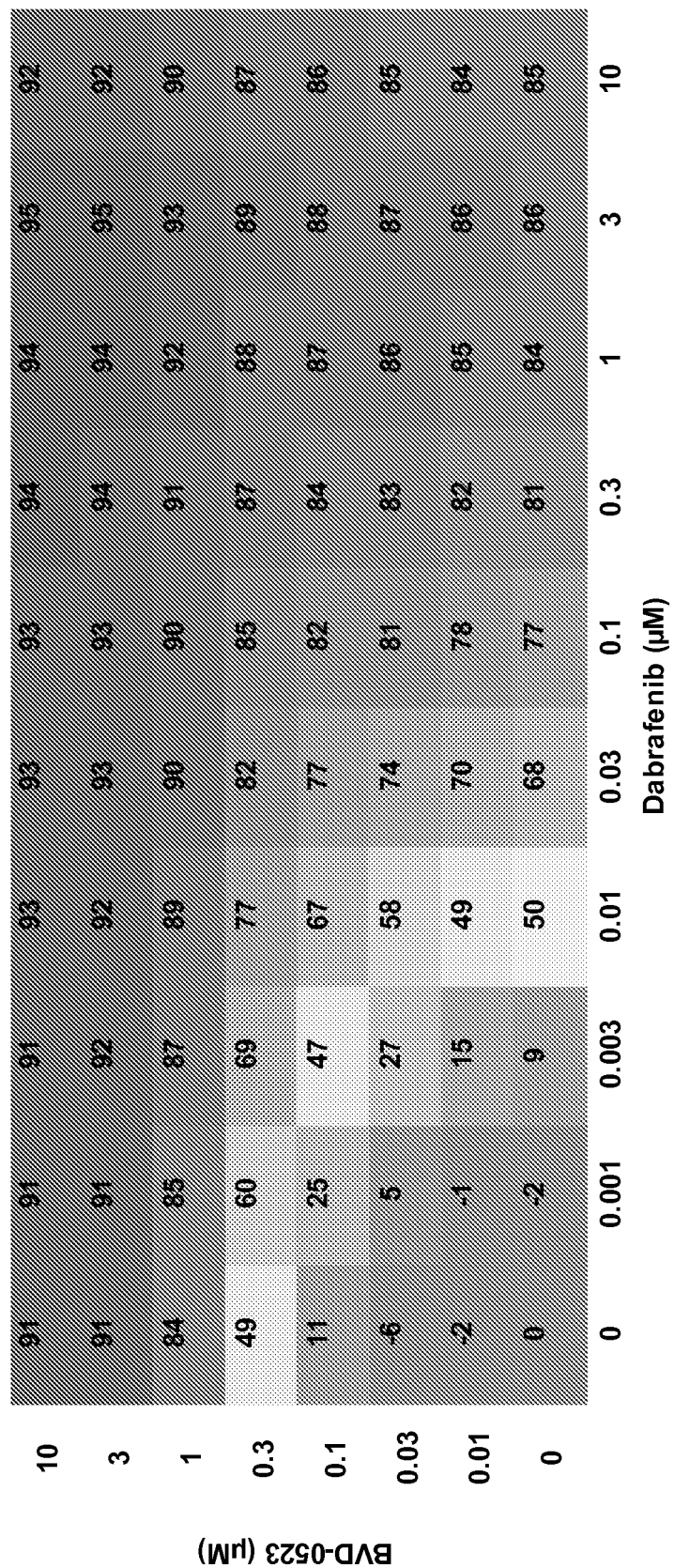
FIG. 12A is a dose matrix showing % inhibition of the BVD-523/dabrafenib combination in A375 cells using the Alamar Blue cell viability assay.
FIG. 12B is a dose matrix showing excess over Bliss for the BVD-523/dabrafenib combination.
FIGS. 12C and 12D show % viability relative to DMSO only treated controls for dabrafenib and BVD-523 single agent treatments in A375 cells using the Alamar Blue cell viability assay.
FIG. 12E shows % viability relative to DMSO only treated controls for dabrafenib and BVD-523 combination treatments in A375 cells using the Alamar Blue cell viability assay.
Figure 13:
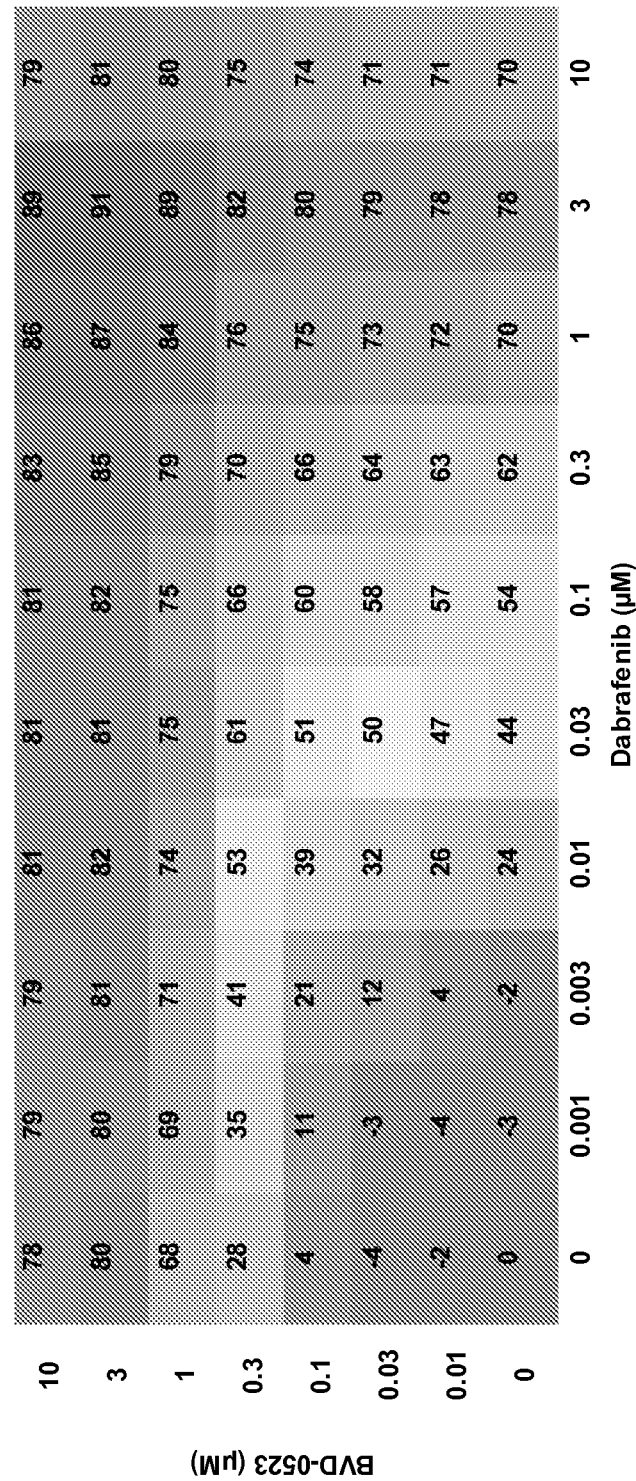
FIG. 13A is a dose matrix showing % inhibition of the BVD-523/dabrafenib combination in A375 cells using the CellTiter-Glo cell viability assay.
FIG. 13B is a dose matrix showing excess over Bliss for the BVD-523/dabrafenib combination.
FIGS. 13C and 13D show % viability relative to DMSO only treated controls for dabrafenib and BVD-523 single agent treatments in A375 cells using the CellTiter-Glo cell viability assay.
FIG. 13E shows % viability relative to DMSO only treated controls for dabrafenib and BVD-523 combination treatments in A375 cells using the CellTiter-Glo cell viability assay.
Figure 14:
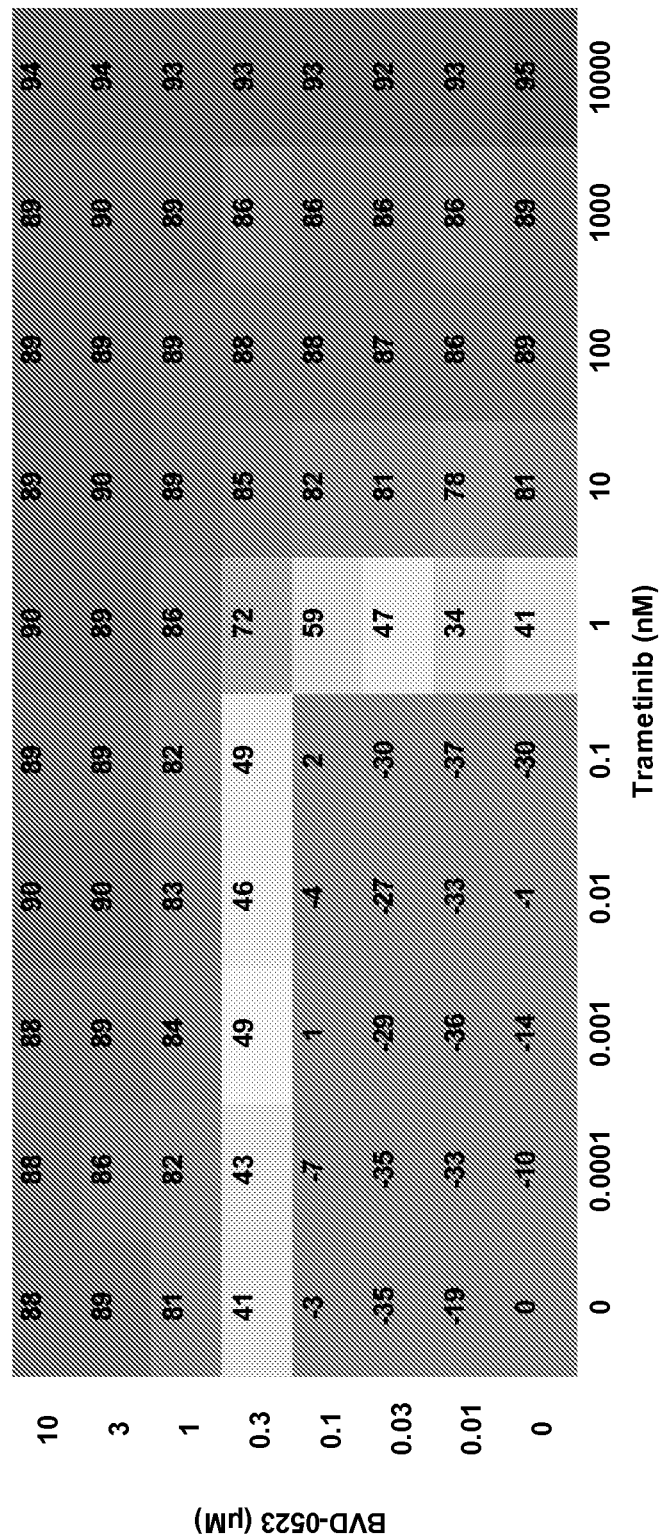
FIG. 14A is a dose matrix showing % inhibition of the trametinib/BVD-523 combination in A375 cells using the Alamar Blue cell viability assay.
FIG. 14B is a dose matrix showing excess over Bliss for the trametinib/BVD-523 combination.
FIGS. 14C and 14D show % viability relative to DMSO only treated controls for BVD-523 and trametinib single agent treatments in A375 cells using the Alamar Blue cell viability assay.
FIG. 14E shows % viability relative to DMSO only treated controls for BVD-523 and trametinib combination treatments in A375 cells using the Alamar Blue cell viability assay.
Figure 15:
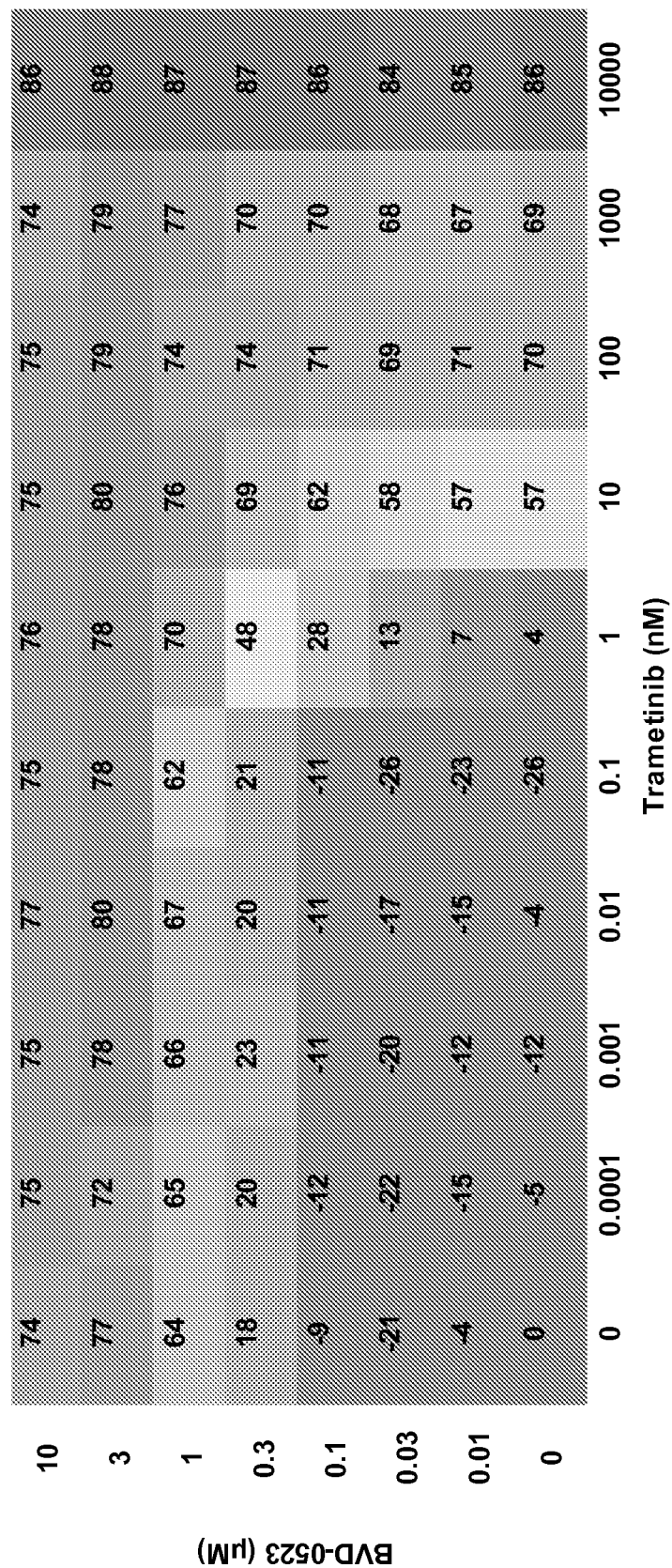
FIG. 15A is a dose matrix showing % inhibition of the trametinib/BVD-523 combination in A375 cells using the CellTiter-Glo cell viability assay.
FIG. 15B is a dose matrix showing excess over Bliss for the trametinib/BVD-523 combination.
FIGS. 15C and 15D show % viability relative to DMSO only treated controls for BVD-523 and trametinib single agent treatments in A375 cells using the CellTiter-Glo cell viability assay.
FIG. 15E shows % viability relative to DMSO only treated controls for BVD-523 and trametinib combination treatments in A375 cells using the CellTiter-Glo cell viability assay.

As expected, A375 cells, which carry a BRAF (V600E) mutation, were sensitive to dabrafenib. Single agent $IC_{50}$ values calculated using Alamar Blue (FIGS. 10, 12, 14) were generally slightly lower for Dabrafenib and BVD-523 compared to those derived using CellTiter-Glo (FIGS. 11, 13, 15). Published $IC_{50}$ values for Dabrafenib and Trametinib in a 72 hour CellTiter-Glo assay were 28±16 nM and 5±3 nM respectively (Greger et al., 2012; King et al., 2013)—the single agent results reported here are consistent with these values. There was some evidence for a window of synergy in all treatments. Variation between triplicates was low, however, there was some evidence of edge effects that likely explains the apparent enhanced growth observed in some treatments versus the no drug control (e.g. particularly apparent in the Trametinib/BVD-523 combination). This makes the interpretation of the Bliss analysis more challenging as in some treatments it may have resulted in the artefactual enhancement in the level of synergy.

The combination assays were repeated for A375 cells. Additionally, HCT116 cells were used in a follow-up combination assay. The results of these experiments are shown in FIGS. 31-41. Single agent BVD-523, Trametinib and Dabrafenib potencies were consistent with those reported in the previous studies.

HCT116 cells are human colorectal cancer cells with mutations in KRAS. Dabrafenib and Trametinib were antagonist at relevant on-target concentrations. In contrast, Trametinib exhibited synergy with AZ628 over a broad range of combinations, and with higher concentrations of Sorafenib. BVD-523 exhibited windows of synergy with both AZ628 and Sorafenib.

In A375 cells, trametinib exhibited pockets of synergy at lower concentrations of Dabrafenib and AZ628. BVD-523 exhibited a window of synergy with the lower concentrations of Sorafenib.

Example 6

BVD-523 Altered Markers of MAPK Kinase Activity and Effector Function

For Western blot studies, HCT116 cells (5×10⁶) were seeded into 10 cm dishes in McCoy's 5A plus 10% FBS. A375 cells (2.5×10⁶) were seeded into 10 cm dishes in DMEM plus 10% FBS. Cells were allowed to adhere overnight prior to addition of the indicated amount of test compound (BVD-523) or vehicle control. Cells were treated for either 4 or 24 hours before isolation of whole-cell protein lysates, as specified below. Cells were harvested by trypsinisation, pelleted and snap frozen. Lysates were prepared with RIPA (Radio-Immunoprecipitation Assay) buffer, clarified by centrifugation and quantitated by bicinchoninic acid assay (BCA) assay. 20-50 µg of protein was resolved by SDS-PAGE electrophoresis, blotted onto PVDF membrane and probed using the antibodies detailed in Table 13 (for the 4-hour treatment) and Table 14 (for the 24-hour treatment) below.

TABLE 13

Antibody Details

| Antigen | Size (kDa) | Supplier | Cat No | Dilution | Incubation/Block Conditions | Secondary |
|---|---|---|---|---|---|---|
| pRSK1/2 pS380 | 90 | Cell Signaling | 9335 | 1:1000 | o/n 4° C. 5% BSA | anti-rabbit |
| pRSK1/2 pS380 | 90 | Cell Signaling | 11989 | 1:2000 | o/n 4° C. 5% BSA | anti-rabbit |
| pRSK-T359/S363 | 90 | Millipore | 04-419 | 1:40000 | o/n 4° C. 5% BSA | anti-rabbit |
| Total RSK | 90 | Cell Signaling | 9333 | 1:1000 | o/n 4° C. 5% BSA | anti-rabbit |
| pErk 1/2 | 42/44 | Cell Signaling | 9106S | 1:500 | o/n 4° C. 5% milk | anti-mouse |
| Total ERK | 42/44 | Cell Signaling | 9102 | 1:2000 | o/n 4° C. 5% milk | anti-rabbit |
| pMEK1/2 | 45 | Cell Signaling | 9154 | 1:1000 | o/n 4° C. 5% BSA | anti-rabbit |
| Total MEK | 45 | Cell Signaling | 9126 | 1:1000 | o/n 4° C. 5% BSA | anti-rabbit |
| pS6-pS235 | 32 | Cell Signaling | 2211S | 1:3000 | o/n 4° C. 5% milk | anti-rabbit |
| Total S6 | 32 | Cell Signaling | 2217 | 1:2000 | o/n 4° C. 5% milk | anti-rabbit |
| DUSP6 | 48 | Cell Signaling | 3058S | 1:1000 | o/n 4° C. 5% BSA | anti-rabbit |
| Total CRAF | 73 | BD Biosciences | 610152 | 1:2000 | o/n 4° C. 5% milk | anti-mouse |
| pCRAF-Ser338 | 73 | Cell Signaling | 9427 | 1:1000 | o/n 4° C. 5% BSA | anti-rabbit |
| pRB (Ser780) | 105 | Cell Signaling | 9307 | 1:2000 | o/n 4° C. 5% BSA | anti-rabbit |
| β-Actin | 42 | Sigma | A5441 | 1:500,000 | o/n 4° C. 5% milk | anti-mouse |

TABLE 14

Antibody details

| Antigen | Size (kDa) | Supplier | Cat No | Dilution | Incubation/Block Conditions | Secondary |
|---|---|---|---|---|---|---|
| pRB (Ser780) | 105 | Cell Signaling | 9307 | 1:2000 | o/n 4° C. 5% BSA | anti-rabbit |
| CCND1 | 34 | Abcam | ab6152 | 1:500 | o/n 4° C. 5% milk | anti-mouse |
| Bim-EL | 23 | Millipore | AB17003 | 1:1000 | o/n 4° C. 5% BSA | anti-rabbit |
| Bim-EL | 23 | Cell Signaling | 2933 | 1:1000 | o/n 4° C. 5% BSA | anti-rabbit |
| BCL-xL | 30 | Cell Signaling | 2762 | 1:2000 | o/n 4° C. 5% BSA | anti-rabbit |
| PARP | 116/89 | Cell Signaling | 9542 | 1:1000 | o/n 4° C. 5% milk | anti-rabbit |
| Cleaved Caspase 3 | 17, 19 | Cell Signaling | 9664X | 1:1000 | o/n 4° C. 5% milk | anti-rabbit |
| DUSP6 | 48 | Cell Signaling | 3058S | 1:1000 | o/n 4° C. 5% BSA | anti-rabbit |
| pRSK1/2 pS380 | 90 | Cell Signaling | 9335 | 1:1000 | o/n 4° C. 5% BSA | anti-rabbit |
| pRSK1/2 pS380 | 90 | Cell Signaling | 11989 | 1:2000 | o/n 4° C. 5% BSA | anti-rabbit |
| pRSK-T359/S363 | 90 | Millipore | 04-419 | 1:40000 | o/n 4° C. 5% BSA | anti-rabbit |

TABLE 14-continued

Antibody details

| Antigen | Size (kDa) | Supplier | Cat No | Dilution | Incubation/ Block Conditions | Secondary |
|---|---|---|---|---|---|---|
| Total RSK | 90 | Cell Signaling | 9333 | 1:1000 | o/n 4° C. 5% BSA | anti-rabbit |
| pErk 1/2 | 42/44 | Cell Signaling | 9106S | 1:500 | o/n 4° C. 5% milk | anti-mouse |
| Total ERK | 42/44 | Cell Signaling | 9102 | 1:2000 | o/n 4° C. 5% milk | anti-rabbit |
| B-Actin | 42 | Sigma | A5441 | 1:500,000 | o/n 4° C. 5% milk | anti-mouse |

Figure 16:
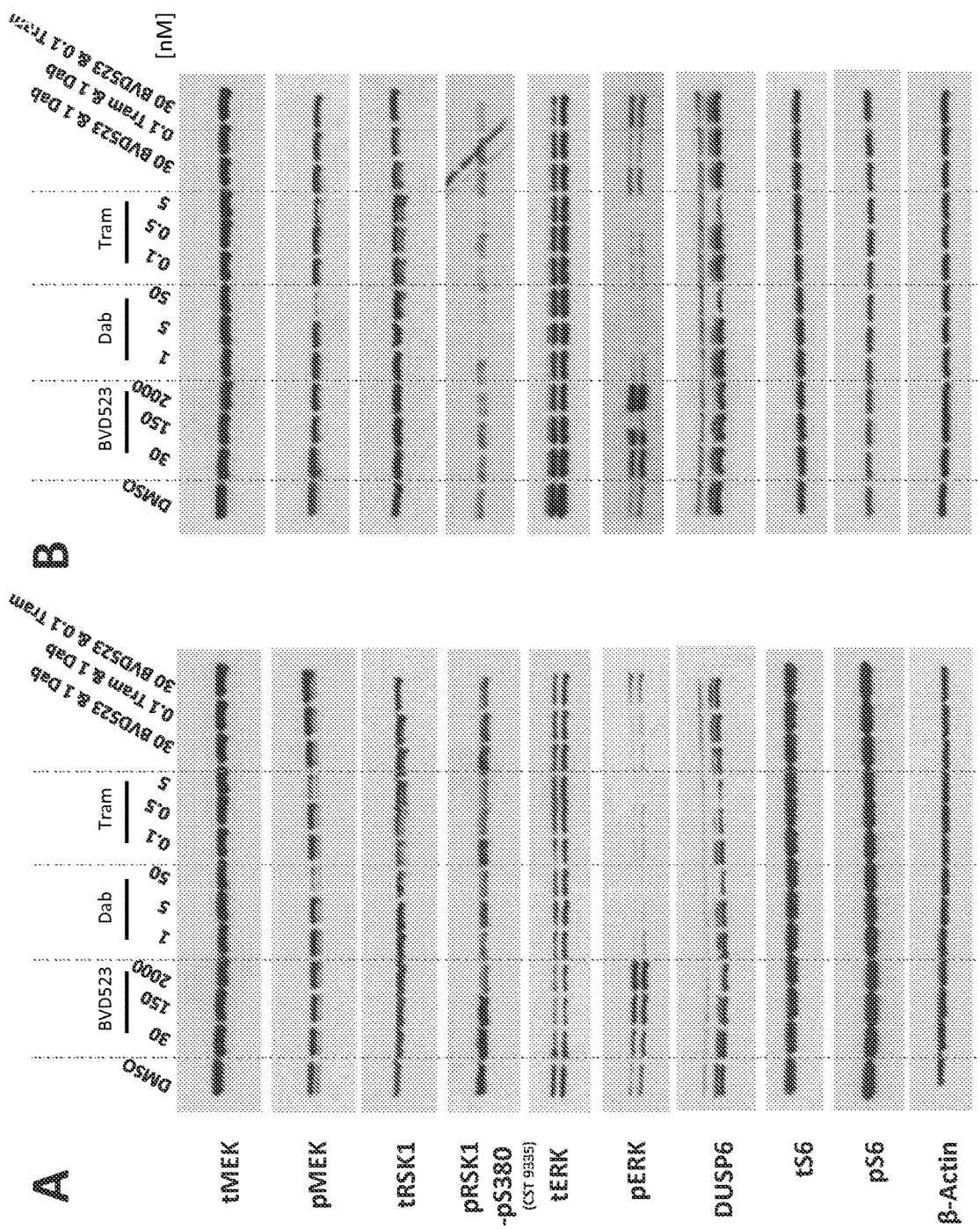
FIGS. 16A-D are a set of images showing Western blot analysis of MAPK signaling in A375 cells after a 4 hour treatment with various concentrations (in nM) of BVD-523, dabrafenib (Dab), and Trametinib (Tram). 40 µg of total protein was loaded in each lane except where indicated otherwise. In this experiment, duplicate samples were collected.
Figure 17:
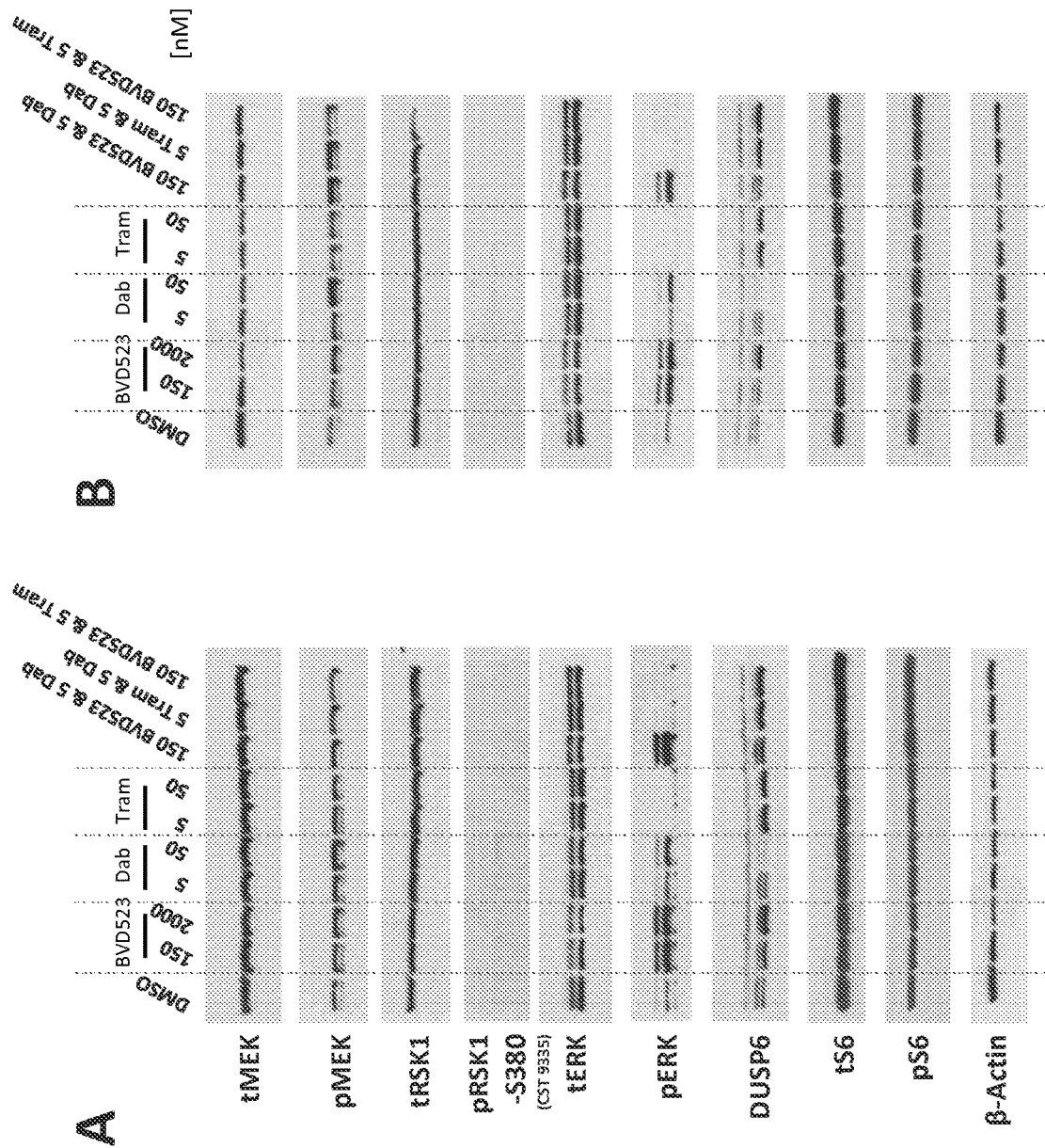
FIGS. 17A-D are a set of images showing Western blot analysis of MAPK signaling in a human colorectal carcinoma cell line (HCT116 cells) after a 4 hour treatment with various concentrations (in nM) of BVD-523, dabrafenib (Dab), and Trametinib (Tram). 40 µg of total protein was loaded in each lane except where indicated otherwise. In this experiment, duplicate samples were collected.

FIGS. 16-18 show Western blot analyses of cells treated with BVD-523 at various concentrations for the following: 1) MAPK signaling components in A375 cells after 4 hours; 2) cell cycle and apoptosis signaling in A375 24 hours treatment with various amounts of BVD-523; and 3) MAPK signaling in HCT-116 cells treated for 4 hours. The results show that acute and prolonged treatment with BVD-523 in RAF and RAS mutant cancer cells in-vitro affects both substrate phosphorylation and effector targets of ERK kinases. The concentrations of BVD-523 required to induce these changes is typically in the low micromolar range.

Changes in several specific activity markers are noteworthy. First, the abundance of slowly migrating isoforms of ERK kinase increase following BVD-523 treatment; modest changes can be observed acutely, and increase following prolonged treatment. While this could indicate an increase in enzymatically active, phosphorylated forms of ERK, it remains noteworthy that multiple proteins subject to both direct and indirect regulation by ERK remain "off" following BVD-523 treatment. First, RSK1/2 proteins exhibit reduced phosphorylation at residues that are strictly dependent on ERK for protein modification (T359/S363). Second, BVD-523 treatment induces complex changes in the MAPK feedback phosphatase, DUSP6: slowly migrating protein isoforms are reduced following acute treatment, while total protein levels are greatly reduced following prolonged BVD-523 treatment. Both of these findings are consistent with reduced activity of ERK kinases, which control DUSP6 function through both post-translational and transcriptional mechanisms. Overall, despite increases in cellular forms of ERK that are typically thought to be active, it appears likely that cellular ERK enzyme activity is fully inhibited following either acute or prolonged treatment with BVD-523.

Consistent with these observations, effector genes that require MAPK pathway signaling are altered following treatment with BVD-523. The G1/S cell-cycle apparatus is regulated at both post-translational and transcriptional levels by MAPK signaling, and cyclin-D1 protein levels are greatly reduced following prolonged BVD-523 treatment. Similarly, gene expression and protein abundance of apoptosis effectors often require intact MAPK signaling, and total levels of Bim-EL increase following prolonged BVD-523 treatment. As noted above, however, PARP protein cleavage and increased apoptosis were not noted in the A375 cell background; this suggests that additional factors may influence whether changes in BVD-523/ERK-dependent effector signaling are translated into definitive events such as cell death and cell cycle arrest.

Consistent with the cellular activity of BVD-523, marker analysis suggests that ERK inhibition alters a variety of molecular signaling events in cancer cells, making them susceptible to both decreased cell proliferation and survival.

In sum, FIGS. 16-18 show that BVD-523 inhibits the MAPK signaling pathway and may be more favorable compared to RAF or MEK inhibition in this setting.

Finally, properties of BVD-523 may make this a preferred agent for use as an ERK inhibitor, compared to other agents with a similar activity. It is known that kinase inhibitor drugs display unique and specific interactions with their enzyme targets, and that drug efficacy is strongly influenced by both the mode of direct inhibition, as well as susceptibility to adaptive changes that occur following treatment. For example, inhibitors of ABL, KIT, EGFR and ALK kinases are effective only when their cognate target is found in active or inactive configurations. Likewise, certain of these inhibitors are uniquely sensitive to either secondary genetic mutation, or post-translational adaptive changes, of the protein target. Finally, RAF inhibitors show differential potency to RAF kinases present in certain protein complexes and/or subcellular localizations. In summary, as ERK kinases are similarly known to exist in diverse, variable, and complex biochemical states, it appears likely that BVD-523 may interact with and inhibit these targets in a fashion that is distinct and highly preferable to other agents.

Example 7

In Vivo Assay

Mice

Female athymic nude mice (Crl:NU(Ncr)-Foxn/$^{nu}$, Charles River) were nine weeks old with a body weight (BW) range of 17.5 to 26.2 grams on Day 1 of the study. The animals were fed ad libitum water (reverse osmosis, 1 ppm Cl), and NIH 31 Modified and Irradiated Lab Diet® consisting of 18.0% crude protein, 5.0% crude fat, and 5.0% crude fiber. The mice were housed on irradiated Enrich-o'cobs™ Laboratory Animal Bedding in static microisolators on a 12-hour light cycle at 20-22° C. (68-72° F.) and 40-60% humidity. The recommendations of the *Guide for Care and Use of Laboratory Animals* with respect to restraint, husbandry, surgical procedures, feed and fluid regulation, and veterinary care were complied with.

In Vivo Implantation and Tumor Growth

Tumor xenografts were initiated with A375 human melanomas by serial subcutaneous transplantation in athymic nude mice. On the day of tumor implant, each test mouse received a 1 mm$^3$ A375 fragment implanted subcutaneously in the right flank, and tumor growth was monitored as the average size approached the target range of 80 to 120 mm$^3$.

Tumors were measured in two dimensions using calipers, and volume was calculated using the formula:

$$\text{Tumor Volume (mm}^3) = \frac{w^2 \times l}{2}$$

where w=width and l=length, in mm, of the tumor. Tumor weight may be estimated with the assumption that 1 mg is equivalent to 1 mm³ of tumor volume.

Ten days after tumor implantation, designated as Day 1 of the study, the animals were sorted into nine groups (Groups 1-9) each consisting of fifteen mice and one group (Group 10) consisting of ten mice. Individual tumor volumes ranged from 75 to 144 mm³ and group mean tumor volumes were 110 or 111 mm³.

Therapeutic Agents

BVD-523 and dabrafenib were supplied as dry powders and were stored at room temperature protected from light.

BVD-523 doses were prepared by suspending the required amount of BVD-523 powder in 1% carboxymethyl cellulose in deionized water ("1% CMC"). A 10 mg/mL BVD-523 stock was prepared, and was used to dose the 100 mg/kg BVD-523 group. Aliquots of the stock were diluted with the vehicle to a concentration of 5.0 mg/mL to provide the 50 mg/kg BVD-523 dosage in a dosing volume of 10 mL/kg. The BVD-523 doses were stored at 4° C. protected from light for up to one week.

Dabrafenib dry powder consisted of 84.5% active compound, which was accounted for when preparing doses. Dabrafenib was formulated in 1% CMC at concentrations of 11.834 and 5.917 mg/mL to yield 100 and 50 mg/kg active compound dosages, respectively, in a dosing volume of 10 mL/kg. The dabrafenib doses were stored protected from light at 4° C. for up to one week.

The 1% CMC vehicle ("Vehicle") was used to dose the control group.

Temozolomide (Temodar®, Schering Corporation, Lot No. 2RSA013) doses were prepared by suspending the contents of the required number of 100 mg Temodar® capsules in deionized water at a concentration of 15 mg/mL, which supplied a 150 mg/kg dosage in a dosing volume of 10 mL/kg. Temozolomide was stored protected from light at 4° C. during the 5-day dosing period.

Treatment

On Day 1 of the study, mice were sorted into nine groups (Group 1-9) each consisting of fifteen mice and one group (Group 10) consisting of ten mice, and dosing was initiated according to the treatment plan summarized in Table 15 below. Each dose was given by oral gavage (p.o.) in a dosing volume of 10 mL/kg (0.2 mL per 20 grams of body weight), scaled to the body weight of each individual animal. The vehicle and dabrafenib doses were to be given once daily until study end (qd to end), whereas the BVD-523 doses were to be given twice daily until study end (bid to end). For bid dosing, dosing was initiated in the afternoon on Day 1, so that one dose was given on the first day ("first day 1 dose").

TABLE 15

Protocol Design for the A375 in vivo Study

| | | Treatment Regimen | | | |
|---|---|---|---|---|---|
| Group | n | Agent | mg/kg | Route | Schedule |
| 1 | 15 | Vehicle | — | po | qd to end |
| 2 | 15 | Dabrafenib | 50 | po | qd to end |
| | | BVD-523 | 50 | po | bid to end |
| 3 | 15 | Dabrafenib | 50 | po | qd to end |
| | | BVD-523 | 100 | po | bid to end |
| 4 | 15 | Dabrafenib | 100 | po | qd to end |
| | | BVD-523 | 50 | po | bid to end |
| 5 | 15 | Dabrafenib | 100 | po | qd to end |
| | | BVD-523 | 100 | po | bid to end |
| 6 | 15 | Dabrafenib | 50 | po | qd to end |
| 7 | 15 | Dabrafenib | 100 | po | qd to end |
| 8 | 15 | BVD-523 | 50 | po | bid to end |
| 9 | 15 | BVD-523 | 100 | po | bid to end |
| 10 | 10 | Temozolomide | 150 | po | qd × 5 |

Vehicle = 1% carboxymethylcellulose (CMC) in DI water
For bid doses, one dose was given in the afternoon on the first day and one dose in the morning on the last day.

Dosing in the combination groups was modified during the study as described below.

Controls

Group 1 received 1% CMC vehicle, and served as the control group for calculation of % TGD. Group 10 received temozolomide at 150 mg/kg once per day for five days (qd×5), and served as a reference group.

Monotherapy Treatments

Groups 6 and 7 received 50 and 100 mg/kg dabrafenib, respectively. Groups 8 and 9 received 50 and 100 mg/kg BVD-523, respectively.

Combination Treatments

Groups 2 and 3 received the combinations of 50 mg/kg dabrafenib with 50 or 100 mg/kg BVD-523, respectively. Groups 4 and 5 received the combinations of 100 mg/kg dabrafenib with 50 or 100 mg/kg BVD-523, respectively. Due to the striking response to combination treatment, dosing in Groups 2-5 was stopped on Day 20 in order to monitor tumor re-growth. Dosing was to be re-initiated in a group when the mean tumor burden reached 1000 mm³. By Day 42, the 1000 mm³ mean tumor burden had not been reached in any of the combination groups. Dosing was re-initiated to permit post-final dose serum and tumor sampling for pharmacokinetic analyses. Beginning on Day 42, Groups 2-5 received dabrafenib given once per day for four days and BVD-523 given twice per day for three days, followed by one BVD-523 dose in the morning on Day 45. The final dosing schedules are shown below in Table 16.

TABLE 16

Response Summary in the A375 in vivo Study

| | | Treatment Regimen | | | | Median | | | Statistical | |
|---|---|---|---|---|---|---|---|---|---|---|
| Group | n | Agent | mg/kg | Route | Schedule | TTE | T-C | % TGD | vs G1 | vs G2 |
| 1 | 14 | Vehicle | — | po | qd to end | 9.2 | — | — | — | — |
| 2 | 15 | Dabrafenib | 50 | po | qd × 20/21 days off/qd × 4 | 45.0 | 35.8 | 389 | *** | — |
| | | BVD-523 | 50 | po | bid ×19/21 days off/bid × 3 then qd × 1 | | | | | |

TABLE 16-continued

Response Summary in the A375 in vivo Study

| | | | | | | | | | | |
|---|---|---|---|---|---|---|---|---|---|---|
| 3 | 14 | Dabrafenib | 50 | po | qd × 20/21 days off/qd × 4 | 45.0 | 35.8 | 389 | *** | — |
| | | BVD-523 | 100 | po | bid ×19/21 days off/bid × 3 then qd × 1 | | | | | |
| 4 | 15 | Dabrafenib | 100 | po | qd × 20/21 days off/qd × 4 | 45.0 | 35.8 | 389 | *** | — |
| | | BVD-523 | 50 | po | bid ×19/21 days off/bid × 3 then qd × 1 | | | | | |
| 5 | 15 | Dabrafenib | 100 | po | qd × 20/21 days off/qd × 4 | 45.0 | 35.8 | 389 | *** | — |
| | | BVD-523 | 100 | po | bid ×19/21 days off/bid × 3 then qd × 1 | | | | | |
| 6 | 15 | Dabrafenib | 50 | po | qd to end | 16.1 | 6.9 | 75 | *** | *** |
| 7 | 15 | Dabrafenib | 100 | po | qd to end | 28.5 | 19.3 | 210 | *** | — |
| 8 | 15 | BVD-523 | 50 | po | bid to end | 8.6 | −0.6 | −7 | ns | *** |
| 9 | 15 | BVD-523 | 100 | po | bid to end | 18.5 | 9.3 | 101 | *** | — |
| 10 | 10 | Temozolomide | 150 | po | qd × 5 | 10.5 | 1.3 | 14 | ns | |

| Group | n | Significance vs G3 | vs G4 | vs G5 | MTV (n) D45 | Regressions PR | CR | TFS | Mean BW Nadir | TR | Deaths NTR |
|---|---|---|---|---|---|---|---|---|---|---|---|
| 1 | 14 | — | — | — | — | 0 | 0 | 0 | — | 0 | 1 |
| 2 | 15 | — | — | — | 0 (10) | 3 | 8 | 7 | — | 0 | 0 |
| 3 | 14 | — | — | — | 0 (14) | 0 | 14 | 14 | — | 0 | 1 |
| 4 | 15 | — | — | — | 0 (15) | 1 | 14 | 14 | — | 0 | 0 |
| 5 | 15 | — | — | — | 0 (15) | 0 | 15 | 15 | — | 0 | 0 |
| 6 | 15 | *** | — | — | — | 0 | 0 | 0 | — | 0 | 0 |
| 7 | 15 | — | *** | *** | 282 (2) | 1 | 0 | 0 | — | 0 | 0 |
| 8 | 15 | — | *** | — | 0 (1) | 0 | 1 | 1 | −0.1% Day 2 | 0 | 0 |
| 9 | 15 | *** | — | *** | 2 (2) | 0 | 2 | 2 | — | 0 | 0 |
| 10 | 10 | | | | — | 0 | 0 | 0 | −1.6% Day 5 | 0 | 0 | n = number of animals in a group not dead from accidental or unknown causes;
Vehicle = 1% carboxymethylcellulose (CMC) in DI water. For bid × 19 and bid to end doses, one dose was given in the afternoon on the first day and one dose in the morning on the last day. The maximum T-C in this study is 35.8 days (389%), compared to Group 1.
Statistical Significance (Logrank test): ne = not evaluated, ns = not significant, * = P <0.05,  = P <0.01, * = P <0.001, compared to group indicated.
MTV (n) = median tumor volume (imd) for the number of animals on the day of TGD analysis (excludes animals attaining tumor volume endpoint).
PR = partial regressions;
CR = total number complete regressions;
TFS = tumor free survivors, i.e., CRs at end of study;
Mean BW Nadir = lowest group mean body weight, as % change from Day 1;
— indicates no decrease in mean body weight was observed;
TR = treatment-related death;
NTR = non-treatment-related death Endpoint and Tumor Growth Delay (TGD) Analysis Tumors were measured using calipers twice per week, and each animal was euthanized when its tumor reached the pre-determined tumor volume endpoint of 2000 mm$^3$ or on the final day, whichever came first. Animals that exited the study for tumor volume endpoint were documented as euthanized for tumor progression (TP), with the date of euthanasia. The time to endpoint (TTE) for analysis was calculated for each mouse by the following equation:

$$TTE = \frac{\log_o (\text{endpoint volume}) - b}{m}$$

where TTE is expressed in days, endpoint volume is expressed in mm$^3$, b is the intercept, and m is the slope of the line obtained by linear regression of a log-transformed tumor growth data set. The data set consists of the first observation that exceeded the endpoint volume used in analysis and the three consecutive observations that immediately preceded the attainment of this endpoint volume. The calculated TTE is usually less than the TP date, the day on which the animal was euthanized for tumor size. Animals with tumors that did not reach the endpoint volume were assigned a TTE value equal to the last day of the study. Any animal classified as having died from NTR (non-treatment-related) causes due to accident (NTRa) or due to unknown etiology (NTRu) were excluded from TTE calculations (and all further analyses). Animals classified as TR (treatment-related) deaths or NTRm (non-treatment-related death due to metastasis) were assigned a TTE value equal to the day of death.

Treatment outcome was evaluated from tumor growth delay (TGD), defined as the increase in the median time to endpoint (TTE) in a treatment group compared to the control group:

TGD=T-C, expressed in days, or as a percentage of the median TTE of the control group:

$$\% \ TGD = \frac{T-C}{C} \times 100$$

where:
T=median TTE for a treatment group, and
C=median TTE for the designated control group.

Criteria for Repression Responses

Treatment efficacy may be determined from the incidence and magnitude of regression responses observed during the study. Treatment may cause partial regression (PR) or complete regression (CR) of the tumor in an animal. In a PR response, the tumor volume was 50% or less of its Day 1 volume for three consecutive measurements during the course of the study, and equal to or greater than 135 mm$^3$ for one or more of these three measurements. In a CR response, the tumor volume was less than 135 mm$^3$ for three consecutive measurements during the course of the study. An animal with a CR response at the termination of a study was additionally classified as a tumor-free survivor (TFS). Animals were monitored for regression responses.

Toxicity

Animals were weighed daily on Days 1-5, then twice per week until completion of the study. The mice were observed frequently for overt signs of any adverse, treatment-related (TR) side effects, and clinical signs were recorded when observed. Individual body weight loss was monitored as per protocol, and any animal that exceeded the limits for acceptable body weight loss was euthanized. Group mean body weight loss also was monitored as per protocol. Dosing was to be suspended in any group that exceeded the limits for acceptable mean body weight loss. If mean body weight recovered, then dosing was to be resumed in that group, but at a lower dosage or less frequent dosing schedule.

Acceptable toxicity for the maximum tolerated dose (MTD) was defined as a group mean body-weight loss of less than 20% during the study and not more than 10% treatment-related (TR) deaths. A death was classified as TR if attributable to treatment side effects as evidenced by clinical signs and/or necropsy, or was also classified as TR if due to unknown causes during the dosing period or within 14 days of the last dose. A death was classified as non-treatment-related (NTR) if there was no evidence that death was related to treatment side effects. NTR deaths were further characterized based on cause of death. A death was classified as NTRa if it resulted from an accident or human error. A death was classified as NTRm if necropsy indicated that it may have resulted from tumor dissemination by invasion and/or metastasis. A death was classified as NTRu if the cause of death was unknown and there was no available evidence of death related to treatment side effects, metastasis, accident or human error, although death due to treatment side effects cannot be excluded.

Sampling

When available, five mice per group were euthanized by terminal cardiac puncture under carbon dioxide anesthesia at 3, 6 and 12 hours post final dose, and the full blood volume of each animal was collected. The serum was separated and stored frozen at −80° C. until shipment. In addition, the tumors of these mice were harvested and divided into two parts. One part was snap frozen and stored at −80° C. The other part was fixed for 16-24 hours in 10% neutral buffered formalin, and then transferred to 70% ethanol. For groups with mice that had no detectable tumor, the implant site including full skin and muscle thickness was collected from three mice per group.

Statistical and Graphical Analyses

Prism (GraphPad) for Windows 3.03 was used for graphical representations and statistical analyses.

The logrank test, which evaluates overall survival experience, was used to analyze the significance of the differences between the TTE values of two groups. Logrank analysis includes the data for all animals in a group except those assessed as NTR deaths. Two-tailed statistical analyses were conducted at significance level P=0.05. The statistical tests were not adjusted for multiple comparisons. Prism summarizes test results as not significant (ns) at P>0.05, significant (symbolized by "*") at 0.01<P<0.05, very significant ("") at 0.001<P<0.01, and extremely significant ("*") at P<0.001. Because tests of statistical significance do not provide an estimate of the magnitude of the difference between groups, all levels of significance were described as either significant or not significant within the text of this report.

A scatter plot was constructed to show TTE values for individual mice, by group. Group mean tumor volumes were plotted as a function of time. When an animal exited the study due to tumor size, the final tumor volume recorded for the animal was included with the data used to calculate the mean volume at subsequent time points. Error bars (when present) indicate one standard error of the mean (SEM). Kaplan-Meier plots show the percentage of animals in each group remaining in the study versus time. The Kaplan-Meier plot and logrank test share the same TTE data sets. Percent mean body weight changes from Day 1 were calculated for each group for each day of body weight measurement, and were plotted as a function of time. Tumor growth and body weight plots excluded the data for NTR deaths, and were truncated after 50% of the assessable animals in a group had exited the study.

Results

Figure 26:
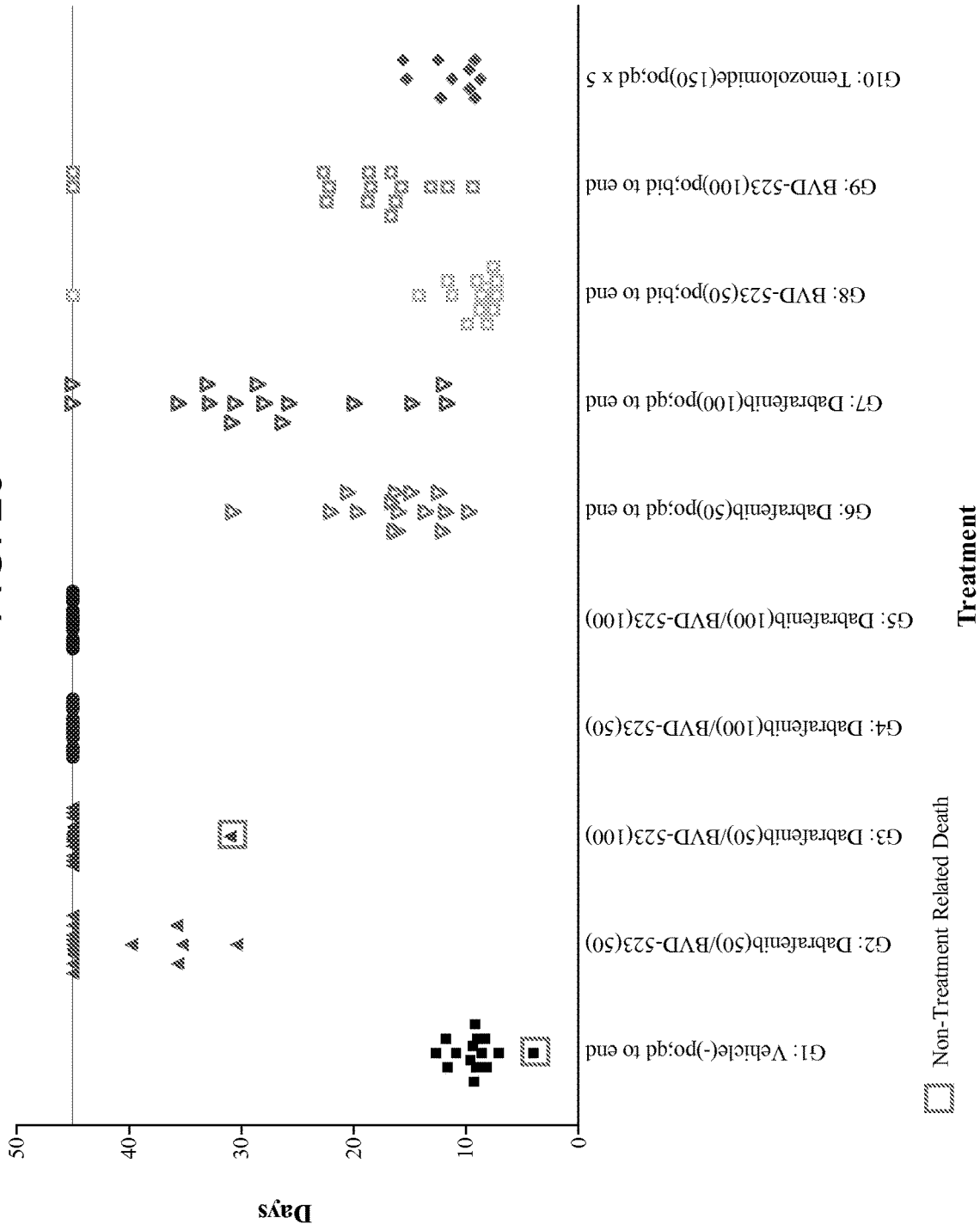
FIG. 26 shows the individual times to endpoint for mice in the study.
Figure 27:
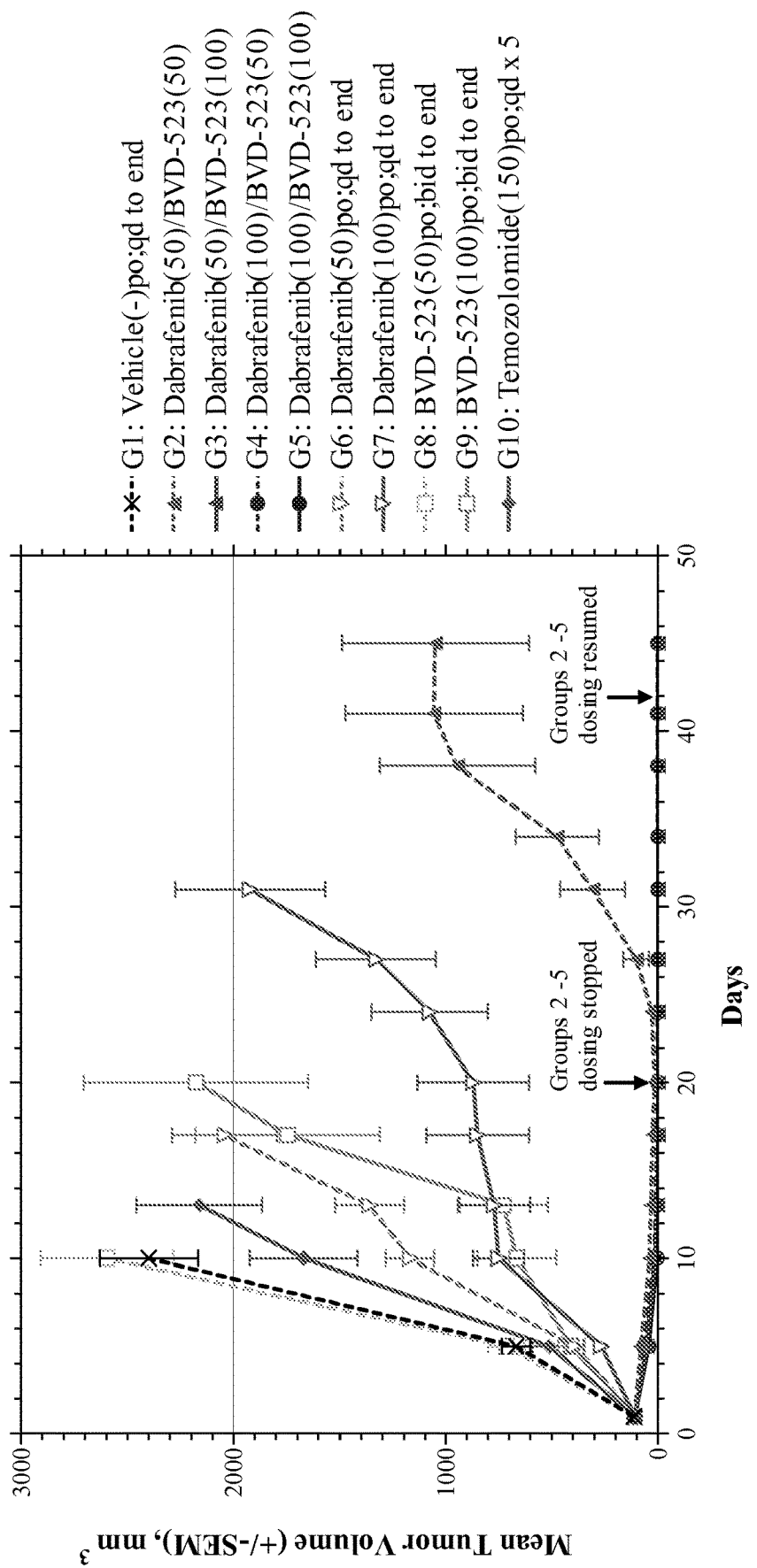
FIG. 27 shows mean tumor growth (FIG. 27A) and Kaplan-Meier plot (FIG. 27B) for the study.
Figure 27:
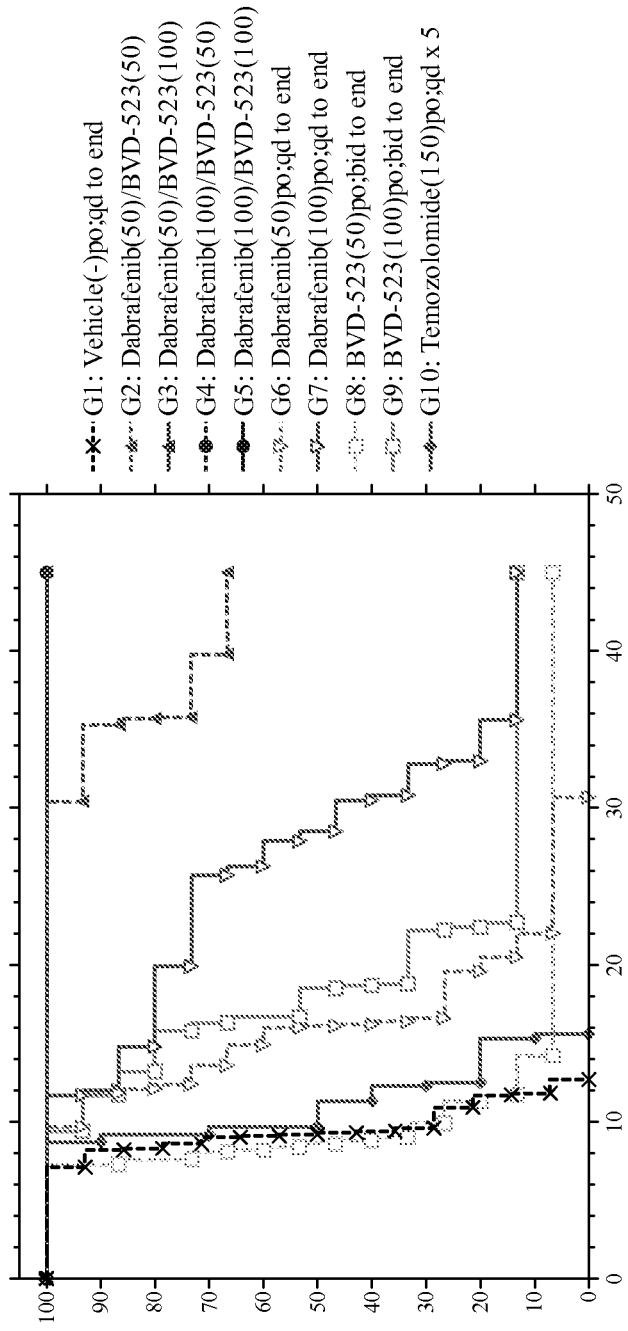
Figure 28:
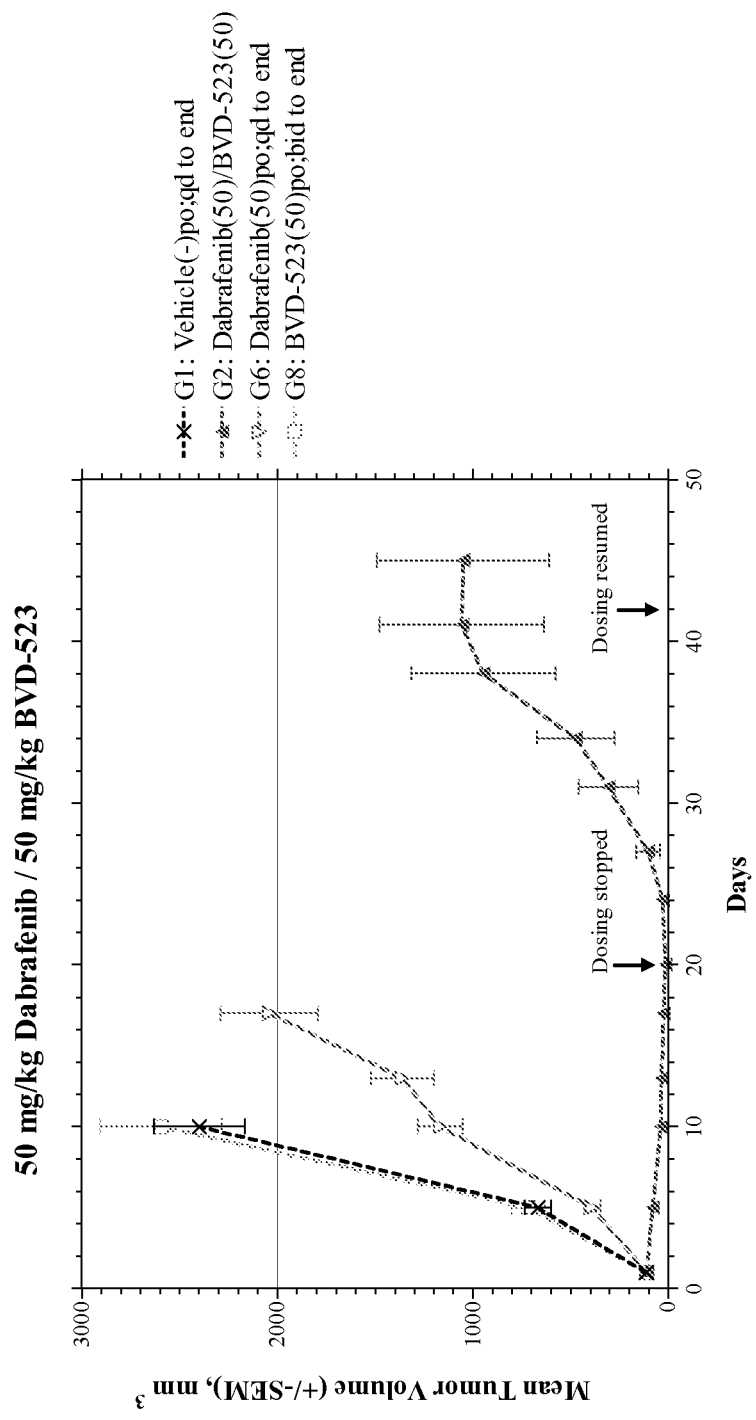
FIGS. 28A-28D show mean tumor growth for various groups of mice administered with dabrafenib/BVD-523 combinations compared to monotherapies.
Figure 29:
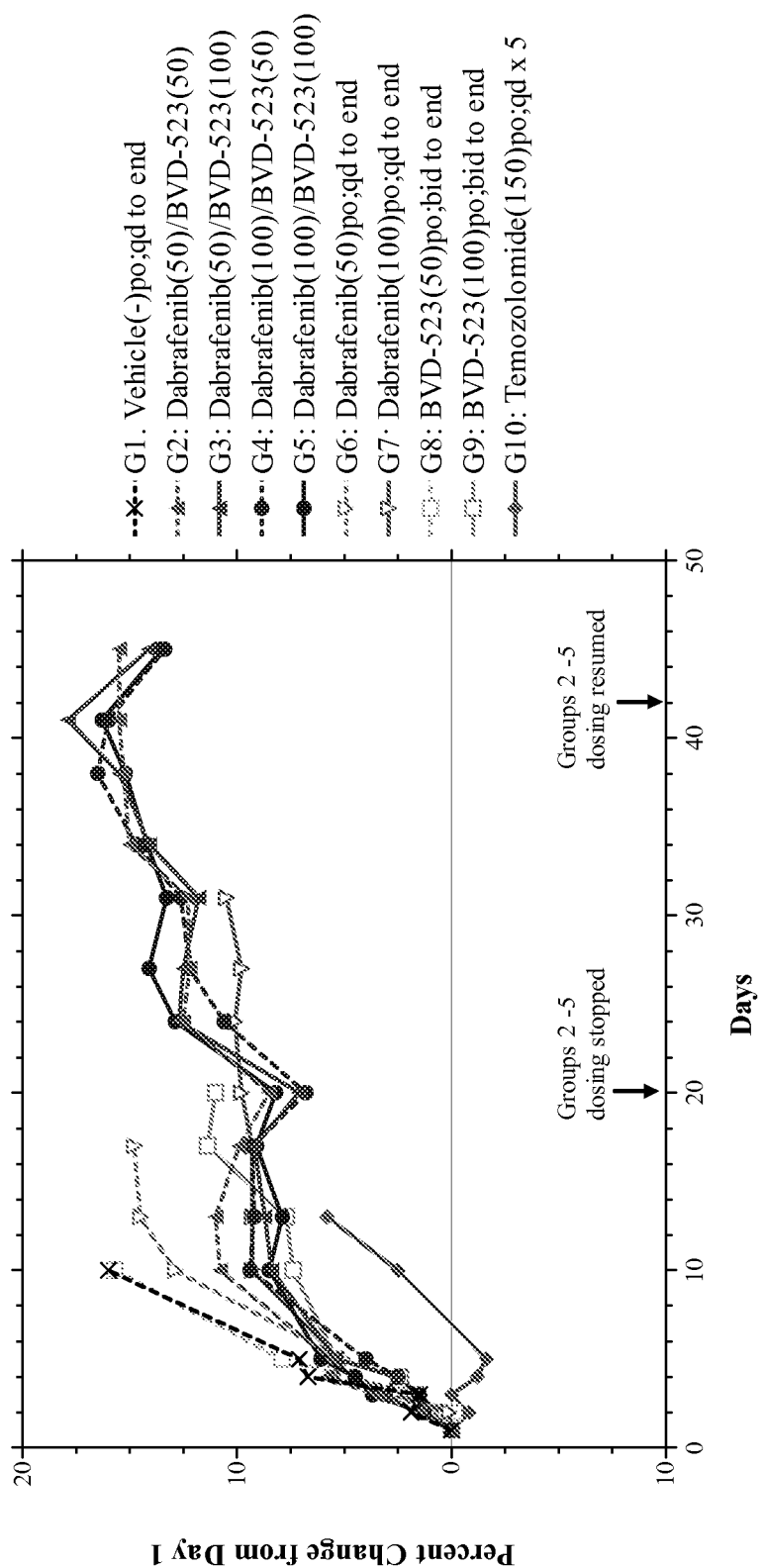
FIG. 29 shows percent mean body weight changes from Day 1 in the in vivo study.

Groups in the A375 in vivo study were treated in accordance with the modified protocol as disclosed in Table 15. The experiment was terminated on Day 45. Table 16 presents a summary of the treatment responses for each group. FIG. 26 is a scatter plot showing the individual TTEs for each group. FIG. 27 presents plots of mean tumor growth (FIG. 27A) and Kaplan-Meier survival (FIG. 27B) for each group in the study. FIGS. 28A-D present mean tumor growth plots for the four combinations compared to their respective monotherapies. FIG. 29 presents plots of percent mean body weight changes from Day 1 for each group.

Efficacy—Growth of A375 Human Melanomas in Control Mice (Group 1)

In Group 1, one control mouse was found dead beyond necropsy on Day 4, and the death was assessed as NTRu. The other fourteen control tumors progressed rapidly and uniformly to the 2000 mm$^3$ endpoint with a median TTE of 9.2 days, establishing a maximum possible TGD of 35.8 days (389%) for the 45-day study (Table 15). The scatter plot shows a cluster of control TTEs (FIG. 26). The mean tumor growth plot for Group 1 illustrated the rapid control tumor growth (FIG. 27A, and FIG. 28A-D).

Efficacy—Response to Dabrafenib as Monotherapy (Groups 6 and 7)

Groups 6 and 7 received dabrafenib as monotherapy at 50 and 100 mg/kg, respectively, p.o. qd to end. The median TTEs for Groups 6 and 7 were 16.1 and 28.5 days, respectively, corresponding to dose-related TGDs of 6.9 days (75%) and 19.3 days (210%), with a significant survival difference for each compared to controls (Group 1 vs. 6 or 7, P<0.001). One PR was recorded in the 100 mg/kg dabrafenib group (Table 16). All Group 6 tumors attained the 2000 mm$^3$ endpoint tumor volume, whereas 13/15 Group 7 tumors attained the endpoint and two remained on Day 45 with a MTV of 282 mm$^3$ (Table 16). The mean tumor growth plots for Groups 6 and 7 illustrated the dose-related delays, although tumors in both groups progressed during treatment (FIG. 27A).

Efficacy—Response to BVD-523 as Monotherapy (Groups 8 and 9)

Groups 8 and 9 received BVD-523 as monotherapy at 50 and 100 mg/kg, respectively, p.o. bid to end. The median TTEs for Groups 8 and 9 were 8.6 and 18.5 days, respectively, which corresponded to no TGD for the 50 mg/kg BVD-523 group and TGD of 9.3 days (101%) for the 100 mg/kg BVD-523 group (Table 16). Logrank analyses detected a significant survival difference only for 100 mg/kg BVD-523 compared to controls (Group 1 vs. 8, P>0.05; Group 1 vs. 9, P<0.001). Group 8 had one CR that remained a TFS on Day 45, while Group 9 had two CRs/TFSs, and all other tumors in these two groups attained the 2000 mm³ endpoint tumor volume (Table 16). The mean tumor growth plot for the 50 mg/kg BVD-523 group was comparable to that for controls, whereas the 100 mg/kg BVD-523 group showed marginal delay with tumors that progressed during treatment (FIG. 27A).

Efficacy—Response to Treatment with Combinations of Dabrafenib and BVD-523 (Groups 2-5)

Groups 2 and 3 received 50 mg/kg dabrafenib with 50 or 100 mg/kg BVD-523, respectively, whereas Groups 4 and 5 received 100 mg/kg dabrafenib with 50 or 100 mg/kg BVD-523, respectively. As indicated in Table 16, the combination regimens were modified so that dosing was ended after Day 20 and then re-initiated on Day 42 (Table 16).

The median TTEs for Groups 2-5 were each 45.0 days, corresponding to the maximum possible TGD for the study (35.8 days, 389%) and a significant overall survival benefit compared to controls (Group 1 vs. 2-5, P<0.001).

Five tumors in Group 2 attained the 2000 mm³ endpoint volume, whereas Groups 3-5 had no tumors that grew to the endpoint volume. Group 2 had three PRs and eight CRs, with seven mice that remained TFSs on Day 45 (Table 16). Group 3 had one NTRu death on Day 31, and the other fourteen mice had CRs and remained TFSs at study end. Group 4 had one PR and fourteen CRs that remained TFSs, whereas Group 5 had 100% TFSs.

Mean tumor burdens were non-detectable in Groups 2-5 by Day 20 when dosing was stopped (FIG. 27A). Mean tumor growth resumed only in the lowest dosage combination group (Group 2), and remained non-detectable through study end in the other three combination groups (FIG. 27AI). The tumor growth plot for each combination group showed noteworthy activity compared to its corresponding monotherapies (FIGS. 28A-D).

Efficacy—Response to Temozolomide Treatment (Group 10)

The temozolomide reference treatment resulted in a median TTE of 10.5 days, which corresponded to negligible TGD (1.3 days, 14%), with no regressions (Table 16). Logrank analyses detected no significant survival difference for the temozolomide group compared to controls (Group 1 vs. 10, P=0.052). The mean tumor growth plot for this group showed negligible delay compared to the plot for Group 1 controls (FIG. 27A).

Side Effects

Table 16 provides a summary of maximum mean BW losses, TR and NTR deaths. FIG. 29 presents plots of percent mean BW changes from Day 1 for each group.

No TR deaths were recorded in the study, but two NTRu deaths were assessed (Table 16). One NTRu death was recorded in Group 1 on Day 4, and a second NTRu death was recorded in Group 3 on Day 31. The Group 1 animal was found dead beyond necropsy with no prior clinical observations, whereas the Group 3 mouse was thin, hunched and lethargic just prior to death, and necropsy revealed a mass of white nodules on the liver suggesting metastatic disease was a possible cause of death. There were negligible or no mean BW losses among groups in the study (Table 16 and FIG. 29), and no noteworthy signs of treatment-related side effects among the BVD-523 and dabrafenib mono- and combination therapy groups.

Summary

The in vivo study evaluated combinations of BVD-523 with dabrafenib for efficacy in the A375 human melanoma xenograft nude mouse model. BVD-523 was administered orally at 50 or 100 mg/kg on a twice daily schedule and dabrafenib was given orally at 50 or 100 mg/kg on a daily schedule, alone and in combination. Due to the striking response to combination treatment, dosing in the combination groups was stopped on Day 20 to monitor for tumor re-growth, and was reinitiated on Day 42 for sample collection at study end on Day 45.

A375 control tumors progressed rapidly and uniformly to the tumor volume endpoint. The median TTE for controls was 9.2 days, establishing a maximum possible TGD of 35.8 days (389%) for the 45-day study. A narrow range of control TTEs, which reflected the uniform control tumor growth, permitted the logrank test to detect small differences between control and treated mice. The temozolomide reference treatment resulted in negligible TGD (1.3 days, 14%) and no regressions, consistent with previous results for temozolomide in this tumor model.

The 50 and 100 mg/kg dabrafenib monotherapies produced dose-related efficacy, with TGDs of 6.9 days (75%) and 19.3 days (210%), respectively, and one PR in the 100 mg/kg dabrafenib group. The 50 mg/kg BVD-523 monotherapy was inactive, producing no TGD and no significant survival difference from controls (P>0.05). The single TFS in this group might have been due to treatment or a spontaneous regression. The 100 mg/kg BVD-523 monotherapy was marginally active, resulting TGD of 9.3 days (101%), a significant survival difference versus controls (P<0.001), and two TFSs that could have been due to treatment or a spontaneous regression.

Each of the four combinations of dabrafenib with BVD-523 tested in this study was highly active, producing the maximum possible TGD, noteworthy regression responses, and statistically superior overall survival compared to their corresponding monotherapies (P<0.001). The lowest dosage combination group (Group 2) produced a noteworthy 7/15 TFSs. The three higher dosage combinations (Groups 3-5) achieved 43/44 tumor-free survivors by study end, including 15/15 TFSs in the highest dosage combination group (Group 5). It is noteworthy that, given a mean doubling time of less than 3 days for control tumors, no tumor re-growth occurred in 43/44 mice among Groups 3-5 during the dosing holiday from Days 21 to 42, which was a duration of time corresponding to approximately 7 tumor doublings. These results were consistent with curative or near-curative activity.

In summary, dabrafenib and BVD-523 each produced marginal dose-related efficacy as monotherapies, but remarkable activity in combination. The combinations of dabrafenib with BVD-523 tested in this study produced noteworthy tumor-free survival, and superior efficacy to either agent given alone.

We show that ERK kinase inhibition, exemplified using BVD-523, is effective in combination with the RAF inhibitor dabrafenib in a model of BRAF mutant melanoma. In cells, combined BVD-523 and dabrafenib treatment induces windows of synergistic inhibition of cell proliferation. When dosed together in a xenograft model, combination treatment causes prominent and durable tumor regression compared to single agent therapy.

Additionally, when A375 cells are induced to exhibit acquired drug resistance following prolonged exposure to inhibitors of the MAPK cascade, ERK inhibition using BVD-523 shows attractive properties. Within weeks following treatment with dabrafenib or trametinib, A375 cells can be isolated that grow rapidly in concentrations greater 10-fold more than the respective compound growth IC50 inhibitory concentration. After 2 months, cells exposed to BVD-523 alone grow poorly, and can only withstand treatment with less than 10-fold increases in drug exposures beyond the IC50. Cells treated with the combination of BVD-523 and dabrafenib similarly exhibit poor growth, and can only be cultured in modestly increased levels of dabrafenib when in combination.

Lastly, BVD-523 was tested in a melanoma xenograft model derived from biopsies obtained from a patient that exhibited disease progression following initial response to vemurafenib. Interestingly, this in vivo model exhibited acquired cross-resistance, appearing insensitive to both dabrafenib and trametinib. BVD-523 appears effective in the model however, and induced a potent anti-tumor response either alone or in combination with dabrafenib.

In total, these results suggest combined ERK and RAF inhibitor treatment is effective in the background of BRAF mutant melanoma. BVD-523 has a novel mode of drug action, and possibly exhibits prolonged duration in models that show both intrinsic sensitivity or acquired resistance to BRAF or MEK inhibitors. The combination of RAF and ERK inhibitors for BRAF mutant cancers inhibits an oncogenic pathway at two control points, which in turn appears to create a difficult barrier against subversion and acquired drug resistance.

These findings indicate that therapy with the combination of ERK and RAF inhibitors may be effective in a variety of cancers, particularly those that harbor oncogenic changes in BRAF, including melanoma, thyroid, lung and colon cancers.

Example 8

Additional Combination Studies

Single Agent Proliferation Assay

Cells were seeded in 96-well plates at the densities and media conditions indicated in Table 17 and allowed to adhere overnight prior to addition of compound or vehicle control. Compounds were prepared from DMSO stocks to give the desired final concentrations. The final DMSO concentration was constant at 0.1%. Test compounds were incubated with the cells for 72 h at 37° C., 5% $CO_2$ in a humidified atmosphere. CellTiter-Glo® reagent (Promega, Madison, Wis.) was added according to manufacturer's instructions and luminescence detected using the BMG FLUOstar plate reader (BMG Labtech, Ortenberg, Germany). The average media only background value was deducted and the data analysed using a 4-parameter logistic equation in GraphPad Prism (GraphPad Software, La Jolla, Calif.).

Combination Proliferation Assay

Cells were seeded in triplicate 96-well plates at the densities and media conditions indicated in Table 17 and allowed to adhere overnight prior to addition of compound or vehicle control. Compounds were prepared from DMSO stocks to give the desired final concentrations. The final DMSO concentration was constant at 0.2%. Combinations were tested using a 10×8 dose matrix. Test compounds were incubated with the cells for 72 h at 37° C., 5% $CO_2$ in a humidified atmosphere. CellTiter-Glo® reagent (Promega, Madison, Wis.) was added according to manufacturer's instructions and luminescence detected using the BMG FLUOstar plate reader (BMG Labtech, Ortenberg, Germany). The average media only background value was deducted and the data analysed.

For the 10×8 combination assays the combination interactions across the dose matrix were determined by the Loewe Additivity and Bliss independence models using Chalice™ Combination Analysis Software (Horizon Discovery Group, Cambridge, Mass.) as outlined in the user manual (available at chalice.horizondiscovery.com/chalice-portal/documentation/analyzer/home.jsp). Synergy is determined by comparing the experimentally observed level of inhibition at each combination point with the value expected for additivity, which is derived from the single-agent responses along the edges of the matrix. Potential synergistic interactions were identified by displaying the calculated excess inhibition over that predicted as being additive across the dose matrix as a heat map, and by reporting a quantitative 'Synergy Score' based on the Loewe model. The single agent data derived from the combination assay plates were presented as dose-response curves generated in GraphPad Prism (GraphPad Software, La Jolla, Calif.) (plotted using percentage viability relative to DMSO only treated controls).

TABLE 17

Cell Line Seeding Density and Growth Media

| Cell Line | Seeding Density (cells/well) | Media |
|---|---|---|
| A375 | 2500 | DMEM + 10% FBS |
| G-361 | 5000 | McCoy's 5A + 10% FBS |

Results

The aim of this study was to assess the effects of combining ERK inhibitors with Type I RAF inhibitors. One novel ERK inhibitor BVD-523 with two Type I RAF inhibitors, Dabrafenib (GSK2118436) and Vemurafenib (PLX4032), and a Type II inhibitor TAK-632, in two BRAF V600E mutant melanoma cell lines, A375 and G-361. A second, mechanistically distinct, ERK inhibitor (SCH772984) also was tested in combination with Dabrafenib (GSK2118436) and Vemurafenib (PLX4032).

Single agent proliferation assays were first performed to select an appropriate concentration range for the combination studies. While both cell lines had a similar level of sensitivity to paclitaxel, G-361 cells appeared 4-to-6-fold less sensitive to both ERK and RAF inhibition compared to A375 cells (FIG. 42). $IC_{50}$ results are summarized in Table 18.

TABLE 18

Single Agent $IC_{50}$ Values for Tested Compounds

| | Cell Line | |
|---|---|---|
| Compound | A375 | G-361 |
| Dabrafenib* | ~0.0007 | ~0.0014 |
| Vemurafenib | 0.047 | 0.248 |
| TAK-632 | 0.026 | 0.164 |
| BVD-523 | 0.087 | 0.344 |
| SCH772984 | 0.032 | 0.180 |
| Paclitaxel | 0.005 | 0.007 |

*The values for dabrafenib should be considered as approximate as the top of the curves were not well defined by the dose range tested.

Combination interactions between two compounds were assessed across an 8×10 matrix of concentrations using the Loewe Additivity and Bliss Independence Models with Chalice™ Bioinformatics Software (Horizon Discovery Group, Cambridge, Mass.). Chalice™ enables potential synergistic interactions to be identified by displaying the calculated excess inhibition over that predicted as being additive across the dose matrix as a heat map, and by reporting a quantitative 'Synergy Score' based on the Loewe model.

In A375 cells (FIG. 43-FIG. 48), analysis using the Loewe model indicated that combinations with BVD-523 appeared mainly additive. Results using the Bliss method were similar, although this method suggested the presence of a region of mild antagonism at higher concentrations for each combination. In contrast, in G-361 cells (FIG. 49-FIG. 54), while most interactions across the dose matrix were also additive, both analysis models also revealed small pockets of modest synergy at the mid concentrations. Similar results were obtained with a second mechanistically distinct ERK inhibitor (SCH772984). This supports the notion that the synergies observed in G-361 are likely to be specifically related to inhibition of ERK and not due off-target effects.

In summary, these results suggest that interactions between BVD-523 and type I and type II RAF inhibitors are at least additive, and in some cases synergistic, in melanoma cell lines carrying a BRAF V600E mutation.

Figure 55:
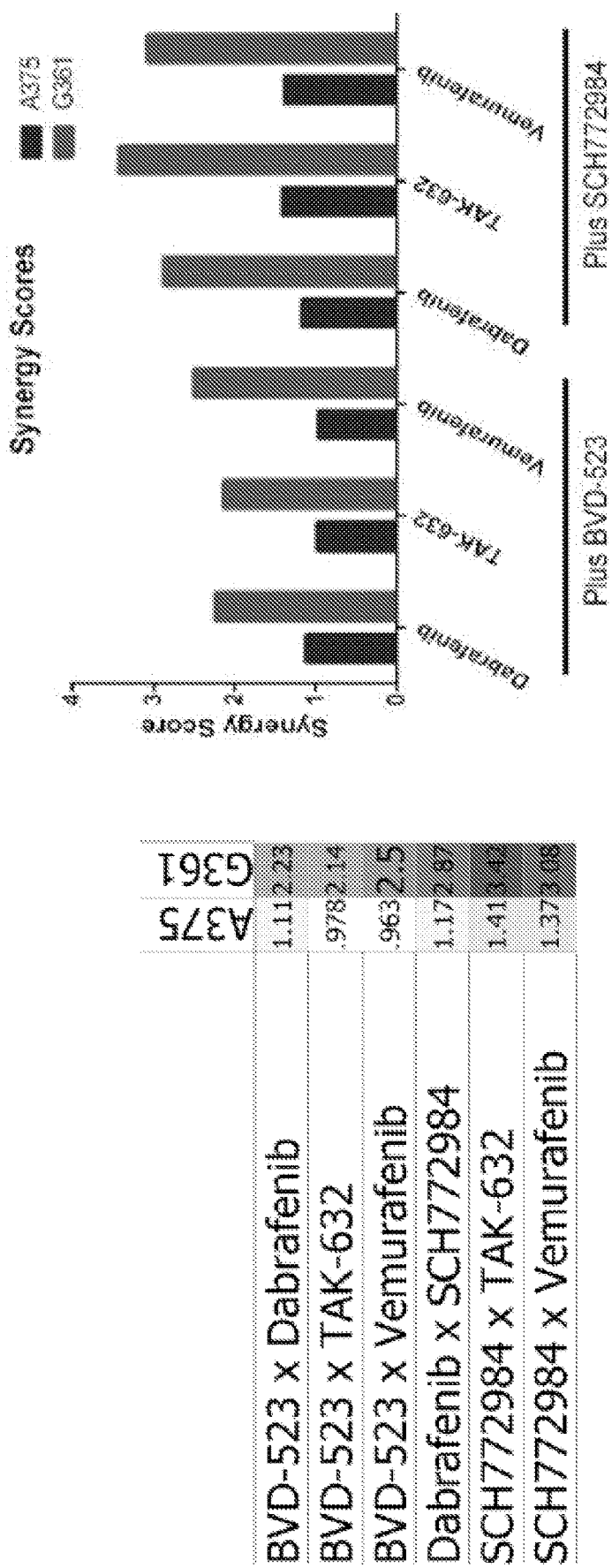
FIG. 55A shows synergy scores for the tested combinations in both A375 and G-361 cells.
FIG. 55B shows a graph of the values presented in FIG. 55A.
Figure 56:
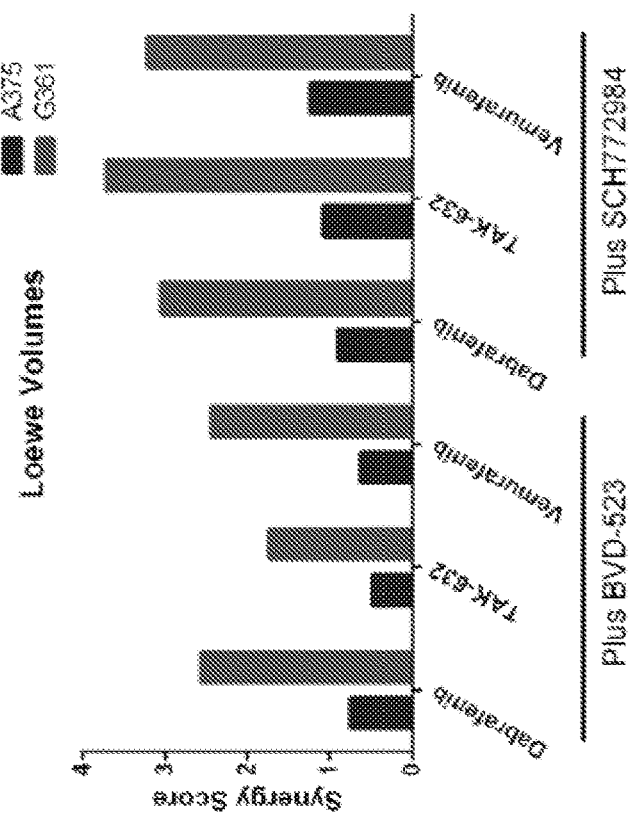
FIG. 56A shows Loewe volumes for the tested combinations in both A375 and G-361 cells.
FIG. 56B shows a graph of the values presented in FIG. 56A.

Synergistic interactions were scored in two ways (FIG. 55-FIG. 57). Excess activity over that predicted if a combination was additive can be calculated using a simple volume score, which calculates the volume between the measured and the predicted response surface. This volume score shows whether the overall response to a combination is synergistic (positive values), antagonistic (negative values) or additive (values ~0). Additionally, a 'Synergy Score' is a positive-gated inhibition-weighted volume over Loewe additivity. This provides an additional prioritization favouring combinations whose synergy occurs at high effect levels, ignoring antagonistic portions of the response surface.

Example 9

Combination Interactions Between ERK Inhibitors

RAF mutant melanoma cell line A375 cells were cultured in DMEM with 10% FBS and seeded into triplicate 96-well plates at an initial density of 2000 cells per well. Combination interactions between ERK inhibitors BVD-523 and SCH772984 were analized after 72 hours as described above in Example 8. Viability was determined using CellTiter-Glo® reagent (Promega, Madison, Wis.) according to manufacturer's instructions and luminescence was detected using the BMG FLUOstar plate reader (BMG Labtech, Ortenberg, Germany).

Visualization of the Loewe and Bliss 'excess inhibition' heat maps suggested that the combination of BVD-523 and SCH772984 was mainly additive with windows of potential synergy in mid-range doses (FIG. 58).

In summary, these results suggest that interactions between BVD-523 and SCH772984 are at least additive, and in some cases synergistic.

DOCUMENTS

AVRUCH, J.; et al. Ras activation of the Raf kinase: tyrosine kinase recruitment of the MAP kinase cascade. Recent Prog. Horm. Res., 2001, 127-155.
BROSE, et al. BRAF and RAS mutations in human lung cancer and melanoma. Cancer Res., 2002, 62, 6997-7000.
DAVIES et al., Mutations of the BRAF gene in human cancer. Nature, 2002, 417, 949-954.
FRANSEN et al., Mutation analysis of the BRAF, ARAF and RAF-1 genes in human colorectal adenocarcinomas. Carcinogenesis, 2004, 25, 527-533.
GARNETT, M. J.; et al. Wildtype and mutant B-RAF activate C-RAF through distinct mechanisms involving heterodimerization. Mol. Cell, 2005, 20, 963-969.
GREGER, James G., et al. "Combinations of BRAF, MEK, and PI3K/mTOR inhibitors overcome acquired resistance to the BRAF inhibitor GSK2118436 dabrafenib, mediated by NRAS or MEK mutations." Molecular cancer therapeutics 11.4 (2012): 909-920.
HOCKER et al., Ultraviolet radiation and melanoma: A systematic review and analysis of reported sequence variants. Hum. Mutat., 2007, 28, 578-588.
KING, Alastair J., et al. "Dabrafenib; preclinical characterization, increased efficacy when combined with trametinib, while BRAF/MEK tool combination reduced skin lesions." PloS one 8.7 (2013): e67583.
LI et al., Recent advances in the research and development of B-Raf Inhibitors. *Current Medicinal Chemistry*, 2010, 17:1618-1634.
LIU, Dingxie, et al. "BRAF V600E maintains proliferation, transformation, and tumorigenicity of BRAF-mutant papillary thyroid cancer cells." Journal of Clinical Endocrinology & Metabolism 92.6 (2007): 2264-2271.
LITTLE, A. S., et al., Amplification of the Driving Oncogene, KRAS or BRAF, Underpins Acquired Resistance to MEK1/2 Inhibitors in Colorectal Cancer Cells. Sci. Signal. 4, ra17 (2011).
LONG G V, Menzies A M, Nagrial A M, et al. Prognostic and Clinicopathologic Associations of Oncogenic BRAF in Metastatic Melanoma. J Clin Oncol. 2011
MANANDHAR S P, Hildebrandt E R, Schmidt W K. Small-molecule inhibitors of the Rce1p CaaX protease. J Biomol Screen. 2007; 12(7):983-993.
MAURER, T, Garrenton, L S, Oh, A, Pitts, K, Anderson, D J, Skelton, N J, Fauber, B P, Pan, B, Malek, S, Stokoe, D, Ludlam, M J C, Bowman, K K, Wu, J, Giannetti, A M, Starovasnik, M A, Mellman, I, Jackson, P K, Rudolph, J, Wang, W, Fang, G. Small-molecule ligands bind to a distinct pocket in Ras and inhibit SOS-mediated nucleotide exchange activity. PNAS. 2012; 109(14):5299-304.
MITTAL, Rohit et al. "The acetyltransferase activity of the bacterial toxin YopJ of Yersinia is activated by eukaryotic host cell inositol hexakisphosphate." Journal of Biological Chemistry 285.26 (2010): 19927-19934.
PATGIRI, A, Yadav, K K, Arora, P S, Bar-Sagi, D. An orthosteric inhibitor of the Ras-Sos interaction. Nat Chem Biol. 2011; 7:585-587.
PORTER S B, Hildebrandt E R, Breevoort S R, Mokry D Z, Dore T M, Schmidt W K. Inhibition of the CaaX proteases Rce1p and Ste24p by peptidyl (acyloxy)methyl ketones. Biochim Biophys Acta.2007; 1773(6):853-862.
RUSHWORTH, L. K.; et al. Regulation and role of Raf-1/B-Raf heterodimerization. Mol. Cell Biol., 2006, 26, 2262-2272.
SETH et al., Concomitant mutations and splice variants in KRAS and BRAF demonstrate complex perturbation of the Ras/Raf signalling pathway in advanced colorectal cancer, Gut 2009; 58:1234-1241
SHIMA, F, Yoshikawa, Y, Ye, M, Araki, M, Matsumoto, S, Liao, J, Hu, L, Sugimoto, T, Ijiri, Y, Takeda, A, Nishiyama, Y, Sato, C, Muraoka, S, Tamura, A, Osoda, T, Tsuda, K-I, Miyakawa, T, Fukunishi, H, Shimada, J, Kumasaka, Yamamoto, M, Kataoka, T. In silico discovery of small-molecule Ras inhibitors that display antitumor activity by blocking the Ras-effector interaction. PNAS. 2013; 110(20):8182-7.
WAN, et al., Mechanism of activation of the RAF-ERK signaling pathway by oncogenic mutations of B-RAF. Cell, 2004, 116, 855-867.
WEBER, C. K.; et al. Active Ras induces heterodimerization of cRaf and BRaf. Cancer Res., 2001, 61, 3595-3598.

Wellbrock et al. The RAF proteins take centre stage. Nat. Rev. Mol. Cell Biol., 2004, 5, 875-885.

XU et al., High prevalence of BRAF gene mutation in papillary thyroid carcinomas and thyroid tumor cell lines. Cancer Res., 2003, 63, 4561-4567.

All documents cited in this application are hereby incorporated by reference as if recited in full herein.

Although illustrative embodiments of the present invention have been described herein, it should be understood that the invention is not limited to those described, and that various other changes or modifications may be made by one skilled in the art without departing from the scope or spirit of the invention.

What is claimed is:

1. A method of treating or ameliorating the effects of a cancer in a subject in need thereof comprising administering to the subject an effective amount of (i) a first anti-cancer agent, which is BVD-523 or a pharmaceutically acceptable salt thereof and (ii) a second anti-cancer agent, which is a type 1 RAF inhibitor or a pharmaceutically acceptable salt thereof, to treat or ameliorate the effects of the cancer,
   wherein the type 1 RAF inhibitor is selected from the group consisting of dabrafenib, vemurafenib, pharmaceutically acceptable salts thereof, and combinations thereof, and
   wherein administration of the first and second anti-cancer agents provides a synergistic effect compared to administration of either anti-cancer agent alone.

2. The method according to claim 1, wherein the subject is a mammal.

3. The method according to claim 2, wherein the mammal is selected from the group consisting of humans, primates, farm animals, and domestic animals.

4. The method according to claim 2, wherein the mammal is a human.

5. The method according to claim 1, wherein the subject with cancer has a somatic BRAF mutation or is refractory to MAPK pathway inhibitor treatment.

6. The method according to claim 1 further comprising administering at least one additional therapeutic agent selected from the group consisting of an antibody or fragment thereof, a cytotoxic agent, a toxin, a radionuclide, an immunomodulator, a photoactive therapeutic agent, a radiosensitizing agent, a hormone, an anti-angiogenesis agent, and combinations thereof.

7. The method according to claim 6, wherein the additional therapeutic agent is an inhibitor of the PI3K/Akt pathway.

8. The method according to claim 7, wherein the inhibitor of the PI3K/Akt pathway is selected from the group consisting of A-674563 (CAS #552325-73-2), AGL 2263, AMG-319, AS-041164 (5-benzo[1,3]dioxol-5-ylmethylene-thiazolidine-2,4-dione), AS-604850 (5-(2,2-Difluoro-benzo[1,3]dioxol-5-ylmethylene)-thiazolidine-2,4-dione), AS-605240 (5-quinoxilin-6-methylene-1,3-thiazolidine-2,4-dione), AT7867 (CAS #857531-00-1), benzimidazole series, BML-257 (CAS #32387-96-5), CAL-120, CAL-129, CAL-130, CAL-253, CAL-263, CAS #612847-09-3, CAS #681281-88-9, CAS #75747-14-7, CAS #925681-41-0, CAS #98510-80-6, CCT128930 (CAS #885499-61-6), CH5132799 (CAS #1007207-67-1), CHR-4432, FPA 124 (CAS #902779-59-3), GS-1101 (CAL-101), GSK 690693 (CAS #937174-76-0), H-89 (CAS #127243-85-0), Honokiol, IC87114, IPI-145, KAR-4139, KAR-4141, KIN-1, KT 5720 (CAS #108068-98-0), Miltefosine, MK-2206 dihydrochloride (CAS #1032350-13-2), ML-9 (CAS #105637-50-1), Naltrindole Hydrochloride, OXY-111A, perifosine, PHT-427 (CAS #1191951-57-1), pictilisib, PIK-90 (CAS #677338-12-4), SC-103980, SF-1126, SH-5, SH-6, Tetrahydro Curcumin, TG100-115, Triciribine, X-339, XL-499, pharmaceutically acceptable salts thereof, and combinations thereof.

9. A method of treating or ameliorating the effects of a cancer in a subject in need thereof comprising administering to the subject an effective amount of (i) a first anti-cancer agent, which is BVD-523 or a pharmaceutically acceptable salt thereof and (ii) a second anti-cancer agent, which is dabrafenib or a pharmaceutically acceptable salt thereof, to treat or ameliorate the effects of the cancer,
wherein administration of the first and second anti-cancer agents provides a synergistic effect compared to administration of either anti-cancer agent alone.

10. The method according to claim 9, wherein the subject is a mammal.

11. The method according to claim 10, wherein the mammal is selected from the group consisting of humans, primates, farm animals, and domestic animals.

12. The method according to claim 10, wherein the mammal is a human.

13. The method according to claim 9, wherein the BVD-523 or a pharmaceutically acceptable salt thereof is administered in the form of a pharmaceutical composition further comprising a pharmaceutically acceptable carrier or diluent.

14. The method according to claim 9, wherein the dabrafenib or a pharmaceutically acceptable salt thereof is administered in the form of a pharmaceutical composition further comprising a pharmaceutically acceptable carrier or diluent.

15. The method according to claim 9, wherein the subject with cancer has a BRAF mutation or is refractory to MAPK pathway inhibitor treatment.

16. The method according to claim 9 further comprising administering at least one additional therapeutic agent selected from the group consisting of an antibody or fragment thereof, a cytotoxic agent, a toxin, a radionuclide, an immunomodulator, a photoactive therapeutic agent, a radiosensitizing agent, a hormone, an anti-angiogenesis agent, and combinations thereof.

17. The method according to claim 16, wherein the additional therapeutic agent is an inhibitor of the PI3K/Akt pathway.

18. The method according to claim 17, wherein the inhibitor of the PI3K/Akt pathway is selected from the group consisting of A-674563 (CAS #552325-73-2), AGL 2263, AMG-319, AS-041164 (5-benzo[1,3]dioxol-5-ylmethylene-thiazolidine-2,4-dione), AS-604850 (5-(2,2-Difluoro-benzo[1,3]dioxol-5-ylmethylene)-thiazolidine-2,4-dione), AS-605240 (5-quinoxilin-6-methylene-1,3-thiazolidine-2,4-dione), AT7867 (CAS #857531-00-1), benzimidazole series, BML-257 (CAS #32387-96-5), CAL-120, CAL-129, CAL-130, CAL-253, CAL-263, CAS #612847-09-3, CAS #681281-88-9, CAS #75747-14-7, CAS #925681-41-0, CAS #98510-80-6, CCT128930 (CAS #885499-61-6), CH5132799 (CAS #1007207-67-1), CHR-4432, FPA 124 (CAS #902779-59-3), GS-1101 (CAL-101), GSK 690693 (CAS #937174-76-0), H-89 (CAS #127243-85-0), Honokiol, IC87114, IPI-145, KAR-4139, KAR-4141, KIN-1, KT 5720 (CAS #108068-98-0), Miltefosine, MK-2206 dihydrochloride (CAS #1032350-13-2), ML-9 (CAS #105637-50-1), Naltrindole Hydrochloride, OXY-111A, perifosine, PHT-427 (CAS #1191951-57-1), pictilisib, PIK-90 (CAS #677338-12-4), SC-103980, SF-1126, SH-5, SH-6, Tetrahydro Curcumin, TG100-115, Triciribine, X-339, XL-499, pharmaceutically acceptable salts thereof, and combinations thereof.

19. A method of effecting cancer cell death comprising contacting the cancer cell with an effective amount of (i) a first anti-cancer agent, which is BVD-523 or a pharmaceutically acceptable salt thereof and (ii) a second anti-cancer agent, which is a type 1 RAF inhibitor or a pharmaceutically acceptable salt thereof,
wherein the type 1 RAF inhibitor is selected from the group consisting of dabrafenib, vemurafenib, pharmaceutically acceptable salts thereof, and combinations thereof, and
wherein administration of the first and second anti-cancer agents provides a synergistic effect compared to administration of either anti-cancer agent alone.

20. The method according to claim 19, wherein the cancer cell is a mammalian cancer cell.

21. The method according to claim 20, wherein the mammalian cancer cell is obtained from a mammal selected from the group consisting of humans, primates, farm animals, and domestic animals.

22. The method according to claim 20, wherein the mammalian cancer cell is a human cancer cell.

23. The method according to claim 19, wherein the type 1 RAF inhibitor is dabrafenib or a pharmaceutically acceptable salt thereof.

24. The method according to claim 19, wherein the subject with cancer has a somatic BRAF mutation or is refractory to MAPK pathway inhibitor treatment.

25. The method according to claim 19 further comprising administering at least one additional therapeutic agent selected from the group consisting of an antibody or fragment thereof, a cytotoxic agent, a toxin, a radionuclide, an immunomodulator, a photoactive therapeutic agent, a radiosensitizing agent, a hormone, an anti-angiogenesis agent, and combinations thereof.

26. The method according to claim 25, wherein the additional therapeutic agent is an inhibitor of the PI3K/Akt pathway.

27. The method according to claim 26, wherein the inhibitor of the PI3K/Akt pathway is selected from the group consisting of A-674563 (CAS #552325-73-2), AGL 2263, AMG-319, AS-041164 (5-benzo[1,3]dioxol-5-ylmethylene-thiazolidine-2,4-dione), AS-604850 (5-(2,2-Difluoro-benzo[1,3]dioxol-5-ylmethylene)-thiazolidine-2,4-dione), AS-605240 (5-quinoxilin-6-methylene-1,3-thiazolidine-2,4-dione), AT7867 (CAS #857531-00-1), benzimidazole series, BML-257 (CAS #32387-96-5), CAL-120, CAL-129, CAL-130, CAL-253, CAL-263, CAS #612847-09-3, CAS #681281-88-9, CAS #75747-14-7, CAS #925681-41-0, CAS #98510-80-6, CCT128930 (CAS #885499-61-6), CH5132799 (CAS #1007207-67-1), CHR-4432, FPA 124 (CAS #902779-59-3), GS-1101 (CAL-101), GSK 690693 (CAS #937174-76-0), H-89 (CAS #127243-85-0), Honokiol, IC87114, IPI-145, KAR-4139, KAR-4141, KIN-1, KT 5720 (CAS #108068-98-0), Miltefosine, MK-2206 dihydrochloride (CAS #1032350-13-2), ML-9 (CAS #105637-50-1), Naltrindole Hydrochloride, OXY-111A, perifosine, PHT-427 (CAS #1191951-57-1), pictilisib, PIK-90 (CAS #677338-12-4), SC-103980, SF-1126, SH-5, SH-6, Tetrahydro Curcumin, TG100-115, Triciribine, X-339, XL-499, pharmaceutically acceptable salts thereof, and combinations thereof.

* * * * *

SEQUENCE LISTING

```
<160> NUMBER OF SEQ ID NOS: 45

<210> SEQ ID NO 1
<211> LENGTH: 5898
<212> TYPE: DNA
<213> ORGANISM: Homo sapiens

<400> SEQUENCE: 1 cgcctcccctt  cccctcccc  gcccgacagc  ggccgctcgg  gccccggctc  tcggttataa      60
gatggcggcg  ctgagcggtg  gcggtggtgg  cggcgcggag  ccgggccagg  ctctgttcaa     120
cggggacatg  gagcccgagg  ccggcgccgg  cgccggcgcc  gcggcctctt  cggctgcgga     180
ccctgccatt  ccggaggagg  tgtggaatat  caaacaaatg  attaagttga  cacaggaaca     240
tatagaggcc  ctattggaca  aatttggtgg  ggagcataat  ccaccatcaa  tatatctgga     300
ggcctatgaa  gaatacacca  gcaagctaga  tgcactccaa  caaagagaac  aacagttatt     360
ggaatctctg  gggaacggaa  ctgatttttc  tgtttctagc  tctgcatcaa  tggataccgt     420
tacatcttct  tcctcttcta  gcctttcagt  gctaccttca  tctcttttcag  tttttcaaaa     480 tcccacagat  gtggcacgga  gcaaccccaa  gtcaccacaa  aaacctatcg  ttagagtctt     540
cctgcccaac  aaacagagga  cagtggtacc  tgcaaggtgt  ggagttacag  tccgagacag     600
tctaaagaaa  gcactgatga  tgagaggtct  aatcccagag  tgctgtgctg  tttacagaat     660
tcaggatgga  gagaagaaac  caattggttg  ggacactgat  atttcctggc  ttactggaga     720
agaattgcat  gtggaagtgt  tggagaatgt  tccacttaca  acacacaact  tgtacgaaa     780 aacgttttc  accttagcat  tttgtgactt  ttgtcgaaag  ctgcttttcc  agggtttccg     840
ctgtcaaaca  tgtggttata  aatttcacca  gcgttgtagt  acagaagttc  cactgatgtg     900
tgttaattat  gaccaacttg  atttgctgtt  tgtctccaag  ttctttgaac  accacccaat     960
accacaggaa  gaggcgtcct  tagcagagac  tgccctaaca  tctggatcat  cccctccgc    1020 acccgcctcg  gactctattg  ggcccaaat  tctcaccagt  ccgtctcctt  caaaatccat    1080
tccaattcca  cagcccttcc  gaccagcaga  tgaagatcat  cgaaatcaat  ttgggcaacg    1140
agaccgatcc  tcatcagctc  ccaatgtgca  tataaacaca  atagaacctg  tcaatattga    1200
tgacttgatt  agagaccaag  gatttcgtgg  tgatggagga  tcaaccacag  gtttgtctgc    1260 tacccccct  gcctcattac  ctggctcact  aactaacgtg  aaagccttac  agaaatctcc    1320
aggacctcag  cgagaaagga  agtcatcttc  atcctcagaa  gacaggaatc  gaatgaaaac    1380
acttggtaga  cgggactcga  gtgatgattg  ggagattcct  gatgggcaga  ttacagtggg    1440
acaaagaatt  ggatctggat  catttggaac  agtctacaag  ggaaagtggc  atggtgatgt    1500
ggcagtgaaa  atgttgaatg  tgacagcacc  tacacctcag  cagttacaag  ccttcaaaaa    1560
tgaagtagga  gtactcagga  aaacacgaca  tgtgaatatc  ctactcttca  tgggctattc    1620
cacaaagcca  caactggcta  ttgttaccca  gtggtgtgag  ggctccagct  tgtatcacca    1680
tctccatatc  attgagacca  aatttgagat  gatcaaactt  atagatattg  cacgacagac    1740
tgcacagggc  atggattact  tacacgccaa  gtcaatcatc  cacagagacc  tcaagagtaa    1800
```

-continued

```
taatatattt cttcatgaag acctcacagt aaaaataggt gattttggtc tagctacagt    1860
gaaatctcga tggagtgggt cccatcagtt tgaacagttg tctggatcca ttttgtggat    1920
ggcaccagaa gtcatcagaa tgcaagataa aaatccatac agctttcagt cagatgtata    1980
tgcatttgga attgttctgt atgaattgat gactggacag ttaccttatt caaacatcaa    2040
caacagggac cagataattt ttatggtggg acgaggatac ctgtctccag atctcagtaa    2100
ggtacggagt aactgtccaa aagccatgaa gagattaatg gcagagtgcc tcaaaaagaa    2160
aagagatgag agaccactct ttccccaaat tctcgcctct attgagctgc tggcccgctc    2220
attgccaaaa attcaccgca gtgcatcaga accctccttg aatcgggctg gtttccaaac    2280
agaggatttt agtctatatg cttgtgcttc tccaaaaaca cccatccagg caggggata    2340
tggtgcgttt cctgtccact gaaacaaatg agtgagagag ttcaggagag tagcaacaaa    2400
aggaaaataa atgaacatat gtttgcttat atgttaaatt gaataaaata ctctctttt    2460
ttttaaggtg aaccaagaa cacttgtgtg gttaaagact agatataatt tttccccaaa    2520
ctaaaattta tacttaacat tggattttta acatccaagg gttaaaatac atagacattg    2580
ctaaaaattg gcagagcctc ttctagaggc tttactttct gttccgggtt tgtatcattc    2640
acttggttat tttaagtagt aaacttcagt ttctcatgca acttttgttg ccagctatca    2700
catgtccact agggactcca gaagaagacc ctacctatgc ctgtgtttgc aggtgagaag    2760
ttggcagtcg gttagcctgg gttagataag gcaaactgaa cagatctaat ttaggaagtc    2820
agtagaattt aataattcta ttattattct taataatttt tctataacta tttcttttta    2880
taacaatttg gaaaatgtgg atgtctttta tttccttgaa gcaataaact aagtttcttt    2940
ttataaaaac gcctccctc ccctccccg cccgacagcg gccgctcggg ccccggctct    3000
cggttataag atggcggcgc tgagcggtgg cggtggtggc ggcgcggagc cgggccaggc    3060
tctgttcaac ggggacatgg agcccgaggc cggcgccggc gccggcgccg cggcctcttc    3120
ggctgcggac cctgccattc cggaggaggt gtggaatatc aaacaaatga ttaagttgac    3180
acaggaacat atagaggccc tattggacaa atttggtggg gagcataatc caccatcaat    3240
atatctggag gcctatgaag aatacaccag caagctagat gcactccaac aaagagaaca    3300
acagttattg gaatctctgg ggaacggaac tgattttttct gtttctagct ctgcatcaat    3360
ggataccgtt acatcttctt cctcttctag cctttcagtg ctaccttcat ctctttcagt    3420
ttttcaaaat cccacagatg tggcacggag caaccccaag tcaccacaaa aacctatcgt    3480
tagagtcttc ctgcccaaca aacagaggac agtggtacct gcaaggtgtg gagttacagt    3540
ccgagacagt ctaaagaaag cactgatgat gagaggtcta atcccagagt gctgtgctgt    3600
ttacagaatt caggatggag agaagaaacc aattggttgg gacactgata tttcctggct    3660
tactggagaa gaattgcatg tggaagtgtt ggagaatgtt ccacttacaa cacacaactt    3720
tgtacgaaaa acgttttca ccttagcatt ttgtgacttt tgtcgaaagc tgcttttcca    3780
gggtttccgc tgtcaaacat gtggttataa atttcaccag cgttgtagta cagaagttcc    3840
actgatgtgt gttaattatg accaacttga tttgctgttt gtctccaagt tctttgaaca    3900
ccacccaata ccacaggaag aggcgtcctt agcagagact gccctaacat ctggatcatc    3960
cccttccgca cccgcctcgg actctattgg gccccaaatt ctcaccagtc cgtctccttc    4020
aaaatccatt ccaattccac agcccttccg accagcagat gaagatcatc gaaatcaatt    4080
tgggcaacga gaccgatcct catcagctcc caatgtgcat ataaacacaa tagaacctgt    4140
caatattgat gacttgatta gagaccaagg atttcgtggt gatggaggat caaccacagg    4200
```

```
tttgtctgct accccccctg cctcattacc tggctcacta actaacgtga aagccttaca    4260
gaaatctcca ggacctcagc gagaaaggaa gtcatcttca tcctcagaag acaggaatcg    4320
aatgaaaaca cttggtagac gggactcgag tgatgattgg gagattcctg atgggcagat    4380
tacagtggga caaagaattg gatctggatc atttggaaca gtctacaagg gaaagtggca    4440
tggtgatgtg gcagtgaaaa tgttgaatgt gacagcacct cacctcagc agttacaagc     4500 cttcaaaaat gaagtaggag tactcaggaa aacacgacat gtgaatatcc tactcttcat    4560
gggctattcc acaaagccac aactggctat tgttacccag tggtgtgagg gctccagctt    4620
gtatcaccat ctccatatca ttgagaccaa atttgagatg atcaaactta tagatattgc    4680
acgacagact gcacagggca tggattactt acacgccaag tcaatcatcc acagagacct    4740
caagagtaat aatatatttc ttcatgaaga cctcacagta aaaataggtg attttggtct    4800
agctacagtg aaatctcgat ggagtgggtc ccatcagttt gaacagttgt ctggatccat    4860
tttgtggatg gcaccagaag tcatcagaat gcaagataaa aatccataca gctttcagtc    4920
agatgtatat gcatttggaa ttgttctgta tgaattgatg actggacagt taccttattc    4980
aaacatcaac aacagggacc agataatttt tatggtggga cgaggatacc tgtctccaga    5040
tctcagtaag gtacggagta actgtccaaa agccatgaag agattaatgg cagagtgcct    5100
caaaaagaaa agagatgaga gaccactctt tccccaaatt ctcgcctcta ttgagctgct    5160
ggcccgctca ttgccaaaaa ttcaccgcag tgcatcagaa ccctccttga atcgggctgg    5220
tttccaaaca gaggatttta gtctatatgc ttgtgcttct ccaaaaacac ccatccaggc    5280 aggggggatat ggtgcgtttc ctgtccactg aaacaaatga gtgagagagt tcaggagagt    5340
agcaacaaaa ggaaaataaa tgaacatatg tttgcttata tgttaaattg aataaaaatac    5400 tctcttttt tttaaggtga accaaagaac acttgtgtgg ttaaagacta gatataattt    5460
ttccccaaac taaaatttat acttaacatt ggatttttaa catccaaggg ttaaaataca    5520
tagacattgc taaaaattgg cagagcctct tctagaggct ttactttctg ttccgggttt    5580
gtatcattca cttggttatt ttaagtagta aacttcagtt tctcatgcaa ctttttgttgc    5640 cagctatcac atgtccacta gggactccag aagaagaccc tacctatgcc tgtgtttgca    5700
ggtgagaagt tggcagtcgg ttagcctggg ttagataagg caaactgaac agatctaatt    5760
taggaagtca gtagaattta ataattctat tattattctt aataatttt ctataactat      5820 ttcttttat aacaatttgg aaaatgtgga tgtctttat ttccttgaag caataaacta       5880
agtttctttt tataaaaa                                                   5898
```

<210> SEQ ID NO 2
<211> LENGTH: 765
<212> TYPE: PRT
<213> ORGANISM: Homo sapiens

<400> SEQUENCE: 2

```
Ala Ala Leu Ser Gly Gly Gly Gly Gly Ala Glu Pro Gly Gln Ala
1               5                   10                  15

Leu Phe Asn Gly Asp Met Glu Pro Glu Ala Gly Ala Gly Ala Gly Ala
                20                  25                  30

Ala Ala Ser Ser Ala Ala Asp Pro Ala Ile Pro Glu Glu Val Trp Asn
            35                  40                  45

Ile Lys Gln Met Ile Lys Leu Thr Gln Glu His Ile Glu Ala Leu Leu
        50                  55                  60
```

-continued

```
Asp Lys Phe Gly Gly Glu His Asn Pro Pro Ser Ile Tyr Leu Glu Ala
 65                  70                  75                  80

Tyr Glu Glu Tyr Thr Ser Lys Leu Asp Ala Leu Gln Gln Arg Glu Gln
             85                  90                  95

Gln Leu Leu Glu Ser Leu Gly Asn Gly Thr Asp Phe Ser Val Ser Ser
        100                 105                 110

Ser Ala Ser Met Asp Thr Val Thr Ser Ser Ser Ser Ser Leu Ser
        115                 120                 125

Val Leu Pro Ser Ser Leu Ser Val Phe Gln Asn Pro Thr Asp Val Ala
130                 135                 140

Arg Ser Asn Pro Lys Ser Pro Gln Lys Pro Ile Val Arg Val Phe Leu
145                 150                 155                 160

Pro Asn Lys Gln Arg Thr Val Val Pro Ala Arg Cys Gly Val Thr Val
                165                 170                 175

Arg Asp Ser Leu Lys Lys Ala Leu Met Met Arg Gly Leu Ile Pro Glu
            180                 185                 190

Cys Cys Ala Val Tyr Arg Ile Gln Asp Gly Glu Lys Lys Pro Ile Gly
        195                 200                 205

Trp Asp Thr Asp Ile Ser Trp Leu Thr Gly Glu Glu Leu His Val Glu
210                 215                 220

Val Leu Glu Asn Val Pro Leu Thr Thr His Asn Phe Val Arg Lys Thr
225                 230                 235                 240

Phe Phe Thr Leu Ala Phe Cys Asp Phe Cys Arg Lys Leu Leu Phe Gln
                245                 250                 255

Gly Phe Arg Cys Gln Thr Cys Gly Tyr Lys Phe His Gln Arg Cys Ser
            260                 265                 270

Thr Glu Val Pro Leu Met Cys Val Asn Tyr Asp Gln Leu Asp Leu Leu
        275                 280                 285

Phe Val Ser Lys Phe Phe Glu His His Pro Ile Pro Gln Glu Glu Ala
        290                 295                 300

Ser Leu Ala Glu Thr Ala Leu Thr Ser Gly Ser Ser Pro Ser Ala Pro
305                 310                 315                 320

Ala Ser Asp Ser Ile Gly Pro Gln Ile Leu Thr Ser Pro Ser Pro Ser
                325                 330                 335

Lys Ser Ile Pro Ile Pro Gln Pro Phe Arg Pro Ala Asp Glu Asp His
            340                 345                 350

Arg Asn Gln Phe Gly Gln Arg Asp Arg Ser Ser Ser Ala Pro Asn Val
        355                 360                 365

His Ile Asn Thr Ile Glu Pro Val Asn Ile Asp Asp Leu Ile Arg Asp
        370                 375                 380

Gln Gly Phe Arg Gly Asp Gly Gly Ser Thr Thr Gly Leu Ser Ala Thr
385                 390                 395                 400

Pro Pro Ala Ser Leu Pro Gly Ser Leu Thr Asn Val Lys Ala Leu Gln
                405                 410                 415

Lys Ser Pro Gly Pro Gln Arg Glu Arg Lys Ser Ser Ser Ser Ser Glu
            420                 425                 430

Asp Arg Asn Arg Met Lys Thr Leu Gly Arg Arg Asp Ser Ser Asp Asp
        435                 440                 445

Trp Glu Ile Pro Asp Gly Gln Ile Thr Val Gly Gln Arg Ile Gly Ser
        450                 455                 460

Gly Ser Phe Gly Thr Val Tyr Lys Gly Lys Trp His Gly Asp Val Ala
465                 470                 475                 480

Val Lys Met Leu Asn Val Thr Ala Pro Thr Pro Gln Gln Leu Gln Ala
```

```
                  485                 490                 495
Phe Lys Asn Glu Val Gly Val Leu Arg Lys Thr Arg His Val Asn Ile
                500                 505                 510

Leu Leu Phe Met Gly Tyr Ser Thr Lys Pro Gln Leu Ala Ile Val Thr
            515                 520                 525

Gln Trp Cys Glu Gly Ser Ser Leu Tyr His His Leu His Ile Ile Glu
        530                 535                 540

Thr Lys Phe Glu Met Ile Lys Leu Ile Asp Ile Ala Arg Gln Thr Ala
545                 550                 555                 560

Gln Gly Met Asp Tyr Leu His Ala Lys Ser Ile Ile His Arg Asp Leu
                565                 570                 575

Lys Ser Asn Asn Ile Phe Leu His Glu Asp Leu Thr Val Lys Ile Gly
            580                 585                 590

Asp Phe Gly Leu Ala Thr Val Lys Ser Arg Trp Ser Gly Ser His Gln
        595                 600                 605

Phe Glu Gln Leu Ser Gly Ser Ile Leu Trp Met Ala Pro Glu Val Ile
    610                 615                 620

Arg Met Gln Asp Lys Asn Pro Tyr Ser Phe Gln Ser Asp Val Tyr Ala
625                 630                 635                 640

Phe Gly Ile Val Leu Tyr Glu Leu Met Thr Gly Gln Leu Pro Tyr Ser
                645                 650                 655

Asn Ile Asn Asn Arg Asp Gln Ile Ile Phe Met Val Gly Arg Gly Tyr
            660                 665                 670

Leu Ser Pro Asp Leu Ser Lys Val Arg Ser Asn Cys Pro Lys Ala Met
        675                 680                 685

Lys Arg Leu Met Ala Glu Cys Leu Lys Lys Lys Arg Asp Glu Arg Pro
    690                 695                 700

Leu Phe Pro Gln Ile Leu Ala Ser Ile Glu Leu Leu Ala Arg Ser Leu
705                 710                 715                 720

Pro Lys Ile His Arg Ser Ala Ser Glu Pro Ser Leu Asn Arg Ala Gly
                725                 730                 735

Phe Gln Thr Glu Asp Phe Ser Leu Tyr Ala Cys Ala Ser Pro Lys Thr
            740                 745                 750

Pro Ile Gln Ala Gly Gly Tyr Gly Ala Phe Pro Val His
        755                 760                 765

<210> SEQ ID NO 3
<211> LENGTH: 3906
<212> TYPE: DNA
<213> ORGANISM: Rattus norvegicus

<400> SEQUENCE: 3
atggcggcgc tgagtggcgg cggtggcagc agcagcggtg gcggtggcgg cggcggcggc      60
ggcggtggtg gcggcggcgg cggcggcgcc gaacagggac aggctctgtt caatggcgac     120
atggagccgg aggccggcgc tggcgccgcg gcctcttcgg ccgcggaccc ggccattcct     180
gaagaggtgt ggaatatcaa gcaaatgatt aagttgacac aggaacatat agaggcccta     240
ttggacaagt tggtgggga gcataaccca ccgtcaatat acctggaggc ctatgaagag     300
tacaccagca gctagatgc ccttcagcag agagagcagc agctgttgga atccctggtt     360
tttcaaactc ccacagatgt gatcacggaa accccaagt caccacagaa acctatcgtt     420
cgtgtcttcc tgcccaacaa acagaggaca gtggtgcccg caagatgtgg tgtaacggtc     480
cgagacagtc taaagaaagc actaatgatg aggggtctca tcccagagtg ctgtgctgtt     540
```

```
tacagaattc aggacggaga gaagaaacca attggctggg acactgacat tcctggctt      600 actggagagg agctacatgt tgaagtacta gagaatgttc ctctgacaac ccacaacttc     660
gtacggaaaa cttttttcac cttagcattt tgtgactttt gccgaaagct gcttttccag    720
ggtttccgct gtcaaacatg tggttataag tttcaccagc gttgtagtac agaggttcca    780
ctgatgtgtg ttaattatga ccaacttgat ttgctgtttg tctccaagtt ctttgagcat    840
cacccagtac cacaggagga ggccttctca gcagagacta cccttccatc tggatgctct    900
tccgcacccc cctcagactc tattgggccc caaatcctca ccagtccatc tccttcaaaa    960
tccattccaa ttccacagcc cttccggcca gcagatgaag atcatcgcaa tcagtttggg   1020
caacgagacc gctcctcctc cgctcccaat gttcatataa acacaatcga acctgtcaat   1080
attgatgaaa aattcccaga agtggaatta caggatcaaa gggatttgat tagagaccag   1140
gggtttcgtg gggatggagc cccttttgaac cagctgatgc gctgtcttcg gaaataccaa   1200
tcccggactc ccagcccct cctccattct gtccccagtg aaatagtgtt tgattttgag   1260 cctgcccag tgttcagagg gtcaaccaca ggcttgtcgg ccaccccacc tgcctcatta    1320
cctggctcac tcactaacgt gaaagcctta cagaaatctc caggacctca gcgggaaagg   1380
aagtcctcct cctcctcctc ctccacgaaa gacagaagtc ggatgaaaac acttggtaga   1440
agagattcaa gtgatgattg ggagattcct gatggacaga ttacagtggg acagagaatt   1500
ggatctgggt cctttggaac tgtctacaag ggaaagtggc atggcgacgt ggcagtgaaa   1560
atgctgaatg tgacagcacc cacacctcag cagttacagg ccttcaaaaa cgaagtcgga   1620
gtactcagga aaactcgaca tgtgaacatc ctccttttca tgggctattc tacaaagcca   1680
cagctggcta ttgttacaca gtggtgtgaa ggctccagct tatatcacca tctccacatc   1740
attgagacca aatttgagat gatcaaactt atagatattg cacggcagac tgcacagggc   1800
atggattact tacacgccaa gtcaatcatc cacagagacc tcaagagtaa taatatattt   1860
cttcatgaag acctcacggt aaaaataggt gactttggtt tagccacagt gaagtcccga   1920
tggagtgggt cccatcagtt tgaacagttg tctggatcta ttttgtggat ggcacccgaa   1980
gtaatcagaa tgcaagataa aaacccatat agctttcagt cagacgtgta tgcatttggg   2040
attgttctgt atgaactgat gactggtcag ctaccttatt caaacatcaa caacagggat   2100
cagataattt ttatggtggg acgaggatac ctatctccag atctcagtaa ggtacggagt   2160
aactgtccaa aagccatgaa gagattaatg gcagagtgcc tcaaaaagaa aagagacgag   2220
agaccactct ttccccaaat tctcgcctct attgagctgc tggcccgctc attgccaaaa   2280
attcaccgca gtgcatcaga ccctccttg aatcgggctg gtttccaaac agaagatttt   2340
agtctgtatg cttgtgcttc tccaaaaaca cccatccaag caggggggata tggagaattt   2400 gcagccttca agtagccact ccatcatggc agcatctact ctttatttct taagtcttgt   2460
gttcatacaa tttgttaaca tcaaaacaca gttctgttcc tcaaattttt tttaaagata   2520
caaaattttc aatgcataag ctcgtgtgga acagaatgga atttcctatt caacaaaaga   2580
gggaagaatg ttttaggaac cagaattctc tgctgcccgt gtttcttctt caacacaaat   2640
atcatgtgca taaactctg cccattccca agaagaaaga ggagagaccc cgaattctgc    2700
ccttttggtg gtcaggcatg atggaaagaa tttgctgctg cagcttggga aaaattgcta   2760
tggaaagtct gccagtcaac tttgcccttc taaccaccag atccatttgt ggctggtcat   2820
ctgatggggc gatttcaatc accaagcatc gttcttgcct gttgtgggat tatgtcgtgg   2880
agcactttcc ctatccacca ccgttaattt ccgagggatg gagtaaatgc agcatacccct  2940
```

-continued

```
ttgtgtagca cctgtccagt cctcaaccaa tgctatcaca gtgaagctct ttaaatttaa   3000
gtggtgggtg agtgttgagg agagactgcc ttggggggcag agaaaagggg atgctgcatc  3060
ttcttcctca cctccagctc tctcacctcg ggttgccttg cacactgggc tccgcctaac   3120
cactcgggct gggcagtgct ggcacacatt gccgccttt ctcattgggt ccagcaattg   3180
agcagagggt tgggggattg tttcctccac aatgtagcaa attctcagga aaatacagtc   3240
catatcttcc tctcagctct tccagtcacc aaatacttac gtggctcctt tgtccaggac   3300
ataaaacacc gtggacaaca cctaattaaa agcctacaaa actgcttact gacagttttg   3360
aatgtgagac atttgtgtaa tttaaatgta aggtacaggt cttaatttct tctattaagt   3420
ttcttctatt tttatttaaa cgaagaaaat aattttcagg tttaattgga ataaacgaat   3480
acttcccaaa agactatata ccctgaaaat tatattttg ttaattgtaa acaactttta   3540
aaaaatggtt attatccttt tctctaccta aaattatggg aaatcttagc ataatgacaa   3600
ttatttatac tttttaaata aatggtactt gctggatcca cactaacatc tttgctaaca   3660
ttcccattgt ttcttccaac ttcactccta cactacatcc tccatcctct ttctagtctt   3720
ttatctataa tatgcaacct aaaataaaag tggtggtgtc tccattcatt cttcttcttc   3780
ctttttccc caagcctggt cttcaaaagg ttgggtaatt tagtagctga gttccctagg   3840
tagaaataga actattaggg acattggggt tgtaggaaag cgtgaggcct gtcaccagtt   3900
gttctt                                                              3906
```

<210> SEQ ID NO 4
<211> LENGTH: 804
<212> TYPE: PRT
<213> ORGANISM: Rattus norvegicus

<400> SEQUENCE: 4

```
Met Ala Ala Leu Ser Gly Gly Gly Ser Ser Gly Gly Gly
1               5                   10              15

Gly Gly Gly Gly Gly Gly Gly Gly Gly Gly Gly Ala Glu Gln
            20                  25                  30

Gly Gln Ala Leu Phe Asn Gly Asp Met Glu Pro Glu Ala Gly Ala Gly
            35                  40                  45

Ala Ala Ala Ser Ser Ala Ala Asp Pro Ala Ile Pro Glu Glu Val Trp
    50                  55                  60

Asn Ile Lys Gln Met Ile Lys Leu Thr Gln Glu His Ile Glu Ala Leu
65                  70                  75                  80

Leu Asp Lys Phe Gly Gly Glu His Asn Pro Pro Ser Ile Tyr Leu Glu
                85                  90                  95

Ala Tyr Glu Glu Tyr Thr Ser Lys Leu Asp Ala Leu Gln Gln Arg Glu
                100                 105                 110

Gln Gln Leu Leu Glu Ser Leu Val Phe Gln Thr Pro Thr Asp Val Ser
            115                 120                 125

Arg Asn Asn Pro Lys Ser Pro Gln Lys Pro Ile Val Arg Val Phe Leu
    130                 135                 140

Pro Asn Lys Gln Arg Thr Val Val Pro Ala Arg Cys Gly Val Thr Val
145                 150                 155                 160

Arg Asp Ser Leu Lys Lys Ala Leu Met Met Arg Gly Leu Ile Pro Glu
                165                 170                 175

Cys Cys Ala Val Tyr Arg Ile Gln Asp Gly Glu Lys Lys Pro Ile Gly
                180                 185                 190
```

```
Trp Asp Thr Asp Ile Ser Trp Leu Thr Gly Glu Glu Leu His Val Glu
            195                 200                 205
Val Leu Glu Asn Val Pro Leu Thr Thr His Asn Phe Val Arg Lys Thr
210                 215                 220
Phe Phe Thr Leu Ala Phe Cys Asp Phe Cys Arg Lys Leu Leu Phe Gln
225                 230                 235                 240
Gly Phe Arg Cys Gln Thr Cys Gly Tyr Lys Phe His Gln Arg Cys Ser
                245                 250                 255
Thr Glu Val Pro Leu Met Cys Val Asn Tyr Asp Gln Leu Asp Leu Leu
            260                 265                 270
Phe Val Ser Lys Phe Glu His His Pro Val Pro Gln Glu Glu Ala
            275                 280                 285
Phe Ser Ala Glu Thr Thr Leu Pro Ser Gly Cys Ser Ser Ala Pro Pro
290                 295                 300
Ser Asp Ser Ile Gly Pro Gln Ile Leu Thr Ser Pro Ser Pro Ser Lys
305                 310                 315                 320
Ser Ile Pro Ile Pro Gln Pro Phe Arg Pro Ala Asp Glu Asp His Arg
                325                 330                 335
Asn Gln Phe Gly Gln Arg Asp Arg Ser Ser Ala Pro Asn Val His
            340                 345                 350
Ile Asn Thr Ile Glu Pro Val Asn Ile Asp Glu Lys Phe Pro Glu Val
            355                 360                 365
Glu Leu Gln Asp Gln Arg Asp Leu Ile Arg Asp Gln Gly Phe Arg Gly
            370                 375                 380
Asp Gly Ala Pro Leu Asn Gln Leu Met Arg Cys Leu Arg Lys Tyr Gln
385                 390                 395                 400
Ser Arg Thr Pro Ser Pro Leu Leu His Ser Val Pro Ser Glu Ile Val
                405                 410                 415
Phe Asp Phe Glu Pro Gly Pro Val Phe Arg Gly Ser Thr Thr Gly Leu
            420                 425                 430
Ser Ala Thr Pro Pro Ala Ser Leu Pro Gly Ser Leu Thr Asn Val Lys
            435                 440                 445
Ala Leu Gln Lys Ser Pro Gly Pro Gln Arg Glu Arg Lys Ser Ser Ser
450                 455                 460
Ser Ser Ser Ser Thr Glu Asp Arg Ser Arg Met Lys Thr Leu Gly Arg
465                 470                 475                 480
Arg Asp Ser Ser Asp Asp Trp Glu Ile Pro Asp Gly Gln Ile Thr Val
                485                 490                 495
Gly Gln Arg Ile Gly Ser Gly Ser Phe Gly Thr Val Tyr Lys Gly Lys
                500                 505                 510
Trp His Gly Asp Val Ala Val Lys Met Leu Asn Val Thr Ala Pro Thr
            515                 520                 525
Pro Gln Gln Leu Gln Ala Phe Lys Asn Glu Val Gly Val Leu Arg Lys
530                 535                 540
Thr Arg His Val Asn Ile Leu Leu Phe Met Gly Tyr Ser Thr Lys Pro
545                 550                 555                 560
Gln Leu Ala Ile Val Thr Gln Trp Cys Glu Gly Ser Ser Leu Tyr His
                565                 570                 575
His Leu His Ile Ile Glu Thr Lys Phe Glu Met Ile Lys Leu Ile Asp
                580                 585                 590
Ile Ala Arg Gln Thr Ala Gln Gly Met Asp Tyr Leu His Ala Lys Ser
            595                 600                 605
Ile Ile His Arg Asp Leu Lys Ser Asn Asn Ile Phe Leu His Glu Asp
```

```
                  610                 615                 620
Leu Thr Val Lys Ile Gly Asp Phe Gly Leu Ala Thr Val Lys Ser Arg
625                 630                 635                 640

Trp Ser Gly Ser His Gln Phe Glu Gln Leu Ser Gly Ser Ile Leu Trp
                    645                 650                 655

Met Ala Pro Glu Val Ile Arg Met Gln Asp Lys Asn Pro Tyr Ser Phe
                660                 665                 670

Gln Ser Asp Val Tyr Ala Phe Gly Ile Val Leu Tyr Glu Leu Met Thr
            675                 680                 685

Gly Gln Leu Pro Tyr Ser Asn Ile Asn Asn Arg Asp Gln Ile Ile Phe
690                 695                 700

Met Val Gly Arg Gly Tyr Leu Ser Pro Asp Leu Ser Lys Val Arg Ser
705                 710                 715                 720

Asn Cys Pro Lys Ala Met Lys Arg Leu Met Ala Glu Cys Leu Lys Lys
                    725                 730                 735

Lys Arg Asp Glu Arg Pro Leu Phe Pro Gln Ile Leu Ala Ser Ile Glu
                740                 745                 750

Leu Leu Ala Arg Ser Leu Pro Lys Ile His Arg Ser Ala Ser Glu Pro
            755                 760                 765

Ser Leu Asn Arg Ala Gly Phe Gln Thr Glu Asp Phe Ser Leu Tyr Ala
770                 775                 780

Cys Ala Ser Pro Lys Thr Pro Ile Gln Ala Gly Gly Tyr Gly Glu Phe
785                 790                 795                 800

Ala Ala Phe Lys

<210> SEQ ID NO 5
<211> LENGTH: 9728
<212> TYPE: DNA
<213> ORGANISM: Mus musculus

<400> SEQUENCE: 5
ccctcaggct cggctgcgcc ggggccgccg gcgggttcca gaggtggcct ccgcccggc       60 cgctccgccc acgcccccg cgcctccgcg cccgcctccg cccgcccgc gcctcccttc      120 cccctccccg ccccgcggcg gccgctcggc ccggctcgcg cttcgaagat ggcggcgctg    180
agtggcggcg gtggcagcag cagcggtggc ggcggcggcg gtgcggcgg cggtggcggt    240 ggcgacggcg gcggcggcgc cgagcagggc caggctctgt tcaatggcga catggagccg    300
gaggccggcg ctggcgccgc ggcctcttcg gctgcggacc cggccattcc tgaagaggta    360
tggaatatca agcaaatgat taagttgaca caggaacata tagaggccct attggacaaa    420
tttggtggag agcataaccc accatcaata tacctggagg cctatgaaga gtacaccagc    480
aagctagatg cccttcagca aagagaacag cagcttttgg aatccctggt ttttcaaact    540
cccacagatg catcacggaa caaccccaag tcaccacaga aacctatcgt tagagtcttc    600
ctgcccaaca acagaggac agtggtaccc gcaagatgtg tgttacagt tcgacagt       660 ctaaagaaag cactgatgat gagaggtctc atcccagaat gctgtgctgt ttacagaatt    720
caggatggag agaagaaacc aattggctgg gacacggaca tttcctggct tactggagag    780
gagttacatg ttgaagtact ggagaatgtc ccacttacaa cacacaactt gtacgaaa    840 actttttca ccttagcatt tgtgactttt tgccgaaagc tgcttttcca gggtttccgt    900
tgtcaaacat gtggttataa atttcaccag cgttgtagta cagaggttcc actgatgtgt    960
gtaaattatg accaacttga tttgctgttt gtctccaagt tctttgagca tcacccagta   1020
```

```
ccacaggagg aggcctcctt cccagagact gcccttccat ctggatcctc ttccgcaccc    1080
ccctcagact ctactgggcc ccaaatcctc accagtccat ctccttcaaa atccattcca    1140
attccacagc ccttccgacc agcagatgaa gatcatcgca atcagtttgg gcaacgagac    1200
cggtcctcct cagctcccaa tgttcatata aacacaattg agcctgtgaa tatcgatgaa    1260
aaattcccag aagtggaatt acaggatcaa agggatttga ttagagacca ggggtttcgt    1320
ggtgatggag cccccttgaa ccaactgatg cgctgtcttc ggaaatacca atcccggact    1380
cccagccccc tcctccattc tgtccccagt gaaatagtgt ttgattttga gcctggccca    1440
gtgttcagag ggtcaaccac aggcttgtcc gccaccccgc ctgcctcatt acctggctca    1500
ctcactaacg tgaaagcctt acagaaatct ccaggtcctc agcgggaaag gaagtcatct    1560
tcttcctcat cctcggagga cagaagtcgg atgaaaacac ttggtagaag agattcaagt    1620
gatgactggg agattcctga tggacagatt acagtgggac agagaattgg atctgggtca    1680
tttggaactg tctacaaggg aaagtggcat ggtgatgtgg cagtgaaaat gttgaatgtg    1740
acagcaccca cacctcaaca gctacaggcc ttcaaaaatg aagtaggagt gctcaggaaa    1800
actcgacatg tgaatatcct ccttttcatg ggctattcta caaagccaca actggcaatt    1860
gttacacagt ggtgtgaggg ctccagctta tatcaccatc tccacatcat tgagaccaaa    1920
tttgagatga tcaaacttat agatattgct cggcagactg cacagggcat ggattactta    1980
cacgccaagt caatcatcca cagagacctc aagagtaata atatatttct tcatgaagac    2040
ctcacggtaa aataggtga ctttggtcta gccacagtga atctcggtg gagtgggtcc    2100 catcagtttg aacagttgtc tggatctatt ttgtggatgg caccagaagt aatcagaatg    2160
caagataaaa acccgtatag ctttcagtca gacgtgtatg cgtttgggat tgttctgtac    2220
gaactgatga ccggccagct accttattca aacatcaaca acaggatca gataattttt    2280 atggtgggac gaggatacct atctccagat ctcagtaagg tacggagtaa ctgtccaaaa    2340
gccatgaaga gattaatggc agagtgcctc aaaaagaaaa gagacgagag accactcttt    2400
ccccaaattc tcgcctccat tgagctgctg gcccgctcat tgccaaaaat tcaccgcagt    2460
gcatcagaac cttccttgaa tcgggctggt ttccaaacag aagattttag tctgtatgct    2520
tgtgcttctc cgaaaacacc catccaagca gggggatatg gagaatttgc agccttcaag    2580
tagccagtcc atcatggcag catctactct ttatttctta agtcttgtgt tcatacagtt    2640
tgttaacatc aaaacacagt tctgttcctc aaaaaatttt ttaaagatac aaaattttca    2700
atgcataagt tcatgtggaa cagaatgaaa tttcctattc aacaaagag ggaagaatgt    2760 tttaggaacc agaattctct gctgcccgtg tttcttcttc aacataacta tcacgtgcat    2820
acaagtctgc ccattcccaa gaagaaagag gagagaccct gaattctgcc cttttggtgg    2880
tcaggcatga tggaaagaat tgctgctgc agcttgggaa aattgctatg gaaagtctgc    2940
cagtcgactt tgcccttcta accaccagat cagcctgtgg ctggtcatct gatggggcga    3000
tttccatcac caagcatcgt tcttgcctat tctgggatta tgttgtggag cactttccct    3060
gtccagcacc gttcatttct gagggatgga gtaaatgcag cattcccttg tgtagcgcct    3120
gttcagtcct cagcagctgc tgtcacacgc aagctttta cagttaagtg gtgggggaga    3180
gttgaggaga gcctgcctcg gggcagagaa aaggggtgc tgcatcttct tcctcacctc    3240
cagctctctc acctcgggtt gccttgctca ctgggctccg cctaaccact caggctgctc    3300
agtgctggca cacattgcct tcttttctca ttgggtccag caattgagga gagggttggg    3360
ggattgtttc ctcctcaatg tagcaaattc tcaggaaaat acagtccata tcttcctctc    3420
```

```
agctcttcca gtcaccaaat acttacgtgg ctcctttgtc caggacataa aacaccgtgg    3480
acaacaccta attaaaagcc tacaaaactg cttactgaca gttttgaatg tgagacactt    3540
gtgtaattta aatgtaaggt acaggtttta atttctgagt ttcttctatt tttatttaaa    3600
agaagaaaat aattttcagt tttaattgga ataaatgagt acttcccaca agactatata    3660
ccctgaaaat tatattttg ttaattgtaa acaactttta aagaataatt attatccttt    3720
tctctaccta aaaattatgg ggaatcttag cataatgaca attatttata cttttaaat    3780 aaatggtact tgctggatcc acactaacat ctttgctaac aatcccattg tttcttccaa    3840
cttaactcct acactacatc ctacatcctc tttctagtct tttatctata atatgcaacc    3900
taaaataaac gtggtggcgt ctccattcat tctccctctt cctgttttcc ccaagcctgg    3960
tcttcaaaag gttgggtaat cggtccctga gctccctagc tggcaatgca actattaggg    4020
acattggagt tgcaggagag caggaagcct gtccccagct gttcttctag aaccctaaat    4080
cttatctttg cacagatcaa aagtatcacc tcgtcacagt tctccttagc ctttacttac    4140
aggtaatata aataaaaatc accatagtag taaagaaaac aactggatgg attgatgacc    4200
agtacctctc agagccagga atcttgaatc tccaggattt atacgtgcaa atttaaggag    4260
atgtacttag caacttcaag ccaagaactt ccaaaatact agcgaatcta aaataaaatg    4320
gaattttgag ttatttttaa agttcaaatt ataattgata ccactatgta tttaagccta    4380
ctcacagcaa gttagatgga ttttgctaaa ctcattgcca gactgtggtg gtggtggtgg    4440
tagtgtgcac ctttaatcca agcaactcag caatcagaat gaggtaaatc tctgtgaata    4500
caaggcctgc ctagtctgca gcgctagttc caggatagcc agggctacac acacaaaaac    4560
cctctctcaa aaaaacaaa attaattagt tgataataaa aaataactaa agtatcatca    4620
aaggaaggcc tactggaagt tttatatatt cccagtaaat tgaaaaatat tctgaagtta    4680
ttaaccagtt agcaacaatg tgttttaag tcttacataa acagagcaaa gtcttcaaat    4740
gtttcagagc tgagaagata attgtgcttg atatgaaaaa tagcctctcc atatgatgtg    4800
ccacattgaa aggcgtcatt acccttttaa atacttctta atgtggcttt gttccctta    4860 cccaggatta gctagaaaga gctaggtagg cttcggccac agttgcacat ttcgggcctg    4920
ctgaagaatg ggagctttga aggctggcct tggtggagga gcccctcagt gctgagggt    4980 ggggcgtgta cgcagcatgg aagtggtcta gacagagtgc aaagggacag acttcttct    5040 cattttagta tagggtgatg tctcacttga aatgagaaag tagagttgat attaaacgaa    5100
gctgtgccca gaaccaggc tcagggtatt gtgagatttt ctttttaaat agagaatata    5160
aaagatagaa ataaatattt aaaccttcct tcttatttc tatcaaatag attttttta    5220 tcatttgcaa acaacataaa aaaggtttc ttttgtgggg ttttctttcc ttctttttt    5280 tttttttttt ttttaagac tgcagataat cttgttgagc tcctcggaaa atacaaggaa    5340
gtccgtgttt tgcagagcg ctttatgagt aactgtatag acagtgtggc tgcttcactc    5400
atcccagagg gctgcagctg tcggcccatg aagtggctgc agtgcctcgt gagatctgct    5460
ttgttttgtt tggagtgaag tctttgaaag gtttgagtgc aactatatag gactgttttt    5520
aaataagtag tattcctcat gaactttctc attgttaagc tacaggaccc aaactctacc    5580
actaagatat tattaacctc aaaatgtagt ttatagaagg aatttgcaaa tagaatatcc    5640
agttcgtact tatatgcatc ttcaacaaag attctctgtg acttgttgga tttggttcct    5700
gaacagccca tttctgtatt tgaggttagg agggcataat gaggcatcct aaaagacaat    5760
```

```
ctgatataaa ctgtatgcta gatgtatgct ggtaggggag aaagcattct gtaaagacat    5820
gatttaagac ttcagctctg tcaaccagaa accttgtaaa tacttcctgt cttggtgcag    5880
ccccgcccct tgatcacac gatgttgtct tgtgcttgtc agacactgtc agagctgctg     5940
ttcgtccctc tgcagatctc acctgtcccc actgcacacc cacctcctgc ctcttgcaga    6000
cctcagcatc tagctttagt tggaaacagt tcagggttca ggtgacttct taaaaaaaaa    6060
aaaaaaccct acctcctcag aatgaggtaa tgaatagtta tttatttaaa gtatgaagag    6120
tcaggagcgc tcgaacatga aggtgattta agatggttcc tttcgtgtgt attgtagctg    6180
agcacttgtt tttgtcctaa agggcattat acatttaagc agtgattctg tttaaagatg    6240
tttttcttta aaggtgtagc tcagagtatc tgttgttgga attggtgcca gagtctgctt    6300
aatagatttc agaatcctaa gcttaagtca gtcgcatgaa gttaagtagt tatggtaaca    6360 cttttgctagc catgatataa ttctactttt taggagtagg tttggcaaaa ctgtatgcct    6420
tcaaagtgag ttggccacag cttttgtcaca tgcacagata ctcatctgaa gagactgccc    6480
agctaagagg gcggaaggat acccttttt cctacgattc gcttctttgt ccacgttggc    6540
attgttagta ctagtttatc agcacccttga ccagcagatg tcaaccaata agctattttt     6600
aaaaccatag ccagagatgg agaggtcact gtgagtagaa acagcaggac gcttacagga    6660
gtgaaatggt gtagggaggc tctagaaaaa tatcttgaca atttgccaaa tgatcttact    6720
gtgccttcat gatgcaataa aaaagctaac attttagcag aaatcagtga tttacgaaga    6780
gagtggccag tctggtttaa ctcagctggg ataatatttt tagagtgcaa tttagactgc    6840
gaagataaat gcactaaaga gtttatagcc aattcacatt tgaaaaataa gaaaatggta    6900
aattttcagt gaaatatttt tttaaagcac ataatcccta gtgtagccag aaatatttac    6960
cacatagagc agctaggctg agatacagtc cagtgacatt tctagagaaa cctttttctac    7020 tcccacgggc tcctcaaagc atggaaattt tatacaaaat gtttgacatt ttaagatact    7080
gctgtagttt agttttgaaa tagtatgtgc tgagcagcaa tcatgtacta actcagagag    7140
agaaaacaac aacaaattgt gcatctgatt tgttttcaga gaaatgctgc caacttagat    7200
actgagttct cagagcttca agtgtaaact tgcctcccaa gtcctgtttg caatgaagt    7260 tggctagtgc tactgactgc tccagcacat gatggaaggc agggggctgt ctctgaagtg    7320
tcttctataa agggacaata gaatagtgag agacctggtc agtgtgtgtc agctggacac    7380
tccatgctat gggacttgca tcttctgtcc tcaccatccc caagacattg tgctttcctc    7440
agttgtcctc tagctgtttc actcagacac caagatgaat tactgatgcc agaaggggcc    7500
aaaatggcca gtgtgttttg ggggttgtat cagttgactg gacaataact ttaatagttt    7560
cagatcattt ttttttacttt ccattttgac agacatttaa atggaaattt agtcctaact    7620
tttgtcattt gaaaggaaaa attaacagtt cctataagat acttttgagg tggaatctga    7680
catcctaatt tttttttcttt tcagtggggtt tgcagcgagg gtcttgtatg cactaggcaa    7740
gggttctacc actaagccac atttcccagg aaataaaatg ttaacagtta aaacatacac    7800
acaaatacac aaacacccttа ttaccacttt agtaaagtga gagatgtgcg tcctttgtct    7860
cagtctccac gatttcagct gccccttgta tgaataactc agtctcgcta aactgtttac    7920
ttttatttac ctggtttgac tagttgcagc tatataacca gttgtgcatg aggacaacag    7980
ccagtgtgtt tgttttgttt ttggtttttt gtggtacatt ttttgtaaag aattctgtag    8040
attgaagtgc tctttgaaaa cagaactgag atatatttat tcttgttagc atcaaaaaac    8100
attttgtgca aatgatttgc ttttcctggc aggctgagta ccatatccag cgcccacaat    8160
```

```
tgcgggttcc catctaccat gtccacaggg gagacagacg ggaagcacat gagggggtgtg    8220 tttacagagt tgtaggagtt atgtagttct cttgttgcct tggaaatcac tgttgtttta    8280
agactgttga acccgtgtgt ttggctgggc tgtgagttac atgaagaaac tgcaaactag    8340
catatgcaga caaagctcac agactaggcg taaatggagg aaaatggacc aaaataaggc    8400
agggtgacac ataaaccttg ggcttcgagg aaaactaagg gtggagatga actataatca    8460
cctgaataca atgtaagagt gcaataagtg tgcttattct aagctgtgaa cttcttttaa    8520
atcattcctt tctaatacat ttatgtatgt tccattgctg actaaaacca gctatgagaa    8580
catatgcctt tttattcatg ttaactacca gtttaagtgg ctaaccttaa tgtcttattt    8640
atcttcattt tgtattagtt tacataccag gtatgtgtgt gtgctgtact cttcttccct    8700
ttatttgaaa acacttttca ctgggtcatc tccttggcca ttccacaaca caactttggt    8760
ttggctttca atgtcacctt atttgatggc ctgtgtccca gtagcagaat ttatggtatt    8820
cccattgctg gctgctcttc cgacccttttg cttctacagc acttgtctct cctaagatag    8880
tcagaaacta actgatcagg ggatggactt caccattcat cgtgtctctt caattctatt    8940
aaatagacca ctcttgggct ttagaccagg aaaaaggaga cagctctagc catctaccaa    9000
gcctcaccct aaaaggtcac ccgtacttct tggtctgagg acaagtctcc actccagtaa    9060
gggagagggg aggaaatgct tcctgtttga aatgcagtga attcctatgg ctcctgtttc    9120
accacccgca cctatggcaa cccatataca ttcctcttgt ctgtaactgc caaaggttgg    9180
gtttatgtca cttcagttcc actcaagcat tgaaaaggtt tcatggagt ctggggtgtg    9240 cccagtgaaa agatggggac ttttttcatta tccacagacc tctctatacc tgctttgcaa    9300
aaattataat ggagtaacta tttttaaagc ttatttttca attcataaga aaaagacatt    9360
tattttcaat caaatggatg atgtctctta tcccttatcc ctcaatgttt gcttgaattt    9420
tgtttgttcc ctatacctac tccctaattc tttagttcct tcctgctcag gtccctttcat    9480 ttgtactttg gagttttttct catgtaaatt tgtataatgg aaaatattgt tcagtttgga    9540
tagaaagcat ggagaaataa ataaaaaaag atagctgaaa atcaaattga agaaatttat    9600
ttctgtgtaa agttatttaa aaactctgta ttatatttaa agaaaaaagc caacccccc    9660 aaaaagtgct atgtaattga tgtgaatatg cgaatactgc tataataaag attgactgca    9720
tggagaaa                                                             9728
```

<210> SEQ ID NO 6
<211> LENGTH: 804
<212> TYPE: PRT
<213> ORGANISM: Mus musculus

<400> SEQUENCE: 6

Met Ala Ala Leu Ser Gly Gly Gly Ser Ser Gly Gly Gly
1               5                   10                  15

Gly Gly Gly Gly Gly Gly Gly Gly Asp Gly Gly Gly Ala Glu
            20                  25                  30

Gln Gly Gln Ala Leu Phe Asn Gly Asp Met Glu Pro Glu Ala Gly Ala
        35                  40                  45

Gly Ala Ala Ala Ser Ser Ala Ala Asp Pro Ala Ile Pro Glu Glu Val
    50                  55                  60

Trp Asn Ile Lys Gln Met Ile Lys Leu Thr Gln Glu His Ile Glu Ala
65                  70                  75                  80

Leu Leu Asp Lys Phe Gly Gly Glu His Asn Pro Pro Ser Ile Tyr Leu

```
                85                  90                  95
Glu Ala Tyr Glu Glu Tyr Thr Ser Lys Leu Asp Ala Leu Gln Gln Arg
            100                 105                 110
Glu Gln Gln Leu Leu Glu Ser Leu Val Phe Gln Thr Pro Thr Asp Ala
            115                 120                 125
Ser Arg Asn Asn Pro Lys Ser Pro Gln Lys Pro Ile Val Arg Val Phe
            130                 135                 140
Leu Pro Asn Lys Gln Arg Thr Val Val Pro Ala Arg Cys Gly Val Thr
145                 150                 155                 160
Val Arg Asp Ser Leu Lys Lys Ala Leu Met Met Arg Gly Leu Ile Pro
                165                 170                 175
Glu Cys Cys Ala Val Tyr Arg Ile Gln Asp Gly Glu Lys Lys Pro Ile
                180                 185                 190
Gly Trp Asp Thr Asp Ile Ser Trp Leu Thr Gly Glu Glu Leu His Val
                195                 200                 205
Glu Val Leu Glu Asn Val Pro Leu Thr Thr His Asn Phe Val Arg Lys
            210                 215                 220
Thr Phe Phe Thr Leu Ala Phe Cys Asp Phe Cys Arg Lys Leu Leu Phe
225                 230                 235                 240
Gln Gly Phe Arg Cys Gln Thr Cys Gly Tyr Lys Phe His Gln Arg Cys
                245                 250                 255
Ser Thr Glu Val Pro Leu Met Cys Val Asn Tyr Asp Gln Leu Asp Leu
            260                 265                 270
Leu Phe Val Ser Lys Phe Phe Glu His His Pro Val Pro Gln Glu Glu
            275                 280                 285
Ala Ser Phe Pro Glu Thr Ala Leu Pro Ser Gly Ser Ser Ser Ala Pro
            290                 295                 300
Pro Ser Asp Ser Thr Gly Pro Gln Ile Leu Thr Ser Pro Ser Pro Ser
305                 310                 315                 320
Lys Ser Ile Pro Ile Pro Gln Pro Phe Arg Pro Ala Asp Glu Asp His
                325                 330                 335
Arg Asn Gln Phe Gly Gln Arg Asp Arg Ser Ser Ser Ala Pro Asn Val
            340                 345                 350
His Ile Asn Thr Ile Glu Pro Val Asn Ile Asp Glu Lys Phe Pro Glu
            355                 360                 365
Val Glu Leu Gln Asp Gln Arg Asp Leu Ile Arg Asp Gln Gly Phe Arg
            370                 375                 380
Gly Asp Gly Ala Pro Leu Asn Gln Leu Met Arg Cys Leu Arg Lys Tyr
385                 390                 395                 400
Gln Ser Arg Thr Pro Ser Pro Leu Leu His Ser Val Pro Ser Glu Ile
            405                 410                 415
Val Phe Asp Phe Glu Pro Gly Pro Val Phe Arg Gly Ser Thr Thr Gly
            420                 425                 430
Leu Ser Ala Thr Pro Pro Ala Ser Leu Pro Gly Ser Leu Thr Asn Val
            435                 440                 445
Lys Ala Leu Gln Lys Ser Pro Gly Pro Gln Arg Glu Arg Lys Ser Ser
            450                 455                 460
Ser Ser Ser Ser Ser Glu Asp Arg Ser Arg Met Lys Thr Leu Gly Arg
465                 470                 475                 480
Arg Asp Ser Ser Asp Asp Trp Glu Ile Pro Asp Gly Gln Ile Thr Val
                485                 490                 495
Gly Gln Arg Ile Gly Ser Gly Ser Phe Gly Thr Val Tyr Lys Gly Lys
            500                 505                 510
```

Trp His Gly Asp Val Ala Val Lys Met Leu Asn Val Thr Ala Pro Thr
          515                 520                 525

Pro Gln Gln Leu Gln Ala Phe Lys Asn Glu Val Gly Val Leu Arg Lys
    530                 535                 540

Thr Arg His Val Asn Ile Leu Leu Phe Met Gly Tyr Ser Thr Lys Pro
545                 550                 555                 560

Gln Leu Ala Ile Val Thr Gln Trp Cys Glu Gly Ser Ser Leu Tyr His
                565                 570                 575

His Leu His Ile Ile Glu Thr Lys Phe Glu Met Ile Lys Leu Ile Asp
            580                 585                 590

Ile Ala Arg Gln Thr Ala Gln Gly Met Asp Tyr Leu His Ala Lys Ser
        595                 600                 605

Ile Ile His Arg Asp Leu Lys Ser Asn Asn Ile Phe Leu His Glu Asp
    610                 615                 620

Leu Thr Val Lys Ile Gly Asp Phe Gly Leu Ala Thr Val Lys Ser Arg
625                 630                 635                 640

Trp Ser Gly Ser His Gln Phe Glu Gln Leu Ser Gly Ser Ile Leu Trp
                645                 650                 655

Met Ala Pro Glu Val Ile Arg Met Gln Asp Lys Asn Pro Tyr Ser Phe
            660                 665                 670

Gln Ser Asp Val Tyr Ala Phe Gly Ile Val Leu Tyr Glu Leu Met Thr
        675                 680                 685

Gly Gln Leu Pro Tyr Ser Asn Ile Asn Asn Arg Asp Gln Ile Ile Phe
    690                 695                 700

Met Val Gly Arg Gly Tyr Leu Ser Pro Asp Leu Ser Lys Val Arg Ser
705                 710                 715                 720

Asn Cys Pro Lys Ala Met Lys Arg Leu Met Ala Glu Cys Leu Lys Lys
                725                 730                 735

Lys Arg Asp Glu Arg Pro Leu Phe Pro Gln Ile Leu Ala Ser Ile Glu
            740                 745                 750

Leu Leu Ala Arg Ser Leu Pro Lys Ile His Arg Ser Ala Ser Glu Pro
        755                 760                 765

Ser Leu Asn Arg Ala Gly Phe Gln Thr Glu Asp Phe Ser Leu Tyr Ala
    770                 775                 780

Cys Ala Ser Pro Lys Thr Pro Ile Gln Ala Gly Gly Tyr Gly Glu Phe
785                 790                 795                 800

Ala Ala Phe Lys

<210> SEQ ID NO 7
<211> LENGTH: 2232
<212> TYPE: DNA
<213> ORGANISM: Oryctolagus cuniculus

<400> SEQUENCE: 7
atggggaatg tgtggaatat caaacaaatg attaagttga cacaggagca tatagaggcc    60
ctattggaca aatttggtgg ggagcataat ccaccatcaa tatatctgga ggcctacgaa   120
gaatacacca gcaagctaga tgccctccaa caaagagaac agcagttatt ggaatcccta   180 gttttcaaa atcccacaga tgtgtcacgg agcaaccca gtcaccaca aaaacctatt    240 gttagagtct tcctgcccaa caaacagagg acagtggtac ctgcaagatg tggagttacg   300
gttcgagaca gtctaaagaa agcgctgatg atgagaggtc tgatcccaga tgctgtgct    360 gtttacagaa ttcaggatgg agagaagaag ccaattggct gggacactga tatttcctgg   420

```
ctcactggag aagagctgca tgtggaagtg ttagagaatg tcccactcac cacacataac    480
tttgtacgga aaactttttt caccttagca ttttgtgact tctgtagaaa gctgcttttc    540
cagggtttcc gctgtcaaac atgtggctac aaatttcacc agcgttgtag tacggaagtt    600
ccactgatgt gtgttaatta tgaccaactt gatttgctgt ttgtctccaa gttctttgaa    660
caccacccag taccacagga ggaggcctcc ttagcagaga ctgccctcac atctgggtca    720
tcgccttccg cacctccctc agactctatt gggcaccaaa ttctcaccag tccgtcccct    780
tcaaaatcca ttccgattcc acagtccttc cgaccagcag atgaagatca tcgaaatcag    840
tttgggcaac gagaccggtc ttcatcagcg cctaatgttc acattaacac aatagaacct    900
gtcaatattg atgaaaaatt cccagaagtg gaattacagg atcaaaggga cttgattaga    960
gaccaagggt ttcgtggtga tggagcccct ttgaaccagc tgatgcgctg tcttcggaaa   1020
taccaatccc ggactcccag tcccctccta ccttctgtcc ccagtgacat agtgtttgat   1080
tttgagcctg gcccagtgtt cagaggatcg accacgggtt tgtctgccac tcccctgcc   1140
tcattacctg gctcactcac tagtgtgaaa gctgtacaga gatccccagg acctcagcga   1200
gagaggaagt cgtcttcctc ctcagaagac aggaatcgaa tgaaaactct tggtagacgg   1260
gattcaagtg atgattggga gattcctgat gggcagatca ccgtgggaca gagaattgga   1320
tctggatcat ttggaaccgt ctacaaggga aaatggcacg gtgatgtggc agtaaaaatg   1380
ttgaatgtga cagcacctac acctcagcag ttacaggcct tcaaaaatga agtaggagta   1440
ctcaggaaaa cacgacatgt gaatatccta ctttcatgg gctattccac aaagccacag   1500
ctggctattg ttacccagtg gtgtgagggc tccagtttat atcaccatct ccacatcatt   1560
gagaccaaat tcgagatgat caaacttata gatattgcac ggcagactgc acagggcatg   1620
gattacttac acgccaagtc aatcatccac agagacctca gagtaataa tatatttctt   1680
catgaagacc tcacagtaaa aataggtgat tttggtctag ccacagtgaa atctcgatgg   1740
agtgggtccc atcagtttga acaattgtct ggatccattt tgtggatggc accagaagta   1800
atcagaatgc aagacaaaaa cccatatagc tttcagtcag atgtatatgc atttgggatt   1860
gttctgtatg aattgatgac tgggcagtta ccttactcaa acatcaacaa cagggaccag   1920
atcattttta tggtgggacg tggctacctg tctccagacc tcagtaaggt acggagtaac   1980
tgtccgaaag ccatgaagag attaatggca gagtgcctca aaagaaaag agatgagaga   2040
ccactctttc cccaaattct cgcctccatt gagctgctgg cccgctcatt gccaaaaatc   2100
caccgcagtg catcagaacc ctccttgaat cgggctggtt tccagacaga ggattttagt   2160
ctatatgctt gtgcttctcc aaaaacaccc atccaggcag ggggatatgg agaatttgca   2220
gccttcaagt ag                                                        2232
```

<210> SEQ ID NO 8
<211> LENGTH: 743
<212> TYPE: PRT
<213> ORGANISM: Oryctolagus cuniculus

<400> SEQUENCE: 8

Met Gly Asn Val Trp Asn Ile Lys Gln Met Ile Lys Leu Thr Gln Glu
1               5                   10                  15

His Ile Glu Ala Leu Leu Asp Lys Phe Gly Gly Glu His Asn Pro Pro
            20                  25                  30

Ser Ile Tyr Leu Glu Ala Tyr Glu Glu Tyr Thr Ser Lys Leu Asp Ala
        35                  40                  45

-continued

```
Leu Gln Gln Arg Glu Gln Gln Leu Leu Glu Ser Leu Val Phe Gln Asn
    50                  55                  60

Pro Thr Asp Val Ser Arg Ser Asn Pro Lys Ser Pro Gln Lys Pro Ile
65                  70                  75                  80

Val Arg Val Phe Leu Pro Asn Lys Gln Arg Thr Val Val Pro Ala Arg
                85                  90                  95

Cys Gly Val Thr Val Arg Asp Ser Leu Lys Lys Ala Leu Met Met Arg
                100                 105                 110

Gly Leu Ile Pro Glu Cys Cys Ala Val Tyr Arg Ile Gln Asp Gly Glu
                115                 120                 125

Lys Lys Pro Ile Gly Trp Asp Thr Asp Ile Ser Trp Leu Thr Gly Glu
    130                 135                 140

Glu Leu His Val Glu Val Leu Glu Asn Val Pro Leu Thr Thr His Asn
145                 150                 155                 160

Phe Val Arg Lys Thr Phe Phe Thr Leu Ala Phe Cys Asp Phe Cys Arg
                165                 170                 175

Lys Leu Leu Phe Gln Gly Phe Arg Cys Gln Thr Cys Gly Tyr Lys Phe
                180                 185                 190

His Gln Arg Cys Ser Thr Glu Val Pro Leu Met Cys Val Asn Tyr Asp
    195                 200                 205

Gln Leu Asp Leu Leu Phe Val Ser Lys Phe Phe Glu His His Pro Val
    210                 215                 220

Pro Gln Glu Glu Ala Ser Leu Ala Glu Thr Ala Leu Thr Ser Gly Ser
225                 230                 235                 240

Ser Pro Ser Ala Pro Pro Ser Asp Ser Ile Gly His Gln Ile Leu Thr
                245                 250                 255

Ser Pro Ser Pro Ser Lys Ser Ile Pro Ile Pro Gln Ser Phe Arg Pro
                260                 265                 270

Ala Asp Glu Asp His Arg Asn Gln Phe Gly Gln Arg Asp Arg Ser Ser
                275                 280                 285

Ser Ala Pro Asn Val His Ile Asn Thr Ile Glu Pro Val Asn Ile Asp
    290                 295                 300

Glu Lys Phe Pro Glu Val Glu Leu Gln Asp Gln Arg Asp Leu Ile Arg
305                 310                 315                 320

Asp Gln Gly Phe Arg Gly Asp Gly Ala Pro Leu Asn Gln Leu Met Arg
                325                 330                 335

Cys Leu Arg Lys Tyr Gln Ser Arg Thr Pro Ser Pro Leu Leu Pro Ser
                340                 345                 350

Val Pro Ser Asp Ile Val Phe Asp Phe Glu Pro Gly Pro Val Phe Arg
                355                 360                 365

Gly Ser Thr Thr Gly Leu Ser Ala Thr Pro Pro Ala Ser Leu Pro Gly
    370                 375                 380

Ser Leu Thr Ser Val Lys Ala Val Gln Arg Ser Pro Gly Pro Gln Arg
385                 390                 395                 400

Glu Arg Lys Ser Ser Ser Ser Glu Asp Arg Asn Arg Met Lys Thr
                405                 410                 415

Leu Gly Arg Arg Asp Ser Ser Asp Asp Trp Glu Ile Pro Asp Gly Gln
                420                 425                 430

Ile Thr Val Gly Gln Arg Ile Gly Ser Gly Ser Phe Gly Thr Val Tyr
                435                 440                 445

Lys Gly Lys Trp His Gly Asp Val Ala Val Lys Met Leu Asn Val Thr
    450                 455                 460

Ala Pro Thr Pro Gln Gln Leu Gln Ala Phe Lys Asn Glu Val Gly Val
```

```
                465                 470                 475                 480
Leu Arg Lys Thr Arg His Val Asn Ile Leu Leu Phe Met Gly Tyr Ser
                    485                 490                 495
Thr Lys Pro Gln Leu Ala Ile Val Thr Gln Trp Cys Glu Gly Ser Ser
                500                 505                 510
Leu Tyr His His Leu His Ile Ile Glu Thr Lys Phe Glu Met Ile Lys
                515                 520                 525
Leu Ile Asp Ile Ala Arg Gln Thr Ala Gln Gly Met Asp Tyr Leu His
                530                 535                 540
Ala Lys Ser Ile Ile His Arg Asp Leu Lys Ser Asn Asn Ile Phe Leu
545                 550                 555                 560
His Glu Asp Leu Thr Val Lys Ile Gly Asp Phe Gly Leu Ala Thr Val
                    565                 570                 575
Lys Ser Arg Trp Ser Gly Ser His Gln Phe Glu Gln Leu Ser Gly Ser
                580                 585                 590
Ile Leu Trp Met Ala Pro Glu Val Ile Arg Met Gln Asp Lys Asn Pro
                595                 600                 605
Tyr Ser Phe Gln Ser Asp Val Tyr Ala Phe Gly Ile Val Leu Tyr Glu
                610                 615                 620
Leu Met Thr Gly Gln Leu Pro Tyr Ser Asn Ile Asn Asn Arg Asp Gln
625                 630                 635                 640
Ile Ile Phe Met Val Gly Arg Gly Tyr Leu Ser Pro Asp Leu Ser Lys
                    645                 650                 655
Val Arg Ser Asn Cys Pro Lys Ala Met Lys Arg Leu Met Ala Glu Cys
                660                 665                 670
Leu Lys Lys Lys Arg Asp Glu Arg Pro Leu Phe Pro Gln Ile Leu Ala
                675                 680                 685
Ser Ile Glu Leu Leu Ala Arg Ser Leu Pro Lys Ile His Arg Ser Ala
                690                 695                 700
Ser Glu Pro Ser Leu Asn Arg Ala Gly Phe Gln Thr Glu Asp Phe Ser
705                 710                 715                 720
Leu Tyr Ala Cys Ala Ser Pro Lys Thr Pro Ile Gln Ala Gly Gly Tyr
                    725                 730                 735
Gly Glu Phe Ala Ala Phe Lys
                740

<210> SEQ ID NO 9
<211> LENGTH: 2186
<212> TYPE: DNA
<213> ORGANISM: Cavia porcellus

<400> SEQUENCE: 9
atggcggcgc tcagcggcgg cggtggcgcg gagcagggcc aggctctgtt caacggggac     60
atggagctcg aggccggcgc cggcgccgca gcctcttcgg ctgcagaccc tgccattccc    120
gaggaggtat ggaatatcaa acaaatgatt aagttgacgc aggaacacat agaggcccta    180
ttggacaaat tggtggaga gcataatcca ccatcaatat acctggaggc ctatgaagaa    240
tacaccagca aactagatgc cctccaacaa agagaacagc agttactgga atccctcggg    300
aatggaactg attttctgt ttctagctct gcatcactgg acaccgttac atcttcttct    360
tcttctagcc tttcagtact accttcatct cttcagtttt tcaaaatcc tacagatgtg    420 tcacggagca accccaaatc accacaaaaa cctattgtta gagtcttcct gcccaacaaa    480
cagaggacag tggtacctgc aaggtgtgga gttacagtcc gagacagtct gaagaaagca    540
```

```
ctcatgatga gaggtcttat cccagagtgc tgtgctgtgt acagaattca ggatggagaa    600
aagaaaccaa ttggctggga cactgacatt tcctggctta ctggggaaga attacatgta    660
gaagtattgg agaatgttcc acttacaaca cacaattttg tatgtatctt tatatttttt    720
ttgctgtttg tctccaagtt ctttgaacac cacccaatac cacaggagga ggcttcctta    780
gcagagacca cccttacatc tggatcatcc ccttctgcac ccccctcaga gtccattggg    840
cccccaattc tcaccagccc atctccttca aaatccattc caattccaca gcctttccgg    900
ccaggagagg aagatcatcg aaatcaattt gggcagcgag accggtcctc atctgctccc    960
aatgtgcata taaacacaat agaacctgtc aatattgatg atttgattag agaccaaggg   1020
tttcgtagtg atggaggatc aactacaggt ttgtctgcca ccccacctgc ctcattacct   1080
ggctcactca ctaatgtgaa agccttacag aaatctccag acctcagcg agaaaggaag    1140
tcatcttcat cctcagaaga cagaaatcga atgaaaacgc ttggtagacg ggactcaagt   1200
gatgattggg agattcctga tgggcagatt acagtgggac aaagaattgg atctgggtca   1260
tttggaacag tctacaaggg gaagtggcat ggtgacgtgg cagtgaaaat gttgaatgtg   1320
acagcaccca cacctcaaca gttacaggcc ttcaaaaatg aagtaggagt actcaggaaa   1380
acacgacatg tgaatatcct actcttcatg ggctattcca caaagccaca gctagctatt   1440
gttacccagt ggtgtgaggg ctccagctta taccaccatc tccacatcat cgagaccaaa   1500
tttgagatga tcaaacttat agatattgca cgacagactg cccagggcat ggattactta   1560
cacgccaagt caatcatcca cagagacctc aagagtaata atatatttct tcacgaagac   1620
ctcacggtta aaataggtga ttttggtcta gccacagtga atctcgatg gagtgggtcc   1680
catcagtttg aacagttgtc tggatccatt ttgtggatgg caccagaagt aatcagaatg   1740
cgagataaaa acccatacag tttttcagtcc gatgtatatg catttgggat tgttctatat   1800
gaattgatga ctgggcagtt accctattca aatatcaaca cagggaccaa gataattttt   1860
atggtgggac gaggatatct atctccagat ctcagcaagg tacggagtaa ctgtccaaaa   1920
gccatgaaga ggttaatggc ggagtgcctc aaaaagaaaa gagatgagag accactcttt   1980
ccccaaattc tcgcctctat tgagctgctg gcccgctcat tgccaaaaat tcaccgcagt   2040
gcatcagaac cctccttgaa tcgggctggt ttccaaacag aggattttag tctctatgct   2100
tgtgcttctc caaaaacacc catccaggca gggggatatg gtgcgtttcc tgtccactga   2160
tgcaaattaa atgagtgaga aataaa                                        2186
```

<210> SEQ ID NO 10
<211> LENGTH: 719
<212> TYPE: PRT
<213> ORGANISM: Cavia porcellus

<400> SEQUENCE: 10

Met Ala Ala Leu Ser Gly Gly Gly Ala Glu Gln Gly Gln Ala Leu
1               5                   10                  15

Phe Asn Gly Asp Met Glu Leu Glu Ala Gly Ala Gly Ala Ala Ala Ser
                20                  25                  30

Ser Ala Ala Asp Pro Ala Ile Pro Glu Glu Val Trp Asn Ile Lys Gln
            35                  40                  45

Met Ile Lys Leu Thr Gln Glu His Ile Glu Ala Leu Leu Asp Lys Phe
        50                  55                  60

Gly Gly Glu His Asn Pro Pro Ser Ile Tyr Leu Glu Ala Tyr Glu Glu
65                  70                  75                  80

```
Tyr Thr Ser Lys Leu Asp Ala Leu Gln Gln Arg Glu Gln Gln Leu Leu
             85                  90                  95

Glu Ser Leu Gly Asn Gly Thr Asp Phe Ser Val Ser Ser Ala Ser
            100                 105                 110

Leu Asp Thr Val Thr Ser Ser Ser Ser Leu Ser Val Leu Pro
            115                 120                 125

Ser Ser Leu Ser Val Phe Gln Asn Pro Thr Asp Val Ser Arg Ser Asn
130                 135                 140

Pro Lys Ser Pro Gln Lys Pro Ile Val Arg Val Phe Leu Pro Asn Lys
145                 150                 155                 160

Gln Arg Thr Val Val Pro Ala Arg Cys Gly Val Thr Val Arg Asp Ser
                165                 170                 175

Leu Lys Lys Ala Leu Met Met Arg Gly Leu Ile Pro Glu Cys Cys Ala
            180                 185                 190

Val Tyr Arg Ile Gln Asp Gly Glu Lys Lys Pro Ile Gly Trp Asp Thr
            195                 200                 205

Asp Ile Ser Trp Leu Thr Gly Glu Glu Leu His Val Glu Val Leu Glu
            210                 215                 220

Asn Val Pro Leu Thr Thr His Asn Phe Val Cys Ile Phe Ile Phe Phe
225                 230                 235                 240

Leu Leu Phe Val Ser Lys Phe Phe Glu His His Pro Ile Pro Gln Glu
                245                 250                 255

Glu Ala Ser Leu Ala Glu Thr Thr Leu Thr Ser Gly Ser Ser Pro Ser
            260                 265                 270

Ala Pro Pro Ser Glu Ser Ile Gly Pro Pro Ile Leu Thr Ser Pro Ser
            275                 280                 285

Pro Ser Lys Ser Ile Pro Ile Pro Gln Pro Phe Arg Pro Gly Glu Glu
            290                 295                 300

Asp His Arg Asn Gln Phe Gly Gln Arg Asp Arg Ser Ser Ser Ala Pro
305                 310                 315                 320

Asn Val His Ile Asn Thr Ile Glu Pro Val Asn Ile Asp Asp Leu Ile
                325                 330                 335

Arg Asp Gln Gly Phe Arg Ser Asp Gly Gly Ser Thr Thr Gly Leu Ser
            340                 345                 350

Ala Thr Pro Pro Ala Ser Leu Pro Gly Ser Leu Thr Asn Val Lys Ala
            355                 360                 365

Leu Gln Lys Ser Pro Gly Pro Gln Arg Glu Arg Lys Ser Ser Ser Ser
            370                 375                 380

Ser Glu Asp Arg Asn Arg Met Lys Thr Leu Gly Arg Arg Asp Ser Ser
385                 390                 395                 400

Asp Asp Trp Glu Ile Pro Asp Gly Gln Ile Thr Val Gly Gln Arg Ile
                405                 410                 415

Gly Ser Gly Ser Phe Gly Thr Val Tyr Lys Gly Lys Trp His Gly Asp
            420                 425                 430

Val Ala Val Lys Met Leu Asn Val Thr Ala Pro Thr Pro Gln Gln Leu
            435                 440                 445

Gln Ala Phe Lys Asn Glu Val Gly Val Leu Arg Lys Thr Arg His Val
450                 455                 460

Asn Ile Leu Leu Phe Met Gly Tyr Ser Thr Lys Pro Gln Leu Ala Ile
465                 470                 475                 480

Val Thr Gln Trp Cys Glu Gly Ser Ser Leu Tyr His His Leu His Ile
                485                 490                 495

Ile Glu Thr Lys Phe Glu Met Ile Lys Leu Ile Asp Ile Ala Arg Gln
```

```
                    500                 505                 510
Thr Ala Gln Gly Met Asp Tyr Leu His Ala Lys Ser Ile Ile His Arg
                515                 520                 525
Asp Leu Lys Ser Asn Asn Ile Phe Leu His Glu Asp Leu Thr Val Lys
            530                 535                 540
Ile Gly Asp Phe Gly Leu Ala Thr Val Lys Ser Arg Trp Ser Gly Ser
545                 550                 555                 560
His Gln Phe Glu Gln Leu Ser Gly Ser Ile Leu Trp Met Ala Pro Glu
                565                 570                 575
Val Ile Arg Met Arg Asp Lys Asn Pro Tyr Ser Phe Gln Ser Asp Val
                580                 585                 590
Tyr Ala Phe Gly Ile Val Leu Tyr Glu Leu Met Thr Gly Gln Leu Pro
            595                 600                 605
Tyr Ser Asn Ile Asn Asn Arg Asp Gln Ile Ile Phe Met Val Gly Arg
        610                 615                 620
Gly Tyr Leu Ser Pro Asp Leu Ser Lys Val Arg Ser Asn Cys Pro Lys
625                 630                 635                 640
Ala Met Lys Arg Leu Met Ala Glu Cys Leu Lys Lys Arg Asp Glu
                645                 650                 655
Arg Pro Leu Phe Pro Gln Ile Leu Ala Ser Ile Glu Leu Leu Ala Arg
                660                 665                 670
Ser Leu Pro Lys Ile His Arg Ser Ala Ser Glu Pro Ser Leu Asn Arg
                675                 680                 685
Ala Gly Phe Gln Thr Glu Asp Phe Ser Leu Tyr Ala Cys Ala Ser Pro
            690                 695                 700
Lys Thr Pro Ile Gln Ala Gly Gly Tyr Gly Ala Phe Pro Val His
705                 710                 715
```

<210> SEQ ID NO 11
<211> LENGTH: 3229
<212> TYPE: DNA
<213> ORGANISM: Canis lupus

<400> SEQUENCE: 11

```
gtaatgctgg attttcatgg aataagtttg acctgtgctg cagtggcctc cagcaaggta      60
cccgcaagat gtggagttac agtccgggac agtctaaaga aagctctgat gatgagaggt     120
ctaatcccag agtgctgtgc tgtttacaga attcaggatg agagaagaa accgattggc     180
tgggacactg atattcctg gctcactgga gaggaattgc atgtagaagt gttggaaaat     240
gttccgctta ccacacacaa ctttgtacgg aaaactttt tcaccttagc attttgtgac     300
ttttgtcgaa agctgctttt ccagggtttt cgctgtcaaa catgtggtta taaatttcac     360
cagcgttgta gtacagaggt tccactgatg tgtgttaatt atgaccaact tgatttgctg     420
tttgtctcca agttctttga acaccaccca ataccacagg aggaggcctc catagcagag     480
actgcccta cgtctggatc atcccttct gctcccccct ccgattctcc tgggcccca      540
attctgacca gtccgtctcc ttcaaaatcc attccaattc cacagccttt ccgaccagca     600
gatgaagatc atcgaaatca gtttggacaa cgagaccggt cctcatcagc tccaaatgtg     660
catataaaca caatagaacc cgtcaacatt gatgacttga ttagagacca agggtttcgt     720
agtgatggag atcaaccac aggtttgtct gccaccccc ctgcctcatt gcctggctca     780
ctcactaatg taaagcatt acagaaatct ccaggacctc agcgggaaag aaaatcatct     840
tcatcctcag aagataggaa tcgaatgaaa acacttggta gacgggattc aagtgatgat     900
```

-continued

```
tgggagatac ctgatgggca gatcacagtg ggacagagaa ttggatccgg gtcatttggg      960
acagtctaca agggaaagtg gcatggtgac gtggcagtga aaatgttgaa tgtgacagca     1020
cccacacctc agcagttaca ggccttcaaa aatgaagtag gagtactcag gaaaactcga     1080
catgtgaata tcctactctt tatgggctat tcaacaaagc cccaactggc tattgttacc     1140
cagtggtgtg agggctccag cttatatcac catctccaca tcattgagac caaatttgag     1200
atgataaagc ttatagatat tgcacggcag actgcacagg gcatggatta cttacacgcc     1260
aagtcaatca tccacagaga cctcaagagt aataatattt ttcttcatga agacctcaca     1320
gtaaaaatag gtgattttgg tctagccaca gtgaaatctc gatggagtgg gtcccatcag     1380
tttgaacagt tgtctggatc cattttgtgg atggcaccag aagtgatccg aatgcaagac     1440
aaaaacccat atagcttcca gtcagatgta tacgcatttg ggattgttct atatgaattg     1500
atgacagggc agttacctta ttcaaacatc aacaacaggg accagataat ttttatggtg     1560
ggacgaggat atcttttctcc agatctcagt aaggtacgga gtaactgtcc aaaagccatg     1620
aagagattga tggcagagtg cctaaaaaag aaaagagatg agaggccact ctttcccccaa     1680
attctcgcct ctattgagct gctggcccgc tcattgccaa aaattcaccg cagtgcatca     1740
gaaccctcct tgaatcgggc tggcttccaa acagaggatt ttagtctcta tgcttgcgct     1800
tctccaaaaa cacccatcca ggcaggggga tacggagaat ttgcagcctt caagtagcca     1860
caccatcatg gcaacaacta ctcttatttc ttaagtcttg tgttcgtaca atttgttaac     1920
atcaaaacac agttctgttc ctcaaatctt ttttttaaga tacagaattt tcaatgcata     1980
agctggtgtg gaacagaatg gaatttccca tccaacaaaa gagggaagaa tgttttagga     2040
accagaattc tctgctgcca gtgtttcttc ttcaacacaa ataccacgtg catacaagtc     2100
tgcccactcc caggaaggaa gaggagagcc tgagttctga ccttttgatg gtcaggcatg     2160
atggaaagaa actgctgcta cagcttggga gattggctgt ggagagcctg cccgtcagct     2220
ctgcccttct aaccgccaga tgagtgtgtg gctggtcacc tgacagggca gctgcaatcg     2280
ccaagcatcg ttctctttcc tgtcctggga ttttgtcgtg gagctctttc cccctagtca     2340
ccaccggttc atttctgagg gatggaacaa aaatgcagca tggccttttct gtgtggtgca     2400
tgtccggtct ttgacaaatt tttatcaagt gaagctcttg tatttaaatg gagaatgaga     2460
ggcgaggggg gggatcacg ttttggtgta ggggcaaagg gaatgctgca tcttttttcct     2520
gacccactgg gtttctggcc tttgtttcct tgctcactga gggtgtctgc ctataaccac     2580
gcaggctgga aagtgctggc acacattgcc ttctcttctc actgggtcca gcaatgaaga     2640
caagtgttgg ggatttttttt ttttgccctc cacaatgtag caagttctca ggaaaataca     2700
gttaatatct tcctcctaag ctcttccagt catcaagtac ttatgtggct actttgtcca     2760
gggcacaaaa tgccatggcg gtatccaatt aaaagcctac aaaactgctt gataacagtt     2820
ttgaatgtgt gagacattta tgtaatttaa atgtaaggta caagttttaa tttctgagtt     2880
tctctattat atttttatta aaagaaaat aattttcaga tttaattgaa ttggaataaa     2940
ataatacttc ccaccagaat tatatatcct ggaaaattgt attttttgtta tataaacaac     3000
ttttaaagaa agatcattat ccttttctct acctaaatat ggggagtctt agcataatga     3060
cagatatttta taattttaa attaatggta cttgctggat ccacactaac atctttgcta     3120
atatctcatg ttttcctcca acttactcct acactacatc ctccatcctc tttccagtct     3180
tttatctaga atatgcaacc taaaataaaa atggtggtgt ctccattca               3229
```

```
<210> SEQ ID NO 12
<211> LENGTH: 617
<212> TYPE: PRT
<213> ORGANISM: Canis lupus

<400> SEQUENCE: 12
```

| | | | | | | | | | | | | | | | |
|---|---|---|---|---|---|---|---|---|---|---|---|---|---|---|---|
| Met | Leu | Asp | Phe | His | Gly | Ile | Ser | Leu | Thr | Cys | Ala | Ala | Val | Ala | Ser |
| 1 | | | | 5 | | | | | 10 | | | | | 15 | |
| Ser | Lys | Val | Pro | Ala | Arg | Cys | Gly | Val | Thr | Val | Arg | Asp | Ser | Leu | Lys |
| | | | 20 | | | | | 25 | | | | | 30 | | |
| Lys | Ala | Leu | Met | Met | Arg | Gly | Leu | Ile | Pro | Glu | Cys | Cys | Ala | Val | Tyr |
| | | | 35 | | | | | 40 | | | | | 45 | | |
| Arg | Ile | Gln | Asp | Gly | Glu | Lys | Lys | Pro | Ile | Gly | Trp | Asp | Thr | Asp | Ile |
| | | 50 | | | | | 55 | | | | | 60 | | | |
| Ser | Trp | Leu | Thr | Gly | Glu | Glu | Leu | His | Val | Glu | Val | Leu | Glu | Asn | Val |
| 65 | | | | | 70 | | | | | 75 | | | | | 80 |
| Pro | Leu | Thr | Thr | His | Asn | Phe | Val | Arg | Lys | Thr | Phe | Phe | Thr | Leu | Ala |
| | | | | 85 | | | | | 90 | | | | | 95 | |
| Phe | Cys | Asp | Phe | Cys | Arg | Lys | Leu | Leu | Phe | Gln | Gly | Phe | Arg | Cys | Gln |
| | | | | 100 | | | | | 105 | | | | | 110 | |
| Thr | Cys | Gly | Tyr | Lys | Phe | His | Gln | Arg | Cys | Ser | Thr | Glu | Val | Pro | Leu |
| | | | | 115 | | | | | 120 | | | | | 125 | |
| Met | Cys | Val | Asn | Tyr | Asp | Gln | Leu | Asp | Leu | Leu | Phe | Val | Ser | Lys | Phe |
| | | 130 | | | | | 135 | | | | | 140 | | | |
| Phe | Glu | His | His | Pro | Ile | Pro | Gln | Glu | Glu | Ala | Ser | Ile | Ala | Glu | Thr |
| 145 | | | | | 150 | | | | | 155 | | | | | 160 |
| Ala | Leu | Thr | Ser | Gly | Ser | Ser | Pro | Ser | Ala | Pro | Pro | Ser | Asp | Ser | Pro |
| | | | | 165 | | | | | 170 | | | | | 175 | |
| Gly | Pro | Pro | Ile | Leu | Thr | Ser | Pro | Ser | Pro | Ser | Lys | Ser | Ile | Pro | Ile |
| | | | | 180 | | | | | 185 | | | | | 190 | |
| Pro | Gln | Pro | Phe | Arg | Pro | Ala | Asp | Glu | Asp | His | Arg | Asn | Gln | Phe | Gly |
| | | | | 195 | | | | | 200 | | | | | 205 | |
| Gln | Arg | Asp | Arg | Ser | Ser | Ser | Ala | Pro | Asn | Val | His | Ile | Asn | Thr | Ile |
| | | 210 | | | | | 215 | | | | | 220 | | | |
| Glu | Pro | Val | Asn | Ile | Asp | Asp | Leu | Ile | Arg | Asp | Gln | Gly | Phe | Arg | Ser |
| 225 | | | | | 230 | | | | | 235 | | | | | 240 |
| Asp | Gly | Gly | Ser | Thr | Thr | Gly | Leu | Ser | Ala | Thr | Pro | Pro | Ala | Ser | Leu |
| | | | | 245 | | | | | 250 | | | | | 255 | |
| Pro | Gly | Ser | Leu | Thr | Asn | Val | Lys | Ala | Leu | Gln | Lys | Ser | Pro | Gly | Pro |
| | | | | 260 | | | | | 265 | | | | | 270 | |
| Gln | Arg | Glu | Arg | Lys | Ser | Ser | Ser | Ser | Glu | Asp | Arg | Asn | Arg | Met | |
| | | | | 275 | | | | | 280 | | | | | 285 | |
| Lys | Thr | Leu | Gly | Arg | Arg | Asp | Ser | Ser | Asp | Asp | Trp | Glu | Ile | Pro | Asp |
| | | | | 290 | | | | | 295 | | | | | 300 | |
| Gly | Gln | Ile | Thr | Val | Gly | Gln | Arg | Ile | Gly | Ser | Gly | Ser | Phe | Gly | Thr |
| 305 | | | | | 310 | | | | | 315 | | | | | 320 |
| Val | Tyr | Lys | Gly | Lys | Trp | His | Gly | Asp | Val | Ala | Val | Lys | Met | Leu | Asn |
| | | | | 325 | | | | | 330 | | | | | 335 | |
| Val | Thr | Ala | Pro | Thr | Pro | Gln | Gln | Leu | Gln | Ala | Phe | Lys | Asn | Glu | Val |
| | | | | 340 | | | | | 345 | | | | | 350 | |
| Gly | Val | Leu | Arg | Lys | Thr | Arg | His | Val | Asn | Ile | Leu | Leu | Phe | Met | Gly |
| | | | | 355 | | | | | 360 | | | | | 365 | |
| Tyr | Ser | Thr | Lys | Pro | Gln | Leu | Ala | Ile | Val | Thr | Gln | Trp | Cys | Glu | Gly |
| | | | | 370 | | | | | 375 | | | | | 380 | |

-continued

```
Ser Ser Leu Tyr His His Leu His Ile Ile Glu Thr Lys Phe Glu Met
385                 390                 395                 400

Ile Lys Leu Ile Asp Ile Ala Arg Gln Thr Ala Gln Gly Met Asp Tyr
            405                 410                 415

Leu His Ala Lys Ser Ile Ile His Arg Asp Leu Lys Ser Asn Asn Ile
        420                 425                 430

Phe Leu His Glu Asp Leu Thr Val Lys Ile Gly Asp Phe Gly Leu Ala
        435                 440                 445

Thr Val Lys Ser Arg Trp Ser Gly Ser His Gln Phe Glu Gln Leu Ser
450                 455                 460

Gly Ser Ile Leu Trp Met Ala Pro Glu Val Ile Arg Met Gln Asp Lys
465                 470                 475                 480

Asn Pro Tyr Ser Phe Gln Ser Asp Val Tyr Ala Phe Gly Ile Val Leu
            485                 490                 495

Tyr Glu Leu Met Thr Gly Gln Leu Pro Tyr Ser Asn Ile Asn Asn Arg
            500                 505                 510

Asp Gln Ile Ile Phe Met Val Gly Arg Gly Tyr Leu Ser Pro Asp Leu
        515                 520                 525

Ser Lys Val Arg Ser Asn Cys Pro Lys Ala Met Lys Arg Leu Met Ala
530                 535                 540

Glu Cys Leu Lys Lys Lys Arg Asp Glu Arg Pro Leu Phe Pro Gln Ile
545                 550                 555                 560

Leu Ala Ser Ile Glu Leu Leu Ala Arg Ser Leu Pro Lys Ile His Arg
                565                 570                 575

Ser Ala Ser Glu Pro Ser Leu Asn Arg Ala Gly Phe Gln Thr Glu Asp
            580                 585                 590

Phe Ser Leu Tyr Ala Cys Ala Ser Pro Lys Thr Pro Ile Gln Ala Gly
        595                 600                 605

Gly Tyr Gly Glu Phe Ala Ala Phe Lys
610                 615

<210> SEQ ID NO 13
<211> LENGTH: 1889
<212> TYPE: DNA
<213> ORGANISM: Canis lupus

<400> SEQUENCE: 13
ggaatatcaa acaaatgatt aagttgacac aggaacatat agaagcccta ttggacaagt      60
ttggtgggga gcataatcca ccatcaatat atctggaggc ctatgaagaa tacaccagca     120
aactagatgc cctccaacag cgagaacaac agttattgga atccctgggg aatgaactg      180 attttctgt ttctagctct gcatcaacgg acaccgttac atcttcttcc tcttctagcc      240
tttcagtgct accttcatct ctttcagttt tcaaaatcc cacagatata tcacggagca      300
atcccaagtc accacaaaaa cctatcgtta gagtcttcct gcccaataaa cagaggacgg     360
tggtacccgc aagatgtgga gttacagtcc gggacagtct aaagaaagct ctgatgatga     420
gaggtctaat cccagagtgc tgtgctgttt acagaattca ggatggagag aagaaaccga     480
ttggctggga cactgatatt tcctggctca ctggagagga attgcatgta gaagtgttgg     540
aaaatgttcc gcttaccaca cacaactttg tacggaaaac ttttttcacc ttagcatttt     600
gtgacttttg tcgaaagctg cttttccagg gttttcgctg tcaaacatgt ggttataaat     660
ttcaccagcg ttgtagtaca gaggttccac tgatgtgtgt taattatgac caacttgatt     720
tgctgtttgt ctccaagttc tttgaacacc acccaatacc acaggaggag gcctccatag     780
```

```
cagagactgc ccttacgtct ggatcatccc cttctgctcc ccctccgat tctcctgggc    840 ccccaattct gaccagtccg tctccttcaa aatccattcc aattccacag cctttccgac    900
cagcagatga agatcatcga aatcagtttg acaacgaga ccggtcctca tcagctccaa    960
atgtgcatat aaacacaata gaaccgtca acattgatga cttgattaga gaccaagggt   1020
ttcgtagtga tggaggatca accacaggtt tgtctgccac cccccctgcc tcattgcctg   1080
gctcactcac taatgtaaaa gcattacaga aatctccagg acctcagcgg gaaagaaaat   1140
catcttcatc ctcagaagat aggaatcgaa tgaaaacact tggtagacgg gattcaagtg   1200
atgattggga gatacctgat gggcagatca cagtgggaca gagaattgga tccgggtcat   1260
ttgggacagt ctacaaggga agtggcatg gtgacgtggc agtgaaaatg ttgaatgtga   1320
cagcacccac acctcagcag ttacaggcct tcaaaaatga agtaggagta ctcaggaaaa   1380
ctcgacatgt gaatatccta ctctttatgg gctattcaac aaagcccaa ctggctattg    1440 ttacccagtg gtgtgagggc tccagcttat atcaccatct ccacatcatt gagaccaaat   1500
ttgagatgat aaagcttata gatattgcac ggcagactgc acagggcatg gattacttac   1560
acgccaagtc aatcatccac agagacctca gagtaataa tattttctt catgaagacc    1620 tcacagtaaa aataggtgat tttggtctag ccacagtgaa atctcgatgg agtgggtccc   1680
atcagtttga acagttgtct ggatccattt tgtggatggc accagaagtg atccgaatgc   1740
aagacaaaaa cccatatagc ttccagtcag atgtatacgc atttgggatt gttctatatg   1800
aattgatgac agggcagtta ccttattcaa acatcaacaa cagggaccag ctcagatcat   1860
gatcacggtg tcatgagatc aagccccac                                    1889
```

<210> SEQ ID NO 14
<211> LENGTH: 615
<212> TYPE: PRT
<213> ORGANISM: Canis lupus

<400> SEQUENCE: 14

```
Met Ile Lys Leu Thr Gln Glu His Ile Glu Ala Leu Leu Asp Lys Phe
1               5                   10                  15

Gly Gly Glu His Asn Pro Pro Ser Ile Tyr Leu Glu Ala Tyr Glu Glu
            20                  25                  30

Tyr Thr Ser Lys Leu Asp Ala Leu Gln Gln Arg Glu Gln Gln Leu Leu
        35                  40                  45

Glu Ser Leu Gly Asn Gly Thr Asp Phe Ser Val Ser Ser Ala Ser
    50                  55                  60

Thr Asp Thr Val Thr Ser Ser Ser Ser Leu Ser Val Leu Pro
65                  70                  75                  80

Ser Ser Leu Ser Val Phe Gln Asn Pro Thr Asp Ile Ser Arg Ser Asn
                85                  90                  95

Pro Lys Ser Pro Gln Lys Pro Ile Val Arg Val Phe Leu Pro Asn Lys
            100                 105                 110

Gln Arg Thr Val Val Pro Ala Arg Cys Gly Val Thr Val Arg Asp Ser
        115                 120                 125

Leu Lys Lys Ala Leu Met Met Arg Gly Leu Ile Pro Glu Cys Cys Ala
    130                 135                 140

Val Tyr Arg Ile Gln Asp Gly Glu Lys Lys Pro Ile Gly Trp Asp Thr
145                 150                 155                 160

Asp Ile Ser Trp Leu Thr Gly Glu Glu Leu His Val Glu Val Leu Glu
                165                 170                 175
```

-continued

Asn Val Pro Leu Thr Thr His Asn Phe Val Arg Lys Thr Phe Phe Thr
            180                 185                 190

Leu Ala Phe Cys Asp Phe Cys Arg Lys Leu Leu Phe Gln Gly Phe Arg
        195                 200                 205

Cys Gln Thr Cys Gly Tyr Lys Phe His Gln Arg Cys Ser Thr Glu Val
        210                 215                 220

Pro Leu Met Cys Val Asn Tyr Asp Gln Leu Asp Leu Leu Phe Val Ser
225                 230                 235                 240

Lys Phe Phe Glu His His Pro Ile Pro Gln Glu Ala Ser Ile Ala
            245                 250                 255

Glu Thr Ala Leu Thr Ser Gly Ser Ser Pro Ser Ala Pro Pro Ser Asp
            260                 265                 270

Ser Pro Gly Pro Pro Ile Leu Thr Ser Pro Ser Pro Ser Lys Ser Ile
            275                 280                 285

Pro Ile Pro Gln Pro Phe Arg Pro Ala Asp Glu Asp His Arg Asn Gln
            290                 295                 300

Phe Gly Gln Arg Asp Arg Ser Ser Ser Ala Pro Asn Val His Ile Asn
305                 310                 315                 320

Thr Ile Glu Pro Val Asn Ile Asp Asp Leu Ile Arg Asp Gln Gly Phe
            325                 330                 335

Arg Ser Asp Gly Gly Ser Thr Thr Gly Leu Ser Ala Thr Pro Pro Ala
            340                 345                 350

Ser Leu Pro Gly Ser Leu Thr Asn Val Lys Ala Leu Gln Lys Ser Pro
            355                 360                 365

Gly Pro Gln Arg Glu Arg Lys Ser Ser Ser Ser Glu Asp Arg Asn
            370                 375                 380

Arg Met Lys Thr Leu Gly Arg Arg Asp Ser Ser Asp Asp Trp Glu Ile
385                 390                 395                 400

Pro Asp Gly Gln Ile Thr Val Gly Gln Arg Ile Gly Ser Gly Ser Phe
            405                 410                 415

Gly Thr Val Tyr Lys Gly Lys Trp His Gly Asp Val Ala Val Lys Met
            420                 425                 430

Leu Asn Val Thr Ala Pro Thr Pro Gln Gln Leu Gln Ala Phe Lys Asn
            435                 440                 445

Glu Val Gly Val Leu Arg Lys Thr Arg His Val Asn Ile Leu Leu Phe
450                 455                 460

Met Gly Tyr Ser Thr Lys Pro Gln Leu Ala Ile Val Thr Gln Trp Cys
465                 470                 475                 480

Glu Gly Ser Ser Leu Tyr His His Leu His Ile Glu Thr Lys Phe
            485                 490                 495

Glu Met Ile Lys Leu Ile Asp Ile Ala Arg Gln Thr Ala Gln Gly Met
            500                 505                 510

Asp Tyr Leu His Ala Lys Ser Ile Ile His Arg Asp Leu Lys Ser Asn
            515                 520                 525

Asn Ile Phe Leu His Glu Asp Leu Thr Val Lys Ile Gly Asp Phe Gly
            530                 535                 540

Leu Ala Thr Val Lys Ser Arg Trp Ser Gly Ser His Gln Phe Glu Gln
545                 550                 555                 560

Leu Ser Gly Ser Ile Leu Trp Met Ala Pro Glu Val Ile Arg Met Gln
            565                 570                 575

Asp Lys Asn Pro Tyr Ser Phe Gln Ser Asp Val Tyr Ala Phe Gly Ile
            580                 585                 590

Val Leu Tyr Glu Leu Met Thr Gly Gln Leu Pro Tyr Ser Asn Ile Asn

```
                         595                 600                 605

Asn Arg Asp Gln Leu Arg Ser
    610                 615

<210> SEQ ID NO 15
<211> LENGTH: 3521
<212> TYPE: DNA
<213> ORGANISM: Felis catus
<220> FEATURE:
<221> NAME/KEY: misc_feature
<222> LOCATION: (630)..(649)
<223> OTHER INFORMATION: n is a, c, g, or t

<400> SEQUENCE: 15
atgcctaacc tcagtctctg ccaccacggc caatttgctc atgtgcccac tgtgtcggca      60
ctgggatatt ttgtgatttg ccttggccat tgtccactgt ccttgacatt gcctgaagga     120
gaaccactga tgctaatgtt gaaggtgacc tttgcaggct ctccactact cataccaaag     180
atgcggcccc ctgataatcc cagagccact gtctgcacat gggcaaaaca ggctacattc     240
tgtgcagact ggggagaaag gttccaagaa cacagtgcca tagttttggg cagagagttt     300
caacacagca tagtgtctat ggcagtatct ggatttggcc gggggaagtg cccaagagga     360
gacagtcagg ctgtgtccta cggccaagga cctgcactta tttttgcatg cagtggttta     420
gcacagggaa gagaacgaag taggaaatcg gagccatgga acggcagag cggaggaaac      480 gtgcacgcgc gagggtgggc acgaaaggaa agaaccctcc ccagaagact gcgcgagggc     540
gctcctagga ttacgtcacg caccccgcga aaactgaaat gtactgtgtg tggtcttttta    600 attgaactat cttccttatg tgcacttaan nnnnnnnnnn nnnnnnnnng cggcggcggc     660
ggtggcgcgg agcagggcca ggctctgttc aacggggaca tggagcccga agccggcgcc     720
gcggcctctt cggctgcgga ccctgccatt cccgaggagg tgtggaatat caaacaaatg     780
attaagttga cacaggaaca tatagaggcc ctattggaca aatttggtgg ggagcataat     840
ccaccatcaa tatatctaga ggcctatgaa gaatacacca gcaagctaga tgccctccaa     900
cagagagaac aacagttatt ggaatccctg gggaatggaa ctgattttttc tgtttctagc    960 tctgcatcaa cagacaccgt tacatcttcc tcctcttcta gcctttcagt gctaccttca    1020
tctctttcag ttttttcaaaa ccccacagat gtgtcacgga gcaatcccaa gtcaccacag    1080
aaacctatcg ttagagtctt cctgcctaat aaacagagga cagtggtacc tgcaagatgt    1140
ggagttacag tccgggacag tctaaagaaa gctctgatga tgagaggtct aatccctgag    1200
tgctgtgctg tttacagaat tcaggatgga gagaagaaac caattggctg ggacactgat    1260
atctcctggc tcaccggaga ggaattgcat gtagaagtgt tggaaaatgt tccacttaca    1320
actcacaact ttgtatgtac ggaaaacgtt tcaccttag cattttgtga cttttgtcga    1380
aagctgcttt tccaaggttt tcgctgtcaa acgtgtggtt ataaatttca ccagcgttgt    1440
agtacagagg ttccactgat gtgtgttaat tatgaccaac ttgatttgct gttttgtctcc    1500 aagttctttg aacaccaccc aataccacag gaggaggcct ccatagcaga gactgcccta    1560
acgtctggat cgtcccctttc tgccccccccc tccgattcta ctgggcccca aattctcacc    1620
agtccgtctc cttcaaaatc cattccaatt ccacagcctt tccgaccagc agatgaagat    1680
catcgaaatc aatttggaca gcgagaccgg tcctcatcag ctccaaatgt gcatataaat    1740
acaatagaac ctgtcaatat tgatgacttg attagagacc aggggtttcg tagtgatgga    1800
ggatcaacca caggcttgtc tgccaccccc cctgcctcat tgccgggctc tctcactaat    1860
```

-continued

```
gtaaaagcat tacagaaatc tccagggcct cagcgggaaa ggaaatcttc ttcatcctca    1920
gaagatagga atcgaatgaa aacacttggt agaagggatt caagtgatga ttgggagatt    1980
cctgatgggc agatcacagt gggacagaga attggatccg ggtcatttgg acagtctac    2040
aagggaaagt ggcatggtga tgtggcagtg aaaatgttga atgtgacagc acccacacct    2100
cagcagttac aggccttcaa aaatgaagta ggagtactca ggaaaactcg gcatgtgaac    2160
atcctgctct tcatgggcta ttcaacaaag ccccagctgg ctattgtcac ccagtggtgt    2220
gagggctcca gcttatacca ccatctccac atcatcgaga ccaaattcga gatgatcaag    2280
ctgatagata ttgctcggca gactgcgcag ggcatggatt acttacacgc caagtcaatc    2340
atccacagag acctcaagag taataatatt tttcttcacg aagacctcac agtaaaaata    2400
ggtgattttg gtctagccac agtgaaatct cgatggagtg ggtcccatca gtttgaacag    2460
ttgtctggat ccattttgtg gatggcacca gaagtaattc gaatgcaaga taaaaaccca    2520
tatagctttc agtcagatgt atatgcattt gggattgttc tatatgaatt gatgactgga    2580
cagttacctt attcaaacat caacaacagg gaccagataa ttttatggt gggacgagga    2640
tatctttctc cagatctcag taaggtacga agtaactgtc caaaagccat gaagagattg    2700
atggcagagt gcctaaaaaa gaaaagagat gagaggccac tgtttcccca aattcttgcc    2760
tctattgagc tgctggcccg ctcattgcca aaaattcacc gcagtgcatc agaaccctcc    2820
ttgaatcggg ctggcttcca gacagaggat tttagtctct atgcttgtgc ttctccaaaa    2880
acacccatcc aggcaggggg atatggtgcg tttcccgtcc actgagataa gttagatgag    2940
tgcgcgagtg caggggccg gggccaagga ggtggaaatg tgcgtgcttc tgtactaagt    3000
tggatagcat cttcttttt aaaaaagat gaaccaaaga atgtgtatgt ttttaaagac    3060
tagatataat tatttcctga tctaaaatgt atacttagct ttggattttc aatatccaag    3120
ggttttcaaa atgcacagac attgctgaac atttgcagta cctcttctgg aggctttact    3180
tcctgttaca aattggtttt gtttactggc ttatcctaat tattaaactt caattaaact    3240
tttctcctgc acctttttgtt atgagctatc acatgtccct tagggactcg caagagcagt    3300
actgcccccg tgtacgggct tgcaggtaga aaggggatga cgggttttaa cacctgtgtg    3360
aggcaaggca gtccgaacag atctcattta ggaagccacg agagttgaat aagttatttt    3420
tattcttagt attttttctg taactacttt ttattataac ttggaaaata tggatgtcct    3480
ttatacacct tagcaataga ctgaatttct ttttataaat t                       3521
```

<210> SEQ ID NO 16
<211> LENGTH: 974
<212> TYPE: PRT
<213> ORGANISM: Felis catus
<220> FEATURE:
<221> NAME/KEY: misc_feature
<222> LOCATION: (210)..(217)
<223> OTHER INFORMATION: Xaa can be any naturally occurring amino acid

<400> SEQUENCE: 16

```
Met Pro Asn Leu Ser Leu Cys His His Gly Gln Phe Ala His Val Pro
1               5                   10                  15

Thr Val Ser Ala Leu Gly Tyr Phe Val Ile Cys Leu Gly His Cys Pro
            20                  25                  30

Leu Ser Leu Thr Leu Pro Glu Gly Glu Pro Leu Met Leu Met Leu Lys
        35                  40                  45

Val Thr Phe Ala Gly Ser Pro Leu Leu Ile Pro Lys Met Arg Pro Pro
    50                  55                  60
```

```
Asp Asn Pro Arg Ala Thr Val Cys Thr Trp Ala Lys Gln Ala Thr Phe
 65                  70                  75                  80

Cys Ala Asp Trp Gly Glu Arg Phe Gln Glu His Ser Ala Ile Val Leu
                 85                  90                  95

Gly Arg Glu Phe Gln His Ser Ile Val Ser Met Ala Val Ser Gly Phe
            100                 105                 110

Gly Arg Gly Lys Cys Pro Arg Gly Asp Ser Gln Ala Val Ser Tyr Gly
        115                 120                 125

Gln Gly Pro Ala Leu Ile Phe Ala Cys Ser Gly Leu Ala Gln Gly Arg
130                 135                 140

Glu Arg Ser Arg Lys Ser Glu Pro Trp Lys Arg Gln Ser Gly Gly Asn
145                 150                 155                 160

Val His Ala Arg Gly Trp Ala Arg Lys Glu Arg Thr Leu Pro Arg Arg
                165                 170                 175

Leu Arg Glu Gly Ala Pro Arg Ile Thr Ser Arg Thr Pro Arg Lys Leu
            180                 185                 190

Lys Cys Thr Val Cys Gly Leu Leu Ile Glu Leu Ser Ser Leu Cys Ala
        195                 200                 205

Leu Xaa Xaa Xaa Xaa Xaa Xaa Xaa Gly Gly Gly Gly Gly Gly Ala Glu
210                 215                 220

Gln Gly Gln Ala Leu Phe Asn Gly Asp Met Glu Pro Glu Ala Gly Ala
225                 230                 235                 240

Ala Ala Ser Ser Ala Ala Asp Pro Ala Ile Pro Glu Glu Val Trp Asn
                245                 250                 255

Ile Lys Gln Met Ile Lys Leu Thr Gln Glu His Ile Glu Ala Leu Leu
            260                 265                 270

Asp Lys Phe Gly Gly Glu His Asn Pro Pro Ser Ile Tyr Leu Glu Ala
        275                 280                 285

Tyr Glu Glu Tyr Thr Ser Lys Leu Asp Ala Leu Gln Gln Arg Glu Gln
290                 295                 300

Gln Leu Leu Glu Ser Leu Gly Asn Gly Thr Asp Phe Ser Val Ser Ser
305                 310                 315                 320

Ser Ala Ser Thr Asp Thr Val Thr Ser Ser Ser Ser Ser Ser Leu Ser
                325                 330                 335

Val Leu Pro Ser Ser Leu Ser Val Phe Gln Asn Pro Thr Asp Val Ser
            340                 345                 350

Arg Ser Asn Pro Lys Ser Pro Gln Lys Pro Ile Val Arg Val Phe Leu
        355                 360                 365

Pro Asn Lys Gln Arg Thr Val Val Pro Ala Arg Cys Gly Val Thr Val
370                 375                 380

Arg Asp Ser Leu Lys Lys Ala Leu Met Met Arg Gly Leu Ile Pro Glu
385                 390                 395                 400

Cys Cys Ala Val Tyr Arg Ile Gln Asp Gly Glu Lys Lys Pro Ile Gly
                405                 410                 415

Trp Asp Thr Asp Ile Ser Trp Leu Thr Gly Glu Glu Leu His Val Glu
            420                 425                 430

Val Leu Glu Asn Val Pro Leu Thr Thr His Asn Phe Val Cys Thr Glu
        435                 440                 445

Asn Val Phe Thr Leu Ala Phe Cys Asp Phe Cys Arg Lys Leu Leu Phe
450                 455                 460

Gln Gly Phe Arg Cys Gln Thr Cys Gly Tyr Lys Phe His Gln Arg Cys
465                 470                 475                 480
```

```
Ser Thr Glu Val Pro Leu Met Cys Val Asn Tyr Asp Gln Leu Asp Leu
                485                 490                 495

Leu Phe Val Ser Lys Phe Phe Glu His His Pro Ile Pro Gln Glu Glu
            500                 505                 510

Ala Ser Ile Ala Glu Thr Ala Leu Thr Ser Gly Ser Ser Pro Ser Ala
            515                 520                 525

Pro Pro Ser Asp Ser Thr Gly Pro Gln Ile Leu Thr Ser Pro Ser Pro
        530                 535                 540

Ser Lys Ser Ile Pro Ile Pro Gln Pro Phe Arg Pro Ala Asp Glu Asp
545                 550                 555                 560

His Arg Asn Gln Phe Gly Gln Arg Asp Arg Ser Ser Ser Ala Pro Asn
                565                 570                 575

Val His Ile Asn Thr Ile Glu Pro Val Asn Ile Asp Asp Leu Ile Arg
            580                 585                 590

Asp Gln Gly Phe Arg Ser Asp Gly Gly Ser Thr Thr Gly Leu Ser Ala
        595                 600                 605

Thr Pro Pro Ala Ser Leu Pro Gly Ser Leu Thr Asn Val Lys Ala Leu
    610                 615                 620

Gln Lys Ser Pro Gly Pro Gln Arg Glu Arg Lys Ser Ser Ser Ser Ser
625                 630                 635                 640

Glu Asp Arg Asn Arg Met Lys Thr Leu Gly Arg Arg Asp Ser Ser Asp
                645                 650                 655

Asp Trp Glu Ile Pro Asp Gly Gln Ile Thr Val Gly Gln Arg Ile Gly
            660                 665                 670

Ser Gly Ser Phe Gly Thr Val Tyr Lys Gly Lys Trp His Gly Asp Val
        675                 680                 685

Ala Val Lys Met Leu Asn Val Thr Ala Pro Thr Pro Gln Gln Leu Gln
    690                 695                 700

Ala Phe Lys Asn Glu Val Gly Val Leu Arg Lys Thr Arg His Val Asn
705                 710                 715                 720

Ile Leu Leu Phe Met Gly Tyr Ser Thr Lys Pro Gln Leu Ala Ile Val
                725                 730                 735

Thr Gln Trp Cys Glu Gly Ser Ser Leu Tyr His His Leu His Ile Ile
            740                 745                 750

Glu Thr Lys Phe Glu Met Ile Lys Leu Ile Asp Ile Ala Arg Gln Thr
        755                 760                 765

Ala Gln Gly Met Asp Tyr Leu His Ala Lys Ser Ile Ile His Arg Asp
    770                 775                 780

Leu Lys Ser Asn Asn Ile Phe Leu His Glu Asp Leu Thr Val Lys Ile
785                 790                 795                 800

Gly Asp Phe Gly Leu Ala Thr Val Lys Ser Arg Trp Ser Gly Ser His
                805                 810                 815

Gln Phe Glu Gln Leu Ser Gly Ser Ile Leu Trp Met Ala Pro Glu Val
            820                 825                 830

Ile Arg Met Gln Asp Lys Asn Pro Tyr Ser Phe Gln Ser Asp Val Tyr
        835                 840                 845

Ala Phe Gly Ile Val Leu Tyr Glu Leu Met Thr Gly Gln Leu Pro Tyr
    850                 855                 860

Ser Asn Ile Asn Asn Arg Asp Gln Ile Ile Phe Met Val Gly Arg Gly
865                 870                 875                 880

Tyr Leu Ser Pro Asp Leu Ser Lys Val Arg Ser Asn Cys Pro Lys Ala
                885                 890                 895

Met Lys Arg Leu Met Ala Glu Cys Leu Lys Lys Lys Arg Asp Glu Arg
```

```
                900             905             910
Pro Leu Phe Pro Gln Ile Leu Ala Ser Ile Glu Leu Leu Ala Arg Ser
            915             920             925

Leu Pro Lys Ile His Arg Ser Ala Ser Glu Pro Ser Leu Asn Arg Ala
        930             935             940

Gly Phe Gln Thr Glu Asp Phe Ser Leu Tyr Ala Cys Ala Ser Pro Lys
945             950             955             960

Thr Pro Ile Gln Ala Gly Gly Tyr Gly Ala Phe Pro Val His
            965             970

<210> SEQ ID NO 17
<211> LENGTH: 3853
<212> TYPE: DNA
<213> ORGANISM: Bos taurus

<400> SEQUENCE: 17
ctcagctgcg ccgggtctca caagacggtt cccgaggtgg cccaggcgcc gtcccaccgc      60
cgacgccgcc cgggccgccc gggccgtccc tccccgctgc ccccgtcctc cgcctccgc     120
ctccccccgc cctcagcctc ccttcccccct cccgcccag cagcggtcgc tcgggcccgg    180
ctctcggtta taagatggcg cgcgctgagtg gcggcggcgg cggcggcggc ggtggcgcgg    240
agcagggcca ggctctgttc aacggggaca tggagcccga ggccggcgcc gcggcctctt    300
cggctgcgga ccccgccatt cccgaggagg tgtggaatat caaacaaatg attaagttga    360
cacaggagca tatagaggcc ctattggaca aatttggtgg ggagcataat ccaccatcaa    420
tatatctgga ggcctatgaa gaatacacca gcaagctaga tgccctccaa caaagagaac    480
aacagttatt ggaatccctg gggaatggaa ctgattttttc tgtttctagc tctgcatcaa    540
cggacaccgt tacatcttct tcctcttcta gcctttcagt gctgccttca tctctttcag    600
ttttttcaaaa tcccacagat gtgtcacgga gcaaccccaa gtcaccacaa aaacctatcg    660
ttagagtctt cctgcccaat aaacagagga cagtggtacc tgcacggtgt ggagtcacag    720
tccgggacag cctgaagaag gcactgatga tgagaggtct aatcccagag tgctgtgctg    780
tttacagaat tcaggatggg gagaagaaac caattggctg gacactgata tttcctggc    840
ttactggaga ggagttgcat gtagaagtgt tggagaatgt tccacttaca acacacaact    900
ttgtacggaa aactttttttc acccttagcat tttgtgactt ctgtagaaag ctgcttttcc    960
agggattccg ctgtcaaaca tgtggttata aatttcacca gcgttgtagt acagaggttc   1020
cactgatgtg tgttaattat gaccaactag atttgctgtt tgtctccaag ttctttgaac   1080
accacccaat accacaggag gaggcctcct tagcagagac tacccttcca tgtggctcat   1140
cccttctgc acccccctcc gattctattg ggccccaat tctcaccagt ccatctcctt   1200
caaaatccat tccaattcca cagccttttcc gaccagcaga tgaagatcat cgaaatcagt   1260
ttggacaacg agaccggtcc tcatcagctc caaatgtgca tataaacaca atagaacccg   1320
tcaatattga tgacttgatt agagaccaag ggtttcgtag tgatggagga tcaaccacag   1380
gtttatccgc cacacccctt gcctcattac ctggctcact ctctaatgtg aaagcattgc   1440
agaaatctcc aggacctcag cgagaaagaa agtcctcttc atcctcagaa gacaggaatc   1500
gaatgaaaac gcttggtaga cgggattcaa gtgacgattg ggagattcct gatggacaga   1560
tcacagtggg acaaagaatt ggatcagggt catttgggac agtctacaag ggaaagtggc   1620
atggtgatgt ggcagtgaaa atgttgaatg tgacagcacc cacacctcag cagttacagg   1680
ccttcaaaaa tgaagtagga gtactcagga aaacgcgaca tgtgaatatc ctcctcttca   1740
```

```
tgggttattc aacaaagcca caactggcta ttgttaccca gtggtgtgag ggctccagtt    1800
tatatcatca tctccacatc attgagacca aattcgagat gatcaaactt atagatattg    1860
cacggcagac tgcacagggc atggattact tacacgccaa gtcaatcatc cacagagacc    1920
tcaagagtaa taatattttt cttcatgaag acctcacagt aaaaataggt gattttggtc    1980
tagccacagt gaaatctcga tggagtgggt cccatcagtt tgaacagttg tctggatcca    2040
ttttgtggat ggcaccagaa gtaatcagaa tgcaagataa aaacccatat agctttcagt    2100
cagatgtata tgcatttggg attgttctgt atgaattgat gaccggacag ttaccttatt    2160
caaatatcaa caacagggac cagataattt ttatggtggg acgaggatat ctgtctccag    2220
atctcagtaa ggtacggagt aactgtccaa aagccatgaa gagattaatg gcagagtgcc    2280
taaaaaagaa aagagatgaa agaccactct tccccaaaat tctcgcctct attgagctgc    2340
tggcccgctc attgccaaaa attcaccgca gtgcatcaga ccctccttg aatcgggctg    2400 gcttccaaac agaggatttt agtctatatg cttgtgcttc tccaaaaaca cccattcagg    2460 caggggata tggtacgttt cctgttcact gaaacaaacc gagtgagtga cagcatgtag    2520
gagggtaggg acaaaagaaa gtgaacaaat gtttgcttat atatttgtta aattgaatag    2580
gattttcttt ttcttttaaag gtgaacaaga gaacatgtgt gttttttaaag tttggatata    2640 gttttcttcc cagtctaaaaa cccatagtta gcattacatt ttcaacatcg aatttttttt    2700
taattcatag acattgctga aaatttataa tacctttttcc agaggcttta cttcccattc    2760
caagtttgtt ttgtttactt ggttagtcta atcattaaac tttaaactttt ccccacctac    2820 cttttgctgt tagctatccc gcatccatta ggggctccaa gaacagcact gtctgcgtgt    2880
gtgtgttggc aggtgggaag ctgatggtaa gttaggctgt gttagtgaag gtaaactgac    2940
caggtctaat taggagtcac tagaattgaa taagcttatt tttattaata ttttttctta    3000
taactatttc ttttttgtaat aatttagaaa atataattgt tctttattcc cttacagcag    3060
tataaattat tggtgcaggt aaccaaagat attactgagg agtggcatgt ttgacatgag    3120
tgacatggtt taactttgga ttttttagtta atatttcttt atatattaag gatgtcttac    3180
acattataga agtcaaattt actgacaaag gtattgcctc ctcttcctcc ccaaaaacac    3240
agcaaaattc tctgggaact cgtagcattg ttggttttct tttggatgac tatggttgcc    3300
aaacaaccaa gtaattgatt tttttttaaat tattattgct ttagattata ctcacctctc    3360
atgatgcctg ttagcaatca cctttatcca tgtgtcttgt aaaatatctt tcctccttat    3420
attctttgcc caacaagagt ctacttgtta tgaatgagta ctattttctt tttttgattc    3480
cccagtataa ttagtatgtt tagtgctttc taggacttcc acttctttat gttaaaaaaa    3540
aaaacaaact aatgtggcag tcagtatatt cttactgtga atcagagtct ttactgggaa    3600
tcaaagtgaa agaagcagct gttctgactt cagagtcagc ctagggacca aaaccagcct    3660
cttaaataca ccttcattta ttcagtttgg atttgtgatg attttcatta tagctgcacg    3720
ttcaaggtta ttcagtggca cacagatagc atctgcataa atgcctttct tcttgaaaat    3780
aaaggagaaa attgggaaga ctttacacca atagtttagt cttaagtac cacagataac    3840 acacaccata aat                                                      3853

<210> SEQ ID NO 18
<211> LENGTH: 764
<212> TYPE: PRT
<213> ORGANISM: Bos taurus
```

<400> SEQUENCE: 18

```
Ala Ala Leu Ser Gly Gly Gly Gly Gly Gly Gly Ala Glu Gln
1               5                   10                  15

Gly Gln Ala Leu Phe Asn Gly Asp Met Glu Pro Glu Ala Gly Ala Ala
            20                  25                  30

Ala Ser Ser Ala Ala Asp Pro Ala Ile Pro Glu Glu Val Trp Asn Ile
            35                  40                  45

Lys Gln Met Ile Lys Leu Thr Gln Glu His Ile Glu Ala Leu Leu Asp
50                  55                  60

Lys Phe Gly Gly Glu His Asn Pro Pro Ser Ile Tyr Leu Glu Ala Tyr
65                  70                  75                  80

Glu Glu Tyr Thr Ser Lys Leu Asp Ala Leu Gln Gln Arg Glu Gln Gln
                85                  90                  95

Leu Leu Glu Ser Leu Gly Asn Gly Thr Asp Phe Ser Val Ser Ser Ser
            100                 105                 110

Ala Ser Thr Asp Thr Val Thr Ser Ser Ser Ser Ser Leu Ser Val
            115                 120                 125

Leu Pro Ser Ser Leu Ser Val Phe Gln Asn Pro Thr Asp Val Ser Arg
    130                 135                 140

Ser Asn Pro Lys Ser Pro Gln Lys Pro Ile Val Arg Val Phe Leu Pro
145                 150                 155                 160

Asn Lys Gln Arg Thr Val Val Pro Ala Arg Cys Gly Val Thr Val Arg
                165                 170                 175

Asp Ser Leu Lys Lys Ala Leu Met Met Arg Gly Leu Ile Pro Glu Cys
            180                 185                 190

Cys Ala Val Tyr Arg Ile Gln Asp Gly Glu Lys Lys Pro Ile Gly Trp
        195                 200                 205

Asp Thr Asp Ile Ser Trp Leu Thr Gly Glu Glu Leu His Val Glu Val
    210                 215                 220

Leu Glu Asn Val Pro Leu Thr Thr His Asn Phe Val Arg Lys Thr Phe
225                 230                 235                 240

Phe Thr Leu Ala Phe Cys Asp Phe Cys Arg Lys Leu Leu Phe Gln Gly
                245                 250                 255

Phe Arg Cys Gln Thr Cys Gly Tyr Lys Phe His Gln Arg Cys Ser Thr
            260                 265                 270

Glu Val Pro Leu Met Cys Val Asn Tyr Asp Gln Leu Asp Leu Leu Phe
        275                 280                 285

Val Ser Lys Phe Phe Glu His His Pro Ile Pro Gln Glu Glu Ala Ser
    290                 295                 300

Leu Ala Glu Thr Thr Leu Pro Cys Gly Ser Ser Pro Ser Ala Pro Pro
305                 310                 315                 320

Ser Asp Ser Ile Gly Pro Pro Ile Leu Thr Ser Pro Ser Pro Ser Lys
                325                 330                 335

Ser Ile Pro Ile Pro Gln Pro Phe Arg Pro Ala Asp Glu Asp His Arg
            340                 345                 350

Asn Gln Phe Gly Gln Arg Asp Arg Ser Ser Ala Pro Asn Val His
        355                 360                 365

Ile Asn Thr Ile Glu Pro Val Asn Ile Asp Asp Leu Ile Arg Asp Gln
    370                 375                 380

Gly Phe Arg Ser Asp Gly Gly Ser Thr Thr Gly Leu Ser Ala Thr Pro
385                 390                 395                 400

Pro Ala Ser Leu Pro Gly Ser Leu Ser Asn Val Lys Ala Leu Gln Lys
                405                 410                 415
```

Ser Pro Gly Pro Gln Arg Glu Arg Lys Ser Ser Ser Ser Glu Asp
        420                 425                 430

Arg Asn Arg Met Lys Thr Leu Gly Arg Arg Asp Ser Ser Asp Asp Trp
        435                 440                 445

Glu Ile Pro Asp Gly Gln Ile Thr Val Gly Gln Arg Ile Gly Ser Gly
        450                 455                 460

Ser Phe Gly Thr Val Tyr Lys Gly Lys Trp His Gly Asp Val Ala Val
465                 470                 475                 480

Lys Met Leu Asn Val Thr Ala Pro Thr Pro Gln Gln Leu Gln Ala Phe
                485                 490                 495

Lys Asn Glu Val Gly Val Leu Arg Lys Thr Arg His Val Asn Ile Leu
            500                 505                 510

Leu Phe Met Gly Tyr Ser Thr Lys Pro Gln Leu Ala Ile Val Thr Gln
        515                 520                 525

Trp Cys Glu Gly Ser Ser Leu Tyr His His Leu His Ile Ile Glu Thr
530                 535                 540

Lys Phe Glu Met Ile Lys Leu Ile Asp Ile Ala Arg Gln Thr Ala Gln
545                 550                 555                 560

Gly Met Asp Tyr Leu His Ala Lys Ser Ile Ile His Arg Asp Leu Lys
                565                 570                 575

Ser Asn Asn Ile Phe Leu His Glu Asp Leu Thr Val Lys Ile Gly Asp
            580                 585                 590

Phe Gly Leu Ala Thr Val Lys Ser Arg Trp Ser Gly Ser His Gln Phe
        595                 600                 605

Glu Gln Leu Ser Gly Ser Ile Leu Trp Met Ala Pro Glu Val Ile Arg
        610                 615                 620

Met Gln Asp Lys Asn Pro Tyr Ser Phe Gln Ser Asp Val Tyr Ala Phe
625                 630                 635                 640

Gly Ile Val Leu Tyr Glu Leu Met Thr Gly Gln Leu Pro Tyr Ser Asn
                645                 650                 655

Ile Asn Asn Arg Asp Gln Ile Ile Phe Met Val Gly Arg Gly Tyr Leu
            660                 665                 670

Ser Pro Asp Leu Ser Lys Val Arg Ser Asn Cys Pro Lys Ala Met Lys
        675                 680                 685

Arg Leu Met Ala Glu Cys Leu Lys Lys Lys Arg Asp Glu Arg Pro Leu
        690                 695                 700

Phe Pro Gln Ile Leu Ala Ser Ile Glu Leu Leu Ala Arg Ser Leu Pro
705                 710                 715                 720

Lys Ile His Arg Ser Ala Ser Glu Pro Ser Leu Asn Arg Ala Gly Phe
                725                 730                 735

Gln Thr Glu Asp Phe Ser Leu Tyr Ala Cys Ala Ser Pro Lys Thr Pro
            740                 745                 750

Ile Gln Ala Gly Gly Tyr Gly Thr Phe Pro Val His
        755                 760

<210> SEQ ID NO 19
<211> LENGTH: 4936
<212> TYPE: DNA
<213> ORGANISM: Bos taurus

<400> SEQUENCE: 19
ctcagctgcg ccgggtctca caagacggtt cccgaggtgg cccaggcgcc gtccaccgc    60 cgacgccgcc cgggccgccc gggccgtccc tcccgctgc ccccgtcct ccgcctccgc    120

```
ctcccccgc cctcagcctc ccttccccct ccccgcccag cagcggtcgc tcgggcccgg       180
ctctcggtta taagatggcg gcgctgagtg gcggcggcgg cggcggcggc ggtggcgcgg       240
agcagggcca ggctctgttc aacggggaca tggagcccga ggccggcgcc gcggcctctt       300
cggctgcgga ccccgccatt cccgaggagg tgtggaatat caaacaaatg attaagttga       360
cacaggagca tatagaggcc ctattggaca aatttggtgg ggagcataat ccaccatcaa       420
tatatctgga ggcctatgaa gaatacacca gcaagctaga tgccctccaa caaagagaac       480
aacagttatt ggaatccctg gggaatggaa ctgatttttc tgtttctagc tctgcatcaa       540
cggacaccgt tacatcttct tcctcttcta gcctttcagt gctgccttca tctctttcag       600
tttttcaaaa tcccacagat gtgtcacgga gcaaccccaa gtcaccacaa aaacctatcg       660
ttagagtctt cctgcccaat aaacagagga cagtggtacc tgcacggtgt ggagtcacag       720
tccgggacag cctgaagaag gcactgatga tgagaggtct aatcccagag tgctgtgctg       780
tttacagaat tcaggatggg gagaagaaac caattggctg ggacactgat atttcctggc       840
ttactggaga ggagttgcat gtagaagtgt tggagaatgt tccacttaca acacacaact       900
ttgtacggaa aactttttc accttagcat tttgtgactt ctgtagaaag ctgcttttcc       960
agggattccg ctgtcaaaca tgtggttata aatttcacca gcgttgtagt acagaggttc      1020
cactgatgtg tgttaattat gaccaactag atttgctgtt tgtctccaag ttctttgaac      1080 accaccccaat accacaggag gaggcctcct tagcagagac tacccttcca tgtggctcat      1140 cccctctgc accccctcc gattctattg ggccccaat tctcaccagt ccatctcctt       1200
caaaatccat tccaattcca cagcctttcc gaccagcaga tgaagatcat cgaaatcagt      1260
ttggacaacg agaccggtcc tcatcagctc caaatgtgca tataaacaca atagaacccg      1320
tcaatattga tgacttgatt agagaccaag ggtttcgtag tgatggagga tcaaccacag      1380
gtttatccgc cacacccct gcctcattac ctggctcact ctctaatgtg aaagcattgc      1440
agaaatctcc aggacctcag cgagaaagaa agtcctcttc atcctcagaa gacaggaatc      1500
gaatgaaaac gcttggtaga cgggattcaa gtgacgattg ggagattcct gatggacaga      1560
tcacagtggg acaaagaatt ggatcagggt catttgggac agtctacaag ggaaagtggc      1620
atggtgatgt ggcagtgaaa atgttgaatg tgacagcacc cacacctcag cagttacagg      1680
ccttcaaaaa tgaagtagga gtactcagga aaacgcgaca tgtgaatatc ctcctcttca      1740
tgggttattc aacaaagcca caactggcta ttgttaccca gtggtgtgag ggctccagtt      1800
tatatcatca tctccacatc attgagacca aattcgagat gatcaaactt atagatattg      1860
cacggcagac tgcacagggc atggattact acacgccaa gtcaatcatc cacagagacc      1920
tcaagagtaa taatattttt cttcatgaag acctcacagt aaaaataggt gattttggtc      1980
tagccacagt gaaatctcga tggagtgggt cccatcagtt tgaacagttg tctggatcca      2040
ttttgtggat ggcaccagaa gtaatcagaa tgcaagataa aaacccatat agctttcagt      2100
cagatgtata tgcatttggg attgttctgt atgaattgat gaccggacag ttaccttatt      2160
caaatatcaa caacagggac cagataattt ttatggtggg acgaggatat ctgtctccag      2220
atctcagtaa ggtacggagt aactgtccaa aagccatgaa gagattaatg gcagagtgcc      2280 taaaaagaa aagagatgaa agaccactct ttccccaagt aggaaagact ctcctaagca      2340
agagacaaaa ttcagaagtt atcagggaaa aagataagca gattctcgcc tctattgagc      2400
tgctggcccg ctcattgcca aaaattcacc gcagtgcatc agaaccctcc ttgaatcggg      2460
ctggcttcca aacagaggat tttagtctat atgcttgtgc ttctccaaaa acacccattc      2520
```

```
aggcaggggg atatgaagca gatttggctc ttacatcaaa taaaaataga gtagaagttg    2580
ggatttagag atttcctgac atgcaagaag gaataagcaa gaaaaaaagg tttgttttcc    2640
ccaaatcata tctattgtct tttacttcta ttttttctta aatttttgt gatttcagag     2700 acatgtagag ttttattgat acctaaacta tgagttcttt tttttttttt tttttcatta    2760
ttttgatttt tttggccaag aggcatatgg gatcttagct tgagaaagca acaattttct    2820
tgatgtcatt ttgggtgagg gcacatattg ctgtgaacag tgtggtgata gccaccaggg    2880
accaaactca cacccgctgc attgaaaggt gaagtcttaa acactggacc agcagagaaa    2940
ttcctactct atgagttctt tttgtcatcc cctccccgca ccctccaccc caacctaaa     3000 gtctgatgat gaaatcaaca actattccat tagaagcagt agattctggt agcatgatct    3060
ttagtttgtt agtaagattt tgtgcttttgt ggggttgtgt cgttttaagg ctaatattta   3120
agtttgtcaa atagaatgct gttcagattg taaaaatgag taataaacat ctgaagtttt    3180
ttttaagtta tttttaacat ggtatataca gttgagctta gagtttatca ttttctgata    3240
ttctcttact tagtagatga attctagcca ttttttataa agatttctgt taagcaaatc    3300
ctgttttcac atgggcttcc tttaagggat tttagattct gctggatatg gtgactgctc    3360
ataagactgt tgaaaattac ttttaagatg tattagaata cttctgaaaa aaaatagcaa    3420
ccttaaaacc ataagcaaaa gtagtaaggg tgtttataca tttctagagt ccctgtttag    3480
gtaatagcct cctatgattg tactttaaat gttttgctct ccaaggtttt agtaacttgg    3540 cttttttttct aatcagtgcc aaactccccc agttttttta actttaaata tgaggtaata   3600
aatcttttac ccttccttga tcttttgact tataatacct tggtcagttg tttcttaaaa    3660
ggaatcctta aatggaaaga gacaatatca ctgtctgcag ttctgattag tagttttatt    3720
cagaatggaa aaacagatta ttcattttg aaaattgttc aggggtatgt tcattgttag     3780
gaccttggac tttggagtca gtgcctagct atgcattcca ggtctgccat tttctggctg    3840
tgaaattttg gacaagttac ttaaccactt taaaccccag ctttaagaag taaattaacc    3900
ccagtaaatt aagaagtaat agcagccact tcgtagagtt gttatgaggc tcagatgcag    3960
tgcaaatgtg tataaagtat tcagggagtc acctggtata ctataataga cactagaata    4020
gttgccaata ttatcagcat acaatctgag gattctgtca gccaatcatt agcaatctgt    4080
tgtttgttgg gacatgccag tgttctccag ttgaaatcag tagcaatcta aaaatggata    4140
gattattcct catttaaata gtgtgttcat ataagtgatt gcttggatcc ttatcagaag    4200
ttgctgttac tgaaaaatga taaggctgac taaattgtga tagttgtcag ttactaacca    4260
actcccagaa atgaataaga ggaacctatc tctagttcct agtagaaggt atggacaaaa    4320
tagtaggtga aaaataatgt cttgaacccc caaattaagt aagctttaaa gagtacaata    4380
cctcaaaggg tctttgcggt ttaaaatttg tatgctgaga atgatgttca ttgacatgtg    4440
cctatatgta atttttttgat agtttaaaag gtgaaatgaa ctacagatgg gagaggtctg   4500
aattttcttg ccttcagtca atgtgtaat gtggacatat tatttgacct gtgaattta     4560 tcttttaaaa aagattaatt cctgcttctt ccttcctaat agttgcatta taataatgaa    4620
aatgagttga taatttgggg ggaaagtatt ctacaaatca accttattat tttaccattg    4680
gtttctgaga aattttgttc atttgaaccg tttatagctt gattagaatc atagcatgta    4740
aaacccaact gagggattat ctgcagactt aatgtagtat tatgtaagtt gtcttctttc    4800
atttcgacct ttttttgcttt tgttgttgct agatctgtag tatgtagcta gtcacctttc   4860
```

```
agcgaggttt cagcgaggct tttctgtgtc tctaggttat ttgagataac tttttaaaa    4920 ttagctcttg tcctcc                                                    4936
```

<210> SEQ ID NO 20
<211> LENGTH: 797
<212> TYPE: PRT
<213> ORGANISM: Bos taurus

<400> SEQUENCE: 20

```
Met Ala Ala Leu Ser Gly Gly Gly Gly Gly Gly Gly Gly Gly Ala Glu
1               5                   10                  15

Gln Gly Gln Ala Leu Phe Asn Gly Asp Met Glu Pro Glu Ala Gly Ala
            20                  25                  30

Ala Ala Ser Ser Ala Ala Asp Pro Ala Ile Pro Glu Glu Val Trp Asn
        35                  40                  45

Ile Lys Gln Met Ile Lys Leu Thr Gln Glu His Ile Glu Ala Leu Leu
 50                 55                  60

Asp Lys Phe Gly Gly Glu His Asn Pro Pro Ser Ile Tyr Leu Glu Ala
65                  70                  75                  80

Tyr Glu Glu Tyr Thr Ser Lys Leu Asp Ala Leu Gln Gln Arg Glu Gln
                85                  90                  95

Gln Leu Leu Glu Ser Leu Gly Asn Gly Thr Asp Phe Ser Val Ser Ser
            100                 105                 110

Ser Ala Ser Thr Asp Thr Val Thr Ser Ser Ser Ser Ser Ser Leu Ser
        115                 120                 125

Val Leu Pro Ser Ser Leu Ser Val Phe Gln Asn Pro Thr Asp Val Ser
130                 135                 140

Arg Ser Asn Pro Lys Ser Pro Gln Lys Pro Ile Val Arg Val Phe Leu
145                 150                 155                 160

Pro Asn Lys Gln Arg Thr Val Val Pro Ala Arg Cys Gly Val Thr Val
                165                 170                 175

Arg Asp Ser Leu Lys Lys Ala Leu Met Met Arg Gly Leu Ile Pro Glu
            180                 185                 190

Cys Cys Ala Val Tyr Arg Ile Gln Asp Gly Glu Lys Lys Pro Ile Gly
        195                 200                 205

Trp Asp Thr Asp Ile Ser Trp Leu Thr Gly Glu Glu Leu His Val Glu
210                 215                 220

Val Leu Glu Asn Val Pro Leu Thr Thr His Asn Phe Val Arg Lys Thr
225                 230                 235                 240

Phe Phe Thr Leu Ala Phe Cys Asp Phe Cys Arg Lys Leu Leu Phe Gln
                245                 250                 255

Gly Phe Arg Cys Gln Thr Cys Gly Tyr Lys Phe His Gln Arg Cys Ser
            260                 265                 270

Thr Glu Val Pro Leu Met Cys Val Asn Tyr Asp Gln Leu Asp Leu Leu
        275                 280                 285

Phe Val Ser Lys Phe Phe Glu His His Pro Ile Pro Gln Glu Glu Ala
290                 295                 300

Ser Leu Ala Glu Thr Thr Leu Pro Cys Gly Ser Ser Pro Ser Ala Pro
305                 310                 315                 320

Pro Ser Asp Ser Ile Gly Pro Pro Ile Leu Thr Ser Pro Ser Pro Ser
                325                 330                 335

Lys Ser Ile Pro Ile Pro Gln Pro Phe Arg Pro Ala Asp Glu Asp His
            340                 345                 350

Arg Asn Gln Phe Gly Gln Arg Asp Arg Ser Ser Ser Ala Pro Asn Val
```

```
                355                 360                 365
His Ile Asn Thr Ile Glu Pro Val Asn Ile Asp Asp Leu Ile Arg Asp
            370                 375                 380

Gln Gly Phe Arg Ser Asp Gly Ser Thr Thr Gly Leu Ser Ala Thr
385                 390                 395                 400

Pro Pro Ala Ser Leu Pro Gly Ser Leu Ser Asn Val Lys Ala Leu Gln
                405                 410                 415

Lys Ser Pro Gly Pro Gln Arg Glu Arg Lys Ser Ser Ser Ser Glu
            420                 425                 430

Asp Arg Asn Arg Met Lys Thr Leu Gly Arg Arg Asp Ser Ser Asp Asp
                435                 440                 445

Trp Glu Ile Pro Asp Gly Gln Ile Thr Val Gly Gln Arg Ile Gly Ser
            450                 455                 460

Gly Ser Phe Gly Thr Val Tyr Lys Gly Lys Trp His Gly Asp Val Ala
465                 470                 475                 480

Val Lys Met Leu Asn Val Thr Ala Pro Thr Pro Gln Gln Leu Gln Ala
                485                 490                 495

Phe Lys Asn Glu Val Gly Val Leu Arg Lys Thr Arg His Val Asn Ile
            500                 505                 510

Leu Leu Phe Met Gly Tyr Ser Thr Lys Pro Gln Leu Ala Ile Val Thr
            515                 520                 525

Gln Trp Cys Glu Gly Ser Ser Leu Tyr His His Leu His Ile Ile Glu
530                 535                 540

Thr Lys Phe Glu Met Ile Lys Leu Ile Asp Ile Ala Arg Gln Thr Ala
545                 550                 555                 560

Gln Gly Met Asp Tyr Leu His Ala Lys Ser Ile Ile His Arg Asp Leu
                565                 570                 575

Lys Ser Asn Asn Ile Phe Leu His Glu Asp Leu Thr Val Lys Ile Gly
            580                 585                 590

Asp Phe Gly Leu Ala Thr Val Lys Ser Arg Trp Ser Gly Ser His Gln
            595                 600                 605

Phe Glu Gln Leu Ser Gly Ser Ile Leu Trp Met Ala Pro Glu Val Ile
            610                 615                 620

Arg Met Gln Asp Lys Asn Pro Tyr Ser Phe Gln Ser Asp Val Tyr Ala
625                 630                 635                 640

Phe Gly Ile Val Leu Tyr Glu Leu Met Thr Gly Gln Leu Pro Tyr Ser
                645                 650                 655

Asn Ile Asn Asn Arg Asp Gln Ile Ile Phe Met Val Gly Arg Gly Tyr
            660                 665                 670

Leu Ser Pro Asp Leu Ser Lys Val Arg Ser Asn Cys Pro Lys Ala Met
            675                 680                 685

Lys Arg Leu Met Ala Glu Cys Leu Lys Lys Lys Arg Asp Glu Arg Pro
            690                 695                 700

Leu Phe Pro Gln Val Gly Lys Thr Leu Leu Ser Lys Arg Gln Asn Ser
705                 710                 715                 720

Glu Val Ile Arg Glu Lys Asp Lys Gln Ile Leu Ala Ser Ile Glu Leu
                725                 730                 735

Leu Ala Arg Ser Leu Pro Lys Ile His Arg Ser Ala Ser Glu Pro Ser
            740                 745                 750

Leu Asn Arg Ala Gly Phe Gln Thr Glu Asp Phe Ser Leu Tyr Ala Cys
            755                 760                 765

Ala Ser Pro Lys Thr Pro Ile Gln Ala Gly Gly Tyr Glu Ala Asp Leu
770                 775                 780
```

Ala Leu Thr Ser Asn Lys Asn Arg Val Glu Val Gly Ile
785                 790                 795

<210> SEQ ID NO 21
<211> LENGTH: 4154
<212> TYPE: DNA
<213> ORGANISM: Bos taurus

<400> SEQUENCE: 21

| | | | | |
|---|---|---|---|---|
| ctcagctgcg | ccgggtctca | caagacggtt | cccgaggtgg | cccaggcgcc gtcccaccgc | 60 |
| cgacgccgcc | cgggccgccc | gggccgtccc | tccccgctgc | ccccgtcct ccgcctccgc | 120 |
| ctccccccgc | cctcagcctc | ccttcccct | ccccgcccag | cagcggtcgc tcgggcccgg | 180 |
| ctctcggtta | taagatggcg | cgcgctgagtg | gcggcggcgg | cggcggcggc ggtggcgcgg | 240 |
| agcagggcca | ggctctgttc | aacggggaca | tggagcccga | ggccggcgcc gcggcctctt | 300 |
| cggctgcgga | ccccgccatt | cccgaggagg | tgtggaatat | caaacaaatg attaagttga | 360 |
| cacaggagca | tatagaggcc | ctattggaca | aatttggtgg | ggagcataat ccaccatcaa | 420 |
| tatatctgga | ggcctatgaa | gaatacacca | gcaagctaga | tgccctccaa caaagagaac | 480 |
| aacagttatt | ggaatccctg | ggaatggaa | ctgattttc | tgtttctagc tctgcatcaa | 540 |
| cggacaccgt | tacatcttct | tcctcttcta | gcctttcagt | gctgccttca tctctttcag | 600 |
| tttttcaaaa | tccacagat | gtgtcacgga | gcaaccccaa | gtcaccacaa aaacctatcg | 660 |
| ttagagtctt | cctgcccaat | aaacagagga | cagtggtacc | tgcacggtgt ggagtcacag | 720 |
| tccgggacag | cctgaagaag | gcactgatga | tgagaggtct | aatcccagag tgctgtgctg | 780 |
| tttacagaat | tcaggatggg | gagaagaaac | caattggctg | ggacactgat atttcctggc | 840 |
| ttactggaga | ggagttgcat | gtagaagtgt | tggagaatgt | tccacttaca acacacaact | 900 |
| ttgtacggaa | aactttttc | accttagcat | tttgtgactt | ctgtagaaag ctgcttttcc | 960 |
| agggattccg | ctgtcaaaca | tgtggttata | aatttcacca | gcgttgtagt acagaggttc | 1020 |
| cactgatgtg | tgttaattat | gaccaactag | atttgctgtt | tgtctccaag ttctttgaac | 1080 |
| accacccaat | accacaggag | gaggcctcct | tagcagagac | tacccttcca tgtggctcat | 1140 |
| ccccttctgc | accccctcc | gattctattg | gccccccaat | tctcaccagt ccatctcctt | 1200 |
| caaaatccat | tccaattcca | cagccttttcc | gaccagcaga | tgaagatcat cgaaatcagt | 1260 |
| ttggacaacg | agaccggtcc | tcatcagctc | caaatgtgca | tataaacaca atagaacccg | 1320 |
| tcaatattga | tgacttgatt | agagaccaag | ggtttcgtag | tgatggagga tcaaccacag | 1380 |
| gtttatccgc | cacaccccct | gcctcattac | ctggctcact | ctctaatgtg aaagcattgc | 1440 |
| agaaatctcc | aggacctcag | cgagaaagaa | agtcctcttc | atcctcagaa gacaggaatc | 1500 |
| gaatgaaaac | gcttggtaga | cgggattcaa | gtgacgattg | ggagattcct gatggacaga | 1560 |
| tcacagtggg | acaaagaatt | ggatcagggt | catttgggac | agtctacaag ggaaagtggc | 1620 |
| atggtgatgt | ggcagtgaaa | atgttgaatg | tgacagcacc | cacacctcag cagttacagg | 1680 |
| ccttcaaaaa | tgaagtagga | gtactcagga | aaacgcgaca | tgtgaatatc ctcctcttca | 1740 |
| tgggttattc | aacaaagcca | caactggcta | ttgttaccca | gtggtgtgag ggctccagtt | 1800 |
| tatatcatca | tctccacatc | attgagacca | aattcgagat | gatcaaactt atagatattg | 1860 |
| cacggcagac | tgcacagggc | atggattact | acacgccaa | gtcaatcatc cacagagacc | 1920 |
| tcaagagtaa | taatatttt | cttcatgaag | acctcacagt | aaaaataggt gattttggtc | 1980 |
| tagccacagt | gaaatctcga | tggagtgggt | cccatcagtt | tgaacagttg tctggatcca | 2040 |

```
ttttgtggat ggcaccagaa gtaatcagaa tgcaagataa aaacccatat agctttcagt      2100
cagatgtata tgcatttggg attgttctgt atgaattgat gaccggacag ttaccttatt      2160
caaatatcaa caacagggac cagataattt ttatggtggg acgaggatat ctgtctccag      2220
atctcagtaa ggtacggagt aactgtccaa aagccatgaa gagattaatg gcagagtgcc      2280
taaaaaagaa aagagatgaa agaccactct ttccccaagt aggaaagact ctcctaagca      2340
agagacaaaa ttcagaagtt atcagggaaa agataagca gattctcgcc tctattgagc       2400
tgctggcccg ctcattgcca aaaattcacc gcagtgcatc agaaccctcc ttgaatcggg      2460
ctggcttcca aacagaggat tttagtctat atgcttgtgc ttctccaaaa acacccattc      2520
aggcaggggg atatggctga gcacattgtc catcacccac aagtggctgg ttctcatcgc      2580
agaatctacg tagggaatcg ggcgtgaaat tcacttaaga gatagagcag aggaagtgtt      2640
ctgtttacag gaatggagat gagagttatg agtaagttgc ttagtcagtt ggctttgttt      2700
tgaaaattat tgtgttatat ttgtgttaac ctacttgtgt tttgacagta tatgtcacat      2760
aggaagaaac ctcagactag cataataaca aagctcagac taggcacaga tgtacacaga      2820
atggaccaaa atgggatggg ggaaggtatg ggaataagtc taggggtagg gaaaaattga      2880
tgtgagggtg ggaaataaac tgtaattacc tgaaataaaa tgtaagagtg caataagtgt      2940 gcttttatt ctaagctgtg aatgggtttt ttaaaaaaag cattccttcc caatgcattt       3000
gcctatgttc catagctgat taaaaccagc tatataaaca tatgcctttt tattcatgtt      3060
aattaccaat ataaatggct aacctttacg tcttatttat cttcatgtta tgttagttta      3120
catacaggga tgtgtgtgtg tgtgtatgct ataaattttc cctccttcgt ttaaaaacgc      3180
gtttgttgga tcctctctgt ttccttaggc catgccacag ctcatagtct cagcttggcc      3240
ttcctgtcac ctgatctgaa ggactatcac agtgacgtag ctcgttcatt ggttgtacac      3300
actctaaccc ttttccttgc tcagcaatta ctgtgtcttc taaaacagga gtgtacaacc      3360
atgagattgc aattaattgt ttgacatatg tccctttgaa ttctatttat tagttatgat      3420
tgattgctct ttggtttgga ccaagaaaaa cgaaatccca cctcccacc ttttcactta       3480 tttcttactt tgaggacaat tctgtaagag agaggaaagg gaactccttc atgtttttaac     3540 tgcagcaagt taatggccct ggtttacacc aaacattatg gtgattcaca ttcacattcc      3600
tctcctctct tgctgccaga ggtttgggtt ttgttcagtt ctgctcaagc actgaaaaag      3660
ttttcatgga gtctggagag tgcccagtga aaagatggtt tttaattgtc cacagacctt      3720
tctgttcctg ctttgcaaaa attacaaagg agtaactatt tttaaagctt atttttcaat      3780
tcataaaaaa gacatttatt ttcagtcaga tgatgtctcc ttgtccctta atcctcaatg      3840
tttgcttgaa tctttttttt tttctgatt ttctcccatc cccacttctt gatacttct        3900 gagttctctt tcctgctcag gtccttcat ttgtactttg gagttttttc tcatgtaaat       3960
ttgtacaatg gaaatattg ttcagtttgg atagaacgca tggagaatta ataaaaaag        4020 atagctgaaa ttcagattga aatttatttg tgtaaagtta tttaaaaact ctgtactata      4080
taaaaggcaa aaaagttct atgtacttga tgtgaatatg cgaatactgc tataataaag       4140
attgactgca tgga                                                        4154
```

<210> SEQ ID NO 22
<211> LENGTH: 781
<212> TYPE: PRT
<213> ORGANISM: Bos taurus

<400> SEQUENCE: 22

```
Met Ala Ala Leu Ser Gly Gly Gly Gly Gly Gly Gly Ala Glu
1               5                   10                  15

Gln Gly Gln Ala Leu Phe Asn Gly Asp Met Glu Pro Glu Ala Gly Ala
            20                  25                  30

Ala Ala Ser Ser Ala Ala Asp Pro Ala Ile Pro Glu Glu Val Trp Asn
        35                  40                  45

Ile Lys Gln Met Ile Lys Leu Thr Gln Glu His Ile Glu Ala Leu Leu
50                  55                  60

Asp Lys Phe Gly Gly Glu His Asn Pro Pro Ser Ile Tyr Leu Glu Ala
65                  70                  75                  80

Tyr Glu Glu Tyr Thr Ser Lys Leu Asp Ala Leu Gln Gln Arg Glu Gln
                85                  90                  95

Gln Leu Leu Glu Ser Leu Gly Asn Gly Thr Asp Phe Ser Val Ser Ser
            100                 105                 110

Ser Ala Ser Thr Asp Thr Val Thr Ser Ser Ser Ser Ser Leu Ser
        115                 120                 125

Val Leu Pro Ser Ser Leu Ser Val Phe Gln Asn Pro Thr Asp Val Ser
130                 135                 140

Arg Ser Asn Pro Lys Ser Pro Gln Lys Pro Ile Val Arg Val Phe Leu
145                 150                 155                 160

Pro Asn Lys Gln Arg Thr Val Val Pro Ala Arg Cys Gly Val Thr Val
                165                 170                 175

Arg Asp Ser Leu Lys Lys Ala Leu Met Met Arg Gly Leu Ile Pro Glu
            180                 185                 190

Cys Cys Ala Val Tyr Arg Ile Gln Asp Gly Glu Lys Lys Pro Ile Gly
        195                 200                 205

Trp Asp Thr Asp Ile Ser Trp Leu Thr Gly Glu Glu Leu His Val Glu
210                 215                 220

Val Leu Glu Asn Val Pro Leu Thr Thr His Asn Phe Val Arg Lys Thr
225                 230                 235                 240

Phe Phe Thr Leu Ala Phe Cys Asp Phe Cys Arg Lys Leu Leu Phe Gln
                245                 250                 255

Gly Phe Arg Cys Gln Thr Cys Gly Tyr Lys Phe His Gln Arg Cys Ser
            260                 265                 270

Thr Glu Val Pro Leu Met Cys Val Asn Tyr Asp Gln Leu Asp Leu Leu
        275                 280                 285

Phe Val Ser Lys Phe Phe Glu His His Pro Ile Pro Gln Glu Glu Ala
290                 295                 300

Ser Leu Ala Glu Thr Thr Leu Pro Cys Gly Ser Ser Pro Ser Ala Pro
305                 310                 315                 320

Pro Ser Asp Ser Ile Gly Pro Ile Leu Thr Ser Pro Ser Pro Ser
                325                 330                 335

Lys Ser Ile Pro Ile Pro Gln Pro Phe Arg Pro Ala Asp Glu Asp His
            340                 345                 350

Arg Asn Gln Phe Gly Gln Arg Asp Arg Ser Ser Ser Ala Pro Asn Val
        355                 360                 365

His Ile Asn Thr Ile Glu Pro Val Asn Ile Asp Asp Leu Ile Arg Asp
370                 375                 380

Gln Gly Phe Arg Ser Asp Gly Gly Ser Thr Thr Gly Leu Ser Ala Thr
385                 390                 395                 400

Pro Pro Ala Ser Leu Pro Gly Ser Leu Ser Asn Val Lys Ala Leu Gln
                405                 410                 415
```

Lys Ser Pro Gly Pro Gln Arg Glu Arg Lys Ser Ser Ser Ser Glu
        420                 425                 430

Asp Arg Asn Arg Met Lys Thr Leu Gly Arg Arg Asp Ser Ser Asp Asp
            435                 440                 445

Trp Glu Ile Pro Asp Gly Gln Ile Thr Val Gly Gln Arg Ile Gly Ser
        450                 455                 460

Gly Ser Phe Gly Thr Val Tyr Lys Gly Lys Trp His Gly Asp Val Ala
465                 470                 475                 480

Val Lys Met Leu Asn Val Thr Ala Pro Thr Pro Gln Gln Leu Gln Ala
                485                 490                 495

Phe Lys Asn Glu Val Gly Val Leu Arg Lys Thr Arg His Val Asn Ile
            500                 505                 510

Leu Leu Phe Met Gly Tyr Ser Thr Lys Pro Gln Leu Ala Ile Val Thr
        515                 520                 525

Gln Trp Cys Glu Gly Ser Ser Leu Tyr His His Leu His Ile Ile Glu
530                 535                 540

Thr Lys Phe Glu Met Ile Lys Leu Ile Asp Ile Ala Arg Gln Thr Ala
545                 550                 555                 560

Gln Gly Met Asp Tyr Leu His Ala Lys Ser Ile Ile His Arg Asp Leu
            565                 570                 575

Lys Ser Asn Asn Ile Phe Leu His Glu Asp Leu Thr Val Lys Ile Gly
        580                 585                 590

Asp Phe Gly Leu Ala Thr Val Lys Ser Arg Trp Ser Gly Ser His Gln
            595                 600                 605

Phe Glu Gln Leu Ser Gly Ser Ile Leu Trp Met Ala Pro Glu Val Ile
        610                 615                 620

Arg Met Gln Asp Lys Asn Pro Tyr Ser Phe Gln Ser Asp Val Tyr Ala
625                 630                 635                 640

Phe Gly Ile Val Leu Tyr Glu Leu Met Thr Gly Gln Leu Pro Tyr Ser
            645                 650                 655

Asn Ile Asn Asn Arg Asp Gln Ile Ile Phe Met Val Gly Arg Gly Tyr
        660                 665                 670

Leu Ser Pro Asp Leu Ser Lys Val Arg Ser Asn Cys Pro Lys Ala Met
        675                 680                 685

Lys Arg Leu Met Ala Glu Cys Leu Lys Lys Lys Arg Asp Glu Arg Pro
690                 695                 700

Leu Phe Pro Gln Val Gly Lys Thr Leu Leu Ser Lys Arg Gln Asn Ser
705                 710                 715                 720

Glu Val Ile Arg Glu Lys Asp Lys Gln Ile Leu Ala Ser Ile Glu Leu
            725                 730                 735

Leu Ala Arg Ser Leu Pro Lys Ile His Arg Ser Ala Ser Glu Pro Ser
        740                 745                 750

Leu Asn Arg Ala Gly Phe Gln Thr Glu Asp Phe Ser Leu Tyr Ala Cys
        755                 760                 765

Ala Ser Pro Lys Thr Pro Ile Gln Ala Gly Gly Tyr Gly
770                 775                 780

<210> SEQ ID NO 23
<211> LENGTH: 7914
<212> TYPE: DNA
<213> ORGANISM: Bos taurus

<400> SEQUENCE: 23
ctcagctgcg ccgggtctca caagacggtt cccgaggtgg cccaggcgcc gtcccaccgc    60

-continued

```
cgacgccgcc cgggccgccc gggccgtccc tcccgctgc ccccgtcct ccgcctccgc   120 ctcccccgc cctcagcctc ccttcccct ccccgcccag cagcggtcgc tcgggcccgg    180
ctctcggtta taagatggcg gcgctgagtg gcggcggcgg cggcggcggc ggtggcgcgg   240
agcagggcca ggctctgttc aacggggaca tggagcccga ggccggcgcc gcggcctctt   300
cggctgcgga ccccgccatt cccgaggagg tgtggaatat caaacaaatg attaagttga   360
cacaggagca tatagaggcc ctattggaca aatttggtgg ggagcataat ccaccatcaa   420
tatatctgga ggcctatgaa gaatacacca gcaagctaga tgccctccaa caaagagaac   480
aacagttatt ggaatccctg gggaatggaa ctgattttc tgtttctagc ctgcatcaa    540 cggacaccgt tacatcttct tcctcttcta gcctttcagt gctgccttca tctctttcag   600
tttttcaaaa tcccacagat gtgtcacgga gcaaccccaa gtcaccacaa aaacctatcg   660
ttagagtctt cctgcccaat aaacagagga cagtggtacc tgcacggtgt ggagtcacag   720
tccgggacag cctgaagaag gcactgatga tgagaggtct aatcccagag tgctgtgctg   780
tttacagaat tcaggatggg gagaagaaac caattggctg ggacactgat atttcctggc   840
ttactggaga ggagttgcat gtagaagtgt tggagaatgt tccacttaca acacacaact   900
ttgtacggaa aacttttttc accttagcat tttgtgactt ctgtagaaag ctgcttttcc   960
agggattccg ctgtcaaaca tgtggttata aatttcacca gcgttgtagt acagaggttc   1020
cactgatgtg tgttaattat gaccaactag atttgctgtt tgtctccaag ttctttgaac   1080
accacccaat accacaggag gaggcctcct tagcagagac tacccttcca tgtggctcat   1140 cccttctgc acccccctcc gattctattg gcccccaat tctcaccagt ccatctcctt     1200
caaaatccat tccaattcca cagcctttcc gaccagcaga tgaagatcat cgaaatcagt   1260
ttggacaacg agaccggtcc tcatcagctc caaatgtgca tataaacaca atagaacccg   1320
tcaatattga tgacttgatt agagaccaag ggtttcgtag tgatggagga tcaaccacag   1380
gtttatccgc cacacccct gcctcattac ctggctcact ctctaatgtg aaagcattgc     1440
agaaatctcc aggacctcag cgagaaagaa agtcctcttc atcctcagaa gacaggaatc   1500
gaatgaaaac gcttggtaga cgggattcaa gtgacgattg ggagattcct gatggacaga   1560
tcacagtggg acaaagaatt ggatcagggt catttgggac agtctacaag ggaaagtggc   1620
atggtgatgt ggcagtgaaa atgttgaatg tgacagcacc cacacctcag cagttacagg   1680
ccttcaaaaa tgaagtagga gtactcagga aaacgcgaca tgtgaatatc ctcctcttca   1740
tgggttattc aacaaagcca caactggcta ttgttaccca gtggtgtgag ggctccagtt   1800
tatatcatca tctccacatc attgagacca aattcgagat gatcaaactt atagatattg   1860
cacggcagac tgcacaggc atggattact tacacgccaa gtcaatcatc cacagagacc    1920
tcaagagtaa taatattttt cttcatgaag acctcacagt aaaaataggt gattttggtc    1980
tagccacagt gaaatctcga tggagtgggt cccatcagtt tgaacagttg tctggatcca   2040
ttttgtggat ggcaccagaa gtaatcagaa tgcaagataa aaacccatat agctttcagt   2100
cagatgtata tgcatttggg attgttctgt atgaattgat gaccggacag ttaccttatt   2160
caaatatcaa caacagggac cagataattt ttatggtggg acgaggatat ctgtctccag    2220
atctcagtaa ggtacggagt aactgtccaa aagccatgaa gagattaatg gcagagtgcc    2280
taaaaaagaa aagagatgaa agaccactct tcccccaaat tctcgcctct attgagctgc   2340
tggcccgctc attgccaaaa attcaccgca gtgcatcaga accctccttg aatcgggctg   2400
```

```
gcttccaaac agaggatttt agtctatatg cttgtgcttc tccaaaaaca cccattcagg    2460
cagggggata tggagaattt gcagccttca agtagccaca ccatcatgac agcatctact    2520
cttatttctt aagtcttgtg ttcgtacaat ttgttaacat caaaacacag ttctgttcct    2580
caactctttt taaagttaaa attttcagt gcataagctg gtgtggaaca gaaggaaatt     2640
tcccatccaa caaaagaggg aagaatgttt taggaaccag aattctctgc tgccagtgtt    2700
tcttcttcaa cacaaatatc acaagtctgc ccactcccag gaagaaagag gagagaccct    2760
gagttctgac cttttgatgg tcaggcatga tggaaagaaa ctgctgctac agcttgggag    2820
atttgctctg ggaagtctgc cagtcaactt tgcccttcta accaccagat caatatgtgg    2880
ctgatcatct gatggggcag ttgcaatcac caagccttgt tctctttcct gttctgggat    2940
tgtgttgtgg aaccctttc cctagccacc accagttcat ttctgaggga tggaacaaaa     3000
atgcagcatg cccttcctgt gtggtgcatg ttcagtcctt gacaaatttt taccaaaatg    3060
aagctacttt atttaaaagg agggtgagag gtgaggaggt cactttgggt gtggcggaaa    3120
gggaatgctg catctttttc ctgggctgct ggggctctgg ccttggcttg ccagccggaa    3180
gcgctggcac gcatcgcctt cttttcccat tgggtccagc aatgaagacg agtgtttggg    3240
gttttttttt tctccaccat gtagcaagtt ctcaggaaaa tacaattgat atcttcctcc    3300
taagctcttc caatcagtca ccaagtactt atgtggttac tttgtccagg gcacaaaatg    3360
cctgtatcta attaaaagcc tacaaaactg cttgataaca gttttgaatg tgagacattt    3420
atgtaattta aatgtaaggt acaagtttta atttctgagt ttcttctatt atattttat     3480 taaaaaaga aaataatttt cagattgaat tggagtaaaa taatattact tcccactaga     3540
attatatatc ctggaaaatt gtatttttgt tacataagca gcttttaaag aaagatcatt    3600
acccttttct ctacataaat atatggggag tcttagccta atgacaaata tttataattt    3660
ttaaattaat ggtacttgct ggatccatac taacatcttt actaatacct cattgtttct    3720
tccaacttac tcctcacta catcctacat cttcttccta gtcttttatc tagaatatgc     3780
aacctcaaat aaaaatggtg gtgtcctcat tcattctcct ccttccttt tcccaagcc      3840 tgatcttcaa aaggttggtt aatttggcag ctgagttcct ccccaggcag agaatagacc    3900
aattttaggt gtattgggac tgagggagga tgtgtaaaga ttaacatcag taaagaaccg    3960
ctgtggagta attaagaact tgttctttta taactggaga atataaccta accctaacat    4020
ccctcagcct ttactaaagt gtggcgtaaa tcacagtagt agcaaagaaa gtgactctgg    4080
atgtgttcct ggccagtacc tcccttatca tgaatgtaga ctctctcatc aagatttagg    4140
aatataaatc aaatcaaatg tgcccagcca agctatgtag taagggactt gaacaatatt    4200
aggcagaacc tataaaataa atcagggaat tagaaattat ttaaagtttt caaattgtaa    4260
attgccccgg tgtctttcag cctactgcca ttatttttgc tacaataccct acatttcaga   4320 ggagggccta ctgaaaattc catgcaagtg gaaataatc ctcaagttat taatgagttt     4380
gaaaagcaat gagttcttaa gtctttgtga gtagagcaag atcctacaaa attcagaaat    4440
agtaaaaatg gattcatgct gatttgaaga gcatctgtgt gcataatata atgctgcatc    4500
tcttttaaaa gcagtctatt tttcttttta aatttgtccc catagatgct tttgaacatg    4560
aacatgctta tgttaccttt tccgaggttg ggaagagcca ggagctctca ggcagggccc    4620
cctccctcag ctgggcagga gctgctcagg aggagctagt tatagaggaa gcttagcgtt    4680
ggcattttca aaattcaagg tgataacgct ttcttcttcc tttctgtttt agaatagatt    4740
gctgtctgat ttgaaaaagg gaaatagatt tgatctcaaa tgaatctgtg cccagaagcc    4800
```

```
aggctcaggg tattcagaga tttgtatagt gccctcaaaa aataacaaaa ttttagcttt    4860
ccttttttct tcttttctcc atcaaattct tttttctcta gtttacaaat gacatggaaa    4920
aggaatttcc cctgagtttt gtatgccttt ttttttttgg cttagactat agataggcgt    4980
gttgagctcc taagaaaata caaggaggaa ctctttgttg tgcagagcac tttatgagta    5040
gtttgtgtgg ataatatgtg actgcttccc tgacgagctt gtgaggctgt acttatgtct    5100
ttcctgtaag gcagcttcag tgccttctgt agtgtatata aggaaagatt acgccttctg    5160
aaaaatctca gagcaaccat aagattattt taaaatatgt agtatgactg atggactttt    5220
tcatcattaa attagtctag catctaaact tttaccactg aaataatatt gaccaaaaag    5280
caatttataa aaggtatttg tgaatagaaa atacaatgtg atcatttgta cttatgtgca    5340
ccttaaaaga ggaattctgt ctagctgtca aattctggtt ccttaacatc cagtccttga    5400
ttgtgattga gatctggtag gacgtgctgg ggcacgctag cagataaaat cccgtatact    5460
ttaggataga tgttacattt atgtcagtgt tggcaaagag cattgtgtag taataaagaa    5520
ttcaagactt cagcaatgtc aacctgaaac tttgtaaata tttcctagat tgttatttga    5580
tgcagtcaca gctctttatc acacaatgtt gtctttccct catcaggcaa ttttagaact    5640
gctgcacacc cctcctcaga tctcacctgc ccctcctgta cattcacctc tccagccttg    5700
tgcacacctc atttagcttt agtttgaaac acattgcagg gttcaggtga cctcttcaaa    5760
aactacctcc tcagaatgag gtaatgaata gttatttatt ttaaaatatg aaaagtcagg    5820
agctctagaa tatgaagatg atctaagatt ttaactttta tgtatacttg ttgagcactc    5880
tccttttgtc ctaaagggca ttatacattt aagcagtaat actgaaaaat gtagctcaga    5940
gtaactgaat gttgttgaaa gtggtgccag aatctgtttt aggggtacgt atcagaatct    6000
taatcttaaa tcggttacat gaaattaaat agttaatggt aacacttgac taacagatat    6060
aattttaatt ttcggtaggc ttttagcaag acagtaagta catcttcata atgagttagc    6120
cacagcttca tcacatgcac agattttcct gttgagagac tgcccagtta agagggtaga    6180
atgatgaacc atttttcagg attctcttct ttgtccaaac tggcattgtg agtgctagaa    6240
tatcagcact ttcaaactag tgattccaac tattaggcta ttaaaaagca aacaaacca    6300 aacaaaccat agccagacat gggaagttta ctatgagtat aaacagcaaa tagcttacag    6360
gtcatacatt gaaatggtgt aggtaaggcg ttagaaaaat accttgacaa tttgccaaat    6420
gatcttactg tgccttcatg atgcaataaa aaaaaaaaa atttagcata aatcagtgat    6480
ttgtgaagag agcagccacc ctggtctaac tcagctgtgt taatatttt tagcgtgcaa    6540 tttagactgc aaagataaat gcactaaaga gtttatagcc aaaatcacat ttaaaaaatg    6600
agagaaaaca caggtaaatt ttcagtgaac aaaattattt ttttaaagta cataatccct    6660
agtatagtca gatatattta tcacatagag caaataggtt gaaatcacaa ttcagtgaca    6720
tttctagaga aacttttct actcccatag gttcttcaaa gcatggaact tttatataac    6780
agaaatgtgt gacggtcatt ttaaattgct gtagtttggg gctgaagtac tgtgtgctgg    6840
gcagcaatca catgtattaa ctagtgagaa aggagaaatt aagatatagg acagaatttg    6900
attttcttgt tcccagatta ctgctgccaa cctagacact gagtttccag aggctgaaac    6960
gtaaacttgc agctcagcaa ctgttttgca aagttagtgg gactgtcctg cttatgctgt    7020
tcaaaaatgc tctgagggcc aggtggggcc tccaggggct cctctctgag ggacatcag    7080 actagctaac gacctggcgg gcggatgtga accggacaca ctccatggtg tgcttcttgt    7140
```

-continued

```
atcggtccct cgccaccctc aagaaaggct tcagcgggtt ctctagacgt ctccactaag    7200
gtgtgttact aacagccatg ggttgttgag cacccgagga gtgcaatagc atctctgcat    7260
gattgtatat tggcccgaag agaatgaagt ggccagtgta ctcatgttcc atgttgctag    7320
ctctggtaaa ctgaaaatac tggtaagatt tttgttttat cagtacacta gagagtaagc    7380
tttgttttgt tgttttttaga taatgttttc acttccattt ggaaagacat ttaaattgag    7440
tttcagtcct aaattttgcc agtcatggta attagcagtt tctatcaggt attttttaagg   7500 tagaagagga tagaaacata agttctaaaa gcttaaggta accgtggttt attttaaaat    7560 gtttagggggt ggttagtctc tacctcaaaa aaagtgagtg aatcttttat ttcagcattc   7620
acaagttcgg ctgttgtttt tgtaatacat tttttttta accttttgac cccccttttac   7680 ctaagtgtca atgtagtttt attaattact aagtcagttt cattaaaatg tttatttagc    7740
agttttgact aattgcaatg attaatatag ccagttgtgc atgaggacac agccagtgag    7800
tatatctggg tttttttttgt gatgcttttt ttcttaagac ttctgtagat ttatgaagta   7860
ctcattgaaa acaactaaaa tacgtttatt cgtgttaata tggaaaaaaa aaaa          7914
```

<210> SEQ ID NO 24
<211> LENGTH: 766
<212> TYPE: PRT
<213> ORGANISM: Bos taurus

<400> SEQUENCE: 24

| Met | Ala | Ala | Leu | Ser | Gly | Gly | Gly | Gly | Gly | Gly | Gly | Gly | Ala | Glu |
|---|---|---|---|---|---|---|---|---|---|---|---|---|---|---|
| 1 | | | | 5 | | | | | 10 | | | | | 15 |

| Gln | Gly | Gln | Ala | Leu | Phe | Asn | Gly | Asp | Met | Glu | Pro | Glu | Ala | Gly | Ala |
| | | | 20 | | | | | 25 | | | | | 30 | | |

Ala Ala Ser Ser Ala Ala Asp Pro Ala Ile Pro Glu Glu Val Trp Asn
        35                  40                  45

Ile Lys Gln Met Ile Lys Leu Thr Gln Glu His Ile Glu Ala Leu Leu
 50                  55                  60

Asp Lys Phe Gly Gly Glu His Asn Pro Pro Ser Ile Tyr Leu Glu Ala
65                  70                  75                  80

Tyr Glu Glu Tyr Thr Ser Lys Leu Asp Ala Leu Gln Gln Arg Glu Gln
                85                  90                  95

Gln Leu Leu Glu Ser Leu Gly Asn Gly Thr Asp Phe Ser Val Ser Ser
            100                 105                 110

Ser Ala Ser Thr Asp Thr Val Thr Ser Ser Ser Ser Ser Ser Leu Ser
        115                 120                 125

Val Leu Pro Ser Ser Leu Ser Val Phe Gln Asn Pro Thr Asp Val Ser
    130                 135                 140

Arg Ser Asn Pro Lys Ser Pro Gln Lys Pro Ile Val Arg Val Phe Leu
145                 150                 155                 160

Pro Asn Lys Gln Arg Thr Val Val Pro Ala Arg Cys Gly Val Thr Val
                165                 170                 175

Arg Asp Ser Leu Lys Lys Ala Leu Met Met Arg Gly Leu Ile Pro Glu
            180                 185                 190

Cys Cys Ala Val Tyr Arg Ile Gln Asp Gly Glu Lys Lys Pro Ile Gly
        195                 200                 205

Trp Asp Thr Asp Ile Ser Trp Leu Thr Gly Glu Glu Leu His Val Glu
    210                 215                 220

Val Leu Glu Asn Val Pro Leu Thr Thr His Asn Phe Val Arg Lys Thr
225                 230                 235                 240

```
Phe Phe Thr Leu Ala Phe Cys Asp Phe Cys Arg Lys Leu Leu Phe Gln
                    245                 250                 255

Gly Phe Arg Cys Gln Thr Cys Gly Tyr Lys Phe His Gln Arg Cys Ser
            260                 265                 270

Thr Glu Val Pro Leu Met Cys Val Asn Tyr Asp Gln Leu Asp Leu Leu
                275                 280                 285

Phe Val Ser Lys Phe Phe Glu His His Pro Ile Pro Gln Glu Glu Ala
            290                 295                 300

Ser Leu Ala Glu Thr Thr Leu Pro Cys Gly Ser Ser Pro Ser Ala Pro
305                 310                 315                 320

Pro Ser Asp Ser Ile Gly Pro Pro Ile Leu Thr Ser Pro Ser Pro Ser
                    325                 330                 335

Lys Ser Ile Pro Ile Pro Gln Pro Phe Arg Pro Ala Asp Glu Asp His
                340                 345                 350

Arg Asn Gln Phe Gly Gln Arg Asp Arg Ser Ser Ala Pro Asn Val
            355                 360                 365

His Ile Asn Thr Ile Glu Pro Val Asn Ile Asp Asp Leu Ile Arg Asp
        370                 375                 380

Gln Gly Phe Arg Ser Asp Gly Gly Ser Thr Thr Gly Leu Ser Ala Thr
385                 390                 395                 400

Pro Pro Ala Ser Leu Pro Gly Ser Leu Ser Asn Val Lys Ala Leu Gln
                405                 410                 415

Lys Ser Pro Gly Pro Gln Arg Glu Arg Lys Ser Ser Ser Ser Ser Glu
                420                 425                 430

Asp Arg Asn Arg Met Lys Thr Leu Gly Arg Arg Asp Ser Ser Asp Asp
            435                 440                 445

Trp Glu Ile Pro Asp Gly Gln Ile Thr Val Gly Gln Arg Ile Gly Ser
        450                 455                 460

Gly Ser Phe Gly Thr Val Tyr Lys Gly Lys Trp His Gly Asp Val Ala
465                 470                 475                 480

Val Lys Met Leu Asn Val Thr Ala Pro Thr Pro Gln Gln Leu Gln Ala
                485                 490                 495

Phe Lys Asn Glu Val Gly Val Leu Arg Lys Thr Arg His Val Asn Ile
                500                 505                 510

Leu Leu Phe Met Gly Tyr Ser Thr Lys Pro Gln Leu Ala Ile Val Thr
            515                 520                 525

Gln Trp Cys Glu Gly Ser Ser Leu Tyr His His Leu His Ile Ile Glu
        530                 535                 540

Thr Lys Phe Glu Met Ile Lys Leu Ile Asp Ile Ala Arg Gln Thr Ala
545                 550                 555                 560

Gln Gly Met Asp Tyr Leu His Ala Lys Ser Ile Ile His Arg Asp Leu
                565                 570                 575

Lys Ser Asn Asn Ile Phe Leu His Glu Asp Leu Thr Val Lys Ile Gly
                580                 585                 590

Asp Phe Gly Leu Ala Thr Val Lys Ser Arg Trp Ser Gly Ser His Gln
            595                 600                 605

Phe Glu Gln Leu Ser Gly Ser Ile Leu Trp Met Ala Pro Glu Val Ile
        610                 615                 620

Arg Met Gln Asp Lys Asn Pro Tyr Ser Phe Gln Ser Asp Val Tyr Ala
625                 630                 635                 640

Phe Gly Ile Val Leu Tyr Glu Leu Met Thr Gly Gln Leu Pro Tyr Ser
                645                 650                 655

Asn Ile Asn Asn Arg Asp Gln Ile Ile Phe Met Val Gly Arg Gly Tyr
```

|  |  |  | 660 |  |  |  | 665 |  |  |  | 670 |  |
|---|---|---|---|---|---|---|---|---|---|---|---|---|
| Leu | Ser | Pro | Asp | Leu | Ser | Lys | Val | Arg | Ser | Asn | Cys | Pro | Lys | Ala | Met |
|  |  |  | 675 |  |  |  | 680 |  |  |  | 685 |  |

| Lys | Arg | Leu | Met | Ala | Glu | Cys | Leu | Lys | Lys | Lys | Arg | Asp | Glu | Arg | Pro |
|  |  | 690 |  |  |  | 695 |  |  |  | 700 |  |

| Leu | Phe | Pro | Gln | Ile | Leu | Ala | Ser | Ile | Glu | Leu | Leu | Ala | Arg | Ser | Leu |
| 705 |  |  |  | 710 |  |  |  | 715 |  |  |  | 720 |

| Pro | Lys | Ile | His | Arg | Ser | Ala | Ser | Glu | Pro | Ser | Leu | Asn | Arg | Ala | Gly |
|  |  |  | 725 |  |  |  | 730 |  |  |  | 735 |  |

| Phe | Gln | Thr | Glu | Asp | Phe | Ser | Leu | Tyr | Ala | Cys | Ala | Ser | Pro | Lys | Thr |
|  |  |  | 740 |  |  |  | 745 |  |  |  | 750 |  |

| Pro | Ile | Gln | Ala | Gly | Gly | Tyr | Gly | Glu | Phe | Ala | Ala | Phe | Lys |
|  | 755 |  |  |  | 760 |  |  |  | 765 |  |

<210> SEQ ID NO 25
<211> LENGTH: 4670
<212> TYPE: DNA
<213> ORGANISM: Bos taurus

<400> SEQUENCE: 25

| ggtgtgtcat | agtgcagcag | attgaatgca | gaagatatga | aaattcagat | gtcttctgtt | 60 |
| aaggtgtgga | atatcaaaca | aatgattaag | ttgacacagg | agcatataga | ggccctattg | 120 |
| gacaaatttg | gtggggagca | taatccacca | tcaatatatc | tggaggccta | tgaagaatac | 180 |
| accagcaagc | tagatgccct | ccaacaaaga | gaacaacagt | tattggaatc | cctggggaat | 240 |
| ggaactgatt | tttctgtttc | tagctctgca | tcaacggaca | ccgttacatc | ttcttcctct | 300 |
| tctagccttt | cagtgctgcc | ttcatctctt | tcagttttc | aaaatcccac | agatgtgtca | 360 |
| cggagcaacc | ccaagtcacc | acaaaaacct | atcgttagag | tcttcctgcc | caataaacag | 420 |
| aggacagtgg | tacctgcacg | gtgtggagtc | acagtccggg | acagcctgaa | gaaggcactg | 480 |
| atgatgagag | gtctaatccc | agagtgctgt | gctgtttaca | gaattcagga | tggggagaag | 540 |
| aaaccaattg | gctgggacac | tgatatttcc | tggcttactg | gagaggagtt | gcatgtagaa | 600 |
| gtgttggaga | atgttccact | tacaacacac | aactttgtac | ggaaaacttt | tttcacctta | 660 |
| gcattttgtg | acttctgtag | aaagctgctt | ttccagggat | tccgctgtca | acatgtggt | 720 |
| tataaatttc | accagcgttg | tagtacagag | gttccactga | tgtgtgttaa | ttatgaccaa | 780 |
| ctagatttgc | tgtttgtctc | caagttcttt | gaacaccacc | aataccaca | ggaggaggcc | 840 |
| tccttagcag | agactaccct | tccatgtggc | tcatccccctt | ctgcaccccc | ctccgattct | 900 |
| attgggcccc | caattctcac | cagtccatct | ccttcaaaat | ccattccaat | tccacagcct | 960 |
| ttccgaccag | cagatgaaga | tcatcgaaat | cagtttggac | aacgagaccg | gtcctcatca | 1020 |
| gctccaaatg | tgcatataaa | cacaatagaa | cccgtcaata | ttgatgactt | gattagagac | 1080 |
| caagggtttc | gtagtgatgg | aggatcaacc | acaggtttat | ccgccacacc | ccctgcctca | 1140 |
| ttacctggct | cactctctaa | tgtgaaagca | ttgcagaaat | ctccaggacc | tcagcgagaa | 1200 |
| agaaagtcct | cttcatcctc | agaagacagg | aatcgaatga | aaacgcttgg | tagacgggat | 1260 |
| tcaagtgacg | attgggagat | tcctgatgga | cagatcacag | tgggacaaag | aattggatca | 1320 |
| gggtcatttg | gacagtctca | aagggaaag | tggcatggtg | atgtggcagt | gaaaatgttg | 1380 |
| aatgtgacag | cacccacacc | tcagcagtta | caggccttca | aaaatgaagt | aggagtactc | 1440 |
| aggaaaacgc | gacatgtgaa | tatcctcctc | ttcatggggt | attcaacaaa | gccacaactg | 1500 |
| gctattgtta | cccagtggtg | tgagggctcc | agtttatatc | atcatctcca | catcattgag | 1560 |

```
accaaattcg agatgatcaa acttatagat attgcacggc agactgcaca gggcatggat   1620
tacttacacg ccaagtcaat catccacaga gacctcaaga gtaataatat ttttcttcat   1680
gaagacctca cagtaaaaat aggtgatttt ggtctagcca cagtgaaatc tcgatggagt   1740
gggtcccatc agtttgaaca gttgtctgga tccatttttgt ggatggcacc agaagtaatc   1800
agaatgcaag ataaaaaccc atatagcttt cagtcagatg tatatgcatt tgggattgtt   1860
ctgtatgaat tgatgaccgg acagttacct tattcaaata tcaacaacag ggaccagata   1920
atttttatgg tgggacgagg atatctgtct ccagatctca gtaaggtacg gagtaactgt   1980
ccaaaagcca tgaagagatt aatggcagag tgcctaaaaa agaaaagaga tgaaagacca   2040
ctctttcccc aagtaggaaa gactctccta agcaagagac aaaattcaga agttatcagg   2100
gaaaaagata agcagattct cgcctctatt gagctgctgg cccgctcatt gccaaaaatt   2160
caccgcagtg catcagaacc ctccttgaat cgggctggct ccaaacaga ggattttagt   2220
ctatatgctt gtgcttctcc aaaaacaccc attcaggcag ggggatatga agcagatttg   2280
gctcttacat caaataaaaa tagagtagaa gttgggattt agagatttcc tgacatgcaa   2340
gaaggaataa gcaagaaaaa aaggtttgtt ttccccaaat catatctatt gtcttttact   2400
tctattttttt cttaaatttt ttgtgatttc agagacatgt agagttttat tgatacctaa   2460
actatgagtt ctttttttttt tttttttttc attattttga ttttttttggc caagaggcat   2520
atgggatctt agcttgagaa agcaacaatt ttcttgatgt catttttgggt gagggcacat   2580
attgctgtga acagtgtggt gatagccacc agggaccaaa ctcacacccg ctgcattgaa   2640
aggtgaagtc ttaaacactg gaccagcaga gaaattccta ctctatgagt tcttttttgtc   2700
atcccctccc cgcacccctcc accccccaacc taaagtctga tgatgaaatc aacaactatt   2760
ccattagaag cagtagattc tggtagcatg atctttagtt tgttagtaag atttttgtgct   2820
ttgtggggtt gtgtcgtttt aaggctaata tttaagtttg tcaaatagaa tgctgttcag   2880
attgtaaaaa tgagtaataa acatctgaag tttttttttaa gttatttttta acatggtata   2940
tacagttgag cttagagttt atcattttct gatattctct tacttagtag atgaattcta   3000
gccatttttt ataaagattt ctgttaagca aatcctgttt tcacatgggc ttcctttaag   3060
ggattttaga ttctgctgga tatggtgact gctcataaga ctgttgaaaa ttacttttaa   3120
gatgtattag aatacttctg aaaaaaaata gcaaccttaa aaccataagc aaaagtagta   3180
agggtgttta tacatttcta gagtccctgt ttaggtaata gcctcctatg attgtacttt   3240
aaatgttttg ctctccaagg ttttagtaac ttggcttttt ttctaatcag tgccaaactc   3300
ccccagtttt tttaacttta aatatgaggt aataaatctt ttacccttcc ttgatctttt   3360
gacttataat accttggtca gttgtttctt aaaaggaatc cttaaatgga aagagacaat   3420
atcactgtct gcagttctga ttagtagttt tattcagaat ggaaaaacag attattcatt   3480
tttgaaaatt gttcaggggt atgttcattg ttaggacctt ggactttgga gtcagtgcct   3540
agctatgcat tccaggtctg ccattttctg gctgtgaaat tttggacaag ttacttaacc   3600
actttaaacc ccagctttaa gaagtaaatt aacccccagta aattaagaag taatagcagc   3660
cacttcgtag agttgttatg aggctcagat gcagtgcaaa tgtgtataaa gtattcaggg   3720
agtcacctgg tatactataa tagacactag aatagttgcc aatattatca gcatacaatc   3780
tgaggattct gtcagccaat cattagcaat ctgttgtttg ttgggacatg ccagtgttct   3840
ccagttgaaa tcagtagcaa tctaaaaatg gatagattat tcctcattta aatagtgtgt   3900
```

| tcatataagt gattgcttgg atccttatca gaagttgctg ttactgaaaa atgataaggc | 3960 |
| tgactaaatt gtgatagttg tcagttacta accaactccc agaaatgaat aagaggaacc | 4020 |
| tatctctagt tcctagtaga aggtatggac aaaatagtag gtgaaaaata atgtcttgaa | 4080 |
| cccccaaatt aagtaagctt taaagagtac aatacctcaa agggtctttg cggtttaaaa | 4140 |
| tttgtatgct gagaatgatg ttcattgaca tgtgcctata tgtaattttt tgatagttta | 4200 |
| aaaggtgaaa tgaactacag atgggagagg tctgaatttt cttgccttca gtcaaatgtg | 4260 |
| taatgtggac atattatttg acctgtgaat tttatctttt aaaaaagatt aattcctgct | 4320 |
| tcttccttcc taatagttgc attataataa tgaaaatgag ttgataattt ggggggaaag | 4380 |
| tattctacaa atcaacctta ttattttacc attggtttct gagaaatttt gttcatttga | 4440 |
| accgtttata gcttgattag aatcatagca tgtaaaaccc aactgaggga ttatctgcag | 4500 |
| acttaatgta gtattatgta agttgtcttc tttcatttcg acctttttg cttttgttgt | 4560 |
| tgctagatct gtagtatgta gctagtcacc tttcagcgag gtttcagcga ggcttttctg | 4620 |
| tgtctctagg ttatttgaga taactttttt aaaattagct cttgtcctcc | 4670 |

```
<210> SEQ ID NO 26
<211> LENGTH: 761
<212> TYPE: PRT
<213> ORGANISM: Bos taurus

<400> SEQUENCE: 26
```

Met Lys Ile Gln Met Ser Ser Val Lys Val Trp Asn Ile Lys Gln Met
1               5                   10                  15

Ile Lys Leu Thr Gln Glu His Ile Glu Ala Leu Leu Asp Lys Phe Gly
            20                  25                  30

Gly Glu His Asn Pro Pro Ser Ile Tyr Leu Glu Ala Tyr Glu Glu Tyr
        35                  40                  45

Thr Ser Lys Leu Asp Ala Leu Gln Gln Arg Glu Gln Gln Leu Leu Glu
    50                  55                  60

Ser Leu Gly Asn Gly Thr Asp Phe Ser Val Ser Ser Ala Ser Thr
65                  70                  75                  80

Asp Thr Val Thr Ser Ser Ser Ser Ser Leu Ser Val Leu Pro Ser
                85                  90                  95

Ser Leu Ser Val Phe Gln Asn Pro Thr Asp Val Ser Arg Ser Asn Pro
            100                 105                 110

Lys Ser Pro Gln Lys Pro Ile Val Arg Val Phe Leu Pro Asn Lys Gln
        115                 120                 125

Arg Thr Val Val Pro Ala Arg Cys Gly Val Thr Val Arg Asp Ser Leu
    130                 135                 140

Lys Lys Ala Leu Met Met Arg Gly Leu Ile Pro Glu Cys Cys Ala Val
145                 150                 155                 160

Tyr Arg Ile Gln Asp Gly Glu Lys Lys Pro Ile Gly Trp Asp Thr Asp
                165                 170                 175

Ile Ser Trp Leu Thr Gly Glu Glu Leu His Val Glu Val Leu Glu Asn
            180                 185                 190

Val Pro Leu Thr Thr His Asn Phe Val Arg Lys Thr Phe Phe Thr Leu
        195                 200                 205

Ala Phe Cys Asp Phe Cys Arg Lys Leu Leu Phe Gln Gly Phe Arg Cys
    210                 215                 220

Gln Thr Cys Gly Tyr Lys Phe His Gln Arg Cys Ser Thr Glu Val Pro
225                 230                 235                 240

```
Leu Met Cys Val Asn Tyr Asp Gln Leu Asp Leu Leu Phe Val Ser Lys
            245                 250                 255

Phe Phe Glu His His Pro Ile Pro Gln Glu Glu Ala Ser Leu Ala Glu
        260                 265                 270

Thr Thr Leu Pro Cys Gly Ser Ser Pro Ser Ala Pro Pro Ser Asp Ser
    275                 280                 285

Ile Gly Pro Pro Ile Leu Thr Ser Pro Ser Pro Ser Lys Ser Ile Pro
290                 295                 300

Ile Pro Gln Pro Phe Arg Pro Ala Asp Glu Asp His Arg Asn Gln Phe
305                 310                 315                 320

Gly Gln Arg Asp Arg Ser Ser Ala Pro Asn Val His Ile Asn Thr
                325                 330                 335

Ile Glu Pro Val Asn Ile Asp Asp Leu Ile Arg Asp Gln Gly Phe Arg
            340                 345                 350

Ser Asp Gly Gly Ser Thr Thr Gly Leu Ser Ala Thr Pro Pro Ala Ser
        355                 360                 365

Leu Pro Gly Ser Leu Ser Asn Val Lys Ala Leu Gln Lys Ser Pro Gly
    370                 375                 380

Pro Gln Arg Glu Arg Lys Ser Ser Ser Ser Glu Asp Arg Asn Arg
385                 390                 395                 400

Met Lys Thr Leu Gly Arg Arg Asp Ser Ser Asp Asp Trp Glu Ile Pro
            405                 410                 415

Asp Gly Gln Ile Thr Val Gly Gln Arg Ile Gly Ser Gly Ser Phe Gly
        420                 425                 430

Thr Val Tyr Lys Gly Lys Trp His Gly Asp Val Ala Val Lys Met Leu
    435                 440                 445

Asn Val Thr Ala Pro Thr Pro Gln Gln Leu Gln Ala Phe Lys Asn Glu
450                 455                 460

Val Gly Val Leu Arg Lys Thr Arg His Val Asn Ile Leu Leu Phe Met
465                 470                 475                 480

Gly Tyr Ser Thr Lys Pro Gln Leu Ala Ile Val Thr Gln Trp Cys Glu
            485                 490                 495

Gly Ser Ser Leu Tyr His His Leu His Ile Ile Glu Thr Lys Phe Glu
        500                 505                 510

Met Ile Lys Leu Ile Asp Ile Ala Arg Gln Thr Ala Gln Gly Met Asp
    515                 520                 525

Tyr Leu His Ala Lys Ser Ile Ile His Arg Asp Leu Lys Ser Asn Asn
530                 535                 540

Ile Phe Leu His Glu Asp Leu Thr Val Lys Ile Gly Asp Phe Gly Leu
545                 550                 555                 560

Ala Thr Val Lys Ser Arg Trp Ser Gly Ser His Gln Phe Glu Gln Leu
            565                 570                 575

Ser Gly Ser Ile Leu Trp Met Ala Pro Glu Val Ile Arg Met Gln Asp
        580                 585                 590

Lys Asn Pro Tyr Ser Phe Gln Ser Asp Val Tyr Ala Phe Gly Ile Val
    595                 600                 605

Leu Tyr Glu Leu Met Thr Gly Gln Leu Pro Tyr Ser Asn Ile Asn Asn
610                 615                 620

Arg Asp Gln Ile Ile Phe Met Val Gly Arg Gly Tyr Leu Ser Pro Asp
625                 630                 635                 640

Leu Ser Lys Val Arg Ser Asn Cys Pro Lys Ala Met Lys Arg Leu Met
            645                 650                 655

Ala Glu Cys Leu Lys Lys Lys Arg Asp Glu Arg Pro Leu Phe Pro Gln
```

```
              660              665              670
Val Gly Lys Thr Leu Leu Ser Lys Arg Gln Asn Ser Glu Val Ile Arg
            675              680              685

Glu Lys Asp Lys Gln Ile Leu Ala Ser Ile Glu Leu Leu Ala Arg Ser
        690              695              700

Leu Pro Lys Ile His Arg Ser Ala Ser Glu Pro Ser Leu Asn Arg Ala
705              710              715              720

Gly Phe Gln Thr Glu Asp Phe Ser Leu Tyr Ala Cys Ala Ser Pro Lys
            725              730              735

Thr Pro Ile Gln Ala Gly Gly Tyr Glu Ala Asp Leu Ala Leu Thr Ser
                740              745              750

Asn Lys Asn Arg Val Glu Val Gly Ile
            755              760

<210> SEQ ID NO 27
<211> LENGTH: 4816
<212> TYPE: DNA
<213> ORGANISM: Bos taurus

<400> SEQUENCE: 27
ctcagctgcg ccgggtctca caagacggtt cccgaggtgg cccaggcgcc gtcccaccgc      60
cgacgccgcc cgggccgccc gggccgtccc tccccgctgc ccccccgtcct ccgcctccgc    120
ctccccccgc cctcagcctc ccttcccccct cccgcccag cagcggtcgc tcgggcccgg    180
ctctcggtta aagatggcg cgcgtgagtg gcggcggcgg cggcggcggc ggtggcgcgg    240
agcagggcca ggctctgttc aacggggaca tggagcccga ggccggcgcc gcggcctctt    300
cggctgcgga ccccgccatt cccgaggagg tgtggaatat caaacaaatg attaagttga    360
cacaggagca tatagaggcc ctattggaca aatttggtgg ggagcataat ccaccatcaa    420
tatatctgga ggcctatgaa aatacacca gcaagctaga tgccctccaa caaagagaac    480
aacagttatt ggaatccctg gggaatggaa ctgattttc tgtttctagc ctgcatcaa    540
cggacaccgt tacatcttct tcctcttcta gcctttcagt gctgccttca tctctttcag    600
tttttcaaaa tcccacagat gtgtcacgga gcaaccccaa gtcaccacaa aaacctatcg    660
ttagagtctt cctgcccaat aaacagagga cagtggtacc tgcacggtgt ggagtcacag    720
tccgggacag cctgaagaag gcactgatga tgagaggtct aatcccagag tgctgtgctg    780
tttacagaat tcaggatggg gagaagaaac caattggctg ggacactgat atttcctggc    840
ttactggaga ggagttgcat gtagaagtgt tggagaatgt tccacttaca acacacaact    900
tgtacggaa aacttttttc accttagcat tttgtgactt ctgtagaaag ctgcttttcc    960
agggattccg ctgtcaaaca tgtggttata aatttcacca gcgttgtagt acagaggttc   1020
cactgatgtg tgttaattat gaccaactag agcccccaat tctcaccagt ccatctcctt   1080
caaaatccat tccaattcca cagcctttcc gaccagcaga tgaagatcat cgaaatcagt   1140
ttggacaacg agaccggtcc tcatcagctc caaatgtgca tataaacaca atagaacccg   1200
tcaatattga tgacttgatt agagaccaag ggtttcgtag tgatggagga tcaaccacag   1260
gtttatccgc cacaccccct gcctcattac ctggctcact ctctaatgtg aaagcattgc   1320
agaaatctcc aggacctcag cgagaaagaa agtcctcttc atcctcagaa gacaggaatc   1380
gaatgaaaac gcttggtaga cgggattcaa gtgacgattg ggagattcct gatggacaga   1440
tcacagtggg acaaagaatt ggatcagggt catttgggac agtctacaag ggaaagtggc   1500
atggtgatgt ggcagtgaaa atgttgaatg tgacagcacc cacacctcag cagttacagg   1560
```

```
ccttcaaaaa tgaagtagga gtactcagga aaacgcgaca tgtgaatatc ctcctcttca    1620
tgggttattc aacaaagcca caactggcta ttgttaccca gtggtgtgag ggctccagtt    1680
tatatcatca tctccacatc attgagacca aattcgagat gatcaaactt atagatattg    1740
cacggcagac tgcacagggc atggattact tacacgccaa gtcaatcatc cacagagacc    1800
tcaagagtaa taatattttt cttcatgaag acctcacagt aaaaataggt gattttggtc    1860
tagccacagt gaaatctcga tggagtgggt cccatcagtt tgaacagttg tctggatcca    1920
ttttgtggat ggcaccagaa gtaatcagaa tgcaagataa aaacccatat agctttcagt    1980
cagatgtata tgcatttggg attgttctgt atgaattgat gaccggacag ttaccttatt    2040
caaatatcaa caacagggac cagataattt ttatggtggg acgaggatat ctgtctccag    2100
atctcagtaa ggtacggagt aactgtccaa aagccatgaa gagattaatg gcagagtgcc    2160 taaaaagaa aagagatgaa agaccactct ttccccaagt aggaaagact ctcctaagca    2220
agagacaaaa ttcagaagtt atcagggaaa aagataagca gattctcgcc tctattgagc    2280
tgctggcccg ctcattgcca aaaattcacc gcagtgcatc agaaccctcc ttgaatcggg    2340
ctggcttcca aacagaggat tttagtctat atgcttgtgc ttctccaaaa acacccattc    2400 aggcagggg atatgaagca gatttggctc ttacatcaaa taaaaataga gtagaagttg    2460
ggatttagag atttcctgac atgcaagaag aataagcaa gaaaaaaagg tttgttttcc    2520
ccaaatcata tctattgtct tttacttcta ttttttctta aatttttgt gatttcagag    2580 acatgtagag ttttattgat acctaaacta tgagttcttt tttttttttt ttttcatta    2640 ttttgatttt tttggccaag aggcatatgg gatcttagct tgagaaagca acaattttct    2700
tgatgtcatt ttgggtgagg gcacatattg ctgtgaacag tgtggtgata gccaccaggg    2760
accaaactca cacccgctgc attgaaaggt gaagtcttaa acactggacc agcagagaaa    2820
ttcctactct atgagttctt tttgtcatcc cctccccgca ccctccaccc caacctaaa    2880 gtctgatgat gaaatcaaca actattccat tagaagcagt agattctggt agcatgatct    2940
ttagtttgtt agtaagattt tgtgcttgt ggggttgtgt cgtttaagg ctaatattta    3000 agtttgtcaa atagaatgct gttcagattg taaaaatgag taataaacat ctgaagtttt    3060
ttttaagtta ttttaacat ggtatataca gttgagctta gagtttatca ttttctgata    3120
ttctcttact tagtagatga attctagcca ttttttataa agatttctgt taagcaaatc    3180
ctgttttcac atgggcttcc tttaagggat tttagattct gctggatatg gtgactgctc    3240
ataagactgt tgaaaattac ttttaagatg tattagaata cttctgaaaa aaaatagcaa    3300
ccttaaaacc ataagcaaaa gtagtaaggg tgtttataca tttctagagt ccctgtttag    3360
gtaatagcct cctatgattg tactttaaat gttttgctct ccaaggtttt agtaacttgg    3420 cttttttct aatcagtgcc aaactccccc agttttttta actttaaata tgaggtaata    3480
aatcttttac ccttccttga tcttttgact tataatacct tggtcagttg tttcttaaaa    3540
ggaatcctta aatggaaaga gacaatatca ctgtctgcag ttctgattag tagttttatt    3600
cagaatggaa aaacagatta ttcattttg aaaattgttc aggggtatgt tcattgttag    3660
gaccttggac tttggagtca gtgcctagct atgcattcca ggtctgccat tttctggctg    3720
tgaaattttg acaagttac ttaaccactt taaaccccag ctttaagaag taaattaacc    3780
ccagtaaatt aagaagtaat agcagccact tcgtagagtt gttatgaggc tcagatgcag    3840
tgcaaatgtg tataaagtat tcagggagtc acctggtata ctataataga cactagaata    3900
```

-continued

```
gttgccaata ttatcagcat acaatctgag gattctgtca gccaatcatt agcaatctgt    3960
tgtttgttgg gacatgccag tgttctccag ttgaaatcag tagcaatcta aaaatggata    4020
gattattcct catttaaata gtgtgttcat ataagtgatt gcttggatcc ttatcagaag    4080
ttgctgttac tgaaaaatga taaggctgac taaattgtga tagttgtcag ttactaacca    4140
actcccagaa atgaataaga ggaacctatc tctagttcct agtagaaggt atggacaaaa    4200
tagtaggtga aaataatgt cttgaacccc caaattaagt aagctttaaa gagtacaata     4260
cctcaaaggg tctttgcggt ttaaaatttg tatgctgaga atgatgttca ttgacatgtg    4320
cctatatgta attttttgat agtttaaaag gtgaaatgaa ctacagatgg gagaggtctg    4380
aattttcttg ccttcagtca aatgtgtaat gtggacatat tatttgacct gtgaatttta    4440
tcttttaaaa aagattaatt cctgcttctt ccttcctaat agttgcatta taataatgaa    4500
aatgagttga taatttgggg ggaaagtatt ctacaaatca accttattat tttaccattg    4560
gtttctgaga aattttgttc atttgaaccg tttatagctt gattagaatc atagcatgta    4620
aaacccaact gagggattat ctgcagactt aatgtagtat tatgtaagtt gtcttctttc    4680
atttcgacct ttttttgcttt tgttgttgct agatctgtag tatgtagcta gtcacctttc   4740
agcgaggttt cagcgaggct tttctgtgtc tctaggttat tttgagataac tttttttaaaa  4800 ttagctcttg tcctcc                                                    4816
```

<210> SEQ ID NO 28
<211> LENGTH: 757
<212> TYPE: PRT
<213> ORGANISM: Bos taurus

<400> SEQUENCE: 28

```
Met Ala Ala Leu Ser Gly Gly Gly Gly Gly Gly Gly Gly Gly Ala Glu
1               5                   10                  15

Gln Gly Gln Ala Leu Phe Asn Gly Asp Met Glu Pro Glu Ala Gly Ala
            20                  25                  30

Ala Ala Ser Ser Ala Ala Asp Pro Ala Ile Pro Glu Glu Val Trp Asn
        35                  40                  45

Ile Lys Gln Met Ile Lys Leu Thr Gln Glu His Ile Glu Ala Leu Leu
    50                  55                  60

Asp Lys Phe Gly Gly Glu His Asn Pro Pro Ser Ile Tyr Leu Glu Ala
65                  70                  75                  80

Tyr Glu Glu Tyr Thr Ser Lys Leu Asp Ala Leu Gln Gln Arg Glu Gln
                85                  90                  95

Gln Leu Leu Glu Ser Leu Gly Asn Gly Thr Asp Phe Ser Val Ser Ser
            100                 105                 110

Ser Ala Ser Thr Asp Thr Val Thr Ser Ser Ser Ser Ser Leu Ser
        115                 120                 125

Val Leu Pro Ser Ser Leu Ser Val Phe Gln Asn Pro Thr Asp Val Ser
    130                 135                 140

Arg Ser Asn Pro Lys Ser Pro Gln Lys Pro Ile Val Arg Val Phe Leu
145                 150                 155                 160

Pro Asn Lys Gln Arg Thr Val Val Pro Ala Arg Cys Gly Val Thr Val
                165                 170                 175

Arg Asp Ser Leu Lys Lys Ala Leu Met Met Arg Gly Leu Ile Pro Glu
            180                 185                 190

Cys Cys Ala Val Tyr Arg Ile Gln Asp Gly Glu Lys Lys Pro Ile Gly
        195                 200                 205
```

```
Trp Asp Thr Asp Ile Ser Trp Leu Thr Gly Glu Glu Leu His Val Glu
    210                 215                 220
Val Leu Glu Asn Val Pro Leu Thr Thr His Asn Phe Val Arg Lys Thr
225                 230                 235                 240
Phe Phe Thr Leu Ala Phe Cys Asp Phe Cys Arg Lys Leu Leu Phe Gln
                245                 250                 255
Gly Phe Arg Cys Gln Thr Cys Gly Tyr Lys Phe His Gln Arg Cys Ser
            260                 265                 270
Thr Glu Val Pro Leu Met Cys Val Asn Tyr Asp Gln Leu Glu Pro Pro
        275                 280                 285
Ile Leu Thr Ser Pro Ser Pro Ser Lys Ser Ile Pro Ile Pro Gln Pro
    290                 295                 300
Phe Arg Pro Ala Asp Glu Asp His Arg Asn Gln Phe Gly Gln Arg Asp
305                 310                 315                 320
Arg Ser Ser Ser Ala Pro Asn Val His Ile Asn Thr Ile Glu Pro Val
                325                 330                 335
Asn Ile Asp Asp Leu Ile Arg Asp Gln Gly Phe Arg Ser Asp Gly Gly
            340                 345                 350
Ser Thr Thr Gly Leu Ser Ala Thr Pro Pro Ala Ser Leu Pro Gly Ser
        355                 360                 365
Leu Ser Asn Val Lys Ala Leu Gln Lys Ser Pro Gly Pro Gln Arg Glu
    370                 375                 380
Arg Lys Ser Ser Ser Ser Glu Asp Arg Asn Arg Met Lys Thr Leu
385                 390                 395                 400
Gly Arg Arg Asp Ser Ser Asp Asp Trp Glu Ile Pro Asp Gly Gln Ile
                405                 410                 415
Thr Val Gly Gln Arg Ile Gly Ser Gly Ser Phe Gly Thr Val Tyr Lys
            420                 425                 430
Gly Lys Trp His Gly Asp Val Ala Val Lys Met Leu Asn Val Thr Ala
        435                 440                 445
Pro Thr Pro Gln Gln Leu Gln Ala Phe Lys Asn Glu Val Gly Val Leu
    450                 455                 460
Arg Lys Thr Arg His Val Asn Ile Leu Leu Phe Met Gly Tyr Ser Thr
465                 470                 475                 480
Lys Pro Gln Leu Ala Ile Val Thr Gln Trp Cys Glu Gly Ser Ser Leu
                485                 490                 495
Tyr His His Leu His Ile Ile Glu Thr Lys Phe Glu Met Ile Lys Leu
            500                 505                 510
Ile Asp Ile Ala Arg Gln Thr Ala Gln Gly Met Asp Tyr Leu His Ala
        515                 520                 525
Lys Ser Ile Ile His Arg Asp Leu Lys Ser Asn Asn Ile Phe Leu His
    530                 535                 540
Glu Asp Leu Thr Val Lys Ile Gly Asp Phe Gly Leu Ala Thr Val Lys
545                 550                 555                 560
Ser Arg Trp Ser Gly Ser His Gln Phe Glu Gln Leu Ser Gly Ser Ile
                565                 570                 575
Leu Trp Met Ala Pro Glu Val Ile Arg Met Gln Asp Lys Asn Pro Tyr
            580                 585                 590
Ser Phe Gln Ser Asp Val Tyr Ala Phe Gly Ile Val Leu Tyr Glu Leu
        595                 600                 605
Met Thr Gly Gln Leu Pro Tyr Ser Asn Ile Asn Asn Arg Asp Gln Ile
    610                 615                 620
Ile Phe Met Val Gly Arg Gly Tyr Leu Ser Pro Asp Leu Ser Lys Val
```

| | | | | | | | | | | |
|---|---|---|---|---|---|---|---|---|---|---|
|625| | | | |630| | | | |635| | | |640|
|Arg|Ser|Asn|Cys|Pro|Lys|Ala|Met|Lys|Arg|Leu|Met|Ala|Glu|Cys|Leu|
| | | | |645| | | | | |650| | | | |655|

Arg Ser Asn Cys Pro Lys Ala Met Lys Arg Leu Met Ala Glu Cys Leu
                    645                 650                 655

Lys Lys Lys Arg Asp Glu Arg Pro Leu Phe Pro Gln Val Gly Lys Thr
                    660                 665                 670

Leu Leu Ser Lys Arg Gln Asn Ser Glu Val Ile Arg Glu Lys Asp Lys
                    675                 680                 685

Gln Ile Leu Ala Ser Ile Glu Leu Leu Ala Arg Ser Leu Pro Lys Ile
            690                 695                 700

His Arg Ser Ala Ser Glu Pro Ser Leu Asn Arg Ala Gly Phe Gln Thr
705                 710                 715                 720

Glu Asp Phe Ser Leu Tyr Ala Cys Ala Ser Pro Lys Thr Pro Ile Gln
                    725                 730                 735

Ala Gly Gly Tyr Glu Ala Asp Leu Ala Leu Thr Ser Asn Lys Asn Arg
            740                 745                 750

Val Glu Val Gly Ile
            755

<210> SEQ ID NO 29
<211> LENGTH: 2499
<212> TYPE: DNA
<213> ORGANISM: Bos taurus

<400> SEQUENCE: 29

```
ctcagctgcg ccgggtctca caagacggtt cccgaggtgg cccaggcgcc gtcccaccgc      60
cgacgccgcc cgggccgccc gggccgtccc tccccgctgc ccccgtcct ccgcctccgc     120
ctcccccgc cctcagcctc ccttccccct ccccgcccag cagcggtcgc tcgggcccgg     180
ctctcggtta aagatggcg gcgctgagtg gcggcggcgg cggcggcggc ggtggcgcgg     240
agcagggcca ggctctgttc aacggggaca tggagcccga ggccggcgcc gcggcctctt     300
cggctgcgga ccccgccatt cccgaggagg tgtggaatat caaacaaatg attaagttga     360
cacaggagca tatagaggcc ctattggaca aatttggtgg ggagcataat ccaccatcaa     420
tatatctgga ggcctatgaa gaatacacca gcaagctaga tgccctccaa caaagagaac     480
aacagttatt ggaatccctg gggaatggaa ctgattttc tgtttctagc tctgcatcaa     540
cggacaccgt tacatcttct tcctcttcta gcctttcagt gctgccttca tctctttcag     600
ttttcaaaa tcccacagat gtgtcacgga gcaaccccaa gtcaccacaa aaacctatcg     660
ttagagtctt cctgcccaat aaacagagga cagtggtacc tgcacggtgt ggagtcacag     720
tccgggacag cctgaagaag gcactgatga tgagaggtct aatcccagag tgctgtgctg     780
tttacagaat tcaggatggg gagaagaaac caattggctg ggacactgat atttcctggc     840
ttactggaga ggagttgcat gtagaagtgt tggagaatgt tccacttaca acacacaact     900
tgtacggaa aactttttc accttagcat tttgtgactt ctgtagaaag ctgcttttcc     960
agggattccg ctgtcaaaca tgtggttata aatttcacca gcgttgtagt acagaggttc    1020
cactgatgtg tgttaattat gaccaactag atttgctgtt tgtctccaag ttctttgaac    1080
accacccaat accacaggag gaggcctcct tagcagagac tacccttcca tgtggctcat    1140
cccttctgc acccccctcc gattctattg gccccccaat tctcaccagt ccatctcctt    1200
caaaatccat tccaattcca cagccttttc gaccagcaga tgaagatcat cgaaatcagt    1260
ttggacaacg agaccggtcc tcatcagctc caaatgtgca tataaacaca atagaacccg    1320
tcaatattga tgacttgatt agagaccaag ggtttcgtag tgatggagga tcaaccacag    1380
```

```
gtttatccgc cacacccct gcctcattac ctggctcact ctctaatgtg aaagcattgc    1440
agaaatctcc aggacctcag cgagaaagaa agtcctcttc atcctcagaa acaggaatc    1500 gaatgaaaac gcttggtaga cgggattcaa gtgacgattg ggagattcct gatggacaga    1560
tcacagtggg acaagaatt ggatcagggt catttgggac agtctacaag ggaaagtggc    1620
atggtgatgt ggcagtgaaa atgttgaatg tgacagcacc cacacctcag cagttacagg    1680
ccttcaaaaa tgaagtagga gtactcagga aaacgcgaca tgtgaatatc ctcctcttca    1740
tgggttattc aacaaagcca caactggcta ttgttaccca gtggtgtgag ggctccagtt    1800
tatatcatca tctccacatc attgagacca aattcgagat gatcaaactt atagatattg    1860
cacggcagac tgcacagggc atggattact tacacgccaa gtcaatcatc cacagagacc    1920
tcaagagtaa taatatttt cttcatgaag acctcacagt aaaaataggt gattttggtc    1980
tagccacagt gaaatctcga tggagtgggt cccatcagtt tgaacagttg tctggatcca    2040
ttttgtggat ggcaccagaa gtaatcagaa tgcaagataa aaacccatat agctttcagt    2100
cagatgtata tgcatttggg attgttctgt atgaattgat gaccggacag ttaccttatt    2160
caaatatcaa caacagggac cagataattt ttatggtggg acgaggatat ctgtctccag    2220
atctcagtaa ggtacggagt aactgtccaa aagccatgaa gagattaatg gcagagtgcc    2280
taaaaaagaa aagagatgaa agaccactct ttccccaagt aggaaagact ctcctaagca    2340
agagacaaaa ttcagaagtt atcagggaaa agataagca ggaaaagtat gtttctttag    2400
tacattccag gcatttggga ttacagtaaa aacaatattc tcgcctctat tgagctgctg    2460
gcccgctcat tgccaaaaat tcaccgcagt gcatcagaa                          2499
```

<210> SEQ ID NO 30
<211> LENGTH: 744
<212> TYPE: PRT
<213> ORGANISM: Bos taurus

<400> SEQUENCE: 30

```
Met Ala Ala Leu Ser Gly Gly Gly Gly Gly Gly Gly Gly Gly Ala Glu
1               5                   10                  15

Gln Gly Gln Ala Leu Phe Asn Gly Asp Met Glu Pro Glu Ala Gly Ala
            20                  25                  30

Ala Ala Ser Ser Ala Ala Asp Pro Ala Ile Pro Glu Glu Val Trp Asn
        35                  40                  45

Ile Lys Gln Met Ile Lys Leu Thr Gln Glu His Ile Glu Ala Leu Leu
    50                  55                  60

Asp Lys Phe Gly Gly Glu His Asn Pro Pro Ser Ile Tyr Leu Glu Ala
65                  70                  75                  80

Tyr Glu Glu Tyr Thr Ser Lys Leu Asp Ala Leu Gln Gln Arg Glu Gln
                85                  90                  95

Gln Leu Leu Glu Ser Leu Gly Asn Gly Thr Asp Phe Ser Val Ser Ser
            100                 105                 110

Ser Ala Ser Thr Asp Thr Val Thr Ser Ser Ser Ser Ser Leu Ser
        115                 120                 125

Val Leu Pro Ser Ser Leu Ser Val Phe Gln Asn Pro Thr Asp Val Ser
    130                 135                 140

Arg Ser Asn Pro Lys Ser Pro Gln Lys Pro Ile Val Arg Val Phe Leu
145                 150                 155                 160

Pro Asn Lys Gln Arg Thr Val Val Pro Ala Arg Cys Gly Val Thr Val
                165                 170                 175
```

```
Arg Asp Ser Leu Lys Lys Ala Leu Met Met Arg Gly Leu Ile Pro Glu
            180                 185                 190

Cys Cys Ala Val Tyr Arg Ile Gln Asp Gly Glu Lys Lys Pro Ile Gly
            195                 200                 205

Trp Asp Thr Asp Ile Ser Trp Leu Thr Gly Glu Glu Leu His Val Glu
210                 215                 220

Val Leu Glu Asn Val Pro Leu Thr Thr His Asn Phe Val Arg Lys Thr
225                 230                 235                 240

Phe Phe Thr Leu Ala Phe Cys Asp Phe Cys Arg Lys Leu Leu Phe Gln
                245                 250                 255

Gly Phe Arg Cys Gln Thr Cys Gly Tyr Lys Phe His Gln Arg Cys Ser
            260                 265                 270

Thr Glu Val Pro Leu Met Cys Val Asn Tyr Asp Gln Leu Asp Leu Leu
            275                 280                 285

Phe Val Ser Lys Phe Phe Glu His His Pro Ile Pro Gln Glu Glu Ala
            290                 295                 300

Ser Leu Ala Glu Thr Thr Leu Pro Cys Gly Ser Ser Pro Ser Ala Pro
305                 310                 315                 320

Pro Ser Asp Ser Ile Gly Pro Pro Ile Leu Thr Ser Pro Ser Pro Ser
                325                 330                 335

Lys Ser Ile Pro Ile Pro Gln Pro Phe Arg Pro Ala Asp Glu Asp His
            340                 345                 350

Arg Asn Gln Phe Gly Gln Arg Asp Arg Ser Ser Ser Ala Pro Asn Val
            355                 360                 365

His Ile Asn Thr Ile Glu Pro Val Asn Ile Asp Asp Leu Ile Arg Asp
            370                 375                 380

Gln Gly Phe Arg Ser Asp Gly Ser Thr Thr Gly Leu Ser Ala Thr
385                 390                 395                 400

Pro Pro Ala Ser Leu Pro Gly Ser Leu Ser Asn Val Lys Ala Leu Gln
                405                 410                 415

Lys Ser Pro Gly Pro Gln Arg Glu Arg Lys Ser Ser Ser Ser Ser Glu
            420                 425                 430

Asp Arg Asn Arg Met Lys Thr Leu Gly Arg Arg Asp Ser Ser Asp Asp
            435                 440                 445

Trp Glu Ile Pro Asp Gly Gln Ile Thr Val Gly Gln Arg Ile Gly Ser
450                 455                 460

Gly Ser Phe Gly Thr Val Tyr Lys Gly Lys Trp His Gly Asp Val Ala
465                 470                 475                 480

Val Lys Met Leu Asn Val Thr Ala Pro Thr Pro Gln Gln Leu Gln Ala
                485                 490                 495

Phe Lys Asn Glu Val Gly Val Leu Arg Lys Thr Arg His Val Asn Ile
            500                 505                 510

Leu Leu Phe Met Gly Tyr Ser Thr Lys Pro Gln Leu Ala Ile Val Thr
            515                 520                 525

Gln Trp Cys Glu Gly Ser Ser Leu Tyr His His Leu His Ile Ile Glu
            530                 535                 540

Thr Lys Phe Glu Met Ile Lys Leu Ile Asp Ile Ala Arg Gln Thr Ala
545                 550                 555                 560

Gln Gly Met Asp Tyr Leu His Ala Lys Ser Ile Ile His Arg Asp Leu
                565                 570                 575

Lys Ser Asn Asn Ile Phe Leu His Glu Asp Leu Thr Val Lys Ile Gly
            580                 585                 590
```

```
Asp Phe Gly Leu Ala Thr Val Lys Ser Arg Trp Ser Gly Ser His Gln
            595                 600                 605

Phe Glu Gln Leu Ser Gly Ser Ile Leu Trp Met Ala Pro Glu Val Ile
        610                 615                 620

Arg Met Gln Asp Lys Asn Pro Tyr Ser Phe Gln Ser Asp Val Tyr Ala
625                 630                 635                 640

Phe Gly Ile Val Leu Tyr Glu Leu Met Thr Gly Gln Leu Pro Tyr Ser
                645                 650                 655

Asn Ile Asn Asn Arg Asp Gln Ile Ile Phe Met Val Gly Arg Gly Tyr
            660                 665                 670

Leu Ser Pro Asp Leu Ser Lys Val Arg Ser Asn Cys Pro Lys Ala Met
        675                 680                 685

Lys Arg Leu Met Ala Glu Cys Leu Lys Lys Arg Asp Glu Arg Pro
690                 695                 700

Leu Phe Pro Gln Val Gly Lys Thr Leu Leu Ser Lys Arg Gln Asn Ser
705                 710                 715                 720

Glu Val Ile Arg Glu Lys Asp Lys Gln Glu Lys Tyr Val Ser Leu Val
                725                 730                 735

His Ser Arg His Leu Gly Leu Gln
            740

<210> SEQ ID NO 31
<211> LENGTH: 2404
<212> TYPE: DNA
<213> ORGANISM: Bos taurus

<400> SEQUENCE: 31
ctcagctgcg ccgggtctca aagacggtt  cccgaggtgg cccaggcgcc gtcccaccgc      60
cgacgccgcc cgggccgccc gggccgtccc tcccgctgc  ccccgtcct  ccgcctccgc     120 ctccccccgc cctcagcctc ccttccccct ccccgcccag cagcggtcgc tcgggcccgg     180
ctctcggtta agatggcg  gcgctgagtg cggcggcgg  cggcggcggc ggtgcgcgg      240 agcagggcca ggctctgttc aacggggaca tggagcccga ggccggcgcc gcggcctctt     300
cggctgcgga ccccgccatt cccgaggagg tgtggaatat caaacaaatg attaagttga     360
cacaggagca tatagaggcc ctattggaca aatttggtgg ggagcataat ccaccatcaa     420
tatatctgga ggcctatgaa gaatacacca gcaagctaga tgccctccaa caaagagaac     480
aacagttatt ggaatccctg ggaatggaa  ctgattttc  tgtttctagc tctgcatcaa     540
cggacaccgt tacatcttct tcctcttcta gcctttcagt gctgccttca tctctttcag     600 ttttttcaaaa tcccacagat gtgtcacgga gcaaccccaa gtcaccacaa aaacctatcg     660
ttagagtctt cctgcccaat aaacagagga cagtggtacc tgcacggtgt ggagtcacag     720
tccgggacag cctgaagaag gcactgatga tgagaggtct aatcccagag tgctgtgctg     780
tttacagaat tcaggatggg gagaagaaac caattggctg ggacactgat atttcctggc     840
ttactggaga ggagttgcat gtagaagtgt tggagaatgt tccacttaca acacacaact     900
ttgtacggaa aactttttc  accttagcat tttgtgactt ctgtagaaag ctgcttttcc     960
agggattccg ctgtcaaaca tgtggttata aatttcacca gcgttgtagt acagaggttc    1020
cactgatgtg tgttaattat gaccaactag atttgctgtt tgtctccaag ttctttgaac    1080
accacccaat accacaggag gaggcctcct tagcagagac tacccttcca tgtggctcat    1140 cccttctgc  acccccctcc gattctattg ggccccaat  tctcaccagt ccatctcctt    1200
caaaatccat tccaattcca cagcctttcc gaccagcaga tgaagatcat cgaaatcagt    1260
```

```
ttggacaacg agaccggtcc tcatcagctc caaatgtgca tataaacaca atagaacccg    1320
tcaatattga tgacttgatt agagaccaag ggtttcgtag tgatggagga tcaaccacag    1380
gtttatccgc cacaccccct gcctcattac ctggctcact ctctaatgtg aaagcattgc    1440
agaaatctcc aggacctcag cgagaaagaa agtcctcttc atcctcagaa acaggaatc     1500
gaatgaaaac gcttggtaga cgggattcaa gtgacgattg ggagattcct gatggacaga    1560
tcacagtggg acaagaatt ggatcagggt catttgggac agtctacaag ggaaagtggc     1620
atggtgatgt ggcagtgaaa atgttgaatg tgacagcacc cacacctcag cagttacagg    1680
ccttcaaaaa tgaagtagga gtactcagga aaacgcgaca tgtgaatatc ctcctcttca    1740
tgggttattc aacaaagcca caactggcta ttgttaccca gtggtgtgag ggctccagtt    1800
tatatcatca tctccacatc attgagacca aattcgagat gatcaaactt atagatattg    1860
cacggcagac tgcacagggc atggattact acacgccaa gtcaatcatc cacagagacc     1920
tcaagagtaa taatatttt cttcatgaag acctcacagt aaaaataggt gattttggtc     1980
tagccacagt gaaatctcga tggagtgggt cccatcagtt tgaacagttg tctggatcca    2040
ttttgtggat ggcaccagaa gtaatcagaa tgcaagataa aaacccatat agctttcagt    2100
cagatgtata tgcatttggg attgttctgt atgaattgat gaccggacag ttaccttatt    2160
caaatatcaa caacagggac cagataattt ttatggtggg acgaggatat ctgtctccag    2220
atctcagtaa ggtacggagt aactgtccaa aagccatgaa gagattaatg gcagagtgcc    2280
taaaaaagaa aagagatgaa agaccactct tcccccaaga tctctcttcc caccatagac    2340
acaaaaattt cagatggcta caggtttaca tgtaaaaaac agaattataa caaatgattt    2400
ttat                                                                 2404

<210> SEQ ID NO 32
<211> LENGTH: 726
<212> TYPE: PRT
<213> ORGANISM: Bos taurus

<400> SEQUENCE: 32

Met Ala Ala Leu Ser Gly Gly Gly Gly Gly Gly Gly Gly Ala Glu
1               5                   10                  15

Gln Gly Gln Ala Leu Phe Asn Gly Asp Met Glu Pro Glu Ala Gly Ala
            20                  25                  30

Ala Ala Ser Ser Ala Ala Asp Pro Ala Ile Pro Glu Glu Val Trp Asn
        35                  40                  45

Ile Lys Gln Met Ile Lys Leu Thr Gln Glu His Ile Glu Ala Leu Leu
    50                  55                  60

Asp Lys Phe Gly Gly Glu His Asn Pro Pro Ser Ile Tyr Leu Glu Ala
65                  70                  75                  80

Tyr Glu Glu Tyr Thr Ser Lys Leu Asp Ala Leu Gln Gln Arg Glu Gln
                85                  90                  95

Gln Leu Leu Glu Ser Leu Gly Asn Gly Thr Asp Phe Ser Val Ser Ser
            100                 105                 110

Ser Ala Ser Thr Asp Thr Val Thr Ser Ser Ser Ser Ser Leu Ser
        115                 120                 125

Val Leu Pro Ser Ser Leu Ser Val Phe Gln Asn Pro Thr Asp Val Ser
    130                 135                 140

Arg Ser Asn Pro Lys Ser Pro Gln Lys Pro Ile Val Arg Val Phe Leu
145                 150                 155                 160
```

```
Pro Asn Lys Gln Arg Thr Val Val Pro Ala Arg Cys Gly Val Thr Val
            165                 170                 175
Arg Asp Ser Leu Lys Lys Ala Leu Met Met Arg Gly Leu Ile Pro Glu
            180                 185                 190
Cys Cys Ala Val Tyr Arg Ile Gln Asp Gly Glu Lys Lys Pro Ile Gly
            195                 200                 205
Trp Asp Thr Asp Ile Ser Trp Leu Thr Gly Glu Glu Leu His Val Glu
            210                 215                 220
Val Leu Glu Asn Val Pro Leu Thr Thr His Asn Phe Val Arg Lys Thr
225                 230                 235                 240
Phe Phe Thr Leu Ala Phe Cys Asp Phe Cys Arg Lys Leu Leu Phe Gln
            245                 250                 255
Gly Phe Arg Cys Gln Thr Cys Gly Tyr Lys Phe His Gln Arg Cys Ser
            260                 265                 270
Thr Glu Val Pro Leu Met Cys Val Asn Tyr Asp Gln Leu Asp Leu Leu
            275                 280                 285
Phe Val Ser Lys Phe Phe Glu His His Pro Ile Pro Gln Glu Glu Ala
            290                 295                 300
Ser Leu Ala Glu Thr Thr Leu Pro Cys Gly Ser Ser Pro Ser Ala Pro
305                 310                 315                 320
Pro Ser Asp Ser Ile Gly Pro Pro Ile Leu Thr Ser Pro Ser Pro Ser
            325                 330                 335
Lys Ser Ile Pro Ile Pro Gln Pro Phe Arg Pro Ala Asp Glu Asp His
            340                 345                 350
Arg Asn Gln Phe Gly Gln Arg Asp Arg Ser Ser Ser Ala Pro Asn Val
            355                 360                 365
His Ile Asn Thr Ile Glu Pro Val Asn Ile Asp Asp Leu Ile Arg Asp
            370                 375                 380
Gln Gly Phe Arg Ser Asp Gly Gly Ser Thr Thr Gly Leu Ser Ala Thr
385                 390                 395                 400
Pro Pro Ala Ser Leu Pro Gly Ser Leu Ser Asn Val Lys Ala Leu Gln
            405                 410                 415
Lys Ser Pro Gly Pro Gln Arg Glu Arg Lys Ser Ser Ser Ser Ser Glu
            420                 425                 430
Asp Arg Asn Arg Met Lys Thr Leu Gly Arg Arg Asp Ser Ser Asp Asp
            435                 440                 445
Trp Glu Ile Pro Asp Gly Gln Ile Thr Val Gly Gln Arg Ile Gly Ser
            450                 455                 460
Gly Ser Phe Gly Thr Val Tyr Lys Gly Lys Trp His Gly Asp Val Ala
465                 470                 475                 480
Val Lys Met Leu Asn Val Thr Ala Pro Thr Pro Gln Gln Leu Gln Ala
            485                 490                 495
Phe Lys Asn Glu Val Gly Val Leu Arg Lys Thr Arg His Val Asn Ile
            500                 505                 510
Leu Leu Phe Met Gly Tyr Ser Thr Lys Pro Gln Leu Ala Ile Val Thr
            515                 520                 525
Gln Trp Cys Glu Gly Ser Ser Leu Tyr His His Leu His Ile Ile Glu
            530                 535                 540
Thr Lys Phe Glu Met Ile Lys Leu Ile Asp Ile Ala Arg Gln Thr Ala
545                 550                 555                 560
Gln Gly Met Asp Tyr Leu His Ala Lys Ser Ile Ile His Arg Asp Leu
            565                 570                 575
Lys Ser Asn Asn Ile Phe Leu His Glu Asp Leu Thr Val Lys Ile Gly
```

```
            580                 585                 590
Asp Phe Gly Leu Ala Thr Val Lys Ser Arg Trp Ser Gly Ser His Gln
            595                 600                 605

Phe Glu Gln Leu Ser Gly Ser Ile Leu Trp Met Ala Pro Glu Val Ile
            610                 615                 620

Arg Met Gln Asp Lys Asn Pro Tyr Ser Phe Gln Ser Asp Val Tyr Ala
625                 630                 635                 640

Phe Gly Ile Val Leu Tyr Glu Leu Met Thr Gly Gln Leu Pro Tyr Ser
                645                 650                 655

Asn Ile Asn Asn Arg Asp Gln Ile Ile Phe Met Val Gly Arg Gly Tyr
                660                 665                 670

Leu Ser Pro Asp Leu Ser Lys Val Arg Ser Asn Cys Pro Lys Ala Met
            675                 680                 685

Lys Arg Leu Met Ala Glu Cys Leu Lys Lys Arg Asp Glu Arg Pro
            690                 695                 700

Leu Phe Pro Gln Asp Leu Ser Ser His His Arg His Lys Asn Phe Arg
705                 710                 715                 720

Trp Leu Gln Val Tyr Met
                725

<210> SEQ ID NO 33
<211> LENGTH: 2331
<212> TYPE: DNA
<213> ORGANISM: Bos taurus

<400> SEQUENCE: 33
ctcagctgcg ccgggtctca caagacggtt cccgaggtgg cccaggcgcc gtcccaccgc      60
cgacgccgcc cgggccgccc gggccgtccc tcccgctgcc ccccgtcctc cgcctccgc     120
ctcccccgc cctcagcctc ccttccccct ccccgcccag cagcggtcgc tcgggcccgg     180
ctctcggtta aagatggcg cgcgtgagtg gcggcggcgg cggcggcggc ggtggcgcgg     240
agcagggcca ggctctgttc aacggggaca tggagcccga ggccggcgcc gcggcctctt     300
cggctgcgga ccccgccatt cccgaggagg tgtggaatat caaacaaatg attaagttga     360
cacaggagca tatagaggcc ctattggaca aatttggtgg ggagcataat ccaccatcaa     420
tatatctgga ggcctatgaa gaatacacca gcaagctaga tgccctccaa caaagagaac     480
aacagttatt ggaatccctg ggaatggaa ctgattttc tgtttctagc tctgcatcaa     540
cggacaccgt tacatcttct tcctcttcta gcctttcagt gctgccttca tctctttcag     600
tttttcaaaa tcccacagat gtgtcacgga caaccccaa gtcaccacaa aaacctatcg     660
ttagagtctt cctgcccaat aaacagagga cagtggtacc tgcacggtgt ggagtcacag     720
tccgggacag cctgaagaag gcactgatga tgagaggtct aatcccagag tgctgtgctg     780
tttacagaat tcaggatggg gagaagaaac caattggctg ggacactgat atttcctggc     840
ttactggaga ggagttgcat gtagaagtgt tggagaatgt tccacttaca acacacaact     900
ttgtacggaa aactttttc accttagcat tttgtgactt ctgtagaaag ctgctttcc     960
agggattccg ctgtcaaaca tgtggttata aatttcacca gcgttgtagt acagaggttc    1020
cactgatgtg tgttaattat gaccaactag atttgctgtt tgtctccaag ttctttgaac    1080
accacccaat accacaggag gaggcctcct agcagagac taccttcca tgtggctcat    1140
ccccttctgc accccctcc gattctattg ggccccaat tctcaccagt ccatctcctt    1200
caaaatccat tccaattcca cagcctttcc gaccagcaga tgaagatcat cgaaatcagt    1260
```

-continued

```
ttggacaacg agaccggtcc tcatcagctc caaatgtgca tataaacaca atagaacccg    1320
tcaatattga tgacttgatt agagaccaag ggtttcgtag tgatggagga tcaaccacag    1380
gtttatccgc cacacccct gcctcattac ctggctcact ctctaatgtg aaagcattgc    1440
agaaatctcc aggacctcag cgagaaagaa agtcctcttc atcctcagaa gacaggaatc    1500
gaatgaaaac gcttggtaga cgggattcaa gtgacgattg ggagattcct gatggacaga    1560
tcacagtggg acaaagaatt ggatcagggt catttgggac agtctacaag ggaaagtggc    1620
atggtgatgt ggcagtgaaa atgttgaatg tgacagcacc cacacctcag cagttacagg    1680
ccttcaaaaa tgaagtagga gtactcagga aaacgcgaca tgtgaatatc ctcctcttca    1740
tgggttattc aacaaagcca caactggcta ttgttaccca gtggtgtgag ggctccagtt    1800
tatatcatca tctccacatc attgagacca aattcgagat gatcaaactt atagatattg    1860
cacggcagac tgcacagggc atggattact tacacgccaa gtcaatcatc cacagagacc    1920
tcaagagtaa taatatttttt cttcatgaag acctcacagt aaaaataggt gattttggtc    1980
tagccacagt gaaatctcga tggagtgggt cccatcagtt tgaacagttg tctggatcca    2040
ttttgtggat ggcaccagaa gtaatcagaa tgcaagataa aaacccatat agctttcagt    2100
cagatgtata tgcatttggg attgttctgt atgaattgat gaccggacag ttaccttatt    2160
caaatatcaa caacagggac caggtgcttt gtcctccatg ggagtgtaat aaatgctgtg    2220
caagggctta cttcccatga gagaagtgag tgaccaacag aaggataatt tttatggtgg    2280
gacgaggata tctgtctcca gatctcagta aggtacggag taactgtcca a             2331
```

<210> SEQ ID NO 34
<211> LENGTH: 681
<212> TYPE: PRT
<213> ORGANISM: Bos taurus

<400> SEQUENCE: 34

```
Met Ala Ala Leu Ser Gly Gly Gly Gly Gly Gly Gly Gly Ala Glu
1               5                   10                  15

Gln Gly Gln Ala Leu Phe Asn Gly Asp Met Glu Pro Glu Ala Gly Ala
                20                  25                  30

Ala Ala Ser Ser Ala Ala Asp Pro Ala Ile Pro Glu Glu Val Trp Asn
            35                  40                  45

Ile Lys Gln Met Ile Lys Leu Thr Gln Glu His Ile Glu Ala Leu Leu
        50                  55                  60

Asp Lys Phe Gly Gly Glu His Asn Pro Pro Ser Ile Tyr Leu Glu Ala
65                  70                  75                  80

Tyr Glu Glu Tyr Thr Ser Lys Leu Asp Ala Leu Gln Gln Arg Glu Gln
                85                  90                  95

Gln Leu Leu Glu Ser Leu Gly Asn Gly Thr Asp Phe Ser Val Ser Ser
            100                 105                 110

Ser Ala Ser Thr Asp Thr Val Thr Ser Ser Ser Ser Ser Leu Ser
            115                 120                 125

Val Leu Pro Ser Ser Leu Ser Val Phe Gln Asn Pro Thr Asp Val Ser
        130                 135                 140

Arg Ser Asn Pro Lys Ser Pro Gln Lys Pro Ile Val Arg Val Phe Leu
145                 150                 155                 160

Pro Asn Lys Gln Arg Thr Val Val Pro Ala Arg Cys Gly Val Thr Val
                165                 170                 175

Arg Asp Ser Leu Lys Lys Ala Leu Met Met Arg Gly Leu Ile Pro Glu
            180                 185                 190
```

```
Cys Cys Ala Val Tyr Arg Ile Gln Asp Gly Glu Lys Lys Pro Ile Gly
            195                 200                 205

Trp Asp Thr Asp Ile Ser Trp Leu Thr Gly Glu Glu Leu His Val Glu
    210                 215                 220

Val Leu Glu Asn Val Pro Leu Thr Thr His Asn Phe Val Arg Lys Thr
225                 230                 235                 240

Phe Phe Thr Leu Ala Phe Cys Asp Phe Cys Arg Lys Leu Leu Phe Gln
                245                 250                 255

Gly Phe Arg Cys Gln Thr Cys Gly Tyr Lys Phe His Gln Arg Cys Ser
                260                 265                 270

Thr Glu Val Pro Leu Met Cys Val Asn Tyr Asp Gln Leu Asp Leu Leu
            275                 280                 285

Phe Val Ser Lys Phe Phe Glu His His Pro Ile Pro Gln Glu Glu Ala
        290                 295                 300

Ser Leu Ala Glu Thr Thr Leu Pro Cys Gly Ser Ser Pro Ser Ala Pro
305                 310                 315                 320

Pro Ser Asp Ser Ile Gly Pro Pro Ile Leu Thr Ser Pro Ser Pro Ser
                325                 330                 335

Lys Ser Ile Pro Ile Pro Gln Pro Phe Arg Pro Ala Asp Glu Asp His
            340                 345                 350

Arg Asn Gln Phe Gly Gln Arg Asp Arg Ser Ser Ser Ala Pro Asn Val
            355                 360                 365

His Ile Asn Thr Ile Glu Pro Val Asn Ile Asp Asp Leu Ile Arg Asp
        370                 375                 380

Gln Gly Phe Arg Ser Asp Gly Gly Ser Thr Thr Gly Leu Ser Ala Thr
385                 390                 395                 400

Pro Pro Ala Ser Leu Pro Gly Ser Leu Ser Asn Val Lys Ala Leu Gln
                405                 410                 415

Lys Ser Pro Gly Pro Gln Arg Glu Arg Lys Ser Ser Ser Ser Ser Glu
            420                 425                 430

Asp Arg Asn Arg Met Lys Thr Leu Gly Arg Arg Asp Ser Ser Asp Asp
            435                 440                 445

Trp Glu Ile Pro Asp Gly Gln Ile Thr Val Gly Gln Arg Ile Gly Ser
    450                 455                 460

Gly Ser Phe Gly Thr Val Tyr Lys Gly Lys Trp His Gly Asp Val Ala
465                 470                 475                 480

Val Lys Met Leu Asn Val Thr Ala Pro Thr Pro Gln Gln Leu Gln Ala
                485                 490                 495

Phe Lys Asn Glu Val Gly Val Leu Arg Lys Thr Arg His Val Asn Ile
            500                 505                 510

Leu Leu Phe Met Gly Tyr Ser Thr Lys Pro Gln Leu Ala Ile Val Thr
        515                 520                 525

Gln Trp Cys Glu Gly Ser Ser Leu Tyr His His Leu His Ile Ile Glu
    530                 535                 540

Thr Lys Phe Glu Met Ile Lys Leu Ile Asp Ile Ala Arg Gln Thr Ala
545                 550                 555                 560

Gln Gly Met Asp Tyr Leu His Ala Lys Ser Ile Ile His Arg Asp Leu
                565                 570                 575

Lys Ser Asn Asn Ile Phe Leu His Glu Asp Leu Thr Val Lys Ile Gly
            580                 585                 590

Asp Phe Gly Leu Ala Thr Val Lys Ser Arg Trp Ser Gly Ser His Gln
            595                 600                 605
```

```
Phe Glu Gln Leu Ser Gly Ser Ile Leu Trp Met Ala Pro Glu Val Ile
610                 615                 620

Arg Met Gln Asp Lys Asn Pro Tyr Ser Phe Gln Ser Asp Val Tyr Ala
625                 630                 635                 640

Phe Gly Ile Val Leu Tyr Glu Leu Met Thr Gly Gln Leu Pro Tyr Ser
                645                 650                 655

Asn Ile Asn Asn Arg Asp Gln Val Leu Cys Pro Pro Trp Glu Cys Asn
                660                 665                 670

Lys Cys Cys Ala Arg Ala Tyr Phe Pro
            675                 680

<210> SEQ ID NO 35
<211> LENGTH: 2319
<212> TYPE: DNA
<213> ORGANISM: Bos taurus

<400> SEQUENCE: 35
```

| | | | | |
|---|---|---|---|---|
| ctcagctgcg | ccgggtctca | caagacggtt | cccgaggtgg | cccaggcgcc | gtcccaccgc | 60 |
| cgacgccgcc | cgggccgccc | gggccgtccc | tccccgctgc | ccccgtcct | ccgcctccgc | 120 |
| ctcccccgc | cctcagcctc | ccttccccct | ccccgcccag | cagcggtcgc | tcgggcccgg | 180 |
| ctctcggtta | taagatggcg | cgcgctgagtg | gcggcggcgg | cggcggcggc | ggtggcgcgg | 240 |
| agcagggcca | ggctctgttc | aacggggaca | tggagcccga | ggccggcgcc | gcggcctctt | 300 |
| cggctgcgga | ccccgccatt | cccgaggagg | tgtggaatat | caaacaaatg | attaagttga | 360 |
| cacaggagca | tatagaggcc | ctattggaca | aatttggtgg | ggagcataat | ccaccatcaa | 420 |
| tatatctgga | ggcctatgaa | aatacacca | gcaagctaga | tgccctccaa | caaagagaac | 480 |
| aacagttatt | ggaatccctg | gggaatggaa | ctgattttc | tgtttctagc | ctgcatcaa | 540 |
| cggacaccgt | tacatcttct | tcctcttcta | gcctttcagt | gctgccttca | tctctttcag | 600 |
| tttttcaaaa | tcccacagat | gtgtcacgga | gcaaccccaa | gtcaccacaa | aaacctatcg | 660 |
| ttagagtctt | cctgcccaat | aaacagagga | cagtggtacc | tgcacggtgt | ggagtcacag | 720 |
| tccgggacag | cctgaagaag | gcactgatga | tgagaggtct | aatcccagag | tgctgtgctg | 780 |
| tttacagaat | tcaggatggg | gagaagaaac | caattggctg | ggacactgat | atttcctggc | 840 |
| ttactggaga | ggagttgcat | gtagaagtgt | tggagaatgt | tccacttaca | acacacaact | 900 |
| ttgtacgaa | aactttttc | acctagcat | ttgtgactt | ctgtagaaag | ctgcttttcc | 960 |
| agggattccg | ctgtcaaaca | tgtggttata | aatttcacca | gcgttgtagt | acagaggttc | 1020 |
| cactgatgtg | tgttaattat | gaccaactag | atttgctgtt | tgtctccaag | ttctttgaac | 1080 |
| accacccaat | accacaggag | gaggcctcct | tagcagagac | tacccttcca | tgtggctcat | 1140 |
| cccttctgc | acccccctcc | gattctattg | gccccccaat | tctcaccagt | ccatctcctt | 1200 |
| caaaatccat | tccaattcca | cagcctttcc | gaccagcaga | tgaagatcat | cgaaatcagt | 1260 |
| ttggacaacg | agaccggtcc | tcatcagctc | caaatgtgca | tataaacaca | atagaacccg | 1320 |
| tcaatattga | tgacttgatt | agagaccaag | ggtttcgtag | tgatggagga | tcaaccacag | 1380 |
| gtttatccgc | cacaccccct | gcctcattac | ctggctcact | ctctaatgtg | aaagcattgc | 1440 |
| agaaatctcc | aggacctcag | cgagaaagaa | agtcctcttc | atcctcagaa | gacaggaatc | 1500 |
| gaatgaaaac | gcttggtaga | cgggattcaa | gtgacgattg | ggagattcct | gatggacaga | 1560 |
| tcacagtggg | acaaagaatt | ggatcagggt | catttgggac | agtctacaag | ggaaagtggc | 1620 |
| atggtgatgt | ggcagtgaaa | atgttgaatg | tgacagcacc | cacacctcag | cagttacagg | 1680 |

```
ccttcaaaaa tgaagtagga gtactcagga aaacgcgaca tgtgaatatc ctcctcttca   1740
tgggttattc aacaaagcca caactggcta ttgttaccca gtggtgtgag ggctccagtt   1800
tatatcatca tctccacatc attgagacca aattcgagat gatcaaactt atagatattg   1860
cacggcagac tgcacagggc atggattact tacacgccaa gtcaatcatc cacagagacc   1920
tcaagagtaa taatattttt cttcatgaag acctcacagt aaaaataggt gattttggtc   1980
tagccacagt gaaatctcga tggagtgggt cccatcagtt tgaacagttg tctggatcca   2040
ttttgtggat ggcaccagaa gtaatcagaa tgcaagataa aaacccatat agctttcagt   2100
cagatgtata tgcatttggg attgttctgt atgaattgat gaccggacag ttaccttatt   2160
caaatatcaa caacagggac caggtgcttt gtcctccatg ggagtgtaat aaatgctgtg   2220
caagggctta cttcccatga gagaagtgag tgaccaacag aaggtctgtg caaggaaaag   2280
agacaaagcc acggatcaga agcacatggc cataactga                          2319
```

<210> SEQ ID NO 36
<211> LENGTH: 681
<212> TYPE: PRT
<213> ORGANISM: Bos taurus

<400> SEQUENCE: 36

```
Met Ala Ala Leu Ser Gly Gly Gly Gly Gly Gly Gly Gly Ala Glu
1               5                   10                  15

Gln Gly Gln Ala Leu Phe Asn Gly Asp Met Glu Pro Glu Ala Gly Ala
            20                  25                  30

Ala Ala Ser Ser Ala Ala Asp Pro Ala Ile Pro Glu Glu Val Trp Asn
        35                  40                  45

Ile Lys Gln Met Ile Lys Leu Thr Gln Glu His Ile Glu Ala Leu Leu
    50                  55                  60

Asp Lys Phe Gly Gly Glu His Asn Pro Pro Ser Ile Tyr Leu Glu Ala
65                  70                  75                  80

Tyr Glu Glu Tyr Thr Ser Lys Leu Asp Ala Leu Gln Gln Arg Glu Gln
                85                  90                  95

Gln Leu Leu Glu Ser Leu Gly Asn Gly Thr Asp Phe Ser Val Ser Ser
            100                 105                 110

Ser Ala Ser Thr Asp Thr Val Thr Ser Ser Ser Ser Ser Leu Ser
        115                 120                 125

Val Leu Pro Ser Ser Leu Ser Val Phe Gln Asn Pro Thr Asp Val Ser
130                 135                 140

Arg Ser Asn Pro Lys Ser Pro Gln Lys Pro Ile Val Arg Val Phe Leu
145                 150                 155                 160

Pro Asn Lys Gln Arg Thr Val Val Pro Ala Arg Cys Gly Val Thr Val
                165                 170                 175

Arg Asp Ser Leu Lys Lys Ala Leu Met Met Arg Gly Leu Ile Pro Glu
            180                 185                 190

Cys Cys Ala Val Tyr Arg Ile Gln Asp Gly Glu Lys Lys Pro Ile Gly
        195                 200                 205

Trp Asp Thr Asp Ile Ser Trp Leu Thr Gly Glu Glu Leu His Val Glu
    210                 215                 220

Val Leu Glu Asn Val Pro Leu Thr Thr His Asn Phe Val Arg Lys Thr
225                 230                 235                 240

Phe Phe Thr Leu Ala Phe Cys Asp Phe Cys Arg Lys Leu Leu Phe Gln
                245                 250                 255

Gly Phe Arg Cys Gln Thr Cys Gly Tyr Lys Phe His Gln Arg Cys Ser
```

```
                260             265             270
Thr Glu Val Pro Leu Met Cys Val Asn Tyr Asp Gln Leu Asp Leu Leu
                275             280             285
Phe Val Ser Lys Phe Phe Glu His His Pro Ile Pro Gln Glu Glu Ala
                290             295             300
Ser Leu Ala Glu Thr Thr Leu Pro Cys Gly Ser Ser Pro Ser Ala Pro
305             310             315             320
Pro Ser Asp Ser Ile Gly Pro Pro Ile Leu Thr Ser Pro Ser Pro Ser
                325             330             335
Lys Ser Ile Pro Ile Pro Gln Pro Phe Arg Pro Ala Asp Glu Asp His
                340             345             350
Arg Asn Gln Phe Gly Gln Arg Asp Arg Ser Ser Ala Pro Asn Val
                355             360             365
His Ile Asn Thr Ile Glu Pro Val Asn Ile Asp Asp Leu Ile Arg Asp
                370             375             380
Gln Gly Phe Arg Ser Asp Gly Gly Ser Thr Thr Gly Leu Ser Ala Thr
385             390             395             400
Pro Pro Ala Ser Leu Pro Gly Ser Leu Ser Asn Val Lys Ala Leu Gln
                405             410             415
Lys Ser Pro Gly Pro Gln Arg Glu Arg Lys Ser Ser Ser Ser Ser Glu
                420             425             430
Asp Arg Asn Arg Met Lys Thr Leu Gly Arg Arg Asp Ser Ser Asp Asp
                435             440             445
Trp Glu Ile Pro Asp Gly Gln Ile Thr Val Gly Gln Arg Ile Gly Ser
                450             455             460
Gly Ser Phe Gly Thr Val Tyr Lys Gly Lys Trp His Gly Asp Val Ala
465             470             475             480
Val Lys Met Leu Asn Val Thr Ala Pro Thr Pro Gln Gln Leu Gln Ala
                485             490             495
Phe Lys Asn Glu Val Gly Val Leu Arg Lys Thr Arg His Val Asn Ile
                500             505             510
Leu Leu Phe Met Gly Tyr Ser Thr Lys Pro Gln Leu Ala Ile Val Thr
                515             520             525
Gln Trp Cys Glu Gly Ser Ser Leu Tyr His His Leu His Ile Ile Glu
                530             535             540
Thr Lys Phe Glu Met Ile Lys Leu Ile Asp Ile Ala Arg Gln Thr Ala
545             550             555             560
Gln Gly Met Asp Tyr Leu His Ala Lys Ser Ile Ile His Arg Asp Leu
                565             570             575
Lys Ser Asn Asn Ile Phe Leu His Glu Asp Leu Thr Val Lys Ile Gly
                580             585             590
Asp Phe Gly Leu Ala Thr Val Lys Ser Arg Trp Ser Gly Ser His Gln
                595             600             605
Phe Glu Gln Leu Ser Gly Ser Ile Leu Trp Met Ala Pro Glu Val Ile
                610             615             620
Arg Met Gln Asp Lys Asn Pro Tyr Ser Phe Gln Ser Asp Val Tyr Ala
625             630             635             640
Phe Gly Ile Val Leu Tyr Glu Leu Met Thr Gly Gln Leu Pro Tyr Ser
                645             650             655
Asn Ile Asn Asn Arg Asp Gln Val Leu Cys Pro Pro Trp Glu Cys Asn
                660             665             670
Lys Cys Cys Ala Arg Ala Tyr Phe Pro
                675             680
```

<210> SEQ ID NO 37
<211> LENGTH: 2661
<212> TYPE: DNA
<213> ORGANISM: Bos taurus

<400> SEQUENCE: 37

| | | | | | |
|---|---|---|---|---|---|
| tcagctgcgc | cgggtctcac | aagacggttc | ccgaggtggc | ccaggcgccg | tcccaccgcc | 60 |
| gacgccgccc | gggccgcccg | ggccgtccct | ccccgctgcc | cccgtcctc | cgcctccgcc | 120 |
| tcccccgcc | ctcagcctcc | cttccccctc | cccgcccagc | agcggtcgct | cgggcccggc | 180 |
| tctcggttat | aagatggcgg | cgctgagtgg | cggcggcggc | ggcggcggcg | gtggcgcgga | 240 |
| gcagggccag | gctctgttca | acggggacat | ggagcccgag | gccggcgccg | cggcctcttc | 300 |
| ggctgcggac | cccgccattc | ccgaggaggt | gtggaatatc | aaacaaatga | ttaagttgac | 360 |
| acaggagcat | atagaggccc | tattggacaa | atttggtggg | gagcataatc | caccatcaat | 420 |
| atatctggag | gcctatgaag | aatacaccag | caagctagat | gccctccaac | aaagagaaca | 480 |
| acagttattg | gaatccctgg | ggaatggaac | tgattttttct | gtttctagct | ctgcatcaac | 540 |
| ggacaccgtt | acatcttctt | cctcttctag | cctttcagtg | ctgccttcat | ctctttcagt | 600 |
| ttttcaaaat | cccacagatg | tgtcacggag | caaccccaag | tcaccacaaa | aacctatcgt | 660 |
| tagagtcttc | ctgcccaata | aacagaggac | agtggtacct | gcacggtgtg | gagtcacagt | 720 |
| ccgggacagc | ctgaagaagg | cactgatgat | gagaggtcta | atcccagagt | gctgtgctgt | 780 |
| ttacagaatt | caggatgggg | agaagaaacc | aattggctgg | gacactgata | tttcctggct | 840 |
| tactggagag | gagttgcatg | tagaagtgtt | ggagaatgtt | ccacttacaa | cacacaactt | 900 |
| tgtacgaaaa | acttttttca | ccttagcatt | ttgtgacttc | tgtagaaagc | tgcttttcca | 960 |
| gggattccgc | tgtcaaacat | gtggttataa | atttcaccag | cgttgtagta | cagaggttcc | 1020 |
| actgatgtgt | gttaattatg | accaactaga | tttgctgttt | gtctccaagt | tctttgaaca | 1080 |
| ccacccaata | ccacaggagg | aggcctcctt | agcagagact | acccttccat | gtggctcatc | 1140 |
| cccttctgca | cccccctccg | attctattgg | gccccaatt | ctcaccagtc | catctccttc | 1200 |
| aaaatccatt | ccaattccac | agccttttccg | accagcagat | gaagatcatc | gaaatcagtt | 1260 |
| tggacaacga | gaccggtcct | catcagctcc | aaatgtgcat | ataaacacaa | tagaacccgt | 1320 |
| caatattgat | gacttgatta | gagaccaagg | gtttcgtagt | gatggaggat | caaccacagg | 1380 |
| tttatccgcc | acaccccctg | cctcattacc | tggctcactc | tctaatgtga | aagcattgca | 1440 |
| gaaatctcca | ggacctcagc | gagaaagaaa | gtcctcttca | tcctcagaag | acaggaatcg | 1500 |
| aatgaaaacg | cttggtagac | gggattcaag | tgacgattgg | gagattcctg | atggacagat | 1560 |
| cacagtggga | caagaattg | gatcagggtc | atttgggaca | gtctacaagg | gaaagtggca | 1620 |
| tggtgatgtg | gcagtgaaaa | tgttgaatgt | gacagcaccc | acacctcagc | agttacaggc | 1680 |
| cttcaaaaat | gaagtaggag | tactcaggaa | acgcgacat | gtgaatatcc | tcctcttcat | 1740 |
| gggttattca | acaaagccac | aactggctat | tgttacccag | tggtgtgagg | gctccagttt | 1800 |
| atatcatcat | ctccacatca | ttgagaccaa | attcgagatg | atcaaactta | tagatattgc | 1860 |
| acggcagact | gcacagggca | tggattactt | acacgccaag | tcaatcatcc | acagagacct | 1920 |
| caagagtaat | aatatttttc | ttcatgaaga | cctcacagta | aaataggtg | attttggtct | 1980 |
| agccacagtg | aaatctcgat | ggagtgggtc | ccatcagttt | gaacagttgt | ctggatccat | 2040 |
| tttgtggatg | gcaccagaag | taatcagaat | gcaagataaa | aacccatata | gctttcagtc | 2100 |

```
agatgtatat gcatttggga ttgttctgta tgaattgatg accggacagt taccttattc    2160
aaatatcaac aacagggacc agtctgtgca aggaaaagag acaaagccac ggatcagaag    2220
cacatggcca taactgaaga ttttgtgaac tctcacaagg aaaaaatttg ctctttgaac    2280
aataagaagg aactcactaa aatgtaactg agaactgttc aacaggttga agctgaaag     2340 atgccattgg aactgacaaa atgtttctta acataaatg atgaaacagt gaaactacat    2400
aatatctcct ctggctgaaa cattcaagaa gtttaaaatg cttaagttaa aaataaaatc    2460
ctagtaaaca atggacttac tgtgcaacat agagaatatc ttacgataac ctgtaatgga    2520
aaagaatctg aaaagaatg tatataactg aatcactttg ctgtaaacta gaatctgaca    2580
caacactgta aatcactaca cttttctgtt gcatgccaaa gattatttaa taacgtcatt    2640
aaaaaattat tttaataatt a                                             2661
```

<210> SEQ ID NO 38
<211> LENGTH: 679
<212> TYPE: PRT
<213> ORGANISM: Bos taurus

<400> SEQUENCE: 38

```
Met Ala Ala Leu Ser Gly Gly Gly Gly Gly Gly Gly Gly Ala Glu
1               5                   10                  15

Gln Gly Gln Ala Leu Phe Asn Gly Asp Met Glu Pro Glu Ala Gly Ala
            20                  25                  30

Ala Ala Ser Ser Ala Ala Asp Pro Ala Ile Pro Glu Glu Val Trp Asn
        35                  40                  45

Ile Lys Gln Met Ile Lys Leu Thr Gln Glu His Ile Glu Ala Leu Leu
    50                  55                  60

Asp Lys Phe Gly Gly Glu His Asn Pro Pro Ser Ile Tyr Leu Glu Ala
65                  70                  75                  80

Tyr Glu Glu Tyr Thr Ser Lys Leu Asp Ala Leu Gln Gln Arg Glu Gln
                85                  90                  95

Gln Leu Leu Glu Ser Leu Gly Asn Gly Thr Asp Phe Ser Val Ser Ser
            100                 105                 110

Ser Ala Ser Thr Asp Thr Val Ser Ser Ser Ser Ser Leu Ser
        115                 120                 125

Val Leu Pro Ser Ser Leu Ser Val Phe Gln Asn Pro Thr Asp Val Ser
    130                 135                 140

Arg Ser Asn Pro Lys Ser Pro Gln Lys Pro Ile Val Arg Val Phe Leu
145                 150                 155                 160

Pro Asn Lys Gln Arg Thr Val Val Pro Ala Arg Cys Gly Val Thr Val
                165                 170                 175

Arg Asp Ser Leu Lys Lys Ala Leu Met Met Arg Gly Leu Ile Pro Glu
            180                 185                 190

Cys Cys Ala Val Tyr Arg Ile Gln Asp Gly Glu Lys Lys Pro Ile Gly
        195                 200                 205

Trp Asp Thr Asp Ile Ser Trp Leu Thr Gly Glu Glu Leu His Val Glu
    210                 215                 220

Val Leu Glu Asn Val Pro Leu Thr Thr His Asn Phe Val Arg Lys Thr
225                 230                 235                 240

Phe Phe Thr Leu Ala Phe Cys Asp Phe Cys Arg Lys Leu Leu Phe Gln
                245                 250                 255

Gly Phe Arg Cys Gln Thr Cys Gly Tyr Lys Phe His Gln Arg Cys Ser
            260                 265                 270
```

-continued

```
Thr Glu Val Pro Leu Met Cys Val Asn Tyr Asp Gln Leu Asp Leu Leu
        275                 280                 285
Phe Val Ser Lys Phe Phe Glu His His Pro Ile Pro Gln Glu Glu Ala
        290                 295                 300
Ser Leu Ala Glu Thr Thr Leu Pro Cys Gly Ser Ser Pro Ser Ala Pro
305                 310                 315                 320
Pro Ser Asp Ser Ile Gly Pro Pro Ile Leu Thr Ser Pro Ser Pro Ser
                325                 330                 335
Lys Ser Ile Pro Ile Pro Gln Pro Phe Arg Pro Ala Asp Glu Asp His
                340                 345                 350
Arg Asn Gln Phe Gly Gln Arg Asp Arg Ser Ser Ser Ala Pro Asn Val
            355                 360                 365
His Ile Asn Thr Ile Glu Pro Val Asn Ile Asp Asp Leu Ile Arg Asp
        370                 375                 380
Gln Gly Phe Arg Ser Asp Gly Gly Ser Thr Thr Gly Leu Ser Ala Thr
385                 390                 395                 400
Pro Pro Ala Ser Leu Pro Gly Ser Leu Ser Asn Val Lys Ala Leu Gln
                405                 410                 415
Lys Ser Pro Gly Pro Gln Arg Glu Arg Lys Ser Ser Ser Ser Ser Glu
                420                 425                 430
Asp Arg Asn Arg Met Lys Thr Leu Gly Arg Arg Asp Ser Ser Asp Asp
            435                 440                 445
Trp Glu Ile Pro Asp Gly Gln Ile Thr Val Gly Gln Arg Ile Gly Ser
        450                 455                 460
Gly Ser Phe Gly Thr Val Tyr Lys Gly Lys Trp His Gly Asp Val Ala
465                 470                 475                 480
Val Lys Met Leu Asn Val Thr Ala Pro Thr Pro Gln Gln Leu Gln Ala
                485                 490                 495
Phe Lys Asn Glu Val Gly Val Leu Arg Lys Thr Arg His Val Asn Ile
                500                 505                 510
Leu Leu Phe Met Gly Tyr Ser Thr Lys Pro Gln Leu Ala Ile Val Thr
            515                 520                 525
Gln Trp Cys Glu Gly Ser Ser Leu Tyr His His Leu His Ile Ile Glu
        530                 535                 540
Thr Lys Phe Glu Met Ile Lys Leu Ile Asp Ile Ala Arg Gln Thr Ala
545                 550                 555                 560
Gln Gly Met Asp Tyr Leu His Ala Lys Ser Ile Ile His Arg Asp Leu
                565                 570                 575
Lys Ser Asn Asn Ile Phe Leu His Glu Asp Leu Thr Val Lys Ile Gly
                580                 585                 590
Asp Phe Gly Leu Ala Thr Val Lys Ser Arg Trp Ser Gly Ser His Gln
            595                 600                 605
Phe Glu Gln Leu Ser Gly Ser Ile Leu Trp Met Ala Pro Glu Val Ile
        610                 615                 620
Arg Met Gln Asp Lys Asn Pro Tyr Ser Phe Gln Ser Asp Val Tyr Ala
625                 630                 635                 640
Phe Gly Ile Val Leu Tyr Glu Leu Met Thr Gly Gln Leu Pro Tyr Ser
                645                 650                 655
Asn Ile Asn Asn Arg Asp Gln Ser Val Gln Gly Lys Glu Thr Lys Pro
                660                 665                 670
Arg Ile Arg Ser Thr Trp Pro
            675
```

```
<210> SEQ ID NO 39
<211> LENGTH: 7434
<212> TYPE: DNA
<213> ORGANISM: Bos taurus

<400> SEQUENCE: 39
acaccgttac atcttcttcc tcttctagcc tttcagtgct gccttcatct ctttcagttt      60
ttcaaaatcc cacagatgtg tcacggagca accccaagtc accacaaaaa cctatcgtta     120
gagtcttcct gcccaataaa cagaggacag tggtacctgc acggtgtgga gtcacagtcc     180
gggacagcct gaagaaggca ctgatgatga gaggtctaat cccagagtgc tgtgctgttt     240
acagaattca ggatggggag aagaaaccaa ttggctggga cactgatatt tcctggctta     300
ctggagagga gttgcatgta gaagtgttgg agaatgttcc acttacaaca cacaactttg     360
tacgaaaaac ttttttcacc ttagcatttt gtgacttctg tagaaagctg cttttccagg     420
gattccgctg tcaaacatgt ggttataaat ttcaccagcg ttgtagtaca gaggttccac     480
tgatgtgtgt taattatgac caactagatt tgctgtttgt ctccaagttc tttgaacacc     540
acccaatacc acaggaggag gcctccttag cagagactac ccttccatgt ggctcatccc     600
cttctgcacc ccctccgat tctattgggc cccaattct caccagtcca tctccttcaa      660
aatccattcc aattccacag cctttccgac cagcagatga agatcatcga aatcagtttg     720
gacaacgaga ccggtcctca tcagctccaa atgtgcatat aaacacaata gaacccgtca     780
atattgatga cttgattaga gaccaagggt ttcgtagtga tggaggatca accacaggtt     840
tatccgccac accccctgcc tcattacctg gctcactctc taatgtgaaa gcattgcaga     900
aatctccagg acctcagcga gaaagaaagt cctcttcatc ctcagaagac aggaatcgaa     960
tgaaaacgct tggtagacgg gattcaagtg acgattggga gattcctgat ggacagatca    1020
cagtgggaca aagaattgga tcagggtcat ttgggacagt ctacaaggga aagtggcatg    1080
gtgatgtggc agtgaaaatg ttgaatgtga cagcacccac acctcagcag ttacaggcct    1140
tcaaaaatga agtaggagta ctcaggaaaa cgcgacatgt gaatatcctc ctcttcatgg    1200
gttattcaac aaaagccacaa ctggctattg ttacccagtg gtgtgagggc tccagtttat    1260
atcatcatct ccacatcatt gagaccaaat tcgagatgat caaacttata gatattgcac    1320
ggcagactgc acagggcatg gattacttac acgccaagtc aatcatccac agagacctca    1380
agagtaataa tattttttctt catgaagacc tcacagtaaa aataggtgat tttggtctag    1440
ccacagtgaa atctcgatgg agtgggtccc atcagtttga acagttgtct ggatccattt    1500
tgtggatggc accagaagta atcagaatgc aagataaaaa cccatatagc tttcagtcag    1560
atgtatatgc atttgggatt gttctgtatg aattgatgac cggacagtta ccttattcaa    1620
atatcaacaa cagggaccag ataatttttta tggtgggacg aggatatctg tctccagatc    1680
tcagtaaggt acggagtaac tgtccaaaag ccatgaagag attaatggca gagtgcctaa    1740
aaaagaaaag agatgaaaga ccactctttc cccaagtagg aaagactctc taagcaagac    1800
gacaaaattc agaagttatc agggaaaaag ataagcagat tctcgcctct attgagctgc    1860
tggcccgctc attgccaaaa attccaccgcga gtgcatcaga accctccttg aatcgggctg    1920
gcttccaaac agaggatttt agtctatatg cttgtgcttc tccaaaaaca cccattcagg    1980
cagggggata tggagaattt gcagccttca gtagccacac ccatcatgac agcatctact    2040
cttatttctt aagtcttgtg ttcgtacaat ttgttaacat caaaacacag ttctgttcct    2100
caactctttt taaagttaaa attttcagt gcataagctg gtgtggaaca gaaggaaatt    2160
```

```
tcccatccaa caaaagaggg aagaatgttt taggaaccag aattctctgc tgccagtgtt    2220
tcttcttcaa cacaaatatc acaagtctgc ccactcccag gaagaaagag gagagaccct    2280
gagttctgac cttttgatgg tcaggcatga tggaaagaaa ctgctgctac agcttgggag    2340
atttgctctg ggaagtctgc cagtcaactt tgcccttcta accaccagat caatatgtgg    2400
ctgatcatct gatggggcag ttgcaatcac caagccttgt tctctttcct gttctgggat    2460
tgtgttgtgg aaccctttc cctagccacc accagttcat ttctgaggga tggaacaaaa    2520
atgcagcatg cccttcctgt gtggtgcatg ttcagtcctt gacaaatttt taccaaaatg    2580
aagctacttt atttaaaagg agggtgagag gtgaggaggt cacttgggt gtggcggaaa     2640 gggaatgctg catcttttc ctgggctgct ggggctctgg ccttggcttg ccagccggaa     2700
gcgctggcac gcatcgcctt cttttcccat tgggtccagc aatgaagacg agtgtttggg    2760 gtttttttt tctccaccat gtagcaagtt ctcaggaaaa tacaattgat atcttcctcc     2820
taagctcttc caatcagtca ccaagtactt atgtggttac tttgtccagg gcacaaaatg    2880
cctgtatcta attaaaagcc tacaaaactg cttgataaca gttttgaatg tgagacattt    2940
atgtaattta aatgtaaggt acaagtttta atttctgagt ttcttctatt atattttat    3000 taaaaaaga aaataatttt cagattgaat tggagtaaaa taatattact tcccactaga     3060
attatatatc ctggaaaatt gtattttgt tacataagca gcttttaaag aaagatcatt     3120
acccttttct ctacataaat atatgggag tcttagccta atgacaaata tttataattt     3180
ttaaattaat ggtacttgct ggatccatac taacatcttt actaataccct cattgtttct    3240 tccaacttac tcctcacta catcctacat cttcttccta gtcttttatc tagaatatgc     3300
aacctcaaat aaaaatggtg gtgtcctcat tcattctcct ccttccttt ttcccaagcc     3360 tgatcttcaa aaggttggtt aatttggcag ctgagttcct ccccaggcag agaatagacc    3420
aattttaggt gtattgggac tgagggagga tgtgtaaaga ttaacatcag taaagaaccg    3480
ctgtggagta attaagaact tgttctttta taactggaga atataaccta accctaacat    3540
ccctcagcct ttactaaagt gtggcgtaaa tcacagtagt agcaaagaaa gtgactctgg    3600
atgtgttcct ggccagtacc tcccttatca tgaatgtaga ctctctcatc aagatttagg    3660
aatataaatc aaatcaaatg tgcccagcca agctatgtag taagggactt gaacaatatt    3720
aggcagaacc tataaaataa atcagggaat tagaaattat ttaagttttt caaattgtaa    3780
attgccccgg tgtctttcag cctactgcca ttattttgc tacaatacct acatttcaga    3840
ggagggccta ctgaaaattc catgcaagtg gaaaataatc ctcaagttat taatgagttt    3900
gaaaagcaat gagttcttaa gtctttgtga gtagagcaag atcctacaaa attcagaaat    3960
agtaaaaatg gattcatgct gatttgaaga gcatctgtgt gcataatata atgctgcatc    4020
tcttttaaaa gcagtctatt tttcttttta aatttgtccc catagatgct tttgaacatg    4080
aacatgctta tgttacccttt tccgaggttg ggaagagcca ggagctctca ggcagggccc    4140
cctccctcag ctgggcagga gctgctcagg aggagctagt tatagaggaa gcttagcgtt    4200
ggcattttca aaattcaagg tgataacgct ttcttcttcc tttctgtttt agaatagatt    4260
gctgtctgat ttgaaaaagg gaaatagatt tgatctcaaa tgaatctgtg cccagaagcc    4320
aggctcaggg tattcagaga tttgtatagt gccctcaaaa aataacaaaa ttttagcttt    4380 cctttttct tcttttctcc atcaaattct ttttctcta gtttacaaat gacatggaaa      4440
aggaatttcc cctgagtttt gtatgccttt tttttttgg cttagactat agataggcgt    4500
gttgagctcc taagaaaata caaggaggaa ctctttgttg tgcagagcac tttatgagta    4560
```

```
gtttgtgtgg ataatatgtg actgcttccc tgacgagctt gtgaggctgt acttatgtct   4620
ttcctgtaag gcagcttcag tgccttctgt agtgtatata aggaaagatt acgccttctg   4680
aaaaatctca gagcaaccat aagattattt taaaatatgt agtatgactg atggactttt   4740
tcatcattaa attagtctag catctaaact tttaccactg aaataatatt gaccaaaaag   4800
caatttataa aaggtatttg tgaatagaaa atacaatgtg atcatttgta cttatgtgca   4860
ccttaaaaga ggaattctgt ctagctgtca aattctggtt ccttaacatc cagtccttga   4920
ttgtgattga gatctggtag gacgtgctgg ggcacgctag cagataaaat cccgtatact   4980
ttaggataga tgttacattt atgtcagtgt tggcaaagag cattgtgtag taataaagaa   5040
ttcaagactt cagcaatgtc aacctgaaac tttgtaaata tttcctagat tgttatttga   5100
tgcagtcaca gctctttatc acacaatgtt gtctttccct catcaggcaa ttttagaact   5160
gctgcacacc cctcctcaga tctcacctgc ccctcctgta cattcacctc tccagccttg   5220
tgcacacctc atttagcttt agtttgaaac acattgcagg gttcaggtga cctcttcaaa   5280
aactacctcc tcagaatgag gtaatgaata gttatttatt ttaaaatatg aaaagtcagg   5340
agctctagaa tatgaagatg atctaagatt ttaacttttta tgtatacttg ttgagcactc   5400
tccttttgtc ctaaagggca ttatacattt aagcagtaat actgaaaaat gtagctcaga   5460
gtaactgaat gttgttgaaa gtggtgccag aatctgtttt aggggtacgt atcagaatct   5520
taatcttaaa tcggttacat gaaattaaat agttaatggt aacacttgac taacagatat   5580
aattttaatt ttcggtaggc ttttagcaag acagtaagta catcttcata atgagttagc   5640
cacagcttca tcacatgcac agattttcct gttgagagac tgcccagtta agagggtaga   5700
atgatgaacc attttttcagg attctcttct ttgtccaaac tggcattgtg agtgctagaa   5760
tatcagcact ttcaaactag tgattccaac tattaggcta ttaaaaagca aaacaaacca   5820
aacaaaccat agccagacat gggaagttta ctatgagtat aaacagcaaa tagcttacag   5880
gtcatacatt gaaatggtgt aggtaaggcg ttagaaaaat accttgacaa tttgccaaat   5940
gatcttactg tgccttcatg atgcaataaa aaaaaaaaaa atttagcata atcagtgat   6000 ttgtgaagag agcagccacc ctggtctaac tcagctgtgt taatattttt tagcgtgcaa   6060
tttagactgc aaagataaat gcactaaaga gtttatagcc aaaatcacat ttaaaaaatg   6120
agagaaaaca caggtaaatt ttcagtgaac aaaattattt ttttaaagta cataatccct   6180
agtatagtca gatatattta tcacatagag caaataggtt gaaatcacaa ttcagtgaca   6240
tttctagaga aactttttct actcccatag gttcttcaaa gcatggaact tttatataac   6300
agaaatgtgt gacggtcatt ttaaattgct gtagtttggg gctgaagtac tgtgtgctgg   6360
gcagcaatca catgtattaa ctagtgagaa aggagaaatt aagatatagg acagaatttg   6420
attttcttgt tcccagatta ctgctgccaa cctagacact gagtttccag aggctgaaac   6480
gtaaacttgc agctcagcaa ctgttttgca aagttagtgg gactgtcctg cttatgctgt   6540
tcaaaaatgc tctgagggcc aggtggggcc tccaggggct cctctctgag gggacatcag   6600
actagctaac gacctggcgg gcggatgtga accggacaca ctccatggtg tgcttccttgt   6660 atcggtccct cgccaccctc aagaaaggct tcagcgggtt ctctagacgt ctccactaag   6720
gtgtgttact aacagccatg ggttgttgag cacccgagga gtgcaatagc atctctgcat   6780
gattgtatat tggcccgaag agaatgaagt ggccagtgta ctcatgttcc atgttgctag   6840
ctctggtaaa ctgaaaatac tggtaagatt tttgttttat cagtacacta gagagtaagc   6900
```

-continued

```
tttgttttgt tgtttttaga taatgttttc acttccattt ggaaagacat ttaaattgag    6960
tttcagtcct aaattttgcc agtcatggta attagcagtt tctatcaggt attttttaagg   7020 tagaagagga tagaaacata agttctaaaa gcttaaggta accgtggttt attttaaaat    7080 gtttagggggg ggttagtctc tacctcaaaa aaagtgagtg aatctttttat ttcagcattc   7140 acaagttcgg ctgttgtttt tgtaatacat ttttttttta accttttgac cccccttttac   7200 ctaagtgtca atgtagtttt attaattact aagtcagttt cattaaaatg tttatttagc    7260
agttttgact aattgcaatg attaatatag ccagttgtgc atgaggacac agccagtgag    7320
tatatctggg ttttttttgt gatgcttttt ttcttaagac ttctgtagat ttatgaagta    7380
ctcattgaaa acaactaaaa tacgtttatt cgtgttaata tggaaaaaaa aaaa          7434
```

<210> SEQ ID NO 40
<211> LENGTH: 603
<212> TYPE: PRT
<213> ORGANISM: Bos taurus

<400> SEQUENCE: 40

```
Met Met Arg Gly Leu Ile Pro Glu Cys Cys Ala Val Tyr Arg Ile Gln
1               5                   10                  15

Asp Gly Glu Lys Lys Pro Ile Gly Trp Asp Thr Asp Ile Ser Trp Leu
                20                  25                  30

Thr Gly Glu Glu Leu His Val Glu Val Leu Glu Asn Val Pro Leu Thr
            35                  40                  45

Thr His Asn Phe Val Arg Lys Thr Phe Phe Thr Leu Ala Phe Cys Asp
        50                  55                  60

Phe Cys Arg Lys Leu Leu Phe Gln Gly Phe Arg Cys Gln Thr Cys Gly
65                  70                  75                  80

Tyr Lys Phe His Gln Arg Cys Ser Thr Glu Val Pro Leu Met Cys Val
                85                  90                  95

Asn Tyr Asp Gln Leu Asp Leu Leu Phe Val Ser Lys Phe Phe Glu His
                100                 105                 110

His Pro Ile Pro Gln Glu Glu Ala Ser Leu Ala Glu Thr Thr Leu Pro
            115                 120                 125

Cys Gly Ser Ser Pro Ser Ala Pro Ser Asp Ser Ile Gly Pro Pro
        130                 135                 140

Ile Leu Thr Ser Pro Ser Pro Ser Lys Ser Ile Pro Ile Pro Gln Pro
145                 150                 155                 160

Phe Arg Pro Ala Asp Glu Asp His Arg Asn Gln Phe Gly Gln Arg Asp
                165                 170                 175

Arg Ser Ser Ser Ala Pro Asn Val His Ile Asn Thr Ile Glu Pro Val
            180                 185                 190

Asn Ile Asp Asp Leu Ile Arg Asp Gln Gly Phe Arg Ser Asp Gly Gly
        195                 200                 205

Ser Thr Thr Gly Leu Ser Ala Thr Pro Pro Ala Ser Leu Pro Gly Ser
    210                 215                 220

Leu Ser Asn Val Lys Ala Leu Gln Lys Ser Pro Gly Pro Gln Arg Glu
225                 230                 235                 240

Arg Lys Ser Ser Ser Ser Glu Asp Arg Asn Arg Met Lys Thr Leu
                245                 250                 255

Gly Arg Arg Asp Ser Ser Asp Asp Trp Glu Ile Pro Asp Gly Gln Ile
            260                 265                 270

Thr Val Gly Gln Arg Ile Gly Ser Gly Ser Phe Gly Thr Val Tyr Lys
        275                 280                 285
```

Gly Lys Trp His Gly Asp Val Ala Val Lys Met Leu Asn Val Thr Ala
    290                 295                 300

Pro Thr Pro Gln Gln Leu Gln Ala Phe Lys Asn Glu Val Gly Val Leu
305                 310                 315                 320

Arg Lys Thr Arg His Val Asn Ile Leu Leu Phe Met Gly Tyr Ser Thr
                325                 330                 335

Lys Pro Gln Leu Ala Ile Val Thr Gln Trp Cys Glu Gly Ser Ser Leu
            340                 345                 350

Tyr His His Leu His Ile Ile Glu Thr Lys Phe Glu Met Ile Lys Leu
        355                 360                 365

Ile Asp Ile Ala Arg Gln Thr Ala Gln Gly Met Asp Tyr Leu His Ala
370                 375                 380

Lys Ser Ile Ile His Arg Asp Leu Lys Ser Asn Asn Ile Phe Leu His
385                 390                 395                 400

Glu Asp Leu Thr Val Lys Ile Gly Asp Phe Gly Leu Ala Thr Val Lys
                405                 410                 415

Ser Arg Trp Ser Gly Ser His Gln Phe Glu Gln Leu Ser Gly Ser Ile
            420                 425                 430

Leu Trp Met Ala Pro Glu Val Ile Arg Met Gln Asp Lys Asn Pro Tyr
        435                 440                 445

Ser Phe Gln Ser Asp Val Tyr Ala Phe Gly Ile Val Leu Tyr Glu Leu
450                 455                 460

Met Thr Gly Gln Leu Pro Tyr Ser Asn Ile Asn Asn Arg Asp Gln Ile
465                 470                 475                 480

Ile Phe Met Val Gly Arg Gly Tyr Leu Ser Pro Asp Leu Ser Lys Val
                485                 490                 495

Arg Ser Asn Cys Pro Lys Ala Met Lys Arg Leu Met Ala Glu Cys Leu
            500                 505                 510

Lys Lys Lys Arg Asp Glu Arg Pro Leu Phe Pro Gln Val Gly Lys Thr
        515                 520                 525

Leu Leu Ser Lys Arg Gln Asn Ser Glu Val Ile Arg Glu Lys Asp Lys
530                 535                 540

Gln Ile Leu Ala Ser Ile Glu Leu Leu Ala Arg Ser Leu Pro Lys Ile
545                 550                 555                 560

His Arg Ser Ala Ser Glu Pro Ser Leu Asn Arg Ala Gly Phe Gln Thr
                565                 570                 575

Glu Asp Phe Ser Leu Tyr Ala Cys Ala Ser Pro Lys Thr Pro Ile Gln
            580                 585                 590

Ala Gly Gly Tyr Gly Glu Phe Ala Ala Phe Lys
        595                 600

<210> SEQ ID NO 41
<211> LENGTH: 2295
<212> TYPE: DNA
<213> ORGANISM: Equus caballus
<220> FEATURE:
<221> NAME/KEY: misc_feature
<222> LOCATION: (79)..(79)
<223> OTHER INFORMATION: n is a, c, g, or t

<400> SEQUENCE: 41
atgaagacgc tgagcggcgg cggcggcggc gcggagcagg gccaggctct gttcaacggg      60
gacatggaac ccgaggcnc cgcgccggcg cccgcggcct cgtcggccgc ggaccctgcc      120
attcccgagg aggtatggaa tatcaaacaa atgattaaat tgacacagga acatatagag      180

```
gccctattgg acaaatttgg tggggagcat aatccaccat caatatatct ggaggcctat    240
gaagaataca ccagcaagct agatgccctc caacaaagag aacaacagtt attggaatcc    300
ctggggaatg gaactgattt ttctgtttct agttctgcat caacggacac cgttacatct    360
tcttcctctt ctagccttc agtgctacct tcatctcttt cagttttca aaatcccaca     420 gatgtgtcac ggagcaaccc taagtcacca caaaaaccta tcgttagagt cttcctgccc    480
aacaaacaga ggacagtggt acctgcaagg tgtggcgtta cagtccggga cagtctaaag    540
aaagcactga tgatgagagg tctaatccca gagtgctgtg ctgtttacag aattcaggat    600
ggagagaaga aaccaattgg ctgggacact gatatttcct ggctcactgg agaggaattg    660
catgtagaag tgttggagaa tgttccactt acaacacaca actttgtacg aaaacttttt    720
ttcaccttag cattttgtga cttttgtcga aagctgcttt tccagggttt ccgctgtcaa    780
acatgtggtt ataaatttca ccagcgttgt agtacagagg ttccactgat gtgtgttaat    840
tatgaccaac ttgatttgct gtttgtctcc aagttctttg aacaccaccc agtatcacag    900
gaggaggcct ccttagcaga gactgccctt acatctggat catcccttc tgcaccccc     960 tccgattcca ttgggcccca aattctcacc agtccatctc cttcaaaatc cattccaatt   1020
ccacagcctt tccgaccagc agatgaagat catcgaaatc agtttggaca acgagaccgg   1080
tcctcatcag ctccaaatgt acatataaac acaatagaac ctgtcaatat tgatgacttg   1140
attagagacc aagggtttcg tagtgatgga ggatcaacca caggtttatc tgccaccccc   1200
cctgcctcat tacctggctc actcactaat gtgaaggcat tacagaaatc tccaggacct   1260
caacgggaaa ggaaatcatc ttcatcctca gaagacagga tcgaatgaa aactcttggt    1320 agacgggatt caagtgacga ttgggagatt cctgatgggc agatcacagt gggacaaaga   1380
attggatctg ggtcatttgg gacagtctac aagggaaagt ggcatggtga tgtggcagtg   1440
aaaatgttga atgtgacagc acccacacct cagcagttac aggccttcaa aaatgaagta   1500
ggagtactca ggaaaactcg acatgtgaat atcctactct tcatgggcta ttcaacaaag   1560
ccacaactgg ctattgttac ccagtggtgt gagggctcca gcttatatca ccatctccac   1620
atcattgaga ccaaatttga gatgatcaaa cttatagata ttgctcggca aactgcacag   1680
ggcatggatt acttacacgc caagtcaatc atccacagag acctcaagag taataatatt   1740
tttcttcatg aagacctcac agtaaaaata ggtgatttg gtctagccac agtgaaatct    1800
cgatggagtg ggtcccatca gtttgaacag ttgtctggat ccatttttgtg gatggcacca   1860 gaagtaatca gaatgcaaga taaaaacccg tatagctttc aatcagatgt atatgccttt   1920
gggattgttc tgtatgaatt gatgactgga cagttacctt attcaaacat caacaacagg   1980
gaccagataa tttttatggt gggaagagga tatctatctc cagatctcag taaggtacgg   2040
agtaactgtc caaaagccat gaagagatta atggcagagt gcctaaaaaa gaaaagagac   2100
gagagaccac tcttccccca aattctcgcc tctattgagc tgctggcccg ctcattgcca   2160
aaaattcacc gcagtgcatc agagccctcc ttgaatcggg ctggcttcca gacagaggat   2220
tttagtctat atgcttgtgc ttctccgaaa acacccatcc aggcaggggg atatggtgcg   2280
tttcctgtcc actga                                                    2295

<210> SEQ ID NO 42
<211> LENGTH: 764
<212> TYPE: PRT
<213> ORGANISM: Equus caballus
<220> FEATURE:
<221> NAME/KEY: misc_feature
```

<222> LOCATION: (27)..(27)
<223> OTHER INFORMATION: Xaa can be any naturally occurring amino acid

<400> SEQUENCE: 42

```
Met Lys Thr Leu Ser Gly Gly Gly Gly Ala Glu Gln Gly Gln Ala
1               5                   10                  15

Leu Phe Asn Gly Asp Met Glu Pro Gly Xaa Ala Pro Ala Pro Ala
            20                  25                  30

Ala Ser Ser Ala Ala Asp Pro Ala Ile Pro Glu Glu Val Trp Asn Ile
        35                  40                  45

Lys Gln Met Ile Lys Leu Thr Gln Glu His Ile Glu Ala Leu Leu Asp
    50                  55                  60

Lys Phe Gly Gly Glu His Asn Pro Pro Ser Ile Tyr Leu Glu Ala Tyr
65                  70                  75                  80

Glu Glu Tyr Thr Ser Lys Leu Asp Ala Leu Gln Gln Arg Glu Gln Gln
                85                  90                  95

Leu Leu Glu Ser Leu Gly Asn Gly Thr Asp Phe Ser Val Ser Ser Ser
            100                 105                 110

Ala Ser Thr Asp Thr Val Thr Ser Ser Ser Ser Ser Leu Ser Val
        115                 120                 125

Leu Pro Ser Ser Leu Ser Val Phe Gln Asn Pro Thr Asp Val Ser Arg
130                 135                 140

Ser Asn Pro Lys Ser Pro Gln Lys Pro Ile Val Arg Val Phe Leu Pro
145                 150                 155                 160

Asn Lys Gln Arg Thr Val Val Pro Ala Arg Cys Gly Val Thr Val Arg
                165                 170                 175

Asp Ser Leu Lys Lys Ala Leu Met Met Arg Gly Leu Ile Pro Glu Cys
            180                 185                 190

Cys Ala Val Tyr Arg Ile Gln Asp Gly Glu Lys Lys Pro Ile Gly Trp
        195                 200                 205

Asp Thr Asp Ile Ser Trp Leu Thr Gly Glu Glu Leu His Val Glu Val
210                 215                 220

Leu Glu Asn Val Pro Leu Thr Thr His Asn Phe Val Arg Lys Thr Phe
225                 230                 235                 240

Phe Thr Leu Ala Phe Cys Asp Phe Cys Arg Lys Leu Leu Phe Gln Gly
                245                 250                 255

Phe Arg Cys Gln Thr Cys Gly Tyr Lys Phe His Gln Arg Cys Ser Thr
            260                 265                 270

Glu Val Pro Leu Met Cys Val Asn Tyr Asp Gln Leu Asp Leu Leu Phe
        275                 280                 285

Val Ser Lys Phe Phe Glu His His Pro Val Ser Gln Glu Glu Ala Ser
290                 295                 300

Leu Ala Glu Thr Ala Leu Thr Ser Gly Ser Ser Pro Ser Ala Pro Pro
305                 310                 315                 320

Ser Asp Ser Ile Gly Pro Gln Ile Leu Thr Ser Pro Ser Pro Ser Lys
                325                 330                 335

Ser Ile Pro Ile Pro Gln Pro Phe Arg Pro Ala Asp Glu Asp His Arg
            340                 345                 350

Asn Gln Phe Gly Gln Arg Asp Arg Ser Ser Ala Pro Asn Val His
        355                 360                 365

Ile Asn Thr Ile Glu Pro Val Asn Ile Asp Asp Leu Ile Arg Asp Gln
370                 375                 380

Gly Phe Arg Ser Asp Gly Gly Ser Thr Thr Gly Leu Ser Ala Thr Pro
385                 390                 395                 400
```

Pro Ala Ser Leu Pro Gly Ser Leu Thr Asn Val Lys Ala Leu Gln Lys
            405                 410                 415

Ser Pro Gly Pro Gln Arg Glu Arg Lys Ser Ser Ser Ser Glu Asp
        420                 425                 430

Arg Asn Arg Met Lys Thr Leu Gly Arg Arg Asp Ser Ser Asp Asp Trp
            435                 440                 445

Glu Ile Pro Asp Gly Gln Ile Thr Val Gly Gln Arg Ile Gly Ser Gly
450                 455                 460

Ser Phe Gly Thr Val Tyr Lys Gly Lys Trp His Gly Asp Val Ala Val
465                 470                 475                 480

Lys Met Leu Asn Val Thr Ala Pro Thr Pro Gln Gln Leu Gln Ala Phe
            485                 490                 495

Lys Asn Glu Val Gly Val Leu Arg Lys Thr Arg His Val Asn Ile Leu
            500                 505                 510

Leu Phe Met Gly Tyr Ser Thr Lys Pro Gln Leu Ala Ile Val Thr Gln
            515                 520                 525

Trp Cys Glu Gly Ser Ser Leu Tyr His His Leu His Ile Ile Glu Thr
        530                 535                 540

Lys Phe Glu Met Ile Lys Leu Ile Asp Ile Ala Arg Gln Thr Ala Gln
545                 550                 555                 560

Gly Met Asp Tyr Leu His Ala Lys Ser Ile Ile His Arg Asp Leu Lys
            565                 570                 575

Ser Asn Asn Ile Phe Leu His Glu Asp Leu Thr Val Lys Ile Gly Asp
            580                 585                 590

Phe Gly Leu Ala Thr Val Lys Ser Arg Trp Ser Gly Ser His Gln Phe
            595                 600                 605

Glu Gln Leu Ser Gly Ser Ile Leu Trp Met Ala Pro Glu Val Ile Arg
        610                 615                 620

Met Gln Asp Lys Asn Pro Tyr Ser Phe Gln Ser Asp Val Tyr Ala Phe
625                 630                 635                 640

Gly Ile Val Leu Tyr Glu Leu Met Thr Gly Gln Leu Pro Tyr Ser Asn
            645                 650                 655

Ile Asn Asn Arg Asp Gln Ile Ile Phe Met Val Gly Arg Gly Tyr Leu
            660                 665                 670

Ser Pro Asp Leu Ser Lys Val Arg Ser Asn Cys Pro Lys Ala Met Lys
            675                 680                 685

Arg Leu Met Ala Glu Cys Leu Lys Lys Lys Arg Asp Glu Arg Pro Leu
690                 695                 700

Phe Pro Gln Ile Leu Ala Ser Ile Glu Leu Leu Ala Arg Ser Leu Pro
705                 710                 715                 720

Lys Ile His Arg Ser Ala Ser Glu Pro Ser Leu Asn Arg Ala Gly Phe
            725                 730                 735

Gln Thr Glu Asp Phe Ser Leu Tyr Ala Cys Ala Ser Pro Lys Thr Pro
            740                 745                 750

Ile Gln Ala Gly Gly Tyr Gly Ala Phe Pro Val His
            755                 760

<210> SEQ ID NO 43
<211> LENGTH: 2678
<212> TYPE: DNA
<213> ORGANISM: Gallus gallus

<400> SEQUENCE: 43 tcccctccc tcgccccagc gcttcgatcc aagatggcgg cgctgagcag cggcagcagc    60

```
gccgaggggg cctcgctctt caacggggac atggagcccg agccgccgcc gcccgtgctg    120
ggcgcctgct acgccgggag cggcggcggc gacccggcca tcccggagga ggtgtggaat    180
atcaaacaga tgattaaatt aacacaagaa catatagaag cgctgttaga caagtttgga    240
ggagagcata acccaccatc aatatattta gaggcctatg aggagtacac cagcaaacta    300
gatgctctac agcagagaga acagcagtta ttggaatcca tgggaaatgg aactgatttc    360
tctgtttcca gttcagcttc aacggacaca gttgcatcat cttcctcctc tagcctctct    420
gtagcacctt catcccttc agtttatcaa atcctactg atatgtcgcg aataaccct     480
aagtctccac agaagcctat tgttagagtc ttcctgccca caagcaaag gactgtggtt     540
ccggcaagat gtgggtgac agtccgagac agcctgaaga aagctctgat gatgagaggt    600
cttattccag aatgctgtgc tgtttacaga atacaggatg agagaagaa gccaattggc    660
tgggacactg acatttcctg ctaaccgga gaggagttac acgtggaggt cttggagaat    720
gtgccactca caacacacaa ttttgtacga aaacattct tcacgttagc gttctgcgac    780
ttctgtcgaa agctgctttt ccagggattc cgatgccaga catgtggcta caaatttcac    840
cagcgctgta gcacagaagt gccactgatg tgtgttaact acgaccaact cgatttgctg    900
tttgtctcca gttctttga acatcacccc atatcgcagg aggagaccac cttaggagag    960
accaccccgg catcgggatc gtacccctca gtgcccccat cagattctgt tggaccacca  1020
attctcccta gtccttctcc ttcaaaatcc attccaatcc acagcccctt ccgaccagca  1080
gatgaagacc atcggaatca gtttgggcaa cgcgaccgat cctcttcagc tcccaatgtt  1140
cacatcaata caattgagcc agtcaatatt gatgacttga ttagagacca gggtgtacga  1200
ggagagggag ccccttttgaa ccagctgatg cgctgtcttc ggaaatacca atcccggact  1260
cccagtcccc tccttcattc tgtccccagt gaaatagtgt ttgattttga gcctggccca  1320
gtgttcagag gttcaactgc aggttttgtct gcaacacctc ctgcatcttt gcctgggtca  1380
cttaccaatg tgaaagcatt acagaaatca ccaggccccc aacgggaaag gaaatcatcc  1440
tcatcctcag aagacagaaa taggatgaaa acccttggtc gacgagattc aagtgatgat  1500
tgggaaatac cagatgggca gatcacagtt ggacaaagga taggatctgg atcatttgga  1560
acagtctaca aggaaagtg gcatggtgac gtggcagtga aaatgttgaa tgttacagca  1620
cccacacctc aacagttaca ggctttcaaa aatgaagtag gagtgctcag gaaaacacgg  1680
catgtgaata tcctactttt tatgggttat tcaacaaaac ctcagttggc tattgttaca  1740
cagtggtgtg agggtccag cttatatcac catctgcaca taattgagac caagtttgaa  1800
atgatcaaac taattgatat tgcacgacag actgcacaag gcatggatta tttgcatgcc  1860
aagtcaatca tccacagaga cctcaagagt aataatattt tcttcatga agacctcaca  1920
gtaaaaatag gtgacttcgg tctggctaca gtgaaatcac gatggagtgg atctcatcaa  1980
tttgaacagt tatctggatc aattctatgg atggcaccgg aagtgatcag gatgcaagac  2040
aaaaacccat atagctttca gtcagatgtg tatgcattcg ggattgtgct ttatgaactg  2100
atgactggac agttaccata ctcaaacatc aacaacaggg accagataat ttttatggtg  2160
ggacgaggat atctatctcc agacctcagt aaagtaagaa gtaactgtcc aaaagctatg  2220
aagagactaa tggcagaatg cttgaaaaag aaaagagatg agagacctct ttttccacag  2280
attcttgcct ccattgagct tctggccggg tcgttgccaa aaattcaccg cagtgcatct  2340
gagccgtcac taaaccgggc tggcttccag accgaggatt cagtctgta tgcttgtgct  2400
```

```
tctccaaaaa cgcccatcca agcaggggga tacggtgggt tccagtaca ctgaaaagaa    2460 atgtgaaagc gtgtgcctgt ttgctcatgt gctggtgtgt tcctgtgtgt gcaacgcata    2520
cgtacgttct cagttcctac cagcgacttt ttaaggttta ctgagggaat gaagactcat    2580
ttcctaacat ggggcattga acgtcctgag cacaagtcag tgctggtaag gaatgtcttg    2640
ggaacagctg gcaagaagaa ttagaaggta cttaaagg                           2678
```

```
<210> SEQ ID NO 44
<211> LENGTH: 806
<212> TYPE: PRT
<213> ORGANISM: Gallus gallus

<400> SEQUENCE: 44
```

| | | | | | | | | | | | | | | |
|---|---|---|---|---|---|---|---|---|---|---|---|---|---|---|
| Met | Ala | Ala | Leu | Ser | Ser | Gly | Ser | Ser | Ala | Glu | Gly | Ala | Ser | Leu | Phe |
| 1 | | | | 5 | | | | | 10 | | | | | 15 | |

Asn Gly Asp Met Glu Pro Glu Pro Pro Pro Val Leu Gly Ala Cys
                20                  25                  30

Tyr Ala Gly Ser Gly Gly Asp Pro Ala Ile Pro Glu Glu Val Trp
        35                  40                  45

Asn Ile Lys Gln Met Ile Lys Leu Thr Gln Glu His Ile Glu Ala Leu
50                  55                  60

Leu Asp Lys Phe Gly Gly Glu His Asn Pro Ser Ile Tyr Leu Glu
65                  70                  75                  80

Ala Tyr Glu Glu Tyr Thr Ser Lys Leu Asp Ala Leu Gln Gln Arg Glu
                85                  90                  95

Gln Gln Leu Leu Glu Ser Met Gly Asn Gly Thr Asp Phe Ser Val Ser
            100                 105                 110

Ser Ser Ala Ser Thr Asp Thr Val Ala Ser Ser Ser Ser Ser Leu
        115                 120                 125

Ser Val Ala Pro Ser Ser Leu Ser Val Tyr Gln Asn Pro Thr Asp Met
130                 135                 140

Ser Arg Asn Asn Pro Lys Ser Pro Gln Lys Pro Ile Val Arg Val Phe
145                 150                 155                 160

Leu Pro Asn Lys Gln Arg Thr Val Val Pro Ala Arg Cys Gly Val Thr
                165                 170                 175

Val Arg Asp Ser Leu Lys Lys Ala Leu Met Met Arg Gly Leu Ile Pro
            180                 185                 190

Glu Cys Cys Ala Val Tyr Arg Ile Gln Asp Gly Glu Lys Lys Pro Ile
        195                 200                 205

Gly Trp Asp Thr Asp Ile Ser Trp Leu Thr Gly Glu Glu Leu His Val
    210                 215                 220

Glu Val Leu Glu Asn Val Pro Leu Thr Thr His Asn Phe Val Arg Lys
225                 230                 235                 240

Thr Phe Phe Thr Leu Ala Phe Cys Asp Phe Cys Arg Lys Leu Leu Phe
                245                 250                 255

Gln Gly Phe Arg Cys Gln Thr Cys Gly Tyr Lys Phe His Gln Arg Cys
            260                 265                 270

Ser Thr Glu Val Pro Leu Met Cys Val Asn Tyr Asp Gln Leu Asp Leu
        275                 280                 285

Leu Phe Val Ser Lys Phe Phe Glu His His Pro Ile Ser Gln Glu Glu
    290                 295                 300

Thr Thr Leu Gly Glu Thr Thr Pro Ala Ser Gly Ser Tyr Pro Ser Val
305                 310                 315                 320

Pro Pro Ser Asp Ser Val Gly Pro Pro Ile Leu Pro Ser Pro Ser Pro

```
            325                 330                 335
Ser Lys Ser Ile Pro Ile Pro Gln Pro Phe Arg Pro Ala Asp Glu Asp
            340                 345                 350
His Arg Asn Gln Phe Gly Gln Arg Asp Arg Ser Ser Ala Pro Asn
            355                 360             365
Val His Ile Asn Thr Ile Glu Pro Val Asn Ile Asp Asp Leu Ile Arg
            370                 375                 380
Asp Gln Gly Val Arg Gly Glu Gly Ala Pro Leu Asn Gln Leu Met Arg
385                 390                 395                 400
Cys Leu Arg Lys Tyr Gln Ser Arg Thr Pro Ser Pro Leu Leu His Ser
                405                 410                 415
Val Pro Ser Glu Ile Val Phe Asp Phe Glu Pro Gly Pro Val Phe Arg
            420                 425                 430
Gly Ser Thr Ala Gly Leu Ser Ala Thr Pro Ala Ser Leu Pro Gly
            435                 440             445
Ser Leu Thr Asn Val Lys Ala Leu Gln Lys Ser Pro Gly Pro Gln Arg
    450                 455                 460
Glu Arg Lys Ser Ser Ser Ser Glu Asp Arg Asn Arg Met Lys Thr
465                 470                 475             480
Leu Gly Arg Arg Asp Ser Ser Asp Asp Trp Glu Ile Pro Asp Gly Gln
                485                 490                 495
Ile Thr Val Gly Gln Arg Ile Gly Ser Gly Ser Phe Gly Thr Val Tyr
            500                 505                 510
Lys Gly Lys Trp His Gly Asp Val Ala Val Lys Met Leu Asn Val Thr
        515                 520                 525
Ala Pro Thr Pro Gln Gln Leu Gln Ala Phe Lys Asn Glu Val Gly Val
    530                 535                 540
Leu Arg Lys Thr Arg His Val Asn Ile Leu Leu Phe Met Gly Tyr Ser
545                 550                 555                 560
Thr Lys Pro Gln Leu Ala Ile Val Thr Gln Trp Cys Glu Gly Ser Ser
                565                 570                 575
Leu Tyr His His Leu His Ile Ile Glu Thr Lys Phe Glu Met Ile Lys
            580                 585                 590
Leu Ile Asp Ile Ala Arg Gln Thr Ala Gln Gly Met Asp Tyr Leu His
        595                 600                 605
Ala Lys Ser Ile Ile His Arg Asp Leu Lys Ser Asn Asn Ile Phe Leu
    610                 615                 620
His Glu Asp Leu Thr Val Lys Ile Gly Asp Phe Gly Leu Ala Thr Val
625                 630                 635                 640
Lys Ser Arg Trp Ser Gly Ser His Gln Phe Glu Gln Leu Ser Gly Ser
                645                 650                 655
Ile Leu Trp Met Ala Pro Glu Val Ile Arg Met Gln Asp Lys Asn Pro
            660                 665                 670
Tyr Ser Phe Gln Ser Asp Val Tyr Ala Phe Gly Ile Val Leu Tyr Glu
        675                 680                 685
Leu Met Thr Gly Gln Leu Pro Tyr Ser Asn Ile Asn Asn Arg Asp Gln
    690                 695             700
Ile Ile Phe Met Val Gly Arg Gly Tyr Leu Ser Pro Asp Leu Ser Lys
705                 710                 715                 720
Val Arg Ser Asn Cys Pro Lys Ala Met Lys Arg Leu Met Ala Glu Cys
                725                 730                 735
Leu Lys Lys Lys Arg Asp Glu Arg Pro Leu Phe Pro Gln Ile Leu Ala
            740                 745                 750
```

```
Ser Ile Glu Leu Leu Ala Arg Ser Leu Pro Lys Ile His Arg Ser Ala
        755                 760                 765

Ser Glu Pro Ser Leu Asn Arg Ala Gly Phe Gln Thr Glu Asp Phe Ser
    770                 775                 780

Leu Tyr Ala Cys Ala Ser Pro Lys Thr Pro Ile Gln Ala Gly Gly Tyr
785                 790                 795                 800

Gly Gly Phe Pro Val His
            805

<210> SEQ ID NO 45
<211> LENGTH: 2949
<212> TYPE: DNA
<213> ORGANISM: Homo sapiens

<400> SEQUENCE: 45
cgcctcccct tcccctcccc gcccgacagc ggccgctcgg gccccggctc tcggttataa      60
gatggcggcg ctgagcggtg gcggtggtgg cggcgcggag ccgggccagg ctctgttcaa     120
cggggacatg gagcccgagg ccggcgccgg cgccggcgcc gcggcctctt cggctgcgga     180
ccctgccatt ccgaggagg tgtggaatat caaacaaatg attaagttga cacaggaaca     240
tatagaggcc ctattggaca aatttggtgg ggagcataat ccaccatcaa tatatctgga     300
ggcctatgaa gaatacacca gcaagctaga tgcactccaa caagagaac aacagttatt     360 ggaatctctg gggaacggaa ctgatttttc tgtttctagc tctgcatcaa tggataccgt     420
tacatcttct tcctcttcta gcctttcagt gctaccttca tctctttcag tttttcaaaa     480
tcccacagat gtggcacgga gcaaccccaa gtcaccacaa aaacctatcg ttagagtctt     540
cctgcccaac aaacagagga cagtggtacc tgcaaggtgt ggagttacag tccgagacag     600
tctaaagaaa gcactgatga tgagaggtct aatcccagag tgctgtgctg tttacagaat     660
tcaggatgga gagaagaaac caattggttg ggacactgat atttcctggc ttactggaga     720
agaattgcat gtggaagtgt tggagaatgt tccacttaca acacacaact ttgtacgaaa     780
aacgtttttc accttagcat tttgtgactt ttgtcgaaag ctgctttttcc agggttttccg     840 ctgtcaaaca tgtggttata aatttcacca gcgttgtagt acagaagttc cactgatgtg     900
tgttaattat gaccaacttg atttgctgtt tgtctccaag ttctttgaac accccaat     960 accacaggaa gaggcgtcct tagcagagac tgccctaaca tctggatcat cccttccgc    1020 acccgcctcg gactctattg ggccccaaat tctcaccagt ccgtctcctt caaaatccat    1080
tccaattcca cagcccttcc gaccagcaga tgaagatcat cgaaatcaat tgggcaacg    1140 agaccgatcc tcatcagctc ccaatgtgca tataaacaca atagaacctg tcaatattga    1200
tgacttgatt agagaccaag gatttcgtgg tgatggagga tcaaccacag gtttgtctgc    1260 tacccccct gcctcattac ctggctcact aactaacgtg aaagccttac agaaatctcc    1320
aggacctcag cgagaaagga agtcatcttc atcctcagaa acaggaatc gaatgaaaac    1380 acttggtaga cgggactcga gtgatgattg ggagattcct gatgggcaga ttacagtggg    1440
acaaagaatt ggatctggat catttggaac agtctacaag ggaaagtggc atggtgatgt    1500
ggcagtgaaa atgttgaatg tgacagcacc tacacctcag cagttacaag ccttcaaaaa    1560
tgaagtagga gtactcagga aaacacgaca tgtgaatatc ctactcttca tgggctattc    1620
cacaaagcca caactggcta ttgttaccca gtggtgtgag ggctccagct tgtatcacca    1680
tctccatatc attgagacca aatttgagat gatcaaactt atagatattg cacgacagac    1740
```

-continued

```
tgcacagggc atggattact tacacgccaa gtcaatcatc cacagagacc tcaagagtaa   1800
taatatattt cttcatgaag acctcacagt aaaaataggt gattttggtc tagctacaga   1860
gaaatctcga tggagtgggt cccatcagtt tgaacagttg tctggatcca ttttgtggat   1920
ggcaccagaa gtcatcagaa tgcaagataa aaatccatac agctttcagt cagatgtata   1980
tgcatttgga attgttctgt atgaattgat gactggacag ttaccttatt caaacatcaa   2040
caacagggac cagataattt ttatggtggg acgaggatac ctgtctccag atctcagtaa   2100
ggtacggagt aactgtccaa aagccatgaa gagattaatg gcagagtgcc tcaaaaagaa   2160
aagagatgag agaccactct ttccccaaat tctcgcctct attgagctgc tggcccgctc   2220
attgccaaaa attcaccgca gtgcatcaga accctccttg aatcgggctg gtttccaaac   2280
agaggatttt agtctatatg cttgtgcttc tccaaaaaca cccatccagg caggggata    2340 tggtgcgttt cctgtccact gaaacaaatg agtgagagag ttcaggagag tagcaacaaa   2400
aggaaaataa atgaacatat gtttgcttat atgttaaatt gaataaaata ctctcttttt   2460
ttttaaggtg aaccaaagaa cacttgtgtg gttaaagact agatataatt tttccccaaa   2520
ctaaaattta tacttaacat tggattttta acatccaagg gttaaaatac atagacattg   2580
ctaaaaattg gcagagcctc ttctagaggc tttactttct gttccgggtt tgtatcattc   2640
acttggttat tttaagtagt aaacttcagt ttctcatgca actttttgttg ccagctatca   2700 catgtccact agggactcca gaagaagacc ctacctatgc ctgtgtttgc aggtgagaag   2760
ttggcagtcg gttagcctgg gttagataag gcaaactgaa cagatctaat ttaggaagtc   2820
agtagaattt aataattcta ttattattct taataatttt tctataacta tttcttttta   2880
taacaatttg gaaaatgtgg atgtctttta tttccttgaa gcaataaact aagtttcttt   2940
ttataaaaa                                                           2949
```